(12) United States Patent
Hotoda et al.

(10) Patent No.: US 7,157,442 B2
(45) Date of Patent: Jan. 2, 2007

(54) ANTIBACTERIAL COMPOUND

(75) Inventors: Hitoshi Hotoda, Urawa (JP); Masakatsu Kaneko, Yokohama (JP); Masatoshi Inukai, Matsudo (JP); Yasunori Muramatsu, Tokyo (JP); Yukio Utsui, Tokorozawa (JP); Satoshi Ohya, Tokyo (JP)

(73) Assignee: Sankyo Company, Limited, Tokyo (JP)

( * ) Notice: Subject to any disclaimer, the term of this patent is extended or adjusted under 35 U.S.C. 154(b) by 710 days.

(21) Appl. No.: 10/080,191

(22) Filed: Feb. 19, 2002

(65) Prior Publication Data

US 2003/0171330 A1 Sep. 11, 2003

Related U.S. Application Data

(63) Continuation of application No. PCT/JP00/05538, filed on Aug. 18, 2000.

(30) Foreign Application Priority Data

Aug. 20, 1999 (JP) .............................. 11-233934

(51) Int. Cl.
  *A61K 31/70* (2006.01)
  *A61K 31/553* (2006.01)
  *A61K 31/504* (2006.01)
  *C07D 239/02* (2006.01)
  *C07D 401/00* (2006.01)

(52) U.S. Cl. .................... 514/49; 514/211.3; 514/269; 544/209; 544/310; 540/488

(58) Field of Classification Search ................ 514/49, 514/211.03, 269; 544/209, 310; 540/488
See application file for complete search history.

(56) References Cited

U.S. PATENT DOCUMENTS 5,034,381 A 7/1991 Hutchinson et al.
6,472,384 B1 10/2002 Inukai et al.

FOREIGN PATENT DOCUMENTS

| EP | 1 095 947 A1 | 5/2001 |
|---|---|---|
| HU | 48904 | 7/1989 |
| HU | 73659 | 9/1996 |
| JP | 60-259190 | 12/1985 |
| JP | 1-265100 A | 10/1989 |
| JP | 5-148293 | 6/1993 |
| JP | 05-148293 A2 | 6/1993 |
| JP | 2001253897 * | 1/2000 |
| JP | 2000-154187 | 6/2000 |
| JP | 2000-159765 | 6/2000 |
| JP | 2001-253828 | 9/2001 |
| WO | WO 94/22887 A1 | 10/1994 |
| WO | WO 00/02892 | 1/2000 |

OTHER PUBLICATIONS

H. Yamaguchi et al., Capuramycin, A New Nucleoside Antibiotic Taxonomy, Fermentation, Isolation and Characterization, *The Journal of Antibiotics*, vol. 39, No. 8, pp. 1047-1053 (1986).
U.S. Appl. No. 09/757,393, filed Jan. 2001, Masatoshi Inukai et al.
H. Seto et al., "The Structure of a New Nucleoside Antibiotic, Capuramycin", *Tetrahedron Letters,* vol. 29, No. 19, pp. 2343-2346 (1988).
H. Seto, "Structural Studies of Natural Products by New NMR Techniques", *Pure and Applied Chemistry,* vol. 61, No. 3, pp. 365-368 (1989).
S. Knapp et al., "Synthesis of Capuramycin", *Journal of Organic Chemistry,* vol. 59, No. 2, pp. 281-283 (1994).

* cited by examiner

*Primary Examiner*—James O. Wilson
*Assistant Examiner*—Paul V. Ward
(74) *Attorney, Agent, or Firm*—Frishauf, Holtz, Goodman & Chick, P.C.

(57) ABSTRACT

The present invention relates to a compound of formula (I) (wherein $R^1$ and $R^2$ represent an aryl group, a heterocyclic group, an alkyl group, an alkenyl group and the like which are optionally substituted, $R^3$ represents a hydrogen atom or a hydroxyl group, and $X^1$ and $X^2$ represent an oxygen atom or a sulfur atom, or a nitrogen atom which may be substituted), a pharmaceutically acceptable derivative thereof or a salt thereof.

The present invention also relates to a pharmaceutical composition comprising a compound described above as an active ingredient for the prevention or treatment of bacterial infections.

The present invention includes the use of a compound described above in order to prepare a medicament effective in the prevention or treatment of bacterial infections.

The present invention is concerned with a method for the prevention or treatment of bacterial infections in warm-blooded animals comprising administering a pharmacologically effective amount of a compound described above to them (I)

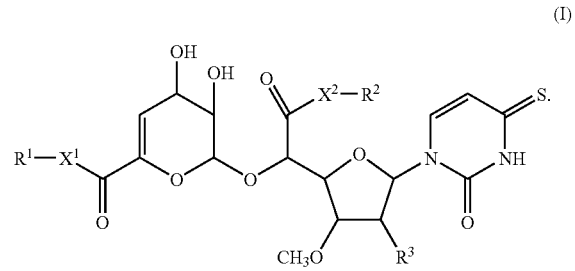

84 Claims, No Drawings

ANTIBACTERIAL COMPOUND

This application is a continuation application of International Patent Application PCT/JP00/05538 filed Aug. 18, 2000 (not published in English). The entire content of PCT/JP00/05538 is hereby incorporated by reference herein.

BACKGROUND OF THE INVENTION

1. Field of the Invention

The present invention relates to compounds of formula (I) which have excellent antibacterial activity and pharmaceutically acceptable derivatives or pharmaceutically acceptable salts thereof.

The present invention also relates to a composition effective to prevent or treat bacterial infections comprising a compound described above as an active ingredient.

The present invention further includes the use of a compound described above in order to prepare a medicament effective to prevent or treat bacterial infections.

The present invention is concerned with a method effective to prevent or treat bacterial infections in warm-blooded animals which comprises administering to them a pharmacologically effective amount of a compound described above.

2. Background Information b-lactam antibiotics, amino-glycosides, quinolone carboxylic acids, isoniazids and rifampicin have conventionally been used in the treatment and prophylaxis of bacterial infections. Recently a lot of bacteria have become resistant to these antibiotics. It is desirable to develop new compounds which have different types of mechanism of antimicrobial action from the conventional ones.

On the other hand, it has been known that capuramycin, having the formula shown below, exhibits anti acid-fast *bacillus* activity without cross-resistance to conventional medicaments. However, its antibacterial activity is not potent enough to enable its use as an antibacterial agent. (J. Antibiotics, 29, (8), 1047–1053 (1986)).

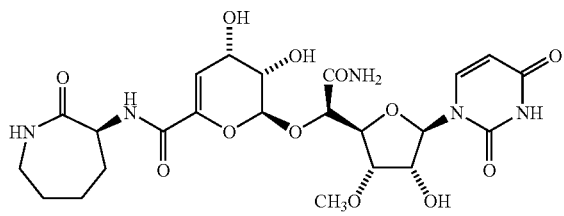

After many compounds were prepared by chemical modification of capuramycin, the present inventors made intensive studies on their pharmacological activities for several years. As a result, they have found that compounds of formula (I), pharmaceutically acceptable derivatives thereof and pharmaceutically acceptable salts thereof exhibit excellent antibacterial activity without cross-resistance to conventional medicaments and are therefore useful as a medicament effective to prevent and treat bacterial infections, and they have accomplished the present invention.

SUMMARY OF THE INVENTION

The present invention includes a compound of formula (I), a pharmaceutically acceptable ester, ether or N-alkyl derivative thereof, or a pharmaceutically acceptable salt thereof; a composition comprising said compound as an active ingredient for the prevention or treatment of a bacterial infection; the use of said compound in order to manufacture a medicament for the prevention or treatment of bacterial infection; and a method for the treatment or prevention of a bacterial infection which comprises administering to a warm-blooded animal an amount of said compound effective to treat or prevent a bacterial infection:

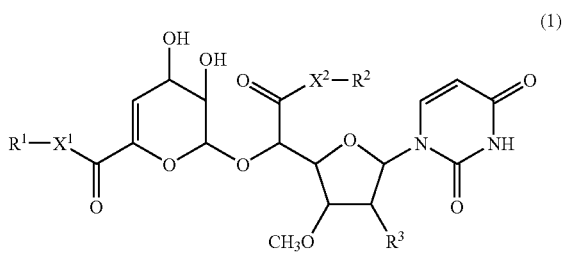

(1)

wherein:

$X^1$ represents an oxygen atom, a sulfur atom or a group of formula —N($R^4$)— (in which $R^4$ is a hydrogen atom, a $C_1$–$C_3$ alkyl group, or $R^4$, together with $R^1$ and the nitrogen atom to which they are attached, forms a 3- to 7-membered cyclic amine which may have a ring oxygen or sulfur atom);

$X^2$ represents an oxygen atom, a sulfur atom or a group of formula —N($R^5$)— (in which $R^5$ is a hydrogen atom, a $C_1$–$C_3$ alkyl group, or $R^5$, together with $R^2$ and the nitrogen atom to which they are attached, forms a 3- to 7-membered cyclic amine which may have a ring oxygen or sulfur atom);

$R^1$ and $R^2$ are the same or different and each represents:

(1) a hydrogen atom;

(2) a $C_6$–$C_{10}$ aryl group which may have one or more substituents [said one or more substituents are selected from Group A, consisting of a halogen atom, a hydroxyl group, an amino group (said amino group may be substituted with one or more $C_1$–$C_6$ alkyl groups), a nitro group, a cyano group, a carboxyl group, a $C_1$–$C_4$ alkoxycarbonyl group, a carbamoyl group, a $C_1$–$C_{10}$ alkylenedioxy group, a $C_7$–$C_{14}$ aralkyloxy group, a $C_1$–$C_{16}$ alkyl group (said alkyl group may be substituted with one or more halogen atoms), a $C_2$–$C_{16}$ alkenyl group, a $C_1$–$C_{16}$ alkoxy group (said alkoxy group may be substituted with one or more halogen atoms), a $C_1$–$C_{16}$ alkylthio group (said alkylthio group may be substituted with one or more halogen atoms), a $C_6$–$C_{10}$ arylazo group, and a heterocyclic group which has 1–4 nitrogen, sulfur or oxygen atoms];

(3) a heterocyclic group which has 1–4 nitrogen, sulfur or oxygen atoms and which may have one or more substituents [said one or more substituents are selected from Group B, consisting of an oxo group, a thiooxo group, an imino group, a halogen atom, a hydroxyl group, an amino group (said amino group may be substituted with one or more $C_1$–$C_{16}$ alkyl groups), a nitro group, a cyano group, a carboxyl group, a $C_1$–$C_4$ alkoxycarbonyl group, a carbamoyl group, a $C_7$–$C_{14}$ aralkyloxy group, a $C_1$–$C_{16}$ alkyl group (said alkyl group may be substituted with one or more halogen atoms), a $C_2$–$C_{16}$ alkenyl group, a $C_1$–$C_{16}$ alkoxy group (said alkoxy group may be substituted with one or more halogen atoms), and a $C_1$–$C_{16}$ alkylthio group (said alkylthio group may be substituted with one ore more halogen atoms)];

(4) a $C_1$–$C_{14}$ alkyl group which is substituted with one to three $C_6$–$C_{10}$ aryl groups, which may be the same or different, and may have one or more substituents [said one or more substituents on the aryl group are selected from Group A];

(5) a $C_1-C_{14}$ alkyl group which is substituted with one to three heterocyclic groups which may be the same or different and each have 1–4 nitrogen, sulfur or oxygen atoms and may have one or more substituents [said one or more substituents on the heterocyclic group are selected from Group B];

(6) a $C_1-C_{22}$ alkyl group which may have one or more substituents [said one or more substituents are selected from Group C, consisting of a halogen atom, a hydroxyl group, an amino group, a nitro group, a cyano group, a carboxyl group, a $C_1-C_4$ alkoxycarbonyl group, a carbamoyl group, a $C_1-C_{16}$ alkoxy group (said alkoxy group may be substituted with one or more halogen atoms), and a $C_1-C_{16}$ alkylthio group (said alkylthio group may be substituted with one or more halogen atoms)];

(7) a $C_2-C_{22}$ alkenyl group which may have one or more substituents [said one or more substituents are selected from those listed in (2) or (3) above or from Group C]; or (8) a group of formula (a)

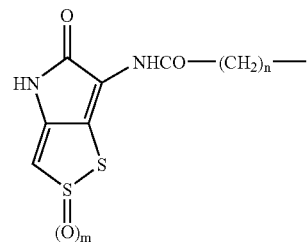

(a)

[in which n represents an integer of 1 to 20 and m represents 0 or 2]; and $R^3$ represents a hydrogen atom or a hydroxyl group;

with the proviso that:

a compound wherein $X^1$ and $X^2$ represents a group of formula —NH—, $R^1$ represents a hydrogen atom or a group of formulae (II), (III), (IV) or (V), $R^2$ is a hydrogen atom and $R^3$ is a hydroxyl group; and a compound wherein $X^1$ is an oxygen atom, $X^2$ represents a group of formula —NH—, $R^1$ represents a hydrogen atom or a methyl group, $R^2$ is a hydrogen atom and $R^3$ is a hydroxyl group;

are excluded.

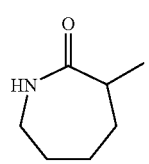

(II)

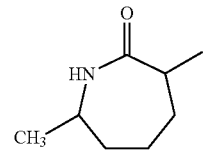

(III)

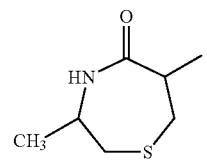

(IV)

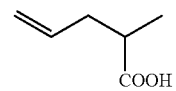

(V)

DETAILED DESCRIPTION OF THE INVENTION

In the compounds of formula (I), examples of the "$C_1-C_3$ alkyl group" in the definition of $R^4$ and $R^5$ in the definition of $X^1$ and $X^2$ include alkyl groups such as methyl, ethyl, propyl or isopropyl, of which the methyl group is preferred.

In the definition of $R^4$ and $R^5$ in $X^1$ and $X^2$, when $R^4$ (or $R^5$), together with $R^1$ (or $R^2$) and the nitrogen atom to which they are attached, forms a 3- to 7-membered cyclic amine which may have an oxygen or sulfur atom, examples of such groups include aziridinyl, azetidinyl, pyrrolidinyl, piperidinyl, morpholinyl or thiomorpholinyl. When $R^4$ (or $R^5$), taken together with $R^1$ (or $R^2$) and the nitrogen atom to which they are attached, forms such a group, a 5- or 6-membered cyclic amine is preferred and pyrrolidinyl is more preferred.

Preferably, $R^4$ in $X^1$ is a hydrogen atom or a $C_1-C_3$ alkyl group, or $R^4$, together with $R^1$ and the nitrogen atom to which they are attached, forms a 5- or 6-membered cyclic amine, of which a hydrogen atom or a $C_1-C_3$ alkyl group is more preferred, and a hydrogen atom is particularly preferred.

As $R^5$ in $X^2$, a hydrogen atom or a $C_1-C_3$ alkyl group is more preferred, and a hydrogen atom is particularly preferred.

As a whole group $X^1$, a group represented by the formula —N($R^4$)— is preferred and a group represented by the formula —N($R^4$)— (wherein $R^4$ is a hydrogen atom, or a $C_1-C_3$ alkyl group, or $R^4$, together with $R^1$ and the nitrogen atom to which they are attached, forms a 5- or 6-membered cyclic amine), is more preferred. A group represented by the formula —N($R^4$)— (wherein $R^4$ is a hydrogen atom or a $C_1-C_3$ alkyl group) is still more preferred and a group represented by the formula —N(H)— is particularly preferred.

As a whole group $X^2$, a group represented by the formula —N($R^5$)— is preferred and a group represented by the formula —N($R^5$)— (wherein $R^5$ is a hydrogen atom or a $C_1-C_3$ alkyl group) is more preferred. A group represented by the formula —N(H)— is particularly preferred.

In the definition of $R^1$ and $R^2$, examples of the "$C_6-C_{10}$ aryl group" include aryl groups such as phenyl, 1-naphthyl or 2-naphthyl, of which phenyl is preferred.

Examples of the "heterocyclic group which has 1–4 nitrogen, sulfur or oxygen atoms" include 5- or 6-membered aromatic heterocyclic groups such as furyl, thienyl, pyrrolyl, pyrazolyl, imidazolyl, oxazolyl, isoxazolyl, thiazolyl, isothiazolyl, triazolyl, tetrazolyl, thiadiazolyl, pyridyl, pyridazinyl, pyrimidinyl and pyrazinyl, and partially or fully reduced heterocyclic groups such as tetrahydrofuryl, morpholinyl, thiomorpholinyl, pyrrolidinyl, pyrrolinyl, imidazolidinyl, pyrazolidinyl, pyrazolinyl, piperidinyl, piperazinyl and pyranyl.

The aforementioned 5- or 6-membered aromatic heterocyclic groups and partially or fully reduced heterocyclic groups may be fused to other cyclic groups such as phenyl. Examples of such fused groups include benzofuranyl, benzothienyl, benzimidazolyl, isobenzothienyl, chromenyl, xanthenyl, phenoxathiinyl, indolizinyl, isoindolyl, indolyl, indazolyl, purinyl, quinolidinyl, isoquinolyl, quinolyl, phthalazinyl, naphthyridinyl, quinoxalinyl, quinazolinyl, carbazolyl, carbolinyl, acridinyl, and isoindolinyl.

Among these heterocyclic groups, 5- or 6-membered aromatic heterocyclic groups or 5- or 6-membered aromatic heterocyclic groups fused to benzene rings are preferred, and furyl, thienyl, pyridinyl, thiazolyl, thiadiazolyl or quinolinyl groups are more preferred.

"$C_1$–$C_{22}$ alkyl group" means a straight or branched chain, or cyclic saturated $C_1$–$C_{22}$ hydrocarbon group. Examples of straight or branched chain alkyl groups include the methyl, ethyl, propyl, isopropyl, butyl, isobutyl, sec-butyl, tert-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 6,6-dimethylheptyl, decyl, 1-methylnonyl, 3-methylnonyl, 8-methylnonyl, 3-ethyloctyl, 3,7-dimethyloctyl, 7,7-dimethyloctyl, undecyl, 4,8-dimethylnonyl, dodecyl, tridecyl, tetradecyl, pentadecyl, 3,7,11-trimethyldodecyl, hexadecyl, 4,8,12-trimethyltridecyl, 1-methylpentadecyl, 14-methylpentadecyl, 13,13-dimethyltetradecyl, heptadecyl, 15-methylhexadecyl, octadecyl, 1-methylheptadecyl, nonadecyl, icosyl, 3,7,11,15-tetramethyhexadecyl, henicosyl and docosyl groups. Examples of a $C_3$–$C_{12}$ cycloalkyl group which is optionally substituted with a group which may have a branched chain or is optionally a fused ring include the cyclopropyl, cyclobutyl, cyclopentyl, cyclohexyl, methylcyclohexyl, dimethylcyclohexyl, ethylcyclohexyl, propylcyclohexyl, butylcyclohexyl, tert-butylcyclohexyl, cycloheptyl, cyclooctyl, cyclononyl, cyclodecyl, cyclododecyl, norbornyl and adamantyl groups. Examples of cycloalkylalkyl groups include the cyclopropylmethyl, cyclopropylethyl, cyclobutylethyl, cyclobutylethyl, cyclopentylmethyl, cyclopentylethyl, cyclohexylmethyl, cyclohexylethyl, cyclohexylpropyl, cyclohexylbutyl and cyclohexylhexyl groups. A $C_1$–$C_{18}$ straight or branched chain alkyl group, or a $C_5$–$C_{12}$ cycloalkyl group, is preferred.

A "$C_1$–$C_{14}$ alkyl group which is substituted with one to three $C_6$–$C_{10}$ aryl groups which may be the same or different" means a "$C_1$–$C_{14}$ alkyl group" which is substituted with one to three aforementioned "$C_6$–$C_{10}$ aryl groups".

A "$C_1$–$C_{14}$ alkyl group which is substituted with one to three heterocyclic groups which may be the same or different and each have 1–4 nitrogen, sulfur or oxygen atoms" means a "$C_1$–$C_{14}$ alkyl group" which is substituted with one to three aforementioned "heterocyclic groups which have 1–4 nitrogen, sulfur or oxygen atoms".

A "$C_2$–$C_{22}$ alkenyl group" means a straight or branched chain or cyclic, unsaturated $C_2$–$C_{22}$ hydrocarbon group with one to three double bonds. Examples of straight or branched chain alkenyl groups include ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl, 5-hexenyl, heptenyl, octenyl, decenyl, dodecenyl, tetradecenyl, hexadecenyl, cis-8-heptadecenyl, cis, cis-8,11-heptadecadienyl, cis,cis,cis-8,11,14-heptadecatrienyl, cis-9-octadecenyl, cis-10-nonadecenyl and cis-12-icosenyl groups. Examples of a cycloalkenyl group which is optionally substituted with a group which may have a branch include the cyclopentenyl, methylcyclopentenyl, cyclohexenyl, methylcyclohexenyl, dimethylcyclohexenyl, ethylcyclohexenyl, butylcyclohexenyl, cycloheptenyl, cyclooctenyl, cyclodecenyl and cyclododecenyl groups. Examples of cycloalkenylalkyl groups include the cyclopentenylmethyl, cyclohexenylmethyl, cyclohexenylethyl and cyclohexenylbutyl groups. A $C_2$–$C_{18}$ straight or branched chain alkenyl group, or a ($C_5$–$C_8$ cycloalkenyl)alkyl group, is preferred.

Examples of the halogen atom in Groups A, B and C include fluorine, chlorine, bromine or iodine, of which fluorine or chlorine is preferred.

Examples of the amino group which may be substituted with one or more $C_1$–$C_{16}$ alkyl groups in Groups A and B include the unsubstituted amino, methylamino, ethylamino, propylamino, butylamino, hexylamino, octylamino, decylamino, dodecylamino, tetradecylamino, dimethylamino, diethylamino, dipropylamino and dibutylamino groups. An amino group which may be substituted with one or more $C_1$–$C_6$ alkyl groups is preferred, an amino group which may be substituted with one or more $C_1$–$C_3$ alkyl groups is more preferred, and an amino or dimethylamino group is particularly preferred.

Examples of the "$C_1$–$C_{10}$ alkylenedioxy group" in Group A include the methylenedioxy, 1,1-ethylenedioxy, 1,2-ethylenedioxy, 1,1-propylenedioxy, 1,1-butylenedioxy, 1,1-hexylenedioxy, 1,1-octylenedioxy and 1,1-decylenedioxy groups. $C_1$–$C_3$ alkylenedioxy groups are preferred and the methylenedioxy group is particularly preferred.

Examples of the "$C_1$–$C_4$ alkoxycarbonyl group" in Groups A, B and C include the methoxycarbonyl, ethoxycarbonyl, propyloxycarbonyl, isopropyloxycarbonyl, butyloxycarbonyl, isobutyloxycarbonyl, sec-butyloxycarbonyl and tert-butyloxycarbonyl groups, of which the methoxycarbonyl and ethoxycarbonyl groups are preferred.

Examples of the "$C_7$–$C_{14}$ aralkyloxy group" in Groups A and B include the benzyloxy, 1-phenethyloxy, 2-phenethyloxy, 3-phenylpropyloxy, 2-phenylpropyloxy, 4-phenylbutyloxy, 1-naphthylmethyloxy, 2-(1-naphthyl)ethyloxy, 3-(1-naphthyl)propyloxy, 4-(1-naphthyl)butyloxy, 2-naphthylmethyloxy, 2-(2-naphthyl)ethyloxy, 3-(2-naphthyl)propyloxy and 4-(2-naphthyl)butyloxy groups. $C_7$–$C_{10}$ phenylalkyloxy groups are preferred, and the benzyloxy and 2-phenethyloxy groups are more preferred.

Examples of the "$C_1$–$C_{16}$ alkyl group (said alkyl group may be substituted with one or more halogen atoms" in Groups A and B include straight or branched chain alkyl groups such as methyl, ethyl, propyl, isopropyl, butyl, isobutyl, sec-butyl, tert-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 6,6-dimethylheptyl, decyl, 1-methylnonyl, 3-methylnonyl, 8-methylnonyl, 3-ethyloctyl, 3,7-dimethyloctyl, 7,7-dimethyloctyl, undecyl, 4,8-dimethylnonyl, dodecyl, tridecyl, tetradecyl, pentadecyl, 3,7,11-trimethyldodecyl, hexadecyl, 4,8,12-trimethyltridecyl, 1-methylpentadecyl, 14-methylpentadecyl, 13,13-dimethyltetradecyl and 15-methylhexadecyl groups; and straight or branched chain alkyl groups which are substituted with halogen atom(s) such as trifluoromethyl, 2-fluoroethyl, 2,2,2-trifluoroethyl, pentafluoroethyl, heptafluoropropyl, nonafluorobutyl, undecafluoropentyl, tridecafluorohexyl, 3-fluoropropyl, 4-fluorobutyl, 5-fluoropentyl, 6-fluorohexyl, chloromethyl, dichloromethyl, 2-chloroethyl, 3-chloropropyl, bromomethyl and 2-bromoethyl groups. $C_1$–$C_{16}$ alkyl groups (said alkyl group may be substituted with one or more fluorine or chlorine atoms) are preferred and $C_1$–$C_{16}$ alkyl groups (said alkyl group may be substituted with one or more fluorine atoms) are more preferred.

Examples of the "$C_2$–$C_{16}$ alkenyl group" in Groups A and B include straight or branched chain alkenyl groups such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl, 5-hexenyl, heptenyl, octenyl, decenyl, dodecenyl, tetradecenyl and hexadecenyl groups, of which $C_2$–$C_{10}$ alkenyl groups are preferred.

Examples of the "$C_1$–$C_{16}$ alkoxy group (said alkoxy group may be substituted with halogen atom(s)" in Groups A, B and C include straight or branched chain alkoxy groups such as methoxy, ethoxy, propyloxy, isopropyloxy, butyloxy, isobutyloxy, sec-butyloxy, tert-butyloxy, pentyloxy, isopentyloxy, 2-methylbutyloxy, neopentyloxy, 1-ethylpropyloxy, hexyloxy, isohexyloxy, 4-methylpentyloxy, 3-methylpentyloxy, 2-methylpentyloxy, 1-methylpentyloxy, 3,3-dimethylbutyloxy, 2,2-dimethylbutyloxy, 1,1-dimethylbutyloxy, 1,2-dimethylbutyloxy, 1,3-dimethylbutyloxy, 2,3-dimethylbutyloxy, 2-ethylbutyloxy, heptyloxy, 1-methylhexyloxy, 2-methylhexyloxy, 3-methylhexyloxy, 4-methylhexyloxy, 5-methylhexyloxy, 1-propylbutyloxy, 4,4-dimethylpentyloxy, octyloxy, 1-methylheptyloxy, 2-methylheptyloxy, 3-methylheptyloxy, 4-methylheptyloxy, 5-methylheptyloxy, 6-methylheptyloxy, 1-propylpentyloxy, 2-ethylhexyloxy, 5,5-dimethylhexyloxy, nonyloxy, 3-methyloctyloxy, 4-methyloctyloxy, 5-methyloctyloxy, 6-methyloctyloxy, 1-propylhexyloxy, 2-ethylheptyloxy, 6,6-dimethylheptyloxy, decyloxy, 1-methylnonyloxy, 3-methylnonyloxy, 8-methylnonyloxy, 3-ethyloctyloxy, 3,7-dimethyloctyloxy, 7,7-dimethyloctyloxy, undecyloxy, 4,8-dimethylnonyloxy, dodecyloxy, tridecyloxy, tetradecyloxy, pentadecyloxy, 3,7,11-trimethyldodecyloxy, hexadecyloxy, 4,8,12-trimethyltridecyloxy, 1-methylpentadecyloxy, 14-methylpentadecyloxy, 13,13-dimethyltetradecyloxy and 15-methylhexadecyloxy groups; and straight or branched chain alkoxy groups which are substituted with halogen atom(s) such as trifluoromethyloxy, 2-fluoroethyloxy, 2,2,2-trifluoroethyloxy, pentafluoroethyloxy, 1,1,2,2-tetrafluoroethyloxy, heptafluoropropyloxy, nonafluorobutyloxy, undecafluoropentyloxy, tridecafluorohexyloxy, 3-fluoropropyloxy, 4-fluorobutyloxy, 5-fluoropentyloxy, 6-fluorohexyloxy, pentafluoroethylmethyloxy, heptafluoropropylmethyloxy, 2-(nonafluorobutyl)ethyloxy, 2-(tridecafluorohexyl)ethyloxy, 2-(heptadecafluorooctyl)ethyloxy, chloromethyloxy, dichloromethyloxy, 2-chloroethyloxy, 3-chloropropyloxy, bromomethyloxy and 2-bromoethyloxy groups. $C_1$–$C_{16}$ alkoxy groups (said alkoxy group may be substituted with one or more fluorine or chlorine atoms) are preferred and $C_1$–$C_{16}$ alkoxy groups (said alkoxy group may be substituted with one or more fluorine atoms) are more preferred.

Examples of the "$C_1$–$C_{16}$ alkylthio group (said alkylthio group may be substituted with one or more halogen atoms" in Groups A, B and C include straight or branched chain alkylthio group such as methylthio, ethylthio, propylthio, isopropylthio, butylthio, isobutylthio, sec-butylthio, tert-butylthio, pentylthio, isopentylthio, 2-methylbutylthio, neopentylthio, 1-ethylpropylthio, hexylthio, isohexylthio, 4-methylpentylthio, 3-methylpentylthio, 2-methylpentylthio, 1-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio, 2-ethylbutylthio, heptylthio, 1-methylhexylthio, 2-methylhexylthio, 3-methylhexylthio, 4-methylhexylthio, 5-methylhexylthio, 1-propylbutylthio, 4,4-dimethylpentylthio, octylthio, 1-methylheptylthio, 2-methylheptylthio, 3-methylheptylthio, 4-methylheptylthio, 5-methylheptylthio, 6-methylheptylthio, 1-propylpentylthio, 2-ethylhexylthio, 5,5-dimethylhexylthio, nonylthio, 3-methyloctylthio, 4-methyloctylthio, 5-methyloctylthio, 6-methyloctylthio, 1-propylhexylthio, 2-ethylheptylthio, 6,6-dimethylheptylthio, decylthio, 1-methylnonylthio, 3-methylnonylthio, 8-methylnonylthio, 3-ethyloctylthio, 3,7-dimethyloctylthio, 7,7-dimethyloctylthio, undecylthio, 4,8-dimethylnonylthio, dodecylthio, tridecylthio, tetradecylthio, pentadecylthio, 3,7,11-trimethyldodecylthio, hexadecylthio, 4,8,12-trimethyltridecylthio, 1-methylpentadecylthio, 14-methylpentadecylthio, 13,13-dimethyltetradecylthio and 15-methylhexadecylthio groups; and straight or branched chain alkylthio groups which are substituted with halogen atom(s) such as trifluoromethylthio, 2-fluoroethylthio, 2,2,2-trifluoroethylthio, pentafluoroethylthio, 1,1,2,2-tetrafluoroethylthio, heptafluoropropylthio, nonafluorobutylthio, undecafluoropentylthio, tridecafluorohexylthio, 3-fluoropropylthio, 4-fluorobutylthio, 5-fluoropentylthio, 6-fluorohexylthio, pentafluoroethylmethylthio, heptafluoropropylmethylthio, 2-(nonafluorobutyl)ethylthio, 2-(tridecafluorohexyl)-ethylthio, 2-(heptadecafluorooctyl)ethylthio, chloromethylthio, dichloromethylthio, 2-chloroethylthio, 3-chloropropylthio, bromomethylthio and 2-bromoethylthio groups. $C_1$–$C_{16}$ alkylthio groups (said alkylthio group may be substituted with one or more fluorine or chlorine atoms) are preferred and $C_1$–$C_{16}$ alkylthio groups (said alkyl groups may be substituted with one or more fluorine or chlorine atoms) are more preferred.

Examples of the "$C_6$–$C_{10}$ arylazo group" in Group A include phenylazo, 1-naphthylazo and 2-naphthylazo, of which phenylazo is preferred.

The "heterocyclic group which has 1–4 nitrogen, sulfur or oxygen atoms" in Group A means the same as mentioned above. 5- or 6-membered heterocyclic groups which have 1–3 nitrogen, sulfur or oxygen atoms are preferred.

Group A is preferably Group A1, consisting of a halogen atom, a hydroxyl group, an amino group (said amino group may be substituted with one or more $C_1$–$C_6$ alkyl groups), a nitro group, a cyano group, a carboxyl group, a $C_1$–$C_4$ alkoxycarbonyl group, a carbamoyl group, a $C_1$–$C_4$ alkylenedioxy group, a benzyloxy group, a $C_1$–$C_{16}$ alkyl group (said alkyl group may be substituted with one or more fluorine or chlorine atoms), a $C_2$–$C_{16}$ alkenyl group, a $C_1$–$C_{16}$ alkoxy group (said alkoxy group may be substituted with one or more fluorine or chlorine atoms), a $C_1$–$C_{16}$ alkylthio group (said alkylthio group may be substituted with one or more fluorine or chlorine atoms), a phenylazo group and a 5- or 6-membered heterocyclic group which has 1–3 nitrogen, sulfur or oxygen atoms.

Group A is more preferably Group A2, consisting of a fluorine or chlorine atom, a hydroxyl group, an amino group (said amino group may be substituted with one or more $C_1$–$C_3$ alkyl groups), a nitro group, a cyano group, a carboxyl group, a $C_1$–$C_4$ alkoxycarbonyl group, a carbamoyl group, a $C_1$–$C_4$ alkylenedioxy group, a benzyloxy group, a $C_1$–$C_{16}$ alkyl group (said alkyl group may be substituted with one or more fluorine atoms), a $C_2$–$C_{16}$ alkenyl group, a $C_1$–$C_{16}$ alkoxy group (said alkoxy group may be substituted with one or more fluorine atoms), a $C_1$–$C_{16}$ alkylthio group (said alkylthio group may be substituted with one or more fluorine atoms), a phenylazo group and a 5- or 6-membered heterocyclic group which has 1–3 nitrogen, sulfur or oxygen atoms.

Group B is preferably Group B1, consisting of an oxo group, a thiooxo group, an imino group, a halogen atom, a hydroxyl group, an amino group (said amino group may be substituted with one or more $C_1$–$C_6$ alkyl groups), a nitro group, a cyano group, a carboxyl group, a $C_1$–$C_4$ alkoxycarbonyl group, a carbamoyl group, a benzyloxy group, a $C_1$–$C_{16}$ alkyl group (said alkyl group may be substituted with one or more fluorine or chlorine atoms), a $C_2$–$C_{16}$ alkenyl group, a $C_1$–$C_{16}$ alkoxy group (said alkoxy group may be substituted with one or more fluorine or chlorine atoms) and a $C_1$–$C_{16}$ alkylthio group (said alkylthio group may be substituted with one or more fluorine or chlorine atoms).

Group B is more preferably Group B2, consisting of a thiooxo group, an imino group, a halogen atom, a hydroxyl group, an amino group (said amino group may be substituted with one or more $C_1$–$C_3$ alkyl groups), a nitro group, a cyano group, a carboxyl group, a $C_1$–$C_4$ alkoxycarbonyl group, a carbamoyl group, a benzyloxy group, a $C_1$–$C_{16}$ alkyl group (said alkyl group may be substituted with one or more fluorine atoms), a $C_2$–$C_{16}$ alkenyl group, $C_1$–$C_{16}$ alkoxy group (said alkoxy group may be substituted with one or more fluorine atoms) and a $C_1$–$C_{16}$ alkylthio group (said alkylthio group may be substituted with one or more fluorine atoms).

Group C is preferably Group C1, consisting of a fluorine or chlorine atom, a hydroxyl group, an amino group, a nitro group, a cyano group, a carboxyl group, a $C_1$–$C_4$ alkoxycarbonyl group, a carbamoyl group, a $C_1$–$C_{16}$ alkoxy group (said alkoxy group may be substituted with one or more fluorine or chlorine atoms) and a $C_1$–$C_{16}$ alkylthio group (said alkylthio group may be substituted with one or more fluorine or chlorine atoms).

Group C is more preferably Group C2, consisting of a fluorine atom, a hydroxyl group, an amino group, a nitro group, a cyano group, a carboxyl group, a $C_1$–$C_4$ alkoxycarbonyl group, a carbamoyl group, a $C_1$–$C_{16}$ alkoxy group (said alkoxy group may be substituted with one or more fluorine atoms) and a $C_1$–$C_{16}$ alkylthio group (said alkylthio group may be substituted with one or more fluorine atoms).

In the formula (a), a favourable value of "m" is 0, and a favourable value of "n" is 1–12 and a more favourable value of "n" is 4–8.

Examples of the "$C_6$–$C_{10}$ aryl group which may have one or more substituents (said one or more substituents are selected from Group A) defined as group (2) in the definition of $R^1$ include the phenyl, 4-methylphenyl, 4-ethylphenyl, 4-propylphenyl, 4-isopropylphenyl, 4-butylphenyl, 4-sec-butylphenyl, 4-pentylphenyl, 4-hexylphenyl, 4-heptylphenyl, 4-octylphenyl, 4-decylphenyl, 3-methylphenyl, 3-ethylphenyl, 3-isopropylphenyl, 2-ethylphenyl, 2-propylphenyl, 2-isopropylphenyl, 2-butylphenyl, 4-vinylphenyl, 4-trifluoromethylphenyl, 2,4-dimethylphenyl, 3,4-dimethylphenyl, 3,5-dimethylphenyl, 2,4,6-trimethylphenyl, 2-methoxyphenyl, 2-ethoxyphenyl, 3-ethoxyphenyl, 2-methoxyphenyl, 2-ethoxyphenyl, 3-ethoxyphenyl, 4-methoxyphenyl, 4-ethoxyphenyl, 3-isopropoxyphenyl, 4-isopropoxyphenyl, 4-butoxyphenyl, 4-pentyloxyphenyl, 4-hexyloxyphenyl, 3-benzyloxyphenyl, 2-methyl-4-methoxyphenyl, 3-phenoxyphenyl, 3,4-methylenedioxyphenyl, 3,5-dimethoxyphenyl, 3,4,5-trimethoxyphenyl, 2-fluorophenyl, 3-fluorophenyl, 4-fluorophenyl, 4-chlorophenyl, 4-bromophenyl, 4-iodophenyl, 3-chlorophenyl, 3-iodophenyl, 2,3-difluorophenyl, 2,4-difluorophenyl, 2,5-difluorophenyl, 2,6-difluorophenyl, 3,4-difluorophenyl, 3,5-difluorophenyl, 2,3,4-trifluorophenyl, 2,3,6-trifluorophenyl, 2,4,6-trifluorophenyl, 2,4,5-trifluorophenyl, 3-chloro-4-fluorophenyl, 3-trifluoromethyl-4-fluorophenyl, 3-trifluoromethoxyphenyl, 4-trifluoromethoxyphenyl, 4-methylthiophenyl, 4-trifluoromethylthiophenyl, 3-methylthiophenyl, 3-fluoro-4-methylphenyl, 3-chloro-4-methylphenyl, 3-methyl-4-bromophenyl, 3-nitro-4-fluorophenyl, 3-nitro-4-chlorophenyl, 4-(pentafluoroethylmethoxy)phenyl, 4-(heptafluoropropylmethoxy)phenyl, 4-{2-(nonafluorobutyl)ethoxy}phenyl, 4-{2-(tridecafluorohexyl)ethoxy}phenyl, 4-{2-(heptadecafluorooctyl)ethoxy}phenyl, 4-(2-fluoroethyl)phenyl, 4-(3-fluoropropyl)phenyl, 4-(4-fluorobutyl)phenyl, 4-(5-fluoropentyl)phenyl, 2-nitrophenyl, 3-nitrophenyl, 4-nitrophenyl, 2-hydroxyphenyl, 3-hydroxyphenyl, 4-hydroxyphenyl, 3-cyanophenyl, 4-morpholinophenyl, 4-phenylazophenyl, naphthalen-1-yl, naphthalen-2-yl, 3-aminophenyl and 4-dimethylaminophenyl groups.

Favourable aryl groups are the phenyl, 4-methylphenyl, 4-ethylphenyl, 4-propylphenyl, 4-isopropylphenyl, 4-butylphenyl, 4-sec-butylphenyl, 4-pentylphenyl, 4-hexylphenyl, 4-heptylphenyl, 4-octylphenyl, 4-decylphenyl, 3-methylphenyl, 3-ethylphenyl, 3-isopropylphenyl, 4-vinylphenyl, 4-trifluoromethylphenyl, 3,4-dimethylphenyl, 3,5-dimethylphenyl, 3-ethoxyphenyl, 4-methoxyphenyl, 4-ethoxyphenyl, 3-isopropoxyphenyl, 4-isopropoxyphenyl, 4-butyloxyphenyl, 4-pentyloxyphenyl, 4-hexyloxyphenyl, 3-benzyloxyphenyl, 3-phenoxyphenyl, 3,4-methylenedioxyphenyl, 3,5-dimethoxyphenyl, 3,4,5-trimethoxyphenyl, 3-fluorophenyl, 4-fluorophenyl, 4-chlorophenyl, 4-bromophenyl, 4-iodophenyl, 3-chlorophenyl, 3-iodophenyl, 3,4-difluorophenyl, 3,5-difluorophenyl, 3-chloro-4-fluorophenyl, 3-trifluoromethyl-4-fluorophenyl, 3-trifluoromethoxyphenyl, 4-trifluoromethoxyphenyl, 4-methylthiophenyl, 4-trifluoromethylthiophenyl, 3-methylthiophenyl, 3-fluoro-4-methylphenyl, 3-chloro-4-methylphenyl, 3-methyl-4-bromophenyl, 3-nitro-4-fluorophenyl, 3-nitro-4-chlorophenyl, 4-(pentafluoroethylmethoxy)phenyl, 4-(heptafluoropropylmethoxy)phenyl, 4-{2-(nonafluorobutyl)ethoxy}phenyl, 4-{2-(tridecafluorohexyl)ethoxy}phenyl, 4-{2-(heptadecafluorooctyl)ethoxy}phenyl, 4-(2-fluoroethyl)phenyl, 4-(3-fluoropropyl)phenyl, 4-(4-fluorobutyl)phenyl, 4-(5-fluoropentyl)phenyl, 2-nitrophenyl, 3-nitrophenyl, 4-nitrophenyl, 2-hydroxyphenyl, 3-hydroxyphenyl, 4-hydroxyphenyl, 3-cyanophenyl, 4-morpholinophenyl and 4-phenylazophenyl groups.

More favourable aryl groups are phenyl, 4-ethylphenyl, 4-propylphenyl, 4-butylphenyl, 4-hexylphenyl, 3-methylphenyl, 3-ethylphenyl, 3-isopropylphenyl, 4-trifluoromethylphenyl, 4-butyloxyphenyl, 4-pentyloxyphenyl, 4-hexyloxyphenyl, 3,5-dimethoxyphenyl, 3,4,5-trimethoxyphenyl, 3-fluorophenyl, 4-fluorophenyl, 4-chlorophenyl, 3-chlorophenyl, 3-iodophenyl, 3,4-difluorophenyl, 3,5-difluorophenyl, 3-chloro-4-fluorophenyl, 3-trifluoromethyl-4-fluorophenyl, 3-trifluoromethoxyphenyl, 4-trifluoromethoxyphenyl, 4-methylthiophenyl, 4-trifluoromethylthiophenyl, 3-methylthiophenyl, 3-fluoro-4-methylphenyl, 3-chloro-4-methylphenyl, 4-(pentafluoroethylmethoxy)phenyl, 4-(heptafluoropropylmethoxy)phenyl, 4-{2-(nonafluorobutyl)ethoxy}phenyl, 4-(2-fluoroethyl)phenyl, 4-(3-fluoropropyl)phenyl, 4-(4-fluorobutyl)phenyl, 4-(5-fluoropentyl)phenyl, 3-methyl-4-bromophenyl, 3-nitro-4-fluorophenyl groups.

Examples of the "heterocyclic group which has 1–4 nitrogen, sulfur or oxygen atoms and may have one or more substituents (said one or more substituents are selected from Group B)" defined as group (3) in the definition of $R^1$ include the 2-pyridyl, 3,5-dichloro-2-pyridyl, 3-benzyloxy-2-pyridyl, 3-methyl-2-pyridyl, 4-methyl-2-pyridyl, 5-chloro-2-pyridyl, 3-pyridyl, 2-chloro-3-pyridyl, 6-methoxy-3-pyridyl, 4-pyridyl, 2,3,5,6-tetrafluoro-4-pyridyl, 3-quinolyl, 2-thienyl, 3-methoxycarbonyl-5-acetyl-2-thienyl, 3-thienyl, 2-methoxycarbonyl-3-thienyl, 2-acetyl-3-thienyl, 2-carbamoyl-3-thienyl, 2-furanyl, 5-methoxycarbonyl-2-furanyl, 2-thiazolyl, 5-nitro-2-thiazolyl and 4-methyl-2-thiazolyl groups.

Favourable heterocyclic groups are the 2-pyridyl, 3-benzyloxy-2-pyridyl, 4-methyl-2-pyridyl, 5-chloro-2-pyridyl, 3-pyridyl, 6-methoxy-3-pyridyl, 4-pyridyl, 2,3,5,6-tetrafluoro-4-pyridyl, 2-thienyl, 3-thienyl, 2-furanyl, 5-methoxycarbonyl-2-furanyl, 2-thiazoyl, 5-nitro-2-thiazolyl and 4-methyl-2-thiazolyl groups.

Examples of the "$C_1$–$C_{14}$ alkyl group which is substituted with one to three $C_6$–$C_{10}$ aryl groups which may be the same or different and may have one or more substituents on the aryl group (said substituents are selected from Group A)" defined as group (4) in the definition of $R^1$ include the benzyl, 2-methylbenzyl, 4-methylbenzyl, 4-fluorobenzyl, 2-methoxybenzyl, 4-methoxybenzyl, 3,4,5-trimethoxybenzyl, 3,4-methylenedioxybenzyl, 1-phenylethyl, 2-naphthylmethyl, 2-phenylethyl, 2-(4-methylphenyl)ethyl, 2-(2-methoxyphenyl)ethyl, 2-(3-methoxyphenyl)ethyl, 2-(4-methoxyphenyl)ethyl, 2-(3,4-dimethoxyphenyl)ethyl, 2-(4-fluorophenyl)ethyl, 2-(2-chlorophenyl)ethyl, 2-(3-chlorophenyl)ethyl, 2-(4-chlorophenyl)ethyl, 2-(2,4-dichlorophenyl)ethyl, 2-(4-hydroxyphenyl)ethyl, 2,2-diphenylethyl, 3-phenylpropyl, 6-phenylhexyl, 10-phenyldecyl and 3-(4-hexyloxyphenyl)propyl groups.

Favourable aralkyl groups are the benzyl, 2-methylbenzyl, 4-methylbenzyl, 4-fluorobenzyl, 2-methoxybenzyl, 2-naphthyl, 2-phenylethyl, 2-(4-methylphenyl)ethyl, 2-(4-methoxyphenyl)ethyl, 2-(3,4-dimethoxyphenyl)ethyl, 2-(4-fluorophenyl)ethyl, 2-(2-chlorophenyl)ethyl, 2-(3-chlorophenyl)ethyl, 2-(4-chlorophenyl)ethyl, 2-(2,4-dichlorophenyl)ethyl, 3-phenylpropyl and 6-phenylhexyl groups.

Examples of the "$C_1$–$C_{14}$ alkyl group which is substituted with one to three heterocyclic groups which may be the same or different and each have 1–4 nitrogen, sulfur or oxygen atoms and may have one or more substituents (said one or more substituents on the heterocyclic group are selected from Group B)" defined as group (5) in the defintion of $R^1$ are the 2-furylmethyl, (3-methyl-2-furyl)methyl, 3-furylmethyl, 2-thienylmethyl, 2-pyridylmethyl, 4-fluoro-2-pyridylmethyl, 2-(2-furyl)ethyl, 2-(3-methyl-2-furyl)ethyl, 2-morpholinoethyl, 3-(1-imidazolyl)propyl, 2-quinolylmethyl and 3-(3-pyridyl)propyl groups.

Favourable heterocyclylalkyl groups are the 2-furylmethyl, 3-furylmethyl, 2-thienylmethyl, 2-pyridylmethyl, 4-fluoro-2-pyridylmethyl, 3-(1-imidazolyl)propyl and 2-quinolylmethyl groups.

Examples of the "$C_1$–$C_{22}$ alkyl group which may have one or more substituents (said one or more substituents are selected from Group C)" defined as group (6) in the definition $R^1$ are the methyl, ethyl, propyl, isopropyl, butyl, sec-butyl, tert-butyl, pentyl, hexyl, heptyl, octyl, nonyl, decyl, undecyl, dodecyl, tridecyl, tetradecyl, pentadecyl, hexadecyl, octadecyl, icosyl, docosyl, 1-methylheptyl, 2-ethylhexyl, cyclohexyl, 4-methylcyclohexyl, 4-tert-butylcyclohexyl, cycloheptyl, cyclooctyl, cyclododecyl, cyclohexylmethyl, 3-ethoxypropyl, 3-methylthiopropyl, 2,2-dimethoxyethyl, 2,2-diethoxyethyl, 2-hydroxyethyl, 2-aminoethyl, 4-hydroxybutyl, 5-hydroxypentyl, 5-fluoropentyl, 3-nitropropyl and 2-cyanoethyl groups.

Favourable alkyl groups are the propyl, isopropyl, butyl, sec-butyl, tert-butyl, pentyl, hexyl, heptyl, octyl, nonyl, decyl, undecyl, dodecyl, tridecyl, cyclohexyl, 4-methylcyclohexyl, cycloheptyl, cyclooctyl, cyclododecyl, 3-ethoxypropyl and 3-methylthiopropyl groups.

Examples of the "$C_2$–$C_{22}$ alkenyl group which may have one or more substituents (said one or more substituents are selected from those listed in (2) or (3) described above or from Group C)" defined as group (7) in the definition of $R^1$ are the vinyl, allyl, trans-2-hexen-1-yl, cis-2-hexen-1-yl, trans-2-penten-1-yl, trans-2,4-hexadien-1-yl, 2-(1-cyclohexenyl)ethyl, 4-methyl-trans-2-hexen-1-yl, 6-chloro-trans-2-hexen-1-yl, 6-nitro-trans-2-hexen-1-yl and 6-cyano-trans-2-hexen-1-yl groups.

Favorable alkenyl groups are the trans-2-hexen-1-yl, cis-2-hexen-1-yl, trans-2-penten-1-yl, trans-2,4-hexadien-1-yl, 4-methyl-trans-2-hexen-1-yl and 6-chloro-trans-2-hexen-1-yl groups.

In the definition of the substituents for the $C_2$–$C_{22}$ alkenyl group in group (7), "one or more substituents are selected from those listed in (2) or (3) above (in the definition of $R^1$) or from Group C" include: (i) a $C_6$–$C_{10}$ aryl group which may have one or more substituents selected from Group A (Substituent Group A); (ii) a heterocyclic group which has 1–4 nitrogen, sulfur or oxygen atoms and which may have one or more substituents selected from Group B (Substituent Group B); and (iii) substituents selected from Group C (Substituent Group C).

In the definiton of group (8), "a group of formula (a) (in this formula, n represents an integer from 1 to 20 and m represents 0 or 2)" in the definition of $R^1$, a group of formula (a) in which m is 0 or 2, and n is an integer from 1 to 12 is preferred, a group of formula (a) in which m is 0 or 2, and n is an integer from 4 to 8 is more preferred, and a group of formula (a) in which m is 0, and n is an integer from 4 to 8 is particularly preferred.

Preferred examples of $R^1$ are (2) a $C_6$–$C_{10}$ aryl group which may have one or more substituents, (4) a $C_1$–$C_{14}$ alkyl group which is substituted with one to three $C_6$–$C_{10}$ aryl groups which may be the same or different and may each have one or more substituents, (5) a $C_1$–$C_{14}$ alkyl group which is substituted with one to three heterocyclic groups which may be the same or different, each have 1–4 nitrogen, sulfur or oxygen atoms and may each have one or more substituents, (6) a $C_1$–$C_{22}$ alkyl group which may have one or more substituents, (7) a $C_2$–$C_{22}$ alkenyl group which may have one or more substituents or (8) a group of formula (a) as described above.

More preferred examples are (2) a $C_6$–$C_{10}$ aryl group which may have one or more substituents, (6) a $C_1$–$C_{22}$ alkyl group which may have one or more substituents, (7) a $C_2$–$C_{22}$ alkenyl group which may have one or more substituents or (8) a group of formula (a).

More preferred examples are (2) a $C_6$–$C_{10}$ aryl group which may have one or more substituents, (6) a $C_1$–$C_{22}$ alkyl group which may have one or more substituents or (7) a $C_2$–$C_{22}$ alkenyl group which may have one or more substituents.

Still more preferred examples are (2) a $C_6$–$C_{10}$ aryl group which may have one or more substituents and (6) a $C_1$–$C_{22}$ alkyl group which may have one or more substituents.

The most preferred example is (2) a $C_6$–$C_{10}$ aryl group which may have one or more substituents.

Preferred examples of $R^2$ are (1) a hydrogen atom, (6) a $C_1$–$C_{22}$ alkyl group which may have one or more substituents or (7) a $C_2$–$C_{22}$ alkenyl group which may have one or more substituents.

More preferred examples are a hydrogen atom, a $C_1$–$C_{22}$ alkyl group which has no substituent or a $C_2$–$C_{22}$ alkenyl group which has no substituent.

More preferred examples are a hydrogen atom, a $C_6$–$C_{20}$ alkyl group which has no substituent, or (7) a $C_{10}$–$C_{20}$ alkenyl group which has no substituent.

Still more preferred examples are a hydrogen atom or a $C_6$–$C_{20}$ alkyl group which has no substituent.

The most preferred example is a hydrogen atom.

A preferred example of $R^3$ is a hydroxyl group.

Preferred compounds of formula (I) are as follows:

(1) (1-1) compounds wherein $X^1$ is —$N(R^4)$—,
(1-2) compounds wherein $X^1$ is —$N(R^4)$— (wherein $R^4$ is hydrogen or $C_1$–$C_3$ alkyl),
(1-3) compounds wherein $X^1$ is —NH—;

(2) (2-1) compounds wherein $X^2$ is —$N(R^5)$—,
(2-2) compounds wherein $X^2$ is —$N(R^5)$— (wherein $R^5$ is hydrogen or $C_1$–$C_3$ alkyl),
(2-3) compounds wherein $X^2$ is —NH—;

(3) (3-1) compounds wherein $R^1$ is hydrogen,
(3-2) compounds wherein $R^1$ is $C_6$–$C_{10}$ aryl which may be substituted with onre or more substituents selected from Group A,
(3-2-1) compounds according to (3-2) wherein the one or more substituents are selected from Group A1,
(3-2-2) compounds according to (3-2) wherein the one or more substituents are selected from Group A2,
(3-2-3) compounds according to (3-2) wherein $R^1$ is phenyl, 1-naphthyl or 2-naphthyl which may be substituted with one or more substituents selected from Group A,
(3-2-4) compounds according to (3-2) wherein $R^1$ is phenyl which may be substituted with one or more substituents selected from Group A,
(3-3) compounds wherein $R^1$ is a heterocyclic group which has 1 to 4 nitrogen, oxygen or sulfur atoms and may be substituted with one or more substituents selected from Group B,
(3-3-1) compounds according to (3-3) wherein the one or more substituents are selected from Group B1,
(3-3-2) compounds according to (3-3) wherein the one or more substituents are selected from Group B2,
(3-3-3) compounds according to (3-3) wherein $R^1$ is a 5- or 6-membered aromatic heterocyclic group or a 5- or 6-membered aromatic heterocyclic group fused to a benzene ring, the heterocycle of which may be substituted with one or more substituents selected from Group B,
(3-4) compounds wherein $R^1$ is a $C_1$–$C_{14}$ alkyl group which is substituted with 1 to 3 $C_6$–$C_{10}$ aryl groups which may be the same or different and each may be substituted with one or more substituents selected from Group A,
(3-4-1) compounds according to (3-4) wherein the one or more substituents are selected from Group A1,
(3-4-2) compounds according to (34) wherein the one or more substituents are selected from Group A2,
(3-4-3) compounds according to (3-4) wherein the aryl moiety is phenyl, 1-naphthyl or 2-naphthyl which may be substituted with one or more substituents selected from Group A,
(3-4-4) compounds according to (34) wherein the aryl moiety is phenyl which may have one or more substituents,
(3-4-5) compounds according to (34) wherein the alkyl moiety is $C_1$–$C_8$ alkyl,
(3-4-6) compounds according to (34) wherein the alkyl moiety is $C_1$–$C_4$ alkyl,
(3-4-7) compounds according to (3-4) wherein the alkyl moiety is $C_1$–$C_2$ alkyl,
(3-4-8) compounds according to (34) wherein the alkyl moiety is $C_2$ alkyl,
(3-5) compounds wherein $R^1$ is $C_1$–$C_{14}$ alkyl which is substituted with 1 to 3 heterocyclic groups which may be the same or different and each have 1–4 nitrogen, sulfur or oxygen atoms and may be substituted with one or more substituents selected from Group B,
(3-5-1) compounds according to (3-5) wherein the one or more substituents are selected from Group B1,
(3-5-2) compounds according to (3-5) wherein the one or more substituents are selected from Group B2,
(3-5-3) compounds according to (3-5) wherein the heterocyclic moiety is a 5- or 6-membered aromatic heterocyclic group or a 5- or 6-membered aromatic heterocyclic group fused to a benzene ring, the heterocycle of which may be substituted with one or more substituents selected from Group B,
(3-5-4) compounds according to (3-5) wherein the alkyl moiety is $C_1$–$C_8$ alkyl,
(3-5-5) compounds according to (3-5) wherein the alkyl moiety is $C_1$–$C_4$ alkyl,
(3-5-6) compounds according to (3-5) wherein the alkyl moiety is $C_1$–$C_2$ alkyl,
(3-5-7) compounds according to (3-5) wherein the alkyl moiety is $C_2$ alkyl,
(3-6) compounds wherein $R^1$ is $C_1$–$C_{22}$ alkyl which may be substituted with one or more substituents selected from Group C, (3-6-1) compounds according to (3-6) wherein the one or more substituents are selected from Group C1,
(3-6-2) compounds according to (3-6) wherein the one or more substituents are selected from Group C2,
(3-6-3) compounds wherein $R^1$ is $C_1$–$C_{18}$ alkyl which may be substituted with one or more substituents selected from Group C,
(3-7) compounds wherein $R^1$ is $C_2$–$C_{22}$ alkenyl which may be substituted with one or more substituents selected from those listed in (2), (3) described above or Group C,
(3-7-1) compounds according to (3-7) wherein $R^1$ is $C_2$–$C_{22}$ alkenyl which may be substituted with one or more substituents selected from Group C,
(3-7-2) compounds according to (3-7) wherein $R^1$ is $C_2$–$C_{22}$ alkenyl,
(3-7-3) compounds according to (3-7) wherein $R^1$ is $C_1$–$C_{18}$ alkenyl,
(3-8) compounds wherein $R^1$ is a group of formula (a),
(3-8-1) compounds according to (3-8) wherein m is 0,
(3-8-2) compounds according to (3-8) wherein n is an integer from 1 to 12,
(3-8-3) compounds according to (3-8) wherein n is an integer from 4 to 8,
(3-8-4) compounds according to (3-8) wherein m is 0 or 2 and n is an integer from 4 to 8,
(3-8-5) compounds according to (3-8) wherein m is 0 and n is an integer from 4 to 8;
(4-1) compounds wherein $R^2$ is hydrogen, $C_1$–$C_{22}$ alkyl which may be substituted with one or more substituents selected from Group C, or $C_2$–$C_{22}$ alkenyl which may be substituted with one or more substituents selected from Group C,
(4-2) compounds wherein $R^2$ is hydrogen, $C_1$–$C_{22}$ alkyl, or $C_2$–$C_{22}$ alkenyl,
(4-3) compounds wherein $R^2$ is hydrogen, $C_6$–$C_{20}$ alkyl, or $C_{10}$–$C_{20}$ alkenyl,
(4-4) compounds wherein $R^2$ is hydrogen or, $C_6$–$C_{20}$ alkyl,
(4-5) compounds wherein $R^2$ is $C_6$–$C_{20}$ alkyl,
(4-6) compounds wherein $R^2$ is hydrogen;
(5-1) compounds wherein $R^3$ is hydrogen, and
(5-2) compounds wherein $R^3$ is hydroxyl.

(6) More preferred compounds of formula (I) are selected from an appropriate combination of definitions of $X^1$, $X^2$, $R^1$, $R^2$ and $R^3$ described above. Typical examples of such combinations are shown below. These examples are intended to illustrate the present invention and are not intended to limit the scope of this invention in any manner.

(6-1) $X^1$ is a group of formula —N($R^4$)—, $X^2$ is a group of formula —N($R^5$)—;
  $R^1$ is selected from (2) $C_6$–$C_{10}$ aryl which may be substituted with one or more substituents selected from Group A, (4) $C_1$–$C_{14}$ alkyl which is substituted with 1 to 3 $C_6$–$C_{10}$ aryl groups which may be the same or different and each may be substituted with one or more substituents selected from Group A, (5) $C_1$–$C_{14}$ alkyl which is substituted with 1 to 3 heterocyclic groups which may be the same or different and each have 1 to 4 nitrogen, sulfur or oxygen atoms and may be substituted with one or more substituents selected from Group B, (6) $C_1$–$C_{22}$ alkyl which may be substituted with one or more substituents selected from Group C, (7) $C_2$–$C_{22}$ alkenyl which may be substituted with one or more substituents selected from those listed in (2) or (3) of the definition of $R^1$ above or Group C, or (8) a group of formula (a);
  $R^2$ is hydrogen or $C_6$–$C_{20}$ alkyl, and $R^3$ is hydrogen or hydroxyl.
(6-2) $X^1$ and $X^2$ are each an —NH— group;
  $R^1$ is (2) $C_6$–$C_{10}$ aryl which may be substituted with one ore more substituents selected from Group A, (4) $C_1$–$C_{14}$ alkyl which is substituted with 1 to 3 $C_6$–$C_{10}$ aryl groups which may be the same or different and each may be substituted with one or more substituents selected from Group A, (5) $C_1$–$C_{14}$ alkyl which is substituted with 1 to 3 heterocyclic groups which be may be the same or different and each have 1 to 4 nitrogen, sulfur or oxygen atoms and each may be substituted with one or more substituents selected from Group B, (6) $C_1$–$C_{22}$ alkyl which may be substituted with one or more substituents selected from Group C, (7) $C_2$–$C_{22}$ alkenyl which may be substituted with one or more substituents selected from those listed in (2) or (3) of the definition of $R^1$ above or Group C, or (8) a group of formula (a);
  $R^2$ is hydrogen or $C_6$–$C_{20}$ alkyl, and
  $R^3$ is hydrogen or hydroxyl.
(6-3) $X^1$ and $X^2$ are each an —NH— group;
  $R^1$ is (2) $C_6$–$C_{10}$ aryl which may be substituted with one or more substituents selected from Group A, (6) $C_1$–$C_{22}$ alkyl which may be substituted with one or more substituents selected from Group C, (7) $C_2$–$C_{22}$ alkenyl which may be substituted with one or more substituents selected from those listed in (2) or (3) of the definition of $R^1$ above or Group C, or (8) a group of formula (a);
  $R^2$ is hydrogen or $C_6$–$C_{20}$ alkyl, and
  $R^3$ is hydrogen or hydroxyl.
(6-4) $X^1$ and $X^2$ are each an —NH— group,
  $R^1$ is (2) $C_6$–$C_{10}$ aryl which may be substituted with one or more substituents selected from Group A or (6) $C_6$–$C_{22}$ alkyl which may be substituted with one or more substituents selected from Group C;
  $R^2$ is hydrogen or $C_6$–$C_{20}$ alkyl, and
  $R^3$ is hydrogen or hydroxyl.
(6-5) $X^1$ and $X^2$ are each an —NH— group;
  $R^1$ is (2) $C_6$–$C_{10}$ aryl which may be substituted with one or more substituents selected from Group A;
  $R^2$ is hydrogen or $C_6$–$C_{20}$ alkyl; and
  $R^3$ is hydrogen or hydroxyl.
(6-6) $X^1$ and $X^2$ are each an —NH— group;
  $R^1$ is phenyl which may be substituted with one or more substituents selected from Group A;
  $R^2$ is hydrogen; and
  $R^3$ is hydroxyl.
(6-7) $X^1$ and $X^2$ are each an —NH— group;
  $R^1$ is phenyl which may be substituted with one or more substituents selected from Group A;
  $R^2$ is $C_6$–$C_{20}$ alkyl, and
  $R^3$ is hydroxyl.
(6-8) $X^1$ and $X^2$ are each an —NH— group,
  $R^1$ is phenyl which may be substituted with one or more substituents selected from Group A,
  $R^2$ is hydrogen, and
  $R^3$ is hydrogen.

"Pharmaceutically acceptable esters, ethers and N-alkyl derivatives" of the compounds of formula (I) are those which do not exhibit significant toxicity and can usually be used as medicaments.

The compounds of formula (I) of this invention have hydroxyl groups: an appropriate hydroxyl group can be converted by chemical modification to an ester or ether thereof which does not exhibit significant toxicity and is pharmaceutically acceptable.

The compounds of formula (I) of this invention have a uracil moiety: the nitrogen atom at the 3-position of the uracil group can be converted by chemical modification to produce an N-alkyl derivative thereof which does not exhibit significant toxicity is pharmaceutically acceptable.

Among these compounds, preferred compounds are pharmaceutically acceptable esters or ethers and esters; are more preferred.

Examples of ester groups include:

a carbonyl or carbonyloxy group to which a straight or branched chain $C_1$–$C_{21}$ alkyl group is attached, wherein the alkyl groups include methyl, ethyl, propyl, isopropyl, butyl, isobutyl, s-butyl, tert-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 6,6-dimethylheptyl, decyl, 1-methylnonyl, 3-methylnonyl, 8-methylnonyl, 3-ethyloctyl, 3,7-dimethyloctyl, 7,7-dimethyloctyl, undecyl, 4,8-dimethylnonyl, dodecyl, tridecyl, tetradecyl, pentadecyl, 3,7,11-trimethyldodecyl, hexadecyl, 4,8,12-trimethyltridecyl, 1-methylpentadecyl, 14-methylpentadecyl, 13,13-dimethyltetradecyl, heptadecyl, 15-methylhexadecyl, octadecyl, 1-methylheptadecyl, nonadecyl, icosyl, 3,7,11,15-tetramethylhexadecyl and henicosyl;

a carbonyl or carbonyloxy group to which a straight or branched chain $C_2$–$C_{21}$ alkenyl or alkynyl group is attached, wherein the alkenyl groups include ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl, 5-hexenyl, cis-8-heptadecenyl, cis, cis-8,11-heptadecadienyl, cis, cis, cis-8,11,14-heptadecatrienyl, cis-10-nonadecenyl and cis-12-icosenyl, and the alkynyl groups include ethynyl, 2-propynyl, 1-methyl-2-propynyl, 2-methyl-2-propynyl, 2-ethyl-2-propynyl, 2-butynyl, 1-methyl-2-butynyl, 2-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 2-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl and 5-hexynyl;

a carbonyl or carbonyloxy group to which is attached a straight or branched chain $C_1$–$C_{21}$ alkyl group which is substituted with one or more substituents selected from the group consisting of $C_1$–$C_4$ alkoxy, halogen (for example fluorine, chlorine, bromine or iodine, of which fluorine or chlorine is preferred), and nitro, wherein the substituted alkyl groups include methoxymethyl, ethoxymethyl, methoxyethyl, ethoxyethyl, trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl, 2,2-dibromoethyl, nitromethyl, dinitromethyl, 1-nitroethyl, 2-nitroethyl and 1,2-dinitroethyl;

a carbonyl or carbonyloxy group to which is attached a $(C_6$–$C_{10})$aryl-$(C_1$–$C_{21})$alkyl group, the aryl moiety of which may be substituted with one or more substituents selected from the group consisting of $C_1$–$C_4$ alkyl, $C_1$–$C_4$ alkoxy, halogen (which is as defined above), and nitro, wherein the aryl-alkyl groups include benzyl, α-naphthylmethyl, β-naphthylmethyl, indenylmethyl, phenanthrenylmethyl, anthracenylmethyl, diphenylmethyl, triphenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylhexyl, 2-naphthylhexyl, 3-naphthylhexyl, 4-naphthylhexyl, 5-naphthylhexyl and 6-naphthylhexyl; and a carbonyl or carbonyloxy group to which is attached a $C_6$–$C_{10}$ aryl group that may be substituted with one or more substituents selected from the group consisting of $C_1$–$C_4$ alkyl, $C_1$–$C_4$ alkoxy, halogen (which is as defined above) and nitro, wherein the aryl groups include phenyl, naphthyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 3,5-difluorophenyl, 2,5-difluorophenyl, 2,6-difluorophenyl, 2,4-difluorophenyl, 3,5-dibromophenyl, 2,5-dibromophenyl, 2,6-dichlorophenyl, 2,4-dichlorophenyl, 2,3,6-trifluorophenyl, 2,3,4-trifluorophenyl, 3,4,5-trifluorophenyl, 2,5,6-trifluorophenyl, 2,4,6-trifluorophenyl, 2,3,6-tribromophenyl, 2,3,4-tribromophenyl, 3,4,5-tribromophenyl, 2,5,6-trichlorophenyl, 2,4,6-trichlorophenyl, 1-fluoro-2-naphthyl, 2-fluoro-1-naphthyl, 3-fluoro-1-naphthyl, 1-chloro-2-naphthyl, 2-chloro-1-naphthyl, 3-bromo-1-naphthyl, 3,8-difluoro-1-naphthyl, 2,3-difluoro-1-naphthyl, 4,8-difluoro-1-naphthyl, 5,6-difluoro-1-naphthyl, 3,8-dichloro-1-naphthyl, 2,3-dichloro-1-naphthyl, 4,8-dibromo-1-naphthyl, 5,6-dibromo-1-naphthyl, 2,3,6-trifluoro-1-naphthyl, 2,3,4-trifluoro-1-naphthyl, 3,4,5-trifluoro-1-naphthyl, 4,5,6-trifluoro-1-naphthyl, 2,4,8-trifluoro-1-naphthyl, 2-methylphenyl, 3-methylphenyl, 4-methylphenyl, 2-ethylphenyl, 3-propylphenyl, 4-ethylphenyl, 2-butylphenyl, 3-pentylphenyl, 4-pentylphenyl, 3,5-dimethylphenyl, 2,5-dimethylphenyl, 2,6-dimethylphenyl, 2,4-dimethylphenyl, 3,5-dibutylphenyl, 2,5-dipentylphenyl, 2,6-dipropylmethylphenyl, 2,4-dipropylphenyl, 2,3,6-trimethylphenyl, 2,3,4-trimethylphenyl, 3,4,5-trimethylphenyl, 2,5,6-trimethylphenyl, 2,4,6-trimethylphenyl, 2,3,6-tributylphenyl, 2,3,4-tripentylphenyl, 3,4,5-tributylphenyl, 2,5,6-tripropylmethylphenyl, 2,4,6-tripropylphenyl, 1-methyl-2-naphthyl, 2-methyl-1-naphthyl, 3-methyl-1-naphthyl, 1-ethyl-2-naphthyl, 2-propyl-1-naphthyl, 3-butyl-1-naphthyl, 3,8-dimethyl-1-naphthyl, 2,3-dimethyl-1-naphthyl, 4,8-dimethyl-1-naphthyl, 5,6-dimethyl-1-naphthyl, 3,8-diethyl-1-naphthyl, 2,3-dipropyl-1-naphthyl, 4,8-dipentyl-1-naphthyl, 5,6-dibutyl-1-naphthyl, 2,3,6-trimethyl-1-naphthyl, 2,3,4-trimethyl-1-naphthyl, 3,4,5-trimethyl-1-naphthyl, 4,5,6-trimethyl-1-naphthyl, 2,4,8-trimethyl-1-naphthyl, 2-methoxyphenyl, 3-methoxyphenyl, 4-methoxyphenyl, 2-ethoxyphenyl, 3-propoxyphenyl, 4-ethoxyphenyl, 2-butoxyphenyl, 3-pentoxyphenyl, 4-pentoxyphenyl, 3,5-dimethoxyphenyl, 2,5-dimethoxyphenyl, 2,6-dimethoxyphenyl, 2,4-dimethoxyphenyl, 3,5-dibutoxyphenyl, 2,5-dipentoxyphenyl, 2,6-dipropoxyphenyl, 2,4-dipropoxyphenyl, 2,3,6-trimethoxyphenyl, 2,3,4-trimethoxyphenyl, 3,4,5-trimethoxyphenyl, 2,5,6-trimethoxyphenyl, 2,4,6-trimethoxyphenyl, 2,3,6-tributoxyphenyl, 2,3,4-tripentoxyphenyl, 3,4,5-tributoxyphenyl, 2,5,6-tripropoxyphenyl, 2,4,6-tripropoxyphenyl, 1-methoxy-2-naphthyl, 2-methoxy-1-naphthyl, 3-methoxy-1-naphthyl, 1-ethoxy-2-naphthyl, 2-propoxy-1-naphthyl, 3-butoxy-1-naphthyl, 3,8-dimethoxy-1-naphthyl, 2,3-dimethoxy-1-naphthyl, 4,8-dimethoxy-1-naphthyl, 5,6-dimethoxy-1-naphthyl, 3,8-diethoxy-1-naphthyl, 2,3-dipropoxy-1-naphthyl, 4,8-dipentoxy-1-naphthyl, 5,6-dibutoxy-1-naphthyl, 2,3,6-trimethoxy-1-naphthyl, 2,3,4-trimethoxy-1-naphthyl, 3,4,5-trimethoxy-1-naphthyl, 4,5,6-trimethoxy-1-naphthyl, 2,4,8-trimethoxy-1-naphthyl, 2-nitrophenyl, 3-nitrophenyl, 4-nitrophenyl, 3,5-dinitrophenyl, 2,5-dinitrophenyl, 2,6-dinitrophenyl, 2,4-dinitrophenyl, 2,3,6-trinitrophenyl, 2,3,4-trinitrophenyl, 3,4,5-trinitrophenyl, 2,5,6-trinitrophenyl, 2,4,6-trinitrophenyl, 1-nitro-2-naphthyl, 2-nitro-1-naphthyl, 3-nitro-1-naphthyl, 3,8-dinitro-1-naphthyl, 2,3-dinitro-1-naphthyl, 4,8-dinitro-1-naphthyl, 5,6-dinitro-1-naphthyl, 2,3,6-trinitro-1-naphthyl, 2,3,4-trinitro-1-naphthyl, 3,4,5-trinitro-1-naphthyl, 4,5,6-trinitro-1-naphthyl and 2,4,8-trinitro-1-naphthyl;

carboxy-($C_1$–$C_{10}$)alkylcarbonyl groups such as succinoyl, glutaroyl, and adipoyl;

monoalkyl- or dialkyl-phosphate residue groups wherein the alkyl moieties may be the same or different and are each $C_2$–$C_{16}$ alkyl; or ester-forming residue groups of amino acids such as glycine, alanine, valine, leucine, isoleucine, phenylalanine, proline, tryptophan, glutamine and glutamic acid.

Among these ester groups, preferred ester groups are carboacyl groups such as $R^aCO$— or $R^aOCO$—, wherein $R^a$ is selected from hydrogen; $C_1$–$C_2$, alkyl; $C_2$–$C_{21}$ alkenyl or alkynyl having 1 to 3 unsaturated bonds; $C_1$–$C_{21}$ alkyl which is substituted with 1 to 4 substituents selected from the group consisting of $C_1$–$C_4$ alkoxy, halogen (which is as defined above) and nitro; $C_1$–$C_{21}$ alkyl which is substituted with 1 to 3 $C_6$–$C_{10}$ aryl groups which may be substituted with 1 to 4 substituents selected from the group consisting of $C_1$–$C_4$ alkyl, $C_1$–$C_4$ alkoxy, halogen (which is as defined above) and nitro; and $C_6$–$C_{10}$ aryl which may be substituted with 1 to 4 substituents selected from the group consisting of $C_1$–$C_4$ alkyl, $C_1$–$C_4$ alkoxy, halogen (which is as defined above) and nitro.

More preferred ester groups are carboacyl groups such as $R^aCO$— or $R^aOCO$—, wherein $R^a$ is $C_6$–$C_{20}$ alkyl; $C_{10}$–$C_{20}$ alkenyl having 1 to 3 double bonds; $C_3$–$C_5$ alkynyl having one triple bond; $C_1$–$C_4$ alkyl which is substituted with one $C_1$–$C_4$ alkoxy group; $C_1$–$C_4$ alkyl which is substituted with 1 or 2 phenyl groups which themselves may be substituted with 1 or 2 substituents selected from the group consisting of $C_1$–$C_2$ alkyl, $C_1$–$C_4$ alkoxy, fluorine and chlorine.

The most preferred ester groups are carboacyl groups such as $R^aCO$— or $R^aOCO$—, wherein $R^a$ is $C_6$–$C_{20}$ alkyl or $C_{10}$–$C_{20}$ alkenyl having 1 to 3 double bonds.

Examples of ether residue groups of pharmaceutically acceptable ethers include:

straight or branched chain $C_1$–$C_2$, alkyl groups such as methyl, ethyl, propyl, isopropyl, butyl, isobutyl, s-butyl, tert-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 6,6-dimethylheptyl, decyl, 1-methylnonyl, 3-methylnonyl, 8-methylnonyl, 3-ethyloctyl, 3,7-dimethyloctyl, 7,7-dimethyloctyl, undecyl, 4,8-dimethylnonyl, dodecyl, tridecyl, tetradecyl, pentadecyl, 3,7,11-trimethyldodecyl, hexadecyl, 4,8,12-trimethyltridecyl, 1-methylpentadecyl, 14-methylpentadecyl, 13,13-dimethyltetradecyl, heptadecyl, 15-methylhexadecyl, octadecyl, 1-methylheptadecyl, nonadecyl, icosyl, 3,7,11,15-tetramethylhexadecyl and henicosyl;

straight or branched chain $C_2$–$C_{21}$ alkenyl or alkynyl groups such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl, 5-hexenyl, cis-8-heptadecenyl, cis, cis-8,11-heptadecadienyl, cis, cis, cis-8,11,14-heptadecatrienyl, cis-10-nonadecenyl, cis-12-icosenyl, ethynyl, 2-propynyl, 1-methyl-2-propynyl, 2-methyl-2-propynyl, 2-ethyl-2-propynyl, 2-butynyl, 1-methyl-2-butynyl, 2-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 2-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl and 5-hexynyl;

straight or branched chain $C_1$–$C_{21}$ alkyl which is substituted with one or more substituents selected from the group consisting of $C_1$–$C_4$ alkoxy, halogen (for example fluorine, chlorine, bromine or iodine, of which fluorine or chlorine is preferred), and nitro, such as methoxymethyl, ethoxymethyl, methoxyethyl, ethoxyethyl, trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl, 2,2-dibromoethyl, nitromethyl, dinitromethyl, 1-nitroethyl, 2-nitroethyl and 1,2-dinitroethyl;

($C_6$–$C_{10}$)aryl —($C_1$–$C_{21}$)alkyl groups, aryl moiety of which may be substituted with one or more substituents selected from the group consisting of $C_1$–$C_4$ alkyl, $C_1$–$C_4$ alkoxy, halogen (which is as defined above) and nitro, such as benzyl, α-naphthylmethyl, β-naphthylmethyl, indenylmethyl, phenanthrenylmethyl, anthracenylmethyl, diphenylmethyl, triphenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylhexyl, 2-naphthylhexyl, 3-naphthylhexyl, 4-naphthylhexyl, 5-naphthylhexyl and 6-naphthylhexyl; and $C_6$–$C_{10}$ aryl groups that may be substituted with one or more substituents selected from the group consisting of $C_1$–$C_4$ alkyl, $C_1$–$C_4$ alkoxy, halogen (which is as defined above) and nitro, such as phenyl, naphthyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 3,5-difluorophenyl, 2,5-difluorophenyl, 2,6-difluorophenyl, 2,4-difluorophenyl, 3,5-dibromophenyl, 2,5-dibromophenyl, 2,6-dichlorophenyl, 2,4-dichlorophenyl, 2,3,6-trifluorophenyl, 2,3,4-trifluorophenyl, 3,4,5-trifluorophenyl, 2,5,6-trifluorophenyl, 2,4,6-trifluorophenyl, 2,3,6-tribromophenyl, 2,3,4-tribromophenyl, 3,4,5-tribromophenyl, 2,5,6-trichlorophenyl, 2,4,6-trichlorophenyl, 1-fluoro-2-naphthyl, 2-fluoro-1-naphthyl, 3-fluoro-1-naphthyl, 1-chloro-2-naphthyl, 2-chloro-1-naphthyl, 3-bromo-1-naphthyl, 3,8-difluoro-1-naphthyl, 2,3-difluoro-1-naphthyl, 4,8-difluoro-1-naphthyl, 5,6-difluoro-1-naphthyl, 3,8-dichloro-1-naphthyl, 2,3-dichloro-1-naphthyl, 4,8-dibromo-1-naphthyl, 5,6-dibromo-1-naphthyl, 2,3,6-trifluoro-1-naphthyl, 2,3,4-trifluoro-1-naphthyl, 3,4,5-trifluoro-1-naphthyl, 4,5,6-trifluoro-1-naphthyl, 2,4,8-trifluoro-1-naphthyl, 2-methylphenyl, 3-methylphenyl, 4-methylphenyl, 2-ethylphenyl, 3-propylphenyl, 4-ethylphenyl, 2-butylphenyl, 3-pentylphenyl, 4-pentylphenyl, 3,5-dimethylphenyl, 2,5-dimethylphenyl, 2,6-dimethylphenyl, 2,4-dimethylphenyl, 3,5-dibutylphenyl, 2,5-dipentylphenyl, 2,6-dipropylmethylphenyl, 2,4-dipropylphenyl, 2,3,6-trimethylphenyl, 2,3,4-trimethylphenyl, 3,4,5-trimethylphenyl, 2,5,6-trimethylphenyl, 2,4,6-trimethylphenyl, 2,3,6-tributylphenyl, 2,3,4-tripentylphenyl, 3,4,5-tributylphenyl, 2,5,6-tripropylmethylphenyl, 2,4,6-tripropylphenyl, 1-methyl-2-naphthyl, 2-methyl-1-naphthyl, 3-methyl-1-naphthyl, 1-ethyl-2-naphthyl, 2-propyl-1-naphthyl, 3-butyl-1-naphthyl, 3,8-dimethyl-1-naphthyl, 2,3-dimethyl-1-naphthyl, 4,8-dimethyl-1-naphthyl, 5,6-dimethyl-1-naphthyl, 3,8-diethyl-1-naphthyl, 2,3-dipropyl-1-naphthyl, 4,8-dipentyl-1-naphthyl, 5,6-dibutyl-1-naphthyl, 2,3,6-trimethyl-1-naphthyl, 2,3,4-trimethyl-1-naphthyl, 3,4,5-trimethyl-1-naphthyl, 4,5,6-trimethyl-1-naphthyl, 2,4,8-trimethyl-1-naphthyl, 2-methoxyphenyl, 3-methoxyphenyl, 4-methoxyphenyl, 2-ethoxyphenyl, 3-propoxyphenyl, 4-ethoxyphenyl, 2-butoxyphenyl, 3-pentoxyphenyl, 4-pentoxyphenyl, 3,5-dimethoxyphenyl, 2,5-dimethoxyphenyl, 2,6-dimethoxyphenyl, 2,4-dimethoxyphenyl, 3,5-dibutoxyphenyl, 2,5-dipentoxyphenyl, 2,6-dipropoxymethoxyphenyl, 2,4-dipropoxyphenyl, 2,3,6-trimethoxyphenyl, 2,3,4-trimethoxyphenyl, 3,4,5-trimethoxyphenyl, 2,5,6-trimethoxyphenyl, 2,4,6-trimethoxyphenyl, 2,3,6-tributoxyphenyl, 2,3,4-tripentoxyphenyl, 3,4,5-tributoxyphenyl, 2,5,6-tripropoxyphenyl, 2,4,6-tripropoxyphenyl, 1-methoxy-2-naphthyl, 2-methoxy-1-naphthyl, 3-methoxy-1-naphthyl, 1-ethoxy-2-naphthyl, 2-propoxy-1-naphthyl, 3-butoxy-1-naphthyl, 3,8-dimethoxy-1-naphthyl, 2,3-dimethoxy-1-naphthyl, 4,8-dimethoxy-1-naphthyl, 5,6-dimethoxy-1-naphthyl, 3,8-diethoxy-1-naphthyl, 2,3-dipropoxy-1-naphthyl, 4,8-dipentoxy-1-naphthyl, 5,6-dibutoxy-1-naphthyl, 2,3,6-trimethoxy-1-naphthyl, 2,3,4-trimethoxy-1-naphthyl, 3,4,5-trimethoxy-1-naphthyl, 4,5,6-trimethoxy-1-naphthyl, 2,4,8-trimethoxy-1-naphthyl, 2-nitrophenyl, 3-nitrophenyl, 4-nitrophenyl, 3,5-dinitrophenyl, 2,5-dinitrophenyl, 2,6-dinitrophenyl, 2,4-dinitrophenyl, 2,3,6-trinitrophenyl, 2,3,4-trinitrophenyl, 3,4,5-trinitrophenyl, 2,5,6-trinitrophenyl, 2,4,6-trinitrophenyl, 1-nitro-2-naphthyl, 2-nitro-1-naphthyl, 3-nitro-1-naphthyl, 3,8-dinitro-1-naphthyl, 2,3-dinitro-1-naphthyl, 4,8-dinitro-1-naphthyl, 5,6-dinitro-1-naphthyl, 2,3,6-trinitro-1-naphthyl, 2,3,4-trinitro-1-naphthyl, 3,4,5-trinitro-1-naphthyl, 4,5,6-trinitro-1-naphthyl, and 2,4,8-trinitro-1-naphthyl.

Among these groups, preferred ether residue groups are $C_1$–$C_{21}$ alkyl; $C_2$–$C_{21}$ alkenyl or alkynyl having 1 to 3 unsaturated bonds; $C_1$–$C_{21}$ alkyl which is substituted with 1 to 4 substituents selected from the group consisting of $C_1$–$C_4$ alkoxy, halogen (which is as defined above) and nitro; $C_1$–$C_{21}$ alkyl which is substituted with 1 to 3 $C_6$–$C_{10}$ aryl groups which may be the same or different and are each substituted with 1 to 4 substituents selected from the group consisting of $C_1$–$C_4$ alkyl, $C_1$–$C_4$ alkoxy, halogen (which is as defined above) and nitro; and $C_6$–$C_{10}$ aryl which may be substituted with 1 to 4 substituents selected from the group consisting of $C_1$–$C_4$ alkyl, $C_1$–$C_4$ alkoxy, halogen (which is as defined above) and nitro.

More preferred ether residue groups are $C_6$–$C_{20}$ alkyl; $C_{10}$–$C_{20}$ alkenyl having 1 to 3 double bonds; $C_3$–$C_5$ alkynyl having one triple bond; $C_1$–$C_4$ alkyl which is substituted with one $C_1$–$C_4$ alkoxy group; and $C_1$–$C_4$ alkyl which is substituted with 1 or 2 phenyl groups which may themselves be substituted with 1 or 2 substituents selected from the group consisting of $C_1$–$C_2$ alkyl, $C_1$–$C_4$ alkoxy, fluorine and chlorine.

The most preferred ether residue groups are $C_6$–$C_{20}$ alkyl and $C_{10}$–$C_{20}$ alkenyl having 1 to 3 double bonds.

The compound of formula (I) has a plurality of hydroxyl groups, which can form ester or ether derivative and locate at the 2-position on the oxolane ring (when $R^3$ is hydroxyl) and at the 3- and 4-positions on the dihydropyran ring. An ester or ether derivative of the compound of formula (I) optionally has a plurality of ester group(s) and/or ether group(s) and each of them may be the same or different ester and/or ether group.

Preferred pharmaceutically acceptable ester derivatives of the compound of formula (I) have one or two ester groups; more preferred ester derivatives have an ester group at the 2-position on the oxolane ring or the 3-position on the dihydropyran ring; and the most preferred esters have an ester group at the 2-position on the oxolane ring.

Preferable pharmaceutically acceptable ether derivatives of the compound of formula (I) have one or two ether groups; more preferable ether derivatives have an ether group at the 2-position on the oxolane ring or the 3-position on the dihydropyran ring; and the most preferred ethers have an ether group at the 2-position on the oxolane ring.

Alkyl groups of the pharmaceutically acceptable N-alkyl derivatives include the straight or branched chain $C_1$–$C_{21}$ alkyl groups described above; the straight or branched chain $C_2$–$C_{21}$ alkenyl or alkynyl groups described above; 1-($C_2$–$C_{20}$ alkanoyloxy)-($C_1$–$C_3$)alkyl groups such as acetyloxymethyl, propionyloxymethyl, butyryloxymethyl, pentanoyloxymethyl, pivaloyloxymethyl, hexanoyloxymethyl, octanoyloxymethyl, decanoyloxymethyl, dodecanoyloxymethyl, tetradecanoyloxymethyl, hexadecanoyloxymethyl, octadecanoyloxymethyl, 1-(acetyloxy)ethyl, 1-(propionyloxy)ethyl, 1-(butyryloxy)ethyl, 1-(pentanoyloxy)ethyl, 1-(hexanoyloxy)ethyl, 1-(octanoyloxy)ethyl, 1-(decanoyloxy)ethyl, 1-(dodecanoyloxy)ethyl, 1-(tetradecanoyloxy)ethyl, 1-(hexadecanoyloxy)ethyl, and 1-(octadecanoyloxy)ethyl;

1-($C_1$–$C_{20}$ alkoxycarbonyloxy)-($C_1$–$C_3$)alkyl groups such as methoxycarbonyloxymethyl, ethoxycarbonyloxymethyl, propoxycarbonyloxymethyl, isopropoxycarbonyloxymethyl, butyloxycarbonyloxymethyl, isobutyloxycarbonyloxymethyl, s-butyloxycarbonyloxymethyl, t-butyloxycarbonyloxymethyl, pentyloxycarbonyloxymethyl, 2-pentyloxycarbonyloxymethyl, 3-pentyloxycarbonyloxymethyl, isopentyloxycarbonyloxymethyl, neopentyloxycarbonyloxymethyl, cyclopentyloxycarbonyloxymethyl, hexyloxycarbonyloxymethyl, 2-hexyloxycarbonyloxymethyl, 3-hexyloxycarbonyloxymethyl, isohexyloxycarbonyloxymethyl, cyclohexyloxycarbonyloxymethyl, heptyloxycarbonyloxymethyl, octyloxycarbonyloxymethyl, decyloxycarbonyloxymethyl, dodecyloxycarbonyloxymethyl, tetradecyloxycarbonyloxymethyl, hexadecyloxycarbonyloxymethyl, octadecyloxycarbonyloxymethyl, 1-(methoxycarbonyloxy)ethyl, 1-(ethoxycarbonyloxy)ethyl, 1-(propoxycarbonyloxy)ethyl, 1-(isopropoxycarbonyloxy)ethyl, 1-(butyloxycarbonyloxy)ethyl, 1-(isobutyloxycarbonyloxy)ethyl, 1-(s-butyloxycarbonyloxy)ethyl, 1-(t-butyloxycarbonyloxy)ethyl, 1-(pentyloxycarbonyloxy)ethyl, 1-(2-pentyloxycarbonyloxy)ethyl, 1-(3-pentyloxycarbonyloxy)ethyl, 1-(isopentyloxycarbonyloxy)ethyl, 1-(neopentyloxycarbonyloxy)ethyl, 1-(cyclopentyloxycarbonyloxy)ethyl, 1-(hexyloxycarbonyloxy)ethyl, 1-(2-hexyloxycarbonyloxy)ethyl, 1-(3-hexyloxycarbonyloxy)ethyl, 1-(isohexyloxycarbonyloxy)ethyl, 1-(cyclohexyloxycarbonyloxy)ethyl, 1-(heptyloxycarbonyloxy)ethyl, 1-(octyloxycarbonyloxy)ethyl, 1-(decyloxycarbonyloxy)ethyl, 1-(dodecyloxycarbonyloxy)ethyl, 1-(tetradecyloxycarbonyloxy)ethyl, 1-(hexadecyloxycarbonyloxy)ethyl and 1-(octadecyloxycarbonyloxy)ethyl; and 1-[5-($C_1$–$C_6$ alkyl or phenyl)-2-oxo-1,3-dioxolen-4-yl]-($C_1$–$C_6$)alkyl groups such as (5-methyl-2-oxo-1,3-dioxolen-4-yl)methyl, 1-(5-methyl-2-oxo-1,3-dioxolen-4-yl)ethyl and (5-phenyl-2-oxo-1,3-dioxolen-4-yl)methyl.

Among these alkyl groups, preferred alkyl groups are 1-($C_2$–$C_{20}$ alkanoyloxy)-($C_1$–$C_3$)alkyl or 1-($C_1$–$C_{20}$ alkoxycarbonyloxy)-($C_1$–$C_3$)alkyl.

When a compound chemically modified by those groups described above is administered, the compound is converted into a corresponding parent compound by enzymatic hydrolysis in vivo.

"Pharmaceutically acceptable salts" of the compound of formula (I) or pharmaceutically acceptable esters, ethers and N-alkyl derivatives thereof are salts which do not exhibit significant toxicity and can usually be used as medicaments.

When a compound of formula (I) or a pharmaceutically acceptable ester, ether or N-alkyl derivative thereof has a basic group such as amino, such a compound can be converted to a pharmaceutically acceptable acid addition salt by treatment with an acid according to a conventional technique. Examples of such salts include inorganic acid salts such as hydrochloride, hydrobromide, sulfate and phosphate; organic acid salts such as acetate, benzoate, oxalate, maleate, fumarate, tartrate, and citrate; and sulfonates such as methanesulfonate, benzenesulfonate and p-toluenesulfonate.

When a compound of formula (I) or a pharmaceutically acceptable ester, ether or N-alkyl derivative thereof has an acidic group such as a carboxyl or phosphoric acid group, such a compound can be converted to a pharmaceutically acceptable base addition salt by treatment with a base according to a conventional technique. Examples of such salts include alkali metal salts such sodium, potassium and lithium salts; alkaline earth metal salts such as calcium and magnesium salts; metal salts such as aluminum, iron, zinc, copper, nickel and cobalt salts, and quaternary ammonium salts such as ammonium and triethylammonium salts.

When certain compounds of formula (I) or pharmaceutically acceptable esters, ethers or N-alkyl derivatives thereof are allowed to stand in the air, the compound absorbs or adsorbs water to form a hydrate. Such hydrates are encompassed in the present invention.

Certain compounds of formula (I) or pharmaceutically acceptable esters, ethers or N-alkyl derivatives thereof may absorb a solvent to form a solvate. Such solvates are encompassed in the present invention.

The compounds of formula (I) and pharmaceutically acceptable esters, ethers and N-alkyl derivatives thereof have asymmetric carbons and exists as stereoisomers wherein each asymmetric carbon has R or S configuration. Each such stereoisomer or a mixture of these isomers in any ratio is encompassed in this invention. A preferred stereoisomer is a compound of the following formula (I').

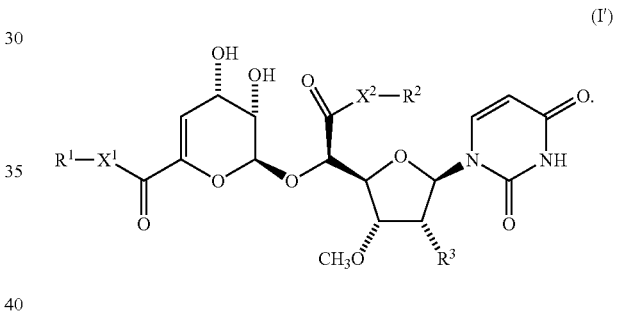

Typical examples of compounds of formula (I) and pharmaceutically acceptable esters, ethers and N-alkyl derivatives thereof are exemplified in Tables 1 to 3. The scope of the present invention is not limited to these exemplification compounds.

TABLE 1

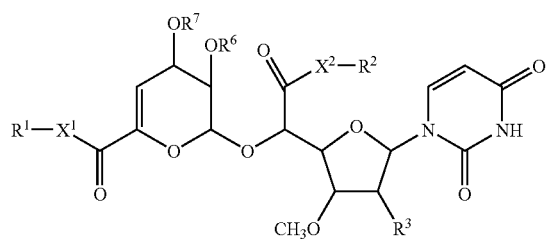

| Exemp. Comp. No. | $R^1$ | $X^1$ | $R^2$ | $X^2$ | $R^3$ | $R^6$ | $R^7$ |
|---|---|---|---|---|---|---|---|
| 1 | Ph | NH | H | NH | H | H | H |
| 2 | Ph | NH | H | NH | OH | H | H |
| 3 | Ph | NH | H | NH | OA6 | H | H |
| 4 | Ph | NH | H | NH | OA8 | H | H |
| 5 | Ph | NH | H | NH | OA9 | H | H |

TABLE 1-continued

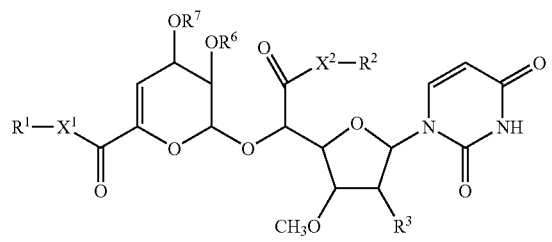

(I-1)

| Exemp. Comp. No. | R¹ | X¹ | R² | X² | R³ | R⁶ | R⁷ |
|---|---|---|---|---|---|---|---|
| 6 | Ph | NH | H | NH | OA10 | H | H |
| 7 | Ph | NH | H | NH | OA12 | H | H |
| 8 | Ph | NH | H | NH | OA14 | H | H |
| 9 | Ph | NH | H | NH | OA16 | H | H |
| 10 | Ph | NH | H | NH | OH | H | A6 |
| 11 | Ph | NH | H | NH | OH | H | A8 |
| 12 | Ph | NH | H | NH | OH | H | A9 |
| 13 | Ph | NH | H | NH | OH | H | A10 |
| 14 | Ph | NH | H | NH | OH | H | A12 |
| 15 | Ph | NH | H | NH | OH | H | A14 |
| 16 | Ph | NH | H | NH | OH | H | A16 |
| 17 | Ph | NH | H | NH | OH | A6 | A6 |
| 18 | Ph | NH | H | NH | OH | A8 | A8 |
| 19 | Ph | NH | H | NH | OH | A10 | A10 |
| 20 | Ph | NH | H | NH | OA2 | A2 | A2 |
| 21 | Ph | NH | H | NH | OA3 | A3 | A3 |
| 22 | Ph | NH | H | NH | OA4 | A4 | A4 |
| 23 | Ph | NH | H | NH | OC6 | H | H |
| 24 | Ph | NH | H | NH | OC7 | H | H |
| 25 | Ph | NH | H | NH | OC8 | H | H |
| 26 | Ph | NH | H | NH | OC10 | H | H |
| 27 | Ph | NH | H | NH | OC11 | H | H |
| 28 | Ph | NH | H | NH | OC12 | H | H |
| 29 | Ph | NH | H | NH | OC14 | H | H |
| 30 | Ph | NH | H | NH | OC16 | H | H |
| 31 | Ph | NH | H | NH | C6CO₃ | H | H |
| 32 | Ph | NH | H | NH | C7CO₃ | H | H |
| 33 | Ph | NH | H | NH | C8CO₃ | H | H |
| 34 | Ph | NH | H | NH | C9CO₃ | H | H |
| 35 | Ph | NH | H | NH | C10CO₃ | H | H |
| 36 | Ph | NH | H | NH | C12CO₃ | H | H |
| 37 | Ph | NH | H | NH | C16CO₃ | H | H |
| 38 | Ph | NH | C8 | NH | OH | H | H |
| 39 | Ph | NH | C9 | NH | OH | H | H |
| 40 | Ph | NH | C10 | NH | OH | H | H |
| 41 | Ph | NH | C12 | NH | OH | H | H |
| 42 | Ph | NH | C16 | NH | OH | H | H |
| 43 | Ph | NH | F1 | NH | OH | H | H |
| 44 | Ph | NH | F2 | NH | OH | H | H |
| 45 | Ph | NH | F3 | NH | OH | H | H |
| 46 | Ph | NH | F4 | NH | OH | H | H |
| 47 | Ph | NH | F5 | NH | OH | H | H |
| 48 | Ph | NH | F6 | NH | OH | H | H |
| 49 | Ph | NH | F7 | NH | OH | H | H |
| 50 | Ph | NH | F8 | NH | OH | H | H |
| 51 | Ph | NH | F9 | NH | OH | H | H |
| 52 | Ph | NH | F10 | NH | OH | H | H |
| 53 | Ph | NH | Ph | NH | OH | H | H |
| 54 | Ph | NH | Bn | NH | OH | H | H |
| 55 | Ph | NH | Pe | NH | OH | H | H |
| 56 | Ph | NH | C12 | NMe | OH | H | H |
| 57 | Ph | NH | C12 | NEt | OH | H | H |
| 58 | Ph | NH | C12 | NPr | OH | H | H |
| 59 | Ph | NH | (CH₂)₃ | N | OH | H | H |
| 60 | Ph | NH | (CH₂)₄ | N | OH | H | H |
| 61 | Ph | NH | (CH₂)₅ | N | OH | H | H |
| 62 | Ph | NH | C12 | O | OH | H | H |
| 63 | Ph | NH | Ph | O | OH | H | H |
| 64 | Ph | NH | C12 | S | OH | H | H |
| 65 | Ph | NH | Ph | S | OH | H | H |
| 66 | Ph | NMe | H | NH | OH | H | H |
| 67 | Ph | NEt | H | NH | OH | H | H |

TABLE 1-continued

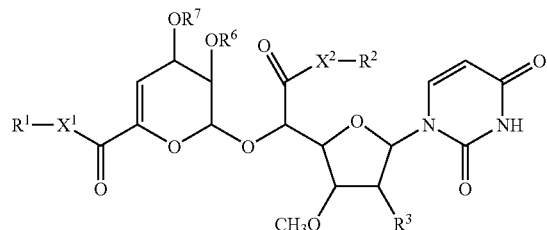

(I-1)

| Exemp. Comp. No. | R¹ | X¹ | R² | X² | R³ | R⁶ | R⁷ |
|---|---|---|---|---|---|---|---|
| 68 | Ph | NPr | H | NH | OH | H | H |
| 69 | Ph | O | H | NH | OH | H | H |
| 70 | Ph | S | H | NH | OH | H | H |
| 71 | 4-Me—Ph | NH | H | NH | H | H | H |
| 72 | 4-Me—Ph | NH | H | NH | OH | H | H |
| 73 | 4-Me—Ph | NH | H | NH | OA6 | H | H |
| 74 | 4-Me—Ph | NH | H | NH | OA8 | H | H |
| 75 | 4-Me—Ph | NH | H | NH | OA9 | H | H |
| 76 | 4-Me—Ph | NH | H | NH | OA10 | H | H |
| 77 | 4-Me—Ph | NH | H | NH | OA12 | H | H |
| 78 | 4-Me—Ph | NH | H | NH | OA14 | H | H |
| 79 | 4-Me—Ph | NH | H | NH | OA16 | H | H |
| 80 | 4-Me—Ph | NH | H | NH | OH | H | A6 |
| 81 | 4-Me—Ph | NH | H | NH | OH | H | A8 |
| 82 | 4-Me—Ph | NH | H | NH | OH | H | A9 |
| 83 | 4-Me—Ph | NH | H | NH | OH | H | A10 |
| 84 | 4-Me—Ph | NH | H | NH | OH | H | A12 |
| 85 | 4-Me—Ph | NH | H | NH | OH | H | A14 |
| 86 | 4-Me—Ph | NH | H | NH | OH | H | A16 |
| 87 | 4-Me—Ph | NH | H | NH | OH | A6 | A6 |
| 88 | 4-Me—Ph | NH | H | NH | OH | A8 | A8 |
| 89 | 4-Me—Ph | NH | H | NH | OH | A10 | A10 |
| 90 | 4-Me—Ph | NH | H | NH | OA2 | A2 | A2 |
| 91 | 4-Me—Ph | NH | H | NH | OA3 | A3 | A3 |
| 92 | 4-Me—Ph | NH | H | NH | OA4 | A4 | A4 |
| 93 | 4-Me—Ph | NH | H | NH | OC6 | H | H |
| 94 | 4-Me—Ph | NH | H | NH | OC7 | H | H |
| 95 | 4-Me—Ph | NH | H | NH | OC8 | H | H |
| 96 | 4-Me—Ph | NH | H | NH | OC10 | H | H |
| 97 | 4-Me—Ph | NH | H | NH | OC11 | H | H |
| 98 | 4-Me—Ph | NH | H | NH | OC12 | H | H |
| 99 | 4-Me—Ph | NH | H | NH | OC14 | H | H |
| 100 | 4-Me—Ph | NH | H | NH | OC16 | H | H |
| 101 | 4-Me—Ph | NH | H | NH | C6CO₃ | H | H |
| 102 | 4-Me—Ph | NH | H | NH | C7CO₃ | H | H |
| 103 | 4-Me—Ph | NH | H | NH | C8CO₃ | H | H |
| 104 | 4-Me—Ph | NH | H | NH | C9CO₃ | H | H |
| 105 | 4-Me—Ph | NH | H | NH | C10CO₃ | H | H |
| 106 | 4-Me—Ph | NH | H | NH | C12CO₃ | H | H |
| 107 | 4-Me—Ph | NH | H | NH | C16CO₃ | H | H |
| 108 | 4-Me—Ph | NH | C8 | NH | OH | H | H |
| 109 | 4-Me—Ph | NH | C9 | NH | OH | H | H |
| 110 | 4-Me—Ph | NH | C10 | NH | OH | H | H |
| 111 | 4-Me—Ph | NH | C12 | NH | OH | H | H |
| 112 | 4-Me—Ph | NH | C16 | NH | OH | H | H |
| 113 | 4-Me—Ph | NH | F1 | NH | OH | H | H |
| 114 | 4-Me—Ph | NH | F2 | NH | OH | H | H |
| 115 | 4-Me—Ph | NH | F3 | NH | OH | H | H |
| 116 | 4-Me—Ph | NH | F4 | NH | OH | H | H |
| 117 | 4-Me—Ph | NH | F5 | NH | OH | H | H |
| 118 | 4-Me—Ph | NH | F6 | NH | OH | H | H |
| 119 | 4-Me—Ph | NH | F7 | NH | OH | H | H |
| 120 | 4-Me—Ph | NH | F8 | NH | OH | H | H |
| 121 | 4-Me—Ph | NH | F9 | NH | OH | H | H |
| 122 | 4-Me—Ph | NH | F10 | NH | OH | H | H |
| 123 | 4-Me—Ph | NH | Ph | NH | OH | H | H |
| 124 | 4-Me—Ph | NH | Bn | NH | OH | H | H |
| 125 | 4-Me—Ph | NH | Pe | NH | OH | H | H |
| 126 | 4-Me—Ph | NH | C12 | NMe | OH | H | H |
| 127 | 4-Me—Ph | NH | C12 | NEt | OH | H | H |
| 128 | 4-Me—Ph | NH | C12 | NPr | OH | H | H |
| 129 | 4-Me—Ph | NH | (CH₂)₃ | N | OH | H | H |

TABLE 1-continued

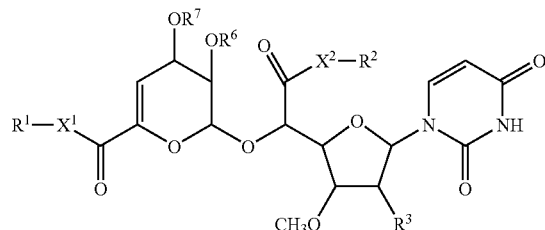

(I-1)

| Exemp. Comp. No. | $R^1$ | $X^1$ | $R^2$ | $X^2$ | $R^3$ | $R^6$ | $R^7$ |
|---|---|---|---|---|---|---|---|
| 130 | 4-Me—Ph | NH | (CH$_2$)$_4$ | N | OH | H | H |
| 131 | 4-Me—Ph | NH | (CH$_2$)$_5$ | N | OH | H | H |
| 132 | 4-Me—Ph | NH | C12 | O | OH | H | H |
| 133 | 4-Me—Ph | NH | Ph | O | OH | H | H |
| 134 | 4-Me—Ph | NH | C12 | S | OH | H | H |
| 135 | 4-Me—Ph | NH | Ph | S | OH | H | H |
| 136 | 4-Me—Ph | NMe | H | NH | OH | H | H |
| 137 | 4-Me—Ph | NEt | H | NH | OH | H | H |
| 138 | 4-Me—Ph | NPr | H | NH | OH | H | H |
| 139 | 4-Me—Ph | O | H | NH | OH | H | H |
| 140 | 4-Me—Ph | S | H | NH | OH | H | H |
| 141 | 4-Et—Ph | NH | H | NH | H | H | H |
| 142 | 4-Et—Ph | NH | H | NH | OH | H | H |
| 143 | 4-Et—Ph | NH | H | NH | OA6 | H | H |
| 144 | 4-Et—Ph | NH | H | NH | OA8 | H | H |
| 145 | 4-Et—Ph | NH | H | NH | OA9 | H | H |
| 146 | 4-Et—Ph | NH | H | NH | OA10 | H | H |
| 147 | 4-Et—Ph | NH | H | NH | OA12 | H | H |
| 148 | 4-Et—Ph | NH | H | NH | OA14 | H | H |
| 149 | 4-Et—Ph | NH | H | NH | OA16 | H | H |
| 150 | 4-Et—Ph | NH | H | NH | OH | H | A6 |
| 151 | 4-Et—Ph | NH | H | NH | OH | H | A8 |
| 152 | 4-Et—Ph | NH | H | NH | OH | H | A9 |
| 153 | 4-Et—Ph | NH | H | NH | OH | H | A10 |
| 154 | 4-Et—Ph | NH | H | NH | OH | H | A12 |
| 155 | 4-Et—Ph | NH | H | NH | OH | H | A14 |
| 156 | 4-Et—Ph | NH | H | NH | OH | H | A16 |
| 157 | 4-Et—Ph | NH | H | NH | OH | A6 | A6 |
| 158 | 4-Et—Ph | NH | H | NH | OH | A8 | A8 |
| 159 | 4-Et—Ph | NH | H | NH | OH | A10 | A10 |
| 160 | 4-Et—Ph | NH | H | NH | OA2 | A2 | A2 |
| 161 | 4-Et—Ph | NH | H | NH | OA3 | A3 | A3 |
| 162 | 4-Et—Ph | NH | H | NH | OA4 | A4 | A4 |
| 163 | 4-Et—Ph | NH | H | NH | OC6 | H | H |
| 164 | 4-Et—Ph | NH | H | NH | OC7 | H | H |
| 165 | 4-Et—Ph | NH | H | NH | OC8 | H | H |
| 166 | 4-Et—Ph | NH | H | NH | OC10 | H | H |
| 167 | 4-Et—Ph | NH | H | NH | OC11 | H | H |
| 168 | 4-Et—Ph | NH | H | NH | OC12 | H | H |
| 169 | 4-Et—Ph | NH | H | NH | OC14 | H | H |
| 170 | 4-Et—Ph | NH | H | NH | OC16 | H | H |
| 171 | 4-Et—Ph | NH | H | NH | C6CO$_3$ | H | H |
| 172 | 4-Et—Ph | NH | H | NH | C7CO$_3$ | H | H |
| 173 | 4-Et—Ph | NH | H | NH | C8CO$_3$ | H | H |
| 174 | 4-Et—Ph | NH | H | NH | C9CO$_3$ | H | H |
| 175 | 4-Et—Ph | NH | H | NH | C10CO$_3$ | H | H |
| 176 | 4-Et—Ph | NH | H | NH | C12CO$_3$ | H | H |
| 177 | 4-Et—Ph | NH | H | NH | C16CO$_3$ | H | H |
| 178 | 4-Et—Ph | NH | C8 | NH | OH | H | H |
| 179 | 4-Et—Ph | NH | C9 | NH | OH | H | H |
| 180 | 4-Et—Ph | NH | C10 | NH | OH | H | H |
| 181 | 4-Et—Ph | NH | C12 | NH | OH | H | H |
| 182 | 4-Et—Ph | NH | C16 | NH | OH | H | H |
| 183 | 4-Et—Ph | NH | F1 | NH | OH | H | H |
| 184 | 4-Et—Ph | NH | F2 | NH | OH | H | H |
| 185 | 4-Et—Ph | NH | F3 | NH | OH | H | H |
| 186 | 4-Et—Ph | NH | F4 | NH | OH | H | H |
| 187 | 4-Et—Ph | NH | F5 | NH | OH | H | H |
| 188 | 4-Et—Ph | NH | F6 | NH | OH | H | H |
| 189 | 4-Et—Ph | NH | F7 | NH | OH | H | H |
| 190 | 4-Et—Ph | NH | F8 | NH | OH | H | H |
| 191 | 4-Et—Ph | NH | F9 | NH | OH | H | H |

TABLE 1-continued

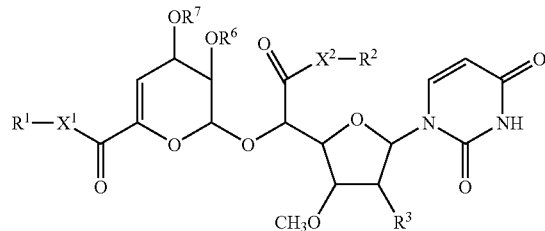

(I-1)

| Exemp. Comp. No. | R¹ | X¹ | R² | X² | R³ | R⁶ | R⁷ |
|---|---|---|---|---|---|---|---|
| 192 | 4-Et—Ph | NH | F10 | NH | OH | H | H |
| 193 | 4-Et—Ph | NH | Ph | NH | OH | H | H |
| 194 | 4-Et—Ph | NH | Bn | NH | OH | H | H |
| 195 | 4-Et—Ph | NH | Pe | NH | OH | H | H |
| 196 | 4-Et—Ph | NH | C12 | NMe | OH | H | H |
| 197 | 4-Et—Ph | NH | C12 | NEt | OH | H | H |
| 198 | 4-Et—Ph | NH | C12 | NPr | OH | H | H |
| 199 | 4-Et—Ph | NH | (CH₂)₃ | N | OH | H | H |
| 200 | 4-Et—Ph | NH | (CH₂)₄ | N | OH | H | H |
| 201 | 4-Et—Ph | NH | (CH₂)₅ | N | OH | H | H |
| 202 | 4-Et—Ph | NH | C12 | O | OH | H | H |
| 203 | 4-Et—Ph | NH | Ph | O | OH | H | H |
| 204 | 4-Et—Ph | NH | C12 | S | OH | H | H |
| 205 | 4-Et—Ph | NH | Ph | S | OH | H | H |
| 206 | 4-Et—Ph | NMe | H | NH | OH | H | H |
| 207 | 4-Et—Ph | NEt | H | NH | OH | H | H |
| 208 | 4-Et—Ph | NPr | H | NH | OH | H | H |
| 209 | 4-Et—Ph | O | H | NH | OH | H | H |
| 210 | 4-Et—Ph | S | H | NH | OH | H | H |
| 211 | 4-Pr—Ph | NH | H | NH | H | H | H |
| 212 | 4-Pr—Ph | NH | H | NH | OH | H | H |
| 213 | 4-Pr—Ph | NH | H | NH | OA6 | H | H |
| 214 | 4-Pr—Ph | NH | H | NH | OA8 | H | H |
| 215 | 4-Pr—Ph | NH | H | NH | OA9 | H | H |
| 216 | 4-Pr—Ph | NH | H | NH | OA10 | H | H |
| 217 | 4-Pr—Ph | NH | H | NH | OA12 | H | H |
| 218 | 4-Pr—Ph | NH | H | NH | OA14 | H | H |
| 219 | 4-Pr—Ph | NH | H | NH | OA16 | H | H |
| 220 | 4-Pr—Ph | NH | H | NH | OH | H | A6 |
| 221 | 4-Pr—Ph | NH | H | NH | OH | H | A8 |
| 222 | 4-Pr—Ph | NH | H | NH | OH | H | A9 |
| 223 | 4-Pr—Ph | NH | H | NH | OH | H | A10 |
| 224 | 4-Pr—Ph | NH | H | NH | OH | H | A12 |
| 225 | 4-Pr—Ph | NH | H | NH | OH | H | A14 |
| 226 | 4-Pr—Ph | NH | H | NH | OH | H | A16 |
| 227 | 4-Pr—Ph | NH | H | NH | OH | A6 | A6 |
| 228 | 4-Pr—Ph | NH | H | NH | OH | A8 | A8 |
| 229 | 4-Pr—Ph | NH | H | NH | OH | A10 | A10 |
| 230 | 4-Pr—Ph | NH | H | NH | OA2 | A2 | A2 |
| 231 | 4-Pr—Ph | NH | H | NH | OA3 | A3 | A3 |
| 232 | 4-Pr—Ph | NH | H | NH | OA4 | A4 | A4 |
| 233 | 4-Pr—Ph | NH | H | NH | OC6 | H | H |
| 234 | 4-Pr—Ph | NH | H | NH | OC7 | H | H |
| 235 | 4-Pr—Ph | NH | H | NH | OC8 | H | H |
| 236 | 4-Pr—Ph | NH | H | NH | OC10 | H | H |
| 237 | 4-Pr—Ph | NH | H | NH | OC11 | H | H |
| 238 | 4-Pr—Ph | NH | H | NH | OC12 | H | H |
| 239 | 4-Pr—Ph | NH | H | NH | OC14 | H | H |
| 240 | 4-Pr—Ph | NH | H | NH | OC16 | H | H |
| 241 | 4-Pr—Ph | NH | H | NH | C6CO₃ | H | H |
| 242 | 4-Pr—Ph | NH | H | NH | C7CO₃ | H | H |
| 243 | 4-Pr—Ph | NH | H | NH | C8CO₃ | H | H |
| 244 | 4-Pr—Ph | NH | H | NH | C9CO₃ | H | H |
| 245 | 4-Pr—Ph | NH | H | NH | C10CO₃ | H | H |
| 246 | 4-Pr—Ph | NH | H | NH | C12CO₃ | H | H |
| 247 | 4-Pr—Ph | NH | H | NH | C16CO₃ | H | H |
| 248 | 4-Pr—Ph | NH | C8 | NH | OH | H | H |
| 249 | 4-Pr—Ph | NH | C9 | NH | OH | H | H |
| 250 | 4-Pr—Ph | NH | C10 | NH | OH | H | H |
| 251 | 4-Pr—Ph | NH | C12 | NH | OH | H | H |
| 252 | 4-Pr—Ph | NH | C16 | NH | OH | H | H |
| 253 | 4-Pr—Ph | NH | F1 | NH | OH | H | H |

TABLE 1-continued

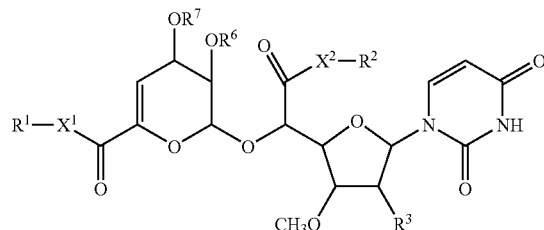

(I-1)

| Exemp. Comp. No. | R¹ | X¹ | R² | X² | R³ | R⁶ | R⁷ |
|---|---|---|---|---|---|---|---|
| 254 | 4-Pr—Ph | NH | F2 | NH | OH | H | H |
| 255 | 4-Pr—Ph | NH | F3 | NH | OH | H | H |
| 256 | 4-Pr—Ph | NH | F4 | NH | OH | H | H |
| 257 | 4-Pr—Ph | NH | F5 | NH | OH | H | H |
| 258 | 4-Pr—Ph | NH | F6 | NH | OH | H | H |
| 259 | 4-Pr—Ph | NH | F7 | NH | OH | H | H |
| 260 | 4-Pr—Ph | NH | F8 | NH | OH | H | H |
| 261 | 4-Pr—Ph | NH | F9 | NH | OH | H | H |
| 262 | 4-Pr—Ph | NH | F10 | NH | OH | H | H |
| 263 | 4-Pr—Ph | NH | Ph | NH | OH | H | H |
| 264 | 4-Pr—Ph | NH | Bn | NH | OH | H | H |
| 265 | 4-Pr—Ph | NH | Pe | NH | OH | H | H |
| 266 | 4-Pr—Ph | NH | C12 | NMe | OH | H | H |
| 267 | 4-Pr—Ph | NH | C12 | NEt | OH | H | H |
| 268 | 4-Pr—Ph | NH | C12 | NPr | OH | H | H |
| 269 | 4-Pr—Ph | NH | $(CH_2)_3$ | N | OH | H | H |
| 270 | 4-Pr—Ph | NH | $(CH_2)_4$ | N | OH | H | H |
| 271 | 4-Pr—Ph | NH | $(CH_2)_5$ | N | OH | H | H |
| 272 | 4-Pr—Ph | NH | C12 | O | OH | H | H |
| 273 | 4-Pr—Ph | NH | Ph | O | OH | H | H |
| 274 | 4-Pr—Ph | NH | C12 | S | OH | H | H |
| 275 | 4-Pr—Ph | NH | Ph | S | OH | H | H |
| 276 | 4-Pr—Ph | NMe | H | NH | OH | H | H |
| 277 | 4-Pr—Ph | NEt | H | NH | OH | H | H |
| 278 | 4-Pr—Ph | NPr | H | NH | OH | H | H |
| 279 | 4-Pr—Ph | O | H | NH | OH | H | H |
| 280 | 4-Pr—Ph | S | H | NH | OH | H | H |
| 281 | 4-iPr—Ph | NH | H | NH | H | H | H |
| 282 | 4-iPr—Ph | NH | H | NH | OH | H | H |
| 283 | 4-iPr—Ph | NH | H | NH | OA6 | H | H |
| 284 | 4-iPr—Ph | NH | H | NH | OA8 | H | H |
| 285 | 4-iPr—Ph | NH | H | NH | OA9 | H | H |
| 286 | 4-iPr—Ph | NH | H | NH | OA10 | H | H |
| 287 | 4-iPr—Ph | NH | H | NH | OA12 | H | H |
| 288 | 4-iPr—Ph | NH | H | NH | OA14 | H | H |
| 289 | 4-iPr—Ph | NH | H | NH | OA16 | H | H |
| 290 | 4-iPr—Ph | NH | H | NH | OH | H | A6 |
| 291 | 4-iPr—Ph | NH | H | NH | OH | H | A8 |
| 292 | 4-iPr—Ph | NH | H | NH | OH | H | A9 |
| 293 | 4-iPr—Ph | NH | H | NH | OH | H | A10 |
| 294 | 4-iPr—Ph | NH | H | NH | OH | H | A12 |
| 295 | 4-iPr—Ph | NH | H | NH | OH | H | A14 |
| 296 | 4-iPr—Ph | NH | H | NH | OH | H | A16 |
| 297 | 4-iPr—Ph | NH | H | NH | OH | A6 | A6 |
| 298 | 4-iPr—Ph | NH | H | NH | OH | A8 | A8 |
| 299 | 4-iPr—Ph | NH | H | NH | OH | A10 | A10 |
| 300 | 4-iPr—Ph | NH | H | NH | OA2 | A2 | A2 |
| 301 | 4-iPr—Ph | NH | H | NH | OA3 | A3 | A3 |
| 302 | 4-iPr—Ph | NH | H | NH | OA4 | A4 | A4 |
| 303 | 4-iPr—Ph | NH | H | NH | OC6 | H | H |
| 304 | 4-iPr—Ph | NH | H | NH | OC7 | H | H |
| 305 | 4-iPr—Ph | NH | H | NH | OC8 | H | H |
| 306 | 4-iPr—Ph | NH | H | NH | OC10 | H | H |
| 307 | 4-iPr—Ph | NH | H | NH | OC11 | H | H |
| 308 | 4-iPr—Ph | NH | H | NH | OC12 | H | H |
| 309 | 4-iPr—Ph | NH | H | NH | OC14 | H | H |
| 310 | 4-iPr—Ph | NH | H | NH | OC16 | H | H |
| 311 | 4-iPr—Ph | NH | H | NH | $C6CO_3$ | H | H |
| 312 | 4-iPr—Ph | NH | H | NH | $C7CO_3$ | H | H |
| 313 | 4-iPr—Ph | NH | H | NH | $C8CO_3$ | H | H |
| 314 | 4-iPr—Ph | NH | H | NH | $C9CO_3$ | H | H |
| 315 | 4-iPr—Ph | NH | H | NH | $C10CO_3$ | H | H |

TABLE 1-continued (I-1)

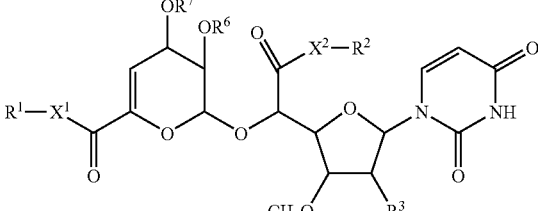

| Exemp. Comp. No. | R¹ | X¹ | R² | X² | R³ | R⁶ | R⁷ |
|---|---|---|---|---|---|---|---|
| 316 | 4-iPr—Ph | NH | H | NH | C12CO₃ | H | H |
| 317 | 4-iPr—Ph | NH | H | NH | C16CO₃ | H | H |
| 318 | 4-iPr—Ph | NH | C8 | NH | OH | H | H |
| 319 | 4-iPr—Ph | NH | C9 | NH | OH | H | H |
| 320 | 4-iPr—Ph | NH | C10 | NH | OH | H | H |
| 321 | 4-iPr—Ph | NH | C12 | NH | OH | H | H |
| 322 | 4-iPr—Ph | NH | C16 | NH | OH | H | H |
| 323 | 4-iPr—Ph | NH | F1 | NH | OH | H | H |
| 324 | 4-iPr—Ph | NH | F2 | NH | OH | H | H |
| 325 | 4-iPr—Ph | NH | F3 | NH | OH | H | H |
| 326 | 4-iPr—Ph | NH | F4 | NH | OH | H | H |
| 327 | 4-iPr—Ph | NH | F5 | NH | OH | H | H |
| 328 | 4-iPr—Ph | NH | F6 | NH | OH | H | H |
| 329 | 4-iPr—Ph | NH | F7 | NH | OH | H | H |
| 330 | 4-iPr—Ph | NH | F8 | NH | OH | H | H |
| 331 | 4-iPr—Ph | NH | F9 | NH | OH | H | H |
| 332 | 4-iPr—Ph | NH | F10 | NH | OH | H | H |
| 333 | 4-iPr—Ph | NH | Ph | NH | OH | H | H |
| 334 | 4-iPr—Ph | NH | Bn | NH | OH | H | H |
| 335 | 4-iPr—Ph | NH | Pe | NH | OH | H | H |
| 336 | 4-iPr—Ph | NH | C12 | NMe | OH | H | H |
| 337 | 4-iPr—Ph | NH | C12 | NEt | OH | H | H |
| 338 | 4-iPr—Ph | NH | C12 | NPr | OH | H | H |
| 339 | 4-iPr—Ph | NH | (CH₂)₃ | N | OH | H | H |
| 340 | 4-iPr—Ph | NH | (CH₂)₄ | N | OH | H | H |
| 341 | 4-iPr—Ph | NH | (CH₂)₅ | N | OH | H | H |
| 342 | 4-iPr—Ph | NH | C12 | O | OH | H | H |
| 343 | 4-iPr—Ph | NH | Ph | O | OH | H | H |
| 344 | 4-iPr—Ph | NH | C12 | S | OH | H | H |
| 345 | 4-iPr—Ph | NH | Ph | S | OH | H | H |
| 346 | 4-iPr—Ph | NMe | H | NH | OH | H | H |
| 347 | 4-iPr—Ph | NEt | H | NH | OH | H | H |
| 348 | 4-iPr—Ph | NPr | H | NH | OH | H | H |
| 349 | 4-iPr—Ph | O | H | NH | OH | H | H |
| 350 | 4-iPr—Ph | S | H | NH | OH | H | H |
| 351 | 4-Bu—Ph | NH | H | NH | H | H | H |
| 352 | 4-Bu—Ph | NH | H | NH | OH | H | H |
| 353 | 4-Bu—Ph | NH | H | NH | OA6 | H | H |
| 354 | 4-Bu—Ph | NH | H | NH | OA8 | H | H |
| 355 | 4-Bu—Ph | NH | H | NH | OA9 | H | H |
| 356 | 4-Bu—Ph | NH | H | NH | OA10 | H | H |
| 357 | 4-Bu—Ph | NH | H | NH | OA12 | H | H |
| 358 | 4-Bu—Ph | NH | H | NH | OA14 | H | H |
| 359 | 4-Bu—Ph | NH | H | NH | OA16 | H | H |
| 360 | 4-Bu—Ph | NH | H | NH | OH | H | A6 |
| 361 | 4-Bu—Ph | NH | H | NH | OH | H | A8 |
| 362 | 4-Bu—Ph | NH | H | NH | OH | H | A9 |
| 363 | 4-Bu—Ph | NH | H | NH | OH | H | A10 |
| 364 | 4-Bu—Ph | NH | H | NH | OH | H | A12 |
| 365 | 4-Bu—Ph | NH | H | NH | OH | H | A14 |
| 366 | 4-Bu—Ph | NH | H | NH | OH | H | A16 |
| 367 | 4-Bu—Ph | NH | H | NH | OH | A6 | A6 |
| 368 | 4-Bu—Ph | NH | H | NH | OH | A8 | A8 |
| 369 | 4-Bu—Ph | NH | H | NH | OH | A10 | A10 |
| 370 | 4-Bu—Ph | NH | H | NH | OA2 | A2 | A2 |
| 371 | 4-Bu—Ph | NH | H | NH | OA3 | A3 | A3 |
| 372 | 4-Bu—Ph | NH | H | NH | OA4 | A4 | A4 |
| 373 | 4-Bu—Ph | NH | H | NH | OC6 | H | H |
| 374 | 4-Bu—Ph | NH | H | NH | OC7 | H | H |
| 375 | 4-Bu—Ph | NH | H | NH | OC8 | H | H |
| 376 | 4-Bu—Ph | NH | H | NH | OC10 | H | H |
| 377 | 4-Bu—Ph | NH | H | NH | OC11 | H | H |

TABLE 1-continued

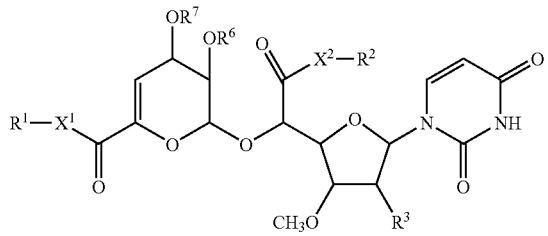

(I-1)

| Exemp. Comp. No. | R¹ | X¹ | R² | X² | R³ | R⁶ | R⁷ |
|---|---|---|---|---|---|---|---|
| 378 | 4-Bu—Ph | NH | H | NH | OC12 | H | H |
| 379 | 4-Bu—Ph | NH | H | NH | OC14 | H | H |
| 380 | 4-Bu—Ph | NH | H | NH | OC16 | H | H |
| 381 | 4-Bu—Ph | NH | H | NH | C6CO$_3$ | H | H |
| 382 | 4-Bu—Ph | NH | H | NH | C7CO$_3$ | H | H |
| 383 | 4-Bu—Ph | NH | H | NH | C8CO$_3$ | H | H |
| 384 | 4-Bu—Ph | NH | H | NH | C9CO$_3$ | H | H |
| 385 | 4-Bu—Ph | NH | H | NH | C10CO$_3$ | H | H |
| 386 | 4-Bu—Ph | NH | H | NH | C12CO$_3$ | H | H |
| 387 | 4-Bu—Ph | NH | H | NH | C16CO$_3$ | H | H |
| 388 | 4-Bu—Ph | NH | C8 | NH | OH | H | H |
| 389 | 4-Bu—Ph | NH | C9 | NH | OH | H | H |
| 390 | 4-Bu—Ph | NH | C10 | NH | OH | H | H |
| 391 | 4-Bu—Ph | NH | C12 | NH | OH | H | H |
| 392 | 4-Bu—Ph | NH | C16 | NH | OH | H | H |
| 393 | 4-Bu—Ph | NH | F1 | NH | OH | H | H |
| 394 | 4-Bu—Ph | NH | F2 | NH | OH | H | H |
| 395 | 4-Bu—Ph | NH | F3 | NH | OH | H | H |
| 396 | 4-Bu—Ph | NH | F4 | NH | OH | H | H |
| 397 | 4-Bu—Ph | NH | F5 | NH | OH | H | H |
| 398 | 4-Bu—Ph | NH | F6 | NH | OH | H | H |
| 399 | 4-Bu—Ph | NH | F7 | NH | OH | H | H |
| 400 | 4-Bu—Ph | NH | F8 | NH | OH | H | H |
| 401 | 4-Bu—Ph | NH | F9 | NH | OH | H | H |
| 402 | 4-Bu—Ph | NH | F10 | NH | OH | H | H |
| 403 | 4-Bu—Ph | NH | Ph | NH | OH | H | H |
| 404 | 4-Bu—Ph | NH | Bn | NH | OH | H | H |
| 405 | 4-Bu—Ph | NH | Pe | NH | OH | H | H |
| 406 | 4-Bu—Ph | NH | C12 | NMe | OH | H | H |
| 407 | 4-Bu—Ph | NH | C12 | NEt | OH | H | H |
| 408 | 4-Bu—Ph | NH | C12 | NPr | OH | H | H |
| 409 | 4-Bu—Ph | NH | (CH$_2$)$_3$ | N | OH | H | H |
| 410 | 4-Bu—Ph | NH | (CH$_2$)$_4$ | N | OH | H | H |
| 411 | 4-Bu—Ph | NH | (CH$_2$)$_5$ | N | OH | H | H |
| 412 | 4-Bu—Ph | NH | C12 | O | OH | H | H |
| 413 | 4-Bu—Ph | NH | Ph | O | OH | H | H |
| 414 | 4-Bu—Ph | NH | C12 | S | OH | H | H |
| 415 | 4-Bu—Ph | NH | Ph | S | OH | H | H |
| 416 | 4-Bu—Ph | NMe | H | NH | OH | H | H |
| 417 | 4-Bu—Ph | NEt | H | NH | OH | H | H |
| 418 | 4-Bu—Ph | NPr | H | NH | OH | H | H |
| 419 | 4-Bu—Ph | O | H | NH | OH | H | H |
| 420 | 4-Bu—Ph | S | H | NH | OH | H | H |
| 421 | 4-tBu—Ph | NH | H | NH | H | H | H |
| 422 | 4-tBu—Ph | NH | H | NH | OH | H | H |
| 423 | 4-tBu—Ph | NH | H | NH | OA6 | H | H |
| 424 | 4-tBu—Ph | NH | H | NH | OA8 | H | H |
| 425 | 4-tBu—Ph | NH | H | NH | OA9 | H | H |
| 426 | 4-tBu—Ph | NH | H | NH | OA10 | H | H |
| 427 | 4-tBu—Ph | NH | H | NH | OA12 | H | H |
| 428 | 4-tBu—Ph | NH | H | NH | OA14 | H | H |
| 429 | 4-tBu—Ph | NH | H | NH | OA16 | H | H |
| 430 | 4-tBu—Ph | NH | H | NH | OH | H | A6 |
| 431 | 4-tBu—Ph | NH | H | NH | OH | H | A8 |
| 432 | 4-tBu—Ph | NH | H | NH | OH | H | A9 |
| 433 | 4-tBu—Ph | NH | H | NH | OH | H | A10 |
| 434 | 4-tBu—Ph | NH | H | NH | OH | H | A12 |
| 435 | 4-tBu—Ph | NH | H | NH | OH | H | A14 |
| 436 | 4-tBu—Ph | NH | H | NH | OH | H | A16 |
| 437 | 4-tBu—Ph | NH | H | NH | OH | A6 | A6 |
| 438 | 4-tBu—Ph | NH | H | NH | OH | A8 | A8 |
| 439 | 4-tBu—Ph | NH | H | NH | OH | A10 | A10 |

TABLE 1-continued

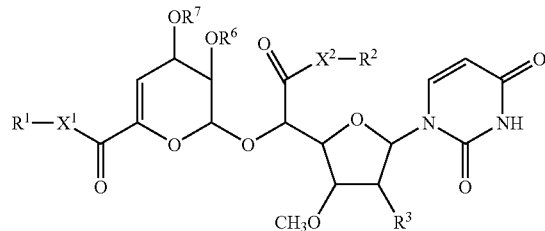

(I-1)

| Exemp. Comp. No. | R¹ | X¹ | R² | X² | R³ | R⁶ | R⁷ |
|---|---|---|---|---|---|---|---|
| 440 | 4-tBu—Ph | NH | H | NH | OA2 | A2 | A2 |
| 441 | 4-tBu—Ph | NH | H | NH | OA3 | A3 | A3 |
| 442 | 4-tBu—Ph | NH | H | NH | OA4 | A4 | A4 |
| 443 | 4-tBu—Ph | NH | H | NH | OC6 | H | H |
| 444 | 4-tBu—Ph | NH | H | NH | OC7 | H | H |
| 445 | 4-tBu—Ph | NH | H | NH | OC8 | H | H |
| 446 | 4-tBu—Ph | NH | H | NH | OC10 | H | H |
| 447 | 4-tBu—Ph | NH | H | NH | OC11 | H | H |
| 448 | 4-tBu—Ph | NH | H | NH | OC12 | H | H |
| 449 | 4-tBu—Ph | NH | H | NH | OC14 | H | H |
| 450 | 4-tBu—Ph | NH | H | NH | OC16 | H | H |
| 451 | 4-tBu—Ph | NH | H | NH | C6CO₃ | H | H |
| 452 | 4-tBu—Ph | NH | H | NH | C7CO₃ | H | H |
| 453 | 4-tBu—Ph | NH | H | NH | C8CO₃ | H | H |
| 454 | 4-tBu—Ph | NH | H | NH | C9CO₃ | H | H |
| 455 | 4-tBu—Ph | NH | H | NH | C10CO₃ | H | H |
| 456 | 4-tBu—Ph | NH | H | NH | C12CO₃ | H | H |
| 457 | 4-tBu—Ph | NH | H | NH | C16CO₃ | H | H |
| 458 | 4-tBu—Ph | NH | C8 | NH | OH | H | H |
| 459 | 4-tBu—Ph | NH | C9 | NH | OH | H | H |
| 460 | 4-tBu—Ph | NH | C10 | NH | OH | H | H |
| 461 | 4-tBu—Ph | NH | C12 | NH | OH | H | H |
| 462 | 4-tBu—Ph | NH | C16 | NH | OH | H | H |
| 463 | 4-tBu—Ph | NH | F1 | NH | OH | H | H |
| 464 | 4-tBu—Ph | NH | F2 | NH | OH | H | H |
| 465 | 4-tBu—Ph | NH | F3 | NH | OH | H | H |
| 466 | 4-tBu—Ph | NH | F4 | NH | OH | H | H |
| 467 | 4-tBu—Ph | NH | F5 | NH | OH | H | H |
| 468 | 4-tBu—Ph | NH | F6 | NH | OH | H | H |
| 469 | 4-tBu—Ph | NH | F7 | NH | OH | H | H |
| 470 | 4-tBu—Ph | NH | F8 | NH | OH | H | H |
| 471 | 4-tBu—Ph | NH | F9 | NH | OH | H | H |
| 472 | 4-tBu—Ph | NH | F10 | NH | OH | H | H |
| 473 | 4-tBu—Ph | NH | Ph | NH | OH | H | H |
| 474 | 4-tBu—Ph | NH | Bn | NH | OH | H | H |
| 475 | 4-tBu—Ph | NH | Pe | NH | OH | H | H |
| 476 | 4-tBu—Ph | NH | C12 | NMe | OH | H | H |
| 477 | 4-tBu—Ph | NH | C12 | NEt | OH | H | H |
| 478 | 4-tBu—Ph | NH | C12 | NPr | OH | H | H |
| 479 | 4-tBu—Ph | NH | (CH₂)₃ | N | OH | H | H |
| 480 | 4-tBu—Ph | NH | (CH₂)₄ | N | OH | H | H |
| 481 | 4-tBu—Ph | NH | (CH₂)₅ | N | OH | H | H |
| 482 | 4-tBu—Ph | NH | C12 | O | OH | H | H |
| 483 | 4-tBu—Ph | NH | Ph | O | OH | H | H |
| 484 | 4-tBu—Ph | NH | C12 | S | OH | H | H |
| 485 | 4-tBu—Ph | NH | Ph | S | OH | H | H |
| 486 | 4-tBu—Ph | NMe | H | NH | OH | H | H |
| 487 | 4-tBu—Ph | NEt | H | NH | OH | H | H |
| 488 | 4-tBu—Ph | NPr | H | NH | OH | H | H |
| 489 | 4-tBu—Ph | O | H | NH | OH | H | H |
| 490 | 4-tBu—Ph | S | H | NH | OH | H | H |
| 491 | 4-sBu—Ph | NH | H | NH | H | H | H |
| 492 | 4-sBu—Ph | NH | H | NH | OH | H | H |
| 493 | 4-sBu—Ph | NH | H | NH | OA6 | H | H |
| 494 | 4-sBu—Ph | NH | H | NH | OA8 | H | H |
| 495 | 4-sBu—Ph | NH | H | NH | OA9 | H | H |
| 496 | 4-sBu—Ph | NH | H | NH | OA10 | H | H |
| 497 | 4-sBu—Ph | NH | H | NH | OA12 | H | H |
| 498 | 4-sBu—Ph | NH | H | NH | OA14 | H | H |
| 499 | 4-sBu—Ph | NH | H | NH | OA16 | H | H |
| 500 | 4-sBu—Ph | NH | H | NH | OH | H | A6 |
| 501 | 4-sBu—Ph | NH | H | NH | OH | H | A8 |

TABLE 1-continued

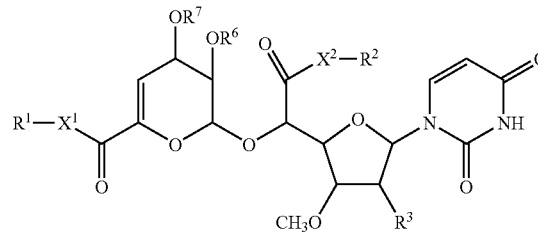

(I-1)

| Exemp. Comp. No. | R¹ | X¹ | R² | X² | R³ | R⁶ | R⁷ |
|---|---|---|---|---|---|---|---|
| 502 | 4-sBu—Ph | NH | H | NH | OH | H | A9 |
| 503 | 4-sBu—Ph | NH | H | NH | OH | H | A10 |
| 504 | 4-sBu—Ph | NH | H | NH | OH | H | A12 |
| 505 | 4-sBu—Ph | NH | H | NH | OH | H | A14 |
| 506 | 4-sBu—Ph | NH | H | NH | OH | H | A16 |
| 507 | 4-sBu—Ph | NH | H | NH | OH | A6 | A6 |
| 508 | 4-sBu—Ph | NH | H | NH | OH | A8 | A8 |
| 509 | 4-sBu—Ph | NH | H | NH | OH | A10 | A10 |
| 510 | 4-sBu—Ph | NH | H | NH | OA2 | A2 | A2 |
| 511 | 4-sBu—Ph | NH | H | NH | OA3 | A3 | A3 |
| 512 | 4-sBu—Ph | NH | H | NH | OA4 | A4 | A4 |
| 513 | 4-sBu—Ph | NH | H | NH | OC6 | H | H |
| 514 | 4-sBu—Ph | NH | H | NH | OC7 | H | H |
| 515 | 4-sBu—Ph | NH | H | NH | OC8 | H | H |
| 516 | 4-sBu—Ph | NH | H | NH | OC10 | H | H |
| 517 | 4-sBu—Ph | NH | H | NH | OC11 | H | H |
| 518 | 4-sBu—Ph | NH | H | NH | OC12 | H | H |
| 519 | 4-sBu—Ph | NH | H | NH | OC14 | H | H |
| 520 | 4-sBu—Ph | NH | H | NH | OC16 | H | H |
| 521 | 4-sBu—Ph | NH | H | NH | $C6CO_3$ | H | H |
| 522 | 4-sBu—Ph | NH | H | NH | $C7CO_3$ | H | H |
| 523 | 4-sBu—Ph | NH | H | NH | $C8CO_3$ | H | H |
| 524 | 4-sBu—Ph | NH | H | NH | $C9CO_3$ | H | H |
| 525 | 4-sBu—Ph | NH | H | NH | $C10CO_3$ | H | H |
| 526 | 4-sBu—Ph | NH | H | NH | $C12CO_3$ | H | H |
| 527 | 4-sBu—Ph | NH | H | NH | $C16CO_3$ | H | H |
| 528 | 4-sBu—Ph | NH | C8 | NH | OH | H | H |
| 529 | 4-sBu—Ph | NH | C9 | NH | OH | H | H |
| 530 | 4-sBu—Ph | NH | C10 | NH | OH | H | H |
| 531 | 4-sBu—Ph | NH | C12 | NH | OH | H | H |
| 532 | 4-sBu—Ph | NH | C16 | NH | OH | H | H |
| 533 | 4-sBu—Ph | NH | F1 | NH | OH | H | H |
| 534 | 4-sBu—Ph | NH | F2 | NH | OH | H | H |
| 535 | 4-sBu—Ph | NH | F3 | NH | OH | H | H |
| 536 | 4-sBu—Ph | NH | F4 | NH | OH | H | H |
| 537 | 4-sBu—Ph | NH | F5 | NH | OH | H | H |
| 538 | 4-sBu—Ph | NH | F6 | NH | OH | H | H |
| 539 | 4-sBu—Ph | NH | F7 | NH | OH | H | H |
| 540 | 4-sBu—Ph | NH | F8 | NH | OH | H | H |
| 541 | 4-sBu—Ph | NH | F9 | NH | OH | H | H |
| 542 | 4-sBu—Ph | NH | F10 | NH | OH | H | H |
| 543 | 4-sBu—Ph | NH | Ph | NH | OH | H | H |
| 544 | 4-sBu—Ph | NH | Bn | NH | OH | H | H |
| 545 | 4-sBu—Ph | NH | Pe | NH | OH | H | H |
| 546 | 4-sBu—Ph | NH | C12 | NMe | OH | H | H |
| 547 | 4-sBu—Ph | NH | C12 | NEt | OH | H | H |
| 548 | 4-sBu—Ph | NH | C12 | NPr | OH | H | H |
| 549 | 4-sBu—Ph | NH | $(CH_2)_3$ | N | OH | H | H |
| 550 | 4-sBu—Ph | NH | $(CH_2)_4$ | N | OH | H | H |
| 551 | 4-sBu—Ph | NH | $(CH_2)_5$ | N | OH | H | H |
| 552 | 4-sBu—Ph | NH | C12 | O | OH | H | H |
| 553 | 4-sBu—Ph | NH | Ph | O | OH | H | H |
| 554 | 4-sBu—Ph | NH | C12 | S | OH | H | H |
| 555 | 4-sBu—Ph | NH | Ph | S | OH | H | H |
| 556 | 4-sBu—Ph | NMe | H | NH | OH | H | H |
| 557 | 4-sBu—Ph | NEt | H | NH | OH | H | H |
| 558 | 4-sBu—Ph | NPr | H | NH | OH | H | H |
| 559 | 4-sBu—Ph | O | H | NH | OH | H | H |
| 560 | 4-sBu—Ph | S | H | NH | OH | H | H |
| 561 | 4-Pen-Ph | NH | H | NH | H | H | H |
| 562 | 4-Pen-Ph | NH | H | NH | OH | H | H |
| 563 | 4-Pen-Ph | NH | H | NH | OA6 | H | H |

TABLE 1-continued (I-1)

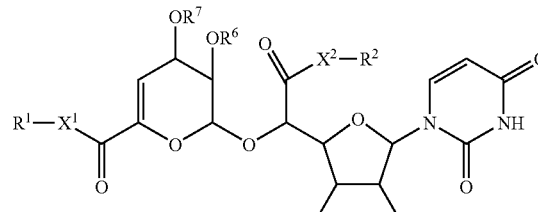

| Exemp. Comp. No. | R¹ | X¹ | R² | X² | R³ | R⁶ | R⁷ |
|---|---|---|---|---|---|---|---|
| 564 | 4-Pen-Ph | NH | H | NH | OA8 | H | H |
| 565 | 4-Pen-Ph | NH | H | NH | OA9 | H | H |
| 566 | 4-Pen-Ph | NH | H | NH | OA10 | H | H |
| 567 | 4-Pen-Ph | NH | H | NH | OA12 | H | H |
| 568 | 4-Pen-Ph | NH | H | NH | OA14 | H | H |
| 569 | 4-Pen-Ph | NH | H | NH | OA16 | H | H |
| 570 | 4-Pen-Ph | NH | H | NH | OH | H | A6 |
| 571 | 4-Pen-Ph | NH | H | NH | OH | H | A8 |
| 572 | 4-Pen-Ph | NH | H | NH | OH | H | A9 |
| 573 | 4-Pen-Ph | NH | H | NH | OH | H | A10 |
| 574 | 4-Pen-Ph | NH | H | NH | OH | H | A12 |
| 575 | 4-Pen-Ph | NH | H | NH | OH | H | A14 |
| 576 | 4-Pen-Ph | NH | H | NH | OH | H | A16 |
| 577 | 4-Pen-Ph | NH | H | NH | OH | A6 | A6 |
| 578 | 4-Pen-Ph | NH | H | NH | OH | A8 | A8 |
| 579 | 4-Pen-Ph | NH | H | NH | OH | A10 | A10 |
| 580 | 4-Pen-Ph | NH | H | NH | OA2 | A2 | A2 |
| 581 | 4-Pen-Ph | NH | H | NH | OA3 | A3 | A3 |
| 582 | 4-Pen-Ph | NH | H | NH | OA4 | A4 | A4 |
| 583 | 4-Pen-Ph | NH | H | NH | OC6 | H | H |
| 584 | 4-Pen-Ph | NH | H | NH | OC7 | H | H |
| 585 | 4-Pen-Ph | NH | H | NH | OC8 | H | H |
| 586 | 4-Pen-Ph | NH | H | NH | OC10 | H | H |
| 587 | 4-Pen-Ph | NH | H | NH | OC11 | H | H |
| 588 | 4-Pen-Ph | NH | H | NH | OC12 | H | H |
| 589 | 4-Pen-Ph | NH | H | NH | OC14 | H | H |
| 590 | 4-Pen-Ph | NH | H | NH | OC16 | H | H |
| 591 | 4-Pen-Ph | NH | H | NH | C6CO$_3$ | H | H |
| 592 | 4-Pen-Ph | NH | H | NH | C7CO$_3$ | H | H |
| 593 | 4-Pen-Ph | NH | H | NH | C8CO$_3$ | H | H |
| 594 | 4-Pen-Ph | NH | H | NH | C9CO$_3$ | H | H |
| 595 | 4-Pen-Ph | NH | H | NH | C10CO$_3$ | H | H |
| 596 | 4-Pen-Ph | NH | H | NH | C12CO$_3$ | H | H |
| 597 | 4-Pen-Ph | NH | H | NH | C16CO$_3$ | H | H |
| 598 | 4-Pen-Ph | NH | C8 | NH | OH | H | H |
| 599 | 4-Pen-Ph | NH | C9 | NH | OH | H | H |
| 600 | 4-Pen-Ph | NH | C10 | NH | OH | H | H |
| 601 | 4-Pen-Ph | NH | C12 | NH | OH | H | H |
| 602 | 4-Pen-Ph | NH | C16 | NH | OH | H | H |
| 603 | 4-Pen-Ph | NH | F1 | NH | OH | H | H |
| 604 | 4-Pen-Ph | NH | F2 | NH | OH | H | H |
| 605 | 4-Pen-Ph | NH | F3 | NH | OH | H | H |
| 606 | 4-Pen-Ph | NH | F4 | NH | OH | H | H |
| 607 | 4-Pen-Ph | NH | F5 | NH | OH | H | H |
| 608 | 4-Pen-Ph | NH | F6 | NH | OH | H | H |
| 609 | 4-Pen-Ph | NH | F7 | NH | OH | H | H |
| 610 | 4-Pen-Ph | NH | F8 | NH | OH | H | H |
| 611 | 4-Pen-Ph | NH | F9 | NH | OH | H | H |
| 612 | 4-Pen-Ph | NH | F10 | NH | OH | H | H |
| 613 | 4-Pen-Ph | NH | Ph | NH | OH | H | H |
| 614 | 4-Pen-Ph | NH | Bn | NH | OH | H | H |
| 615 | 4-Pen-Ph | NH | Pe | NH | OH | H | H |
| 616 | 4-Pen-Ph | NH | C12 | NMe | OH | H | H |
| 617 | 4-Pen-Ph | NH | C12 | NEt | OH | H | H |
| 618 | 4-Pen-Ph | NH | C12 | NPr | OH | H | H |
| 619 | 4-Pen-Ph | NH | (CH$_2$)$_3$ | N | OH | H | H |
| 620 | 4-Pen-Ph | NH | (CH$_2$)$_4$ | N | OH | H | H |
| 621 | 4-Pen-Ph | NH | (CH$_2$)$_5$ | N | OH | H | H |
| 622 | 4-Pen-Ph | NH | C12 | O | OH | H | H |
| 623 | 4-Pen-Ph | NH | Ph | O | OH | H | H |
| 624 | 4-Pen-Ph | NH | C12 | S | OH | H | H |
| 625 | 4-Pen-Ph | NH | Ph | S | OH | H | H |

TABLE 1-continued

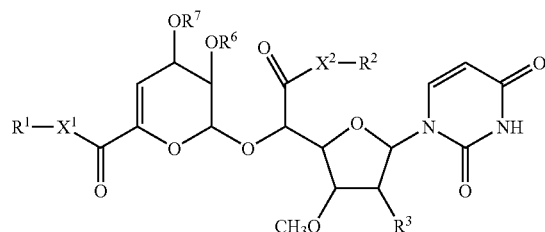

(I-1)

| Exemp. Comp. No. | R¹ | X¹ | R² | X² | R³ | R⁶ | R⁷ |
|---|---|---|---|---|---|---|---|
| 626 | 4-Pen-Ph | NMe | H | NH | OH | H | H |
| 627 | 4-Pen-Ph | NEt | H | NH | OH | H | H |
| 628 | 4-Pen-Ph | NPr | H | NH | OH | H | H |
| 629 | 4-Pen-Ph | O | H | NH | OH | H | H |
| 630 | 4-Pen-Ph | S | H | NH | OH | H | H |
| 631 | 4-Hex-Ph | NH | H | NH | H | H | H |
| 632 | 4-Hex-Ph | NH | H | NH | OH | H | H |
| 633 | 4-Hex-Ph | NH | H | NH | OA6 | H | H |
| 634 | 4-Hex-Ph | NH | H | NH | OA8 | H | H |
| 635 | 4-Hex-Ph | NH | H | NH | OA9 | H | H |
| 636 | 4-Hex-Ph | NH | H | NH | OA10 | H | H |
| 637 | 4-Hex-Ph | NH | H | NH | OA12 | H | H |
| 638 | 4-Hex-Ph | NH | H | NH | OA14 | H | H |
| 639 | 4-Hex-Ph | NH | H | NH | OA16 | H | H |
| 640 | 4-Hex-Ph | NH | H | NH | OH | H | A6 |
| 641 | 4-Hex-Ph | NH | H | NH | OH | H | A8 |
| 642 | 4-Hex-Ph | NH | H | NH | OH | H | A9 |
| 643 | 4-Hex-Ph | NH | H | NH | OH | H | A10 |
| 644 | 4-Hex-Ph | NH | H | NH | OH | H | A12 |
| 645 | 4-Hex-Ph | NH | H | NH | OH | H | A14 |
| 646 | 4-Hex-Ph | NH | H | NH | OH | H | A16 |
| 647 | 4-Hex-Ph | NH | H | NH | OH | A6 | A6 |
| 648 | 4-Hex-Ph | NH | H | NH | OH | A8 | A8 |
| 649 | 4-Hex-Ph | NH | H | NH | OH | A10 | A10 |
| 650 | 4-Hex-Ph | NH | H | NH | OA2 | A2 | A2 |
| 651 | 4-Hex-Ph | NH | H | NH | OA3 | A3 | A3 |
| 652 | 4-Hex-Ph | NH | H | NH | OA4 | A4 | A4 |
| 653 | 4-Hex-Ph | NH | H | NH | OC6 | H | H |
| 654 | 4-Hex-Ph | NH | H | NH | OC7 | H | H |
| 655 | 4-Hex-Ph | NH | H | NH | OC8 | H | H |
| 656 | 4-Hex-Ph | NH | H | NH | OC10 | H | H |
| 657 | 4-Hex-Ph | NH | H | NH | OC11 | H | H |
| 658 | 4-Hex-Ph | NH | H | NH | OC12 | H | H |
| 659 | 4-Hex-Ph | NH | H | NH | OC14 | H | H |
| 660 | 4-Hex-Ph | NH | H | NH | OC16 | H | H |
| 661 | 4-Hex-Ph | NH | H | NH | $C6CO_3$ | H | H |
| 662 | 4-Hex-Ph | NH | H | NH | $C7CO_3$ | H | H |
| 663 | 4-Hex-Ph | NH | H | NH | $C8CO_3$ | H | H |
| 664 | 4-Hex-Ph | NH | H | NH | $C9CO_3$ | H | H |
| 665 | 4-Hex-Ph | NH | H | NH | $C10CO_3$ | H | H |
| 666 | 4-Hex-Ph | NH | H | NH | $C12CO_3$ | H | H |
| 667 | 4-Hex-Ph | NH | H | NH | $C16CO_3$ | H | H |
| 668 | 4-Hex-Ph | NH | C8 | NH | OH | H | H |
| 669 | 4-Hex-Ph | NH | C9 | NH | OH | H | H |
| 670 | 4-Hex-Ph | NH | C10 | NH | OH | H | H |
| 671 | 4-Hex-Ph | NH | C12 | NH | OH | H | H |
| 672 | 4-Hex-Ph | NH | C16 | NH | OH | H | H |
| 673 | 4-Hex-Ph | NH | F1 | NH | OH | H | H |
| 674 | 4-Hex-Ph | NH | F2 | NH | OH | H | H |
| 675 | 4-Hex-Ph | NH | F3 | NH | OH | H | H |
| 676 | 4-Hex-Ph | NH | F4 | NH | OH | H | H |
| 677 | 4-Hex-Ph | NH | F5 | NH | OH | H | H |
| 678 | 4-Hex-Ph | NH | F6 | NH | OH | H | H |
| 679 | 4-Hex-Ph | NH | F7 | NH | OH | H | H |
| 680 | 4-Hex-Ph | NH | F8 | NH | OH | H | H |
| 681 | 4-Hex-Ph | NH | F9 | NH | OH | H | H |
| 682 | 4-Hex-Ph | NH | F10 | NH | OH | H | H |
| 683 | 4-Hex-Ph | NH | Ph | NH | OH | H | H |
| 684 | 4-Hex-Ph | NH | Bn | NH | OH | H | H |
| 685 | 4-Hex-Ph | NH | Pe | NH | OH | H | H |
| 686 | 4-Hex-Ph | NH | C12 | NMe | OH | H | H |
| 687 | 4-Hex-Ph | NH | C12 | NEt | OH | H | H |

TABLE 1-continued (I-1)

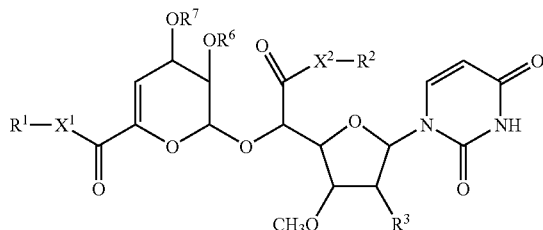

| Exemp. Comp. No. | R¹ | X¹ | R² | X² | R³ | R⁶ | R⁷ |
|---|---|---|---|---|---|---|---|
| 688 | 4-Hex-Ph | NH | C12 | NPr | OH | H | H |
| 689 | 4-Hex-Ph | NH | (CH₂)₃ | N | OH | H | H |
| 690 | 4-Hex-Ph | NH | (CH₂)₄ | N | OH | H | H |
| 691 | 4-Hex-Ph | NH | (CH₂)₅ | N | OH | H | H |
| 692 | 4-Hex-Ph | NH | C12 | O | OH | H | H |
| 693 | 4-Hex-Ph | NH | Ph | O | OH | H | H |
| 694 | 4-Hex-Ph | NH | C12 | S | OH | H | H |
| 695 | 4-Hex-Ph | NH | Ph | S | OH | H | H |
| 696 | 4-Hex-Ph | NMe | H | NH | OH | H | H |
| 697 | 4-Hex-Ph | NEt | H | NH | OH | H | H |
| 698 | 4-Hex-Ph | NPr | H | NH | OH | H | H |
| 699 | 4-Hex-Ph | O | H | NH | OH | H | H |
| 700 | 4-Hex-Ph | S | H | NH | OH | H | H |
| 701 | 4-Hep-Ph | NH | H | NH | H | H | H |
| 702 | 4-Hep-Ph | NH | H | NH | OH | H | H |
| 703 | 4-Hep-Ph | NH | H | NH | OA6 | H | H |
| 704 | 4-Hep-Ph | NH | H | NH | OA8 | H | H |
| 705 | 4-Hep-Ph | NH | H | NH | OA9 | H | H |
| 706 | 4-Hep-Ph | NH | H | NH | OA10 | H | H |
| 707 | 4-Hep-Ph | NH | H | NH | OA12 | H | H |
| 708 | 4-Hep-Ph | NH | H | NH | OA14 | H | H |
| 709 | 4-Hep-Ph | NH | H | NH | OA16 | H | H |
| 710 | 4-Hep-Ph | NH | H | NH | OH | H | A6 |
| 711 | 4-Hep-Ph | NH | H | NH | OH | H | A8 |
| 712 | 4-Hep-Ph | NH | H | NH | OH | H | A9 |
| 713 | 4-Hep-Ph | NH | H | NH | OH | H | A10 |
| 714 | 4-Hep-Ph | NH | H | NH | OH | H | A12 |
| 715 | 4-Hep-Ph | NH | H | NH | OH | H | A14 |
| 716 | 4-Hep-Ph | NH | H | NH | OH | H | A16 |
| 717 | 4-Hep-Ph | NH | H | NH | OH | A6 | A6 |
| 718 | 4-Hep-Ph | NH | H | NH | OH | A8 | A8 |
| 719 | 4-Hep-Ph | NH | H | NH | OH | A10 | A10 |
| 720 | 4-Hep-Ph | NH | H | NH | OA2 | A2 | A2 |
| 721 | 4-Hep-Ph | NH | H | NH | OA3 | A3 | A3 |
| 722 | 4-Hep-Ph | NH | H | NH | OA4 | A4 | A4 |
| 723 | 4-Hep-Ph | NH | H | NH | OC6 | H | H |
| 724 | 4-Hep-Ph | NH | H | NH | OC7 | H | H |
| 725 | 4-Hep-Ph | NH | H | NH | OC8 | H | H |
| 726 | 4-Hep-Ph | NH | H | NH | OC10 | H | H |
| 727 | 4-Hep-Ph | NH | H | NH | OC11 | H | H |
| 728 | 4-Hep-Ph | NH | H | NH | OC12 | H | H |
| 729 | 4-Hep-Ph | NH | H | NH | OC14 | H | H |
| 730 | 4-Hep-Ph | NH | H | NH | OC16 | H | H |
| 731 | 4-Hep-Ph | NH | H | NH | C6CO₃ | H | H |
| 732 | 4-Hep-Ph | NH | H | NH | C7CO₃ | H | H |
| 733 | 4-Hep-Ph | NH | H | NH | C8CO₃ | H | H |
| 734 | 4-Hep-Ph | NH | H | NH | C9CO₃ | H | H |
| 735 | 4-Hep-Ph | NH | H | NH | C10CO₃ | H | H |
| 736 | 4-Hep-Ph | NH | H | NH | C12CO₃ | H | H |
| 737 | 4-Hep-Ph | NH | H | NH | C16CO₃ | H | H |
| 738 | 4-Hep-Ph | NH | C8 | NH | OH | H | H |
| 739 | 4-Hep-Ph | NH | C9 | NH | OH | H | H |
| 740 | 4-Hep-Ph | NH | C10 | NH | OH | H | H |
| 741 | 4-Hep-Ph | NH | C12 | NH | OH | H | H |
| 742 | 4-Hep-Ph | NH | C16 | NH | OH | H | H |
| 743 | 4-Hep-Ph | NH | F1 | NH | OH | H | H |
| 744 | 4-Hep-Ph | NH | F2 | NH | OH | H | H |
| 745 | 4-Hep-Ph | NH | F3 | NH | OH | H | H |
| 746 | 4-Hep-Ph | NH | F4 | NH | OH | H | H |
| 747 | 4-Hep-Ph | NH | F5 | NH | OH | H | H |
| 748 | 4-Hep-Ph | NH | F6 | NH | OH | H | H |
| 749 | 4-Hep-Ph | NH | F7 | NH | OH | H | H |

TABLE 1-continued (I-1)

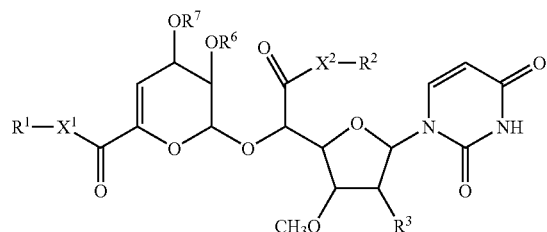

| Exemp. Comp. No. | R¹ | X¹ | R² | X² | R³ | R⁶ | R⁷ |
|---|---|---|---|---|---|---|---|
| 750 | 4-Hep-Ph | NH | F8 | NH | OH | H | H |
| 751 | 4-Hep-Ph | NH | F9 | NH | OH | H | H |
| 752 | 4-Hep-Ph | NH | F10 | NH | OH | H | H |
| 753 | 4-Hep-Ph | NH | Ph | NH | OH | H | H |
| 754 | 4-Hep-Ph | NH | Bn | NH | OH | H | H |
| 755 | 4-Hep-Ph | NH | Pe | NH | OH | H | H |
| 756 | 4-Hep-Ph | NH | C12 | NMe | OH | H | H |
| 757 | 4-Hep-Ph | NH | C12 | NEt | OH | H | H |
| 758 | 4-Hep-Ph | NH | C12 | NPr | OH | H | H |
| 759 | 4-Hep-Ph | NH | (CH₂)₃ | N | OH | H | H |
| 760 | 4-Hep-Ph | NH | (CH₂)₄ | N | OH | H | H |
| 761 | 4-Hep-Ph | NH | (CH₂)₅ | N | OH | H | H |
| 762 | 4-Hep-Ph | NH | C12 | O | OH | H | H |
| 763 | 4-Hep-Ph | NH | Ph | O | OH | H | H |
| 764 | 4-Hep-Ph | NH | C12 | S | OH | H | H |
| 765 | 4-Hep-Ph | NH | Ph | S | OH | H | H |
| 766 | 4-Hep-Ph | NMe | H | NH | OH | H | H |
| 767 | 4-Hep-Ph | NEt | H | NH | OH | H | H |
| 768 | 4-Hep-Ph | NPr | H | NH | OH | H | H |
| 769 | 4-Hep-Ph | O | H | NH | OH | H | H |
| 770 | 4-Hep-Ph | S | H | NH | OH | H | H |
| 771 | 4-Oct-Ph | NH | H | NH | H | H | H |
| 772 | 4-Oct-Ph | NH | H | NH | OH | H | H |
| 773 | 4-Oct-Ph | NH | H | NH | OA6 | H | H |
| 774 | 4-Oct-Ph | NH | H | NH | OA8 | H | H |
| 775 | 4-Oct-Ph | NH | H | NH | OA9 | H | H |
| 776 | 4-Oct-Ph | NH | H | NH | OA10 | H | H |
| 777 | 4-Oct-Ph | NH | H | NH | OA12 | H | H |
| 778 | 4-Oct-Ph | NH | H | NH | OA14 | H | H |
| 779 | 4-Oct-Ph | NH | H | NH | OA16 | H | H |
| 780 | 4-Oct-Ph | NH | H | NH | OH | H | A6 |
| 781 | 4-Oct-Ph | NH | H | NH | OH | H | A8 |
| 782 | 4-Oct-Ph | NH | H | NH | OH | H | A9 |
| 783 | 4-Oct-Ph | NH | H | NH | OH | H | A10 |
| 784 | 4-Oct-Ph | NH | H | NH | OH | H | A12 |
| 785 | 4-Oct-Ph | NH | H | NH | OH | H | A14 |
| 786 | 4-Oct-Ph | NH | H | NH | OH | H | A16 |
| 787 | 4-Oct-Ph | NH | H | NH | OH | A6 | A6 |
| 788 | 4-Oct-Ph | NH | H | NH | OH | A8 | A8 |
| 789 | 4-Oct-Ph | NH | H | NH | OH | A10 | A10 |
| 790 | 4-Oct-Ph | NH | H | NH | OA2 | A2 | A2 |
| 791 | 4-Oct-Ph | NH | H | NH | OA3 | A3 | A3 |
| 792 | 4-Oct-Ph | NH | H | NH | OA4 | A4 | A4 |
| 793 | 4-Oct-Ph | NH | H | NH | OC6 | H | H |
| 794 | 4-Oct-Ph | NH | H | NH | OC7 | H | H |
| 795 | 4-Oct-Ph | NH | H | NH | OC8 | H | H |
| 796 | 4-Oct-Ph | NH | H | NH | OC10 | H | H |
| 797 | 4-Oct-Ph | NH | H | NH | OC11 | H | H |
| 798 | 4-Oct-Ph | NH | H | NH | OC12 | H | H |
| 799 | 4-Oct-Ph | NH | H | NH | OC14 | H | H |
| 800 | 4-Oct-Ph | NH | H | NH | OC16 | H | H |
| 801 | 4-Oct-Ph | NH | H | NH | C6CO₃ | H | H |
| 802 | 4-Oct-Ph | NH | H | NH | C7CO₃ | H | H |
| 803 | 4-Oct-Ph | NH | H | NH | C8CO₃ | H | H |
| 804 | 4-Oct-Ph | NH | H | NH | C9CO₃ | H | H |
| 805 | 4-Oct-Ph | NH | H | NH | C10CO₃ | H | H |
| 806 | 4-Oct-Ph | NH | H | NH | C12CO₃ | H | H |
| 807 | 4-Oct-Ph | NH | H | NH | C16CO₃ | H | H |
| 808 | 4-Oct-Ph | NH | C8 | NH | OH | H | H |
| 809 | 4-Oct-Ph | NH | C9 | NH | OH | H | H |
| 810 | 4-Oct-Ph | NH | C10 | NH | OH | H | H |
| 811 | 4-Oct-Ph | NH | C12 | NH | OH | H | H |

TABLE 1-continued

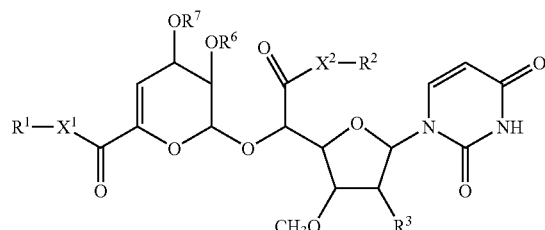

(I-1)

| Exemp. Comp. No. | $R^1$ | $X^1$ | $R^2$ | $X^2$ | $R^3$ | $R^6$ | $R^7$ |
|---|---|---|---|---|---|---|---|
| 812 | 4-Oct-Ph | NH | C16 | NH | OH | H | H |
| 813 | 4-Oct-Ph | NH | F1 | NH | OH | H | H |
| 814 | 4-Oct-Ph | NH | F2 | NH | OH | H | H |
| 815 | 4-Oct-Ph | NH | F3 | NH | OH | H | H |
| 816 | 4-Oct-Ph | NH | F4 | NH | OH | H | H |
| 817 | 4-Oct-Ph | NH | F5 | NH | OH | H | H |
| 818 | 4-Oct-Ph | NH | F6 | NH | OH | H | H |
| 819 | 4-Oct-Ph | NH | F7 | NH | OH | H | H |
| 820 | 4-Oct-Ph | NH | F8 | NH | OH | H | H |
| 821 | 4-Oct-Ph | NH | F9 | NH | OH | H | H |
| 822 | 4-Oct-Ph | NH | F10 | NH | OH | H | H |
| 823 | 4-Oct-Ph | NH | Ph | NH | OH | H | H |
| 824 | 4-Oct-Ph | NH | Bn | NH | OH | H | H |
| 825 | 4-Oct-Ph | NH | Pe | NH | OH | H | H |
| 826 | 4-Oct-Ph | NH | C12 | NMe | OH | H | H |
| 827 | 4-Oct-Ph | NH | C12 | NEt | OH | H | H |
| 828 | 4-Oct-Ph | NH | C12 | NPr | OH | H | H |
| 829 | 4-Oct-Ph | NH | $(CH_2)_3$ | N | OH | H | H |
| 830 | 4-Oct-Ph | NH | $(CH_2)_4$ | N | OH | H | H |
| 831 | 4-Oct-Ph | NH | $(CH_2)_5$ | N | OH | H | H |
| 832 | 4-Oct-Ph | NH | C12 | O | OH | H | H |
| 833 | 4-Oct-Ph | NH | Ph | O | OH | H | H |
| 834 | 4-Oct-Ph | NH | C12 | S | OH | H | H |
| 835 | 4-Oct-Ph | NH | Ph | S | OH | H | H |
| 836 | 4-Oct-Ph | NMe | H | NH | OH | H | H |
| 837 | 4-Oct-Ph | NEt | H | NH | OH | H | H |
| 838 | 4-Oct-Ph | NPr | H | NH | OH | H | H |
| 839 | 4-Oct-Ph | O | H | NH | OH | H | H |
| 840 | 4-Oct-Ph | S | H | NH | OH | H | H |
| 841 | 4-Dec-Ph | NH | H | NH | H | H | H |
| 842 | 4-Dec-Ph | NH | H | NH | OH | H | H |
| 843 | 4-Dec-Ph | NH | H | NH | OA6 | H | H |
| 844 | 4-Dec-Ph | NH | H | NH | OA8 | H | H |
| 845 | 4-Dec-Ph | NH | H | NH | OA9 | H | H |
| 846 | 4-Dec-Ph | NH | H | NH | OA10 | H | H |
| 847 | 4-Dec-Ph | NH | H | NH | OA12 | H | H |
| 848 | 4-Dec-Ph | NH | H | NH | OA14 | H | H |
| 849 | 4-Dec-Ph | NH | H | NH | OA16 | H | H |
| 850 | 4-Dec-Ph | NH | H | NH | OH | H | A6 |
| 851 | 4-Dec-Ph | NH | H | NH | OH | H | A8 |
| 852 | 4-Dec-Ph | NH | H | NH | OH | H | A9 |
| 853 | 4-Dec-Ph | NH | H | NH | OH | H | A10 |
| 854 | 4-Dec-Ph | NH | H | NH | OH | H | A12 |
| 855 | 4-Dec-Ph | NH | H | NH | OH | H | A14 |
| 856 | 4-Dec-Ph | NH | H | NH | OH | H | A16 |
| 857 | 4-Dec-Ph | NH | H | NH | OH | A6 | A6 |
| 858 | 4-Dec-Ph | NH | H | NH | OH | A8 | A8 |
| 859 | 4-Dec-Ph | NH | H | NH | OH | A10 | A10 |
| 860 | 4-Dec-Ph | NH | H | NH | OA2 | A2 | A2 |
| 861 | 4-Dec-Ph | NH | H | NH | OA3 | A3 | A3 |
| 862 | 4-Dec-Ph | NH | H | NH | OA4 | A4 | A4 |
| 863 | 4-Dec-Ph | NH | H | NH | OC6 | H | H |
| 864 | 4-Dec-Ph | NH | H | NH | OC7 | H | H |
| 865 | 4-Dec-Ph | NH | H | NH | OC8 | H | H |
| 866 | 4-Dec-Ph | NH | H | NH | OC10 | H | H |
| 867 | 4-Dec-Ph | NH | H | NH | OC11 | H | H |
| 868 | 4-Dec-Ph | NH | H | NH | OC12 | H | H |
| 869 | 4-Dec-Ph | NH | H | NH | OC14 | H | H |
| 870 | 4-Dec-Ph | NH | H | NH | OC16 | H | H |
| 871 | 4-Dec-Ph | NH | H | NH | $C6CO_3$ | H | H |
| 872 | 4-Dec-Ph | NH | H | NH | $C7CO_3$ | H | H |
| 873 | 4-Dec-Ph | NH | H | NH | $C8CO_3$ | H | H |

TABLE 1-continued (I-1)

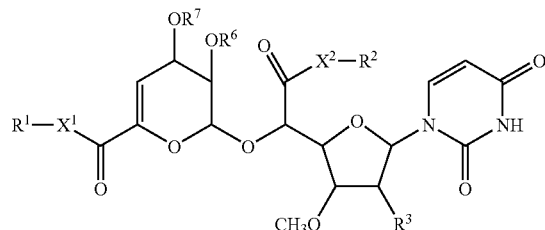

| Exemp. Comp. No. | R¹ | X¹ | R² | X² | R³ | R⁶ | R⁷ |
|---|---|---|---|---|---|---|---|
| 874 | 4-Dec-Ph | NH | H | NH | C9CO₃ | H | H |
| 875 | 4-Dec-Ph | NH | H | NH | C10CO₃ | H | H |
| 876 | 4-Dec-Ph | NH | H | NH | C12CO₃ | H | H |
| 877 | 4-Dec-Ph | NH | H | NH | C16CO₃ | H | H |
| 878 | 4-Dec-Ph | NH | C8 | NH | OH | H | H |
| 879 | 4-Dec-Ph | NH | C9 | NH | OH | H | H |
| 880 | 4-Dec-Ph | NH | C10 | NH | OH | H | H |
| 881 | 4-Dec-Ph | NH | C12 | NH | OH | H | H |
| 882 | 4-Dec-Ph | NH | C16 | NH | OH | H | H |
| 883 | 4-Dec-Ph | NH | F1 | NH | OH | H | H |
| 884 | 4-Dec-Ph | NH | F2 | NH | OH | H | H |
| 885 | 4-Dec-Ph | NH | F3 | NH | OH | H | H |
| 886 | 4-Dec-Ph | NH | F4 | NH | OH | H | H |
| 887 | 4-Dec-Ph | NH | F5 | NH | OH | H | H |
| 888 | 4-Dec-Ph | NH | F6 | NH | OH | H | H |
| 889 | 4-Dec-Ph | NH | F7 | NH | OH | H | H |
| 890 | 4-Dec-Ph | NH | F8 | NH | OH | H | H |
| 891 | 4-Dec-Ph | NH | F9 | NH | OH | H | H |
| 892 | 4-Dec-Ph | NH | F10 | NH | OH | H | H |
| 893 | 4-Dec-Ph | NH | Ph | NH | OH | H | H |
| 894 | 4-Dec-Ph | NH | Bn | NH | OH | H | H |
| 895 | 4-Dec-Ph | NH | Pe | NH | OH | H | H |
| 896 | 4-Dec-Ph | NH | C12 | NMe | OH | H | H |
| 897 | 4-Dec-Ph | NH | C12 | NEt | OH | H | H |
| 898 | 4-Dec-Ph | NH | C12 | NPr | OH | H | H |
| 899 | 4-Dec-Ph | NH | (CH₂)₃ | N | OH | H | H |
| 900 | 4-Dec-Ph | NH | (CH₂)₄ | N | OH | H | H |
| 901 | 4-Dec-Ph | NH | (CH₂)₅ | N | OH | H | H |
| 902 | 4-Dec-Ph | NH | C12 | O | OH | H | H |
| 903 | 4-Dec-Ph | NH | Ph | O | OH | H | H |
| 904 | 4-Dec-Ph | NH | C12 | S | OH | H | H |
| 905 | 4-Dec-Ph | NH | Ph | S | OH | H | H |
| 906 | 4-Dec-Ph | NMe | H | NH | OH | H | H |
| 907 | 4-Dec-Ph | NEt | H | NH | OH | H | H |
| 908 | 4-Dec-Ph | NPr | H | NH | OH | H | H |
| 909 | 4-Dec-Ph | O | H | NH | OH | H | H |
| 910 | 4-Dec-Ph | S | H | NH | OH | H | H |
| 911 | 3-Me—Ph | NH | H | NH | H | H | H |
| 912 | 3-Me—Ph | NH | H | NH | OH | H | H |
| 913 | 3-Me—Ph | NH | H | NH | OA6 | H | H |
| 914 | 3-Me—Ph | NH | H | NH | OA8 | H | H |
| 915 | 3-Me—Ph | NH | H | NH | OA9 | H | H |
| 916 | 3-Me—Ph | NH | H | NH | OA10 | H | H |
| 917 | 3-Me—Ph | NH | H | NH | OA12 | H | H |
| 918 | 3-Me—Ph | NH | H | NH | OA14 | H | H |
| 919 | 3-Me—Ph | NH | H | NH | OA16 | H | H |
| 920 | 3-Me—Ph | NH | H | NH | OH | H | A6 |
| 921 | 3-Me—Ph | NH | H | NH | OH | H | A8 |
| 922 | 3-Me—Ph | NH | H | NH | OH | H | A9 |
| 923 | 3-Me—Ph | NH | H | NH | OH | H | A10 |
| 924 | 3-Me—Ph | NH | H | NH | OH | H | A12 |
| 925 | 3-Me—Ph | NH | H | NH | OH | H | A14 |
| 926 | 3-Me—Ph | NH | H | NH | OH | H | A16 |
| 927 | 3-Me—Ph | NH | H | NH | OH | A6 | A6 |
| 928 | 3-Me—Ph | NH | H | NH | OH | A8 | A8 |
| 929 | 3-Me—Ph | NH | H | NH | OH | A10 | A10 |
| 930 | 3-Me—Ph | NH | H | NH | OA2 | A2 | A2 |
| 931 | 3-Me—Ph | NH | H | NH | OA3 | A3 | A3 |
| 932 | 3-Me—Ph | NH | H | NH | OA4 | A4 | A4 |
| 933 | 3-Me—Ph | NH | H | NH | OC6 | H | H |
| 934 | 3-Me—Ph | NH | H | NH | OC7 | H | H |
| 935 | 3-Me—Ph | NH | H | NH | OC8 | H | H |

TABLE 1-continued

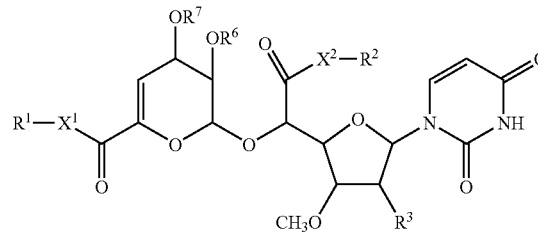

(I-1)

| Exemp. Comp. No. | R¹ | X¹ | R² | X² | R³ | R⁶ | R⁷ |
|---|---|---|---|---|---|---|---|
| 936 | 3-Me—Ph | NH | H | NH | OC10 | H | H |
| 937 | 3-Me—Ph | NH | H | NH | OC11 | H | H |
| 938 | 3-Me—Ph | NH | H | NH | OC12 | H | H |
| 939 | 3-Me—Ph | NH | H | NH | OC14 | H | H |
| 940 | 3-Me—Ph | NH | H | NH | OC16 | H | H |
| 941 | 3-Me—Ph | NH | H | NH | C6CO$_3$ | H | H |
| 942 | 3-Me—Ph | NH | H | NH | C7CO$_3$ | H | H |
| 943 | 3-Me—Ph | NH | H | NH | C8CO$_3$ | H | H |
| 944 | 3-Me—Ph | NH | H | NH | C9CO$_3$ | H | H |
| 945 | 3-Me—Ph | NH | H | NH | C10CO$_3$ | H | H |
| 946 | 3-Me—Ph | NH | H | NH | C12CO$_3$ | H | H |
| 947 | 3-Me—Ph | NH | H | NH | C16CO$_3$ | H | H |
| 948 | 3-Me—Ph | NH | C8 | NH | OH | H | H |
| 949 | 3-Me—Ph | NH | C9 | NH | OH | H | H |
| 950 | 3-Me—Ph | NH | C10 | NH | OH | H | H |
| 951 | 3-Me—Ph | NH | C12 | NH | OH | H | H |
| 952 | 3-Me—Ph | NH | C16 | NH | OH | H | H |
| 953 | 3-Me—Ph | NH | F1 | NH | OH | H | H |
| 954 | 3-Me—Ph | NH | F2 | NH | OH | H | H |
| 955 | 3-Me—Ph | NH | F3 | NH | OH | H | H |
| 956 | 3-Me—Ph | NH | F4 | NH | OH | H | H |
| 957 | 3-Me—Ph | NH | F5 | NH | OH | H | H |
| 958 | 3-Me—Ph | NH | F6 | NH | OH | H | H |
| 959 | 3-Me—Ph | NH | F7 | NH | OH | H | H |
| 960 | 3-Me—Ph | NH | F8 | NH | OH | H | H |
| 961 | 3-Me—Ph | NH | F9 | NH | OH | H | H |
| 962 | 3-Me—Ph | NH | F10 | NH | OH | H | H |
| 963 | 3-Me—Ph | NH | Ph | NH | OH | H | H |
| 964 | 3-Me—Ph | NH | Bn | NH | OH | H | H |
| 965 | 3-Me—Ph | NH | Pe | NH | OH | H | H |
| 966 | 3-Me—Ph | NH | C12 | NMe | OH | H | H |
| 967 | 3-Me—Ph | NH | C12 | NEt | OH | H | H |
| 968 | 3-Me—Ph | NH | C12 | NPr | OH | H | H |
| 969 | 3-Me—Ph | NH | (CH$_2$)$_3$ | N | OH | H | H |
| 970 | 3-Me—Ph | NH | (CH$_2$)$_4$ | N | OH | H | H |
| 971 | 3-Me—Ph | NH | (CH$_2$)$_5$ | N | OH | H | H |
| 972 | 3-Me—Ph | NH | C12 | O | OH | H | H |
| 973 | 3-Me—Ph | NH | Ph | O | OH | H | H |
| 974 | 3-Me—Ph | NH | C12 | S | OH | H | H |
| 975 | 3-Me—Ph | NH | Ph | S | OH | H | H |
| 976 | 3-Me—Ph | NMe | H | NH | OH | H | H |
| 977 | 3-Me—Ph | NEt | H | NH | OH | H | H |
| 978 | 3-Me—Ph | NPr | H | NH | OH | H | H |
| 979 | 3-Me—Ph | O | H | NH | OH | H | H |
| 980 | 3-Me—Ph | S | H | NH | OH | H | H |
| 981 | 3-Et—Ph | NH | H | NH | H | H | H |
| 982 | 3-Et—Ph | NH | H | NH | OH | H | H |
| 983 | 3-Et—Ph | NH | H | NH | OA6 | H | H |
| 984 | 3-Et—Ph | NH | H | NH | OA8 | H | H |
| 985 | 3-Et—Ph | NH | H | NH | OA9 | H | H |
| 986 | 3-Et—Ph | NH | H | NH | OA10 | H | H |
| 987 | 3-Et—Ph | NH | H | NH | OA12 | H | H |
| 988 | 3-Et—Ph | NH | H | NH | OA14 | H | H |
| 989 | 3-Et—Ph | NH | H | NH | OA16 | H | H |
| 990 | 3-Et—Ph | NH | H | NH | OH | H | A6 |
| 991 | 3-Et—Ph | NH | H | NH | OH | H | A8 |
| 992 | 3-Et—Ph | NH | H | NH | OH | H | A9 |
| 993 | 3-Et—Ph | NH | H | NH | OH | H | A10 |
| 994 | 3-Et—Ph | NH | H | NH | OH | H | A12 |
| 995 | 3-Et—Ph | NH | H | NH | OH | H | A14 |
| 996 | 3-Et—Ph | NH | H | NH | OH | H | A16 |
| 997 | 3-Et—Ph | NH | H | NH | OH | A6 | A6 |

TABLE 1-continued

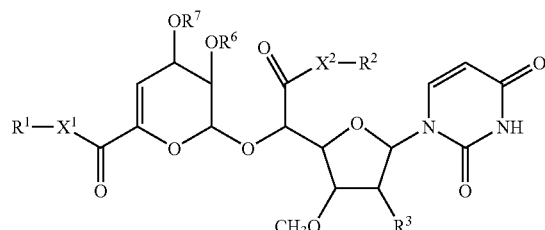

(I-1)

| Exemp. Comp. No. | R¹ | X¹ | R² | X² | R³ | R⁶ | R⁷ |
|---|---|---|---|---|---|---|---|
| 998 | 3-Et—Ph | NH | H | NH | OH | A8 | A8 |
| 999 | 3-Et—Ph | NH | H | NH | OH | A10 | A10 |
| 1000 | 3-Et—Ph | NH | H | NH | OA2 | A2 | A2 |
| 1001 | 3-Et—Ph | NH | H | NH | OA3 | A3 | A3 |
| 1002 | 3-Et—Ph | NH | H | NH | OA4 | A4 | A4 |
| 1003 | 3-Et—Ph | NH | H | NH | OC6 | H | H |
| 1004 | 3-Et—Ph | NH | H | NH | OC7 | H | H |
| 1005 | 3-Et—Ph | NH | H | NH | OC8 | H | H |
| 1006 | 3-Et—Ph | NH | H | NH | OC10 | H | H |
| 1007 | 3-Et—Ph | NH | H | NH | OC11 | H | H |
| 1008 | 3-Et—Ph | NH | H | NH | OC12 | H | H |
| 1009 | 3-Et—Ph | NH | H | NH | OC14 | H | H |
| 1010 | 3-Et—Ph | NH | H | NH | OC16 | H | H |
| 1011 | 3-Et—Ph | NH | H | NH | C6CO₃ | H | H |
| 1012 | 3-Et—Ph | NH | H | NH | C7CO₃ | H | H |
| 1013 | 3-Et—Ph | NH | H | NH | C8CO₃ | H | H |
| 1014 | 3-Et—Ph | NH | H | NH | C9CO₃ | H | H |
| 1015 | 3-Et—Ph | NH | H | NH | C10CO₃ | H | H |
| 1016 | 3-Et—Ph | NH | H | NH | C12CO₃ | H | H |
| 1017 | 3-Et—Ph | NH | H | NH | C16CO₃ | H | H |
| 1018 | 3-Et—Ph | NH | C8 | NH | OH | H | H |
| 1019 | 3-Et—Ph | NH | C9 | NH | OH | H | H |
| 1020 | 3-Et—Ph | NH | C10 | NH | OH | H | H |
| 1021 | 3-Et—Ph | NH | C12 | NH | OH | H | H |
| 1022 | 3-Et—Ph | NH | C16 | NH | OH | H | H |
| 1023 | 3-Et—Ph | NH | F1 | NH | OH | H | H |
| 1024 | 3-Et—Ph | NH | F2 | NH | OH | H | H |
| 1025 | 3-Et—Ph | NH | F3 | NH | OH | H | H |
| 1026 | 3-Et—Ph | NH | F4 | NH | OH | H | H |
| 1027 | 3-Et—Ph | NH | F5 | NH | OH | H | H |
| 1028 | 3-Et—Ph | NH | F6 | NH | OH | H | H |
| 1029 | 3-Et—Ph | NH | F7 | NH | OH | H | H |
| 1030 | 3-Et—Ph | NH | F8 | NH | OH | H | H |
| 1031 | 3-Et—Ph | NH | F9 | NH | OH | H | H |
| 1032 | 3-Et—Ph | NH | F10 | NH | OH | H | H |
| 1033 | 3-Et—Ph | NH | Ph | NH | OH | H | H |
| 1034 | 3-Et—Ph | NH | Bn | NH | OH | H | H |
| 1035 | 3-Et—Ph | NH | Pe | NH | OH | H | H |
| 1036 | 3-Et—Ph | NH | C12 | NMe | OH | H | H |
| 1037 | 3-Et—Ph | NH | C12 | NEt | OH | H | H |
| 1038 | 3-Et—Ph | NH | C12 | NPr | OH | H | H |
| 1039 | 3-Et—Ph | NH | (CH₂)₃ | N | OH | H | H |
| 1040 | 3-Et—Ph | NH | (CH₂)₄ | N | OH | H | H |
| 1041 | 3-Et—Ph | NH | (CH₂)₅ | N | OH | H | H |
| 1042 | 3-Et—Ph | NH | C12 | O | OH | H | H |
| 1043 | 3-Et—Ph | NH | Ph | O | OH | H | H |
| 1044 | 3-Et—Ph | NH | C12 | S | OH | H | H |
| 1045 | 3-Et—Ph | NH | Ph | S | OH | H | H |
| 1046 | 3-Et—Ph | NMe | H | NH | OH | H | H |
| 1047 | 3-Et—Ph | NEt | H | NH | OH | H | H |
| 1048 | 3-Et—Ph | NPr | H | NH | OH | H | H |
| 1049 | 3-Et—Ph | O | H | NH | OH | H | H |
| 1050 | 3-Et—Ph | S | H | NH | OH | H | H |
| 1051 | 3-iPr—Ph | NH | H | NH | H | H | H |
| 1052 | 3-iPr—Ph | NH | H | NH | OH | H | H |
| 1053 | 3-iPr—Ph | NH | H | NH | OA6 | H | H |
| 1054 | 3-iPr—Ph | NH | H | NH | OA8 | H | H |
| 1055 | 3-iPr—Ph | NH | H | NH | OA9 | H | H |
| 1056 | 3-iPr—Ph | NH | H | NH | OA10 | H | H |
| 1057 | 3-iPr—Ph | NH | H | NH | OA12 | H | H |
| 1058 | 3-iPr—Ph | NH | H | NH | OA14 | H | H |
| 1059 | 3-iPr—Ph | NH | H | NH | OA16 | H | H |

TABLE 1-continued

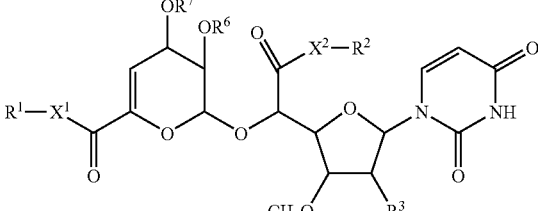

(I-1)

| Exemp. Comp. No. | R¹ | X¹ | R² | X² | R³ | R⁶ | R⁷ |
|---|---|---|---|---|---|---|---|
| 1060 | 3-iPr—Ph | NH | H | NH | OH | H | A6 |
| 1061 | 3-iPr—Ph | NH | H | NH | OH | H | A8 |
| 1062 | 3-iPr—Ph | NH | H | NH | OH | H | A9 |
| 1063 | 3-iPr—Ph | NH | H | NH | OH | H | A10 |
| 1064 | 3-iPr—Ph | NH | H | NH | OH | H | A12 |
| 1065 | 3-iPr—Ph | NH | H | NH | OH | H | A14 |
| 1066 | 3-iPr—Ph | NH | H | NH | OH | H | A16 |
| 1067 | 3-iPr—Ph | NH | H | NH | OH | A6 | A6 |
| 1068 | 3-iPr—Ph | NH | H | NH | OH | A8 | A8 |
| 1069 | 3-iPr—Ph | NH | H | NH | OH | A10 | A10 |
| 1070 | 3-iPr—Ph | NH | H | NH | OA2 | A2 | A2 |
| 1071 | 3-iPr—Ph | NH | H | NH | OA3 | A3 | A3 |
| 1072 | 3-iPr—Ph | NH | H | NH | OA4 | A4 | A4 |
| 1073 | 3-iPr—Ph | NH | H | NH | OC6 | H | H |
| 1074 | 3-iPr—Ph | NH | H | NH | OC7 | H | H |
| 1075 | 3-iPr—Ph | NH | H | NH | OC8 | H | H |
| 1076 | 3-iPr—Ph | NH | H | NH | OC10 | H | H |
| 1077 | 3-iPr—Ph | NH | H | NH | OC11 | H | H |
| 1078 | 3-iPr—Ph | NH | H | NH | OC12 | H | H |
| 1079 | 3-iPr—Ph | NH | H | NH | OC14 | H | H |
| 1080 | 3-iPr—Ph | NH | H | NH | OC16 | H | H |
| 1081 | 3-iPr—Ph | NH | H | NH | C6CO$_3$ | H | H |
| 1082 | 3-iPr—Ph | NH | H | NH | C7CO$_3$ | H | H |
| 1083 | 3-iPr—Ph | NH | H | NH | C8CO$_3$ | H | H |
| 1084 | 3-iPr—Ph | NH | H | NH | C9CO$_3$ | H | H |
| 1085 | 3-iPr—Ph | NH | H | NH | C10CO$_3$ | H | H |
| 1086 | 3-iPr—Ph | NH | H | NH | C12CO$_3$ | H | H |
| 1087 | 3-iPr—Ph | NH | H | NH | C16CO$_3$ | H | H |
| 1088 | 3-iPr—Ph | NH | C8 | NH | OH | H | H |
| 1089 | 3-iPr—Ph | NH | C9 | NH | OH | H | H |
| 1090 | 3-iPr—Ph | NH | C10 | NH | OH | H | H |
| 1091 | 3-iPr—Ph | NH | C12 | NH | OH | H | H |
| 1092 | 3-iPr—Ph | NH | C16 | NH | OH | H | H |
| 1093 | 3-iPr—Ph | NH | F1 | NH | OH | H | H |
| 1094 | 3-iPr—Ph | NH | F2 | NH | OH | H | H |
| 1095 | 3-iPr—Ph | NH | F3 | NH | OH | H | H |
| 1096 | 3-iPr—Ph | NH | F4 | NH | OH | H | H |
| 1097 | 3-iPr—Ph | NH | F5 | NH | OH | H | H |
| 1098 | 3-iPr—Ph | NH | F6 | NH | OH | H | H |
| 1099 | 3-iPr—Ph | NH | F7 | NH | OH | H | H |
| 1100 | 3-iPr—Ph | NH | F8 | NH | OH | H | H |
| 1101 | 3-iPr—Ph | NH | F9 | NH | OH | H | H |
| 1102 | 3-iPr—Ph | NH | F10 | NH | OH | H | H |
| 1103 | 3-iPr—Ph | NH | Ph | NH | OH | H | H |
| 1104 | 3-iPr—Ph | NH | Bn | NH | OH | H | H |
| 1105 | 3-iPr—Ph | NH | Pe | NH | OH | H | H |
| 1106 | 3-iPr—Ph | NH | C12 | NMe | OH | H | H |
| 1107 | 3-iPr—Ph | NH | C12 | NEt | OH | H | H |
| 1108 | 3-iPr—Ph | NH | C12 | NPr | OH | H | H |
| 1109 | 3-iPr—Ph | NH | (CH$_2$)$_3$ | N | OH | H | H |
| 1110 | 3-iPr—Ph | NH | (CH$_2$)$_4$ | N | OH | H | H |
| 1111 | 3-iPr—Ph | NH | (CH$_2$)$_5$ | N | OH | H | H |
| 1112 | 3-iPr—Ph | NH | C12 | O | OH | H | H |
| 1113 | 3-iPr—Ph | NH | Ph | O | OH | H | H |
| 1114 | 3-iPr—Ph | NH | C12 | S | OH | H | H |
| 1115 | 3-iPr—Ph | NH | Ph | S | OH | H | H |
| 1116 | 3-iPr—Ph | NMe | H | NH | OH | H | H |
| 1117 | 3-iPr—Ph | NEt | H | NH | OH | H | H |
| 1118 | 3-iPr—Ph | NPr | H | NH | OH | H | H |
| 1119 | 3-iPr—Ph | O | H | NH | OH | H | H |
| 1120 | 3-iPr—Ph | S | H | NH | OH | H | H |
| 1121 | 2-Et—Ph | NH | H | NH | H | H | H |

TABLE 1-continued

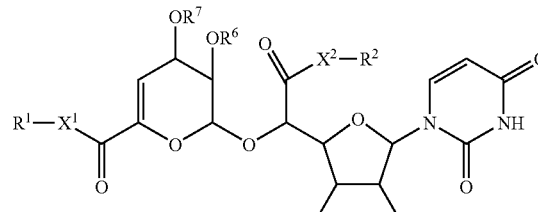

(I-1)

| Exemp. Comp. No. | $R^1$ | $X^1$ | $R^2$ | $X^2$ | $R^3$ | $R^6$ | $R^7$ |
|---|---|---|---|---|---|---|---|
| 1122 | 2-Et—Ph | NH | H | NH | OH | H | H |
| 1123 | 2-Et—Ph | NH | H | NH | OA6 | H | H |
| 1124 | 2-Et—Ph | NH | H | NH | OA8 | H | H |
| 1125 | 2-Et—Ph | NH | H | NH | OA9 | H | H |
| 1126 | 2-Et—Ph | NH | H | NH | OA10 | H | H |
| 1127 | 2-Et—Ph | NH | H | NH | OA12 | H | H |
| 1128 | 2-Et—Ph | NH | H | NH | OA14 | H | H |
| 1129 | 2-Et—Ph | NH | H | NH | OA16 | H | H |
| 1130 | 2-Et—Ph | NH | H | NH | OH | H | A6 |
| 1131 | 2-Et—Ph | NH | H | NH | OH | H | A8 |
| 1132 | 2-Et—Ph | NH | H | NH | OH | H | A9 |
| 1133 | 2-Et—Ph | NH | H | NH | OH | H | A10 |
| 1134 | 2-Et—Ph | NH | H | NH | OH | H | A12 |
| 1135 | 2-Et—Ph | NH | H | NH | OH | H | A14 |
| 1136 | 2-Et—Ph | NH | H | NH | OH | H | A16 |
| 1137 | 2-Et—Ph | NH | H | NH | OH | A6 | A6 |
| 1138 | 2-Et—Ph | NH | H | NH | OH | A8 | A8 |
| 1139 | 2-Et—Ph | NH | H | NH | OH | A10 | A10 |
| 1140 | 2-Et—Ph | NH | H | NH | OA2 | A2 | A2 |
| 1141 | 2-Et—Ph | NH | H | NH | OA3 | A3 | A3 |
| 1142 | 2-Et—Ph | NH | H | NH | OA4 | A4 | A4 |
| 1143 | 2-Et—Ph | NH | H | NH | OC6 | H | H |
| 1144 | 2-Et—Ph | NH | H | NH | OC7 | H | H |
| 1145 | 2-Et—Ph | NH | H | NH | OC8 | H | H |
| 1146 | 2-Et—Ph | NH | H | NH | OC10 | H | H |
| 1147 | 2-Et—Ph | NH | H | NH | OC11 | H | H |
| 1148 | 2-Et—Ph | NH | H | NH | OC12 | H | H |
| 1149 | 2-Et—Ph | NH | H | NH | OC14 | H | H |
| 1150 | 2-Et—Ph | NH | H | NH | OC16 | H | H |
| 1151 | 2-Et—Ph | NH | H | NH | $C6CO_3$ | H | H |
| 1152 | 2-Et—Ph | NH | H | NH | $C7CO_3$ | H | H |
| 1153 | 2-Et—Ph | NH | H | NH | $C8CO_3$ | H | H |
| 1154 | 2-Et—Ph | NH | H | NH | $C9CO_3$ | H | H |
| 1155 | 2-Et—Ph | NH | H | NH | $C10CO_3$ | H | H |
| 1156 | 2-Et—Ph | NH | H | NH | $C12CO_3$ | H | H |
| 1157 | 2-Et—Ph | NH | H | NH | $C16CO_3$ | H | H |
| 1158 | 2-Et—Ph | NH | C8 | NH | OH | H | H |
| 1159 | 2-Et—Ph | NH | C9 | NH | OH | H | H |
| 1160 | 2-Et—Ph | NH | C10 | NH | OH | H | H |
| 1161 | 2-Et—Ph | NH | C12 | NH | OH | H | H |
| 1162 | 2-Et—Ph | NH | C16 | NH | OH | H | H |
| 1163 | 2-Et—Ph | NH | F1 | NH | OH | H | H |
| 1164 | 2-Et—Ph | NH | F2 | NH | OH | H | H |
| 1165 | 2-Et—Ph | NH | F3 | NH | OH | H | H |
| 1166 | 2-Et—Ph | NH | F4 | NH | OH | H | H |
| 1167 | 2-Et—Ph | NH | F5 | NH | OH | H | H |
| 1168 | 2-Et—Ph | NH | F6 | NH | OH | H | H |
| 1169 | 2-Et—Ph | NH | F7 | NH | OH | H | H |
| 1170 | 2-Et—Ph | NH | F8 | NH | OH | H | H |
| 1171 | 2-Et—Ph | NH | F9 | NH | OH | H | H |
| 1172 | 2-Et—Ph | NH | F10 | NH | OH | H | H |
| 1173 | 2-Et—Ph | NH | Ph | NH | OH | H | H |
| 1174 | 2-Et—Ph | NH | Bn | NH | OH | H | H |
| 1175 | 2-Et—Ph | NH | Pe | NH | OH | H | H |
| 1176 | 2-Et—Ph | NH | C12 | NMe | OH | H | H |
| 1177 | 2-Et—Ph | NH | C12 | NEt | OH | H | H |
| 1178 | 2-Et—Ph | NH | C12 | NPr | OH | H | H |
| 1179 | 2-Et—Ph | NH | $(CH_2)_3$ | N | OH | H | H |
| 1180 | 2-Et—Ph | NH | $(CH_2)_4$ | N | OH | H | H |
| 1181 | 2-Et—Ph | NH | $(CH_2)_5$ | N | OH | H | H |
| 1182 | 2-Et—Ph | NH | C12 | O | OH | H | H |
| 1183 | 2-Et—Ph | NH | Ph | O | OH | H | H |

TABLE 1-continued

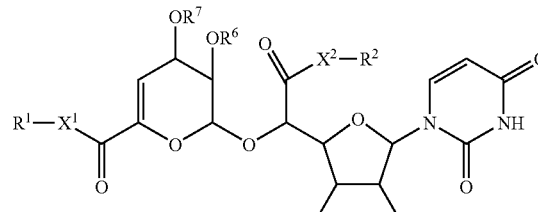

(I-1)

| Exemp. Comp. No. | R¹ | X¹ | R² | X² | R³ | R⁶ | R⁷ |
|---|---|---|---|---|---|---|---|
| 1184 | 2-Et—Ph | NH | C12 | S | OH | H | H |
| 1185 | 2-Et—Ph | NH | Ph | S | OH | H | H |
| 1186 | 2-Et—Ph | NMe | H | NH | OH | H | H |
| 1187 | 2-Et—Ph | NEt | H | NH | OH | H | H |
| 1188 | 2-Et—Ph | NPr | H | NH | OH | H | H |
| 1189 | 2-Et—Ph | O | H | NH | OH | H | H |
| 1190 | 2-Et—Ph | S | H | NH | OH | H | H |
| 1191 | 2-Pr—Ph | NH | H | NH | H | H | H |
| 1192 | 2-Pr—Ph | NH | H | NH | OH | H | H |
| 1193 | 2-Pr—Ph | NH | H | NH | OA6 | H | H |
| 1194 | 2-Pr—Ph | NH | H | NH | OA8 | H | H |
| 1195 | 2-Pr—Ph | NH | H | NH | OA9 | H | H |
| 1196 | 2-Pr—Ph | NH | H | NH | OA10 | H | H |
| 1197 | 2-Pr—Ph | NH | H | NH | OA12 | H | H |
| 1198 | 2-Pr—Ph | NH | H | NH | OA14 | H | H |
| 1199 | 2-Pr—Ph | NH | H | NH | OA16 | H | H |
| 1200 | 2-Pr—Ph | NH | H | NH | OH | H | A6 |
| 1201 | 2-Pr—Ph | NH | H | NH | OH | H | A8 |
| 1202 | 2-Pr—Ph | NH | H | NH | OH | H | A9 |
| 1203 | 2-Pr—Ph | NH | H | NH | OH | H | A10 |
| 1204 | 2-Pr—Ph | NH | H | NH | OH | H | A12 |
| 1205 | 2-Pr—Ph | NH | H | NH | OH | H | A14 |
| 1206 | 2-Pr—Ph | NH | H | NH | OH | H | A16 |
| 1207 | 2-Pr—Ph | NH | H | NH | OH | A6 | A6 |
| 1208 | 2-Pr—Ph | NH | H | NH | OH | A8 | A8 |
| 1209 | 2-Pr—Ph | NH | H | NH | OH | A10 | A10 |
| 1210 | 2-Pr—Ph | NH | H | NH | OA2 | A2 | A2 |
| 1211 | 2-Pr—Ph | NH | H | NH | OA3 | A3 | A3 |
| 1212 | 2-Pr—Ph | NH | H | NH | OA4 | A4 | A4 |
| 1213 | 2-Pr—Ph | NH | H | NH | OC6 | H | H |
| 1214 | 2-Pr—Ph | NH | H | NH | OC7 | H | H |
| 1215 | 2-Pr—Ph | NH | H | NH | OC8 | H | H |
| 1216 | 2-Pr—Ph | NH | H | NH | OC10 | H | H |
| 1217 | 2-Pr—Ph | NH | H | NH | OC11 | H | H |
| 1218 | 2-Pr—Ph | NH | H | NH | OC12 | H | H |
| 1219 | 2-Pr—Ph | NH | H | NH | OC14 | H | H |
| 1220 | 2-Pr—Ph | NH | H | NH | OC16 | H | H |
| 1221 | 2-Pr—Ph | NH | H | NH | C6CO₃ | H | H |
| 1222 | 2-Pr—Ph | NH | H | NH | C7CO₃ | H | H |
| 1223 | 2-Pr—Ph | NH | H | NH | C8CO₃ | H | H |
| 1224 | 2-Pr—Ph | NH | H | NH | C9CO₃ | H | H |
| 1225 | 2-Pr—Ph | NH | H | NH | C10CO₃ | H | H |
| 1226 | 2-Pr—Ph | NH | H | NH | C12CO₃ | H | H |
| 1227 | 2-Pr—Ph | NH | H | NH | C16CO₃ | H | H |
| 1228 | 2-Pr—Ph | NH | C8 | NH | OH | H | H |
| 1229 | 2-Pr—Ph | NH | C9 | NH | OH | H | H |
| 1230 | 2-Pr—Ph | NH | C10 | NH | OH | H | H |
| 1231 | 2-Pr—Ph | NH | C12 | NH | OH | H | H |
| 1232 | 2-Pr—Ph | NH | C16 | NH | OH | H | H |
| 1233 | 2-Pr—Ph | NH | F1 | NH | OH | H | H |
| 1234 | 2-Pr—Ph | NH | F2 | NH | OH | H | H |
| 1235 | 2-Pr—Ph | NH | F3 | NH | OH | H | H |
| 1236 | 2-Pr—Ph | NH | F4 | NH | OH | H | H |
| 1237 | 2-Pr—Ph | NH | F5 | NH | OH | H | H |
| 1238 | 2-Pr—Ph | NH | F6 | NH | OH | H | H |
| 1239 | 2-Pr—Ph | NH | F7 | NH | OH | H | H |
| 1240 | 2-Pr—Ph | NH | F8 | NH | OH | H | H |
| 1241 | 2-Pr—Ph | NH | F9 | NH | OH | H | H |
| 1242 | 2-Pr—Ph | NH | F10 | NH | OH | H | H |
| 1243 | 2-Pr—Ph | NH | Ph | NH | OH | H | H |
| 1244 | 2-Pr—Ph | NH | Bn | NH | OH | H | H |
| 1245 | 2-Pr—Ph | NH | Pe | NH | OH | H | H |

TABLE 1-continued

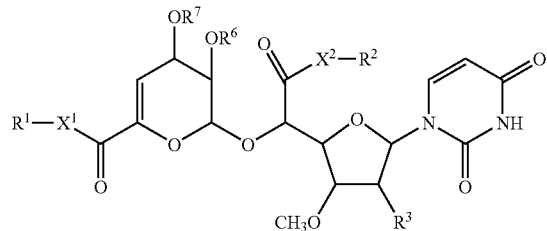

(I-1)

| Exemp. Comp. No. | R¹ | X¹ | R² | X² | R³ | R⁶ | R⁷ |
|---|---|---|---|---|---|---|---|
| 1246 | 2-Pr—Ph | NH | C12 | NMe | OH | H | H |
| 1247 | 2-Pr—Ph | NH | C12 | NEt | OH | H | H |
| 1248 | 2-Pr—Ph | NH | C12 | NPr | OH | H | H |
| 1249 | 2-Pr—Ph | NH | (CH$_2$)$_3$ | N | OH | H | H |
| 1250 | 2-Pr—Ph | NH | (CH$_2$)$_4$ | N | OH | H | H |
| 1251 | 2-Pr—Ph | NH | (CH$_2$)$_5$ | N | OH | H | H |
| 1252 | 2-Pr—Ph | NH | C12 | O | OH | H | H |
| 1253 | 2-Pr—Ph | NH | Ph | O | OH | H | H |
| 1254 | 2-Pr—Ph | NH | C12 | S | OH | H | H |
| 1255 | 2-Pr—Ph | NH | Ph | S | OH | H | H |
| 1256 | 2-Pr—Ph | NMe | H | NH | OH | H | H |
| 1257 | 2-Pr—Ph | NEt | H | NH | OH | H | H |
| 1258 | 2-Pr—Ph | NPr | H | NH | OH | H | H |
| 1259 | 2-Pr—Ph | O | H | NH | OH | H | H |
| 1260 | 2-Pr—Ph | S | H | NH | OH | H | H |
| 1261 | 2-iPr—Ph | NH | H | NH | H | H | H |
| 1262 | 2-iPr—Ph | NH | H | NH | OH | H | H |
| 1263 | 2-iPr—Ph | NH | H | NH | OA6 | H | H |
| 1264 | 2-iPr—Ph | NH | H | NH | OA8 | H | H |
| 1265 | 2-iPr—Ph | NH | H | NH | OA9 | H | H |
| 1266 | 2-iPr—Ph | NH | H | NH | OA10 | H | H |
| 1267 | 2-iPr—Ph | NH | H | NH | OA12 | H | H |
| 1268 | 2-iPr—Ph | NH | H | NH | OA14 | H | H |
| 1269 | 2-iPr—Ph | NH | H | NH | OA16 | H | H |
| 1270 | 2-iPr—Ph | NH | H | NH | OH | H | A6 |
| 1271 | 2-iPr—Ph | NH | H | NH | OH | H | A8 |
| 1272 | 2-iPr—Ph | NH | H | NH | OH | H | A9 |
| 1273 | 2-iPr—Ph | NH | H | NH | OH | H | A10 |
| 1274 | 2-iPr—Ph | NH | H | NH | OH | H | A12 |
| 1275 | 2-iPr—Ph | NH | H | NH | OH | H | A14 |
| 1276 | 2-iPr—Ph | NH | H | NH | OH | H | A16 |
| 1277 | 2-iPr—Ph | NH | H | NH | OH | A6 | A6 |
| 1278 | 2-iPr—Ph | NH | H | NH | OH | A8 | A8 |
| 1279 | 2-iPr—Ph | NH | H | NH | OH | A10 | A10 |
| 1280 | 2-iPr—Ph | NH | H | NH | OA2 | A2 | A2 |
| 1281 | 2-iPr—Ph | NH | H | NH | OA3 | A3 | A3 |
| 1282 | 2-iPr—Ph | NH | H | NH | OA4 | A4 | A4 |
| 1283 | 2-iPr—Ph | NH | H | NH | OC6 | H | H |
| 1284 | 2-iPr—Ph | NH | H | NH | OC7 | H | H |
| 1285 | 2-iPr—Ph | NH | H | NH | OC8 | H | H |
| 1286 | 2-iPr—Ph | NH | H | NH | OC10 | H | H |
| 1287 | 2-iPr—Ph | NH | H | NH | OC11 | H | H |
| 1288 | 2-iPr—Ph | NH | H | NH | OC12 | H | H |
| 1289 | 2-iPr—Ph | NH | H | NH | OC14 | H | H |
| 1290 | 2-iPr—Ph | NH | H | NH | OC16 | H | H |
| 1291 | 2-iPr—Ph | NH | H | NH | C6CO$_3$ | H | H |
| 1292 | 2-iPr—Ph | NH | H | NH | C7CO$_3$ | H | H |
| 1293 | 2-iPr—Ph | NH | H | NH | C8CO$_3$ | H | H |
| 1294 | 2-iPr—Ph | NH | H | NH | C9CO$_3$ | H | H |
| 1295 | 2-iPr—Ph | NH | H | NH | C10CO$_3$ | H | H |
| 1296 | 2-iPr—Ph | NH | H | NH | C12CO$_3$ | H | H |
| 1297 | 2-iPr—Ph | NH | H | NH | C16CO$_3$ | H | H |
| 1298 | 2-iPr—Ph | NH | C8 | NH | OH | H | H |
| 1299 | 2-iPr—Ph | NH | C9 | NH | OH | H | H |
| 1300 | 2-iPr—Ph | NH | C10 | NH | OH | H | H |
| 1301 | 2-iPr—Ph | NH | C12 | NH | OH | H | H |
| 1302 | 2-iPr—Ph | NH | C16 | NH | OH | H | H |
| 1303 | 2-iPr—Ph | NH | F1 | NH | OH | H | H |
| 1304 | 2-iPr—Ph | NH | F2 | NH | OH | H | H |
| 1305 | 2-iPr—Ph | NH | F3 | NH | OH | H | H |
| 1306 | 2-iPr—Ph | NH | F4 | NH | OH | H | H |
| 1307 | 2-iPr—Ph | NH | F5 | NH | OH | H | H |

TABLE 1-continued (I-1)

| Exemp. Comp. No. | R¹ | X¹ | R² | X² | R³ | R⁶ | R⁷ |
|---|---|---|---|---|---|---|---|
| 1308 | 2-iPr—Ph | NH | F6 | NH | OH | H | H |
| 1309 | 2-iPr—Ph | NH | F7 | NH | OH | H | H |
| 1310 | 2-iPr—Ph | NH | F8 | NH | OH | H | H |
| 1311 | 2-iPr—Ph | NH | F9 | NH | OH | H | H |
| 1312 | 2-iPr—Ph | NH | F10 | NH | OH | H | H |
| 1313 | 2-iPr—Ph | NH | Ph | NH | OH | H | H |
| 1314 | 2-iPr—Ph | NH | Bn | NH | OH | H | H |
| 1315 | 2-iPr—Ph | NH | Pe | NH | OH | H | H |
| 1316 | 2-iPr—Ph | NH | C12 | NMe | OH | H | H |
| 1317 | 2-iPr—Ph | NH | C12 | NEt | OH | H | H |
| 1318 | 2-iPr—Ph | NH | C12 | NPr | OH | H | H |
| 1319 | 2-iPr—Ph | NH | (CH₂)₃ | N | OH | H | H |
| 1320 | 2-iPr—Ph | NH | (CH₂)₄ | N | OH | H | H |
| 1321 | 2-iPr—Ph | NH | (CH₂)₅ | N | OH | H | H |
| 1322 | 2-iPr—Ph | NH | C12 | O | OH | H | H |
| 1323 | 2-iPr—Ph | NH | Ph | O | OH | H | H |
| 1324 | 2-iPr—Ph | NH | C12 | S | OH | H | H |
| 1325 | 2-iPr—Ph | NH | Ph | S | OH | H | H |
| 1326 | 2-iPr—Ph | NMe | H | NH | OH | H | H |
| 1327 | 2-iPr—Ph | NEt | H | NH | OH | H | H |
| 1328 | 2-iPr—Ph | NPr | H | NH | OH | H | H |
| 1329 | 2-iPr—Ph | O | H | NH | OH | H | H |
| 1330 | 2-iPr—Ph | S | H | NH | OH | H | H |
| 1331 | 2-Bu—Ph | NH | H | NH | H | H | H |
| 1332 | 2-Bu—Ph | NH | H | NH | OH | H | H |
| 1333 | 2-Bu—Ph | NH | H | NH | OA6 | H | H |
| 1334 | 2-Bu—Ph | NH | H | NH | OA8 | H | H |
| 1335 | 2-Bu—Ph | NH | H | NH | OA9 | H | H |
| 1336 | 2-Bu—Ph | NH | H | NH | OA10 | H | H |
| 1337 | 2-Bu—Ph | NH | H | NH | OA12 | H | H |
| 1338 | 2-Bu—Ph | NH | H | NH | OA14 | H | H |
| 1339 | 2-Bu—Ph | NH | H | NH | OA16 | H | H |
| 1340 | 2-Bu—Ph | NH | H | NH | OH | H | A6 |
| 1341 | 2-Bu—Ph | NH | H | NH | OH | H | A8 |
| 1342 | 2-Bu—Ph | NH | H | NH | OH | H | A9 |
| 1343 | 2-Bu—Ph | NH | H | NH | OH | H | A10 |
| 1344 | 2-Bu—Ph | NH | H | NH | OH | H | A12 |
| 1345 | 2-Bu—Ph | NH | H | NH | OH | H | A14 |
| 1346 | 2-Bu—Ph | NH | H | NH | OH | H | A16 |
| 1347 | 2-Bu—Ph | NH | H | NH | OH | A6 | A6 |
| 1348 | 2-Bu—Ph | NH | H | NH | OH | A8 | A8 |
| 1349 | 2-Bu—Ph | NH | H | NH | OH | A10 | A10 |
| 1350 | 2-Bu—Ph | NH | H | NH | OA2 | A2 | A2 |
| 1351 | 2-Bu—Ph | NH | H | NH | OA3 | A3 | A3 |
| 1352 | 2-Bu—Ph | NH | H | NH | OA4 | A4 | A4 |
| 1353 | 2-Bu—Ph | NH | H | NH | OC6 | H | H |
| 1354 | 2-Bu—Ph | NH | H | NH | OC7 | H | H |
| 1355 | 2-Bu—Ph | NH | H | NH | OC8 | H | H |
| 1356 | 2-Bu—Ph | NH | H | NH | OC10 | H | H |
| 1357 | 2-Bu—Ph | NH | H | NH | OC11 | H | H |
| 1358 | 2-Bu—Ph | NH | H | NH | OC12 | H | H |
| 1359 | 2-Bu—Ph | NH | H | NH | OC14 | H | H |
| 1360 | 2-Bu—Ph | NH | H | NH | OC16 | H | H |
| 1361 | 2-Bu—Ph | NH | H | NH | C6CO₃ | H | H |
| 1362 | 2-Bu—Ph | NH | H | NH | C7CO₃ | H | H |
| 1363 | 2-Bu—Ph | NH | H | NH | C8CO₃ | H | H |
| 1364 | 2-Bu—Ph | NH | H | NH | C9CO₃ | H | H |
| 1365 | 2-Bu—Ph | NH | H | NH | C10CO₃ | H | H |
| 1366 | 2-Bu—Ph | NH | H | NH | C12CO₃ | H | H |
| 1367 | 2-Bu—Ph | NH | H | NH | C16CO₃ | H | H |
| 1368 | 2-Bu—Ph | NH | C8 | NH | OH | H | H |
| 1369 | 2-Bu—Ph | NH | C9 | NH | OH | H | H |

TABLE 1-continued

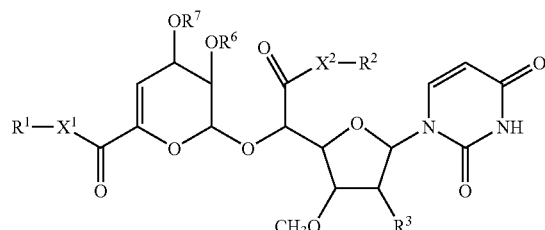

(I-1)

| Exemp. Comp. No. | R$^1$ | X$^1$ | R$^2$ | X$^2$ | R$^3$ | R$^6$ | R$^7$ |
|---|---|---|---|---|---|---|---|
| 1370 | 2-Bu—Ph | NH | C10 | NH | OH | H | H |
| 1371 | 2-Bu—Ph | NH | C12 | NH | OH | H | H |
| 1372 | 2-Bu—Ph | NH | C16 | NH | OH | H | H |
| 1373 | 2-Bu—Ph | NH | F1 | NH | OH | H | H |
| 1374 | 2-Bu—Ph | NH | F2 | NH | OH | H | H |
| 1375 | 2-Bu—Ph | NH | F3 | NH | OH | H | H |
| 1376 | 2-Bu—Ph | NH | F4 | NH | OH | H | H |
| 1377 | 2-Bu—Ph | NH | F5 | NH | OH | H | H |
| 1378 | 2-Bu—Ph | NH | F6 | NH | OH | H | H |
| 1379 | 2-Bu—Ph | NH | F7 | NH | OH | H | H |
| 1380 | 2-Bu—Ph | NH | F8 | NH | OH | H | H |
| 1381 | 2-Bu—Ph | NH | F9 | NH | OH | H | H |
| 1382 | 2-Bu—Ph | NH | F10 | NH | OH | H | H |
| 1383 | 2-Bu—Ph | NH | Ph | NH | OH | H | H |
| 1384 | 2-Bu—Ph | NH | Bn | NH | OH | H | H |
| 1385 | 2-Bu—Ph | NH | Pe | NH | OH | H | H |
| 1386 | 2-Bu—Ph | NH | C12 | NMe | OH | H | H |
| 1387 | 2-Bu—Ph | NH | C12 | NEt | OH | H | H |
| 1388 | 2-Bu—Ph | NH | C12 | NPr | OH | H | H |
| 1389 | 2-Bu—Ph | NH | (CH$_2$)$_3$ | N | OH | H | H |
| 1390 | 2-Bu—Ph | NH | (CH$_2$)$_4$ | N | OH | H | H |
| 1391 | 2-Bu—Ph | NH | (CH$_2$)$_5$ | N | OH | H | H |
| 1392 | 2-Bu—Ph | NH | C12 | O | OH | H | H |
| 1393 | 2-Bu—Ph | NH | Ph | O | OH | H | H |
| 1394 | 2-Bu—Ph | NH | C12 | S | OH | H | H |
| 1395 | 2-Bu—Ph | NH | Ph | S | OH | H | H |
| 1396 | 2-Bu—Ph | NMe | H | NH | OH | H | H |
| 1397 | 2-Bu—Ph | NEt | H | NH | OH | H | H |
| 1398 | 2-Bu—Ph | NPr | H | NH | OH | H | H |
| 1399 | 2-Bu—Ph | O | H | NH | OH | H | H |
| 1400 | 2-Bu—Ph | S | H | NH | OH | H | H |
| 1401 | 4-Vin-Ph | NH | H | NH | H | H | H |
| 1402 | 4-Vin-Ph | NH | H | NH | OH | H | H |
| 1403 | 4-Vin-Ph | NH | H | NH | OA6 | H | H |
| 1404 | 4-Vin-Ph | NH | H | NH | OA8 | H | H |
| 1405 | 4-Vin-Ph | NH | H | NH | OA9 | H | H |
| 1406 | 4-Vin-Ph | NH | H | NH | OA10 | H | H |
| 1407 | 4-Vin-Ph | NH | H | NH | OA12 | H | H |
| 1408 | 4-Vin-Ph | NH | H | NH | OA14 | H | H |
| 1409 | 4-Vin-Ph | NH | H | NH | OA16 | H | H |
| 1410 | 4-Vin-Ph | NH | H | NH | OH | H | A6 |
| 1411 | 4-Vin-Ph | NH | H | NH | OH | H | A8 |
| 1412 | 4-Vin-Ph | NH | H | NH | OH | H | A9 |
| 1413 | 4-Vin-Ph | NH | H | NH | OH | H | A10 |
| 1414 | 4-Vin-Ph | NH | H | NH | OH | H | A12 |
| 1415 | 4-Vin-Ph | NH | H | NH | OH | H | A14 |
| 1416 | 4-Vin-Ph | NH | H | NH | OH | H | A16 |
| 1417 | 4-Vin-Ph | NH | H | NH | OH | A6 | A6 |
| 1418 | 4-Vin-Ph | NH | H | NH | OH | A8 | A8 |
| 1419 | 4-Vin-Ph | NH | H | NH | OH | A10 | A10 |
| 1420 | 4-Vin-Ph | NH | H | NH | OA2 | A2 | A2 |
| 1421 | 4-Vin-Ph | NH | H | NH | OA3 | A3 | A3 |
| 1422 | 4-Vin-Ph | NH | H | NH | OA4 | A4 | A4 |
| 1423 | 4-Vin-Ph | NH | H | NH | OC6 | H | H |
| 1424 | 4-Vin-Ph | NH | H | NH | OC7 | H | H |
| 1425 | 4-Vin-Ph | NH | H | NH | OC8 | H | H |
| 1426 | 4-Vin-Ph | NH | H | NH | OC10 | H | H |
| 1427 | 4-yin-Ph | NH | H | NH | OC11 | H | H |
| 1428 | 4-Vin-Ph | NH | H | NH | OC12 | H | H |
| 1429 | 4-Vin-Ph | NH | H | NH | OC14 | H | H |
| 1430 | 4-Vin-Ph | NH | H | NH | OC16 | H | H |
| 1431 | 4-Vin-Ph | NH | H | NH | C6CO$_3$ | H | H |

TABLE 1-continued (I-1)

| Exemp. Comp. No. | R¹ | X¹ | R² | X² | R³ | R⁶ | R⁷ |
|---|---|---|---|---|---|---|---|
| 1432 | 4-Vin-Ph | NH | H | NH | C7CO₃ | H | H |
| 1433 | 4-Vin-Ph | NH | H | NH | C8CO₃ | H | H |
| 1434 | 4-Vin-Ph | NH | H | NH | C9CO₃ | H | H |
| 1435 | 4-Vin-Ph | NH | H | NH | C10CO₃ | H | H |
| 1436 | 4-Vin-Ph | NH | H | NH | C12CO₃ | H | H |
| 1437 | 4-Vin-Ph | NH | H | NH | C16CO₃ | H | H |
| 1438 | 4-Vin-Ph | NH | C8 | NH | OH | H | H |
| 1439 | 4-Vin-Ph | NH | C9 | NH | OH | H | H |
| 1440 | 4-Vin-Ph | NH | C10 | NH | OH | H | H |
| 1441 | 4-Vin-Ph | NH | C12 | NH | OH | H | H |
| 1442 | 4-Vin-Ph | NH | C16 | NH | OH | H | H |
| 1443 | 4-Vin-Ph | NH | F1 | NH | OH | H | H |
| 1444 | 4-Vin-Ph | NH | F2 | NH | OH | H | H |
| 1445 | 4-Vin-Ph | NH | F3 | NH | OH | H | H |
| 1446 | 4-Vin-Ph | NH | F4 | NH | OH | H | H |
| 1447 | 4-Vin-Ph | NH | F5 | NH | OH | H | H |
| 1448 | 4-Vin-Ph | NH | F6 | NH | OH | H | H |
| 1449 | 4-Vin-Ph | NH | F7 | NH | OH | H | H |
| 1450 | 4-Vin-Ph | NH | F8 | NH | OH | H | H |
| 1451 | 4-Vin-Ph | NH | F9 | NH | OH | H | H |
| 1452 | 4-Vin-Ph | NH | F10 | NH | OH | H | H |
| 1453 | 4-Vin-Ph | NH | Ph | NH | OH | H | H |
| 1454 | 4-Vin-Ph | NH | Bn | NH | OH | H | H |
| 1455 | 4-Vin-Ph | NH | Pe | NH | OH | H | H |
| 1456 | 4-Vin-Ph | NH | C12 | NMe | OH | H | H |
| 1457 | 4-Vin-Ph | NH | C12 | NEt | OH | H | H |
| 1458 | 4-Vin-Ph | NH | C12 | NPr | OH | H | H |
| 1459 | 4-Vin-Ph | NH | (CH₂)₃ | N | OH | H | H |
| 1460 | 4-Vin-Ph | NH | (CH₂)₄ | N | OH | H | H |
| 1461 | 4-Vin-Ph | NH | (CH₂)₅ | N | OH | H | H |
| 1462 | 4-Vin-Ph | NH | C12 | O | OH | H | H |
| 1463 | 4-Vin-Ph | NH | Ph | O | OH | H | H |
| 1464 | 4-Vin-Ph | NH | C12 | S | OH | H | H |
| 1465 | 4-Vin-Ph | NH | Ph | S | OH | H | H |
| 1466 | 4-Vin-Ph | NMe | H | NH | OH | H | H |
| 1467 | 4-Vin-Ph | NEt | H | NH | OH | H | H |
| 1468 | 4-Vin-Ph | NPr | H | NH | OH | H | H |
| 1469 | 4-Vin-Ph | O | H | NH | OH | H | H |
| 1470 | 4-Vin-Ph | S | H | NH | OH | H | H |
| 1471 | 4-CF₃—Ph | NH | H | NH | H | H | H |
| 1472 | 4-CF₃—Ph | NH | H | NH | OH | H | H |
| 1473 | 4-CF₃—Ph | NH | H | NH | OA6 | H | H |
| 1474 | 4-CF₃—Ph | NH | H | NH | OA8 | H | H |
| 1475 | 4-CF₃—Ph | NH | H | NH | OA9 | H | H |
| 1476 | 4-CF₃—Ph | NH | H | NH | OA10 | H | H |
| 1477 | 4-CF₃—Ph | NH | H | NH | OA12 | H | H |
| 1478 | 4-CF₃—Ph | NH | H | NH | OA14 | H | H |
| 1479 | 4-CF₃—Ph | NH | H | NH | OA16 | H | H |
| 1480 | 4-CF₃—Ph | NH | H | NH | OH | H | A6 |
| 1481 | 4-CF₃—Ph | NH | H | NH | OH | H | A8 |
| 1482 | 4-CF₃—Ph | NH | H | NH | OH | H | A9 |
| 1483 | 4-CF₃—Ph | NH | H | NH | OH | H | A10 |
| 1484 | 4-CF₃—Ph | NH | H | NH | OH | H | A12 |
| 1485 | 4-CF₃—Ph | NH | H | NH | OH | H | A14 |
| 1486 | 4-CF₃—Ph | NH | H | NH | OH | H | A16 |
| 1487 | 4-CF₃—Ph | NH | H | NH | OH | A6 | A6 |
| 1488 | 4-CF₃—Ph | NH | H | NH | OH | A8 | A8 |
| 1489 | 4-CF₃—Ph | NH | H | NH | OH | A10 | A10 |
| 1490 | 4-CF₃—Ph | NH | H | NH | OA2 | A2 | A2 |
| 1491 | 4-CF₃—Ph | NH | H | NH | OA3 | A3 | A3 |
| 1492 | 4-CF₃—Ph | NH | H | NH | OA4 | A4 | A4 |
| 1493 | 4-CF₃—Ph | NH | H | NH | OC6 | H | H |

TABLE 1-continued (I-1)

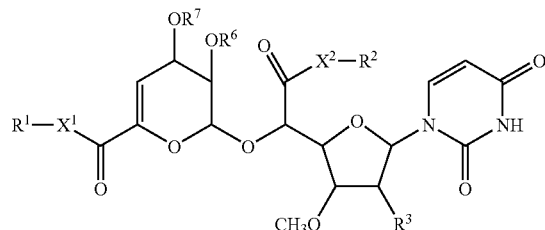

| Exemp. Comp. No. | R¹ | X¹ | R² | X² | R³ | R⁶ | R⁷ |
|---|---|---|---|---|---|---|---|
| 1494 | 4-CF₃—Ph | NH | H | NH | OC7 | H | H |
| 1495 | 4-CF₃—Ph | NH | H | NH | OC8 | H | H |
| 1496 | 4-CF₃—Ph | NH | H | NH | OC10 | H | H |
| 1497 | 4-CF₃—Ph | NH | H | NH | OC11 | H | H |
| 1498 | 4-CF₃—Ph | NH | H | NH | OC12 | H | H |
| 1499 | 4-CF₃—Ph | NH | H | NH | OC14 | H | H |
| 1500 | 4-CF₃—Ph | NH | H | NH | OC16 | H | H |
| 1501 | 4-CF₃—Ph | NH | H | NH | C6CO₃ | H | H |
| 1502 | 4-CF₃—Ph | NH | H | NH | C7CO₃ | H | H |
| 1503 | 4-CF₃—Ph | NH | H | NH | C8CO₃ | H | H |
| 1504 | 4-CF₃—Ph | NH | H | NH | C9CO₃ | H | H |
| 1505 | 4-CF₃—Ph | NH | H | NH | C10CO₃ | H | H |
| 1506 | 4-CF₃—Ph | NH | H | NH | C12CO₃ | H | H |
| 1507 | 4-CF₃—Ph | NH | H | NH | C16CO₃ | H | H |
| 1508 | 4-CF₃—Ph | NH | C8 | NH | OH | H | H |
| 1509 | 4-CF₃—Ph | NH | C9 | NH | OH | H | H |
| 1510 | 4-CF₃—Ph | NH | C10 | NH | OH | H | H |
| 1511 | 4-CF₃—Ph | NH | C12 | NH | OH | H | H |
| 1512 | 4-CF₃—Ph | NH | C16 | NH | OH | H | H |
| 1513 | 4-CF₃—Ph | NH | F1 | NH | OH | H | H |
| 1514 | 4-CF₃—Ph | NH | F2 | NH | OH | H | H |
| 1515 | 4-CF₃—Ph | NH | F3 | NH | OH | H | H |
| 1516 | 4-CF₃—Ph | NH | F4 | NH | OH | H | H |
| 1517 | 4-CF₃—Ph | NH | F5 | NH | OH | H | H |
| 1518 | 4-CF₃—Ph | NH | F6 | NH | OH | H | H |
| 1519 | 4-CF₃—Ph | NH | F7 | NH | OH | H | H |
| 1520 | 4-CF₃—Ph | NH | F8 | NH | OH | H | H |
| 1521 | 4-CF₃—Ph | NH | F9 | NH | OH | H | H |
| 1522 | 4-CF₃—Ph | NH | F10 | NH | OH | H | H |
| 1523 | 4-CF₃—Ph | NH | Ph | NH | OH | H | H |
| 1524 | 4-CF₃—Ph | NH | Bn | NH | OH | H | H |
| 1525 | 4-CF₃—Ph | NH | Pe | NH | OH | H | H |
| 1526 | 4-CF₃—Ph | NH | C12 | NMe | OH | H | H |
| 1527 | 4-CF₃—Ph | NH | C12 | NEt | OH | H | H |
| 1528 | 4-CF₃—Ph | NH | C12 | NPr | OH | H | H |
| 1529 | 4-CF₃—Ph | NH | (CH₂)₃ | N | OH | H | H |
| 1530 | 4-CF₃—Ph | NH | (CH₂)₄ | N | OH | H | H |
| 1531 | 4-CF₃—Ph | NH | (CH₂)₅ | N | OH | H | H |
| 1532 | 4-CF₃—Ph | NH | C12 | O | OH | H | H |
| 1533 | 4-CF₃—Ph | NH | Ph | O | OH | H | H |
| 1534 | 4-CF₃—Ph | NH | C12 | S | OH | H | H |
| 1535 | 4-CF₃—Ph | NH | Ph | S | OH | H | H |
| 1536 | 4-CF₃—Ph | NMe | H | NH | OH | H | H |
| 1537 | 4-CF₃—Ph | NEt | H | NH | OH | H | H |
| 1538 | 4-CF₃—Ph | NPr | H | NH | OH | H | H |
| 1539 | 4-CF₃—Ph | O | H | NH | OH | H | H |
| 1540 | 4-CF₃—Ph | S | H | NH | OH | H | H |
| 1541 | 2,4-Me₂—Ph | NH | H | NH | H | H | H |
| 1542 | 2,4-Me₂—Ph | NH | H | NH | OH | H | H |
| 1543 | 2,4-Me₂—Ph | NH | H | NH | OA6 | H | H |
| 1544 | 2,4-Me₂—Ph | NH | H | NH | OA8 | H | H |
| 1545 | 2,4-Me₂—Ph | NH | H | NH | OA9 | H | H |
| 1546 | 2,4-Me₂—Ph | NH | H | NH | OA10 | H | H |
| 1547 | 2,4-Me₂—Ph | NH | H | NH | OA12 | H | H |
| 1548 | 2,4-Me₂—Ph | NH | H | NH | OA14 | H | H |
| 1549 | 2,4-Me₂—Ph | NH | H | NH | OA16 | H | H |
| 1550 | 2,4-Me₂—Ph | NH | H | NH | OH | H | A6 |
| 1551 | 2,4-Me₂—Ph | NH | H | NH | OH | H | A8 |
| 1552 | 2,4-Me₂—Ph | NH | H | NH | OH | H | A9 |
| 1553 | 2,4-Me₂—Ph | NH | H | NH | OH | H | A10 |
| 1554 | 2,4-Me₂—Ph | NH | H | NH | OH | H | A12 |
| 1555 | 2,4-Me₂—Ph | NH | H | NH | OH | H | A14 |

TABLE 1-continued (I-1)

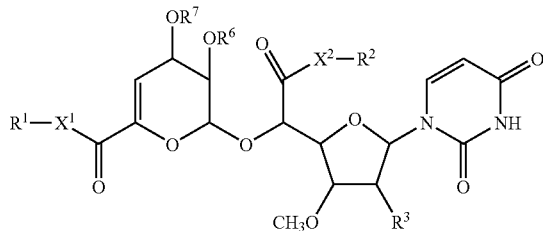

| Exemp. Comp. No. | $R^1$ | $X^1$ | $R^2$ | $X^2$ | $R^3$ | $R^6$ | $R^7$ |
|---|---|---|---|---|---|---|---|
| 1556 | 2,4-Me$_2$—Ph | NH | H | NH | OH | H | A16 |
| 1557 | 2,4-Me$_2$—Ph | NH | H | NH | OH | A6 | A6 |
| 1558 | 2,4-Me$_2$—Ph | NH | H | NH | OH | A8 | A8 |
| 1559 | 2,4-Me$_2$—Ph | NH | H | NH | OH | A10 | A10 |
| 1560 | 2,4-Me$_2$—Ph | NH | H | NH | OA2 | A2 | A2 |
| 1561 | 2,4-Me$_2$—Ph | NH | H | NH | OA3 | A3 | A3 |
| 1562 | 2,4-Me$_2$—Ph | NH | H | NH | OA4 | A4 | A4 |
| 1563 | 2,4-Me$_2$—Ph | NH | H | NH | OC6 | H | H |
| 1564 | 2,4-Me$_2$—Ph | NH | H | NH | OC7 | H | H |
| 1565 | 2,4-Me$_2$—Ph | NH | H | NH | OC8 | H | H |
| 1566 | 2,4-Me$_2$—Ph | NH | H | NH | OC10 | H | H |
| 1567 | 2,4-Me$_2$—Ph | NH | H | NH | OC11 | H | H |
| 1568 | 2,4-Me$_2$—Ph | NH | H | NH | OC12 | H | H |
| 1569 | 2,4-Me$_2$—Ph | NH | H | NH | OC14 | H | H |
| 1570 | 2,4-Me$_2$—Ph | NH | H | NH | OC16 | H | H |
| 1571 | 2,4-Me$_2$—Ph | NH | H | NH | C6CO$_3$ | H | H |
| 1572 | 2,4-Me$_2$—Ph | NH | H | NH | C7CO$_3$ | H | H |
| 1573 | 2,4-Me$_2$—Ph | NH | H | NH | C8CO$_3$ | H | H |
| 1574 | 2,4-Me$_2$—Ph | NH | H | NH | C9CO$_3$ | H | H |
| 1575 | 2,4-Me$_2$—Ph | NH | H | NH | C10CO$_3$ | H | H |
| 1576 | 2,4-Me$_2$—Ph | NH | H | NH | C12CO$_3$ | H | H |
| 1577 | 2,4-Me$_2$—Ph | NH | H | NH | C16CO$_3$ | H | H |
| 1578 | 2,4-Me$_2$—Ph | NH | C8 | NH | OH | H | H |
| 1579 | 2,4-Me$_2$—Ph | NH | C9 | NH | OH | H | H |
| 1580 | 2,4-Me$_2$—Ph | NH | C10 | NH | OH | H | H |
| 1581 | 2,4-Me$_2$—Ph | NH | C12 | NH | OH | H | H |
| 1582 | 2,4-Me$_2$—Ph | NH | C16 | NH | OH | H | H |
| 1583 | 2,4-Me$_2$—Ph | NH | F1 | NH | OH | H | H |
| 1584 | 2,4-Me$_2$—Ph | NH | F2 | NH | OH | H | H |
| 1585 | 2,4-Me$_2$—Ph | NH | F3 | NH | OH | H | H |
| 1586 | 2,4-Me$_2$—Ph | NH | F4 | NH | OH | H | H |
| 1587 | 2,4-Me$_2$—Ph | NH | F5 | NH | OH | H | H |
| 1588 | 2,4-Me$_2$—Ph | NH | F6 | NH | OH | H | H |
| 1589 | 2,4-Me$_2$—Ph | NH | F7 | NH | OH | H | H |
| 1590 | 2,4-Me$_2$—Ph | NH | F8 | NH | OH | H | H |
| 1591 | 2,4-Me$_2$—Ph | NH | F9 | NH | OH | H | H |
| 1592 | 2,4-Me$_2$—Ph | NH | F10 | NH | OH | H | H |
| 1593 | 2,4-Me$_2$—Ph | NH | Ph | NH | OH | H | H |
| 1594 | 2,4-Me$_2$—Ph | NH | Bn | NH | OH | H | H |
| 1595 | 2,4-Me$_2$—Ph | NH | Pe | NH | OH | H | H |
| 1596 | 2,4-Me$_2$—Ph | NH | C12 | NMe | OH | H | H |
| 1597 | 2,4-Me$_2$—Ph | NH | C12 | NEt | OH | H | H |
| 1598 | 2,4-Me$_2$—Ph | NH | C12 | NPr | OH | H | H |
| 1599 | 2,4-Me$_2$—Ph | NH | (CH$_2$)$_3$ | N | OH | H | H |
| 1600 | 2,4-Me$_2$—Ph | NH | (CH$_2$)$_4$ | N | OH | H | H |
| 1601 | 2,4-Me$_2$—Ph | NH | (CH$_2$)$_5$ | N | OH | H | H |
| 1602 | 2,4-Me$_2$—Ph | NH | C12 | O | OH | H | H |
| 1603 | 2,4-Me$_2$—Ph | NH | Ph | O | OH | H | H |
| 1604 | 2,4-Me$_2$—Ph | NH | C12 | S | OH | H | H |
| 1605 | 2,4-Me$_2$—Ph | NH | Ph | S | OH | H | H |
| 1606 | 2,4-Me$_2$—Ph | NMe | H | NH | OH | H | H |
| 1607 | 2,4-Me$_2$—Ph | NEt | H | NH | OH | H | H |
| 1608 | 2,4-Me$_2$—Ph | NPr | H | NH | OH | H | H |
| 1609 | 2,4-Me$_2$—Ph | O | H | NH | OH | H | H |
| 1610 | 2,4-Me$_2$—Ph | S | H | NH | OH | H | H |
| 1611 | 3,4-Me$_2$—Ph | NH | H | NH | H | H | H |
| 1612 | 3,4-Me$_2$—Ph | NH | H | NH | OH | H | H |
| 1613 | 3,4-Me$_2$—Ph | NH | H | NH | OA6 | H | H |
| 1614 | 3,4-Me$_2$—Ph | NH | H | NH | OA8 | H | H |
| 1615 | 3,4-Me$_2$—Ph | NH | H | NH | OA9 | H | H |
| 1616 | 3,4-Me$_2$—Ph | NH | H | NH | OA10 | H | H |
| 1617 | 3,4-Me$_2$—Ph | NH | H | NH | OA12 | H | H |

TABLE 1-continued

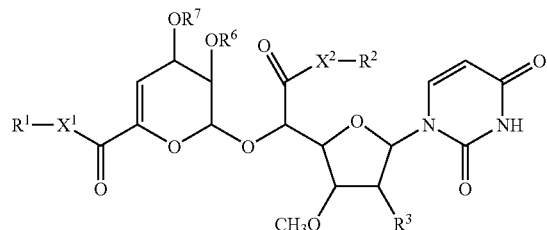

(I-1)

| Exemp. Comp. No. | R¹ | X¹ | R² | X² | R³ | R⁶ | R⁷ |
|---|---|---|---|---|---|---|---|
| 1618 | 3,4-Me₂—Ph | NH | H | NH | OA14 | H | H |
| 1619 | 3,4-Me₂—Ph | NH | H | NH | OA16 | H | H |
| 1620 | 3,4-Me₂—Ph | NH | H | NH | OH | H | A6 |
| 1621 | 3,4-Me₂—Ph | NH | H | NH | OH | H | A8 |
| 1622 | 3,4-Me₂—Ph | NH | H | NH | OH | H | A9 |
| 1623 | 3,4-Me₂—Ph | NH | H | NH | OH | H | A10 |
| 1624 | 3,4-Me₂—Ph | NH | H | NH | OH | H | A12 |
| 1625 | 3,4-Me₂—Ph | NH | H | NH | OH | H | A14 |
| 1626 | 3,4-Me₂—Ph | NH | H | NH | OH | H | A16 |
| 1627 | 3,4-Me₂—Ph | NH | H | NH | OH | A6 | A6 |
| 1628 | 3,4-Me₂—Ph | NH | H | NH | OH | A8 | A8 |
| 1629 | 3,4-Me₂—Ph | NH | H | NH | OH | A10 | A10 |
| 1630 | 3,4-Me₂—Ph | NH | H | NH | OA2 | A2 | A2 |
| 1631 | 3,4-Me₂—Ph | NH | H | NH | OA3 | A3 | A3 |
| 1632 | 3,4-Me₂—Ph | NH | H | NH | OA4 | A4 | A4 |
| 1633 | 3,4-Me₂—Ph | NH | H | NH | OC6 | H | H |
| 1634 | 3,4-Me₂—Ph | NH | H | NH | OC7 | H | H |
| 1635 | 3,4-Me₂—Ph | NH | H | NH | OC8 | H | H |
| 1636 | 3,4-Me₂—Ph | NH | H | NH | OC10 | H | H |
| 1637 | 3,4-Me₂—Ph | NH | H | NH | OC11 | H | H |
| 1638 | 3,4-Me₂—Ph | NH | H | NH | OC12 | H | H |
| 1639 | 3,4-Me₂—Ph | NH | H | NH | OC14 | H | H |
| 1640 | 3,4-Me₂—Ph | NH | H | NH | OC16 | H | H |
| 1641 | 3,4-Me₂—Ph | NH | H | NH | C6CO₃ | H | H |
| 1642 | 3,4-Me₂—Ph | NH | H | NH | C7CO₃ | H | H |
| 1643 | 3,4-Me₂—Ph | NH | H | NH | C8CO₃ | H | H |
| 1644 | 3,4-Me₂—Ph | NH | H | NH | C9CO₃ | H | H |
| 1645 | 3,4-Me₂—Ph | NH | H | NH | C10CO₃ | H | H |
| 1646 | 3,4-Me₂—Ph | NH | H | NH | C12CO₃ | H | H |
| 1647 | 3,4-Me₂—Ph | NH | H | NH | C16CO₃ | H | H |
| 1648 | 3,4-Me₂—Ph | NH | C8 | NH | OH | H | H |
| 1649 | 3,4-Me₂—Ph | NH | C9 | NH | OH | H | H |
| 1650 | 3,4-Me₂—Ph | NH | C10 | NH | OH | H | H |
| 1651 | 3,4-Me₂—Ph | NH | C12 | NH | OH | H | H |
| 1652 | 3,4-Me₂—Ph | NH | C16 | NH | OH | H | H |
| 1653 | 3,4-Me₂—Ph | NH | F1 | NH | OH | H | H |
| 1654 | 3,4-Me₂—Ph | NH | F2 | NH | OH | H | H |
| 1655 | 3,4-Me₂—Ph | NH | F3 | NH | OH | H | H |
| 1656 | 3,4-Me₂—Ph | NH | F4 | NH | OH | H | H |
| 1657 | 3,4-Me₂—Ph | NH | F5 | NH | OH | H | H |
| 1658 | 3,4-Me₂—Ph | NH | F6 | NH | OH | H | H |
| 1659 | 3,4-Me₂—Ph | NH | F7 | NH | OH | H | H |
| 1660 | 3,4-Me₂—Ph | NH | F8 | NH | OH | H | H |
| 1661 | 3,4-Me₂—Ph | NH | F9 | NH | OH | H | H |
| 1662 | 3,4-Me₂—Ph | NH | F10 | NH | OH | H | H |
| 1663 | 3,4-Me₂—Ph | NH | Ph | NH | OH | H | H |
| 1664 | 3,4-Me₂—Ph | NH | Bn | NH | OH | H | H |
| 1665 | 3,4-Me₂—Ph | NH | Pe | NH | OH | H | H |
| 1666 | 3,4-Me₂—Ph | NH | C12 | NMe | OH | H | H |
| 1667 | 3,4-Me₂—Ph | NH | C12 | NEt | OH | H | H |
| 1668 | 3,4-Me₂—Ph | NH | C12 | NPr | OH | H | H |
| 1669 | 3,4-Me₂—Ph | NH | (CH₂)₃ | N | OH | H | H |
| 1670 | 3,4-Me₂—Ph | NH | (CH₂)₄ | N | OH | H | H |
| 1671 | 3,4-Me₂—Ph | NH | (CH₂)₅ | N | OH | H | H |
| 1672 | 3,4-Me₂—Ph | NH | C12 | O | OH | H | H |
| 1673 | 3,4-Me₂—Ph | NH | Ph | O | OH | H | H |
| 1674 | 3,4-Me₂—Ph | NH | C12 | S | OH | H | H |
| 1675 | 3,4-Me₂—Ph | NH | Ph | S | OH | H | H |
| 1676 | 3,4-Me₂—Ph | NMe | H | NH | OH | H | H |
| 1677 | 3,4-Me₂—Ph | NEt | H | NH | OH | H | H |
| 1678 | 3,4-Me₂—Ph | NPr | H | NH | OH | H | H |
| 1679 | 3,4-Me₂—Ph | O | H | NH | OH | H | H |

TABLE 1-continued

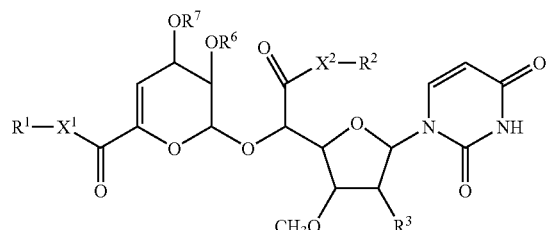

(I-1)

| Exemp. Comp. No. | $R^1$ | $X^1$ | $R^2$ | $X^2$ | $R^3$ | $R^6$ | $R^7$ |
|---|---|---|---|---|---|---|---|
| 1680 | 3,4-Me$_2$—Ph | S | H | NH | OH | H | H |
| 1681 | 3,5-Me$_2$—Ph | NH | H | NH | H | H | H |
| 1682 | 3,5-Me$_2$—Ph | NH | H | NH | OH | H | H |
| 1683 | 3,5-Me$_2$—Ph | NH | H | NH | OA6 | H | H |
| 1684 | 3,5-Me$_2$—Ph | NH | H | NH | OA8 | H | H |
| 1685 | 3,5-Me$_2$—Ph | NH | H | NH | OA9 | H | H |
| 1686 | 3,5-Me$_2$—Ph | NH | H | NH | OA10 | H | H |
| 1687 | 3,5-Me$_2$—Ph | NH | H | NH | OA12 | H | H |
| 1688 | 3,5-Me$_2$—Ph | NH | H | NH | OA14 | H | H |
| 1689 | 3,5-Me$_2$—Ph | NH | H | NH | OA16 | H | H |
| 1690 | 3,5-Me$_2$—Ph | NH | H | NH | OH | H | A6 |
| 1691 | 3,5-Me$_2$—Ph | NH | H | NH | OH | H | A8 |
| 1692 | 3,5-Me$_2$—Ph | NH | H | NH | OH | H | A9 |
| 1693 | 3,5-Me$_2$—Ph | NH | H | NH | OH | H | A10 |
| 1694 | 3,5-Me$_2$—Ph | NH | H | NH | OH | H | A12 |
| 1695 | 3,5-Me$_2$—Ph | NH | H | NH | OH | H | A14 |
| 1696 | 3,5-Me$_2$—Ph | NH | H | NH | OH | H | A16 |
| 1697 | 3,5-Me$_2$—Ph | NH | H | NH | OH | A6 | A6 |
| 1698 | 3,5-Me$_2$—Ph | NH | H | NH | OH | A8 | A8 |
| 1699 | 3,5-Me$_2$—Ph | NH | H | NH | OH | A10 | A10 |
| 1700 | 3,5-Me$_2$—Ph | NH | H | NH | OA2 | A2 | A2 |
| 1701 | 3,5-Me$_2$—Ph | NH | H | NH | OA3 | A3 | A3 |
| 1702 | 3,5-Me$_2$—Ph | NH | H | NH | OA4 | A4 | A4 |
| 1703 | 3,5-Me$_2$—Ph | NH | H | NH | OC6 | H | H |
| 1704 | 3,5-Me$_2$—Ph | NH | H | NH | OC7 | H | H |
| 1705 | 3,5-Me$_2$—Ph | NH | H | NH | OC8 | H | H |
| 1706 | 3,5-Me$_2$—Ph | NH | H | NH | OC10 | H | H |
| 1707 | 3,5-Me$_2$—Ph | NH | H | NH | OC11 | H | H |
| 1708 | 3,5-Me$_2$—Ph | NH | H | NH | OC12 | H | H |
| 1709 | 3,5-Me$_2$—Ph | NH | H | NH | OC14 | H | H |
| 1710 | 3,5-Me$_2$—Ph | NH | H | NH | OC16 | H | H |
| 1711 | 3,5-Me$_2$—Ph | NH | H | NH | C6CO$_3$ | H | H |
| 1712 | 3,5-Me$_2$—Ph | NH | H | NH | C7CO$_3$ | H | H |
| 1713 | 3,5-Me$_2$—Ph | NH | H | NH | C8CO$_3$ | H | H |
| 1714 | 3,5-Me$_2$—Ph | NH | H | NH | C9CO$_3$ | H | H |
| 1715 | 3,5-Me$_2$—Ph | NH | H | NH | C10CO$_3$ | H | H |
| 1716 | 3,5-Me$_2$—Ph | NH | H | NH | C12CO$_3$ | H | H |
| 1717 | 3,5-Me$_2$—Ph | NH | H | NH | C16CO$_3$ | H | H |
| 1718 | 3,5-Me$_2$—Ph | NH | C8 | NH | OH | H | H |
| 1719 | 3,5-Me$_2$—Ph | NH | C9 | NH | OH | H | H |
| 1720 | 3,5-Me$_2$—Ph | NH | C10 | NH | OH | H | H |
| 1721 | 3,5-Me$_2$—Ph | NH | C12 | NH | OH | H | H |
| 1722 | 3,5-Me$_2$—Ph | NH | C16 | NH | OH | H | H |
| 1723 | 3,5-Me$_2$—Ph | NH | F1 | NH | OH | H | H |
| 1724 | 3,5-Me$_2$—Ph | NH | F2 | NH | OH | H | H |
| 1725 | 3,5-Me$_2$—Ph | NH | F3 | NH | OH | H | H |
| 1726 | 3,5-Me$_2$—Ph | NH | F4 | NH | OH | H | H |
| 1727 | 3,5-Me$_2$—Ph | NH | F5 | NH | OH | H | H |
| 1728 | 3,5-Me$_2$—Ph | NH | F6 | NH | OH | H | H |
| 1729 | 3,5-Me$_2$—Ph | NH | F7 | NH | OH | H | H |
| 1730 | 3,5-Me$_2$—Ph | NH | F8 | NH | OH | H | H |
| 1731 | 3,5-Me$_2$—Ph | NH | F9 | NH | OH | H | H |
| 1732 | 3,5-Me$_2$—Ph | NH | F10 | NH | OH | H | H |
| 1733 | 3,5-Me$_2$—Ph | NH | Ph | NH | OH | H | H |
| 1734 | 3,5-Me$_2$—Ph | NH | Bn | NH | OH | H | H |
| 1735 | 3,5-Me$_2$—Ph | NH | Pe | NH | OH | H | H |
| 1736 | 3,5-Me$_2$—Ph | NH | C12 | NMe | OH | H | H |
| 1737 | 3,5-Me$_2$—Ph | NH | C12 | NEt | OH | H | H |
| 1738 | 3,5-Me$_2$—Ph | NH | C12 | NPr | OH | H | H |
| 1739 | 3,5-Me$_2$—Ph | NH | (CH$_2$)$_3$ | N | OH | H | H |
| 1740 | 3,5-Me$_2$—Ph | NH | (CH$_2$)$_4$ | N | OH | H | H |
| 1741 | 3,5-Me$_2$—Ph | NH | (CH$_2$)$_5$ | N | OH | H | H |

TABLE 1-continued (I-1)

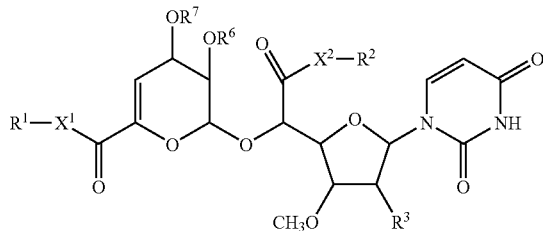

| Exemp. Comp. No. | $R^1$ | $X^1$ | $R^2$ | $X^2$ | $R^3$ | $R^6$ | $R^7$ |
|---|---|---|---|---|---|---|---|
| 1742 | 3,5-Me$_2$—Ph | NH | C12 | O | OH | H | H |
| 1743 | 3,5-Me$_2$—Ph | NH | Ph | O | OH | H | H |
| 1744 | 3,5-Me$_2$—Ph | NH | C12 | S | OH | H | H |
| 1745 | 3,5-Me$_2$—Ph | NH | Ph | S | OH | H | H |
| 1746 | 3,5-Me$_2$—Ph | NMe | H | NH | OH | H | H |
| 1747 | 3,5-Me$_2$—Ph | NEt | H | NH | OH | H | H |
| 1748 | 3,5-Me$_2$—Ph | NPr | H | NH | OH | H | H |
| 1749 | 2,4,6-Me$_3$—Ph | O | H | NH | OH | H | H |
| 1750 | 2,4,6-Me$_3$—Ph | S | H | NH | OH | H | H |
| 1751 | 2,4,6-Me$_3$—Ph | NH | H | NH | H | H | H |
| 1752 | 2,4,6-Me$_3$—Ph | NH | H | NH | OH | H | H |
| 1753 | 2,4,6-Me$_3$—Ph | NH | H | NH | OA6 | H | H |
| 1754 | 2,4,6-Me$_3$—Ph | NH | H | NH | OA8 | H | H |
| 1755 | 2,4,6-Me$_3$—Ph | NH | H | NH | OA9 | H | H |
| 1756 | 2,4,6-Me$_3$—Ph | NH | H | NH | OA10 | H | H |
| 1757 | 2,4,6-Me$_3$—Ph | NH | H | NH | OA12 | H | H |
| 1758 | 2,4,6-Me$_3$—Ph | NH | H | NH | OA14 | H | H |
| 1759 | 2,4,6-Me$_3$—Ph | NH | H | NH | OA16 | H | H |
| 1760 | 2,4,6-Me$_3$—Ph | NH | H | NH | OH | H | A6 |
| 1761 | 2,4,6-Me$_3$—Ph | NH | H | NH | OH | H | A8 |
| 1762 | 2,4,6-Me$_3$—Ph | NH | H | NH | OH | H | A9 |
| 1763 | 2,4,6-Me$_3$—Ph | NH | H | NH | OH | H | A10 |
| 1764 | 2,4,6-Me$_3$—Ph | NH | H | NH | OH | H | A12 |
| 1765 | 2,4,6-Me$_3$—Ph | NH | H | NH | OH | H | A14 |
| 1766 | 2,4,6-Me$_3$—Ph | NH | H | NH | OH | H | A16 |
| 1767 | 2,4,6-Me$_3$—Ph | NH | H | NH | OH | A6 | A6 |
| 1768 | 2,4,6-Me$_3$—Ph | NH | H | NH | OH | A8 | A8 |
| 1769 | 2,4,6-Me$_3$—Ph | NH | H | NH | OH | A10 | A10 |
| 1770 | 2,4,6-Me$_3$—Ph | NH | H | NH | OA2 | A2 | A2 |
| 1771 | 2,4,6-Me$_3$—Ph | NH | H | NH | OA3 | A3 | A3 |
| 1772 | 2,4,6-Me$_3$—Ph | NH | H | NH | OA4 | A4 | A4 |
| 1773 | 2,4,6-Me$_3$—Ph | NH | H | NH | OC6 | H | H |
| 1774 | 2,4,6-Me$_3$—Ph | NH | H | NH | OC7 | H | H |
| 1775 | 2,4,6-Me$_3$—Ph | NH | H | NH | OC8 | H | H |
| 1776 | 2,4,6-Me$_3$—Ph | NH | H | NH | OC10 | H | H |
| 1777 | 2,4,6-Me$_3$—Ph | NH | H | NH | OC11 | H | H |
| 1778 | 2,4,6-Me$_3$—Ph | NH | H | NH | OC12 | H | H |
| 1779 | 2,4,6-Me$_3$—Ph | NH | H | NH | OC14 | H | H |
| 1780 | 2,4,6-Me$_3$—Ph | NH | H | NH | OC16 | H | H |
| 1781 | 2,4,6-Me$_3$—Ph | NH | H | NH | C6CO$_3$ | H | H |
| 1782 | 2,4,6-Me$_3$—Ph | NH | H | NH | C7CO$_3$ | H | H |
| 1783 | 2,4,6-Me$_3$—Ph | NH | H | NH | C8CO$_3$ | H | H |
| 1784 | 2,4,6-Me$_3$—Ph | NH | H | NH | C9CO$_3$ | H | H |
| 1785 | 2,4,6-Me$_3$—Ph | NH | H | NH | C10CO$_3$ | H | H |
| 1786 | 2,4,6-Me$_3$—Ph | NH | H | NH | C12CO$_3$ | H | H |
| 1787 | 2,4,6-Me$_3$—Ph | NH | H | NH | C16CO$_3$ | H | H |
| 1788 | 2,4,6-Me$_3$—Ph | NH | C8 | NH | OH | H | H |
| 1789 | 2,4,6-Me$_3$—Ph | NH | C9 | NH | OH | H | H |
| 1790 | 2,4,6-Me$_3$—Ph | NH | C10 | NH | OH | H | H |
| 1791 | 2,4,6-Me$_3$—Ph | NH | C12 | NH | OH | H | H |
| 1792 | 2,4,6-Me$_3$—Ph | NH | C16 | NH | OH | H | H |
| 1793 | 2,4,6-Me$_3$—Ph | NH | F1 | NH | OH | H | H |
| 1794 | 2,4,6-Me$_3$—Ph | NH | F2 | NH | OH | H | H |
| 1795 | 2,4,6-Me$_3$—Ph | NH | F3 | NH | OH | H | H |
| 1796 | 2,4,6-Me$_3$—Ph | NH | F4 | NH | OH | H | H |
| 1797 | 2,4,6-Me$_3$—Ph | NH | F5 | NH | OH | H | H |
| 1798 | 2,4,6-Me$_3$—Ph | NH | F6 | NH | OH | H | H |
| 1799 | 2,4,6-Me$_3$—Ph | NH | F7 | NH | OH | H | H |
| 1800 | 2,4,6-Me$_3$—Ph | NH | F8 | NH | OH | H | H |
| 1801 | 2,4,6-Me$_3$—Ph | NH | F9 | NH | OH | H | H |
| 1802 | 2,4,6-Me$_3$—Ph | NH | F10 | NH | OH | H | H |
| 1803 | 2,4,6-Me$_3$—Ph | NH | Ph | NH | OH | H | H |

TABLE 1-continued

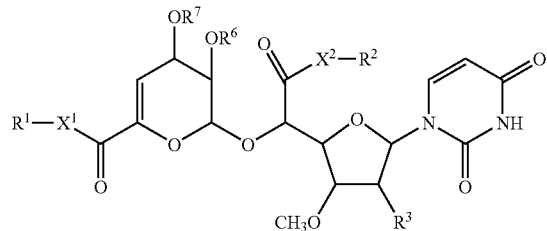

(I-1)

| Exemp. Comp. No. | R¹ | X¹ | R² | X² | R³ | R⁶ | R⁷ |
|---|---|---|---|---|---|---|---|
| 1804 | 2,4,6-Me₃—Ph | NH | Bn | NH | OH | H | H |
| 1805 | 2,4,6-Me₃—Ph | NH | Pe | NH | OH | H | H |
| 1806 | 2,4,6-Me₃—Ph | NH | C12 | NMe | OH | H | H |
| 1807 | 2,4,6-Me₃—Ph | NH | C12 | NEt | OH | H | H |
| 1808 | 2,4,6-Me₃—Ph | NH | C12 | NPr | OH | H | H |
| 1809 | 2,4,6-Me₃—Ph | NH | (CH₂)₃ | N | OH | H | H |
| 1810 | 2,4,6-Me₃—Ph | NH | (CH₂)₄ | N | OH | H | H |
| 1811 | 2,4,6-Me₃—Ph | NH | (CH₂)₅ | N | OH | H | H |
| 1812 | 2,4,6-Me₃—Ph | NH | C12 | O | OH | H | H |
| 1813 | 2,4,6-Me₃—Ph | NH | Ph | O | OH | H | H |
| 1814 | 2,4,6-Me₃—Ph | NH | C12 | S | OH | H | H |
| 1815 | 2,4,6-Me₃—Ph | NH | Ph | S | OH | H | H |
| 1816 | 2,4,6-Me₃—Ph | NMe | H | NH | OH | H | H |
| 1817 | 2,4,6-Me₃—Ph | NEt | H | NH | OH | H | H |
| 1818 | 2,4,6-Me₃—Ph | NPr | H | NH | OH | H | H |
| 1819 | 2,4,6-Me₃—Ph | O | H | NH | OH | H | H |
| 1820 | 2,4,6-Me₃—Ph | S | H | NH | OH | H | H |
| 1821 | 2-MeO—Ph | NH | H | NH | H | H | H |
| 1822 | 2-MeO—Ph | NH | H | NH | OH | H | H |
| 1823 | 2-MeO—Ph | NH | H | NH | OA6 | H | H |
| 1824 | 2-MeO—Ph | NH | H | NH | OA8 | H | H |
| 1825 | 2-MeO—Ph | NH | H | NH | OA9 | H | H |
| 1826 | 2-MeO—Ph | NH | H | NH | OA10 | H | H |
| 1827 | 2-MeO—Ph | NH | H | NH | OA12 | H | H |
| 1828 | 2-MeO—Ph | NH | H | NH | OA14 | H | H |
| 1829 | 2-MeO—Ph | NH | H | NH | OA16 | H | H |
| 1830 | 2-MeO—Ph | NH | H | NH | OH | H | A6 |
| 1831 | 2-MeO—Ph | NH | H | NH | OH | H | A8 |
| 1832 | 2-MeO—Ph | NH | H | NH | OH | H | A9 |
| 1833 | 2-MeO—Ph | NH | H | NH | OH | H | A10 |
| 1834 | 2-MeO—Ph | NH | H | NH | OH | H | A12 |
| 1835 | 2-MeO—Ph | NH | H | NH | OH | H | A14 |
| 1836 | 2-MeO—Ph | NH | H | NH | OH | H | A16 |
| 1837 | 2-MeO—Ph | NH | H | NH | OH | A6 | A6 |
| 1838 | 2-MeO—Ph | NH | H | NH | OH | A8 | A8 |
| 1839 | 2-MeO—Ph | NH | H | NH | OH | A10 | A10 |
| 1840 | 2-MeO—Ph | NH | H | NH | OA2 | A2 | A2 |
| 1841 | 2-MeO—Ph | NH | H | NH | OA3 | A3 | A3 |
| 1842 | 2-MeO—Ph | NH | H | NH | OA4 | A4 | A4 |
| 1843 | 2-MeO—Ph | NH | H | NH | OC6 | H | H |
| 1844 | 2-MeO—Ph | NH | H | NH | OC7 | H | H |
| 1845 | 2-MeO—Ph | NH | H | NH | OC8 | H | H |
| 1846 | 2-MeO—Ph | NH | H | NH | OC10 | H | H |
| 1847 | 2-MeO—Ph | NH | H | NH | OC11 | H | H |
| 1848 | 2-MeO—Ph | NH | H | NH | OC12 | H | H |
| 1849 | 2-MeO—Ph | NH | H | NH | OC14 | H | H |
| 1850 | 2-MeO—Ph | NH | H | NH | OC16 | H | H |
| 1851 | 2-MeO—Ph | NH | H | NH | C6CO₃ | H | H |
| 1852 | 2-MeO—Ph | NH | H | NH | C7CO₃ | H | H |
| 1853 | 2-MeO—Ph | NH | H | NH | C8CO₃ | H | H |
| 1854 | 2-MeO—Ph | NH | H | NH | C9CO₃ | H | H |
| 1855 | 2-MeO—Ph | NH | H | NH | C10CO₃ | H | H |
| 1856 | 2-MeO—Ph | NH | H | NH | C12CO₃ | H | H |
| 1857 | 2-MeO—Ph | NH | H | NH | C16CO₃ | H | H |
| 1858 | 2-MeO—Ph | NH | C8 | NH | OH | H | H |
| 1859 | 2-MeO—Ph | NH | C9 | NH | OH | H | H |
| 1860 | 2-MeO—Ph | NH | C10 | NH | OH | H | H |
| 1861 | 2-MeO—Ph | NH | C12 | NH | OH | H | H |
| 1862 | 2-MeO—Ph | NH | C16 | NH | OH | H | H |
| 1863 | 2-MeO—Ph | NH | F1 | NH | OH | H | H |
| 1864 | 2-MeO—Ph | NH | F2 | NH | OH | H | H |
| 1865 | 2-MeO—Ph | NH | F3 | NH | OH | H | H |

TABLE 1-continued

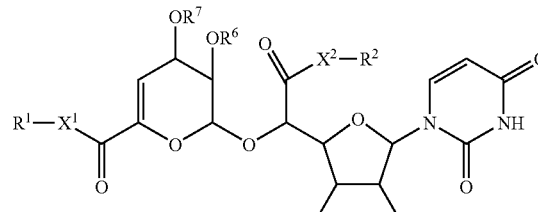

(I-1)

| Exemp. Comp. No. | R¹ | X¹ | R² | X² | R³ | R⁶ | R⁷ |
|---|---|---|---|---|---|---|---|
| 1866 | 2-MeO—Ph | NH | F4 | NH | OH | H | H |
| 1867 | 2-MeO—Ph | NH | F5 | NH | OH | H | H |
| 1868 | 2-MeO—Ph | NH | F6 | NH | OH | H | H |
| 1869 | 2-MeO—Ph | NH | F7 | NH | OH | H | H |
| 1870 | 2-MeO—Ph | NH | F8 | NH | OH | H | H |
| 1871 | 2-MeO—Ph | NH | F9 | NH | OH | H | H |
| 1872 | 2-MeO—Ph | NH | F10 | NH | OH | H | H |
| 1873 | 2-MeO—Ph | NH | Ph | NH | OH | H | H |
| 1874 | 2-MeO—Ph | NH | Bn | NH | OH | H | H |
| 1875 | 2-MeO—Ph | NH | Pe | NH | OH | H | H |
| 1876 | 2-MeO—Ph | NH | C12 | NMe | OH | H | H |
| 1877 | 2-MeO—Ph | NH | C12 | NEt | OH | H | H |
| 1878 | 2-MeO—Ph | NH | C12 | NPr | OH | H | H |
| 1879 | 2-MeO—Ph | NH | (CH$_2$)$_3$ | N | OH | H | H |
| 1880 | 2-MeO—Ph | NH | (CH$_2$)$_4$ | N | OH | H | H |
| 1881 | 2-MeO—Ph | NH | (CH$_2$)$_5$ | N | OH | H | H |
| 1882 | 2-MeO—Ph | NH | C12 | O | OH | H | H |
| 1883 | 2-MeO—Ph | NH | Ph | O | OH | H | H |
| 1884 | 2-MeO—Ph | NH | C12 | S | OH | H | H |
| 1885 | 2-MeO—Ph | NH | Ph | S | OH | H | H |
| 1886 | 2-MeO—Ph | NMe | H | NH | OH | H | H |
| 1887 | 2-MeO—Ph | NEt | H | NH | OH | H | H |
| 1888 | 2-MeO—Ph | NPr | H | NH | OH | H | H |
| 1889 | 2-MeO—Ph | O | H | NH | OH | H | H |
| 1890 | 2-MeO—Ph | S | H | NH | OH | H | H |
| 1891 | 2-EtO—Ph | NH | H | NH | H | H | H |
| 1892 | 2-EtO—Ph | NH | H | NH | OH | H | H |
| 1893 | 2-EtO—Ph | NH | H | NH | OA6 | H | H |
| 1894 | 2-EtO—Ph | NH | H | NH | OA8 | H | H |
| 1895 | 2-EtO—Ph | NH | H | NH | OA9 | H | H |
| 1896 | 2-EtO—Ph | NH | H | NH | OA10 | H | H |
| 1897 | 2-EtO—Ph | NH | H | NH | OA12 | H | H |
| 1898 | 2-EtO—Ph | NH | H | NH | OA14 | H | H |
| 1899 | 2-EtO—Ph | NH | H | NH | OA16 | H | H |
| 1900 | 2-EtO—Ph | NH | H | NH | OH | H | A6 |
| 1901 | 2-EtO—Ph | NH | H | NH | OH | H | A8 |
| 1902 | 2-EtO—Ph | NH | H | NH | OH | H | A9 |
| 1903 | 2-EtO—Ph | NH | H | NH | OH | H | A10 |
| 1904 | 2-EtO—Ph | NH | H | NH | OH | H | A12 |
| 1905 | 2-EtO—Ph | NH | H | NH | OH | H | A14 |
| 1906 | 2-EtO—Ph | NH | H | NH | OH | H | A16 |
| 1907 | 2-EtO—Ph | NH | H | NH | OH | A6 | A6 |
| 1908 | 2-EtO—Ph | NH | H | NH | OH | A8 | A8 |
| 1909 | 2-EtO—Ph | NH | H | NH | OH | A10 | A10 |
| 1910 | 2-EtO—Ph | NH | H | NH | OA2 | A2 | A2 |
| 1911 | 2-EtO—Ph | NH | H | NH | OA3 | A3 | A3 |
| 1912 | 2-EtO—Ph | NH | H | NH | OA4 | A4 | A4 |
| 1913 | 2-EtO—Ph | NH | H | NH | OC6 | H | H |
| 1914 | 2-EtO—Ph | NH | H | NH | OC7 | H | H |
| 1915 | 2-EtO—Ph | NH | H | NH | OC8 | H | H |
| 1916 | 2-EtO—Ph | NH | H | NH | OC10 | H | H |
| 1917 | 2-EtO—Ph | NH | H | NH | OC11 | H | H |
| 1918 | 2-EtO—Ph | NH | H | NH | OC12 | H | H |
| 1919 | 2-EtO—Ph | NH | H | NH | OC14 | H | H |
| 1920 | 2-EtO—Ph | NH | H | NH | OC16 | H | H |
| 1921 | 2-EtO—Ph | NH | H | NH | C6CO$_3$ | H | H |
| 1922 | 2-EtO—Ph | NH | H | NH | C7CO$_3$ | H | H |
| 1923 | 2-EtO—Ph | NH | H | NH | C8CO$_3$ | H | H |
| 1924 | 2-EtO—Ph | NH | H | NH | C9CO$_3$ | H | H |
| 1925 | 2-EtO—Ph | NH | H | NH | C10CO$_3$ | H | H |
| 1926 | 2-EtO—Ph | NH | H | NH | C12CO$_3$ | H | H |
| 1927 | 2-EtO—Ph | NH | H | NH | C16CO$_3$ | H | H |

TABLE 1-continued

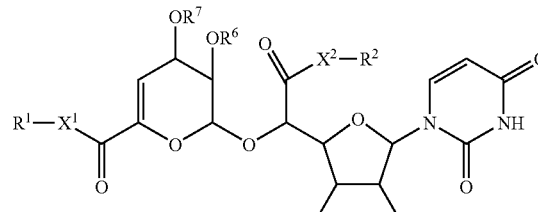

(I-1)

| Exemp. Comp. No. | $R^1$ | $X^1$ | $R^2$ | $X^2$ | $R^3$ | $R^6$ | $R^7$ |
|---|---|---|---|---|---|---|---|
| 1928 | 2-EtO—Ph | NH | C8 | NH | OH | H | H |
| 1929 | 2-EtO—Ph | NH | C9 | NH | OH | H | H |
| 1930 | 2-EtO—Ph | NH | C10 | NH | OH | H | H |
| 1931 | 2-EtO—Ph | NH | C12 | NH | OH | H | H |
| 1932 | 2-EtO—Ph | NH | C16 | NH | OH | H | H |
| 1933 | 2-EtO—Ph | NH | F1 | NH | OH | H | H |
| 1934 | 2-EtO—Ph | NH | F2 | NH | OH | H | H |
| 1935 | 2-EtO—Ph | NH | F3 | NH | OH | H | H |
| 1936 | 2-EtO—Ph | NH | F4 | NH | OH | H | H |
| 1937 | 2-EtO—Ph | NH | F5 | NH | OH | H | H |
| 1938 | 2-EtO—Ph | NH | F6 | NH | OH | H | H |
| 1939 | 2-EtO—Ph | NH | F7 | NH | OH | H | H |
| 1940 | 2-EtO—Ph | NH | F8 | NH | OH | H | H |
| 1941 | 2-EtO—Ph | NH | F9 | NH | OH | H | H |
| 1942 | 2-EtO—Ph | NH | F10 | NH | OH | H | H |
| 1943 | 2-EtO—Ph | NH | Ph | NH | OH | H | H |
| 1944 | 2-EtO—Ph | NH | Bn | NH | OH | H | H |
| 1945 | 2-EtO—Ph | NH | Pe | NH | OH | H | H |
| 1946 | 2-EtO—Ph | NH | C12 | NMe | OH | H | H |
| 1947 | 2-EtO—Ph | NH | C12 | NEt | OH | H | H |
| 1948 | 2-EtO—Ph | NH | C12 | NPr | OH | H | H |
| 1949 | 2-EtO—Ph | NH | $(CH_2)_3$ | N | OH | H | H |
| 1950 | 2-EtO—Ph | NH | $(CH_2)_4$ | N | OH | H | H |
| 1951 | 2-EtO—Ph | NH | $(CH_2)_5$ | N | OH | H | H |
| 1952 | 2-EtO—Ph | NH | C12 | O | OH | H | H |
| 1953 | 2-EtO—Ph | NH | Ph | O | OH | H | H |
| 1954 | 2-EtO—Ph | NH | C12 | S | OH | H | H |
| 1955 | 2-EtO—Ph | NH | Ph | S | OH | H | H |
| 1956 | 2-EtO—Ph | NMe | H | NH | OH | H | H |
| 1957 | 2-EtO—Ph | NEt | H | NH | OH | H | H |
| 1958 | 2-EtO—Ph | NPr | H | NH | OH | H | H |
| 1959 | 2-EtO—Ph | O | H | NH | OH | H | H |
| 1960 | 2-EtO—Ph | S | H | NH | OH | H | H |
| 1961 | 3-EtO—Ph | NH | H | NH | H | H | H |
| 1962 | 3-EtO—Ph | NH | H | NH | OH | H | H |
| 1963 | 3-EtO—Ph | NH | H | NH | OA6 | H | H |
| 1964 | 3-EtO—Ph | NH | H | NH | OA8 | H | H |
| 1965 | 3-EtO—Ph | NH | H | NH | OA9 | H | H |
| 1966 | 3-EtO—Ph | NH | H | NH | OA10 | H | H |
| 1967 | 3-EtO—Ph | NH | H | NH | OA12 | H | H |
| 1968 | 3-EtO—Ph | NH | H | NH | OA14 | H | H |
| 1969 | 3-EtO—Ph | NH | H | NH | OA16 | H | H |
| 1970 | 3-EtO—Ph | NH | H | NH | OH | H | A6 |
| 1971 | 3-EtO—Ph | NH | H | NH | OH | H | A8 |
| 1972 | 3-EtO—Ph | NH | H | NH | OH | H | A9 |
| 1973 | 3-EtO—Ph | NH | H | NH | OH | H | A10 |
| 1974 | 3-EtO—Ph | NH | H | NH | OH | H | A12 |
| 1975 | 3-EtO—Ph | NH | H | NH | OH | H | A14 |
| 1976 | 3-EtO—Ph | NH | H | NH | OH | H | A16 |
| 1977 | 3-EtO—Ph | NH | H | NH | OH | A6 | A6 |
| 1978 | 3-EtO—Ph | NH | H | NH | OH | A8 | A8 |
| 1979 | 3-EtO—Ph | NH | H | NH | OH | A10 | A10 |
| 1980 | 3-EtO—Ph | NH | H | NH | OA2 | A2 | A2 |
| 1981 | 3-EtO—Ph | NH | H | NH | AO3 | A3 | A3 |
| 1982 | 3-EtO—Ph | NH | H | NH | OA4 | A4 | A4 |
| 1983 | 3-EtO—Ph | NH | H | NH | OC6 | H | H |
| 1984 | 3-EtO—Ph | NH | H | NH | OC7 | H | H |
| 1985 | 3-EtO—Ph | NH | H | NH | OC8 | H | H |
| 1986 | 3-EtO—Ph | NH | H | NH | OC10 | H | H |
| 1987 | 3-EtO—Ph | NH | H | NH | OC11 | H | H |
| 1988 | 3-EtO—Ph | NH | H | NH | OC12 | H | H |
| 1989 | 3-EtO—Ph | NH | H | NH | OC14 | H | H |

TABLE 1-continued

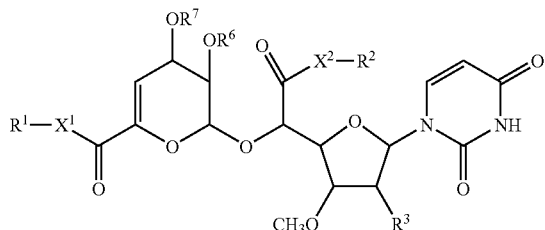

(I-1)

| Exemp. Comp. No. | R$^1$ | X$^1$ | R$^2$ | X$^2$ | R$^3$ | R$^6$ | R$^7$ |
|---|---|---|---|---|---|---|---|
| 1990 | 3-EtO—Ph | NH | H | NH | OC16 | H | H |
| 1991 | 3-EtO—Ph | NH | H | NH | C6CO$_3$ | H | H |
| 1992 | 3-EtO—Ph | NH | H | NH | C7CO$_3$ | H | H |
| 1993 | 3-EtO—Ph | NH | H | NH | C8CO$_3$ | H | H |
| 1994 | 3-EtO—Ph | NH | H | NH | C9CO$_3$ | H | H |
| 1995 | 3-EtO—Ph | NH | H | NH | C10CO$_3$ | H | H |
| 1996 | 3-EtO—Ph | NH | H | NH | C12CO$_3$ | H | H |
| 1997 | 3-EtO—Ph | NH | H | NH | C16CO$_3$ | H | H |
| 1998 | 3-EtO—Ph | NH | C8 | NH | OH | H | H |
| 1999 | 3-EtO—Ph | NH | C9 | NH | OH | H | H |
| 2000 | 3-EtO—Ph | NH | C10 | NH | OH | H | H |
| 2001 | 3-EtO—Ph | NH | C12 | NH | OH | H | H |
| 2002 | 3-EtO—Ph | NH | C16 | NH | OH | H | H |
| 2003 | 3-EtO—Ph | NH | F1 | NH | OH | H | H |
| 2004 | 3-EtO—Ph | NH | F2 | NH | OH | H | H |
| 2005 | 3-EtO—Ph | NH | F3 | NH | OH | H | H |
| 2006 | 3-EtO—Ph | NH | F4 | NH | OH | H | H |
| 2007 | 3-EtO—Ph | NH | F5 | NH | OH | H | H |
| 2008 | 3-EtO—Ph | NH | F6 | NH | OH | H | H |
| 2009 | 3-EtO—Ph | NH | F7 | NH | OH | H | H |
| 2010 | 3-EtO—Ph | NH | F8 | NH | OH | H | H |
| 2011 | 3-EtO—Ph | NH | F9 | NH | OH | H | H |
| 2012 | 3-EtO—Ph | NH | F10 | NH | OH | H | H |
| 2013 | 3-EtO—Ph | NH | Ph | NH | OH | H | H |
| 2014 | 3-EtO—Ph | NH | Bn | NH | OH | H | H |
| 2015 | 3-EtO—Ph | NH | Pe | NH | OH | H | H |
| 2016 | 3-EtO—Ph | NH | C12 | NMe | OH | H | H |
| 2017 | 3-EtO—Ph | NH | C12 | NEt | OH | H | H |
| 2018 | 3-EtO—Ph | NH | C12 | NPr | OH | H | H |
| 2019 | 3-EtO—Ph | NH | (CH$_2$)$_3$ | N | OH | H | H |
| 2020 | 3-EtO—Ph | NH | (CH$_2$)$_4$ | N | OH | H | H |
| 2021 | 3-EtO—Ph | NH | (CH$_2$)$_5$ | N | OH | H | H |
| 2022 | 3-EtO—Ph | NH | C12 | O | OH | H | H |
| 2023 | 3-EtO—Ph | NH | Ph | O | OH | H | H |
| 2024 | 3-EtO—Ph | NH | C12 | S | OH | H | H |
| 2025 | 3-EtO—Ph | NH | Ph | S | OH | H | H |
| 2026 | 3-EtO—Ph | NMe | H | NH | OH | H | H |
| 2027 | 3-EtO—Ph | NEt | H | NH | OH | H | H |
| 2028 | 3-EtO—Ph | NPr | H | NH | OH | H | H |
| 2029 | 3-EtO—Ph | O | H | NH | OH | H | H |
| 2030 | 3-EtO—Ph | S | H | NH | OH | H | H |
| 2031 | 4-EtO—Ph | NH | H | NH | H | H | H |
| 2032 | 4-EtO—Ph | NH | H | NH | OH | H | H |
| 2033 | 4-EtO—Ph | NH | H | NH | OA6 | H | H |
| 2034 | 4-EtO—Ph | NH | H | NH | OA8 | H | H |
| 2035 | 4-EtO—Ph | NH | H | NH | OA9 | H | H |
| 2036 | 4-EtO—Ph | NH | H | NH | OA10 | H | H |
| 2037 | 4-EtO—Ph | NH | H | NH | OA12 | H | H |
| 2038 | 4-EtO—Ph | NH | H | NH | OA14 | H | H |
| 2039 | 4-EtO—Ph | NH | H | NH | OA16 | H | H |
| 2040 | 4-EtO—Ph | NH | H | NH | OH | H | A6 |
| 2041 | 4-EtO—Ph | NH | H | NH | OH | H | A8 |
| 2042 | 4-EtO—Ph | NH | H | NH | OH | H | A9 |
| 2043 | 4-EtO—Ph | NH | H | NH | OH | H | A10 |
| 2044 | 4-EtO—Ph | NH | H | NH | OH | H | A12 |
| 2045 | 4-EtO—Ph | NH | H | NH | OH | H | A14 |
| 2046 | 4-EtO—Ph | NH | H | NH | OH | H | A16 |
| 2047 | 4-EtO—Ph | NH | H | NH | OH | A6 | A6 |
| 2048 | 4-EtO—Ph | NH | H | NH | OH | A8 | A8 |
| 2049 | 4-EtO—Ph | NH | H | NH | OH | A10 | A10 |
| 2050 | 4-EtO—Ph | NH | H | NH | OA2 | A2 | A2 |
| 2051 | 4-EtO—Ph | NH | H | NH | OA3 | A3 | A3 |

TABLE 1-continued

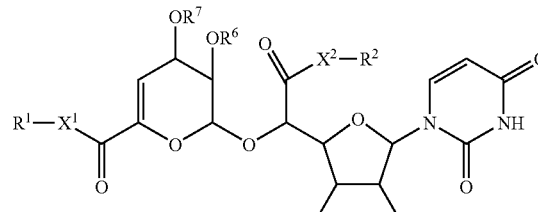

(I-1)

| Exemp. Comp. No. | R¹ | X¹ | R² | X² | R³ | R⁶ | R⁷ |
|---|---|---|---|---|---|---|---|
| 2052 | 4-EtO—Ph | NH | H | NH | OA4 | A4 | A4 |
| 2053 | 4-EtO—Ph | NH | H | NH | OC6 | H | H |
| 2054 | 4-EtO—Ph | NH | H | NH | OC7 | H | H |
| 2055 | 4-EtO—Ph | NH | H | NH | OC8 | H | H |
| 2056 | 4-EtO—Ph | NH | H | NH | OC10 | H | H |
| 2057 | 4-EtO—Ph | NH | H | NH | OC11 | H | H |
| 2058 | 4-EtO—Ph | NH | H | NH | OC12 | H | H |
| 2059 | 4-EtO—Ph | NH | H | NH | OC14 | H | H |
| 2060 | 4-EtO—Ph | NH | H | NH | OC16 | H | H |
| 2061 | 4-EtO—Ph | NH | H | NH | C6CO₃ | H | H |
| 2062 | 4-EtO—Ph | NH | H | NH | C7CO₃ | H | H |
| 2063 | 4-EtO—Ph | NH | H | NH | C8CO₃ | H | H |
| 2064 | 4-EtO—Ph | NH | H | NH | C9CO₃ | H | H |
| 2065 | 4-EtO—Ph | NH | H | NH | C10CO₃ | H | H |
| 2066 | 4-EtO—Ph | NH | H | NH | C12CO₃ | H | H |
| 2067 | 4-EtO—Ph | NH | H | NH | C16CO₃ | H | H |
| 2068 | 4-EtO—Ph | NH | C8 | NH | OH | H | H |
| 2069 | 4-EtO—Ph | NH | C9 | NH | OH | H | H |
| 2070 | 4-EtO—Ph | NH | C10 | NH | OH | H | H |
| 2071 | 4-EtO—Ph | NH | C12 | NH | OH | H | H |
| 2072 | 4-EtO—Ph | NH | C16 | NH | OH | H | H |
| 2073 | 4-EtO—Ph | NH | F1 | NH | OH | H | H |
| 2074 | 4-EtO—Ph | NH | F2 | NH | OH | H | H |
| 2075 | 4-EtO—Ph | NH | F3 | NH | OH | H | H |
| 2076 | 4-EtO—Ph | NH | F4 | NH | OH | H | H |
| 2077 | 4-EtO—Ph | NH | F5 | NH | OH | H | H |
| 2078 | 4-EtO—Ph | NH | F6 | NH | OH | H | H |
| 2079 | 4-EtO—Ph | NH | F7 | NH | OH | H | H |
| 2080 | 4-EtO—Ph | NH | F8 | NH | OH | H | H |
| 2081 | 4-EtO—Ph | NH | F9 | NH | OH | H | H |
| 2082 | 4-EtO—Ph | NH | F10 | NH | OH | H | H |
| 2083 | 4-EtO—Ph | NH | Ph | NH | OH | H | H |
| 2084 | 4-EtO—Ph | NH | Bn | NH | OH | H | H |
| 2085 | 4-EtO—Ph | NH | Pe | NH | OH | H | H |
| 2086 | 4-EtO—Ph | NH | C12 | NMe | OH | H | H |
| 2087 | 4-EtO—Ph | NH | C12 | NEt | OH | H | H |
| 2088 | 4-EtO—Ph | NH | C12 | NPr | OH | H | H |
| 2089 | 4-EtO—Ph | NH | (CH₂)₃ | N | OH | H | H |
| 2090 | 4-EtO—Ph | NH | (CH₂)₄ | N | OH | H | H |
| 2091 | 4-EtO—Ph | NH | (CH₂)₅ | N | OH | H | H |
| 2092 | 4-EtO—Ph | NH | C12 | O | OH | H | H |
| 2093 | 4-EtO—Ph | NH | Ph | O | OH | H | H |
| 2094 | 4-EtO—Ph | NH | C12 | S | OH | H | H |
| 2095 | 4-EtO—Ph | NH | Ph | S | OH | H | H |
| 2096 | 4-EtO—Ph | NMe | H | NH | OH | H | H |
| 2097 | 4-EtO—Ph | NEt | H | NH | OH | H | H |
| 2098 | 4-EtO—Ph | NPr | H | NH | OH | H | H |
| 2099 | 4-EtO—Ph | O | H | NH | OH | H | H |
| 2100 | 4-EtO—Ph | S | H | NH | OH | H | H |
| 2101 | 3-iPrO—Ph | NH | H | NH | H | H | H |
| 2102 | 3-iPrO—Ph | NH | H | NH | OH | H | H |
| 2103 | 3-iPrO—Ph | NH | H | NH | OA6 | H | H |
| 2104 | 3-iPrO—Ph | NH | H | NH | OA8 | H | H |
| 2105 | 3-iPrO—Ph | NH | H | NH | OA9 | H | H |
| 2106 | 3-iPrO—Ph | NH | H | NH | OA10 | H | H |
| 2107 | 3-iPrO—Ph | NH | H | NH | OA12 | H | H |
| 2108 | 3-iPrO—Ph | NH | H | NH | OA14 | H | H |
| 2109 | 3-iPrO—Ph | NH | H | NH | OA16 | H | H |
| 2110 | 3-iPrO—Ph | NH | H | NH | OH | H | A6 |
| 2111 | 3-iPrO—Ph | NH | H | NH | OH | H | A8 |
| 2112 | 3-iPrO—Ph | NH | H | NH | OH | H | A9 |
| 2113 | 3-iPrO—Ph | NH | H | NH | OH | H | A10 |

TABLE 1-continued

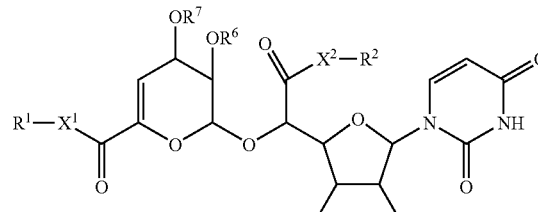

(I-1)

| Exemp. Comp. No. | R¹ | X¹ | R² | X² | R³ | R⁶ | R⁷ |
|---|---|---|---|---|---|---|---|
| 2114 | 3-iPrO—Ph | NH | H | NH | OH | H | A12 |
| 2115 | 3-iPrO—Ph | NH | H | NH | OH | H | A14 |
| 2116 | 3-iPrO—Ph | NH | H | NH | OH | H | A16 |
| 2117 | 3-iPrO—Ph | NH | H | NH | OH | A6 | A6 |
| 2118 | 3-iPrO—Ph | NH | H | NH | OH | A8 | A8 |
| 2119 | 3-iPrO—Ph | NH | H | NH | OH | A10 | A10 |
| 2120 | 3-iPrO—Ph | NH | H | NH | OA2 | A2 | A2 |
| 2121 | 3-iPrO—Ph | NH | H | NH | OA3 | A3 | A3 |
| 2122 | 3-iPrO—Ph | NH | H | NH | OA4 | A4 | A4 |
| 2123 | 3-iPrO—Ph | NH | H | NH | OC6 | H | H |
| 2124 | 3-iPrO—Ph | NH | H | NH | OC7 | H | H |
| 2125 | 3-iPrO—Ph | NH | H | NH | OC8 | H | H |
| 2126 | 3-iPrO—Ph | NH | H | NH | OC10 | H | H |
| 2127 | 3-iPrO—Ph | NH | H | NH | OC11 | H | H |
| 2128 | 3-iPrO—Ph | NH | H | NH | OC12 | H | H |
| 2129 | 3-iPrO—Ph | NH | H | NH | OC14 | H | H |
| 2130 | 3-iPrO—Ph | NH | H | NH | OC16 | H | H |
| 2131 | 3-iPrO—Ph | NH | H | NH | C6CO$_3$ | H | H |
| 2132 | 3-iPrO—Ph | NH | H | NH | C7CO$_3$ | H | H |
| 2133 | 3-iPrO—Ph | NH | H | NH | C8CO$_3$ | H | H |
| 2134 | 3-iPrO—Ph | NH | H | NH | C9CO$_3$ | H | H |
| 2135 | 3-iPrO—Ph | NH | H | NH | C10CO$_3$ | H | H |
| 2136 | 3-iPrO—Ph | NH | H | NH | C12CO$_3$ | H | H |
| 2137 | 3-iPrO—Ph | NH | H | NH | C16CO$_3$ | H | H |
| 2138 | 3-iPrO—Ph | NH | C8 | NH | OH | H | H |
| 2139 | 3-iPrO—Ph | NH | C9 | NH | OH | H | H |
| 2140 | 3-iPrO—Ph | NH | C10 | NH | OH | H | H |
| 2141 | 3-iPrO—Ph | NH | C12 | NH | OH | H | H |
| 2142 | 3-iPrO—Ph | NH | C16 | NH | OH | H | H |
| 2143 | 3-iPrO—Ph | NH | F1 | NH | OH | H | H |
| 2144 | 3-iPrO—Ph | NH | F2 | NH | OH | H | H |
| 2145 | 3-iPrO—Ph | NH | F3 | NH | OH | H | H |
| 2146 | 3-iPrO—Ph | NH | F4 | NH | OH | H | H |
| 2147 | 3-iPrO—Ph | NH | F5 | NH | OH | H | H |
| 2148 | 3-iPrO—Ph | NH | F6 | NH | OH | H | H |
| 2149 | 3-iPrO—Ph | NH | F7 | NH | OH | H | H |
| 2150 | 3-iPrO—Ph | NH | F8 | NH | OH | H | H |
| 2151 | 3-iPrO—Ph | NH | F9 | NH | OH | H | H |
| 2152 | 3-iPrO—Ph | NH | F10 | NH | OH | H | H |
| 2153 | 3-iPrO—Ph | NH | Ph | NH | OH | H | H |
| 2154 | 3-iPrO—Ph | NH | Bn | NH | OH | H | H |
| 2155 | 3-tPrO—Ph | NH | Pe | NH | OH | H | H |
| 2156 | 3-iPrO—Ph | NH | C12 | NMe | OH | H | H |
| 2157 | 3-iPrO—Ph | NH | C12 | NEt | OH | H | H |
| 2158 | 3-iPrO—Ph | NH | C12 | NPr | OH | H | H |
| 2159 | 3-iPrO—Ph | NH | (CH$_2$)$_3$ | N | OH | H | H |
| 2160 | 3-iPrO—Ph | NH | (CH$_2$)$_4$ | N | OH | H | H |
| 2161 | 3-iPrO—Ph | NH | (CH$_2$)$_5$ | N | OH | H | H |
| 2162 | 3-iPrO—Ph | NH | C12 | O | OH | H | H |
| 2163 | 3-iPrO—Ph | NH | Ph | O | OH | H | H |
| 2164 | 3-iPrO—Ph | NH | C12 | S | OH | H | H |
| 2165 | 3-iPrO—Ph | NH | Ph | S | OH | H | H |
| 2166 | 3-iPrO—Ph | NMe | H | NH | OH | H | H |
| 2167 | 3-iPrO—Ph | NEt | H | NH | OH | H | H |
| 2168 | 3-iPrO—Ph | NPr | H | NH | OH | H | H |
| 2169 | 3-iPrO—Ph | O | H | NH | OH | H | H |
| 2170 | 3-iPrO—Ph | S | H | NH | OH | H | H |
| 2171 | 4-iPrO—Ph | NH | H | NH | H | H | H |
| 2172 | 4-iPrO—Ph | NH | H | NH | OH | H | H |
| 2173 | 4-iPrO—Ph | NH | H | NH | OA6 | H | H |
| 2174 | 4-iPrO—Ph | NH | H | NH | OA8 | H | H |
| 2175 | 4-iPrO—Ph | NH | H | NH | OA9 | H | H |

TABLE 1-continued

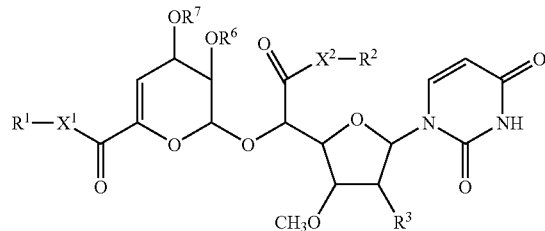

(I-1)

| Exemp. Comp. No. | R¹ | X¹ | R² | X² | R³ | R⁶ | R⁷ |
|---|---|---|---|---|---|---|---|
| 2176 | 4-iPrO—Ph | NH | H | NH | OA10 | H | H |
| 2177 | 4-iPrO—Ph | NH | H | NH | OA12 | H | H |
| 2178 | 4-iPrO—Ph | NH | H | NH | OA14 | H | H |
| 2179 | 4-iPrO—Ph | NH | H | NH | OA16 | H | H |
| 2180 | 4-iPrO—Ph | NH | H | NH | OH | H | A6 |
| 2181 | 4-iPrO—Ph | NH | H | NH | OH | H | A8 |
| 2182 | 4-iPrO—Ph | NH | H | NH | OH | H | A9 |
| 2183 | 4-iPrO—Ph | NH | H | NH | OH | H | A10 |
| 2184 | 4-iPrO—Ph | NH | H | NH | OH | H | A12 |
| 2185 | 4-iPrO—Ph | NH | H | NH | OH | H | A14 |
| 2186 | 4-iPrO—Ph | NH | H | NH | OH | H | A16 |
| 2187 | 4-iPrO—Ph | NH | H | NH | OH | A6 | A6 |
| 2188 | 4-iPrO—Ph | NH | H | NH | OH | A8 | A8 |
| 2189 | 4-iPrO—Ph | NH | H | NH | OH | A10 | A10 |
| 2190 | 4-iPrO—Ph | NH | H | NH | OA2 | A2 | A2 |
| 2191 | 4-iPrO—Ph | NH | H | NH | OA3 | A3 | A3 |
| 2192 | 4-iPrO—Ph | NH | H | NH | OA4 | A4 | A4 |
| 2193 | 4-iPrO—Ph | NH | H | NH | OC6 | H | H |
| 2194 | 4-iPrO—Ph | NH | H | NH | OC7 | H | H |
| 2195 | 4-iPrO—Ph | NH | H | NH | OC8 | H | H |
| 2196 | 4-iPrO—Ph | NH | H | NH | OC10 | H | H |
| 2197 | 4-iPrO—Ph | NH | H | NH | OC11 | H | H |
| 2198 | 4-iPrO—Ph | NH | H | NH | OC12 | H | H |
| 2199 | 4-iPrO—Ph | NH | H | NH | OC14 | H | H |
| 2200 | 4-iPrO—Ph | NH | H | NH | OC16 | H | H |
| 2201 | 4-iPrO—Ph | NH | H | NH | $C6CO_3$ | H | H |
| 2202 | 4-iPrO—Ph | NH | H | NH | $C7CO_3$ | H | H |
| 2203 | 4-iPrO—Ph | NH | H | NH | $C8CO_3$ | H | H |
| 2204 | 4-iPrO—Ph | NH | H | NH | $C9CO_3$ | H | H |
| 2205 | 4-iPrO—Ph | NH | H | NH | $C10CO_3$ | H | H |
| 2206 | 4-iPrO—Ph | NH | H | NH | $C12CO_3$ | H | H |
| 2207 | 4-iPrO—Ph | NH | H | NH | $C16CO_3$ | H | H |
| 2208 | 4-iPrO—Ph | NH | C8 | NH | OH | H | H |
| 2209 | 4-iPrO—Ph | NH | C9 | NH | OH | H | H |
| 2210 | 4-iPrO—Ph | NH | C10 | NH | OH | H | H |
| 2211 | 4-iPrO—Ph | NH | C12 | NH | OH | H | H |
| 2212 | 4-iPrO—Ph | NH | C16 | NH | OH | H | H |
| 2213 | 4-iPrO—Ph | NH | F1 | NH | OH | H | H |
| 2214 | 4-iPrO—Ph | NH | F2 | NH | OH | H | H |
| 2215 | 4-iPrO—Ph | NH | F3 | NH | OH | H | H |
| 2216 | 4-iPrO—Ph | NH | F4 | NH | OH | H | H |
| 2217 | 4-iPrO—Ph | NH | F5 | NH | OH | H | H |
| 2218 | 4-iPrO—Ph | NH | F6 | NH | OH | H | H |
| 2219 | 4-iPrO—Ph | NH | F7 | NH | OH | H | H |
| 2220 | 4-iPrO—Ph | NH | F8 | NH | OH | H | H |
| 2221 | 4-iPrO—Ph | NH | F9 | NH | OH | H | H |
| 2222 | 4-iPrO—Ph | NH | F10 | NH | OH | H | H |
| 2223 | 4-iPrO—Ph | NH | Ph | NH | OH | H | H |
| 2224 | 4-iPrO—Ph | NH | Bn | NH | OH | H | H |
| 2225 | 4-iPrO—Ph | NH | Pe | NH | OH | H | H |
| 2226 | 4-iPrO—Ph | NH | C12 | NMe | OH | H | H |
| 2227 | 4-iPrO—Ph | NH | C12 | NEt | OH | H | H |
| 2228 | 4-iPrO—Ph | NH | C12 | NPr | OH | H | H |
| 2229 | 4-iPrO—Ph | NH | $(CH_2)_3$ | N | OH | H | H |
| 2230 | 4-iPrO—Ph | NH | $(CH_2)_4$ | N | OH | H | H |
| 2231 | 4-iPrO—Ph | NH | $(CH_2)_5$ | N | OH | H | H |
| 2232 | 4-iPrO—Ph | NH | C12 | O | OH | H | H |
| 2233 | 4-iPrO—Ph | NH | Ph | O | OH | H | H |
| 2234 | 4-iPrO—Ph | NH | C12 | S | OH | H | H |
| 2235 | 4-iPrO—Ph | NH | Ph | S | OH | H | H |
| 2236 | 4-iPrO—Ph | NMe | H | NH | OH | H | H |
| 2237 | 4-iPrO—Ph | NEt | H | NH | OH | H | H |

TABLE 1-continued (I-1)

| Exemp. Comp. No. | R¹ | X¹ | R² | X² | R³ | R⁶ | R⁷ |
|---|---|---|---|---|---|---|---|
| 2238 | 4-iPrO—Ph | NPr | H | NH | OH | H | H |
| 2239 | 4-iPrO—Ph | O | H | NH | OH | H | H |
| 2240 | 4-iPrO—Ph | S | H | NH | OH | H | H |
| 2241 | 4-BuO—Ph | NH | H | NH | H | H | H |
| 2242 | 4-BuO—Ph | NH | H | NH | OH | H | H |
| 2243 | 4-BuO—Ph | NH | H | NH | OA6 | H | H |
| 2244 | 4-BuO—Ph | NH | H | NH | OA8 | H | H |
| 2245 | 4-BuO—Ph | NH | H | NH | OA9 | H | H |
| 2246 | 4-BuO—Ph | NH | H | NH | OA10 | H | H |
| 2247 | 4-BuO—Ph | NH | H | NH | OA12 | H | H |
| 2248 | 4-BuO—Ph | NH | H | NH | OA14 | H | H |
| 2249 | 4-BuO—Ph | NH | H | NH | OA16 | H | H |
| 2250 | 4-BuO—Ph | NH | H | NH | OH | H | A6 |
| 2251 | 4-BuO—Ph | NH | H | NH | OH | H | A8 |
| 2252 | 4-BuO—Ph | NH | H | NH | OH | H | A9 |
| 2253 | 4-BuO—Ph | NH | H | NH | OH | H | A10 |
| 2254 | 4-BuO—Ph | NH | H | NH | OH | H | A12 |
| 2255 | 4-BuO—Ph | NH | H | NH | OH | H | A14 |
| 2256 | 4-BuO—Ph | NH | H | NH | OH | H | A16 |
| 2257 | 4-BuO—Ph | NH | H | NH | OH | A6 | A6 |
| 2258 | 4-BuO—Ph | NH | H | NH | OH | A8 | A8 |
| 2259 | 4-BuO—Ph | NH | H | NH | OH | A10 | A10 |
| 2260 | 4-BuO—Ph | NH | H | NH | OA2 | A2 | A2 |
| 2261 | 4-BuO—Ph | NH | H | NH | OA3 | A3 | A3 |
| 2262 | 4-BuO—Ph | NH | H | NH | OA4 | A4 | A4 |
| 2263 | 4-BuO—Ph | NH | H | NH | OC6 | H | H |
| 2264 | 4-BuO—Ph | NH | H | NH | OC7 | H | H |
| 2265 | 4-BuO—Ph | NH | H | NH | OC8 | H | H |
| 2266 | 4-BuO—Ph | NH | H | NH | OC10 | H | H |
| 2267 | 4-BuO—Ph | NH | H | NH | OC11 | H | H |
| 2268 | 4-BuO—Ph | NH | H | NH | OC12 | H | H |
| 2269 | 4-BuO—Ph | NH | H | NH | OC14 | H | H |
| 2270 | 4-BuO—Ph | NH | H | NH | OC16 | H | H |
| 2271 | 4-BuO—Ph | NH | H | NH | C6CO₃ | H | H |
| 2272 | 4-BuO—Ph | NH | H | NH | C7CO₃ | H | H |
| 2273 | 4-BuO—Ph | NH | H | NH | C8CO₃ | H | H |
| 2274 | 4-BuO—Ph | NH | H | NH | C9CO₃ | H | H |
| 2275 | 4-BuO—Ph | NH | H | NH | C10CO₃ | H | H |
| 2276 | 4-BuO—Ph | NH | H | NH | C12CO₃ | H | H |
| 2277 | 4-BuO—Ph | NH | H | NH | C16CO₃ | H | H |
| 2278 | 4-BuO—Ph | NH | C8 | NH | OH | H | H |
| 2279 | 4-BuO—Ph | NH | C9 | NH | OH | H | H |
| 2280 | 4-BuO—Ph | NH | C10 | NH | OH | H | H |
| 2281 | 4-BuO—Ph | NH | C12 | NH | OH | H | H |
| 2282 | 4-BuO—Ph | NH | C16 | NH | OH | H | H |
| 2283 | 4-BuO—Ph | NH | F1 | NH | OH | H | H |
| 2284 | 4-BuO—Ph | NH | F2 | NH | OH | H | H |
| 2285 | 4-BuO—Ph | NH | F3 | NH | OH | H | H |
| 2286 | 4-BuO—Ph | NH | F4 | NH | OH | H | H |
| 2287 | 4-BuO—Ph | NH | F5 | NH | OH | H | H |
| 2288 | 4-BuO—Ph | NH | F6 | NH | OH | H | H |
| 2289 | 4-BuO—Ph | NH | F7 | NH | OH | H | H |
| 2290 | 4-BuO—Ph | NH | F8 | NH | OH | H | H |
| 2291 | 4-BuO—Ph | NH | F9 | NH | OH | H | H |
| 2292 | 4-BuO—Ph | NH | F10 | NH | OH | H | H |
| 2293 | 4-BuO—Ph | NH | Ph | NH | OH | H | H |
| 2294 | 4-BuO—Ph | NH | Bn | NH | OH | H | H |
| 2295 | 4-BuO—Ph | NH | Pe | NH | OH | H | H |
| 2296 | 4-BuO—Ph | NH | C12 | NMe | OH | H | H |
| 2297 | 4-BuO—Ph | NH | C12 | NEt | OH | H | H |
| 2298 | 4-BuO—Ph | NH | C12 | NPr | OH | H | H |
| 2299 | 4-BuO—Ph | NH | (CH₂)₃ | N | OH | H | H |

TABLE 1-continued (I-1)

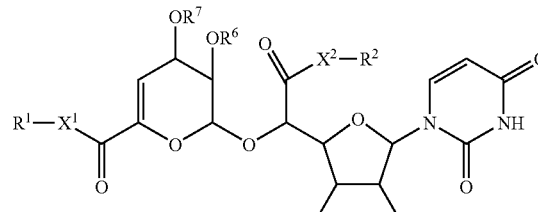

| Exemp. Comp. No. | R¹ | X¹ | R² | X² | R³ | R⁶ | R⁷ |
|---|---|---|---|---|---|---|---|
| 2300 | 4-BuO—Ph | NH | (CH₂)₄ | N | OH | H | H |
| 2301 | 4-BuO—Ph | NH | (CH₂)₅ | N | OH | H | H |
| 2302 | 4-BuO—Ph | NH | C12 | O | OH | H | H |
| 2303 | 4-BuO—Ph | NH | Ph | O | OH | H | H |
| 2304 | 4-BuO—Ph | NH | C12 | S | OH | H | H |
| 2305 | 4-BuO—Ph | NH | Ph | S | OH | H | H |
| 2306 | 4-BuO—Ph | NMe | H | NH | OH | H | H |
| 2307 | 4-BuO—Ph | NEt | H | NH | OH | H | H |
| 2308 | 4-BuO—Ph | NPr | H | NH | OH | H | H |
| 2309 | 4-BuO—Ph | O | H | NH | OH | H | H |
| 2310 | 4-BuO—Ph | S | H | NH | OH | H | H |
| 2311 | 4-PenO—Ph | NH | H | NH | H | H | H |
| 2312 | 4-PenO—Ph | NH | H | NH | OH | H | H |
| 2313 | 4-PenO—Ph | NH | H | NH | OA6 | H | H |
| 2314 | 4-PenO—Ph | NH | H | NH | OA8 | H | H |
| 2315 | 4-PenO—Ph | NH | H | NH | OA9 | H | H |
| 2316 | 4-PenO—Ph | NH | H | NH | OA10 | H | H |
| 2317 | 4-PenO—Ph | NH | H | NH | OA12 | H | H |
| 2318 | 4-PenO—Ph | NH | H | NH | OA14 | H | H |
| 2319 | 4-PenO—Ph | NH | H | NH | OA16 | H | H |
| 2320 | 4-PenO—Ph | NH | H | NH | OH | H | A6 |
| 2321 | 4-PenO—Ph | NH | H | NH | OH | H | A8 |
| 2322 | 4-PenO—Ph | NH | H | NH | OH | H | A9 |
| 2323 | 4-PenO—Ph | NH | H | NH | OH | H | A10 |
| 2324 | 4-PenO—Ph | NH | H | NH | OH | H | A12 |
| 2325 | 4-PenO—Ph | NH | H | NH | OH | H | A14 |
| 2326 | 4-PenO—Ph | NH | H | NH | OH | H | A16 |
| 2327 | 4-PenO—Ph | NH | H | NH | OH | A6 | A6 |
| 2328 | 4-PenO—Ph | NH | H | NH | OH | A8 | A8 |
| 2329 | 4-PenO—Ph | NH | H | NH | OH | A10 | A10 |
| 2330 | 4-PenO—Ph | NH | H | NH | OA2 | A2 | A2 |
| 2331 | 4-PenO—Ph | NH | H | NH | OA3 | A3 | A3 |
| 2332 | 4-PenO—Ph | NH | H | NH | OA4 | A4 | A4 |
| 2333 | 4-PenO—Ph | NH | H | NH | OC6 | H | H |
| 2334 | 4-PenO—Ph | NH | H | NH | OC7 | H | H |
| 2335 | 4-PenO—Ph | NH | H | NH | OC8 | H | H |
| 2336 | 4-PenO—Ph | NH | H | NH | OC10 | H | H |
| 2337 | 4-PenO—Ph | NH | H | NH | OC11 | H | H |
| 2338 | 4-PenO—Ph | NH | H | NH | OC12 | H | H |
| 2339 | 4-PenO—Ph | NH | H | NH | OC14 | H | H |
| 2340 | 4-PenO—Ph | NH | H | NH | OC16 | H | H |
| 2341 | 4-PenO—Ph | NH | H | NH | C6CO₃ | H | H |
| 2342 | 4-PenO—Ph | NH | H | NH | C7CO₃ | H | H |
| 2343 | 4-PenO—Ph | NH | H | NH | C8CO₃ | H | H |
| 2344 | 4-PenO—Ph | NH | H | NH | C9CO₃ | H | H |
| 2345 | 4-PenO—Ph | NH | H | NH | C10CO₃ | H | H |
| 2346 | 4-PenO—Ph | NH | H | NH | C12CO₃ | H | H |
| 2347 | 4-PenO—Ph | NH | H | NH | C16CO₃ | H | H |
| 2348 | 4-PenO—Ph | NH | C8 | NH | OH | H | H |
| 2349 | 4-PenO—Ph | NH | C9 | NH | OH | H | H |
| 2350 | 4-PenO—Ph | NH | C10 | NH | OH | H | H |
| 2351 | 4-PenO—Ph | NH | C12 | NH | OH | H | H |
| 2352 | 4-PenO—Ph | NH | C16 | NH | OH | H | H |
| 2353 | 4-PenO—Ph | NH | F1 | NH | OH | H | H |
| 2354 | 4-PenO—Ph | NH | F2 | NH | OH | H | H |
| 2355 | 4-PenO—Ph | NH | F3 | NH | OH | H | H |
| 2356 | 4-PenO—Ph | NH | F4 | NH | OH | H | H |
| 2357 | 4-PenO—Ph | NH | F5 | NH | OH | H | H |
| 2358 | 4-PenO—Ph | NH | F6 | NH | OH | H | H |
| 2359 | 4-PenO—Ph | NH | F7 | NH | OH | H | H |
| 2360 | 4-PenO—Ph | NH | F8 | NH | OH | H | H |
| 2361 | 4-PenO—Ph | NH | F9 | NH | OH | H | H |

TABLE 1-continued

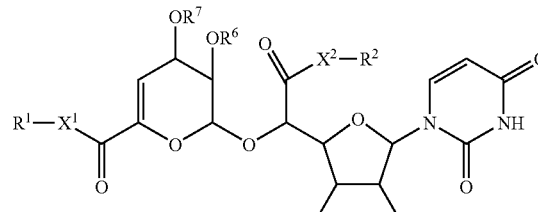

(I-1)

| Exemp. Comp. No. | R¹ | X¹ | R² | X² | R³ | R⁶ | R⁷ |
|---|---|---|---|---|---|---|---|
| 2362 | 4-PenO—Ph | NH | F10 | NH | OH | H | H |
| 2363 | 4-PenO—Ph | NH | Ph | NH | OH | H | H |
| 2364 | 4-PenO—Ph | NH | Bn | NH | OH | H | H |
| 2365 | 4-PenO—Ph | NH | Pe | NH | OH | H | H |
| 2366 | 4-PenO—Ph | NH | C12 | NMe | OH | H | H |
| 2367 | 4-PenO—Ph | NH | C12 | NEt | OH | H | H |
| 2368 | 4-PenO—Ph | NH | C12 | NPr | OH | H | H |
| 2369 | 4-PenO—Ph | NH | (CH₂)₃ | N | OH | H | H |
| 2370 | 4-PenO—Ph | NH | (CH₂)₄ | N | OH | H | H |
| 2371 | 4-PenO—Ph | NH | (CH₂)₅ | N | OH | H | H |
| 2372 | 4-PenO—Ph | NH | C12 | O | OH | H | H |
| 2373 | 4-PenO—Ph | NH | Ph | O | OH | H | H |
| 2374 | 4-PenO—Ph | NH | C12 | S | OH | H | H |
| 2375 | 4-PenO—Ph | NH | Ph | S | OH | H | H |
| 2376 | 4-PenO—Ph | NMe | H | NH | OH | H | H |
| 2377 | 4-PenO—Ph | NEt | H | NH | OH | H | H |
| 2378 | 4-PenO—Ph | NPr | H | NH | OH | H | H |
| 2379 | 4-PenO—Ph | O | H | NH | OH | H | H |
| 2380 | 4-PenO—Ph | S | H | NH | OH | H | H |
| 2381 | 4-HexO—Ph | NH | H | NH | H | H | H |
| 2382 | 4-HexO—Ph | NH | H | NH | OH | H | H |
| 2383 | 4-HexO—Ph | NH | H | NH | OA6 | H | H |
| 2384 | 4-HexO—Ph | NH | H | NH | OA8 | H | H |
| 2385 | 4-HexO—Ph | NH | H | NH | OA9 | H | H |
| 2386 | 4-HexO—Ph | NH | H | NH | OA10 | H | H |
| 2387 | 4-HexO—Ph | NH | H | NH | OA12 | H | H |
| 2388 | 4-HexO—Ph | NH | H | NH | OA14 | H | H |
| 2389 | 4-HexO—Ph | NH | H | NH | OA16 | H | H |
| 2390 | 4-HexO—Ph | NH | H | NH | OH | H | A6 |
| 2391 | 4-HexO—Ph | NH | H | NH | OH | H | A8 |
| 2392 | 4-HexO—Ph | NH | H | NH | OH | H | A9 |
| 2393 | 4-HexO—Ph | NH | H | NH | OH | H | A10 |
| 2394 | 4-HexO—Ph | NH | H | NH | OH | H | A12 |
| 2395 | 4-HexO—Ph | NH | H | NH | OH | H | A14 |
| 2396 | 4-HexO—Ph | NH | H | NH | OH | H | A16 |
| 2397 | 4-HexO—Ph | NH | H | NH | OH | A6 | A6 |
| 2398 | 4-HexO—Ph | NH | H | NH | OH | A8 | A8 |
| 2399 | 4-HexO—Ph | NH | H | NH | OH | A10 | A10 |
| 2400 | 4-HexO—Ph | NH | H | NH | OA2 | A2 | A2 |
| 2401 | 4-HexO—Ph | NH | H | NH | OA3 | A3 | A3 |
| 2402 | 4-HexO—Ph | NH | H | NH | OA4 | A4 | A4 |
| 2403 | 4-HexO—Ph | NH | H | NH | OC6 | H | H |
| 2404 | 4-HexO—Ph | NH | H | NH | OC7 | H | H |
| 2405 | 4-HexO—Ph | NH | H | NH | OC8 | H | H |
| 2406 | 4-HexO—Ph | NH | H | NH | OC10 | H | H |
| 2407 | 4-HexO—Ph | NH | H | NH | OC11 | H | H |
| 2408 | 4-HexO—Ph | NH | H | NH | OC12 | H | H |
| 2409 | 4-HexO—Ph | NH | H | NH | OC14 | H | H |
| 2410 | 4-HexO—Ph | NH | H | NH | OC16 | H | H |
| 2411 | 4-HexO—Ph | NH | H | NH | C6CO₃ | H | H |
| 2412 | 4-HexO—Ph | NH | H | NH | C7CO₃ | H | H |
| 2413 | 4-HexO—Ph | NH | H | NH | C8CO₃ | H | H |
| 2414 | 4-HexO—Ph | NH | H | NH | C9CO₃ | H | H |
| 2415 | 4-HexO—Ph | NH | H | NH | C10CO₃ | H | H |
| 2416 | 4-HexO—Ph | NH | H | NH | C12CO₃ | H | H |
| 2417 | 4-HexO—Ph | NH | H | NH | C16CO₃ | H | H |
| 2418 | 4-HexO—Ph | NH | C8 | NH | OH | H | H |
| 2419 | 4-HexO—Ph | NH | C9 | NH | OH | H | H |
| 2420 | 4-HexO—Ph | NH | C10 | NH | OH | H | H |
| 2421 | 4-HexO—Ph | NH | C12 | NH | OH | H | H |
| 2422 | 4-HexO—Ph | NH | C16 | NH | OH | H | H |
| 2423 | 4-HexO—Ph | NH | F1 | NH | OH | H | H |

TABLE 1-continued (I-1)

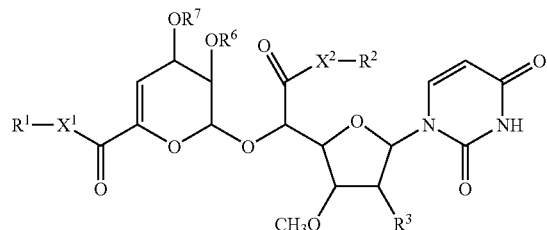

| Exemp. Comp. No. | R¹ | X¹ | R² | X² | R³ | R⁶ | R⁷ |
|---|---|---|---|---|---|---|---|
| 2424 | 4-HexO—Ph | NH | F2 | NH | OH | H | H |
| 2425 | 4-HexO—Ph | NH | F3 | NH | OH | H | H |
| 2426 | 4-HexO—Ph | NH | F4 | NH | OH | H | H |
| 2427 | 4-HexO—Ph | NH | F5 | NH | OH | H | H |
| 2428 | 4-HexO—Ph | NH | F6 | NH | OH | H | H |
| 2429 | 4-HexO—Ph | NH | F7 | NH | OH | H | H |
| 2430 | 4-HexO—Ph | NH | F8 | NH | OH | H | H |
| 2431 | 4-HexO—Ph | NH | F9 | NH | OH | H | H |
| 2432 | 4-HexO—Ph | NH | F10 | NH | OH | H | H |
| 2433 | 4-HexO—Ph | NH | Ph | NH | OH | H | H |
| 2434 | 4-HexO—Ph | NH | Bn | NH | OH | H | H |
| 2435 | 4-HexO—Ph | NH | Pe | NH | OH | H | H |
| 2436 | 4-HexO—Ph | NH | C12 | NMe | OH | H | H |
| 2437 | 4-HexO—Ph | NH | C12 | NEt | OH | H | H |
| 2438 | 4-HexO—Ph | NH | C12 | NPr | OH | H | H |
| 2439 | 4-HexO—Ph | NH | $(CH_2)_3$ | N | OH | H | H |
| 2440 | 4-HexO—Ph | NH | $(CH_2)_4$ | N | OH | H | H |
| 2441 | 4-HexO—Ph | NH | $(CH_2)_5$ | N | OH | H | H |
| 2442 | 4-HexO—Ph | NH | C12 | O | OH | H | H |
| 2443 | 4-HexO—Ph | NH | Ph | O | OH | H | H |
| 2444 | 4-HexO—Ph | NH | C12 | S | OH | H | H |
| 2445 | 4-HexO—Ph | NH | Ph | S | OH | H | H |
| 2446 | 4-HexO—Ph | NMe | H | NH | OH | H | H |
| 2447 | 4-HexO—Ph | NEt | H | NH | OH | H | H |
| 2448 | 4-HexO—Ph | NPr | H | NH | OH | H | H |
| 2449 | 4-HexO—Ph | O | H | NH | OH | H | H |
| 2450 | 4-HexO—Ph | S | H | NH | OH | H | H |
| 2451 | 3-BnO—Ph | NH | H | NH | H | H | H |
| 2452 | 3-BnO—Ph | NH | H | NH | OH | H | H |
| 2453 | 3-BnO—Ph | NH | H | NH | OA6 | H | H |
| 2454 | 3-BnO—Ph | NH | H | NH | OA8 | H | H |
| 2455 | 3-BnO—Ph | NH | H | NH | OA9 | H | H |
| 2456 | 3-BnO—Ph | NH | H | NH | OA10 | H | H |
| 2457 | 3-BnO—Ph | NH | H | NH | OA12 | H | H |
| 2458 | 3-BnO—Ph | NH | H | NH | OA14 | H | H |
| 2459 | 3-BnO—Ph | NH | H | NH | OA16 | H | H |
| 2460 | 3-BnO—Ph | NH | H | NH | OH | H | A6 |
| 2461 | 3-BnO—Ph | NH | H | NH | OH | H | A8 |
| 2462 | 3-BnO—Ph | NH | H | NH | OH | H | A9 |
| 2463 | 3-BnO—Ph | NH | H | NH | OH | H | A10 |
| 2464 | 3-BnO—Ph | NH | H | NH | OH | H | A12 |
| 2465 | 3-BnO—Ph | NH | H | NH | OH | H | A14 |
| 2466 | 3-BnO—Ph | NH | H | NH | OH | H | A16 |
| 2467 | 3-BnO—Ph | NH | H | NH | OH | A6 | A6 |
| 2468 | 3-BnO—Ph | NH | H | NH | OH | A8 | A8 |
| 2469 | 3-BnO—Ph | NH | H | NH | OH | A10 | A10 |
| 2470 | 3-BnO—Ph | NH | H | NH | OA2 | A2 | A2 |
| 2471 | 3-BnO—Ph | NH | H | NH | OA3 | A3 | A3 |
| 2472 | 3-BnO—Ph | NH | H | NH | OA4 | A4 | A4 |
| 2473 | 3-BnO—Ph | NH | H | NH | OC6 | H | H |
| 2474 | 3-BnO—Ph | NH | H | NH | OC7 | H | H |
| 2475 | 3-BnO—Ph | NH | H | NH | OC8 | H | H |
| 2476 | 3-BnO—Ph | NH | H | NH | OC10 | H | H |
| 2477 | 3-BnO—Ph | NH | H | NH | OC11 | H | H |
| 2478 | 3-BnO—Ph | NH | H | NH | OC12 | H | H |
| 2479 | 3-BnO—Ph | NH | H | NH | OC14 | H | H |
| 2480 | 3-BnO—Ph | NH | H | NH | OC16 | H | H |
| 2481 | 3-BnO—Ph | NH | H | NH | $C6CO_3$ | H | H |
| 2482 | 3-BnO—Ph | NH | H | NH | $C7CO_3$ | H | H |
| 2483 | 3-BnO—Ph | NH | H | NH | $C8CO_3$ | H | H |
| 2484 | 3-BnO—Ph | NH | H | NH | $C9CO_3$ | H | H |
| 2485 | 3-BnO—Ph | NH | H | NH | $C10CO_3$ | H | H |

TABLE 1-continued (I-1)

| Exemp. Comp. No. | R¹ | X¹ | R² | X² | R³ | R⁶ | R⁷ |
|---|---|---|---|---|---|---|---|
| 2486 | 3-BnO—Ph | NH | H | NH | C12CO₃ | H | H |
| 2487 | 3-BnO—Ph | NH | H | NH | C16CO₃ | H | H |
| 2488 | 3-BnO—Ph | NH | C8 | NH | OH | H | H |
| 2489 | 3-BnO—Ph | NH | C9 | NH | OH | H | H |
| 2490 | 3-BnO—Ph | NH | C10 | NH | OH | H | H |
| 2491 | 3-BnO—Ph | NH | C12 | NH | OH | H | H |
| 2492 | 3-BnO—Ph | NH | C16 | NH | OH | H | H |
| 2493 | 3-BnO—Ph | NH | F1 | NH | OH | H | H |
| 2494 | 3-BnO—Ph | NH | F2 | NH | OH | H | H |
| 2495 | 3-BnO—Ph | NH | F3 | NH | OH | H | H |
| 2496 | 3-BnO—Ph | NH | F4 | NH | OH | H | H |
| 2497 | 3-BnO—Ph | NH | F5 | NH | OH | H | H |
| 2498 | 3-BnO—Ph | NH | F6 | NH | OH | H | H |
| 2499 | 3-BnO—Ph | NH | F7 | NH | OH | H | H |
| 2500 | 3-BnO—Ph | NH | F8 | NH | OH | H | H |
| 2501 | 3-BnO—Ph | NH | F9 | NH | OH | H | H |
| 2502 | 3-BnO—Ph | NH | F10 | NH | OH | H | H |
| 2503 | 3-BnO—Ph | NH | Ph | NH | OH | H | H |
| 2504 | 3-BnO—Ph | NH | Bn | NH | OH | H | H |
| 2505 | 3-BnO—Ph | NH | Pe | NH | OH | H | H |
| 2506 | 3-BnO—Ph | NH | C12 | NMe | OH | H | H |
| 2507 | 3-BnO—Ph | NH | C12 | NEt | OH | H | H |
| 2508 | 3-BnO—Ph | NH | C12 | NPr | OH | H | H |
| 2509 | 3-BnO—Ph | NH | (CH₂)₃ | N | OH | H | H |
| 2510 | 3-BnO—Ph | NH | (CH₂)₄ | N | OH | H | H |
| 2511 | 3-BnO—Ph | NH | (CH₂)₅ | N | OH | H | H |
| 2512 | 3-BnO—Ph | NH | C12 | O | OH | H | H |
| 2513 | 3-BnO—Ph | NH | Ph | O | OH | H | H |
| 2514 | 3-BnO—Ph | NH | C12 | S | OH | H | H |
| 2515 | 3-BnO—Ph | NH | Ph | S | OH | H | H |
| 2516 | 3-BnO—Ph | NMe | H | NH | OH | H | H |
| 2517 | 3-BnO—Ph | NEt | H | NH | OH | H | H |
| 2518 | 3-BnO—Ph | NPr | H | NH | OH | H | H |
| 2519 | 3-BnO—Ph | O | H | NH | OH | H | H |
| 2520 | 3-BnO—Ph | S | H | NH | OH | H | H |
| 2521 | 2-Me-4-MeO—Ph | NH | H | NH | H | H | H |
| 2522 | 2-Me-4-MeO—Ph | NH | H | NH | OH | H | H |
| 2523 | 2-Me-4-MeO—Ph | NH | H | NH | OA6 | H | H |
| 2524 | 2-Me-4-MeO—Ph | NH | H | NH | OA8 | H | H |
| 2525 | 2-Me-4-MeO—Ph | NH | H | NH | OA9 | H | H |
| 2526 | 2-Me-4-MeO—Ph | NH | H | NH | OA10 | H | H |
| 2527 | 2-Me-4-MeO—Ph | NH | H | NH | OA12 | H | H |
| 2528 | 2-Me-4-MeO—Ph | NH | H | NH | OA14 | H | H |
| 2529 | 2-Me-4-MeO—Ph | NH | H | NH | OA16 | H | H |
| 2530 | 2-Me-4-MeO—Ph | NH | H | NH | OH | H | A6 |
| 2531 | 2-Me-4-MeO—Ph | NH | H | NH | OH | H | A8 |
| 2532 | 2-Me-4-MeO—Ph | NH | H | NH | OH | H | A9 |
| 2533 | 2-Me-4-MeO—Ph | NH | H | NH | OH | H | A10 |
| 2534 | 2-Me-4-MeO—Ph | NH | H | NH | OH | H | A12 |
| 2535 | 2-Me-4-MeO—Ph | NH | H | NH | OH | H | A14 |
| 2536 | 2-Me-4-MeO—Ph | NH | H | NH | OH | H | A16 |
| 2537 | 2-Me-4-MeO—Ph | NH | H | NH | OH | A6 | A6 |
| 2538 | 2-Me-4-MeO—Ph | NH | H | NH | OH | A8 | A8 |
| 2539 | 2-Me-4-MeO—Ph | NH | H | NH | OH | A10 | A10 |
| 2540 | 2-Me-4-MeO—Ph | NH | H | NH | OA2 | A2 | A2 |
| 2541 | 2-Me-4-MeO—Ph | NH | H | NH | OA3 | A3 | A3 |
| 2542 | 2-Me-4-MeO—Ph | NH | H | NH | OA4 | A4 | A4 |
| 2543 | 2-Me-4-MeO—Ph | NH | H | NH | OC6 | H | H |
| 2544 | 2-Me-4-MeO—Ph | NH | H | NH | OC7 | H | H |
| 2545 | 2-Me-4-MeO—Ph | NH | H | NH | OC8 | H | H |
| 2546 | 2-Me-4-MeO—Ph | NH | H | NH | OC10 | H | H |
| 2547 | 2-Me-4-MeO—Ph | NH | H | NH | OC11 | H | H |

TABLE 1-continued (I-1)

| Exemp. Comp. No. | R¹ | X¹ | R² | X² | R³ | R⁶ | R⁷ |
|---|---|---|---|---|---|---|---|
| 2548 | 2-Me-4-MeO—Ph | NH | H | NH | OC12 | H | H |
| 2549 | 2-Me-4-MeO—Ph | NH | H | NH | OC14 | H | H |
| 2550 | 2-Me-4-MeO—Ph | NH | H | NH | OC16 | H | H |
| 2551 | 2-Me-4-MeO—Ph | NH | H | NH | C6CO₃ | H | H |
| 2552 | 2-Me-4-MeO—Ph | NH | H | NH | C7CO₃ | H | H |
| 2553 | 2-Me-4-MeO—Ph | NH | H | NH | C8CO₃ | H | H |
| 2554 | 2-Me-4-MeO—Ph | NH | H | NH | C9CO₃ | H | H |
| 2555 | 2-Me-4-MeO—Ph | NH | H | NH | C10CO₃ | H | H |
| 2556 | 2-Me-4-MeO—Ph | NH | H | NH | C12CO₃ | H | H |
| 2557 | 2-Me-4-MeO—Ph | NH | H | NH | C16CO₃ | H | H |
| 2558 | 2-Me-4-MeO—Ph | NH | C8 | NH | OH | H | H |
| 2559 | 2-Me-4-MeO—Ph | NH | C9 | NH | OH | H | H |
| 2560 | 2-Me-4-MeO—Ph | NH | C10 | NH | OH | H | H |
| 2561 | 2-Me-4-MeO—Ph | NH | C12 | NH | OH | H | H |
| 2562 | 2-Me-4-MeO—Ph | NH | C16 | NH | OH | H | H |
| 2563 | 2-Me-4-MeO—Ph | NH | F1 | NH | OH | H | H |
| 2464 | 2-Me-4-MeO—Ph | NH | F2 | NH | OH | H | H |
| 2565 | 2-Me-4-MeO—Ph | NH | F3 | NH | OH | H | H |
| 2566 | 2-Me-4-MeO—Ph | NH | F4 | NH | OH | H | H |
| 2S67 | 2-Me-4-MeO—Ph | NH | F5 | NH | OH | H | H |
| 2568 | 2-Me-4-MeO—Ph | NH | F6 | NH | OH | H | H |
| 2569 | 2-Me-4-MeO—Ph | NH | F7 | NH | OH | H | H |
| 2570 | 2-Me-4-MeO—Ph | NH | F8 | NH | OH | H | H |
| 2571 | 2-Me-4-MeO—Ph | NH | F9 | NH | OH | H | H |
| 2572 | 2-Me-4-MeO—Ph | NH | F10 | NH | OH | H | H |
| 2573 | 2-Me-4-MeO—Ph | NH | Ph | NH | OH | H | H |
| 2574 | 2-Me-4-MeO—Ph | NH | Bn | NH | OH | H | H |
| 2575 | 2-Me-4-MeO—Ph | NH | Pe | NH | OH | H | H |
| 2576 | 2-Me-4-MeO—Ph | NH | C12 | NMe | OH | H | H |
| 2577 | 2-Me-4-MeO—Ph | NH | C12 | NEt | OH | H | H |
| 2578 | 2-Me-4-MeO—Ph | NH | C12 | NPr | OH | H | H |
| 2579 | 2-Me-4-MeO—Ph | NH | (CH₂)₃ | N | OH | H | H |
| 2580 | 2-Me-4-MeO—Ph | NH | (CH₂)₄ | N | OH | H | H |
| 2581 | 2-Me-4-MeO—Ph | NH | (CH₂)₅ | N | OH | H | H |
| 2582 | 2-Me-4-MeO—Ph | NH | C12 | O | OH | H | H |
| 2583 | 2-Me-4-MeO—Ph | NH | Ph | O | OH | H | H |
| 2584 | 2-Me-4-MeO—Ph | NH | C12 | S | OH | H | H |
| 2585 | 2-Me-4-MeO—Ph | NH | Ph | S | OH | H | H |
| 2586 | 2-Me-4-MeO—Ph | NMe | H | NH | OH | H | H |
| 2587 | 2-Me-4-MeO—Ph | NEt | H | NH | OH | H | H |
| 2588 | 2-Me-4-MeO—Ph | NPr | H | NH | OH | H | H |
| 2589 | 2-Me-4-MeO—Ph | O | H | NH | OH | H | H |
| 2590 | 2-Me-4-MeO—Ph | S | H | NH | OH | H | H |
| 2591 | 3-PhO—Ph | NH | H | NH | H | H | H |
| 2592 | 3-PhO—Ph | NH | H | NH | OH | H | H |
| 2593 | 3-PhO—Ph | NH | H | NH | OA6 | H | H |
| 2594 | 3-PhO—Ph | NH | H | NH | OA8 | H | H |
| 2595 | 3-PhO—Ph | NH | H | NH | OA9 | H | H |
| 2596 | 3-PhO—Ph | NH | H | NH | OA10 | H | H |
| 2597 | 3-PhO—Ph | NH | H | NH | OA12 | H | H |
| 2598 | 3-PhO—Ph | NH | H | NH | OA14 | H | H |
| 2599 | 3-PhO—Ph | NH | H | NH | OA16 | H | H |
| 2600 | 3-PhO—Ph | NH | H | NH | OH | H | A6 |
| 2601 | 3-PhO—Ph | NH | H | NH | OH | H | A8 |
| 2602 | 3-PhO—Ph | NH | H | NH | OH | H | A9 |
| 2603 | 3-PhO—Ph | NH | H | NH | OH | H | A10 |
| 2604 | 3-PhO—Ph | NH | H | NH | OH | H | A12 |
| 2605 | 3-PhO—Ph | NH | H | NH | OH | H | A14 |
| 2606 | 3-PhO—Ph | NH | H | NH | OH | H | A16 |
| 2607 | 3-PhO—Ph | NH | H | NH | OH | A6 | A6 |
| 2608 | 3-PhO—Ph | NH | H | NH | OH | A8 | A8 |
| 2609 | 3-PhO—Ph | NH | H | NH | OH | A10 | A10 |

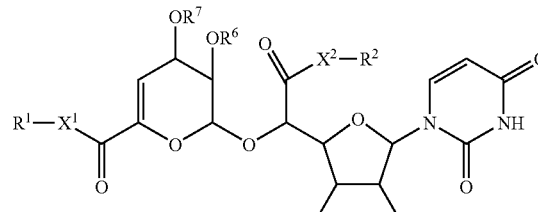

(I-1)

| Exemp. Comp. No. | $R^1$ | $X^1$ | $R^2$ | $X^2$ | $R^3$ | $R^6$ | $R^7$ |
|---|---|---|---|---|---|---|---|
| 2610 | 3-PhO—Ph | NH | H | NH | OA2 | A2 | A2 |
| 2611 | 3-PhO—Ph | NH | H | NH | OA3 | A3 | A3 |
| 2612 | 3-PhO—Ph | NH | H | NH | OA4 | A4 | A4 |
| 2613 | 3-PhO—Ph | NH | H | NH | OC6 | H | H |
| 2614 | 3-PhO—Ph | NH | H | NH | OC7 | H | H |
| 2615 | 3-PhO—Ph | NH | H | NH | OC8 | H | H |
| 2616 | 3-PhO—Ph | NH | H | NH | OC10 | H | H |
| 2617 | 3-PhO—Ph | NH | H | NH | OC11 | H | H |
| 2618 | 3-PhO—Ph | NH | H | NH | OC12 | H | H |
| 2619 | 3-PhO—Ph | NH | H | NH | OC14 | H | H |
| 2620 | 3-PhO—Ph | NH | H | NH | OC16 | H | H |
| 2621 | 3-PhO—Ph | NH | H | NH | C6CO$_3$ | H | H |
| 2622 | 3-PhO—Ph | NH | H | NH | C7CO$_3$ | H | H |
| 2623 | 3-PhO—Ph | NH | H | NH | C8CO$_3$ | H | H |
| 2624 | 3-PhO—Ph | NH | H | NH | C9CO$_3$ | H | H |
| 2625 | 3-PhO—Ph | NH | H | NH | C10CO$_3$ | H | H |
| 2626 | 3-PhO—Ph | NH | H | NH | C12CO$_3$ | H | H |
| 2627 | 3-PhO—Ph | NH | H | NH | C16CO$_3$ | H | H |
| 2628 | 3-PhO—Ph | NH | C8 | NH | OH | H | H |
| 2629 | 3-PhO—Ph | NH | C9 | NH | OH | H | H |
| 2630 | 3-PhO—Ph | NH | C10 | NH | OH | H | H |
| 2631 | 3-PhO—Ph | NH | C12 | NH | OH | H | H |
| 2632 | 3-PhO—Ph | NH | C16 | NH | OH | H | H |
| 2633 | 3-PhO—Ph | NH | F1 | NH | OH | H | H |
| 2634 | 3-PhO—Ph | NH | F2 | NH | OH | H | H |
| 2635 | 3-PhO—Ph | NH | F3 | NH | OH | H | H |
| 2636 | 3-PhO—Ph | NH | F4 | NH | OH | H | H |
| 2637 | 3-PhO—Ph | NH | F5 | NH | OH | H | H |
| 2638 | 3-PhO—Ph | NH | F6 | NH | OH | H | H |
| 2639 | 3-PhO—Ph | NH | F7 | NH | OH | H | H |
| 2640 | 3-PhO—Ph | NH | F8 | NH | OH | H | H |
| 2641 | 3-PhO—Ph | NH | F9 | NH | OH | H | H |
| 2642 | 3-PhO—Ph | NH | F10 | NH | OH | H | H |
| 2643 | 3-PhO—Ph | NH | Ph | NH | OH | H | H |
| 2644 | 3-PhO—Ph | NH | Bn | NH | OH | H | H |
| 2645 | 3-PhO—Ph | NH | Pe | NH | OH | H | H |
| 2646 | 3-PhO—Ph | NH | C12 | NMe | OH | H | H |
| 2647 | 3-PhO—Ph | NH | C12 | NEt | OH | H | H |
| 2648 | 3-PhO—Ph | NH | C12 | NPr | OH | H | H |
| 2649 | 3-PhO—Ph | NH | (CH$_2$)$_3$ | N | OH | H | H |
| 2650 | 3-PhO—Ph | NH | (CH$_2$)$_4$ | N | OH | H | H |
| 2651 | 3-PhO—Ph | NH | (CH$_2$)$_5$ | N | OH | H | H |
| 2652 | 3-PhO—Ph | NH | C12 | O | OH | H | H |
| 2653 | 3-PhO—Ph | NH | Ph | O | OH | H | H |
| 2654 | 3-PhO—Ph | NH | C12 | S | OH | H | H |
| 2655 | 3-PhO—Ph | NH | Ph | S | OH | H | H |
| 2656 | 3-PhO—Ph | NMe | H | NH | OH | H | H |
| 2657 | 3-PhO—Ph | NEt | H | NH | OH | H | H |
| 2658 | 3-PhO—Ph | NPr | H | NH | OH | H | H |
| 2659 | 3-PhO—Ph | O | H | NH | OH | H | H |
| 2660 | 3-PhO—Ph | S | H | NH | OH | H | H |
| 2661 | 3,4-(OCH$_2$O)—Ph | NH | H | NH | H | H | H |
| 2662 | 3,4-(OCH$_2$O)—Ph | NH | H | NH | OH | H | H |
| 2663 | 3,4-(OCH$_2$O)—Ph | NH | H | NH | OA6 | H | H |
| 2664 | 3,4-(OCH$_2$O)—Ph | NH | H | NH | OA8 | H | H |
| 2665 | 3,4-(OCH$_2$O)—Ph | NH | H | NH | OA9 | H | H |
| 2666 | 3,4-(OCH$_2$O)—Ph | NH | H | NH | OA10 | H | H |
| 2667 | 3,4-(OCH$_2$O)—Ph | NH | H | NH | OA12 | H | H |
| 2668 | 3,4-(OCH$_2$O)—Ph | NH | H | NH | OA14 | H | H |
| 2669 | 3,4-(OCH$_2$O)—Ph | NH | H | NH | OA16 | H | H |
| 2670 | 3,4-(OCH$_2$O)—Ph | NH | H | NH | OH | H | A6 |
| 2671 | 3,4-(OCH$_2$O)—Ph | NH | H | NH | OH | H | A8 |

TABLE 1-continued

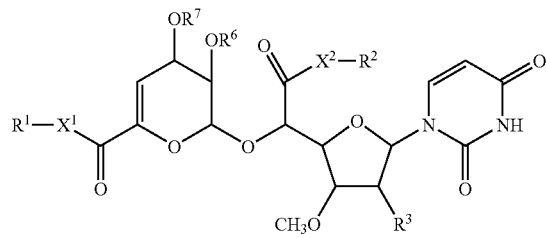
(I-1)

| Exemp. Comp. No. | R¹ | X¹ | R² | X² | R³ | R⁶ | R⁷ |
|---|---|---|---|---|---|---|---|
| 2672 | 3,4-(OCH₂O)—Ph | NH | H | NH | OH | H | A9 |
| 2673 | 3,4-(OCH₂O)—Ph | NH | H | NH | OH | H | A10 |
| 2674 | 3,4-(OCH₂O)—Ph | NH | H | NH | OH | H | A12 |
| 2675 | 3,4-(OCH₂O)—Ph | NH | H | NH | OH | H | A14 |
| 2676 | 3,4-(OCH₂O)—Ph | NH | H | NH | OH | H | A16 |
| 2677 | 3,4-(OCH₂O)—Ph | NH | H | NH | OH | A6 | A6 |
| 2678 | 3,4-(OCH₂O)—Ph | NH | H | NH | OH | A8 | A8 |
| 2679 | 3,4-(OCH₂O)—Ph | NH | H | NH | OH | A10 | A10 |
| 2680 | 3,4-(OCH₂O)—Ph | NH | H | NH | OA2 | A2 | A2 |
| 2681 | 3,4-(OCH₂O)—Ph | NH | H | NH | OA3 | A3 | A3 |
| 2682 | 3,4-(OCH₂O)—Ph | NH | H | NH | OA4 | A4 | A4 |
| 2683 | 3,4-(OCH₂O)—Ph | NH | H | NH | OC6 | H | H |
| 2684 | 3,4-(OCH₂O)—Ph | NH | H | NH | OC7 | H | H |
| 2685 | 3,4-(OCH₂O)—Ph | NH | H | NH | OC8 | H | H |
| 2686 | 3,4-(OCH₂O)—Ph | NH | H | NH | OC10 | H | H |
| 2687 | 3,4-(OCH₂O)—Ph | NH | H | NH | OC11 | H | H |
| 2688 | 3,4-(OCH₂O)—Ph | NH | H | NH | OC12 | H | H |
| 2689 | 3,4-(OCH₂O)—Ph | NH | H | NH | OC14 | H | H |
| 2690 | 3,4-(OCH₂O)—Ph | NH | H | NH | OC16 | H | H |
| 2691 | 3,4-(OCH₂O)—Ph | NH | H | NH | C6CO₃ | H | H |
| 2692 | 3,4-(OCH₂O)—Ph | NH | H | NH | C7CO₃ | H | H |
| 2693 | 3,4-(OCH₂O)—Ph | NH | H | NH | C8CO₃ | H | H |
| 2694 | 3,4-(OCH₂O)—Ph | NH | H | NH | C9CO₃ | H | H |
| 2695 | 3,4-(OCH₂O)—Ph | NH | H | NH | C10CO₃ | H | H |
| 2696 | 3,4-(OCH₂O)—Ph | NH | H | NH | C12CO₃ | H | H |
| 2697 | 3,4-(OCH₂O)—Ph | NH | H | NH | C16CO₃ | H | H |
| 2698 | 3,4-(OCH₂O)—Ph | NH | C8 | NH | OH | H | H |
| 2699 | 3,4-(OCH₂O)—Ph | NH | C9 | NH | OH | H | H |
| 2700 | 3,4-(OCH₂O)—Ph | NH | C10 | NH | OH | H | H |
| 2701 | 3,4-(OCH₂O)—Ph | NH | C12 | NH | OH | H | H |
| 2702 | 3,4-(OCH₂O)—Ph | NH | C16 | NH | OH | H | H |
| 2703 | 3,4-(OCH₂O)—Ph | NH | F1 | NH | OH | H | H |
| 2704 | 3,4-(OCH₂O)—Ph | NH | F2 | NH | OH | H | H |
| 2705 | 3,4-(OCH₂O)—Ph | NH | F3 | NH | OH | H | H |
| 2706 | 3,4-(OCH₂O)—Ph | NH | F4 | NH | OH | H | H |
| 2707 | 3,4-(OCH₂O)—Ph | NH | F5 | NH | OH | H | H |
| 2708 | 3,4-(OCH₂O)—Ph | NH | F6 | NH | OH | H | H |
| 2709 | 3,4-(OCH₂O)—Ph | NH | F7 | NH | OH | H | H |
| 2710 | 3,4-(OCH₂O)—Ph | NH | F8 | NH | OH | H | H |
| 2711 | 3,4-(OCH₂O)—Ph | NH | F9 | NH | OH | H | H |
| 2712 | 3,4-(OCH₂O)—Ph | NH | F10 | NH | OH | H | H |
| 2713 | 3,4-(OCH₂O)—Ph | NH | Ph | NH | OH | H | H |
| 2714 | 3,4-(OCH₂O)—Ph | NH | Bn | NH | OH | H | H |
| 2715 | 3,4-(OCH₂O)—Ph | NH | Pe | NH | OH | H | H |
| 2716 | 3,4-(OCH₂O)—Ph | NH | C12 | NMe | OH | H | H |
| 2717 | 3,4-(OCH₂O)—Ph | NH | C12 | NEt | OH | H | H |
| 2718 | 3,4-(OCH₂O)—Ph | NH | C12 | NPr | OH | H | H |
| 2719 | 3,4-(OCH₂O)—Ph | NH | (CH₂)₃ | N | OH | H | H |
| 2720 | 3,4-(OCH₂O)—Ph | NH | (CH₂)₄ | N | OH | H | H |
| 2721 | 3,4-(OCH₂O)—Ph | NH | (CH₂)₅ | N | OH | H | H |
| 2722 | 3,4-(OCH₂O)—Ph | NH | C12 | O | OH | H | H |
| 2723 | 3,4-(OCH₂O)—Ph | NH | Ph | O | OH | H | H |
| 2724 | 3,4-(OCH₂O)—Ph | NH | C12 | S | OH | H | H |
| 2725 | 3,4-(OCH₂O)—Ph | NH | Ph | S | OH | H | H |
| 2726 | 3,4-(OCH₂O)—Ph | NMe | H | NH | OH | H | H |
| 2727 | 3,4-(OCH₂O)—Ph | NEt | H | NH | OH | H | H |
| 2728 | 3,4-(OCH₂O)—Ph | NPr | H | NH | OH | H | H |
| 2729 | 3,4-(OCH₂O)—Ph | O | H | NH | OH | H | H |
| 2730 | 3,4-(OCH₂O)—Ph | S | H | NH | OH | H | H |
| 2731 | 3,5-(MeO)₂—Ph | NH | H | NH | H | H | H |
| 2732 | 3,5-(MeO)₂—Ph | NH | H | NH | OH | H | H |
| 2733 | 3,5-(MeO)₂—Ph | NH | H | NH | OA6 | H | H |

TABLE 1-continued (I-1)

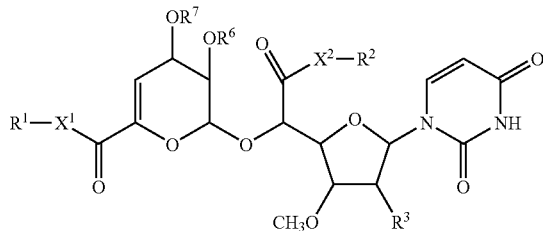

| Exemp. Comp. No. | R¹ | X¹ | R² | X² | R³ | R⁶ | R⁷ |
|---|---|---|---|---|---|---|---|
| 2734 | 3,5-(MeO)₂—Ph | NH | H | NH | OA8 | H | H |
| 2735 | 3,5-(MeO)₂—Ph | NH | H | NH | OA9 | H | H |
| 2736 | 3,5-(MeO)₂—Ph | NH | H | NH | OA10 | H | H |
| 2737 | 3,5-(MeO)₂—Ph | NH | H | NH | OA12 | H | H |
| 2738 | 3,5-(MeO)₂—Ph | NH | H | NH | OA14 | H | H |
| 2739 | 3,5-(MeO)₂—Ph | NH | H | NH | OA16 | H | H |
| 2740 | 3,5-(MeO)₂—Ph | NH | H | NH | OH | H | A6 |
| 2741 | 3,5-(MeO)₂—Ph | NH | H | NH | OH | H | A8 |
| 2742 | 3,5-(MeO)₂—Ph | NH | H | NH | OH | H | A9 |
| 2743 | 3,5-(MeO)₂—Ph | NH | H | NH | OH | H | A10 |
| 2744 | 3,5-(MeO)₂—Ph | NH | H | NH | OH | H | A12 |
| 2745 | 3,5-(MeO)₂—Ph | NH | H | NH | OH | H | A14 |
| 2746 | 3,5-(MeO)₂—Ph | NH | H | NH | OH | H | A16 |
| 2747 | 3,5-(MeO)₂—Ph | NH | H | NH | OH | A6 | A6 |
| 2748 | 3,5-(MeO)₂—Ph | NH | H | NH | OH | A8 | A8 |
| 2749 | 3,5-(MeO)₂—Ph | NH | H | NH | OH | A10 | A10 |
| 2750 | 3,5-(MeO)₂—Ph | NH | H | NH | OA2 | A2 | A2 |
| 2751 | 3,5-(MeO)₂—Ph | NH | H | NH | OA3 | A3 | A3 |
| 2752 | 3,5-(MeO)₂—Ph | NH | H | NH | OA4 | A4 | A4 |
| 2753 | 3,5-(MeO)₂—Ph | NH | H | NH | OC6 | H | H |
| 2754 | 3,5-(MeO)₂—Ph | NH | H | NH | OC7 | H | H |
| 2755 | 3,5-(MeO)₂—Ph | NH | H | NH | OC8 | H | H |
| 2756 | 3,5-(MeO)₂—Ph | NH | H | NH | OC10 | H | H |
| 2757 | 3,5-(MeO)₂—Ph | NH | H | NH | OC11 | H | H |
| 2758 | 3,5-(MeO)₂—Ph | NH | H | NH, | OC12 | H | H |
| 2759 | 3,5-(MeO)₂—Ph | NH | H | NH | OC14 | H | H |
| 2760 | 3,5-(MeO)₂—Ph | NH | H | NH | OC16 | H | H |
| 2761 | 3,5-(MeO)₂—Ph | NH | H | NH | C6CO₃ | H | H |
| 2762 | 3,5-(MeO)₂—Ph | NH | H | NH | C7CO₃ | H | H |
| 2763 | 3,5-(MeO)₂—Ph | NH | H | NH | C8CO₃ | H | H |
| 2764 | 3,5-(MeO)₂—Ph | NH | H | NH | C9CO₃ | H | H |
| 2765 | 3,5-(MeO)₂—Ph | NH | H | NH | C10CO₃ | H | H |
| 2766 | 3,5-(MeO)₂—Ph | NH | H | NH | C12CO₃ | H | H |
| 2767 | 3,5-(MeO)₂—Ph | NH | H | NH | C16CO₃ | H | H |
| 2768 | 3,5-(MeO)₂—Ph | NH | C8 | NH | OH | H | H |
| 2769 | 3,5-(MeO)₂—Ph | NH | C9 | NH | OH | H | H |
| 2770 | 3,5-(MeO)₂—Ph | NH | C10 | NH | OH | H | H |
| 2771 | 3,5-(MeO)₂—Ph | NH | C12 | NH | OH | H | H |
| 2772 | 3,5-(MeO)₂—Ph | NH | C16 | NH | OH | H | H |
| 2773 | 3,5-(MeO)₂—Ph | NH | F1 | NH | OH | H | H |
| 2774 | 3,5-(MeO)₂—Ph | NH | F2 | NH | OH | H | H |
| 2775 | 3,5-(MeO)₂—Ph | NH | F3 | NH | OH | H | H |
| 2776 | 3,5-(MeO)₂—Ph | NH | F4 | NH | OH | H | H |
| 2777 | 3,5-(MeO)₂—Ph | NH | F5 | NH | OH | H | H |
| 2778 | 3,5-(MeO)₂—Ph | NH | F6 | NH | OH | H | H |
| 2779 | 3,5-(MeO)₂—Ph | NH | F7 | NH | OH | H | H |
| 2780 | 3,5-(MeO)₂—Ph | NH | F8 | NH | OH | H | H |
| 2781 | 3,5-(MeO)₂—Ph | NH | F9 | NH | OH | H | H |
| 2782 | 3,5-(MeO)₂—Ph | NH | F10 | NH | OH | H | H |
| 2783 | 3,5-(MeO)₂—Ph | NH | Ph | NH | OH | H | H |
| 2784 | 3,5-(MeO)₂—Ph | NH | Bn | NH | OH | H | H |
| 2785 | 3,5-(MeO)₂—Ph | NH | Pe | NH | OH | H | H |
| 2786 | 3,5-(MeO)₂—Ph | NH | C12 | NMe | OH | H | H |
| 2787 | 3,5-(MeO)₂—Ph | NH | C12 | NEt | OH | H | H |
| 2788 | 3,5-(MeO)₂—Ph | NH | C12 | NPr | OH | H | H |
| 2789 | 3,5-(MeO)₂—Ph | NH | (CH₂)₃ | N | OH | H | H |
| 2790 | 3,5-(MeO)₂—Ph | NH | (CH₂)₄ | N | OH | H | H |
| 2791 | 3,5-(MeO)₂—Ph | NH | (CH₂)₅ | N | OH | H | H |
| 2792 | 3,5-(MeO)₂—Ph | NH | C12 | O | OH | H | H |
| 2793 | 3,5-(MeO)₂—Ph | NH | Ph | O | OH | H | H |
| 2794 | 3,5-(MeO)₂—Ph | NH | C12 | S | OH | H | H |
| 2795 | 3,5-(MeO)₂—Ph | NH | Ph | S | OH | H | H |

TABLE 1-continued (I-1)

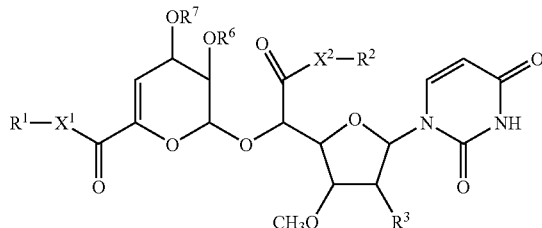

| Exemp. Comp. No. | R¹ | X¹ | R² | X² | R³ | R⁶ | R⁷ |
|---|---|---|---|---|---|---|---|
| 2796 | 3,5-(MeO)₂—Ph | NMe | H | NH | OH | H | H |
| 2797 | 3,5-(MeO)₂—Ph | NEt | H | NH | OH | H | H |
| 2798 | 3,5-(MeO)₂—Ph | NPr | H | NH | OH | H | H |
| 2799 | 3,5-(MeO)₂—Ph | O | H | NH | OH | H | H |
| 2800 | 3,5-(MeO)₂—Ph | S | H | NH | OH | H | H |
| 2801 | 3,4,5-(MeO)₃—Ph | NH | H | NH | H | H | H |
| 2802 | 3,4,5-(MeO)₃—Ph | NH | H | NH | OH | H | H |
| 2803 | 3,4,5-(MeO)₃—Ph | NH | H | NH | OA6 | H | H |
| 2804 | 3,4,5-(MeO)₃—Ph | NH | H | NH | OA8 | H | H |
| 2805 | 3,4,5-(MeO)₃—Ph | NH | H | NH | OA9 | H | H |
| 2806 | 3,4,5-(MeO)₃—Ph | NH | H | NH | OA10 | H | H |
| 2807 | 3,4,5-(MeO)₃—Ph | NH | H | NH | OA12 | H | H |
| 2808 | 3,4,5-(MeO)₃—Ph | NH | H | NH | OA14 | H | H |
| 2809 | 3,4,5-(MeO)₃—Ph | NH | H | NH | OA16 | H | H |
| 2810 | 3,4,5-(MeO)₃—Ph | NH | H | NH | OH | H | A6 |
| 2811 | 3,4,5-(MeO)₃—Ph | NH | H | NH | OH | H | A8 |
| 2812 | 3,4,5-(MeO)₃—Ph | NH | H | NH | OH | H | A9 |
| 2813 | 3,4,5-(MeO)₃—Ph | NH | H | NH | OH | H | A10 |
| 2814 | 3,4,5-(MeO)₃—Ph | NH | H | NH | OH | H | A12 |
| 2815 | 3,4,5-(MeO)₃—Ph | NH | H | NH | OH | H | A14 |
| 2816 | 3,4,5-(MeO)₃—Ph | NH | H | NH | OH | H | A16 |
| 2817 | 3,4,5-(MeO)₃—Ph | NH | H | NH | OH | A6 | A6 |
| 2818 | 3,4,5-(MeO)₃—Ph | NH | H | NH | OH | A8 | A8 |
| 2819 | 3,4,5-(MeO)₃—Ph | NH | H | NH | OH | A10 | A10 |
| 2820 | 3,4,5-(MeO)₃—Ph | NH | H | NH | OA2 | A2 | A2 |
| 2821 | 3,4,5-(MeO)₃—Ph | NH | H | NH | OA3 | A3 | A3 |
| 2822 | 3,4,5-(MeO)₃—Ph | NH | H | NH | OA4 | A4 | A4 |
| 2823 | 3,4,5-(MeO)₃—Ph | NH | H | NH | OC6 | H | H |
| 2824 | 3,4,5-(MeO)₃—Ph | NH | H | NH | OC7 | H | H |
| 2825 | 3,4,5-(MeO)₃—Ph | NH | H | NH | OC8 | H | H |
| 2826 | 3,4,5-(MeO)₃—Ph | NH | H | NH | OC10 | H | H |
| 2827 | 3,4,5-(MeO)₃—Ph | NH | H | NH | OC11 | H | H |
| 2828 | 3,4,5-(MeO)₃—Ph | NH | H | NH | OC12 | H | H |
| 2829 | 3,4,5-(MeO)₃—Ph | NH | H | NH | OC14 | H | H |
| 2830 | 3,4,5-(MeO)₃—Ph | NH | H | NH | OC16 | H | H |
| 2831 | 3,4,5-(MeO)₃—Ph | NH | H | NH | C6CO₃ | H | H |
| 2832 | 3,4,5-(MeO)₃—Ph | NH | H | NH | C7CO₃ | H | H |
| 2833 | 3,4,5-(MeO)₃—Ph | NH | H | NH | C8CO₃ | H | H |
| 2834 | 3,4,5-(MeO)₃—Ph | NH | H | NH | C9CO₃ | H | H |
| 2835 | 3,4,5-(MeO)₃—Ph | NH | H | NH | C10CO₃ | H | H |
| 2836 | 3,4,5-(MeO)₃—Ph | NH | H | NH | C12CO₃ | H | H |
| 2837 | 3,4,5-(MeO)₃—Ph | NH | H | NH | C16CO₃ | H | H |
| 2838 | 3,4,5-(MeO)₃—Ph | NH | C8 | NH | OH | H | H |
| 2839 | 3,4,5-(MeO)₃—Ph | NH | C9 | NH | OH | H | H |
| 2840 | 3,4,5-(MeO)₃—Ph | NH | C10 | NH | OH | H | H |
| 2841 | 3,4,5-(MeO)₃—Ph | NH | C12 | NH | OH | H | H |
| 2842 | 3,4,5-(MeO)₃—Ph | NH | C16 | NH | OH | H | H |
| 2843 | 3,4,5-(MeO)₃—Ph | NH | F1 | NH | OH | H | H |
| 2844 | 3,4,5-(MeO)₃—Ph | NH | F2 | NH | OH | H | H |
| 2845 | 3,4,5-(MeO)₃—Ph | NH | F3 | NH | OH | H | H |
| 2846 | 3,4,5-(MeO)₃—Ph | NH | F4 | NH | OH | H | H |
| 2847 | 3,4,5-(MeO)₃—Ph | NH | F5 | NH | OH | H | H |
| 2848 | 3,4,5-(MeO)₃—Ph | NH | F6 | NH | OH | H | H |
| 2849 | 3,4,5-(MeO)₃—Ph | NH | F7 | NH | OH | H | H |
| 2850 | 3,4,5-(MeO)₃—Ph | NH | F8 | NH | OH | H | H |
| 2851 | 3,4,5-(MeO)₃—Ph | NH | F9 | NH | OH | H | H |
| 2852 | 3,4,5-(MeO)₃—Ph | NH | F10 | NH | OH | H | H |
| 2853 | 3,4,5-(MeO)₃—Ph | NH | Ph | NH | OH | H | H |
| 2854 | 3,4,5-(MeO)₃—Ph | NH | Bn | NH | OH | H | H |
| 2855 | 3,4,5-(MeO)₃—Ph | NH | Pe | NH | OH | H | H |
| 2856 | 3,4,5-(MeO)₃—Ph | NH | C12 | NMe | OH | H | H |
| 2857 | 3,4,5-(MeO)₃—Ph | NH | C12 | NEt | OH | H | H |

TABLE 1-continued (I-1)

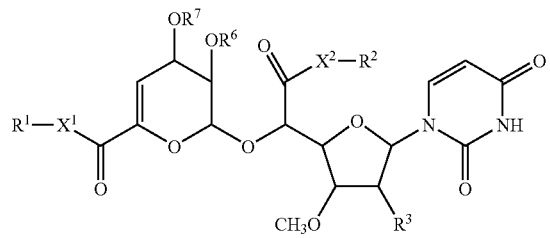

| Exemp. Comp. No. | R¹ | X¹ | R² | X² | R³ | R⁶ | R⁷ |
|---|---|---|---|---|---|---|---|
| 2858 | 3,4,5-(MeO)₃—Ph | NH | C12 | NPr | OH | H | H |
| 2859 | 3,4,5-(MeO)₃—Ph | NH | (CH₂)₃ | N | OH | H | H |
| 2860 | 3,4,5-(MeO)₃—Ph | NH | (CH₂)₄ | N | OH | H | H |
| 2861 | 3,4,5-(MeO)₃—Ph | NH | (CH₂)₅ | N | OH | H | H |
| 2862 | 3,4,5-(MeO)₃—Ph | NH | C12 | O | OH | H | H |
| 2863 | 3,4,5-(MeO)₃—Ph | NH | Ph | O | OH | H | H |
| 2864 | 3,4,5-(MeO)₃—Ph | NH | C12 | S | OH | H | H |
| 2865 | 3,4,5-(MeO)₃—Ph | NH | Ph | S | OH | H | H |
| 2866 | 3,4,5-(MeO)₃—Ph | NMe | H | NH | OH | H | H |
| 2867 | 3,4,5-(MeO)₃—Ph | NEt | H | NH | OH | H | H |
| 2868 | 3,4,5-(MeO)₃—Ph | NPr | H | NH | OH | H | H |
| 2869 | 3,4,5-(MeO)₃—Ph | O | H | NH | OH | H | H |
| 2870 | 3,4,5-(MeO)₃—Ph | S | H | NH | OH | H | H |
| 2871 | 2-F—Ph | NH | H | NH | H | H | H |
| 2872 | 2-F—Ph | NH | H | NH | OH | H | H |
| 2873 | 2-F—Ph | NH | H | NH | OA6 | H | H |
| 2874 | 2-F—Ph | NH | H | NH | OA8 | H | H |
| 2875 | 2-F—Ph | NH | H | NH | OA9 | H | H |
| 2876 | 2-F—Ph | NH | H | NH | OA10 | H | H |
| 2877 | 2-F—Ph | NH | H | NH | OA12 | H | H |
| 2878 | 2-F—Ph | NH | H | NH | OA14 | H | H |
| 2879 | 2-F—Ph | NH | H | NH | OA16 | H | H |
| 2880 | 2-F—Ph | NH | H | NH | OH | H | A6 |
| 2881 | 2-F—Ph | NH | H | NH | OH | H | A8 |
| 2882 | 2-F—Ph | NH | H | NH | OH | H | A9 |
| 2883 | 2-F—Ph | NH | H | NH | OH | H | A10 |
| 2884 | 2-F—Ph | NH | H | NH | OH | H | A12 |
| 2885 | 2-F—Ph | NH | H | NH | OH | H | A14 |
| 2886 | 2-F—Ph | NH | H | NH | OH | H | A16 |
| 2887 | 2-F—Ph | NH | H | NH | OH | A6 | A6 |
| 2888 | 2-F—Ph | NH | H | NH | OH | A8 | A8 |
| 2889 | 2-F—Ph | NH | H | NH | OH | A10 | A10 |
| 2890 | 2-F—Ph | NH | H | NH | OA2 | A2 | A2 |
| 2891 | 2-F—Ph | NH | H | NH | OA3 | A3 | A3 |
| 2892 | 2-F—Ph | NH | H | NH | OA4 | A4 | A4 |
| 2893 | 2-F—Ph | NH | H | NH | OC6 | H | H |
| 2894 | 2-F—Ph | NH | H | NH | OC7 | H | H |
| 2895 | 2-F—Ph | NH | H | NH | OC8 | H | H |
| 2896 | 2-F—Ph | NH | H | NH | OC10 | H | H |
| 2897 | 2-F—Ph | NH | H | NH | OC11 | H | H |
| 2898 | 2-F—Ph | NH | H | NH | OC12 | H | H |
| 2899 | 2-F—Ph | NH | H | NH | OC14 | H | H |
| 2900 | 2-F—Ph | NH | H | NH | OC16 | H | H |
| 2901 | 2-F—Ph | NH | H | NH | C6CO₃ | H | H |
| 2902 | 2-F—Ph | NH | H | NH | C7CO₃ | H | H |
| 2903 | 2-F—Ph | NH | H | NH | C8CO₃ | H | H |
| 2904 | 2-F—Ph | NH | H | NH | C9CO₃ | H | H |
| 2905 | 2-F—Ph | NH | H | NH | C10CO₃ | H | H |
| 2906 | 2-F—Ph | NH | H | NH | C12CO₃ | H | H |
| 2907 | 2-F—Ph | NH | H | NH | C16CO₃ | H | H |
| 2908 | 2-F—Ph | NH | C8 | NH | OH | H | H |
| 2909 | 2-F—Ph | NH | C9 | NH | OH | H | H |
| 2910 | 2-F—Ph | NH | C10 | NH | OH | H | H |
| 2911 | 2-F—Ph | NH | C12 | NH | OH | H | H |
| 2912 | 2-F—Ph | NH | C16 | NH | OH | H | H |
| 2913 | 2-F—Ph | NH | F1 | NH | OH | H | H |
| 2914 | 2-F—Ph | NH | F2 | NH | OH | H | H |
| 2915 | 2-F—Ph | NH | F3 | NH | OH | H | H |
| 2916 | 2-F—Ph | NH | F4 | NH | OH | H | H |
| 2917 | 2-F—Ph | NH | F5 | NH | OH | H | H |
| 2918 | 2-F—Ph | NH | F6 | NH | OH | H | H |
| 2919 | 2-F—Ph | NH | F7 | NH | OH | H | H |

TABLE 1-continued (I-1)

| Exemp. Comp. No. | R¹ | X¹ | R² | X² | R³ | R⁶ | R⁷ |
|---|---|---|---|---|---|---|---|
| 2920 | 2-F—Ph | NH | F8 | NH | OH | H | H |
| 2921 | 2-F—Ph | NH | F9 | NH | OH | H | H |
| 2922 | 2-F—Ph | NH | F10 | NH | OH | H | H |
| 2923 | 2-F—Ph | NH | Ph | NH | OH | H | H |
| 2924 | 2-F—Ph | NH | Bn | NH | OH | H | H |
| 2925 | 2-F—Ph | NH | Pe | NH | OH | H | H |
| 2926 | 2-F—Ph | NH | C12 | NMe | OH | H | H |
| 2927 | 2-F—Ph | NH | C12 | NEt | OH | H | H |
| 2928 | 2-F—Ph | NH | C12 | NPr | OH | H | H |
| 2929 | 2-F—Ph | NH | (CH₂)₃ | N | OH | H | H |
| 2930 | 2-F—Ph | NH | (CH₂)₄ | N | OH | H | H |
| 2931 | 2-F—Ph | NH | (CH₂)₅ | N | OH | H | H |
| 2932 | 2-F—Ph | NH | C12 | O | OH | H | H |
| 2933 | 2-F—Ph | NH | Ph | O | OH | H | H |
| 2934 | 2-F—Ph | NH | C12 | S | OH | H | H |
| 2935 | 2-F—Ph | NH | Ph | S | OH | H | H |
| 2936 | 2-F—Ph | NMe | H | NH | OH | H | H |
| 2937 | 2-F—Ph | NEt | H | NH | OH | H | H |
| 2938 | 2-F—Ph | NPr | H | NH | OH | H | H |
| 2939 | 2-F—Ph | O | H | NH | OH | H | H |
| 2940 | 2-F—Ph | S | H | NH | OH | H | H |
| 2941 | 3-F—Ph | NH | H | NH | H | H | H |
| 2942 | 3-F—Ph | NH | H | NH | OH | H | H |
| 2943 | 3-F—Ph | NH | H | NH | OA6 | H | H |
| 2944 | 3-F—Ph | NH | H | NH | OA8 | H | H |
| 2945 | 3-F—Ph | NH | H | NH | OA9 | H | H |
| 2946 | 3-F—Ph | NH | H | NH | OA10 | H | H |
| 2947 | 3-F—Ph | NH | H | NH | OA12 | H | H |
| 2948 | 3-F—Ph | NH | H | NH | OA14 | H | H |
| 2949 | 3-F—Ph | NH | H | NH | OA16 | H | H |
| 2950 | 3-F—Ph | NH | H | NH | OH | H | A6 |
| 2951 | 3-F—Ph | NH | H | NH | OH | H | A8 |
| 2952 | 3-F—Ph | NH | H | NH | OH | H | A9 |
| 2953 | 3-F—Ph | NH | H | NH | OH | H | A10 |
| 2954 | 3-F—Ph | NH | H | NH | OH | H | A12 |
| 2955 | 3-F—Ph | NH | H | NH | OH | H | A14 |
| 2956 | 3-F—Ph | NH | H | NH | OH | H | A16 |
| 2957 | 3-F—Ph | NH | H | NH | OH | A6 | A6 |
| 2958 | 3-F—Ph | NH | H | NH | OH | A8 | A8 |
| 2959 | 3-F—Ph | NH | H | NH | OH | A10 | A10 |
| 2960 | 3-F—Ph | NH | H | NH | OA2 | A2 | A2 |
| 2961 | 3-F—Ph | NH | H | NH | OA3 | A3 | A3 |
| 2962 | 3-F—Ph | NH | H | NH | OA4 | A4 | A4 |
| 2963 | 3-F—Ph | NH | H | NH | OC6 | H | H |
| 2964 | 3-F—Ph | NH | H | NH | OC7 | H | H |
| 2965 | 3-F—Ph | NH | H | NH | OC8 | H | H |
| 2966 | 3-F—Ph | NH | H | NH | OC10 | H | H |
| 2967 | 3-F—Ph | NH | H | NH | OC11 | H | H |
| 2968 | 3-F—Ph | NH | H | NH | OC12 | H | H |
| 2969 | 3-F—Ph | NH | H | NH | OC14 | H | H |
| 2970 | 3-F—Ph | NH | H | NH | OC16 | H | H |
| 2971 | 3-F—Ph | NH | H | NH | C6CO₃ | H | H |
| 2972 | 3-F—Ph | NH | H | NH | C7CO₃ | H | H |
| 2973 | 3-F—Ph | NH | H | NH | C8CO₃ | H | H |
| 2974 | 3-F—Ph | NH | H | NH | C9CO₃ | H | H |
| 2975 | 3-F—Ph | NH | H | NH | C10CO₃ | H | H |
| 2976 | 3-F—Ph | NH | H | NH | C12CO₃ | H | H |
| 2977 | 3-F—Ph | NH | H | NH | C16CO₃ | H | H |
| 2978 | 3-F—Ph | NH | C8 | NH | OH | H | H |
| 2979 | 3-F—Ph | NH | C9 | NH | OH | H | H |
| 2980 | 3-F—Ph | NH | C10 | NH | OH | H | H |
| 2981 | 3-F—Ph | NH | C12 | NH | OH | H | H |

TABLE 1-continued

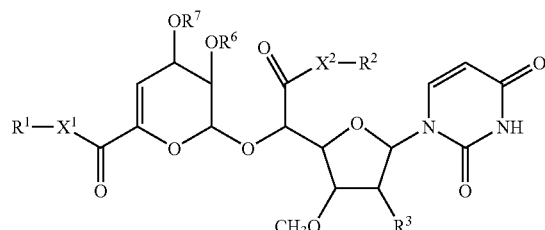

(I-1)

| Exemp. Comp. No. | R$^1$ | X$^1$ | R$^2$ | X$^2$ | R$^3$ | R$^6$ | R$^7$ |
|---|---|---|---|---|---|---|---|
| 2982 | 3-F—Ph | NH | C16 | NH | OH | H | H |
| 2983 | 3-F—Ph | NH | F1 | NH | OH | H | H |
| 2984 | 3-F—Ph | NH | F2 | NH | OH | H | H |
| 2985 | 3-F—Ph | NH | F3 | NH | OH | H | H |
| 2986 | 3-F—Ph | NH | F4 | NH | OH | H | H |
| 2987 | 3-F—Ph | NH | F5 | NH | OH | H | H |
| 2988 | 3-F—Ph | NH | F6 | NH | OH | H | H |
| 2989 | 3-F—Ph | NH | F7 | NH | OH | H | H |
| 2990 | 3-F—Ph | NH | F8 | NH | OH | H | H |
| 2991 | 3-F—Ph | NH | F9 | NH | OH | H | H |
| 2992 | 3-F—Ph | NH | F10 | NH | OH | H | H |
| 2993 | 3-F—Ph | NH | Ph | NH | OH | H | H |
| 2994 | 3-F—Ph | NH | Bn | NH | OH | H | H |
| 2995 | 3-F—Ph | NH | Pe | NH | OH | H | H |
| 2996 | 3-F—Ph | NH | C12 | NMe | OH | H | H |
| 2997 | 3-F—Ph | NH | C12 | NEt | OH | H | H |
| 2998 | 3-F—Ph | NH | C12 | NPr | OH | H | H |
| 2999 | 3-F—Ph | NH | (CH$_2$)$_3$ | N | OH | H | H |
| 3000 | 3-F—Ph | NH | (CH$_2$)$_4$ | N | OH | H | H |
| 3001 | 3-F—Ph | NH | (CH$_2$)$_5$ | N | OH | H | H |
| 3002 | 3-F—Ph | NH | C12 | O | OH | H | H |
| 3003 | 3-F—Ph | NH | Ph | O | OH | H | H |
| 3004 | 3-F—Ph | NH | C12 | S | OH | H | H |
| 3005 | 3-F—Ph | NH | Ph | S | OH | H | H |
| 3006 | 3-F—Ph | NMe | H | NH | OH | H | H |
| 3007 | 3-F—Ph | NEt | H | NH | OH | H | H |
| 3008 | 3-F—Ph | NPr | H | NH | OH | H | H |
| 3009 | 3-F—Ph | O | H | NH | OH | H | H |
| 3010 | 3-F—Ph | S | H | NH | OH | H | H |
| 3011 | 4-F—Ph | NH | H | NH | H | H | H |
| 3012 | 4-F—Ph | NH | H | NH | OH | H | H |
| 3013 | 4-F—Ph | NH | H | NH | OA6 | H | H |
| 3014 | 4-F—Ph | NH | H | NH | OA8 | H | H |
| 3015 | 4-F—Ph | NH | H | NH | OA9 | H | H |
| 3016 | 4-F—Ph | NH | H | NH | OA10 | H | H |
| 3017 | 4-F—Ph | NH | H | NH | OA12 | H | H |
| 3018 | 4-F—Ph | NH | H | NH | OA14 | H | H |
| 3019 | 4-F—Ph | NH | H | NH | OA16 | H | H |
| 3020 | 4-F—Ph | NH | H | NH | OH | H | A6 |
| 3021 | 4-F—Ph | NH | H | NH | OH | H | A8 |
| 3022 | 4-F—Ph | NH | H | NH | OH | H | A9 |
| 3023 | 4-F—Ph | NH | H | NH | OH | H | A10 |
| 3024 | 4-F—Ph | NH | H | NH | OH | H | A12 |
| 3025 | 4-F—Ph | NH | H | NH | OH | H | A14 |
| 3026 | 4-F—Ph | NH | H | NH | OH | H | A16 |
| 3027 | 4-F—Ph | NH | H | NH | OH | A6 | A6 |
| 3028 | 4-F—Ph | NH | H | NH | OH | A8 | A8 |
| 3029 | 4-F—Ph | NH | H | NH | OH | A10 | A10 |
| 3030 | 4-F—Ph | NH | H | NH | OA2 | A2 | A2 |
| 3031 | 4-F—Ph | NH | H | NH | OA3 | A3 | A3 |
| 3032 | 4-F—Ph | NH | H | NH | OA4 | A4 | A4 |
| 3033 | 4-F—Ph | NH | H | NH | OC6 | H | H |
| 3034 | 4-F—Ph | NH | H | NH | OC7 | H | H |
| 3035 | 4-F—Ph | NH | H | NH | OC8 | H | H |
| 3036 | 4-F—Ph | NH | H | NH | OC10 | H | H |
| 3037 | 4-F—Ph | NH | H | NH | OC11 | H | H |
| 3038 | 4-F—Ph | NH | H | NH | OC12 | H | H |
| 3039 | 4-F—Ph | NH | H | NH | OC14 | H | H |
| 3040 | 4-F—Ph | NH | H | NH | OC16 | H | H |
| 3041 | 4-F—Ph | NH | H | NH | C6CO$_3$ | H | H |
| 3042 | 4-F—Ph | NH | H | NH | C7CO$_3$ | H | H |
| 3043 | 4-F—Ph | NH | H | NH | C8CO$_3$ | H | H |

TABLE 1-continued (I-1)

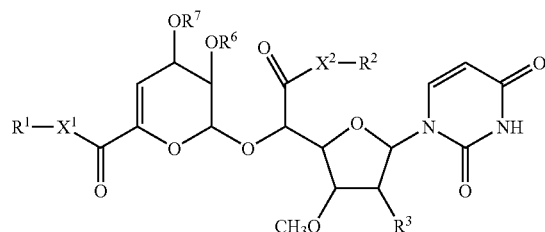

| Exemp. Comp. No. | R$^1$ | X$^1$ | R$^2$ | X$^2$ | R$^3$ | R$^6$ | R$^7$ |
|---|---|---|---|---|---|---|---|
| 3044 | 4-F—Ph | NH | H | NH | C9CO$_3$ | H | H |
| 3045 | 4-F—Ph | NH | H | NH | C10CO$_3$ | H | H |
| 3046 | 4-F—Ph | NH | H | NH | C12CO$_3$ | H | H |
| 3047 | 4-F—Ph | NH | H | NH | C16CO$_3$ | H | H |
| 3048 | 4-F—Ph | NH | C8 | NH | OH | H | H |
| 3049 | 4-F—Ph | NH | C9 | NH | OH | H | H |
| 3050 | 4-F—Ph | NH | C10 | NH | OH | H | H |
| 3051 | 4-F—Ph | NH | C12 | NH | OH | H | H |
| 3052 | 4-F—Ph | NH | C16 | NH | OH | H | H |
| 3053 | 4-F—Ph | NH | F1 | NH | OH | H | H |
| 3054 | 4-F—Ph | NH | F2 | NH | OH | H | H |
| 3055 | 4-F—Ph | NH | F3 | NH | OH | H | H |
| 3056 | 4-F—Ph | NH | F4 | NH | OH | H | H |
| 3057 | 4-F—Ph | NH | F5 | NH | OH | H | H |
| 3058 | 4-F—Ph | NH | F6 | NH | OH | H | H |
| 3059 | 4-F—Ph | NH | F7 | NH | OH | H | H |
| 3060 | 4-F—Ph | NH | F8 | NH | OH | H | H |
| 3061 | 4-F—Ph | NH | F9 | NH | OH | H | H |
| 3062 | 4-F—Ph | NH | F10 | NH | OH | H | H |
| 3063 | 4-F—Ph | NH | Ph | NH | OH | H | H |
| 3064 | 4-F—Ph | NH | Bn | NH | OH | H | H |
| 3065 | 4-F—Ph | NH | Pe | NH | OH | H | H |
| 3066 | 4-F—Ph | NH | C12 | NMe | OH | H | H |
| 3067 | 4-F—Ph | NH | C12 | NEt | OH | H | H |
| 3068 | 4-F—Ph | NH | C12 | NPr | OH | H | H |
| 3069 | 4-F—Ph | NH | (CH$_2$)$_3$ | N | OH | H | H |
| 3070 | 4-F—Ph | NH | (CH$_2$)$_4$ | N | OH | H | H |
| 3071 | 4-F—Ph | NH | (CH$_2$)$_5$ | N | OH | H | H |
| 3072 | 4-F—Ph | NH | C12 | O | OH | H | H |
| 3073 | 4-F—Ph | NH | Ph | O | OH | H | H |
| 3074 | 4-F—Ph | NH | C12 | S | OH | H | H |
| 3075 | 4-F—Ph | NH | Ph | S | OH | H | H |
| 3076 | 4-F—Ph | NMe | H | NH | OH | H | H |
| 3077 | 4-F—Ph | NEt | H | NH | OH | H | H |
| 3078 | 4-F—Ph | NPr | H | NH | OH | H | H |
| 3079 | 4-F—Ph | O | H | NH | OH | H | H |
| 3080 | 4-F—Ph | S | H | NH | OH | H | H |
| 3081 | 4-Cl—Ph | NH | H | NH | H | H | H |
| 3082 | 4-Cl—Ph | NH | H | NH | OH | H | H |
| 3083 | 4-Cl—Ph | NH | H | NH | OA6 | H | H |
| 3084 | 4-Cl—Ph | NH | H | NH | OA8 | H | H |
| 3085 | 4-Cl—Ph | NH | H | NH | OA9 | H | H |
| 3086 | 4-Cl—Ph | NH | H | NH | OA10 | H | H |
| 3087 | 4-Cl—Ph | NH | H | NH | OA12 | H | H |
| 3088 | 4-Cl—Ph | NH | H | NH | OA14 | H | H |
| 3089 | 4-Cl—Ph | NH | H | NH | OA16 | H | H |
| 3090 | 4-Cl—Ph | NH | H | NH | OH | H | A6 |
| 3091 | 4-Cl—Ph | NH | H | NH | OH | H | A8 |
| 3092 | 4-Cl—Ph | NH | H | NH | OH | H | A9 |
| 3093 | 4-Cl—Ph | NH | H | NH | OH | H | A10 |
| 3094 | 4-Cl—Ph | NH | H | NH | OH | H | A12 |
| 3095 | 4-Cl—Ph | NH | H | NH | OH | H | A14 |
| 3096 | 4-Cl—Ph | NH | H | NH | OH | H | A16 |
| 3097 | 4-Cl—Ph | NH | H | NH | OH | A6 | A6 |
| 3098 | 4-Cl—Ph | NH | H | NH | OH | A8 | A8 |
| 3099 | 4-Cl—Ph | NH | H | NH | OH | A10 | A10 |
| 3100 | 4-Cl—Ph | NH | H | NH | OA2 | A2 | A2 |
| 3101 | 4-Cl—Ph | NH | H | NH | OA3 | A3 | A3 |
| 3102 | 4-Cl—Ph | NH | H | NH | OA4 | A4 | A4 |
| 3103 | 4-Cl—Ph | NH | H | NH | OC6 | H | H |
| 3104 | 4-Cl—Ph | NH | H | NH | OC7 | H | H |
| 3105 | 4-Cl—Ph | NH | H | NH | OC8 | H | H |

TABLE 1-continued (I-1)

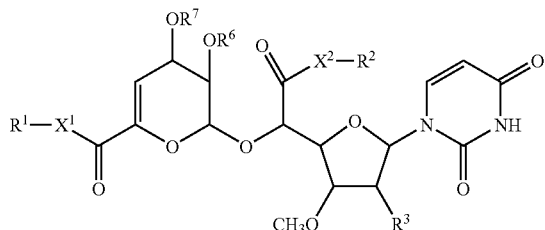

| Exemp. Comp. No. | R¹ | X¹ | R² | X² | R³ | R⁶ | R⁷ |
|---|---|---|---|---|---|---|---|
| 3106 | 4-Cl—Ph | NH | H | NH | OC10 | H | H |
| 3107 | 4-Cl—Ph | NH | H | NH | OC11 | H | H |
| 3108 | 4-Cl—Ph | NH | H | NH | OC12 | H | H |
| 3109 | 4-Cl—Ph | NH | H | NH | OC14 | H | H |
| 3110 | 4-Cl—Ph | NH | H | NH | OC16 | H | H |
| 3111 | 4-Cl—Ph | NH | H | NH | C6CO$_3$ | H | H |
| 3112 | 4-Cl—Ph | NH | H | NH | C7CO$_3$ | H | H |
| 3113 | 4-Cl—Ph | NH | H | NH | C8CO$_3$ | H | H |
| 3114 | 4-Cl—Ph | NH | H | NH | C9CO$_3$ | H | H |
| 3115 | 4-Cl—Ph | NH | H | NH | C10CO$_3$ | H | H |
| 3116 | 4-Cl—Ph | NH | H | NH | C12CO$_3$ | H | H |
| 3117 | 4-Cl—Ph | NH | H | NH | C16CO$_3$ | H | H |
| 3118 | 4-Cl—Ph | NH | C8 | NH | OH | H | H |
| 3119 | 4-Cl—Ph | NH | C9 | NH | OH | H | H |
| 3120 | 4-Cl—Ph | NH | C10 | NH | OH | H | H |
| 3121 | 4-Cl—Ph | NH | C12 | NH | OH | H | H |
| 3122 | 4-Cl—Ph | NH | C16 | NH | OH | H | H |
| 3123 | 4-Cl—Ph | NH | F1 | NH | OH | H | H |
| 3124 | 4-Cl—Ph | NH | F2 | NH | OH | H | H |
| 3125 | 4-Cl—Ph | NH | F3 | NH | OH | H | H |
| 3126 | 4-Cl—Ph | NH | F4 | NH | OH | H | H |
| 3127 | 4-Cl—Ph | NH | F5 | NH | OH | H | H |
| 3128 | 4-Cl—Ph | NH | F6 | NH | OH | H | H |
| 3129 | 4-Cl—Ph | NH | F7 | NH | OH | H | H |
| 3130 | 4-Cl—Ph | NH | F8 | NH | OH | H | H |
| 3131 | 4-Cl—Ph | NH | F9 | NH | OH | H | H |
| 3132 | 4-Cl—Ph | NH | F10 | NH | OH | H | H |
| 3133 | 4-Cl—Ph | NH | Ph | NH | OH | H | H |
| 3134 | 4-Cl—Ph | NH | Bn | NH | OH | H | H |
| 3135 | 4-Cl—Ph | NH | Pe | NH | OH | H | H |
| 3136 | 4-Cl—Ph | NH | C12 | NMe | OH | H | H |
| 3137 | 4-Cl—Ph | NH | C12 | NEt | OH | H | H |
| 3138 | 4-Cl—Ph | NH | C12 | NPr | OH | H | H |
| 3139 | 4-Cl—Ph | NH | (CH$_2$)$_3$ | N | OH | H | H |
| 3140 | 4-Cl—Ph | NH | (CH$_2$)$_4$ | N | OH | H | H |
| 3141 | 4-Cl—Ph | NH | (CH$_2$)$_5$ | N | OH | H | H |
| 3142 | 4-Cl—Ph | NH | C12 | O | OH | H | H |
| 3143 | 4-Cl—Ph | NH | Ph | O | OH | H | H |
| 3144 | 4-Cl—Ph | NH | C12 | S | OH | H | H |
| 3145 | 4-Cl—Ph | NH | Ph | S | OH | H | H |
| 3146 | 4-Cl—Ph | NMe | H | NH | OH | H | H |
| 3147 | 4-Cl—Ph | NEt | H | NH | OH | H | H |
| 3148 | 4-Cl—Ph | NPr | H | NH | OH | H | H |
| 3149 | 4-Cl—Ph | O | H | NH | OH | H | H |
| 3150 | 4-Cl—Ph | S | H | NH | OH | H | H |
| 3151 | 4-Br—Ph | NH | H | NH | H | H | H |
| 3152 | 4-Br—Ph | NH | H | NH | OH | H | H |
| 3153 | 4-Br—Ph | NH | H | NH | OA6 | H | H |
| 3154 | 4-Br—Ph | NH | H | NH | OA8 | H | H |
| 3155 | 4-Br—Ph | NH | H | NH | OA9 | H | H |
| 3156 | 4-Br—Ph | NH | H | NH | OA10 | H | H |
| 3157 | 4-Br—Ph | NH | H | NH | OA12 | H | H |
| 3158 | 4-Br—Ph | NH | H | NH | OA14 | H | H |
| 3159 | 4-Br—Ph | NH | H | NH | OA16 | H | H |
| 3160 | 4-Br—Ph | NH | H | NH | OH | H | A6 |
| 3161 | 4-Br—Ph | NH | H | NH | OH | H | A8 |
| 3162 | 4-Br—Ph | NH | H | NH | OH | H | A9 |
| 3163 | 4-Br—Ph | NH | H | NH | OH | H | A10 |
| 3164 | 4-Br—Ph | NH | H | NH | OH | H | A12 |
| 3165 | 4-Br—Ph | NH | H | NH | OH | H | A14 |
| 3166 | 4-Br—Ph | NH | H | NH | OH | H | A16 |
| 3167 | 4-Br—Ph | NH | H | NH | OH | A6 | A6 |

TABLE 1-continued (I-1)

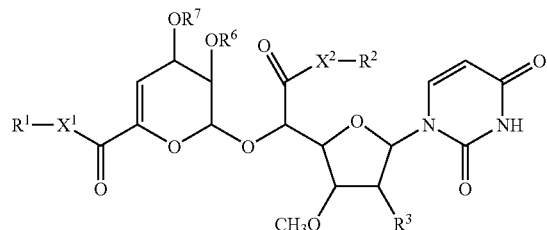

| Exemp. Comp. No. | R¹ | X¹ | R² | X² | R³ | R⁶ | R⁷ |
|---|---|---|---|---|---|---|---|
| 3168 | 4-Br—Ph | NH | H | NH | OH | A8 | A8 |
| 3169 | 4-Br—Ph | NH | H | NH | OH | A10 | A10 |
| 3170 | 4-Br—Ph | NH | H | NH | OA2 | A2 | A2 |
| 3171 | 4-Br—Ph | NH | H | NH | OA3 | A3 | A3 |
| 3172 | 4-Br—Ph | NH | H | NH | OA4 | A4 | A4 |
| 3173 | 4-Br—Ph | NH | H | NH | OC6 | H | H |
| 3174 | 4-Br—Ph | NH | H | NH | OC7 | H | H |
| 3175 | 4-Br—Ph | NH | H | NH | OC8 | H | H |
| 3176 | 4-Br—Ph | NH | H | NH | OC10 | H | H |
| 3177 | 4-Br—Ph | NH | H | NH | OC11 | H | H |
| 3178 | 4-Br—Ph | NH | H | NH | OC12 | H | H |
| 3179 | 4-Br—Ph | NH | H | NH | OC14 | H | H |
| 3180 | 4-Br—Ph | NH | H | NH | OC16 | H | H |
| 3181 | 4-Br—Ph | NH | H | NH | C6CO$_3$ | H | H |
| 3182 | 4-Br—Ph | NH | H | NH | C7CO$_3$ | H | H |
| 3183 | 4-Br—Ph | NH | H | NH | C8CO$_3$ | H | H |
| 3184 | 4-Br—Ph | NH | H | NH | C9CO$_3$ | H | H |
| 3185 | 4-Br—Ph | NH | H | NH | C10CO$_3$ | H | H |
| 3186 | 4-Br—Ph | NH | H | NH | C12CO$_3$ | H | H |
| 3187 | 4-Br—Ph | NH | H | NH | C16CO$_3$ | H | H |
| 3188 | 4-Br—Ph | NH | C8 | NH | OH | H | H |
| 3189 | 4-Br—Ph | NH | C9 | NH | OH | H | H |
| 3190 | 4-Br—Ph | NH | C10 | NH | OH | H | H |
| 3191 | 4-Br—Ph | NH | C12 | NH | OH | H | H |
| 3192 | 4-Br—Ph | NH | C16 | NH | OH | H | H |
| 3193 | 4-Br—Ph | NH | F1 | NH | OH | H | H |
| 3194 | 4-Br—Ph | NH | F2 | NH | OH | H | H |
| 3195 | 4-Br—Ph | NH | F3 | NH | OH | H | H |
| 3196 | 4-Br—Ph | NH | F4 | NH | OH | H | H |
| 3197 | 4-Br—Ph | NH | F5 | NH | OH | H | H |
| 3198 | 4-Br—Ph | NH | F6 | NH | OH | H | H |
| 3199 | 4-Br—Ph | NH | F7 | NH | OH | H | H |
| 3200 | 4-Br—Ph | NH | F8 | NH | OH | H | H |
| 3201 | 4-Br—Ph | NH | F9 | NH | OH | H | H |
| 3202 | 4-Br—Ph | NH | F10 | NH | OH | H | H |
| 3203 | 4-Br—Ph | NH | Ph | NH | OH | H | H |
| 3204 | 4-Br—Ph | NH | Bn | NH | OH | H | H |
| 3205 | 4-Br—Ph | NH | Pe | NH | OH | H | H |
| 3206 | 4-Br—Ph | NH | C12 | NMe | OH | H | H |
| 3207 | 4-Br—Ph | NH | C12 | NEt | OH | H | H |
| 3208 | 4-Br—Ph | NH | C12 | NPr | OH | H | H |
| 3209 | 4-Br—Ph | NH | (CH$_2$)$_3$ | N | OH | H | H |
| 3210 | 4-Br—Ph | NH | (CH$_2$)$_4$ | N | OH | H | H |
| 3211 | 4-Br—Ph | NH | (CH$_2$)$_5$ | N | OH | H | H |
| 3212 | 4-Br—Ph | NH | C12 | O | OH | H | H |
| 3213 | 4-Br—Ph | NH | Ph | O | OH | H | H |
| 3214 | 4-Br—Ph | NH | C12 | S | OH | H | H |
| 3215 | 4-Br—Ph | NH | Ph | S | OH | H | H |
| 3216 | 4-Br—Ph | NMe | H | NH | OH | H | H |
| 3217 | 4-Br—Ph | NEt | H | NH | OH | H | H |
| 3218 | 4-Br—Ph | NPr | H | NH | OH | H | H |
| 3219 | 4-Br—Ph | O | H | NH | OH | H | H |
| 3220 | 4-Br—Ph | S | H | NH | OH | H | H |
| 3221 | 4-I—Ph | NH | H | NH | H | H | H |
| 3222 | 4-I—Ph | NH | H | NH | OH | H | H |
| 3223 | 4-I—Ph | NH | H | NH | OA6 | H | H |
| 3224 | 4-I—Ph | NH | H | NH | OA8 | H | H |
| 3225 | 4-I—Ph | NH | H | NH | OA9 | H | H |
| 3226 | 4-I—Ph | NH | H | NH | OA10 | H | H |
| 3227 | 4-I—Ph | NH | H | NH | OA12 | H | H |
| 3228 | 4-I—Ph | NH | H | NH | OA14 | H | H |
| 3229 | 4-I—Ph | NH | H | NH | OA16 | H | H |

TABLE 1-continued (I-1)

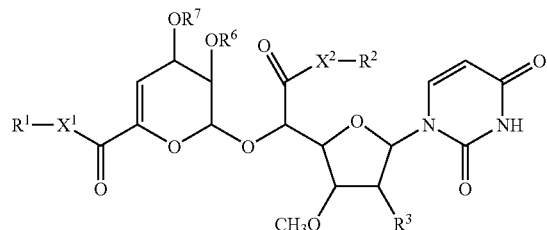

| Exemp. Comp. No. | R¹ | X¹ | R² | X² | R³ | R⁶ | R⁷ |
|---|---|---|---|---|---|---|---|
| 3230 | 4-I—Ph | NH | H | NH | OH | H | A6 |
| 3231 | 4-I—Ph | NH | H | NH | OH | H | A8 |
| 3232 | 4-I—Ph | NH | H | NH | OH | H | A9 |
| 3233 | 4-I—Ph | NH | H | NH | OH | H | A10 |
| 3234 | 4-I—Ph | NH | H | NH | OH | H | A12 |
| 3235 | 4-I—Ph | NH | H | NH | OH | H | A14 |
| 3236 | 4-I—Ph | NH | H | NH | OH | H | A16 |
| 3237 | 4-I—Ph | NH | H | NH | OH | A6 | A6 |
| 3238 | 4-I—Ph | NH | H | NH | OH | A8 | A8 |
| 3239 | 4-I—Ph | NH | H | NH | OH | A10 | A10 |
| 3240 | 4-I—Ph | NH | H | NH | OA2 | A2 | A2 |
| 3241 | 4-I—Ph | NH | H | NH | OA3 | A3 | A3 |
| 3242 | 4-I—Ph | NH | H | NH | OA4 | A4 | A4 |
| 3243 | 4-I—Ph | NH | H | NH | OC6 | H | H |
| 3244 | 4-I—Ph | NH | H | NH | OC7 | H | H |
| 3245 | 4-I—Ph | NH | H | NH | OC8 | H | H |
| 3246 | 4-I—Ph | NH | H | NH | OC10 | H | H |
| 3247 | 4-I—Ph | NH | H | NH | OC11 | H | H |
| 3248 | 4-I—Ph | NH | H | NH | OC12 | H | H |
| 3249 | 4-I—Ph | NH | H | NH | OC14 | H | H |
| 3250 | 4-I—Ph | NH | H | NH | OC16 | H | H |
| 3251 | 4-I—Ph | NH | H | NH | C6CO$_3$ | H | H |
| 3252 | 4-I—Ph | NH | H | NH | C7CO$_3$ | H | H |
| 3253 | 4-I—Ph | NH | H | NH | C8CO$_3$ | H | H |
| 3254 | 4-I—Ph | NH | H | NH | C9CO$_3$ | H | H |
| 3255 | 4-I—Ph | NH | H | NH | C10CO$_3$ | H | H |
| 3256 | 4-I—Ph | NH | H | NH | C12CO$_3$ | H | H |
| 3257 | 4-I—Ph | NH | H | NH | C16CO$_3$ | H | H |
| 3258 | 4-I—Ph | NH | C8 | NH | OH | H | H |
| 3259 | 4-I—Ph | NH | C9 | NH | OH | H | H |
| 3260 | 4-I—Ph | NH | C10 | NH | OH | H | H |
| 3261 | 4-I—Ph | NH | C12 | NH | OH | H | H |
| 3262 | 4-I—Ph | NH | C16 | NH | OH | H | H |
| 3263 | 4-I—Ph | NH | F1 | NH | OH | H | H |
| 3264 | 4-I—Ph | NH | F2 | NH | OH | H | H |
| 3265 | 4-I—Ph | NH | F3 | NH | OH | H | H |
| 3266 | 4-I—Ph | NH | F4 | NH | OH | H | H |
| 3267 | 4-I—Ph | NH | F5 | NH | OH | H | H |
| 3268 | 4-I—Ph | NH | F6 | NH | OH | H | H |
| 3269 | 4-I—Ph | NH | F7 | NH | OH | H | H |
| 3270 | 4-I—Ph | NH | F8 | NH | OH | H | H |
| 3271 | 4-I—Ph | NH | F9 | NH | OH | H | H |
| 3272 | 4-I—Ph | NH | F10 | NH | OH | H | H |
| 3273 | 4-I—Ph | NH | Ph | NH | OH | H | H |
| 3274 | 4-I—Ph | NH | Bn | NH | OH | H | H |
| 3275 | 4-I—Ph | NH | Pe | NH | OH | H | H |
| 3276 | 4-I—Ph | NH | C12 | NMe | OH | H | H |
| 3277 | 4-I—Ph | NH | C12 | NEt | OH | H | H |
| 3278 | 4-I—Ph | NH | C12 | NPr | OH | H | H |
| 3279 | 4-I—Ph | NH | (CH$_2$)$_3$ | N | OH | H | H |
| 3280 | 4-I—Ph | NH | (CH$_2$)$_4$ | N | OH | H | H |
| 3281 | 4-I—Ph | NH | (CH$_2$)$_5$ | N | OH | H | H |
| 3282 | 4-I—Ph | NH | C12 | O | OH | H | H |
| 3283 | 4-I—Ph | NH | Ph | O | OH | H | H |
| 3284 | 4-I—Ph | NH | C12 | S | OH | H | H |
| 3285 | 4-I—Ph | NH | Ph | S | OH | H | H |
| 3286 | 4-I—Ph | NMe | H | NH | OH | H | H |
| 3287 | 4-I—Ph | NEt | H | NH | OH | H | H |
| 3288 | 4-I—Ph | NPr | H | NH | OH | H | H |
| 3289 | 4-I—Ph | O | H | NH | OH | H | H |
| 3290 | 4-I—Ph | S | H | NH | OH | H | H |
| 3291 | 3-Cl—Ph | NH | H | NH | H | H | H |

TABLE 1-continued

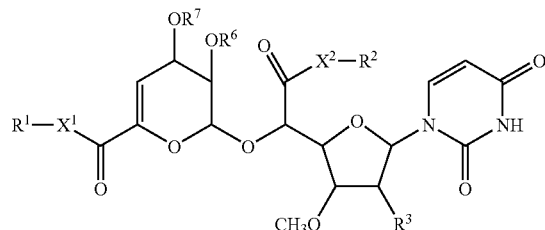

(I-1)

| Exemp. Comp. No. | R¹ | X¹ | R² | X² | R³ | R⁶ | R⁷ |
|---|---|---|---|---|---|---|---|
| 3292 | 3-Cl—Ph | NH | H | NH | OH | H | H |
| 3293 | 3-Cl—Ph | NH | H | NH | OA6 | H | H |
| 3294 | 3-Cl—Ph | NH | H | NH | OA8 | H | H |
| 3295 | 3-Cl—Ph | NH | H | NH | OA9 | H | H |
| 3296 | 3-Cl—Ph | NH | H | NH | OA10 | H | H |
| 3297 | 3-Cl—Ph | NH | H | NH | OA12 | H | H |
| 3298 | 3-Cl—Ph | NH | H | NH | OA14 | H | H |
| 3299 | 3-Cl—Ph | NH | H | NH | OA16 | H | H |
| 3300 | 3-Cl—Ph | NH | H | NH | OH | H | A6 |
| 3301 | 3-Cl—Ph | NH | H | NH | OH | H | A8 |
| 3302 | 3-Cl—Ph | NH | H | NH | OH | H | A9 |
| 3303 | 3-Cl—Ph | NH | H | NH | OH | H | A10 |
| 3304 | 3-Cl—Ph | NH | H | NH | OH | H | A12 |
| 3305 | 3-Cl—Ph | NH | H | NH | OH | H | A14 |
| 3306 | 3-Cl—Ph | NH | H | NH | OH | H | A16 |
| 3307 | 3-Cl—Ph | NH | H | NH | OH | A6 | A6 |
| 3308 | 3-Cl—Ph | NH | H | NH | OH | A8 | A8 |
| 3309 | 3-Cl—Ph | NH | H | NH | OH | A10 | A10 |
| 3310 | 3-Cl—Ph | NH | H | NH | OA2 | A2 | A2 |
| 3311 | 3-Cl—Ph | NH | H | NH | OA3 | A3 | A3 |
| 3312 | 3-Cl—Ph | NH | H | NH | OA4 | A4 | A4 |
| 3313 | 3-Cl—Ph | NH | H | NH | OC6 | H | H |
| 3314 | 3-Cl—Ph | NH | H | NH | OC7 | H | H |
| 3315 | 3-Cl—Ph | NH | H | NH | OC8 | H | H |
| 3316 | 3-Cl—Ph | NH | H | NH | OC10 | H | H |
| 3317 | 3-Cl—Ph | NH | H | NH | OC11 | H | H |
| 3318 | 3-Cl—Ph | NH | H | NH | OC12 | H | H |
| 3319 | 3-Cl—Ph | NH | H | NH | OC14 | H | H |
| 3320 | 3-Cl—Ph | NH | H | NH | OC16 | H | H |
| 3321 | 3-Cl—Ph | NH | H | NH | C6CO$_3$ | H | H |
| 3322 | 3-Cl—Ph | NH | H | NH | C7CO$_3$ | H | H |
| 3323 | 3-Cl—Ph | NH | H | NH | C8CO$_3$ | H | H |
| 3324 | 3-Cl—Ph | NH | H | NH | C9CO$_3$ | H | H |
| 3325 | 3-Cl—Ph | NH | H | NH | C10CO3 | H | H |
| 3326 | 3-Cl—Ph | NH | H | NH | C12CO$_3$ | H | H |
| 3327 | 3-Cl—Ph | NH | H | NH | C16CO$_3$ | H | H |
| 3328 | 3-Cl—Ph | NH | C8 | NH | OH | H | H |
| 3329 | 3-Cl—Ph | NH | C9 | NH | OH | H | H |
| 3330 | 3-Cl—Ph | NH | C10 | NH | OH | H | H |
| 3331 | 3-Cl—Ph | NH | C12 | NH | OH | H | H |
| 3332 | 3-Cl—Ph | NH | C16 | NH | OH | H | H |
| 3333 | 3-Cl—Ph | NH | F1 | NH | OH | H | H |
| 3334 | 3-Cl—Ph | NH | F2 | NH | OH | H | H |
| 3335 | 3-Cl—Ph | NH | F3 | NH | OH | H | H |
| 3336 | 3-Cl—Ph | NH | F4 | NH | OH | H | H |
| 3337 | 3-Cl—Ph | NH | F5 | NH | OH | H | H |
| 3338 | 3-Cl—Ph | NH | F6 | NH | OH | H | H |
| 3339 | 3-Cl—Ph | NH | F7 | NH | OH | H | H |
| 3340 | 3-Cl—Ph | NH | F8 | NH | OH | H | H |
| 3341 | 3-Cl—Ph | NH | F9 | NH | OH | H | H |
| 3342 | 3-Cl—Ph | NH | F10 | NH | OH | H | H |
| 3343 | 3-Cl—Ph | NH | Ph | NH | OH | H | H |
| 3344 | 3-Cl—Ph | NH | Bn | NH | OH | H | H |
| 3345 | 3-Cl—Ph | NH | Pe | NH | OH | H | H |
| 3346 | 3-Cl—Ph | NH | C12 | NMe | OH | H | H |
| 3347 | 3-Cl—Ph | NH | C12 | NEt | OH | H | H |
| 3348 | 3-Cl—Ph | NH | C12 | NPr | OH | H | H |
| 3349 | 3-Cl—Ph | NH | (CH$_2$)$_3$ | N | OH | H | H |
| 3350 | 3-Cl—Ph | NH | (CH$_2$)$_4$ | N | OH | H | H |
| 3351 | 3-Cl—Ph | NH | (CH$_2$)$_5$ | N | OH | H | H |
| 3352 | 3-Cl—Ph | NH | C12 | O | OH | H | H |
| 3353 | 3-Cl—Ph | NH | Ph | O | OH | H | H |

TABLE 1-continued

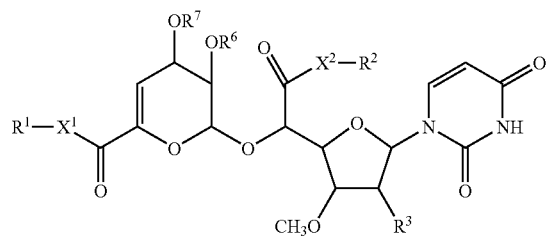

(I-1)

| Exemp. Comp. No. | R¹ | X¹ | R² | X² | R³ | R⁶ | R⁷ |
| --- | --- | --- | --- | --- | --- | --- | --- |
| 3354 | 3-Cl—Ph | NH | C12 | S | OH | H | H |
| 3355 | 3-Cl—Ph | NH | Ph | S | OH | H | H |
| 3356 | 3-Cl—Ph | NMe | H | NH | OH | H | H |
| 3357 | 3-Cl—Ph | NEt | H | NH | OH | H | H |
| 3358 | 3-Cl—Ph | NPr | H | NH | OH | H | H |
| 3359 | 3-Cl—Ph | O | H | NH | OH | H | H |
| 3360 | 3-Cl—Ph | S | H | NH | OH | H | H |
| 3361 | 3-I—Ph | NH | H | NH | H | H | H |
| 3362 | 3-I—Ph | NH | H | NH | OH | H | H |
| 3363 | 3-I—Ph | NH | H | NH | OA6 | H | H |
| 3364 | 3-I—Ph | NH | H | NH | OA8 | H | H |
| 3365 | 3-I—Ph | NH | H | NH | OA9 | H | H |
| 3366 | 3-I—Ph | NH | H | NH | OA10 | H | H |
| 3367 | 3-I—Ph | NH | H | NH | OA12 | H | H |
| 3368 | 3-I—Ph | NH | H | NH | OA14 | H | H |
| 3369 | 3-I—Ph | NH | H | NH | OA16 | H | H |
| 3370 | 3-I—Ph | NH | H | NH | OH | H | A6 |
| 3371 | 3-I—Ph | NH | H | NH | OH | H | A8 |
| 3372 | 3-I—Ph | NH | H | NH | OH | H | A9 |
| 3373 | 3-I—Ph | NH | H | NH | OH | H | A10 |
| 3374 | 3-I—Ph | NH | H | NH | OH | H | A12 |
| 3375 | 3-I—Ph | NH | H | NH | OH | H | A14 |
| 3376 | 3-I—Ph | NH | H | NH | OH | H | A16 |
| 3377 | 3-I—Ph | NH | H | NH | OH | A6 | A6 |
| 3378 | 3-I—Ph | NH | H | NH | OH | A8 | A8 |
| 3379 | 3-I—Ph | NH | H | NH | OH | A10 | A10 |
| 3380 | 3-I—Ph | NH | H | NH | OA2 | A2 | A2 |
| 3381 | 3-I—Ph | NH | H | NH | OA3 | A3 | A3 |
| 3382 | 3-I—Ph | NH | H | NH | OA4 | A4 | A4 |
| 3383 | 3-I—Ph | NH | H | NH | OC6 | H | H |
| 3384 | 3-I—Ph | NH | H | NH | OC7 | H | H |
| 3385 | 3-I—Ph | NH | H | NH | OC8 | H | H |
| 3386 | 3-I—Ph | NH | H | NH | OC10 | H | H |
| 3387 | 3-I—Ph | NH | H | NH | OC11 | H | H |
| 3388 | 3-I—Ph | NH | H | NH | OC12 | H | H |
| 3389 | 3-I—Ph | NH | H | NH | OC14 | H | H |
| 3390 | 3-I—Ph | NH | H | NH | OC16 | H | H |
| 3391 | 3-I—Ph | NH | H | NH | C6CO$_3$ | H | H |
| 3392 | 3-I—Ph | NH | H | NH | C7CO$_3$ | H | H |
| 3393 | 3-I—Ph | NH | H | NH | C8CO$_3$ | H | H |
| 3394 | 3-I—Ph | NH | H | NH | C9CO$_3$ | H | H |
| 3395 | 3-I—Ph | NH | H | NH | C10CO$_3$ | H | H |
| 3396 | 3-I—Ph | NH | H | NH | C12CO$_3$ | H | H |
| 3397 | 3-I—Ph | NH | H | NH | C16CO$_3$ | H | H |
| 3398 | 3-I—Ph | NH | C8 | NH | OH | H | H |
| 3399 | 3-I—Ph | NH | C9 | NH | OH | H | H |
| 3400 | 3-I—Ph | NH | C10 | NH | OH | H | H |
| 3401 | 3-I—Ph | NH | C12 | NH | OH | H | H |
| 3402 | 3-I—Ph | NH | C16 | NH | OH | H | H |
| 3403 | 3-I—Ph | NH | F1 | NH | OH | H | H |
| 3404 | 3-I—Ph | NH | F2 | NH | OH | H | H |
| 3405 | 3-I—Ph | NH | F3 | NH | OH | H | H |
| 3406 | 3-I—Ph | NH | F4 | NH | OH | H | H |
| 3407 | 3-I—Ph | NH | F5 | NH | OH | H | H |
| 3408 | 3-I—Ph | NH | F6 | NH | OH | H | H |
| 3409 | 3-I—Ph | NH | F7 | NH | OH | H | H |
| 3410 | 3-I—Ph | NH | F8 | NH | OH | H | H |
| 3411 | 3-I—Ph | NH | F9 | NH | OH | H | H |
| 3412 | 3-I—Ph | NH | F10 | NH | OH | H | H |
| 3413 | 3-I—Ph | NH | Ph | NH | OH | H | H |
| 3414 | 3-I—Ph | NH | Bn | NH | OH | H | H |
| 3415 | 3-I—Ph | NH | Pe | NH | OH | H | H |

TABLE 1-continued (I-1)

| Exemp. Comp. No. | R¹ | X¹ | R² | X² | R³ | R⁶ | R⁷ |
|---|---|---|---|---|---|---|---|
| 3416 | 3-I—Ph | NH | C12 | NMe | OH | H | H |
| 3417 | 3-I—Ph | NH | C12 | NEt | OH | H | H |
| 3418 | 3-I—Ph | NH | C12 | NPr | OH | H | H |
| 3419 | 3-I—Ph | NH | (CH₂)₃ | N | OH | H | H |
| 3420 | 3-I—Ph | NH | (CH₂)₄ | N | OH | H | H |
| 3421 | 3-I—Ph | NH | (CH₂)₅ | N | OH | H | H |
| 3422 | 3-I—Ph | NH | C12 | O | OH | H | H |
| 3423 | 3-I—Ph | NH | Ph | O | OH | H | H |
| 3424 | 3-I—Ph | NH | C12 | S | OH | H | H |
| 3425 | 3-I—Ph | NH | Ph | S | OH | H | H |
| 3426 | 3-I—Ph | NMe | H | NH | OH | H | H |
| 3427 | 3-I—Ph | NEt | H | NH | OH | H | H |
| 3428 | 3-I—Ph | NPr | H | NH | OH | H | H |
| 3429 | 3-I—Ph | O | H | NH | OH | H | H |
| 3430 | 3-I—Ph | S | H | NH | OH | H | H |
| 3431 | 2,3-F₂—Ph | NH | H | NH | H | H | H |
| 3432 | 2,3-F₂—Ph | NH | H | NH | OH | H | H |
| 3433 | 2,3-F₂—Ph | NH | H | NH | OA6 | H | H |
| 3434 | 2,3-F₂—Ph | NH | H | NH | OA8 | H | H |
| 3435 | 2,3-F₂—Ph | NH | H | NH | OA9 | H | H |
| 3436 | 2,3-F₂—Ph | NH | H | NH | OA10 | H | H |
| 3437 | 2,3-F₂—Ph | NH | H | NH | OA12 | H | H |
| 3438 | 2,3-F₂—Ph | NH | H | NH | OA14 | H | H |
| 3439 | 2,3-F₂—Ph | NH | H | NH | OA16 | H | H |
| 3440 | 2,3-F₂—Ph | NH | H | NH | OH | H | A6 |
| 3441 | 2,3-F₂—Ph | NH | H | NH | OH | H | A8 |
| 3442 | 2,3-F₂—Ph | NH | H | NH | OH | H | A9 |
| 3443 | 2,3-F₂—Ph | NH | H | NH | OH | H | A10 |
| 3444 | 2,3-F₂—Ph | NH | H | NH | OH | H | A12 |
| 3445 | 2,3-F₂—Ph | NH | H | NH | OH | H | A14 |
| 3446 | 2,3-F₂—Ph | NH | H | NH | OH | H | A16 |
| 3447 | 2,3-F₂—Ph | NH | H | NH | OH | A6 | A6 |
| 3448 | 2,3-F₂—Ph | NH | H | NH | OH | A8 | A8 |
| 3449 | 2,3-F₂—Ph | NH | H | NH | OH | A10 | A10 |
| 3450 | 2,3-F₂—Ph | NH | H | NH | OA2 | A2 | A2 |
| 3451 | 2,3-F₂—Ph | NH | H | NH | OA3 | A3 | A3 |
| 3452 | 2,3-F₂—Ph | NH | H | NH | OA4 | A4 | A4 |
| 3453 | 2,3-F₂—Ph | NH | H | NH | OC6 | H | H |
| 3454 | 2,3-F₂—Ph | NH | H | NH | OC7 | H | H |
| 3455 | 2,3-F₂—Ph | NH | H | NH | OC8 | H | H |
| 3456 | 2,3-F₂—Ph | NH | H | NH | OC10 | H | H |
| 3457 | 2,3-F₂—Ph | NH | H | NH | OC11 | H | H |
| 3458 | 2,3-F₂—Ph | NH | H | NH | OC12 | H | H |
| 3459 | 2,3-F₂—Ph | NH | H | NH | OC14 | H | H |
| 3460 | 2,3-F₂—Ph | NH | H | NH | OC16 | H | H |
| 3461 | 2,3-F₂—Ph | NH | H | NH | C6CO₃ | H | H |
| 3462 | 2,3-F₂—Ph | NH | H | NH | C7CO₃ | H | H |
| 3463 | 2,3-F₂—Ph | NH | H | NH | C8CO₃ | H | H |
| 3464 | 2,3-F₂—Ph | NH | H | NH | C9CO₃ | H | H |
| 3465 | 2,3-F₂—Ph | NH | H | NH | C10CO₃ | H | H |
| 3466 | 2,3-F₂—Ph | NH | H | NH | C12CO₃ | H | H |
| 3467 | 2,3-F₂—Ph | NH | H | NH | C16CO₃ | H | H |
| 3468 | 2,3-F₂—Ph | NH | C8 | NH | OH | H | H |
| 3469 | 2,3-F₂—Ph | NH | C9 | NH | OH | H | H |
| 3470 | 2,3-F₂—Ph | NH | C10 | NH | OH | H | H |
| 3471 | 2,3-F₂—Ph | NH | C12 | NH | OH | H | H |
| 3472 | 2,3-F₂—Ph | NH | C16 | NH | OH | H | H |
| 3473 | 2,3-F₂—Ph | NH | F1 | NH | OH | H | H |
| 3474 | 2,3-F₂—Ph | NH | F2 | NH | OH | H | H |
| 3475 | 2,3-F₂—Ph | NH | F3 | NH | OH | H | H |
| 3476 | 2,3-F₂—Ph | NH | F4 | NH | OH | H | H |
| 3477 | 2,3-F₂—Ph | NH | F5 | NH | OH | H | H |

TABLE 1-continued (I-1)

| Exemp. Comp. No. | R¹ | X¹ | R² | X² | R³ | R⁶ | R⁷ |
|---|---|---|---|---|---|---|---|
| 3478 | 2,3-F₂—Ph | NH | F6 | NH | OH | H | H |
| 3479 | 2,3-F₂—Ph | NH | F7 | NH | OH | H | H |
| 3480 | 2,3-F₂—Ph | NH | F8 | NH | OH | H | H |
| 3481 | 2,3-F₂—Ph | NH | F9 | NH | OH | H | H |
| 3482 | 2,3-F₂—Ph | NH | F10 | NH | OH | H | H |
| 3483 | 2,3-F₂—Ph | NH | Ph | NH | OH | H | H |
| 3484 | 2,3-F₂—Ph | NH | Bn | NH | OH | H | H |
| 3485 | 2,3-F₂—Ph | NH | Pe | NH | OH | H | H |
| 3486 | 2,3-F₂—Ph | NH | C12 | NMe | OH | H | H |
| 3487 | 2,3-F₂—Ph | NH | C12 | NEt | OH | H | H |
| 3488 | 2,3-F₂—Ph | NH | C12 | NPr | OH | H | H |
| 3489 | 2,3-F₂—Ph | NH | (CH₂)₃ | N | OH | H | H |
| 3490 | 2,3-F₂—Ph | NH | (CH₂)₄ | N | OH | H | H |
| 3491 | 2,3-F₂—Ph | NH | (CH₂)₅ | N | OH | H | H |
| 3492 | 2,3-F₂—Ph | NH | C12 | O | OH | H | H |
| 3493 | 2,3-F₂—Ph | NH | Ph | O | OH | H | H |
| 3494 | 2,3-F₂—Ph | NH | C12 | S | OH | H | H |
| 3495 | 2,3-F₂—Ph | NH | Ph | S | OH | H | H |
| 3496 | 2,3-F₂—Ph | NMe | H | NH | OH | H | H |
| 3497 | 2,3-F₂—Ph | NEt | H | NH | OH | H | H |
| 3498 | 2,3-F₂—Ph | NPr | H | NH | OH | H | H |
| 3499 | 2,3-F₂—Ph | O | H | NH | OH | H | H |
| 3500 | 2,3-F₂—Ph | S | H | NH | OH | H | H |
| 3501 | 2,4-F₂—Ph | NH | H | NH | H | H | H |
| 3502 | 2,4-F₂—Ph | NH | H | NH | OH | H | H |
| 3503 | 2,4-F₂—Ph | NH | H | NH | OA6 | H | H |
| 3504 | 2,4-F₂—Ph | NH | H | NH | OA8 | H | H |
| 3505 | 2,4-F₂—Ph | NH | H | NH | OA9 | H | H |
| 3506 | 2,4-F₂—Ph | NH | H | NH | OA10 | H | H |
| 3507 | 2,4-F₂—Ph | NH | H | NH | OA12 | H | H |
| 3508 | 2,4-F₂—Ph | NH | H | NH | OA14 | H | H |
| 3509 | 2,4-F₂—Ph | NH | H | NH | OA16 | H | H |
| 3510 | 2,4-F₂—Ph | NH | H | NH | OH | H | A6 |
| 3511 | 2,4-F₂—Ph | NH | H | NH | OH | H | A8 |
| 3512 | 2,4-F₂—Ph | NH | H | NH | OH | H | A9 |
| 3513 | 2,4-F₂—Ph | NH | H | NH | OH | H | A10 |
| 3514 | 2,4-F₂—Ph | NH | H | NH | OH | H | A12 |
| 3515 | 2,4-F₂—Ph | NH | H | NH | OH | H | A14 |
| 3516 | 2,4-F₂—Ph | NH | H | NH | OH | H | A16 |
| 3517 | 2,4-F₂—Ph | NH | H | NH | OH | A6 | A6 |
| 3518 | 2,4-F₂—Ph | NH | H | NH | OH | A8 | A8 |
| 3519 | 2,4-F₂—Ph | NH | H | NH | OH | A10 | A10 |
| 3520 | 2,4-F₂—Ph | NH | H | NH | OA2 | A2 | A2 |
| 3521 | 2,4-F₂—Ph | NH | H | NH | OA3 | A3 | A3 |
| 3522 | 2,4-F₂—Ph | NH | H | NH | OA4 | A4 | A4 |
| 3523 | 2,4-F₂—Ph | NH | H | NH | OC6 | H | H |
| 3524 | 2,4-F₂—Ph | NH | H | NH | OC7 | H | H |
| 3525 | 2,4-F₂—Ph | NH | H | NH | OC8 | H | H |
| 3526 | 2,4-F₂—Ph | NH | H | NH | OC10 | H | H |
| 3527 | 2,4-F₂—Ph | NH | H | NH | OC11 | H | H |
| 3528 | 2,4-F₂—Ph | NH | H | NH | OC12 | H | H |
| 3529 | 2,4-F₂—Ph | NH | H | NH | OC14 | H | H |
| 3530 | 2,4-F₂—Ph | NH | H | NH | OC16 | H | H |
| 3531 | 2,4-F₂—Ph | NH | H | NH | C6CO₃ | H | H |
| 3532 | 2,4-F₂—Ph | NH | H | NH | C7CO₃ | H | H |
| 3533 | 2,4-F₂—Ph | NH | H | NH | C8CO₃ | H | H |
| 3534 | 2,4-F₂—Ph | NH | H | NH | C9CO₃ | H | H |
| 3535 | 2,4-F₂—Ph | NH | H | NH | C10CO₃ | H | H |
| 3536 | 2,4-F₂—Ph | NH | H | NH | C12CO₃ | H | H |
| 3537 | 2,4-F₂—Ph | NH | H | NH | C16CO₃ | H | H |
| 3538 | 2,4-F₂—Ph | NH | C8 | NH | OH | H | H |
| 3539 | 2,4-F₂—Ph | NH | C9 | NH | OH | H | H |

TABLE 1-continued

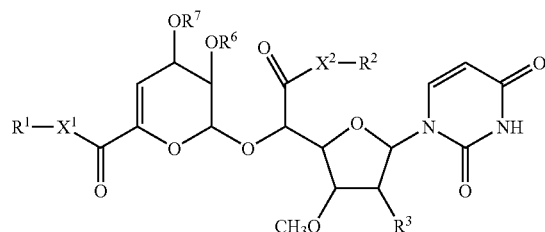

(I-1)

| Exemp. Comp. No. | R¹ | X¹ | R² | X² | R³ | R⁶ | R⁷ |
|---|---|---|---|---|---|---|---|
| 3540 | 2,4-F₂—Ph | NH | C10 | NH | OH | H | H |
| 3541 | 2,4-F₂—Ph | NH | C12 | NH | OH | H | H |
| 3542 | 2,4-F₂—Ph | NH | C16 | NH | OH | H | H |
| 3543 | 2,4-F₂—Ph | NH | F1 | NH | OH | H | H |
| 3544 | 2,4-F₂—Ph | NH | F2 | NH | OH | H | H |
| 3545 | 2,4-F₂—Ph | NH | F3 | NH | OH | H | H |
| 3546 | 2,4-F₂—Ph | NH | F4 | NH | OH | H | H |
| 3547 | 2,4-F₂—Ph | NH | F5 | NH | OH | H | H |
| 3548 | 2,4-F₂—Ph | NH | F6 | NH | OH | H | H |
| 3549 | 2,4-F₂—Ph | NH | F7 | NH | OH | H | H |
| 3550 | 2,4-F₂—Ph | NH | F8 | NH | OH | H | H |
| 3551 | 2,4-F₂—Ph | NH | F9 | NH | OH | H | H |
| 3552 | 2,4-F₂—Ph | NH | F10 | NH | OH | H | H |
| 3553 | 2,4-F₂—Ph | NH | Ph | NH | OH | H | H |
| 3554 | 2,4-F₂—Ph | NH | Bn | NH | OH | H | H |
| 3555 | 2,4-F₂—Ph | NH | Pe | NH | OH | H | H |
| 3556 | 2,4-F₂—Ph | NH | C12 | NMe | OH | H | H |
| 3557 | 2,4-F₂—Ph | NH | C12 | NEt | OH | H | H |
| 3558 | 2,4-F₂—Ph | NH | C12 | NPr | OH | H | H |
| 3559 | 2,4-F₂—Ph | NH | (CH₂)₃ | N | OH | H | H |
| 3560 | 2,4-F₂—Ph | NH | (CH₂)₄ | N | OH | H | H |
| 3561 | 2,4-F₂—Ph | NH | (CH₂)₅ | N | OH | H | H |
| 3562 | 2,4-F₂—Ph | NH | C12 | O | OH | H | H |
| 3563 | 2,4-F₂—Ph | NH | Ph | O | OH | H | H |
| 3564 | 2,4-F₂—Ph | NH | C12 | S | OH | H | H |
| 3565 | 2,4-F₂—Ph | NH | Ph | S | OH | H | H |
| 3566 | 2,4-F₂—Ph | NMe | H | NH | OH | H | H |
| 3567 | 2,4-F₂—Ph | NEt | H | NH | OH | H | H |
| 3568 | 2,4-F₂—Ph | NPr | H | NH | OH | H | H |
| 3569 | 2,4-F₂—Ph | O | H | NH | OH | H | H |
| 3570 | 2,4-F₂—Ph | S | H | NH | OH | H | H |
| 3571 | 2,5-F₂—Ph | NH | H | NH | H | H | H |
| 3572 | 2,5-F₂—Ph | NH | H | NH | OH | H | H |
| 3573 | 2,5-F₂—Ph | NH | H | NH | OA6 | H | H |
| 3574 | 2,5-F₂—Ph | NH | H | NH | OA8 | H | H |
| 3575 | 2,5-F₂—Ph | NH | H | NH | OA9 | H | H |
| 3576 | 2,5-F₂—Ph | NH | H | NH | OA10 | H | H |
| 3577 | 2,5-F₂—Ph | NH | H | NH | OA12 | H | H |
| 3578 | 2,5-F₂—Ph | NH | H | NH | OA14 | H | H |
| 3579 | 2,5-F₂—Ph | NH | H | NH | OA16 | H | H |
| 3580 | 2,5-F₂—Ph | NH | H | NH | OH | H | A6 |
| 3581 | 2,5-F₂—Ph | NH | H | NH | OH | H | A8 |
| 3582 | 2,5-F₂—Ph | NH | H | NH | OH | H | A9 |
| 3583 | 2,5-F₂—Ph | NH | H | NH | OH | H | A10 |
| 3584 | 2,5-F₂—Ph | NH | H | NH | OH | H | A12 |
| 3585 | 2,5-F₂—Ph | NH | H | NH | OH | H | A14 |
| 3586 | 2,5-F₂—Ph | NH | H | NH | OH | H | A16 |
| 3587 | 2,5-F₂—Ph | NH | H | NH | OH | A6 | A6 |
| 3588 | 2,5-F₂—Ph | NH | H | NH | OH | A8 | A8 |
| 3589 | 2,5-F₂—Ph | NH | H | NH | OH | A10 | A10 |
| 3590 | 2,5-F₂—Ph | NH | H | NH | OA2 | A2 | A2 |
| 3591 | 2,5-F₂—Ph | NH | H | NH | OA3 | A3 | A3 |
| 3592 | 2,5-F₂—Ph | NH | H | NH | OA4 | A4 | A4 |
| 3593 | 2,5-F₂—Ph | NH | H | NH | OC6 | H | H |
| 3594 | 2,5-F₂—Ph | NH | H | NH | OC7 | H | H |
| 3595 | 2,5-F₂—Ph | NH | H | NH | OC8 | H | H |
| 3596 | 2,5-F₂—Ph | NH | H | NH | OC10 | H | H |
| 3597 | 2,5-F₂—Ph | NH | H | NH | OC11 | H | H |
| 3598 | 2,5-F₂—Ph | NH | H | NH | OC12 | H | H |
| 3599 | 2,5-F₂—Ph | NH | H | NH | OC14 | H | H |
| 3600 | 2,5-F₂—Ph | NH | H | NH | OC16 | H | H |
| 3601 | 2,5-F₂—Ph | NH | H | NH | C6CO₃ | H | H |

TABLE 1-continued

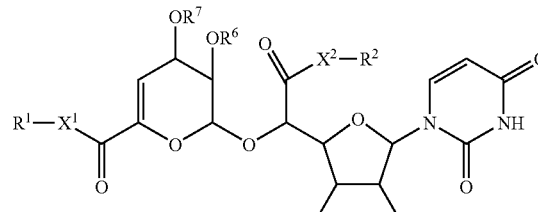

(I-1)

| Exemp. Comp. No. | R¹ | X¹ | R² | X² | R³ | R⁶ | R⁷ |
|---|---|---|---|---|---|---|---|
| 3602 | 2,5-F$_2$—Ph | NH | H | NH | C7CO$_3$ | H | H |
| 3603 | 2,5-F$_2$—Ph | NH | H | NH | C8CO$_3$ | H | H |
| 3604 | 2,5-F$_2$—Ph | NH | H | NH | C9CO$_3$ | H | H |
| 3605 | 2,5-F$_2$—Ph | NH | H | NH | C10CO$_3$ | H | H |
| 3606 | 2,5-F$_2$—Ph | NH | H | NH | C12CO$_3$ | H | H |
| 3607 | 2,5-F$_2$—Ph | NH | H | NH | C16CO$_3$ | H | H |
| 3608 | 2,5-F$_2$—Ph | NH | C8 | NH | OH | H | H |
| 3609 | 2,5-F$_2$—Ph | NH | C9 | NH | OH | H | H |
| 3610 | 2,5-F$_2$—Ph | NH | C10 | NH | OH | H | H |
| 3611 | 2,5-F$_2$—Ph | NH | C12 | NH | OH | H | H |
| 3612 | 2,5-F$_2$—Ph | NH | C16 | NH | OH | H | H |
| 3613 | 2,5-F$_2$—Ph | NH | F1 | NH | OH | H | H |
| 3614 | 2,5-F$_2$—Ph | NH | F2 | NH | OH | H | H |
| 3615 | 2,5-F$_2$—Ph | NH | F3 | NH | OH | H | H |
| 3616 | 2,5-F$_2$—Ph | NH | F4 | NH | OH | H | H |
| 3617 | 2,5-F$_2$—Ph | NH | F5 | NH | OH | H | H |
| 3618 | 2,5-F$_2$—Ph | NH | F6 | NH | OH | H | H |
| 3619 | 2,5-F$_2$—Ph | NH | F7 | NH | OH | H | H |
| 3620 | 2,5-F$_2$—Ph | NH | F8 | NH | OH | H | H |
| 3621 | 2,5-F$_2$—Ph | NH | F9 | NH | OH | H | H |
| 3622 | 2,5-F$_2$—Ph | NH | F10 | NH | OH | H | H |
| 3623 | 2,5-F$_2$—Ph | NH | Ph | NH | OH | H | H |
| 3624 | 2,5-F$_2$—Ph | NH | Bn | NH | OH | H | H |
| 3625 | 2,5-F$_2$—Ph | NH | Pe | NH | OH | H | H |
| 3626 | 2,5-F$_2$—Ph | NH | C12 | NMe | OH | H | H |
| 3627 | 2,5-F$_2$—Ph | NH | C12 | NEt | OH | H | H |
| 3628 | 2,5-F$_2$—Ph | NH | C12 | NPr | OH | H | H |
| 3629 | 2,5-F$_2$—Ph | NH | (CH$_2$)$_3$ | N | OH | H | H |
| 3630 | 2,5-F$_2$—Ph | NH | (CH$_2$)$_4$ | N | OH | H | H |
| 3631 | 2,5-F$_2$—Ph | NH | (CH$_2$)$_5$ | N | OH | H | H |
| 3632 | 2,5-F$_2$—Ph | NH | C12 | O | OH | H | H |
| 3633 | 2,5-F$_2$—Ph | NH | Ph | O | OH | H | H |
| 3634 | 2,5-F$_2$—Ph | NH | C12 | S | OH | H | H |
| 3635 | 2,5-F$_2$—Ph | NH | Ph | S | OH | H | H |
| 3636 | 2,5-F$_2$—Ph | NMe | H | NH | OH | H | H |
| 3637 | 2,5-F$_2$—Ph | NEt | H | NH | OH | H | H |
| 3638 | 2,5-F$_2$—Ph | NPr | H | NH | OH | H | H |
| 3639 | 2,5-F$_2$—Ph | O | H | NH | OH | H | H |
| 3640 | 2,5-F$_2$—Ph | S | H | NH | OH | H | H |
| 3641 | 2,6-F$_2$—Ph | NH | H | NH | H | H | H |
| 3642 | 2,6-F$_2$—Ph | NH | H | NH | OH | H | H |
| 3643 | 2,6-F$_2$—Ph | NH | H | NH | OA6 | H | H |
| 3644 | 2,6-F$_2$—Ph | NH | H | NH | OA8 | H | H |
| 3645 | 2,6-F$_2$—Ph | NH | H | NH | OA9 | H | H |
| 3646 | 2,6-F$_2$—Ph | NH | H | NH | OA10 | H | H |
| 3647 | 2,6-F$_2$—Ph | NH | H | NH | OA12 | H | H |
| 3648 | 2,6-F$_2$—Ph | NH | H | NH | OA14 | H | H |
| 3649 | 2,6-F$_2$—Ph | NH | H | NH | OA16 | H | H |
| 3650 | 2,6-F$_2$—Ph | NH | H | NH | OH | H | A6 |
| 3651 | 2,6-F$_2$—Ph | NH | H | NH | OH | H | A8 |
| 3652 | 2,6-F$_2$—Ph | NH | H | NH | OH | H | A9 |
| 3653 | 2,6-F$_2$—Ph | NH | H | NH | OH | H | A10 |
| 3654 | 2,6-F$_2$—Ph | NH | H | NH | OH | H | A12 |
| 3655 | 2,6-F$_2$—Ph | NH | H | NH | OH | H | A14 |
| 3656 | 2,6-F$_2$—Ph | NH | H | NH | OH | H | A16 |
| 3657 | 2,6-F$_2$—Ph | NH | H | NH | OH | A6 | A6 |
| 3658 | 2,6-F$_2$—Ph | NH | H | NH | OH | A8 | A8 |
| 3659 | 2,6-F$_2$—Ph | NH | H | NH | OH | A10 | A10 |
| 3660 | 2,6-F$_2$—Ph | NH | H | NH | OA2 | A2 | A2 |
| 3661 | 2,6-F$_2$—Ph | NH | H | NH | OA3 | A3 | A3 |
| 3662 | 2,6-F$_2$—Ph | NH | H | NH | OA4 | A4 | A4 |
| 3663 | 2,6-F$_2$—Ph | NH | H | NH | OC6 | H | H |

TABLE 1-continued (I-1)

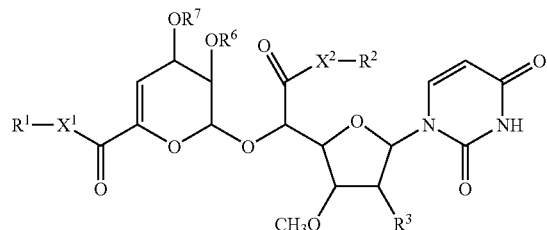

| Exemp. Comp. No. | R¹ | X¹ | R² | X² | R³ | R⁶ | R⁷ |
|---|---|---|---|---|---|---|---|
| 3664 | 2,6-F₂—Ph | NH | H | NH | OC7 | H | H |
| 3665 | 2,6-F₂—Ph | NH | H | NH | OC8 | H | H |
| 3666 | 2,6-F₂—Ph | NH | H | NH | OC10 | H | H |
| 3667 | 2,6-F₂—Ph | NH | H | NH | OC11 | H | H |
| 3668 | 2,6-F₂—Ph | NH | H | NH | OC12 | H | H |
| 3669 | 2,6-F₂—Ph | NH | H | NH | OC14 | H | H |
| 3670 | 2,6-F₂—Ph | NH | H | NH | OC16 | H | H |
| 3671 | 2,6-F₂—Ph | NH | H | NH | C6CO₃ | H | H |
| 3672 | 2,6-F₂—Ph | NH | H | NH | C7CO₃ | H | H |
| 3673 | 2,6-F₂—Ph | NH | H | NH | C8CO₃ | H | H |
| 3674 | 2,6-F₂—Ph | NH | H | NH | C9CO₃ | H | H |
| 3675 | 2,6-F₂—Ph | NH | H | NH | C10CO₃ | H | H |
| 3676 | 2,6-F₂—Ph | NH | H | NH | C12CO₃ | H | H |
| 3677 | 2,6-F₂—Ph | NH | H | NH | C16CO₃ | H | H |
| 3678 | 2,6-F₂—Ph | NH | C8 | NH | OH | H | H |
| 3679 | 2,6-F₂—Ph | NH | C9 | NH | OH | H | H |
| 3680 | 2,6-F₂—Ph | NH | C10 | NH | OH | H | H |
| 3681 | 2,6-F₂—Ph | NH | C12 | NH | OH | H | H |
| 3682 | 2,6-F₂—Ph | NH | C16 | NH | OH | H | H |
| 3683 | 2,6-F₂—Ph | NH | F1 | NH | OH | H | H |
| 3684 | 2,6-F₂—Ph | NH | F2 | NH | OH | H | H |
| 3685 | 2,6-F₂—Ph | NH | F3 | NH | OH | H | H |
| 3686 | 2,6-F₂—Ph | NH | F4 | NH | OH | H | H |
| 3687 | 2,6-F₂—Ph | NH | F5 | NH | OH | H | H |
| 3688 | 2,6-F₂—Ph | NH | F6 | NH | OH | H | H |
| 3689 | 2,6-F₂—Ph | NH | F7 | NH | OH | H | H |
| 3690 | 2,6-F₂—Ph | NH | F8 | NH | OH | H | H |
| 3691 | 2,6-F₂—Ph | NH | F9 | NH | OH | H | H |
| 3692 | 2,6-F₂—Ph | NH | F10 | NH | OH | H | H |
| 3693 | 2,6-F₂—Ph | NH | Ph | NH | OH | H | H |
| 3694 | 2,6-F₂—Ph | NH | Bn | NH | OH | H | H |
| 3695 | 2,6-F₂—Ph | NH | Pe | NH | OH | H | H |
| 3696 | 2,6-F₂—Ph | NH | C12 | NMe | OH | H | H |
| 3697 | 2,6-F₂—Ph | NH | C12 | NEt | OH | H | H |
| 3698 | 2,6-F₂—Ph | NH | C12 | NPr | OH | H | H |
| 3699 | 2,6-F₂—Ph | NH | (CH₂)₃ | N | OH | H | H |
| 3700 | 2,6-F₂—Ph | NH | (CH₂)₄ | N | OH | H | H |
| 3701 | 2,6-F₂—Ph | NH | (CH₂)₅ | N | OH | H | H |
| 3702 | 2,6-F₂—Ph | NH | C12 | O | OH | H | H |
| 3703 | 2,6-F₂—Ph | NH | Ph | O | OH | H | H |
| 3704 | 2,6-F₂—Ph | NH | C12 | S | OH | H | H |
| 3705 | 2,6-F₂—Ph | NH | Ph | S | OH | H | H |
| 3706 | 2,6-F₂—Ph | NMe | H | NH | OH | H | H |
| 3707 | 2,6-F₂—Ph | NEt | H | NH | OH | H | H |
| 3708 | 2,6-F₂—Ph | NPr | H | NH | OH | H | H |
| 3709 | 2,6-F₂—Ph | O | H | NH | OH | H | H |
| 3710 | 2,6-F₂—Ph | S | H | NH | OH | H | H |
| 3711 | 3,4-F₂—Ph | NH | H | NH | H | H | H |
| 3712 | 3,4-F₂—Ph | NH | H | NH | OH | H | H |
| 3713 | 3,4-F₂—Ph | NH | H | NH | OA6 | H | H |
| 3714 | 3,4-F₂—Ph | NH | H | NH | OA8 | H | H |
| 3715 | 3,4-F₂—Ph | NH | H | NH | OA9 | H | H |
| 3716 | 3,4-F₂—Ph | NH | H | NH | OA10 | H | H |
| 3717 | 3,4-F₂—Ph | NH | H | NH | OA12 | H | H |
| 3718 | 3,4-F₂—Ph | NH | H | NH | OA14 | H | H |
| 3719 | 3,4-F₂—Ph | NH | H | NH | OA16 | H | H |
| 3720 | 3,4-F₂—Ph | NH | H | NH | OH | H | A6 |
| 3721 | 3,4-F₂—Ph | NH | H | NH | OH | H | A8 |
| 3722 | 3,4-F₂—Ph | NH | H | NH | OH | H | A9 |
| 3723 | 3,4-F₂—Ph | NH | H | NH | OH | H | A10 |
| 3724 | 3,4-F₂—Ph | NH | H | NH | OH | H | A12 |
| 3725 | 3,4-F₂—Ph | NH | H | NH | OH | H | A14 |

TABLE 1-continued (I-1)

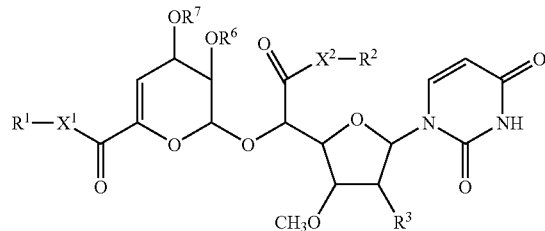

| Exemp. Comp. No. | R[1] | X[1] | R[2] | X[2] | R[3] | R[6] | R[7] |
|---|---|---|---|---|---|---|---|
| 3726 | 3,4-F$_2$—Ph | NH | H | NH | OH | H | A16 |
| 3727 | 3,4-F$_2$—Ph | NH | H | NH | OH | A6 | A6 |
| 3728 | 3,4-F$_2$—Ph | NH | H | NH | OH | A8 | A8 |
| 3729 | 3,4-F$_2$—Ph | NH | H | NH | OH | A10 | A10 |
| 3730 | 3,4-F$_2$—Ph | NH | H | NH | OA2 | A2 | A2 |
| 3731 | 3,4-F$_2$—Ph | NH | H | NH | OA3 | A3 | A3 |
| 3732 | 3,4-F$_2$—Ph | NH | H | NH | OA4 | A4 | A4 |
| 3733 | 3,4-F$_2$—Ph | NH | H | NH | OC6 | H | H |
| 3734 | 3,4-F$_2$—Ph | NH | H | NH | OC7 | H | H |
| 3735 | 3,4-F$_2$—Ph | NH | H | NH | OC8 | H | H |
| 3736 | 3,4-F$_2$—Ph | NH | H | NH | OC10 | H | H |
| 3737 | 3,4-F$_2$—Ph | NH | H | NH | OC11 | H | H |
| 3738 | 3,4-F$_2$—Ph | NH | H | NH | OC12 | H | H |
| 3739 | 3,4-F$_2$—Ph | NH | H | NH | OC14 | H | H |
| 3740 | 3,4-F$_2$—Ph | NH | H | NH | OC16 | H | H |
| 3741 | 3,4-F$_2$—Ph | NH | H | NH | C6CO$_3$ | H | H |
| 3742 | 3,4-F$_2$—Ph | NH | H | NH | C7CO$_3$ | H | H |
| 3743 | 3,4-F$_2$—Ph | NH | H | NH | C8CO$_3$ | H | H |
| 3744 | 3,4-F$_2$—Ph | NH | H | NH | C9CO$_3$ | H | H |
| 3745 | 3,4-F$_2$—Ph | NH | H | NH | C10CO$_3$ | H | H |
| 3746 | 3,4-F$_2$—Ph | NH | H | NH | C12CO$_3$ | H | H |
| 3747 | 3,4-F$_2$—Ph | NH | H | NH | C16CO$_3$ | H | H |
| 3748 | 3,4-F$_2$—Ph | NH | C8 | NH | OH | H | H |
| 3749 | 3,4-F$_2$—Ph | NH | C9 | NH | OH | H | H |
| 3750 | 3,4-F$_2$—Ph | NH | C10 | NH | OH | H | H |
| 3751 | 3,4-F$_2$—Ph | NH | C12 | NH | OH | H | H |
| 3752 | 3,4-F$_2$—Ph | NH | C16 | NH | OH | H | H |
| 3753 | 3,4-F$_2$—Ph | NH | F1 | NH | OH | H | H |
| 3754 | 3,4-F$_2$—Ph | NH | F2 | NH | OH | H | H |
| 3755 | 3,4-F$_2$—Ph | NH | F3 | NH | OH | H | H |
| 3756 | 3,4-F$_2$—Ph | NH | F4 | NH | OH | H | H |
| 3757 | 3,4-F$_2$—Ph | NH | F5 | NH | OH | H | H |
| 3758 | 3,4-F$_2$—Ph | NH | F6 | NH | OH | H | H |
| 3759 | 3,4-F$_2$—Ph | NH | F7 | NH | OH | H | H |
| 3760 | 3,4-F$_2$—Ph | NH | F8 | NH | OH | H | H |
| 3761 | 3,4-F$_2$—Ph | NH | F9 | NH | OH | H | H |
| 3762 | 3,4-F$_2$—Ph | NH | F10 | NH | OH | H | H |
| 3763 | 3,4-F$_2$—Ph | NH | Ph | NH | OH | H | H |
| 3764 | 3,4-F$_2$—Ph | NH | Bn | NH | OH | H | H |
| 3765 | 3,4-F$_2$—Ph | NH | Pe | NH | OH | H | H |
| 3766 | 3,4-F$_2$—Ph | NH | C12 | NMe | OH | H | H |
| 3767 | 3,4-F$_2$—Ph | NH | C12 | NEt | OH | H | H |
| 3768 | 3,4-F$_2$—Ph | NH | C12 | NPr | OH | H | H |
| 3769 | 3,4-F$_2$—Ph | NH | (CH$_2$)$_3$ | N | OH | H | H |
| 3770 | 3,4-F$_2$—Ph | NH | (CH$_2$)$_4$ | N | OH | H | H |
| 3771 | 3,4-F$_2$—Ph | NH | (CH$_2$)$_5$ | N | OH | H | H |
| 3772 | 3,4-F$_2$—Ph | NH | C12 | O | OH | H | H |
| 3773 | 3,4-F$_2$—Ph | NH | Ph | O | OH | H | H |
| 3774 | 3,4-F$_2$—Ph | NH | C12 | S | OH | H | H |
| 3775 | 3,4-F$_2$—Ph | NH | Ph | S | OH | H | H |
| 3776 | 3,4-F$_2$—Ph | NMe | H | NH | OH | H | H |
| 3777 | 3,4-F$_2$—Ph | NEt | H | NH | OH | H | H |
| 3778 | 3,4-F$_2$—Ph | NPr | H | NH | OH | H | H |
| 3779 | 3,4-F$_2$—Ph | O | H | NH | OH | H | H |
| 3780 | 3,4-F$_2$—Ph | S | H | NH | OH | H | H |
| 3781 | 3,5-F$_2$—Ph | NH | H | NH | H | H | H |
| 3782 | 3,5-F$_2$—Ph | NH | H | NH | OH | H | H |
| 3783 | 3,5-F$_2$—Ph | NH | H | NH | OA6 | H | H |
| 3784 | 3,5-F$_2$—Ph | NH | H | NH | OA8 | H | H |
| 3785 | 3,5-F$_2$—Ph | NH | H | NH | OA9 | H | H |
| 3786 | 3,5-F$_2$—Ph | NH | H | NH | OA10 | H | H |
| 3787 | 3,5-F$_2$—Ph | NH | H | NH | OA12 | H | H |

TABLE 1-continued (I-1)

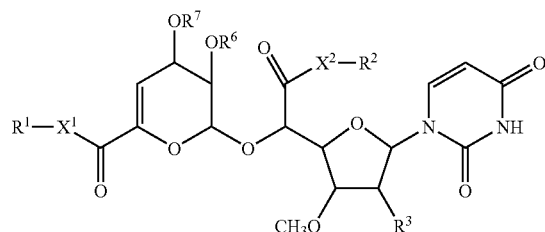

| Exemp. Comp. No. | R¹ | X¹ | R² | X² | R³ | R⁶ | R⁷ |
|---|---|---|---|---|---|---|---|
| 3788 | 3,5-F₂—Ph | NH | H | NH | OA14 | H | H |
| 3789 | 3,5-F₂—Ph | NH | H | NH | OA16 | H | H |
| 3790 | 3,5-F₂—Ph | NH | H | NH | OH | H | A6 |
| 3791 | 3,5-F₂—Ph | NH | H | NH | OH | H | A8 |
| 3792 | 3,5-F₂—Ph | NH | H | NH | OH | H | A9 |
| 3793 | 3,5-F₂—Ph | NH | H | NH | OH | H | A10 |
| 3794 | 3,5-F₂—Ph | NH | H | NH | OH | H | A12 |
| 3795 | 3,5-F₂—Ph | NH | H | NH | OH | H | A14 |
| 3796 | 3,5-F₂—Ph | NH | H | NH | OH | H | A16 |
| 3797 | 3,5-F₂—Ph | NH | H | NH | OH | A6 | A6 |
| 3798 | 3,5-F₂—Ph | NH | H | NH | OH | A8 | A8 |
| 3799 | 3,5-F₂—Ph | NH | H | NH | OH | A10 | A10 |
| 3800 | 3,5-F₂—Ph | NH | H | NH | OA2 | A2 | A2 |
| 3801 | 3,5-F₂—Ph | NH | H | NH | OA3 | A3 | A3 |
| 3802 | 3,5-F₂—Ph | NH | H | NH | OA4 | A4 | A4 |
| 3803 | 3,5-F₂—Ph | NH | H | NH | OC6 | H | H |
| 3804 | 3,5-F₂—Ph | NH | H | NH | OC7 | H | H |
| 3805 | 3,5-F₂—Ph | NH | H | NH | OC8 | H | H |
| 3806 | 3,5-F₂—Ph | NH | H | NH | OC10 | H | H |
| 3807 | 3,5-F₂—Ph | NH | H | NH | OC11 | H | H |
| 3808 | 3,5-F₂—Ph | NH | H | NH | OC12 | H | H |
| 3809 | 3,5-F₂—Ph | NH | H | NH | OC14 | H | H |
| 3810 | 3,5-F₂—Ph | NH | H | NH | OC16 | H | H |
| 3811 | 3,5-F₂—Ph | NH | H | NH | C6CO₃ | H | H |
| 3812 | 3,5-F₂—Ph | NH | H | NH | C7CO₃ | H | H |
| 3813 | 3,5-F₂—Ph | NH | H | NH | C8CO₃ | H | H |
| 3814 | 3,5-F₂—Ph | NH | H | NH | C9CO₃ | H | H |
| 3815 | 3,5-F₂—Ph | NH | H | NH | C10CO₃ | H | H |
| 3816 | 3,5-F₂—Ph | NH | H | NH | C12CO₃ | H | H |
| 3817 | 3,5-F₂—Ph | NH | H | NH | C16CO₃ | H | H |
| 3818 | 3,5-F₂—Ph | NH | C8 | NH | OH | H | H |
| 3819 | 3,5-F₂—Ph | NH | C9 | NH | OH | H | H |
| 3820 | 3,5-F₂—Ph | NH | C10 | NH | OH | H | H |
| 3821 | 3,5-F₂—Ph | NH | C12 | NH | OH | H | H |
| 3822 | 3,5-F₂—Ph | NH | C16 | NH | OH | H | H |
| 3823 | 3,5-F₂—Ph | NH | F1 | NH | OH | H | H |
| 3824 | 3,5-F₂—Ph | NH | F2 | NH | OH | H | H |
| 3825 | 3,5-F₂—Ph | NH | F3 | NH | OH | H | H |
| 3826 | 3,5-F₂—Ph | NH | F4 | NH | OH | H | H |
| 3827 | 3,5-F₂—Ph | NH | F5 | NH | OH | H | H |
| 3828 | 3,5-F₂—Ph | NH | F6 | NH | OH | H | H |
| 3829 | 3,5-F₂—Ph | NH | F7 | NH | OH | H | H |
| 3830 | 3,5-F₂—Ph | NH | F8 | NH | OH | H | H |
| 3831 | 3,5-F₂—Ph | NH | F9 | NH | OH | H | H |
| 3832 | 3,5-F₂—Ph | NH | F10 | NH | OH | H | H |
| 3833 | 3,5-F₂—Ph | NH | Ph | NH | OH | H | H |
| 3834 | 3,5-F₂—Ph | NH | Bn | NH | OH | H | H |
| 3835 | 3,5-F₂—Ph | NH | Pe | NH | OH | H | H |
| 3836 | 3,5-F₂—Ph | NH | C12 | NMe | OH | H | H |
| 3837 | 3,5-F₂—Ph | NH | C12 | NEt | OH | H | H |
| 3838 | 3,5-F₂—Ph | NH | C12 | NPr | OH | H | H |
| 3839 | 3,5-F₂—Ph | NH | (CH₂)₃ | N | OH | H | H |
| 3840 | 3,5-F₂—Ph | NH | (CH₂)₄ | N | OH | H | H |
| 3841 | 3,5-F₂—Ph | NH | (CH₂)₅ | N | OH | H | H |
| 3842 | 3,5-F₂—Ph | NH | C12 | O | OH | H | H |
| 3843 | 3,5-F₂—Ph | NH | Ph | O | OH | H | H |
| 3844 | 3,5-F₂—Ph | NH | C12 | S | OH | H | H |
| 3845 | 3,5-F₂—Ph | NH | Ph | S | OH | H | H |
| 3846 | 3,5-F₂—Ph | NMe | H | NH | OH | H | H |
| 3847 | 3,5-F₂—Ph | NEt | H | NH | OH | H | H |
| 3848 | 3,5-F₂—Ph | NPr | H | NH | OH | H | H |
| 3849 | 3,5-F₂—Ph | O | H | NH | OH | H | H |

TABLE 1-continued (I-1)

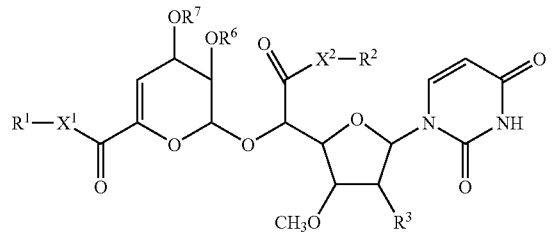

| Exemp. Comp. No. | $R^1$ | $X^1$ | $R^2$ | $X^2$ | $R^3$ | $R^6$ | $R^7$ |
|---|---|---|---|---|---|---|---|
| 3850 | 3,5-$F_2$—Ph | S | H | NH | OH | H | H |
| 3851 | 2,3,4-$F_3$—Ph | NH | H | NH | H | H | H |
| 3852 | 2,3,4-$F_3$—Ph | NH | H | NH | OH | H | H |
| 3853 | 2,3,4-$F_3$—Ph | NH | H | NH | OA6 | H | H |
| 3854 | 2,3,4-$F_3$—Ph | NH | H | NH | OA8 | H | H |
| 3855 | 2,3,4-$F_3$—Ph | NH | H | NH | OA9 | H | H |
| 3856 | 2,3,4-$F_3$—Ph | NH | H | NH | OA10 | H | H |
| 3857 | 2,3,4-$F_3$—Ph | NH | H | NH | OA12 | H | H |
| 3858 | 2,3,4-$F_3$—Ph | NH | H | NH | OA14 | H | H |
| 3859 | 2,3,4-$F_3$—Ph | NH | H | NH | OA16 | H | H |
| 3860 | 2,3,4-$F_3$—Ph | NH | H | NH | OH | H | A6 |
| 3861 | 2,3,4-$F_3$—Ph | NH | H | NH | OH | H | A8 |
| 3862 | 2,3,4-$F_3$—Ph | NH | H | NH | OH | H | A9 |
| 3863 | 2,3,4-$F_3$—Ph | NH | H | NH | OH | H | A10 |
| 3864 | 2,3,4-$F_3$—Ph | NH | H | NH | OH | H | A12 |
| 3865 | 2,3,4-$F_3$—Ph | NH | H | NH | OH | H | A14 |
| 3866 | 2,3,4-$F_3$—Ph | NH | H | NH | OH | H | A16 |
| 3867 | 2,3,4-$F_3$—Ph | NH | H | NH | OH | A6 | A6 |
| 3868 | 2,3,4-$F_3$—Ph | NH | H | NH | OH | A8 | A8 |
| 3869 | 2,3,4-$F_3$—Ph | NH | H | NH | OH | A10 | A10 |
| 3870 | 2,3,4-$F_3$—Ph | NH | H | NH | OA2 | A2 | A2 |
| 3871 | 2,3,4-$F_3$—Ph | NH | H | NH | OA3 | A3 | A3 |
| 3872 | 2,3,4-$F_3$—Ph | NH | H | NH | OA4 | A4 | A4 |
| 3873 | 2,3,4-$F_3$—Ph | NH | H | NH | OC6 | H | H |
| 3874 | 2,3,4-$F_3$—Ph | NH | H | NH | OC7 | H | H |
| 3875 | 2,3,4-$F_3$—Ph | NH | H | NH | OC8 | H | H |
| 3876 | 2,3,4-$F_3$—Ph | NH | H | NH | OC10 | H | H |
| 3877 | 2,3,4-$F_3$—Ph | NH | H | NH | OC11 | H | H |
| 3878 | 2,3,4-$F_3$—Ph | NH | H | NH | OC12 | H | H |
| 3879 | 2,3,4-$F_3$—Ph | NH | H | NH | OC14 | H | H |
| 3880 | 2,3,4-$F_3$—Ph | NH | H | NH | OC16 | H | H |
| 3881 | 2,3,4-$F_3$—Ph | NH | H | NH | $C6CO_3$ | H | H |
| 3882 | 2,3,4-$F_3$—Ph | NH | H | NH | $C7CO_3$ | H | H |
| 3883 | 2,3,4-$F_3$—Ph | NH | H | NH | $C8CO_3$ | H | H |
| 3884 | 2,3,4-$F_3$—Ph | NH | H | NH | $C9CO_3$ | H | H |
| 3885 | 2,3,4-$F_3$—Ph | NH | H | NH | $C10CO_3$ | H | H |
| 3886 | 2,3,4-$F_3$—Ph | NH | H | NH | $C12CO_3$ | H | H |
| 3887 | 2,3,4-$F_3$—Ph | NH | H | NH | $C16CO_3$ | H | H |
| 3888 | 2,3,4-$F_3$—Ph | NH | C8 | NH | OH | H | H |
| 3889 | 2,3,4-$F_3$—Ph | NH | C9 | NH | OH | H | H |
| 3890 | 2,3,4-$F_3$—Ph | NH | C10 | NH | OH | H | H |
| 3891 | 2,3,4-$F_3$—Ph | NH | C12 | NH | OH | H | H |
| 3892 | 2,3,4-$F_3$—Ph | NH | C16 | NH | OH | H | H |
| 3893 | 2,3,4-$F_3$—Ph | NH | F1 | NH | OH | H | H |
| 3894 | 2,3,4-$F_3$—Ph | NH | F2 | NH | OH | H | H |
| 3895 | 2,3,4-$F_3$—Ph | NH | F3 | NH | OH | H | H |
| 3896 | 2,3,4-$F_3$—Ph | NH | F4 | NH | OH | H | H |
| 3897 | 2,3,4-$F_3$—Ph | NH | F5 | NH | OH | H | H |
| 3898 | 2,3,4-$F_3$—Ph | NH | F6 | NH | OH | H | H |
| 3899 | 2,3,4-$F_3$—Ph | NH | F7 | NH | OH | H | H |
| 3900 | 2,3,4-$F_3$—Ph | NH | F8 | NH | OH | H | H |
| 3901 | 2,3,4-$F_3$—Ph | NH | F9 | NH | OH | H | H |
| 3902 | 2,3,4-$F_3$—Ph | NH | F10 | NH | OH | H | H |
| 3903 | 2,3,4-$F_3$—Ph | NH | Ph | NH | OH | H | H |
| 3904 | 2,3,4-$F_3$—Ph | NH | Bn | NH | OH | H | H |
| 3905 | 2,3,4-$F_3$—Ph | NH | Pe | NH | OH | H | H |
| 3906 | 2,3,4-$F_3$—Ph | NH | C12 | NMe | OH | H | H |
| 3907 | 2,3,4-$F_3$—Ph | NH | C12 | NEt | OH | H | H |
| 3908 | 2,3,4-$F_3$—Ph | NH | C12 | NPr | OH | H | H |
| 3909 | 2,3,4-$F_3$—Ph | NH | $(CH_2)_3$ | N | OH | H | H |
| 3910 | 2,3,4-$F_3$—Ph | NH | $(CH_2)_4$ | N | OH | H | H |
| 3911 | 2,3,4-$F_3$—Ph | NH | $(CH_2)_5$ | N | OH | H | H |

TABLE 1-continued (I-1)

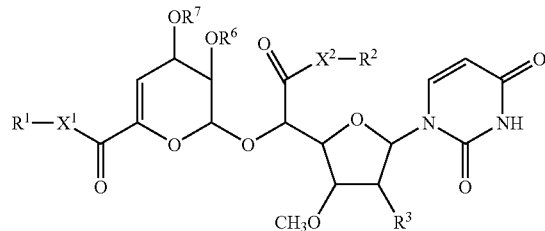

| Exemp. Comp. No. | R¹ | X¹ | R² | X² | R³ | R⁶ | R⁷ |
|---|---|---|---|---|---|---|---|
| 3912 | 2,3,4-F₃—Ph | NH | C12 | O | OH | H | H |
| 3913 | 2,3,4-F₃—Ph | NH | Ph | O | OH | H | H |
| 3914 | 2,3,4-F₃—Ph | NH | C12 | S | OH | H | H |
| 3915 | 2,3,4-F₃—Ph | NH | Ph | S | OH | H | H |
| 3916 | 2,3,4-F₃—Ph | NMe | H | NH | OH | H | H |
| 3917 | 2,3,4-F₃—Ph | NEt | H | NH | OH | H | H |
| 3918 | 2,3,4-F₃—Ph | NPr | H | NH | OH | H | H |
| 3919 | 2,3,4-F₃—Ph | O | H | NH | OH | H | H |
| 3920 | 2,3,4-F₃—Ph | S | H | NH | OH | H | H |
| 3921 | 2,3,6-F₃—Ph | NH | H | NH | H | H | H |
| 3922 | 2,3,6-F₃—Ph | NH | H | NH | OH | H | H |
| 3923 | 2,3,6-F₃—Ph | NH | H | NH | OA6 | H | H |
| 3924 | 2,3,6-F₃—Ph | NH | H | NH | OA8 | H | H |
| 3925 | 2,3,6-F₃—Ph | NH | H | NH | OA9 | H | H |
| 3926 | 2,3,6-F₃—Ph | NH | H | NH | OA10 | H | H |
| 3927 | 2,3,6-F₃—Ph | NH | H | NH | OA12 | H | H |
| 3928 | 2,3,6-F₃—Ph | NH | H | NH | OA14 | H | H |
| 3929 | 2,3,6-F₃—Ph | NH | H | NH | OA16 | H | H |
| 3930 | 2,3,6-F₃—Ph | NH | H | NH | OH | H | A6 |
| 3931 | 2,3,6-F₃—Ph | NH | H | NH | OH | H | A8 |
| 3932 | 2,3,6-F₃—Ph | NH | H | NH | OH | H | A9 |
| 3933 | 2,3,6-F₃—Ph | NH | H | NH | OH | H | A10 |
| 3934 | 2,3,6-F₃—Ph | NH | H | NH | OH | H | A12 |
| 3935 | 2,3,6-F₃—Ph | NH | H | NH | OH | H | A14 |
| 3936 | 2,3,6-F₃—Ph | NH | H | NH | OH | H | A16 |
| 3937 | 2,3,6-F₃—Ph | NH | H | NH | OH | A6 | A6 |
| 3938 | 2,3,6-F₃—Ph | NH | H | NH | OH | A8 | A8 |
| 3939 | 2,3,6-F₃—Ph | NH | H | NH | OH | A10 | A10 |
| 3940 | 2,3,6-F₃—Ph | NH | H | NH | OA2 | A2 | A2 |
| 3941 | 2,3,6-F₃—Ph | NH | H | NH | OA3 | A3 | A3 |
| 3942 | 2,3,6-F₃—Ph | NH | H | NH | OA4 | A4 | A4 |
| 3943 | 2,3,6-F₃—Ph | NH | H | NH | OC6 | H | H |
| 3944 | 2,3,6-F₃—Ph | NH | H | NH | OC7 | H | H |
| 3945 | 2,3,6-F₃—Ph | NH | H | NH | OC8 | H | H |
| 3946 | 2,3,6-F₃—Ph | NH | H | NH | OC10 | H | H |
| 3947 | 2,3,6-F₃—Ph | NH | H | NH | OC11 | H | H |
| 3948 | 2,3,6-F₃—Ph | NH | H | NH | OC12 | H | H |
| 3949 | 2,3,6-F₃—Ph | NH | H | NH | OC14 | H | H |
| 3950 | 2,3,6-F₃—Ph | NH | H | NH | OC16 | H | H |
| 3951 | 2,3,6-F₃—Ph | NH | H | NH | C6CO₃ | H | H |
| 3952 | 2,3,6-F₃—Ph | NH | H | NH | C7CO₃ | H | H |
| 3953 | 2,3,6-F₃—Ph | NH | H | NH | C8CO₃ | H | H |
| 3954 | 2,3,6-F₃—Ph | NH | H | NH | C9CO₃ | H | H |
| 3955 | 2,3,6-F₃—Ph | NH | H | NH | C10CO₃ | H | H |
| 3956 | 2,3,6-F₃—Ph | NH | H | NH | C12CO₃ | H | H |
| 3957 | 2,3,6-F₃—Ph | NH | H | NH | C16CO₃ | H | H |
| 3958 | 2,3,6-F₃—Ph | NH | C8 | NH | OH | H | H |
| 3959 | 2,3,6-F₃—Ph | NH | C9 | NH | OH | H | H |
| 3960 | 2,3,6-F₃—Ph | NH | C10 | NH | OH | H | H |
| 3961 | 2,3,6-F₃—Ph | NH | C12 | NH | OH | H | H |
| 3962 | 2,3,6-F₃—Ph | NH | C16 | NH | OH | H | H |
| 3963 | 2,3,6-F₃—Ph | NH | F1 | NH | OH | H | H |
| 3964 | 2,3,6-F₃—Ph | NH | F2 | NH | OH | H | H |
| 3965 | 2,3,6-F₃—Ph | NH | F3 | NH | OH | H | H |
| 3966 | 2,3,6-F₃—Ph | NH | F4 | NH | OH | H | H |
| 3967 | 2,3,6-F₃—Ph | NH | F5 | NH | OH | H | H |
| 3968 | 2,3,6-F₃—Ph | NH | F6 | NH | OH | H | H |
| 3969 | 2,3,6-F₃—Ph | NH | F7 | NH | OH | H | H |
| 3970 | 2,3,6-F₃—Ph | NH | F8 | NH | OH | H | H |
| 3971 | 2,3,6-F₃—Ph | NH | F9 | NH | OH | H | H |
| 3972 | 2,3,6-F₃—Ph | NH | F10 | NH | OH | H | H |
| 3973 | 2,3,6-F₃—Ph | NH | Ph | NH | OH | H | H |

TABLE 1-continued (I-1)

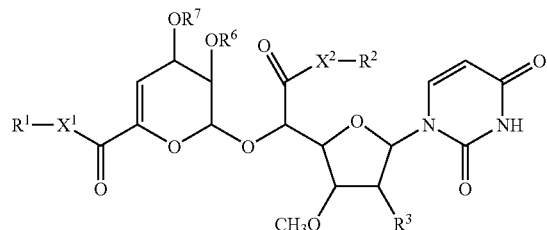

| Exemp. Comp. No. | R¹ | X¹ | R² | X² | R³ | R⁶ | R⁷ |
|---|---|---|---|---|---|---|---|
| 3974 | 2,3,6-F₃—Ph | NH | Bn | NH | OH | H | H |
| 3975 | 2,3,6-F₃—Ph | NH | Pe | NH | OH | H | H |
| 3976 | 2,3,6-F₃—Ph | NH | C12 | NMe | OH | H | H |
| 3977 | 2,3,6-F₃—Ph | NH | C12 | NEt | OH | H | H |
| 3978 | 2,3,6-F₃—Ph | NH | C12 | NPr | OH | H | H |
| 3979 | 2,3,6-F₃—Ph | NH | (CH₂)₃ | N | OH | H | H |
| 3980 | 2,3,6-F₃—Ph | NH | (CH₂)₄ | N | OH | H | H |
| 3981 | 2,3,6-F₃—Ph | NH | (CH₂)₅ | N | OH | H | H |
| 3982 | 2,3,6-F₃—Ph | NH | C12 | O | OH | H | H |
| 3983 | 2,3,6-F₃—Ph | NH | Ph | O | OH | H | H |
| 3984 | 2,3,6-F₃—Ph | NH | C12 | S | OH | H | H |
| 3985 | 2,3,6-F₃—Ph | NH | Ph | S | OH | H | H |
| 3986 | 2,3,6-F₃—Ph | NMe | H | NH | OH | H | H |
| 3987 | 2,3,6-F₃—Ph | NEt | H | NH | OH | H | H |
| 3988 | 2,3,6-F₃—Ph | NPr | H | NH | OH | H | H |
| 3989 | 2,3,6-F₃—Ph | O | H | NH | OH | H | H |
| 3990 | 2,3,6-F₃—Ph | S | H | NH | OH | H | H |
| 3991 | 2,4,6-F₃—Ph | NH | H | NH | H | H | H |
| 3992 | 2,4,6-F₃—Ph | NH | H | NH | OH | H | H |
| 3993 | 2,4,6-F₃—Ph | NH | H | NH | OA6 | H | H |
| 3994 | 2,4,6-F₃—Ph | NH | H | NH | OA8 | H | H |
| 3995 | 2,4,6-F₃—Ph | NH | H | NH | OA9 | H | H |
| 3996 | 2,4,6-F₃—Ph | NH | H | NH | OA10 | H | H |
| 3997 | 2,4,6-F₃—Ph | NH | H | NH | OA12 | H | H |
| 3998 | 2,4,6-F₃—Ph | NH | H | NH | OA14 | H | H |
| 3999 | 2,4,6-F₃—Ph | NH | H | NH | OA16 | H | H |
| 4000 | 2,4,6-F₃—Ph | NH | H | NH | OH | H | A6 |
| 4001 | 2,4,6-F₃—Ph | NH | H | NH | OH | H | A8 |
| 4002 | 2,4,6-F₃—Ph | NH | H | NH | OH | H | A9 |
| 4003 | 2,4,6-F₃—Ph | NH | H | NH | OH | H | A10 |
| 4004 | 2,4,6-F₃—Ph | NH | H | NH | OH | H | A12 |
| 4005 | 2,4,6-F₃—Ph | NH | H | NH | OH | H | A14 |
| 4006 | 2,4,6-F₃—Ph | NH | H | NH | OH | H | A16 |
| 4007 | 2,4,6-F₃—Ph | NH | H | NH | OH | A6 | A6 |
| 4008 | 2,4,6-F₃—Ph | NH | H | NH | OH | A8 | A8 |
| 4009 | 2,4,6-F₃—Ph | NH | H | NH | OH | A10 | A10 |
| 4010 | 2,4,6-F₃—Ph | NH | H | NH | OA2 | A2 | A2 |
| 4011 | 2,4,6-F₃—Ph | NH | H | NH | OA3 | A3 | A3 |
| 4012 | 2,4,6-F₃—Ph | NH | H | NH | OA4 | A4 | A4 |
| 4013 | 2,4,6-F₃—Ph | NH | H | NH | OC6 | H | H |
| 4014 | 2,4,6-F₃—Ph | NH | H | NH | OC7 | H | H |
| 4015 | 2,4,6-F₃—Ph | NH | H | NH | OC8 | H | H |
| 4016 | 2,4,6-F₃—Ph | NH | H | NH | OC10 | H | H |
| 4017 | 2,4,6-F₃—Ph | NH | H | NH | OC11 | H | H |
| 4018 | 2,4,6-F₃—Ph | NH | H | NH | OC12 | H | H |
| 4019 | 2,4,6-F₃—Ph | NH | H | NH | OC14 | H | H |
| 4020 | 2,4,6-F₃—Ph | NH | H | NH | OC16 | H | H |
| 4021 | 2,4,6-F₃—Ph | NH | H | NH | C6CO₃ | H | H |
| 4022 | 2,4,6-F₃—Ph | NH | H | NH | C7CO₃ | H | H |
| 4023 | 2,4,6-F₃—Ph | NH | H | NH | C8CO₃ | H | H |
| 4024 | 2,4,6-F₃—Ph | NH | H | NH | C9CO₃ | H | H |
| 4025 | 2,4,6-F₃—Ph | NH | H | NH | C10CO₃ | H | H |
| 4026 | 2,4,6-F₃—Ph | NH | H | NH | C12CO₃ | H | H |
| 4027 | 2,4,6-F₃—Ph | NH | H | NH | C16CO₃ | H | H |
| 4028 | 2,4,6-F₃—Ph | NH | C8 | NH | OH | H | H |
| 4029 | 2,4,6-F₃—Ph | NH | C9 | NH | OH | H | H |
| 4030 | 2,4,6-F₃—Ph | NH | C10 | NH | OH | H | H |
| 4031 | 2,4,6-F₃—Ph | NH | C12 | NH | OH | H | H |
| 4032 | 2,4,6-F₃—Ph | NH | C16 | NH | OH | H | H |
| 4033 | 2,4,6-F₃—Ph | NH | F1 | NH | OH | H | H |
| 4034 | 2,4,6-F₃—Ph | NH | F2 | NH | OH | H | H |
| 4035 | 2,4,6-F₃—Ph | NH | F3 | NH | OH | H | H |

TABLE 1-continued (I-1)

| Exemp. Comp. No. | R¹ | X¹ | R² | X² | R³ | R⁶ | R⁷ |
|---|---|---|---|---|---|---|---|
| 4036 | 2,4,6-$F_3$—Ph | NH | F4 | NH | OH | H | H |
| 4037 | 2,4,6-$F_3$—Ph | NH | F5 | NH | OH | H | H |
| 4038 | 2,4,6-$F_3$—Ph | NH | F6 | NH | OH | H | H |
| 4039 | 2,4,6-$F_3$—Ph | NH | F7 | NH | OH | H | H |
| 4040 | 2,4,6-$F_3$—Ph | NH | F8 | NH | OH | H | H |
| 4041 | 2,4,6-$F_3$—Ph | NH | F9 | NH | OH | H | H |
| 4042 | 2,4,6-$F_3$—Ph | NH | F10 | NH | OH | H | H |
| 4043 | 2,4,6-$F_3$—Ph | NH | Ph | NH | OH | H | H |
| 4044 | 2,4,6-$F_3$—Ph | NH | Bn | NH | OH | H | H |
| 4045 | 2,4,6-$F_3$—Ph | NH | Pe | NH | OH | H | H |
| 4046 | 2,4,6-$F_3$—Ph | NH | C12 | NMe | OH | H | H |
| 4047 | 2,4,6-$F_3$—Ph | NH | C12 | NEt | OH | H | H |
| 4048 | 2,4,6-$F_3$—Ph | NH | C12 | NPr | OH | H | H |
| 4049 | 2,4,6-$F_3$—Ph | NH | $(CH_2)_3$ | N | OH | H | H |
| 4050 | 2,4,6-$F_3$—Ph | NH | $(CH_2)_4$ | N | OH | H | H |
| 4051 | 2,4,6-$F_3$—Ph | NH | $(CH_2)_5$ | N | OH | H | H |
| 4052 | 2,4,6-$F_3$—Ph | NH | C12 | O | OH | H | H |
| 4053 | 2,4,6-$F_3$—Ph | NH | Ph | O | OH | H | H |
| 4054 | 2,4,6-$F_3$—Ph | NH | C12 | S | OH | H | H |
| 4055 | 2,4,6-$F_3$—Ph | NH | Ph | S | OH | H | H |
| 4056 | 2,4,6-$F_3$—Ph | NMe | H | NH | OH | H | H |
| 4057 | 2,4,6-$F_3$—Ph | NEt | H | NH | OH | H | H |
| 4058 | 2,4,6-$F_3$—Ph | NPr | H | NH | OH | H | H |
| 4059 | 2,4,6-$F_3$—Ph | O | H | NH | OH | H | H |
| 4060 | 2,4,6-$F_3$—Ph | S | H | NH | OH | H | H |
| 4061 | 2,4,5-$F_3$—Ph | NH | H | NH | H | H | H |
| 4062 | 2,4,5-$F_3$—Ph | NH | H | NH | OH | H | H |
| 4063 | 2,4,5-$F_3$—Ph | NH | H | NH | OA6 | H | H |
| 4064 | 2,4,5-$F_3$—Ph | NH | H | NH | OA8 | H | H |
| 4065 | 2,4,5-$F_3$—Ph | NH | H | NH | OA9 | H | H |
| 4066 | 2,4,5-$F_3$—Ph | NH | H | NH | OA10 | H | H |
| 4067 | 2,4,5-$F_3$—Ph | NH | H | NH | OA12 | H | H |
| 4068 | 2,4,5-$F_3$—Ph | NH | H | NH | OA14 | H | H |
| 4069 | 2,4,5-$F_3$—Ph | NH | H | NH | OA16 | H | H |
| 4070 | 2,4,5-$F_3$—Ph | NH | H | NH | OH | H | A6 |
| 4071 | 2,4,5-$F_3$—Ph | NH | H | NH | OH | H | A8 |
| 4072 | 2,4,5-$F_3$—Ph | NH | H | NH | OH | H | A9 |
| 4073 | 2,4,5-$F_3$—Ph | NH | H | NH | OH | H | A10 |
| 4074 | 2,4,5-$F_3$—Ph | NH | H | NH | OH | H | A12 |
| 4075 | 2,4,5-$F_3$—Ph | NH | H | NH | OH | H | A14 |
| 4076 | 2,4,5-$F_3$—Ph | NH | H | NH | OH | H | A16 |
| 4077 | 2,4,5-$F_3$—Ph | NH | H | NH | OH | A6 | A6 |
| 4078 | 2,4,5-$F_3$—Ph | NH | H | NH | OH | A8 | A8 |
| 4079 | 2,4,5-$F_3$—Ph | NH | H | NH | OH | A10 | A10 |
| 4080 | 2,4,5-$F_3$—Ph | NH | H | NH | OA2 | A2 | A2 |
| 4081 | 2,4,5-$F_3$—Ph | NH | H | NH | OA3 | A3 | A3 |
| 4082 | 2,4,5-$F_3$—Ph | NH | H | NH | OA4 | A4 | A4 |
| 4083 | 2,4,5-$F_3$—Ph | NH | H | NH | OC6 | H | H |
| 4084 | 2,4,5-$F_3$—Ph | NH | H | NH | OC7 | H | H |
| 4085 | 2,4,5-$F_3$—Ph | NH | H | NH | OC8 | H | H |
| 4086 | 2,4,5-$F_3$—Ph | NH | H | NH | OC10 | H | H |
| 4087 | 2,4,5-$F_3$—Ph | NH | H | NH | OC11 | H | H |
| 4088 | 2,4,5-$F_3$—Ph | NH | H | NH | OC12 | H | H |
| 4089 | 2,4,5-$F_3$—Ph | NH | H | NH | OC14 | H | H |
| 4090 | 2,4,5-$F_3$—Ph | NH | H | NH | OC16 | H | H |
| 4091 | 2,4,5-$F_3$—Ph | NH | H | NH | C6CO$_3$ | H | H |
| 4092 | 2,4,5-$F_3$—Ph | NH | H | NH | C7CO$_3$ | H | H |
| 4093 | 2,4,5-$F_3$—Ph | NH | H | NH | C8CO$_3$ | H | H |
| 4094 | 2,4,5-$F_3$—Ph | NH | H | NH | C9CO$_3$ | H | H |
| 4095 | 2,4,5-$F_3$—Ph | NH | H | NH | C10CO$_3$ | H | H |
| 4096 | 2,4,5-$F_3$—Ph | NH | H | NH | C12CO$_3$ | H | H |
| 4097 | 2,4,5-$F_3$—Ph | NH | H | NH | C16CO$_3$ | H | H |

TABLE 1-continued

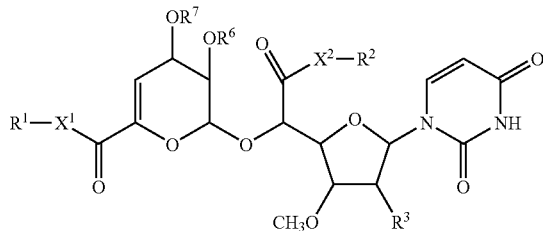

(I-1)

| Exemp. Comp. No. | R¹ | X¹ | R² | X² | R³ | R⁶ | R⁷ |
|---|---|---|---|---|---|---|---|
| 4098 | 2,4,5-F₃—Ph | NH | C8 | NH | OH | H | H |
| 4099 | 2,4,5-F₃—Ph | NH | C9 | NH | OH | H | H |
| 4100 | 2,4,5-F₃—Ph | NH | C10 | NH | OH | H | H |
| 4101 | 2,4,5-F₃—Ph | NH | C12 | NH | OH | H | H |
| 4102 | 2,4,5-F₃—Ph | NH | C16 | NH | OH | H | H |
| 4103 | 2,4,5-F₃—Ph | NH | F1 | NH | OH | H | H |
| 4104 | 2,4,5-F₃—Ph | NH | F2 | NH | OH | H | H |
| 4105 | 2,4,5-F₃—Ph | NH | F3 | NH | OH | H | H |
| 4106 | 2,4,5-F₃—Ph | NH | F4 | NH | OH | H | H |
| 4107 | 2,4,5-F₃—Ph | NH | F5 | NH | OH | H | H |
| 4108 | 2,4,5-F₃—Ph | NH | F6 | NH | OH | H | H |
| 4109 | 2,4,5-F₃—Ph | NH | F7 | NH | OH | H | H |
| 4110 | 2,4,5-F₃—Ph | NH | F8 | NH | OH | H | H |
| 4111 | 2,4,5-F₃—Ph | NH | F9 | NH | OH | H | H |
| 4112 | 2,4,5-F₃—Ph | NH | F10 | NH | OH | H | H |
| 4113 | 2,4,5-F₃—Ph | NH | Ph | NH | OH | H | H |
| 4114 | 2,4,5-F₃—Ph | NH | Bn | NH | OH | H | H |
| 4115 | 2,4,5-F₃—Ph | NH | Pe | NH | OH | H | H |
| 4116 | 2,4,5-F₃—Ph | NH | C12 | NMe | OH | H | H |
| 4117 | 2,4,5-F₃—Ph | NH | C12 | NEt | OH | H | H |
| 4118 | 2,4,5-F₃—Ph | NH | C12 | NPr | OH | H | H |
| 4119 | 2,4,5-F₃—Ph | NH | (CH₂)₃ | N | OH | H | H |
| 4120 | 2,4,5-F₃—Ph | NH | (CH₂)₄ | N | OH | H | H |
| 4121 | 2,4,5-F₃—Ph | NH | (CH₂)₅ | N | OH | H | H |
| 4122 | 2,4,5-F₃—Ph | NH | C12 | O | OH | H | H |
| 4123 | 2,4,5-F₃—Ph | NH | Ph | O | OH | H | H |
| 4124 | 2,4,5-F₃—Ph | NH | C12 | S | OH | H | H |
| 4125 | 2,4,5-F₃—Ph | NH | Ph | S | OH | H | H |
| 4126 | 2,4,5-F₃—Ph | NMe | H | NH | OH | H | H |
| 4127 | 2,4,5-F₃—Ph | NEt | H | NH | OH | H | H |
| 4128 | 2,4,5-F₃—Ph | NPr | H | NH | OH | H | H |
| 4129 | 2,4,5-F₃—Ph | O | H | NH | OH | H | H |
| 4130 | 2,4,5-F₃—Ph | S | H | NH | OH | H | H |
| 4131 | 3-Cl-4-F—Ph | NH | H | NH | H | H | H |
| 4132 | 3-Cl-4-F—Ph | NH | H | NH | OH | H | H |
| 4133 | 3-Cl-4-F—Ph | NH | H | NH | OA6 | H | H |
| 4134 | 3-Cl-4-F—Ph | NH | H | NH | OA8 | H | H |
| 4135 | 3-Cl-4-F—Ph | NH | H | NH | OA9 | H | H |
| 4136 | 3-Cl-4-F—Ph | NH | H | NH | OA10 | H | H |
| 4137 | 3-Cl-4-F—Ph | NH | H | NH | OA12 | H | H |
| 4138 | 3-Cl-4-F—Ph | NH | H | NH | OA14 | H | H |
| 4139 | 3-Cl-4-F—Ph | NH | H | NH | OA16 | H | H |
| 4140 | 3-Cl-4-F—Ph | NH | H | NH | OH | H | A6 |
| 4141 | 3-Cl-4-F—Ph | NH | H | NH | OH | H | A8 |
| 4142 | 3-Cl-4-F—Ph | NH | H | NH | OH | H | A9 |
| 4143 | 3-Cl-4-F—Ph | NH | H | NH | OH | H | A10 |
| 4144 | 3-Cl-4-F—Ph | NH | H | NH | OH | H | A12 |
| 4145 | 3-Cl-4-F—Ph | NH | H | NH | OH | H | A14 |
| 4146 | 3-Cl-4-F—Ph | NH | H | NH | OH | H | A16 |
| 4147 | 3-Cl-4-F—Ph | NH | H | NH | OH | A6 | A6 |
| 4148 | 3-Cl-4-F—Ph | NH | H | NH | OH | A8 | A8 |
| 4149 | 3-Cl-4-F—Ph | NH | H | NH | OH | A10 | A10 |
| 4150 | 3-Cl-4-F—Ph | NH | H | NH | OA2 | A2 | A2 |
| 4151 | 3-Cl-4-F—Ph | NH | H | NH | OA3 | A3 | A3 |
| 4152 | 3-Cl-4-F—Ph | NH | H | NH | OA4 | A4 | A4 |
| 4153 | 3-Cl-4-F—Ph | NH | H | NH | OC6 | H | H |
| 4154 | 3-Cl-4-F—Ph | NH | H | NH | OC7 | H | H |
| 4155 | 3-Cl-4-F—Ph | NH | H | NH | OC8 | H | H |
| 4156 | 3-Cl-4-F—Ph | NH | H | NH | OC10 | H | H |
| 4157 | 3-Cl-4-F—Ph | NH | H | NH | OC11 | H | H |
| 4158 | 3-Cl-4-F—Ph | NH | H | NH | OC12 | H | H |
| 4159 | 3-Cl-4-F—Ph | NH | H | NH | OC14 | H | H |

TABLE 1-continued (I-1)

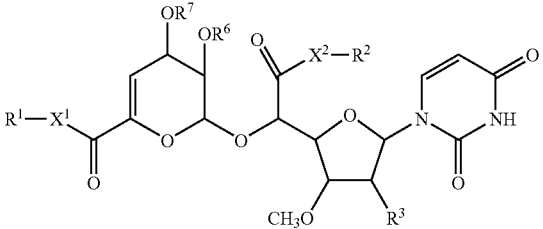

| Exemp. Comp. No. | $R^1$ | $X^1$ | $R^2$ | $X^2$ | $R^3$ | $R^6$ | $R^7$ |
|---|---|---|---|---|---|---|---|
| 4160 | 3-Cl-4-F—Ph | NH | H | NH | OC16 | H | H |
| 4161 | 3-Cl-4-F—Ph | NH | H | NH | C6CO$_3$ | H | H |
| 4162 | 3-Cl-4-F—Ph | NH | H | NH | C7CO$_3$ | H | H |
| 4163 | 3-Cl-4-F—Ph | NH | H | NH | C8CO$_3$ | H | H |
| 4164 | 3-Cl-4-F—Ph | NH | H | NH | C9CO$_3$ | H | H |
| 4165 | 3-Cl-4-F—Ph | NH | H | NH | C10CO$_3$ | H | H |
| 4166 | 3-Cl-4-F—Ph | NH | H | NH | C12CO$_3$ | H | H |
| 4167 | 3-Cl-4-F—Ph | NH | H | NH | C16CO$_3$ | H | H |
| 4168 | 3-Cl-4-F—Ph | NH | C8 | NH | OH | H | H |
| 4169 | 3-Cl-4-F—Ph | NH | C9 | NH | OH | H | H |
| 4170 | 3-Cl-4-F—Ph | NH | C10 | NH | OH | H | H |
| 4171 | 3-Cl-4-F—Ph | NH | C12 | NH | OH | H | H |
| 4172 | 3-Cl-4-F—Ph | NH | C16 | NH | OH | H | H |
| 4173 | 3-Cl-4-F—Ph | NH | F1 | NH | OH | H | H |
| 4174 | 3-Cl-4-F—Ph | NH | F2 | NH | OH | H | H |
| 4175 | 3-Cl-4-F—Ph | NH | F3 | NH | OH | H | H |
| 4176 | 3-Cl-4-F—Ph | NH | F4 | NH | OH | H | H |
| 4177 | 3-Cl-4-F—Ph | NH | F5 | NH | OH | H | H |
| 4178 | 3-Cl-4-F—Ph | NH | F6 | NH | OH | H | H |
| 4179 | 3-Cl-4-F—Ph | NH | F7 | NH | OH | H | H |
| 4180 | 3-Cl-4-F—Ph | NH | F8 | NH | OH | H | H |
| 4181 | 3-Cl-4-F—Ph | NH | F9 | NH | OH | H | H |
| 4182 | 3-Cl-4-F—Ph | NH | F10 | NH | OH | H | H |
| 4183 | 3-Cl-4-F—Ph | NH | Ph | NH | OH | H | H |
| 4184 | 3-Cl-4-F—Ph | NH | Bn | NH | OH | H | H |
| 4185 | 3-Cl-4-F—Ph | NH | Pe | NH | OH | H | H |
| 4186 | 3-Cl-4-F—Ph | NH | C12 | NMe | OH | H | H |
| 4187 | 3-Cl-4-F—Ph | NH | C12 | NEt | OH | H | H |
| 4188 | 3-Cl-4-F—Ph | NH | C12 | NPr | OH | H | H |
| 4189 | 3-Cl-4-F—Ph | NH | (CH$_2$)$_3$ | N | OH | H | H |
| 4190 | 3-Cl-4-F—Ph | NH | (CH$_2$)$_4$ | N | OH | H | H |
| 4191 | 3-Cl-4-F—Ph | NH | (CH$_2$)$_5$ | N | OH | H | H |
| 4192 | 3-Cl-4-F—Ph | NH | C12 | O | OH | H | H |
| 4193 | 3-Cl-4-F—Ph | NH | Ph | O | OH | H | H |
| 4194 | 3-Cl-4-F—Ph | NH | C12 | S | OH | H | H |
| 4195 | 3-Cl-4-F—Ph | NH | Ph | S | OH | H | H |
| 4196 | 3-Cl-4-F—Ph | NMe | H | NH | OH | H | H |
| 4197 | 3-Cl-4-F—Ph | NEt | H | NH | OH | H | H |
| 4198 | 3-Cl-4-F—Ph | NPr | H | NH | OH | H | H |
| 4199 | 3-Cl-4-F—Ph | O | H | NH | OH | H | H |
| 4200 | 3-Cl-4-F—Ph | S | H | NH | OH | H | H |
| 4201 | 3-CF$_3$-4-F—Ph | NH | H | NH | H | H | H |
| 4202 | 3-CF$_3$-4-F—Ph | NH | H | NH | OH | H | H |
| 4203 | 3-CF$_3$-4-F—Ph | NH | H | NH | OA6 | H | H |
| 4204 | 3-CF$_3$-4-F—Ph | NH | H | NH | OA8 | H | H |
| 4205 | 3-CF$_3$-4-F—Ph | NH | H | NH | OA9 | H | H |
| 4206 | 3-CF$_3$-4-F—Ph | NH | H | NH | OA10 | H | H |
| 4207 | 3-CF$_3$-4-F—Ph | NH | H | NH | OA12 | H | H |
| 4208 | 3-CF$_3$-4-F—Ph | NH | H | NH | OA14 | H | H |
| 4209 | 3-CF$_3$-4-F—Ph | NH | H | NH | OA16 | H | H |
| 4210 | 3-CF$_3$-4-F—Ph | NH | H | NH | OH | H | A6 |
| 4211 | 3-CF$_3$-4-F—Ph | NH | H | NH | OH | H | A8 |
| 4212 | 3-CF$_3$-4-F—Ph | NH | H | NH | OH | H | A9 |
| 4213 | 3-CF$_3$-4-F—Ph | NH | H | NH | OH | H | A10 |
| 4214 | 3-CF$_3$-4-F—Ph | NH | H | NH | OH | H | A12 |
| 4215 | 3-CF$_3$-4-F—Ph | NH | H | NH | OH | H | A14 |
| 4216 | 3-CF$_3$-4-F—Ph | NH | H | NH | OH | H | A16 |
| 4217 | 3-CF$_3$-4-F—Ph | NH | H | NH | OH | A6 | A6 |
| 4218 | 3-CF$_3$-4-F—Ph | NH | H | NH | OH | A8 | A8 |
| 4219 | 3-CF$_3$-4-F—Ph | NH | H | NH | OH | A10 | A10 |
| 4220 | 3-CF$_3$-4-F—Ph | NH | H | NH | OA2 | A2 | A2 |
| 4221 | 3-CF$_3$-4-F—Ph | NH | H | NH | OA3 | A3 | A3 |

TABLE 1-continued (I-1)

| Exemp. Comp. No. | R¹ | X¹ | R² | X² | R³ | R⁶ | R⁷ |
|---|---|---|---|---|---|---|---|
| 4222 | 3-CF₃-4-F—Ph | NH | H | NH | OA4 | A4 | A4 |
| 4223 | 3-CF₃-4-F—Ph | NH | H | NH | OC6 | H | H |
| 4224 | 3-CF₃-4-F—Ph | NH | H | NH | OC7 | H | H |
| 4225 | 3-CF₃-4-F—Ph | NH | H | NH | OC8 | H | H |
| 4226 | 3-CF₃-4-F—Ph | NH | H | NH | OC10 | H | H |
| 4227 | 3-CF₃-4-F—Ph | NH | H | NH | OC11 | H | H |
| 4228 | 3-CF₃-4-F—Ph | NH | H | NH | OC12 | H | H |
| 4229 | 3-CF₃-4-F—Ph | NH | H | NH | OC14 | H | H |
| 4230 | 3-CF₃-4-F—Ph | NH | H | NH | OC16 | H | H |
| 4231 | 3-CF₃-4-F—Ph | NH | H | NH | C6CO₃ | H | H |
| 4232 | 3-CF₃-4-F—Ph | NH | H | NH | C7CO₃ | H | H |
| 4233 | 3-CF₃-4-F—Ph | NH | H | NH | C8CO₃ | H | H |
| 4234 | 3-CF₃-4-F—Ph | NH | H | NH | C9CO₃ | H | H |
| 4235 | 3-CF₃-4-F—Ph | NH | H | NH | C10CO₃ | H | H |
| 4236 | 3-CF₃-4-F—Ph | NH | H | NH | C12CO₃ | H | H |
| 4237 | 3-CF₃-4-F—Ph | NH | H | NH | C16CO₃ | H | H |
| 4238 | 3-CF₃-4-F—Ph | NH | C8 | NH | OH | H | H |
| 4239 | 3-CF₃-4-F—Ph | NH | C9 | NH | OH | H | H |
| 4240 | 3-CF₃-4-F—Ph | NH | C10 | NH | OH | H | H |
| 4241 | 3-CF₃-4-F—Ph | NH | C12 | NH | OH | H | H |
| 4242 | 3-CF₃-4-F—Ph | NH | C16 | NH | OH | H | H |
| 4243 | 3-CF₃-4-F—Ph | NH | F1 | NH | OH | H | H |
| 4244 | 3-CF₃-4-F—Ph | NH | F2 | NH | OH | H | H |
| 4245 | 3-CF₃-4-F—Ph | NH | F3 | NH | OH | H | H |
| 4246 | 3-CF₃-4-F—Ph | NH | F4 | NH | OH | H | H |
| 4247 | 3-CF₃-4-F—Ph | NH | F5 | NH | OH | H | H |
| 4248 | 3-CF₃-4-F—Ph | NH | F6 | NH | OH | H | H |
| 4249 | 3-CF₃-4-F—Ph | NH | F7 | NH | OH | H | H |
| 4250 | 3-CF₃-4-F—Ph | NH | F8 | NH | OH | H | H |
| 4251 | 3-CF₃-4-F—Ph | NH | F9 | NH | OH | H | H |
| 4252 | 3-CF₃-4-F—Ph | NH | F10 | NH | OH | H | H |
| 4253 | 3-CF₃-4-F—Ph | NH | Ph | NH | OH | H | H |
| 4254 | 3-CF₃-4-F—Ph | NH | Bn | NH | OH | H | H |
| 4255 | 3-CF₃-4-F—Ph | NH | Pe | NH | OH | H | H |
| 4256 | 3-CF₃-4-F—Ph | NH | C12 | NMe | OH | H | H |
| 4257 | 3-CF₃-4-F—Ph | NH | C12 | NEt | OH | H | H |
| 4258 | 3-CF₃-4-F—Ph | NH | C12 | NPr | OH | H | H |
| 4259 | 3-CF₃-4-F—Ph | NH | (CH₂)₃ | N | OH | H | H |
| 4260 | 3-CF₃-4-F—Ph | NH | (CH₂)₄ | N | OH | H | H |
| 4261 | 3-CF₃-4-F—Ph | NH | (CH₂)₅ | N | OH | H | H |
| 4262 | 3-CF₃-4-F—Ph | NH | C12 | O | OH | H | H |
| 4263 | 3-CF₃-4-F—Ph | NH | Ph | O | OH | H | H |
| 4264 | 3-CF₃-4-F—Ph | NH | C12 | S | OH | H | H |
| 4265 | 3-CF₃-4-F—Ph | NH | Ph | S | OH | H | H |
| 4266 | 3-CF₃-4-F—Ph | NMe | H | NH | OH | H | H |
| 4267 | 3-CF₃-4-F—Ph | NEt | H | NH | OH | H | H |
| 4268 | 3-CF₃-4-F—Ph | NPr | H | NH | OH | H | H |
| 4269 | 3-CF₃-4-F—Ph | O | H | NH | OH | H | H |
| 4270 | 3-CF₃-4-F—Ph | S | H | NH | OH | H | H |
| 4271 | 3-CF₃O—Ph | NH | H | NH | H | H | H |
| 4272 | 3-CF₃O—Ph | NH | H | NH | OH | H | H |
| 4273 | 3-CF₃O—Ph | NH | H | NH | OA6 | H | H |
| 4274 | 3-CF₃O—Ph | NH | H | NH | OA8 | H | H |
| 4275 | 3-CF₃O—Ph | NH | H | NH | OA9 | H | H |
| 4276 | 3-CF₃O—Ph | NH | H | NH | OA10 | H | H |
| 4277 | 3-CF₃O—Ph | NH | H | NH | OA12 | H | H |
| 4278 | 3-CF₃O—Ph | NH | H | NH | OA14 | H | H |
| 4279 | 3-CF₃O—Ph | NH | H | NH | OA16 | H | H |
| 4280 | 3-CF₃O—Ph | NH | H | NH | OH | H | A6 |
| 4281 | 3-CF₃O—Ph | NH | H | NH | OH | H | A8 |
| 4282 | 3-CF₃O—Ph | NH | H | NH | OH | H | A9 |
| 4283 | 3-CF₃O—Ph | NH | H | NH | OH | H | A10 |

TABLE 1-continued

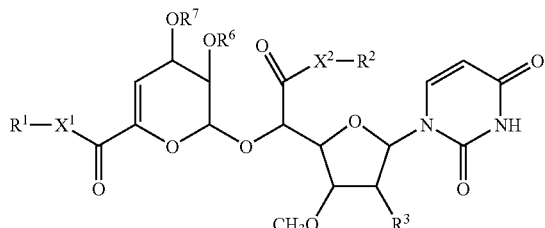

(I-1)

| Exemp. Comp. No. | $R^1$ | $X^1$ | $R^2$ | $X^2$ | $R^3$ | $R^6$ | $R^7$ |
|---|---|---|---|---|---|---|---|
| 4284 | 3-CF$_3$O—Ph | NH | H | NH | OH | H | A12 |
| 4285 | 3-CF$_3$O—Ph | NH | H | NH | OH | H | A14 |
| 4286 | 3-CF$_3$O—Ph | NH | H | NH | OH | H | A16 |
| 4287 | 3-CF$_3$O—Ph | NH | H | NH | OH | A6 | A6 |
| 4288 | 3-CF$_3$O—Ph | NH | H | NH | OH | A8 | A8 |
| 4289 | 3-CF$_3$O—Ph | NH | H | NH | OH | A10 | A10 |
| 4290 | 3-CF$_3$O—Ph | NH | H | NH | OA2 | A2 | A2 |
| 4291 | 3-CF$_3$O—Ph | NH | H | NH | OA3 | A3 | A3 |
| 4292 | 3-CF$_3$O—Ph | NH | H | NH | OA4 | A4 | A4 |
| 4293 | 3-CF$_3$O—Ph | NH | H | NH | OC6 | H | H |
| 4294 | 3-CF$_3$O—Ph | NH | H | NH | OC7 | H | H |
| 4295 | 3-CF$_3$O—Ph | NH | H | NH | OC8 | H | H |
| 4296 | 3-CF$_3$O—Ph | NH | H | NH | OC10 | H | H |
| 4297 | 3-CF$_3$O—Ph | NH | H | NH | OC11 | H | H |
| 4298 | 3-CF$_3$O—Ph | NH | H | NH | OC12 | H | H |
| 4299 | 3-CF$_3$O—Ph | NH | H | NH | OC14 | H | H |
| 4300 | 3-CF$_3$O—Ph | NH | H | NH | OC16 | H | H |
| 4301 | 3-CF$_3$O—Ph | NH | H | NH | C6CO$_3$ | H | H |
| 4302 | 3-CF$_3$O—Ph | NH | H | NH | C7CO$_3$ | H | H |
| 4303 | 3-CF$_3$O—Ph | NH | H | NH | C8CO$_3$ | H | H |
| 4304 | 3-CF$_3$O—Ph | NH | H | NH | C9CO$_3$ | H | H |
| 4305 | 3-CF$_3$O—Ph | NH | H | NH | C10CO$_3$ | H | H |
| 4306 | 3-CF$_3$O—Ph | NH | H | NH | C12CO$_3$ | H | H |
| 4307 | 3-CF$_3$O—Ph | NH | H | NH | C16CO$_3$ | H | H |
| 4308 | 3-CF$_3$O—Ph | NH | C8 | NH | OH | H | H |
| 4309 | 3-CF$_3$O—Ph | NH | C9 | NH | OH | H | H |
| 4310 | 3-CF$_3$O—Ph | NH | C10 | NH | OH | H | H |
| 4311 | 3-CF$_3$O—Ph | NH | C12 | NH | OH | H | H |
| 4312 | 3-CF$_3$O—Ph | NH | C16 | NH | OH | H | H |
| 4313 | 3-CF$_3$O—Ph | NH | F1 | NH | OH | H | H |
| 4314 | 3-CF$_3$O—Ph | NH | F2 | NH | OH | H | H |
| 4315 | 3-CF$_3$O—Ph | NH | F3 | NH | OH | H | H |
| 4316 | 3-CF$_3$O—Ph | NH | F4 | NH | OH | H | H |
| 4317 | 3-CF$_3$O—Ph | NH | F5 | NH | OH | H | H |
| 4318 | 3-CF$_3$O—Ph | NH | F6 | NH | OH | H | H |
| 4319 | 3-CF$_3$O—Ph | NH | F7 | NH | OH | H | H |
| 4320 | 3-CF$_3$O—Ph | NH | F8 | NH | OH | H | H |
| 4321 | 3-CF$_3$O—Ph | NH | F9 | NH | OH | H | H |
| 4322 | 3-CF$_3$O—Ph | NH | F10 | NH | OH | H | H |
| 4323 | 3-CF$_3$O—Ph | NH | Ph | NH | OH | H | H |
| 4324 | 3-CF$_3$O—Ph | NH | Bn | NH | OH | H | H |
| 4325 | 3-CF$_3$O—Ph | NH | Pe | NH | OH | H | H |
| 4326 | 3-CF$_3$O—Ph | NH | C12 | NMe | OH | H | H |
| 4327 | 3-CF$_3$O—Ph | NH | C12 | NEt | OH | H | H |
| 4328 | 3-CF$_3$O—Ph | NH | C12 | NPr | OH | H | H |
| 4329 | 3-CF$_3$O—Ph | NH | (CH$_2$)$_3$ | N | OH | H | H |
| 4330 | 3-CF$_3$O—Ph | NH | (CH$_2$)$_4$ | N | OH | H | H |
| 4331 | 3-CF$_3$O—Ph | NH | (CH$_2$)$_5$ | N | OH | H | H |
| 4332 | 3-CF$_3$O—Ph | NH | C12 | O | OH | H | H |
| 4333 | 3-CF$_3$O—Ph | NH | Ph | O | OH | H | H |
| 4334 | 3-CF$_3$O—Ph | NH | C12 | S | OH | H | H |
| 4335 | 3-CF$_3$O—Ph | NH | Ph | S | OH | H | H |
| 4336 | 3-CF$_3$O—Ph | NMe | H | NH | OH | H | H |
| 4337 | 3-CF$_3$O—Ph | NEt | H | NH | OH | H | H |
| 4338 | 3-CF$_3$O—Ph | NPr | H | NH | OH | H | H |
| 4339 | 3-CF$_3$—Ph | O | H | NH | OH | H | H |
| 4340 | 3-CF$_3$O—Ph | S | H | NH | OH | H | H |
| 4341 | 4-CF$_3$O—Ph | NH | H | NH | H | H | H |
| 4342 | 4-CF$_3$O—Ph | NH | H | NH | OH | H | H |
| 4343 | 4-CF$_3$O—Ph | NH | H | NH | OA6 | H | H |
| 4344 | 4-CF$_3$O—Ph | NH | H | NH | OA8 | H | H |
| 4345 | 4-CF$_3$O—Ph | NH | H | NH | OA9 | H | H |

TABLE 1-continued (I-1)

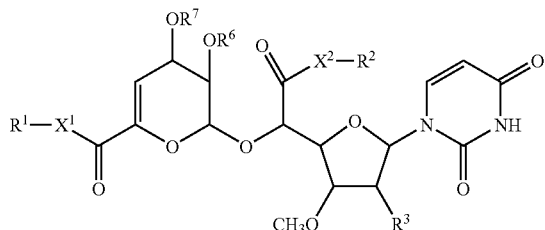

| Exemp. Comp. No. | R¹ | X¹ | R² | X² | R³ | R⁶ | R⁷ |
|---|---|---|---|---|---|---|---|
| 4346 | 4-CF₃O—Ph | NH | H | NH | OA10 | H | H |
| 4347 | 4-CF₃O—Ph | NH | H | NH | OA12 | H | H |
| 4348 | 4-CF₃O—Ph | NH | H | NH | OA14 | H | H |
| 4349 | 4-CF₃O—Ph | NH | H | NH | OA16 | H | H |
| 4350 | 4-CF₃O—Ph | NH | H | NH | OH | H | A6 |
| 4351 | 4-CF₃O—Ph | NH | H | NH | OH | H | A8 |
| 4352 | 4-CF₃O—Ph | NH | H | NH | OH | H | A9 |
| 4353 | 4-CF₃O—Ph | NH | H | NH | OH | H | A10 |
| 4354 | 4-CF₃O—Ph | NH | H | NH | OH | H | A12 |
| 4355 | 4-CF₃O—Ph | NH | H | NH | OH | H | A14 |
| 4356 | 4-CF₃O—Ph | NH | H | NH | OH | H | A16 |
| 4357 | 4-CF₃O—Ph | NH | H | NH | OH | A6 | A6 |
| 4358 | 4-CF₃O—Ph | NH | H | NH | OH | A8 | A8 |
| 4359 | 4-CF₃O—Ph | NH | H | NH | OH | A10 | A10 |
| 4360 | 4-CF₃O—Ph | NH | H | NH | OA2 | A2 | A2 |
| 4361 | 4-CF₃O—Ph | NH | H | NH | OA3 | A3 | A3 |
| 4362 | 4-CF₃O—Ph | NH | H | NH | OA4 | A4 | A4 |
| 4363 | 4-CF₃O—Ph | NH | H | NH | OC6 | H | H |
| 4364 | 4-CF₃O—Ph | NH | H | NH | OC7 | H | H |
| 4365 | 4-CF₃O—Ph | NH | H | NH | OC8 | H | H |
| 4366 | 4-CF₃O—Ph | NH | H | NH | OC10 | H | H |
| 4367 | 4-CF₃O—Ph | NH | H | NH | OC11 | H | H |
| 4368 | 4-CF₃O—Ph | NH | H | NH | OC12 | H | H |
| 4369 | 4-CF₃O—Ph | NH | H | NH | OC14 | H | H |
| 4370 | 4-CF₃O—Ph | NH | H | NH | OC16 | H | H |
| 4371 | 4-CF₃O—Ph | NH | H | NH | C6CO₃ | H | H |
| 4372 | 4-CF₃O—Ph | NH | H | NH | C7CO₃ | H | H |
| 4373 | 4-CF₃O—Ph | NH | H | NH | C8CO₃ | H | H |
| 4374 | 4-CF₃O—Ph | NH | H | NH | C9CO₃ | H | H |
| 4375 | 4-CF₃O—Ph | NH | H | NH | C10CO₃ | H | H |
| 4376 | 4-CF₃O—Ph | NH | H | NH | C12CO₃ | H | H |
| 4377 | 4-CF₃O—Ph | NH | H | NH | C16CO₃ | H | H |
| 4378 | 4-CF₃O—Ph | NH | C8 | NH | OH | H | H |
| 4379 | 4-CF₃O—Ph | NH | C9 | NH | OH | H | H |
| 4380 | 4-CF₃O—Ph | NH | C10 | NH | OH | H | H |
| 4381 | 4-CF₃O—Ph | NH | C12 | NH | OH | H | H |
| 4382 | 4-CF₃O—Ph | NH | C16 | NH | OH | H | H |
| 4383 | 4-CF₃O—Ph | NH | F1 | NH | OH | H | H |
| 4384 | 4-CF₃O—Ph | NH | F2 | NH | OH | H | H |
| 4385 | 4-CF₃O—Ph | NH | F3 | NH | OH | H | H |
| 4386 | 4-CF₃O—Ph | NH | F4 | NH | OH | H | H |
| 4387 | 4-CF₃O—Ph | NH | F5 | NH | OH | H | H |
| 4388 | 4-CF₃O—Ph | NH | F6 | NH | OH | H | H |
| 4389 | 4-CF₃O—Ph | NH | F7 | NH | OH | H | H |
| 4390 | 4-CF₃O—Ph | NH | F8 | NH | OH | H | H |
| 4391 | 4-CF₃O—Ph | NH | F9 | NH | OH | H | H |
| 4392 | 4-CF₃O—Ph | NH | F10 | NH | OH | H | H |
| 4393 | 4-CF₃O—Ph | NH | Ph | NH | OH | H | H |
| 4394 | 4-CF₃O—Ph | NH | Bn | NH | OH | H | H |
| 4395 | 4-CF₃O—Ph | NH | Pe | NH | OH | H | H |
| 4396 | 4-CF₃O—Ph | NH | C12 | NMe | OH | H | H |
| 4397 | 4-CF₃O—Ph | NH | C12 | NEt | OH | H | H |
| 4398 | 4-CF₃O—Ph | NH | C12 | NPr | OH | H | H |
| 4399 | 4-CF₃O—Ph | NH | (CH₂)₃ | N | OH | H | H |
| 4400 | 4-CF₃O—Ph | NH | (CH₂)₄ | N | OH | H | H |
| 4401 | 4-CF₃O—Ph | NH | (CH₂)₅ | N | OH | H | H |
| 4402 | 4-CF₃O—Ph | NH | C12 | O | OH | H | H |
| 4403 | 4-CF₃O—Ph | NH | Ph | O | OH | H | H |
| 4404 | 4-CF₃O—Ph | NH | C12 | S | OH | H | H |
| 4405 | 4-CF₃O—Ph | NH | Ph | S | OH | H | H |
| 4406 | 4-CF₃O—Ph | NMe | H | NH | OH | H | H |
| 4407 | 4-CF₃O—Ph | NEt | H | NH | OH | H | H |

TABLE 1-continued (I-1)

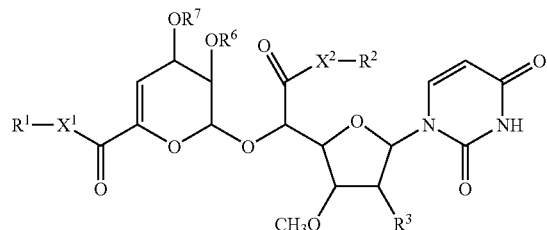

| Exemp. Comp. No. | R¹ | X¹ | R² | X² | R³ | R⁶ | R⁷ |
|---|---|---|---|---|---|---|---|
| 4408 | 4-CF₃O—Ph | NPr | H | NH | OH | H | H |
| 4409 | 4-CF₃O—Ph | O | H | NH | OH | H | H |
| 4410 | 4-CF₃O—Ph | S | H | NH | OH | H | H |
| 4411 | 4-CH₃S—Ph | NH | H | NH | H | H | H |
| 4412 | 4-CH₃S—Ph | NH | H | NH | OH | H | H |
| 4413 | 4-CH₃S—Ph | NH | H | NH | OA6 | H | H |
| 4414 | 4-CH₃S—Ph | NH | H | NH | OA8 | H | H |
| 4415 | 4-CH₃S—Ph | NH | H | NH | OA9 | H | H |
| 4416 | 4-CH₃S—Ph | NH | H | NH | OA10 | H | H |
| 4417 | 4-CH₃S—Ph | NH | H | NH | OA12 | H | H |
| 4418 | 4-CH₃S—Ph | NH | H | NH | OA14 | H | H |
| 4419 | 4-CH₃S—Ph | NH | H | NH | OA16 | H | H |
| 4420 | 4-CH₃S—Ph | NH | H | NH | OH | H | A6 |
| 4421 | 4-CH₃S—Ph | NH | H | NH | OH | H | A8 |
| 4422 | 4-CH₃S—Ph | NH | H | NH | OH | H | A9 |
| 4423 | 4-CH₃S—Ph | NH | H | NH | OH | H | A10 |
| 4424 | 4-CH₃S—Ph | NH | H | NH | OH | H | A12 |
| 4425 | 4-CH₃S—Ph | NH | H | NH | OH | H | A14 |
| 4426 | 4-CH₃S—Ph | NH | H | NH | OH | H | A16 |
| 4427 | 4-CH₃S—Ph | NH | H | NH | OH | A6 | A6 |
| 4428 | 4-CH₃S—Ph | NH | H | NH | OH | A8 | A8 |
| 4429 | 4-CH₃S—Ph | NH | H | NH | OH | A10 | A10 |
| 4430 | 4-CH₃S—Ph | NH | H | NH | OA2 | A2 | A2 |
| 4431 | 4-CH₃S—Ph | NH | H | NH | OA3 | A3 | A3 |
| 4432 | 4-CH₃S—Ph | NH | H | NH | OA4 | A4 | A4 |
| 4433 | 4-CH₃S—Ph | NH | H | NH | OC6 | H | H |
| 4434 | 4-CH₃S—Ph | NH | H | NH | OC7 | H | H |
| 4435 | 4-CH₃S—Ph | NH | H | NH | OC8 | H | H |
| 4436 | 4-CH₃S—Ph | NH | H | NH | OC10 | H | H |
| 4437 | 4-CH₃S—Ph | NH | H | NH | OC11 | H | H |
| 4438 | 4-CH₃S—Ph | NH | H | NH | OC12 | H | H |
| 4439 | 4-CH₃S—Ph | NH | H | NH | OC14 | H | H |
| 4440 | 4-CH₃S—Ph | NH | H | NH | OC16 | H | H |
| 4441 | 4-CH₃S—Ph | NH | H | NH | C6CO₃ | H | H |
| 4442 | 4-CH₃S—Ph | NH | H | NH | C7CO₃ | H | H |
| 4443 | 4-CH₃S—Ph | NH | H | NH | C8CO₃ | H | H |
| 4444 | 4-CH₃S—Ph | NH | H | NH | C9CO₃ | H | H |
| 4445 | 4-CH₃S—Ph | NH | H | NH | C10CO₃ | H | H |
| 4446 | 4-CH₃S—Ph | NH | H | NH | C12CO₃ | H | H |
| 4447 | 4-CH₃S—Ph | NH | H | NH | C16CO₃ | H | H |
| 4448 | 4-CH₃S—Ph | NH | C8 | NH | OH | H | H |
| 4449 | 4-CH₃S—Ph | NH | C9 | NH | OH | H | H |
| 4450 | 4-CH₃S—Ph | NH | C10 | NH | OH | H | H |
| 4451 | 4-CH₃S—Ph | NH | C12 | NH | OH | H | H |
| 4452 | 4-CH₃S—Ph | NH | C16 | NH | OH | H | H |
| 4453 | 4-CH₃S—Ph | NH | F1 | NH | OH | H | H |
| 4454 | 4-CH₃S—Ph | NH | F2 | NH | OH | H | H |
| 4455 | 4-CH₃S—Ph | NH | F3 | NH | OH | H | H |
| 4456 | 4-CH₃S—Ph | NH | F4 | NH | OH | H | H |
| 4457 | 4-CH₃S—Ph | NH | F5 | NH | OH | H | H |
| 4458 | 4-CH₃S—Ph | NH | F6 | NH | OH | H | H |
| 4459 | 4-CH₃S—Ph | NH | F7 | NH | OH | H | H |
| 4460 | 4-CH₃S—Ph | NH | F8 | NH | OH | H | H |
| 4461 | 4-CH₃S—Ph | NH | F9 | NH | OH | H | H |
| 4462 | 4-CH₃S—Ph | NH | F10 | NH | OH | H | H |
| 4463 | 4-CH₃S—Ph | NH | Ph | NH | OH | H | H |
| 4464 | 4-CH₃S—Ph | NH | Bn | NH | OH | H | H |
| 4465 | 4-CH₃S—Ph | NH | Pe | NH | OH | H | H |
| 4466 | 4-CH₃S—Ph | NH | C12 | NMe | OH | H | H |
| 4467 | 4-CH₃S—Ph | NH | C12 | NEt | OH | H | H |
| 4468 | 4-CH₃S—Ph | NH | C12 | NPr | OH | H | H |
| 4469 | 4-CH₃S—Ph | NH | (CH₂)₃ | N | OH | H | H |

TABLE 1-continued (I-1)

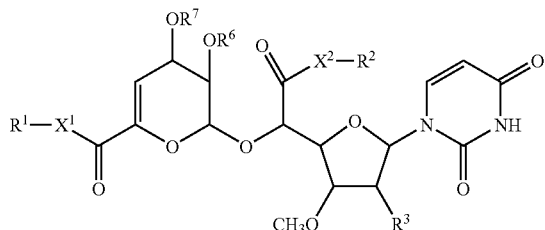

| Exemp. Comp. No. | R[1] | X[1] | R[2] | X[2] | R[3] | R[6] | R[7] |
|---|---|---|---|---|---|---|---|
| 4470 | 4-OH$_3$S—Ph | NH | (CH$_2$)$_4$ | N | OH | H | H |
| 4471 | 4-CH$_3$S—Ph | NH | (CH$_2$)$_5$ | N | OH | H | H |
| 4472 | 4-CH$_3$S—Ph | NH | C12 | O | OH | H | H |
| 4473 | 4-CH$_3$S—Ph | NH | Ph | O | OH | H | H |
| 4474 | 4-CH$_3$S—Ph | NH | C12 | S | OH | H | H |
| 4475 | 4-CH$_3$S—Ph | NH | Ph | S | OH | H | H |
| 4476 | 4-CH$_3$S—Ph | NMe | H | NH | OH | H | H |
| 4477 | 4-CH$_3$S—Ph | NEt | H | NH | OH | H | H |
| 4478 | 4-CH$_3$S—Ph | NPr | H | NH | OH | H | H |
| 4479 | 4-CH$_3$S—Ph | O | H | NH | OH | H | H |
| 4480 | 4-CH$_3$S—Ph | S | H | NH | OH | H | H |
| 4481 | 4-CF$_3$S—Ph | NH | H | NH | H | H | H |
| 4482 | 4-CF$_3$S—Ph | NH | H | NH | OH | H | H |
| 4483 | 4-CF$_3$S—Ph | NH | H | NH | OA6 | H | H |
| 4484 | 4-CF$_3$S—Ph | NH | H | NH | OA8 | H | H |
| 4485 | 4-CF$_3$S—Ph | NH | H | NH | OA9 | H | H |
| 4486 | 4-CF$_3$S—Ph | NH | H | NH | OA10 | H | H |
| 4487 | 4-CF$_3$S—Ph | NH | H | NH | OA12 | H | H |
| 4488 | 4-CF$_3$S—Ph | NH | H | NH | OA14 | H | H |
| 4489 | 4-CF$_3$S—Ph | NH | H | NH | OA16 | H | H |
| 4490 | 4-CF$_3$S—Ph | NH | H | NH | OH | H | A6 |
| 4491 | 4-CF$_3$S—Ph | NH | H | NH | OH | H | A8 |
| 4492 | 4-CF$_3$S—Ph | NH | H | NH | OH | H | A9 |
| 4493 | 4-CF$_3$S—Ph | NH | H | NH | OH | H | A10 |
| 4494 | 4-CF$_3$S—Ph | NH | H | NH | OH | H | A12 |
| 4495 | 4-CF$_3$S—Ph | NH | H | NH | OH | H | A14 |
| 4496 | 4-CF$_3$S—Ph | NH | H | NH | OH | H | A16 |
| 4497 | 4-CF$_3$S—Ph | NH | H | NH | OH | A6 | A6 |
| 4498 | 4-CF$_3$S—Ph | NH | H | NH | OH | A8 | A8 |
| 4499 | 4-CF$_3$S—Ph | NH | H | NH | OH | A10 | A10 |
| 4500 | 4-CF$_3$S—Ph | NH | H | NH | OA2 | A2 | A2 |
| 4501 | 4-CF$_3$S—Ph | NH | H | NH | OA3 | A3 | A3 |
| 4502 | 4-CF$_3$S—Ph | NH | H | NH | OA4 | A4 | A4 |
| 4503 | 4-CF$_3$S—Ph | NH | H | NH | OC6 | H | H |
| 4504 | 4-CF$_3$S—Ph | NH | H | NH | OC7 | H | H |
| 4505 | 4-CF$_3$S—Ph | NH | H | NH | OC8 | H | H |
| 4506 | 4-CF$_3$S—Ph | NH | H | NH | OC10 | H | H |
| 4507 | 4-CF$_3$S—Ph | NH | H | NH | OC11 | H | H |
| 4508 | 4-CF$_3$S—Ph | NH | H | NH | OC12 | H | H |
| 4509 | 4-CF$_3$S—Ph | NH | H | NH | OC14 | H | H |
| 4510 | 4-CF$_3$S—Ph | NH | H | NH | OC16 | H | H |
| 4511 | 4-CF$_3$S—Ph | NH | H | NH | C6CO$_3$ | H | H |
| 4512 | 4-CF$_3$S—Ph | NH | H | NH | C7CO$_3$ | H | H |
| 4513 | 4-CF$_3$S—Ph | NH | H | NH | C8CO$_3$ | H | H |
| 4514 | 4-CF$_3$S—Ph | NH | H | NH | C9CO$_3$ | H | H |
| 4515 | 4-CF$_3$S—Ph | NH | H | NH | C10CO$_3$ | H | H |
| 4516 | 4-CF$_3$S—Ph | NH | H | NH | C12CO$_3$ | H | H |
| 4517 | 4-CF$_3$S—Ph | NH | H | NH | C16CO$_3$ | H | H |
| 4518 | 4-CF$_3$S—Ph | NH | C8 | NH | OH | H | H |
| 4519 | 4-CF$_3$S—Ph | NH | C9 | NH | OH | H | H |
| 4520 | 4-CF$_3$S—Ph | NH | C10 | NH | OH | H | H |
| 4521 | 4-CF$_3$S—Ph | NH | C12 | NH | OH | H | H |
| 4522 | 4-CF$_3$S—Ph | NH | C16 | NH | OH | H | H |
| 4523 | 4-CF$_3$S—Ph | NH | F1 | NH | OH | H | H |
| 4524 | 4-CF$_3$S—Ph | NH | F2 | NH | OH | H | H |
| 4525 | 4-CF$_3$S—Ph | NH | F3 | NH | OH | H | H |
| 4526 | 4-CF$_3$S—Ph | NH | F4 | NH | OH | H | H |
| 4527 | 4-CF$_3$S—Ph | NH | F5 | NH | OH | H | H |
| 4528 | 4-CF$_3$S—Ph | NH | F6 | NH | OH | H | H |
| 4529 | 4-CF$_3$S—Ph | NH | F7 | NH | OH | H | H |
| 4530 | 4-CF$_3$S—Ph | NH | F8 | NH | OH | H | H |
| 4531 | 4-CF$_3$S—Ph | NH | F9 | NH | OH | H | H |

TABLE 1-continued

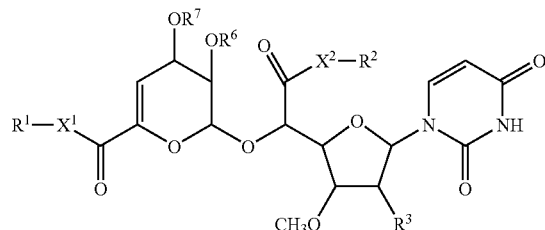

(I-1)

| Exemp. Comp. No. | R¹ | X¹ | R² | X² | R³ | R⁶ | R⁷ |
|---|---|---|---|---|---|---|---|
| 4532 | 4-CF₃S—Ph | NH | F10 | NH | OH | H | H |
| 4533 | 4-CF₃S—Ph | NH | Ph | NH | OH | H | H |
| 4534 | 4-CF₃S—Ph | NH | Bn | NH | OH | H | H |
| 4535 | 4-CF₃S—Ph | NH | Pe | NH | OH | H | H |
| 4536 | 4-CF₃S—Ph | NH | C12 | NMe | OH | H | H |
| 4537 | 4-CF₃S—Ph | NH | C12 | NEt | OH | H | H |
| 4538 | 4-CF₃S—Ph | NH | C12 | NPr | OH | H | H |
| 4539 | 4-CF₃S—Ph | NH | (CH₂)₃ | N | OH | H | H |
| 4540 | 4-CF₃S—Ph | NH | (CH₂)₄ | N | OH | H | H |
| 4541 | 4-CF₃S—Ph | NH | (CH₂)₅ | N | OH | H | H |
| 4542 | 4-CF₃S—Ph | NH | C12 | O | OH | H | H |
| 4543 | 4-CF₃S—Ph | NH | Ph | O | OH | H | H |
| 4544 | 4-CF₃S—Ph | NH | C12 | S | OH | H | H |
| 4545 | 4-CF₃S—Ph | NH | Ph | S | OH | H | H |
| 4546 | 4-CF₃S—Ph | NMe | H | NH | OH | H | H |
| 4547 | 4-CF₃S—Ph | NEt | H | NH | OH | H | H |
| 4548 | 4-CF₃S—Ph | NPr | H | NH | OH | H | H |
| 4549 | 4-CF₃S—Ph | O | H | NH | OH | H | H |
| 4550 | 4-CF₃S—Ph | S | H | NH | OH | H | H |
| 4551 | 3-CH₃S—Ph | NH | H | NH | H | H | H |
| 4552 | 3-CH₃S—Ph | NH | H | NH | OH | H | H |
| 4553 | 3-CH₃S—Ph | NH | H | NH | OA6 | H | H |
| 4554 | 3-CH₃S—Ph | NH | H | NH | OA8 | H | H |
| 4555 | 3-CH₃S—Ph | NH | H | NH | OA9 | H | H |
| 4556 | 3-CH₃S—Ph | NH | H | NH | OA10 | H | H |
| 4557 | 3-CH₃S—Ph | NH | H | NH | OA12 | H | H |
| 4558 | 3-CH₃S—Ph | NH | H | NH | OA14 | H | H |
| 4559 | 3-CH₃S—Ph | NH | H | NH | OA16 | H | H |
| 4560 | 3-CH₃S—Ph | NH | H | NH | OH | H | A6 |
| 4561 | 3-CH₃S—Ph | NH | H | NH | OH | H | A8 |
| 4562 | 3-CH₃S—Ph | NH | H | NH | OH | H | A9 |
| 4563 | 3-CH₃S—Ph | NH | H | NH | OH | H | A10 |
| 4564 | 3-CH₃S—Ph | NH | H | NH | OH | H | A12 |
| 4565 | 3-CH₃S—Ph | NH | H | NH | OH | H | A14 |
| 4566 | 3-CH₃S—Ph | NH | H | NH | OH | H | A16 |
| 4567 | 3-CH₃S—Ph | NH | H | NH | OH | A6 | A6 |
| 4568 | 3-CH₃S—Ph | NH | H | NH | OH | A8 | A8 |
| 4569 | 3-CH₃S—Ph | NH | H | NH | OH | A10 | A10 |
| 4570 | 3-CH₃S—Ph | NH | H | NH | OA2 | A2 | A2 |
| 4571 | 3-CH₃S—Ph | NH | H | NH | OA3 | A3 | A3 |
| 4572 | 3-CH₃S—Ph | NH | H | NH | OA4 | A4 | A4 |
| 4573 | 3-CH₃S—Ph | NH | H | NH | OC6 | H | H |
| 4574 | 3-CH₃S—Ph | NH | H | NH | OC7 | H | H |
| 4575 | 3-CH₃S—Ph | NH | H | NH | OC8 | H | H |
| 4576 | 3-CH₃S—Ph | NH | H | NH | OC10 | H | H |
| 4577 | 3-CH₃S—Ph | NH | H | NH | OC11 | H | H |
| 4578 | 3-CH₃S—Ph | NH | H | NH | OC12 | H | H |
| 4579 | 3-CH₃S—Ph | NH | H | NH | OC14 | H | H |
| 4580 | 3-CH₃S—Ph | NH | H | NH | OC16 | H | H |
| 4581 | 3-CH₃S—Ph | NH | H | NH | C6CO₃ | H | H |
| 4582 | 3-CH₃S—Ph | NH | H | NH | C7CO₃ | H | H |
| 4583 | 3-CH₃S—Ph | NH | H | NH | C8CO₃ | H | H |
| 4584 | 3-CH₃S—Ph | NH | H | NH | C9CO₃ | H | H |
| 4585 | 3-CH₃S—Ph | NH | H | NH | C10CO₃ | H | H |
| 4586 | 3-CH₃S—Ph | NH | H | NH | C12CO₃ | H | H |
| 4587 | 3-CH₃S—Ph | NH | H | NH | C16CO₃ | H | H |
| 4588 | 3-CH₃S—Ph | NH | C8 | NH | OH | H | H |
| 4589 | 3-CH₃S—Ph | NH | C9 | NH | OH | H | H |
| 4590 | 3-CH₃S—Ph | NH | C10 | NH | OH | H | H |
| 4591 | 3-CH₃S—Ph | NH | C12 | NH | OH | H | H |
| 4592 | 3-CH₃S—Ph | NH | C16 | NH | OH | H | H |
| 4593 | 3-CH₃S—Ph | NH | F1 | NH | OH | H | H |

TABLE 1-continued (I-1)

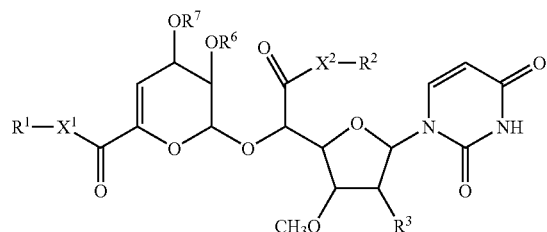

| Exemp. Comp. No. | R¹ | X¹ | R² | X² | R³ | R⁶ | R⁷ |
|---|---|---|---|---|---|---|---|
| 4594 | 3-CH₃S—Ph | NH | F2 | NH | OH | H | H |
| 4595 | 3-CH₃S—Ph | NH | F3 | NH | OH | H | H |
| 4596 | 3-CH₃S—Ph | NH | F4 | NH | OH | H | H |
| 4597 | 3-CH₃S—Ph | NH | F5 | NH | OH | H | H |
| 4598 | 3-CH₃S—Ph | NH | F6 | NH | OH | H | H |
| 4599 | 3-CH₃S—Ph | NH | F7 | NH | OH | H | H |
| 4600 | 3-CH₃S—Ph | NH | F8 | NH | OH | H | H |
| 4601 | 3-CH₃S—Ph | NH | F9 | NH | OH | H | H |
| 4602 | 3-CH₃S—Ph | NH | F10 | NH | OH | H | H |
| 4603 | 3-CH₃S—Ph | NH | Ph | NH | OH | H | H |
| 4604 | 3-CH₃S—Ph | NH | Bn | NH | OH | H | H |
| 4605 | 3-CH₃S—Ph | NH | Pe | NH | OH | H | H |
| 4606 | 3-CH₃S—Ph | NH | C12 | NMe | OH | H | H |
| 4607 | 3-CH₃S—Ph | NH | C12 | NEt | OH | H | H |
| 4608 | 3-CH₃S—Ph | NH | C12 | NPr | OH | H | H |
| 4609 | 3-CH₃S—Ph | NH | (CH₂)₃ | N | OH | H | H |
| 4610 | 3-CH₃S—Ph | NH | (CH₂)₄ | N | OH | H | H |
| 4611 | 3-CH₃S—Ph | NH | (CH₂)₅ | N | OH | H | H |
| 4612 | 3-CH₃S—Ph | NH | C12 | O | OH | H | H |
| 4613 | 3-CH₃S—Ph | NH | Ph | O | OH | H | H |
| 4614 | 3-CH₃S—Ph | NH | C12 | S | OH | H | H |
| 4615 | 3-CH₃S—Ph | NH | Ph | S | OH | H | H |
| 4616 | 3-CH₃S—Ph | NMe | H | NH | OH | H | H |
| 4617 | 3-CH₃S—Ph | NEt | H | NH | OH | H | H |
| 4618 | 3-CH₃S—Ph | NPr | H | NH | OH | H | H |
| 4619 | 3-CH₃S—Ph | O | H | NH | OH | H | H |
| 4620 | 3-CH₃S—Ph | S | H | NH | OH | H | H |
| 4621 | 3-F-4-Me—Ph | NH | H | NH | H | H | H |
| 4622 | 3-F-4-Me—Ph | NH | H | NH | OH | H | H |
| 4623 | 3-F-4-Me—Ph | NH | H | NH | OA6 | H | H |
| 4624 | 3-F-4-Me—Ph | NH | H | NH | OA8 | H | H |
| 4625 | 3-F-4-Me—Ph | NH | H | NH | OA9 | H | H |
| 4626 | 3-F-4-Me—Ph | NH | H | NH | OA10 | H | H |
| 4627 | 3-F-4-Me—Ph | NH | H | NH | OA12 | H | H |
| 4628 | 3-F-4-Me—Ph | NH | H | NH | OA14 | H | H |
| 4629 | 3-F-4-Me—Ph | NH | H | NH | OA16 | H | H |
| 4630 | 3-F-4-Me—Ph | NH | H | NH | OH | H | A6 |
| 4631 | 3-F-4-Me—Ph | NH | H | NH | OH | H | A8 |
| 4632 | 3-F-4-Me—Ph | NH | H | NH | OH | H | A9 |
| 4633 | 3-F-4-Me—Ph | NH | H | NH | OH | H | A10 |
| 4634 | 3-F-4-Me—Ph | NH | H | NH | OH | H | A12 |
| 4635 | 3-F-4-Me—Ph | NH | H | NH | OH | H | A14 |
| 4636 | 3-F-4-Me—Ph | NH | H | NH | OH | H | A16 |
| 4637 | 3-F-4-Me—Ph | NH | H | NH | OH | A6 | A6 |
| 4638 | 3-F-4-Me—Ph | NH | H | NH | OH | A8 | A8 |
| 4639 | 3-F-4-Me—Ph | NH | H | NH | OH | A10 | A10 |
| 4640 | 3-F-4-Me—Ph | NH | H | NH | OA2 | A2 | A2 |
| 4641 | 3-F-4-Me—Ph | NH | H | NH | OA3 | A3 | A3 |
| 4642 | 3-F-4-Me—Ph | NH | H | NH | OA4 | A4 | A4 |
| 4643 | 3-F-4-Me—Ph | NH | H | NH | OC6 | H | H |
| 4644 | 3-F-4-Me—Ph | NH | H | NH | OC7 | H | H |
| 4645 | 3-F-4-Me—Ph | NH | H | NH | OC8 | H | H |
| 4646 | 3-F-4-Me—Ph | NH | H | NH | OC10 | H | H |
| 4647 | 3-F-4-Me—Ph | NH | H | NH | OC11 | H | H |
| 4648 | 3-F-4-Me—Ph | NH | H | NH | OC12 | H | H |
| 4649 | 3-F-4-Me—Ph | NH | H | NH | OC14 | H | H |
| 4650 | 3-F-4-Me—Ph | NH | H | NH | OC16 | H | H |
| 4651 | 3-F-4-Me—Ph | NH | H | NH | C6CO₃ | H | H |
| 4652 | 3-F-4-Me—Ph | NH | H | NH | C7CO₃ | H | H |
| 4653 | 3-F-4-Me—Ph | NH | H | NH | C8CO₃ | H | H |
| 4654 | 3-F-4-Me—Ph | NH | H | NH | C9CO₃ | H | H |
| 4655 | 3-F-4-Me—Ph | NH | H | NH | C10CO₃ | H | H |

TABLE 1-continued (I-1)

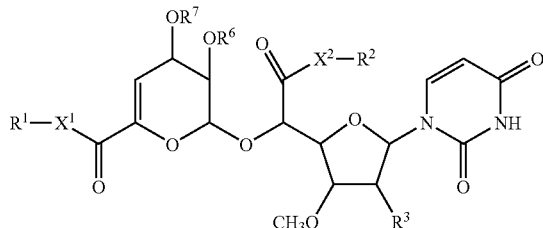

| Exemp. Comp. No. | $R^1$ | $X^1$ | $R^2$ | $X^2$ | $R^3$ | $R^6$ | $R^7$ |
|---|---|---|---|---|---|---|---|
| 4656 | 3-F-4-Me—Ph | NH | H | NH | C12CO$_3$ | H | H |
| 4657 | 3-F-4-Me—Ph | NH | H | NH | C16CO$_3$ | H | H |
| 4658 | 3-F-4-Me—Ph | NH | C8 | NH | OH | H | H |
| 4659 | 3-F-4-Me—Ph | NH | C9 | NH | OH | H | H |
| 4660 | 3-F-4-Me—Ph | NH | C10 | NH | OH | H | H |
| 4661 | 3-F-4-Me—Ph | NH | C12 | NH | OH | H | H |
| 4662 | 3-F-4-Me—Ph | NH | C16 | NH | OH | H | H |
| 4663 | 3-F-4-Me—Ph | NH | F1 | NH | OH | H | H |
| 4664 | 3-F-4-Me—Ph | NH | F2 | NH | OH | H | H |
| 4665 | 3-F-4-Me—Ph | NH | F3 | NH | OH | H | H |
| 4666 | 3-F-4-Me—Ph | NH | F4 | NH | OH | H | H |
| 4667 | 3-F-4-Me—Ph | NH | E5 | NH | OH | H | H |
| 4668 | 3-F-4-Me—Ph | NH | F6 | NH | OH | H | H |
| 4669 | 3-F-4-Me—Ph | NH | F7 | NH | OH | H | H |
| 4670 | 3-F-4-Me—Ph | NH | F8 | NH | OH | H | H |
| 4671 | 3-F-4-Me—Ph | NH | F9 | NH | OH | H | H |
| 4672 | 3-F-4-Me—Ph | NH | F10 | NH | OH | H | H |
| 4673 | 3-F-4-Me—Ph | NH | Ph | NH | OH | H | H |
| 4674 | 3-F-4-Me—Ph | NH | Bn | NH | OH | H | H |
| 4675 | 3-F-4-Me—Ph | NH | Pe | NH | OH | H | H |
| 4676 | 3-F-4-Me—Ph | NH | C12 | NMe | OH | H | H |
| 4677 | 3-F-4-Me—Ph | NH | C12 | NEt | OH | H | H |
| 4678 | 3-F-4-Me—Ph | NH | C12 | NPr | OH | H | H |
| 4679 | 3-F-4-Me—Ph | NH | (CH$_2$)$_3$ | N | OH | H | H |
| 4680 | 3-F-4-Me—Ph | NH | (CH$_2$)$_4$ | N | OH | H | H |
| 4681 | 3-F-4-Me—Ph | NH | (CH$_2$)$_5$ | N | OH | H | H |
| 4682 | 3-F-4-Me—Ph | NH | C12 | O | OH | H | H |
| 4683 | 3-F-4-Me—Ph | NH | Ph | O | OH | H | H |
| 4684 | 3-F-4-Me—Ph | NH | C12 | S | OH | H | H |
| 4685 | 3-F-4-Me—Ph | NH | Ph | S | OH | H | H |
| 4686 | 3-F-4-Me—Ph | NMe | H | NH | OH | H | H |
| 4687 | 3-F-4-Me—Ph | NEt | H | NH | OH | H | H |
| 4688 | 3-F-4-Me—Ph | NPr | H | NH | OH | H | H |
| 4689 | 3-F-4-Me—Ph | O | H | NH | OH | H | H |
| 4690 | 3-F-4-Me—Ph | S | H | NH | OH | H | H |
| 4691 | 3-Cl-4-Me—Ph | NH | H | NH | H | H | H |
| 4692 | 3-Cl-4-Me—Ph | NH | H | NH | OH | H | H |
| 4693 | 3-Cl-4-Me—Ph | NH | H | NH | OA6 | H | H |
| 4694 | 3-Cl-4-Me—Ph | NH | H | NH | OA8 | H | H |
| 4695 | 3-Cl-4-Me—Ph | NH | H | NH | OA9 | H | H |
| 4696 | 3-Cl-4-Me—Ph | NH | H | NH | OA10 | H | H |
| 4697 | 3-Cl-4-Me—Ph | NH | H | NH | OA12 | H | H |
| 4698 | 3-Cl-4-Me—Ph | NH | H | NH | OA14 | H | H |
| 4699 | 3-Cl-4-Me—Ph | NH | H | NH | OA16 | H | H |
| 4700 | 3-Cl-4-Me—Ph | NH | H | NH | OH | H | A6 |
| 4701 | 3-Cl-4-Me—Ph | NH | H | NH | OH | H | A8 |
| 4702 | 3-Cl-4-Me—Ph | NH | H | NH | OH | H | A9 |
| 4703 | 3-Cl-4-Me—Ph | NH | H | NH | OH | H | A10 |
| 4704 | 3-Cl-4-Me—Ph | NH | H | NH | OH | H | A12 |
| 4705 | 3-Cl-4-Me—Ph | NH | H | NH | OH | H | A14 |
| 4706 | 3-Cl-4-Me—Ph | NH | H | NH | OH | H | A16 |
| 4707 | 3-Cl-4-Me—Ph | NH | H | NH | OH | A6 | A6 |
| 4708 | 3-Cl-4-Me—Ph | NH | H | NH | OH | A8 | A8 |
| 4709 | 3-Cl-4-Me—Ph | NH | H | NH | OH | A10 | A10 |
| 4710 | 3-Cl-4-Me—Ph | NH | H | NH | OA2 | A2 | A2 |
| 4711 | 3-Cl-4-Me—Ph | NH | H | NH | OA3 | A3 | A3 |
| 4712 | 3-Cl-4-Me—Ph | NH | H | NH | OA4 | A4 | A4 |
| 4713 | 3-Cl-4-Me—Ph | NH | H | NH | OC6 | H | H |
| 4714 | 3-Cl-4-Me—Ph | NH | H | NH | OC7 | H | H |
| 4715 | 3-Cl-4-Me—Ph | NH | H | NH | OC8 | H | H |
| 4716 | 3-Cl-4-Me—Ph | NH | H | NH | OC10 | H | H |
| 4717 | 3-Cl-4-Me—Ph | NH | H | NH | OC11 | H | H |

TABLE 1-continued (I-1)

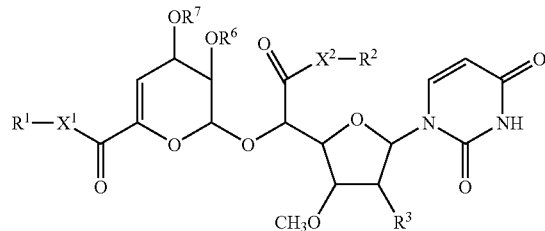

| Exemp. Comp. No. | R$^1$ | X$^1$ | R$^2$ | X$^2$ | R$^3$ | R$^6$ | R$^7$ |
|---|---|---|---|---|---|---|---|
| 4718 | 3-Cl-4-Me—Ph | NH | H | NH | OC12 | H | H |
| 4719 | 3-Cl-4-Me—Ph | NH | H | NH | OC14 | H | H |
| 4720 | 3-Cl-4-Me—Ph | NH | H | NH | OC16 | H | H |
| 4721 | 3-Cl-4-Me—Ph | NH | H | NH | C6CO$_3$ | H | H |
| 4722 | 3-Cl-4-Me—Ph | NH | H | NH | C7CO$_3$ | H | H |
| 4723 | 3-Cl-4-Me—Ph | NH | H | NH | C8CO$_3$ | H | H |
| 4724 | 3-Cl-4-Me—Ph | NH | H | NH | C9CO$_3$ | H | H |
| 4725 | 3-Cl-4-Me—Ph | NH | H | NH | C10CO$_3$ | H | H |
| 4726 | 3-Cl-4-Me—Ph | NH | H | NH | C12CO$_3$ | H | H |
| 4727 | 3-Cl-4-Me—Ph | NH | H | NH | C16CO$_3$ | H | H |
| 4728 | 3-Cl-4-Me—Ph | NH | C8 | NH | OH | H | H |
| 4729 | 3-Cl-4-Me—Ph | NH | C9 | NH | OH | H | H |
| 4730 | 3-Cl-4-Me—Ph | NH | C10 | NH | OH | H | H |
| 4731 | 3-Cl-4-Me—Ph | NH | C12 | NH | OH | H | H |
| 4732 | 3-Cl-4-Me—Ph | NH | C16 | NH | OH | H | H |
| 4733 | 3-Cl-4-Me—Ph | NH | F1 | NH | OH | H | H |
| 4734 | 3-Cl-4-Me—Ph | NH | F2 | NH | OH | H | H |
| 4735 | 3-Cl-4-Me—Ph | NH | F3 | NH | OH | H | H |
| 4736 | 3-Cl-4-Me—Ph | NH | F4 | NH | OH | H | H |
| 4737 | 3-Cl-4-Me—Ph | NH | F5 | NH | OH | H | H |
| 4738 | 3-Cl-4-Me—Ph | NH | F6 | NH | OH | H | H |
| 4739 | 3-Cl-4-Me—Ph | NH | F7 | NH | OH | H | H |
| 4740 | 3-Cl-4-Me—Ph | NH | F8 | NH | OH | H | H |
| 4741 | 3-Cl-4-Me—Ph | NH | F9 | NH | OH | H | H |
| 4742 | 3-Cl-4-Me—Ph | NH | F10 | NH | OH | H | H |
| 4743 | 3-Cl-4-Me—Ph | NH | Ph | NH | OH | H | H |
| 4744 | 3-Cl-4-Me—Ph | NH | Bn | NH | OH | H | H |
| 4745 | 3-Cl-4-Me—Ph | NH | Pe | NH | OH | H | H |
| 4746 | 3-Cl-4-Me—Ph | NH | C12 | NMe | OH | H | H |
| 4747 | 3-Cl-4-Me—Ph | NH | C12 | NEt | OH | H | H |
| 4748 | 3-Cl-4-Me—Ph | NH | C12 | NPr | OH | H | H |
| 4749 | 3-Cl-4-Me—Ph | NH | (CH$_2$)$_3$ | N | OH | H | H |
| 4750 | 3-Cl-4-Me—Ph | NH | (CH$_2$)$_4$ | N | OH | H | H |
| 4751 | 3-Cl-4-Me—Ph | NH | (CH$_2$)$_5$ | N | OH | H | H |
| 4752 | 3-Cl-4-Me—Ph | NH | C12 | O | OH | H | H |
| 4753 | 3-Cl-4-Me—Ph | NH | Ph | O | OH | H | H |
| 4754 | 3-Cl-4-Me—Ph | NH | C12 | S | OH | H | H |
| 4755 | 3-Cl-4-Me—Ph | NH | Ph | S | OH | H | H |
| 4756 | 3-Cl-4-Me—Ph | NMe | H | NH | OH | H | H |
| 4757 | 3-Cl-4-Me—Ph | NEt | H | NH | OH | H | H |
| 4758 | 3-Cl-4-Me—Ph | NPr | H | NH | OH | H | H |
| 4759 | 3-Cl-4-Me—Ph | O | H | NH | OH | H | H |
| 4760 | 3-Cl-4-Me—Ph | S | H | NH | OH | H | H |
| 4761 | 3-Me-4-Br—Ph | NH | H | NH | H | H | H |
| 4762 | 3-Me-4-Br—Ph | NH | H | NH | OH | H | H |
| 4763 | 3-Me-4-Br—Ph | NH | H | NH | OA6 | H | H |
| 4764 | 3-Me-4-Br—Ph | NH | H | NH | OA8 | H | H |
| 4765 | 3-Me-4-Br—Ph | NH | H | NH | OA9 | H | H |
| 4766 | 3-Me-4-Br—Ph | NH | H | NH | OA10 | H | H |
| 4767 | 3-Me-4-Br—Ph | NH | H | NH | OA12 | H | H |
| 4768 | 3-Me-4-Br—Ph | NH | H | NH | OA14 | H | H |
| 4769 | 3-Me-4-Br—Ph | NH | H | NH | OA16 | H | H |
| 4770 | 3-Me-4-Br—Ph | NH | H | NH | OH | H | A6 |
| 4771 | 3-Me-4-Br—Ph | NH | H | NH | OH | H | A8 |
| 4772 | 3-Me-4-Br—Ph | NH | H | NH | OH | H | A9 |
| 4773 | 3-Me-4-Br—Ph | NH | H | NH | OH | H | A10 |
| 4774 | 3-Me-4-Br—Ph | NH | H | NH | OH | H | A12 |
| 4775 | 3-Me-4-Br—Ph | NH | H | NH | OH | H | A14 |
| 4776 | 3-Me-4-Br—Ph | NH | H | NH | OH | H | A16 |
| 4777 | 3-Me-4-Br—Ph | NH | H | NH | OH | A6 | A6 |
| 4778 | 3-Me-4-Br—Ph | NH | H | NH | OH | A8 | A8 |
| 4779 | 3-Me-4-Br—Ph | NH | H | NH | OH | A10 | A10 |

TABLE 1-continued

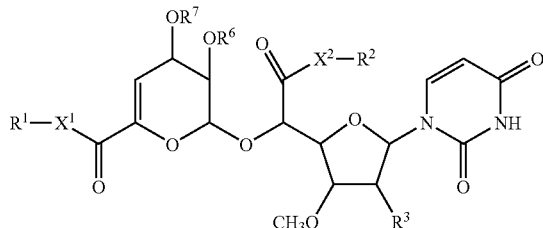

(I-1)

| Exemp. Comp. No. | R¹ | X¹ | R² | X² | R³ | R⁶ | R⁷ |
|---|---|---|---|---|---|---|---|
| 4780 | 3-Me-4-Br—Ph | NH | H | NH | OA2 | A2 | A2 |
| 4781 | 3-Me-4-Br—Ph | NH | H | NH | OA3 | A3 | A3 |
| 4782 | 3-Me-4-Br—Ph | NH | H | NH | OA4 | A4 | A4 |
| 4783 | 3-Me-4-Br—Ph | NH | H | NH | OC6 | H | H |
| 4784 | 3-Me-4-Br—Ph | NH | H | NH | OC7 | H | H |
| 4785 | 3-Me-4-Br—Ph | NH | H | NH | OC8 | H | H |
| 4786 | 3-Me-4-Br—Ph | NH | H | NH | OC10 | H | H |
| 4787 | 3-Me-4-Br—Ph | NH | H | NH | OC11 | H | H |
| 4788 | 3-Me-4-Br—Ph | NH | H | NH | OC12 | H | H |
| 4789 | 3-Me-4-Br—Ph | NH | H | NH | OC14 | H | H |
| 4790 | 3-Me-4-Br—Ph | NH | H | NH | OC16 | H | H |
| 4791 | 3-Me-4-Br—Ph | NH | H | NH | C6CO$_3$ | H | H |
| 4792 | 3-Me-4-Br—Ph | NH | H | NH | C7CO$_3$ | H | H |
| 4793 | 3-Me-4-Br—Ph | NH | H | NH | C8CO$_3$ | H | H |
| 4794 | 3-Me-4-Br—Ph | NH | H | NH | C9CO$_3$ | H | H |
| 4795 | 3-Me-4-Br—Ph | NH | H | NH | C10CO$_3$ | H | H |
| 4796 | 3-Me-4-Br—Ph | NH | H | NH | C12CO$_3$ | H | H |
| 4797 | 3-Me-4-Br—Ph | NH | H | NH | C16CO$_3$ | H | H |
| 4798 | 3-Me-4-Br—Ph | NH | C8 | NH | OH | H | H |
| 4799 | 3-Me-4-Br—Ph | NH | C9 | NH | OH | H | H |
| 4800 | 3-Me-4-Br—Ph | NH | C10 | NH | OH | H | H |
| 4801 | 3-Me-4-Br—Ph | NH | C12 | NH | OH | H | H |
| 4802 | 3-Me-4-Br—Ph | NH | C16 | NH | OH | H | H |
| 4803 | 3-Me-4-Br—Ph | NH | F1 | NH | OH | H | H |
| 4804 | 3-Me-4-Br—Ph | NH | F2 | NH | OH | H | H |
| 4805 | 3-Me-4-Br—Ph | NH | F3 | NH | OH | H | H |
| 4806 | 3-Me-4-Br—Ph | NH | F4 | NH | OH | H | H |
| 4807 | 3-Me-4-Br—Ph | NH | F5 | NH | OH | H | H |
| 4808 | 3-Me-4-Br—Ph | NH | F6 | NH | OH | H | H |
| 4809 | 3-Me-4-Br—Ph | NH | F7 | NH | OH | H | H |
| 4810 | 3-Me-4-Br—Ph | NH | F8 | NH | OH | H | H |
| 4811 | 3-Me-4-Br—Ph | NH | F9 | NH | OH | H | H |
| 4812 | 3-Me-4-Br—Ph | NH | F10 | NH | OH | H | H |
| 4813 | 3-Me-4-Br—Ph | NH | Ph | NH | OH | H | H |
| 4814 | 3-Me-4-Br—Ph | NH | Bn | NH | OH | H | H |
| 4815 | 3-Me-4-Br—Ph | NH | Pe | NH | OH | H | H |
| 4816 | 3-Me-4-Br—Ph | NH | C12 | NMe | OH | H | H |
| 4817 | 3-Me-4-Br—Ph | NH | C12 | NEt | OH | H | H |
| 4818 | 3-Me-4-Br—Ph | NH | C12 | NPr | OH | H | H |
| 4819 | 3-Me-4-Br—Ph | NH | (CH$_2$)$_3$ | N | OH | H | H |
| 4820 | 3-Me-4-Br—Ph | NH | (CH$_2$)$_4$ | N | OH | H | H |
| 4821 | 3-Me-4-Br—Ph | NH | (CH$_2$)$_5$ | N | OH | H | H |
| 4822 | 3-Me-4-Br—Ph | NH | C12 | O | OH | H | H |
| 4823 | 3-Me-4-Br—Ph | NH | Ph | O | OH | H | H |
| 4824 | 3-Me-4-Br—Ph | NH | C12 | S | OH | H | H |
| 4825 | 3-Me-4-Br—Ph | NH | Ph | S | OH | H | H |
| 4826 | 3-Me-4-Br—Ph | NMe | H | NH | OH | H | H |
| 4827 | 3-Me-4-Br—Ph | NEt | H | NH | OH | H | H |
| 4828 | 3-Me-4-Br—Ph | NPr | H | NH | OH | H | H |
| 4829 | 3-Me-4-Br—Ph | O | H | NH | OH | H | H |
| 4830 | 3-Me-4-Br—Ph | S | H | NH | OH | H | H |
| 4831 | 3-NO$_2$-4-F—Ph | NH | H | NH | H | H | H |
| 4832 | 3-NO$_2$-4-F—Ph | NH | H | NH | OH | H | H |
| 4833 | 3-NO$_2$-4-F—Ph | NH | H | NH | OA6 | H | H |
| 4834 | 3-NO$_2$-4-F—Ph | NH | H | NH | OA8 | H | H |
| 4835 | 3-NO$_2$-4-F—Ph | NH | H | NH | OA9 | H | H |
| 4836 | 3-NO$_2$-4-F—Ph | NH | H | NH | OA10 | H | H |
| 4837 | 3-NO$_2$-4-F—Ph | NH | H | NH | OA12 | H | H |
| 4838 | 3-NO$_2$-4-F—Ph | NH | H | NH | OA14 | H | H |
| 4839 | 3-NO$_2$-4-F—Ph | NH | H | NH | OA16 | H | H |
| 4840 | 3-NO$_2$-4-F—Ph | NH | H | NH | OH | H | A6 |
| 4841 | 3-NO$_2$-4-F—Ph | NH | H | NH | OH | H | A8 |

TABLE 1-continued

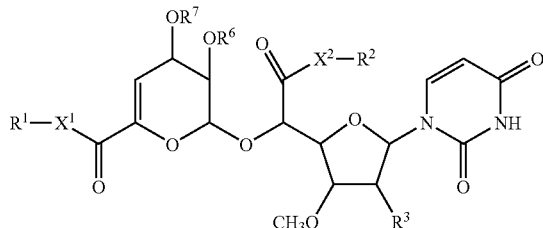

(I-1)

| Exemp. Comp. No. | R¹ | X¹ | R² | X² | R³ | R⁶ | R⁷ |
|---|---|---|---|---|---|---|---|
| 4842 | 3-NO$_2$-4-F—Ph | NH | H | NH | OH | H | A9 |
| 4843 | 3-NO$_2$-4-F—Ph | NH | H | NH | OH | H | A10 |
| 4844 | 3-NO$_2$-4-F—Ph | NH | H | NH | OH | H | A12 |
| 4845 | 3-NO$_2$-4-F—Ph | NH | H | NH | OH | H | A14 |
| 4846 | 3-NO$_2$-4-F—Ph | NH | H | NH | OH | H | A16 |
| 4847 | 3-NO$_2$-4-F—Ph | NH | H | NH | OH | A6 | A6 |
| 4848 | 3-NO$_2$-4-F—Ph | NH | H | NH | OH | A8 | A8 |
| 4849 | 3-NO$_2$-4-F—Ph | NH | H | NH | OH | A10 | A10 |
| 4850 | 3-NO$_2$-4-F—Ph | NH | H | NH | OA2 | A2 | A2 |
| 4851 | 3-NO$_2$-4-F—Ph | NH | H | NH | OA3 | A3 | A3 |
| 4852 | 3-NO$_2$-4-F—Ph | NH | H | NH | OA4 | A4 | A4 |
| 4853 | 3-NO$_2$-4-F—Ph | NH | H | NH | OC6 | H | H |
| 4854 | 3-NO$_2$-4-F—Ph | NH | H | NH | OC7 | H | H |
| 4855 | 3-NO$_2$-4-F—Ph | NH | H | NH | OC8 | H | H |
| 4856 | 3-NO$_2$-4-F—Ph | NH | H | NH | OC10 | H | H |
| 4857 | 3-NO$_2$-4-F—Ph | NH | H | NH | OC11 | H | H |
| 4858 | 3-NO$_2$-4-F—Ph | NH | H | NH | OC12 | H | H |
| 4859 | 3-NO$_2$-4-F—Ph | NH | H | NH | OC14 | H | H |
| 4860 | 3-NO$_2$-4-F—Ph | NH | H | NH | OC16 | H | H |
| 4861 | 3-NO$_2$-4-F—Ph | NH | H | NH | C6CO$_3$ | H | H |
| 4862 | 3-NO$_2$-4-F—Ph | NH | H | NH | C7CO$_3$ | H | H |
| 4863 | 3-NO$_2$-4-F—Ph | NH | H | NH | C8CO$_3$ | H | H |
| 4864 | 3-NO$_2$-4-F—Ph | NH | H | NH | C9CO$_3$ | H | H |
| 4865 | 3-NO$_2$-4-F—Ph | NH | H | NH | C10CO$_3$ | H | H |
| 4866 | 3-NO$_2$-4-F—Ph | NH | H | NH | C12CO$_3$ | H | H |
| 4867 | 3-NO$_2$-4-F—Ph | NH | H | NH | C16CO$_3$ | H | H |
| 4868 | 3-NO$_2$-4-F—Ph | NH | C8 | NH | OH | H | H |
| 4869 | 3-NO$_2$-4-F—Ph | NH | C9 | NH | OH | H | H |
| 4870 | 3-NO$_2$-4-F—Ph | NH | C10 | NH | OH | H | H |
| 4871 | 3-NO$_2$-4-F—Ph | NH | C12 | NH | OH | H | H |
| 4872 | 3-NO$_2$-4-F—Ph | NH | C16 | NH | OH | H | H |
| 4873 | 3-NO$_2$-4-F—Ph | NH | F1 | NH | OH | H | H |
| 4874 | 3-NO$_2$-4-F—Ph | NH | F2 | NH | OH | H | H |
| 4875 | 3-NO$_2$-4-F—Ph | NH | F3 | NH | OH | H | H |
| 4876 | 3-NO$_2$-4-F—Ph | NH | F4 | NH | OH | H | H |
| 4877 | 3-NO$_2$-4-F—Ph | NH | F5 | NH | OH | H | H |
| 4878 | 3-NO$_2$-4-F—Ph | NH | F6 | NH | OH | H | H |
| 4879 | 3-NO$_2$-4-F—Ph | NH | F7 | NH | OH | H | H |
| 4880 | 3-NO$_2$-4-F—Ph | NH | F8 | NH | OH | H | H |
| 4881 | 3-NO$_2$-4-F—Ph | NH | F9 | NH | OH | H | H |
| 4882 | 3-NO$_2$-4-F—Ph | NH | F10 | NH | OH | H | H |
| 4883 | 3-NO$_2$-4-F—Ph | NH | Ph | NH | OH | H | H |
| 4884 | 3-NO$_2$-4-F—Ph | NH | Bn | NH | OH | H | H |
| 4885 | 3-NO$_2$-4-F—Ph | NH | Pe | NH | OH | H | H |
| 4886 | 3-NO$_2$-4-F—Ph | NH | C12 | NMe | OH | H | H |
| 4887 | 3-NO$_2$-4-F—Ph | NH | C12 | NEt | OH | H | H |
| 4888 | 3-NO$_2$-4-F—Ph | NH | C12 | NPr | OH | H | H |
| 4889 | 3-NO$_2$-4-F—Ph | NH | (CH$_2$)$_3$ | N | OH | H | H |
| 4890 | 3-NO$_2$-4-F—Ph | NH | (CH$_2$)$_4$ | N | OH | H | H |
| 4891 | 3-NO$_2$-4-F—Ph | NH | (CH$_2$)$_5$ | N | OH | H | H |
| 4892 | 3-NO$_2$-4-F—Ph | NH | C12 | O | OH | H | H |
| 4893 | 3-NO$_2$-4-F—Ph | NH | Ph | O | OH | H | H |
| 4894 | 3-NO$_2$-4-F—Ph | NH | C12 | S | OH | H | H |
| 4895 | 3-NO$_2$-4-F—Ph | NH | Ph | S | OH | H | H |
| 4896 | 3-NO$_2$-4-F—Ph | NMe | H | NH | OH | H | H |
| 4897 | 3-NO$_2$-4-F—Ph | NEt | H | NH | OH | H | H |
| 4898 | 3-NO$_2$-4-F—Ph | NPr | H | NH | OH | H | H |
| 4899 | 3-NO$_2$-4-F—Ph | O | H | NH | OH | H | H |
| 4900 | 3-NO$_2$-4-F—Ph | S | H | NH | OH | H | H |
| 4901 | 3-NO$_2$-4-Cl—Ph | NH | H | NH | H | H | H |
| 4902 | 3-NO$_2$-4-Cl—Ph | NH | H | NH | OH | H | H |
| 4903 | 3-NO$_2$-4-Cl—Ph | NH | H | NH | OA6 | H | H |

TABLE 1-continued (I-1)

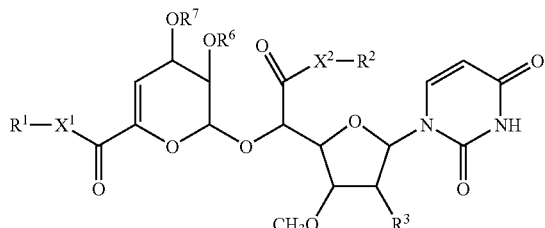

| Exemp. Comp. No. | R¹ | X¹ | R² | X² | R³ | R⁶ | R⁷ |
|---|---|---|---|---|---|---|---|
| 4904 | 3-NO₂-4-Cl—Ph | NH | H | NH | OA8 | H | H |
| 4905 | 3-NO₂-4-Cl—Ph | NH | H | NH | OA9 | H | H |
| 4906 | 3-NO₂-4-Cl—Ph | NH | H | NH | OA10 | H | H |
| 4907 | 3-NO₂-4-Cl—Ph | NH | H | NH | OA12 | H | H |
| 4908 | 3-NO₂-4-Cl—Ph | NH | H | NH | OA14 | H | H |
| 4909 | 3-NO₂-4-Cl—Ph | NH | H | NH | OA16 | H | H |
| 4910 | 3-NO₂-4-Cl—Ph | NH | H | NH | OH | H | A6 |
| 4911 | 3-NO₂-4-Cl—Ph | NH | H | NH | OH | H | A8 |
| 4912 | 3-NO₂-4-Cl—Ph | NH | H | NH | OH | H | A9 |
| 4913 | 3-NO₂-4-Cl—Ph | NH | H | NH | OH | H | A10 |
| 4914 | 3-NO₂-4-Cl—Ph | NH | H | NH | OH | H | A12 |
| 4915 | 3-NO₂-4-Cl—Ph | NH | H | NH | OH | H | A14 |
| 4916 | 3-NO₂-4-Cl—Ph | NH | H | NH | OH | H | A16 |
| 4917 | 3-NO₂-4-Cl—Ph | NH | H | NH | OH | A6 | A6 |
| 4918 | 3-NO₂-4-Cl—Ph | NH | H | NH | OH | A8 | A8 |
| 4919 | 3-NO₂-4-Cl—Ph | NH | H | NH | OH | A10 | A10 |
| 4920 | 3-NO₂-4-Cl—Ph | NH | H | NH | OA2 | A2 | A2 |
| 4921 | 3-NO₂-4-Cl—Ph | NH | H | NH | OA3 | A3 | A3 |
| 4922 | 3-NO₂-4-Cl—Ph | NH | H | NH | OA4 | A4 | A4 |
| 4923 | 3-NO₂-4-Cl—Ph | NH | H | NH | OC6 | H | H |
| 4924 | 3-NO₂-4-Cl—Ph | NH | H | NH | OC7 | H | H |
| 4925 | 3-NO₂-4-Cl—Ph | NH | H | NH | OC8 | H | H |
| 4926 | 3-NO₂-4-Cl—Ph | NH | H | NH | OC10 | H | H |
| 4927 | 3-NO₂-4-Cl—Ph | NH | H | NH | OC11 | H | H |
| 4928 | 3-NO₂-4-Cl—Ph | NH | H | NH | OC12 | H | H |
| 4929 | 3-NO₂-4-Cl—Ph | NH | H | NH | OC14 | H | H |
| 4930 | 3-NO₂-4-Cl—Ph | NH | H | NH | OC16 | H | H |
| 4931 | 3-NO₂-4-Cl—Ph | NH | H | NH | C6CO₃ | H | H |
| 4932 | 3-NO₂-4-Cl—Ph | NH | H | NH | C7CO₃ | H | H |
| 4933 | 3-NO₂-4-Cl—Ph | NH | H | NH | C8CO₃ | H | H |
| 4934 | 3-NO₂-4-Cl—Ph | NH | H | NH | C9CO₃ | H | H |
| 4935 | 3-NO₂-4-Cl—Ph | NH | H | NH | C10CO₃ | H | H |
| 4936 | 3-NO₂-4-Cl—Ph | NH | H | NH | C12CO₃ | H | H |
| 4937 | 3-NO₂-4-Cl—Ph | NH | H | NH | C16CO₃ | H | H |
| 4938 | 3-NO₂-4-Cl—Ph | NH | C8 | NH | OH | H | H |
| 4939 | 3-NO₂-4-Cl—Ph | NH | C9 | NH | OH | H | H |
| 4940 | 3-NO₂-4-Cl—Ph | NH | C10 | NH | OH | H | H |
| 4941 | 3-NO₂-4-Cl—Ph | NH | C12 | NH | OH | H | H |
| 4942 | 3-NO₂-4-Cl—Ph | NH | C16 | NH | OH | H | H |
| 4943 | 3-NO₂-4-Cl—Ph | NH | F1 | NH | OH | H | H |
| 4944 | 3-NO₂-4-Cl—Ph | NH | F2 | NH | OH | H | H |
| 4945 | 3-NO₂-4-Cl—Ph | NH | F3 | NH | OH | H | H |
| 4946 | 3-NO₂-4-Cl—Ph | NH | F4 | NH | OH | H | H |
| 4947 | 3-NO₂-4-Cl—Ph | NH | F5 | NH | OH | H | H |
| 4948 | 3-NO₂-4-Cl—Ph | NH | F6 | NH | OH | H | H |
| 4949 | 3-NO₂-4-Cl—Ph | NH | F7 | NH | OH | H | H |
| 4950 | 3-NO₂-4-Cl—Ph | NH | F8 | NH | OH | H | H |
| 4951 | 3-NO₂-4-Cl—Ph | NH | F9 | NH | OH | H | H |
| 4952 | 3-NO₂-4-Cl—Ph | NH | F10 | NH | OH | H | H |
| 4953 | 3-NO₂-4-Cl—Ph | NH | Ph | NH | OH | H | H |
| 4954 | 3-NO₂-4-Cl—Ph | NH | Bn | NH | OH | H | H |
| 4955 | 3-NO₂-4-Cl—Ph | NH | Pe | NH | OH | H | H |
| 4956 | 3-NO₂-4-Cl—Ph | NH | C12 | NMe | OH | H | H |
| 4957 | 3-NO₂-4-Cl—Ph | NH | C12 | NEt | OH | H | H |
| 4958 | 3-NO₂-4-Cl—Ph | NH | C12 | NPr | OH | H | H |
| 4959 | 3-NO₂-4-Cl—Ph | NH | (CH₂)₃ | N | OH | H | H |
| 4960 | 3-NO₂-4-Cl—Ph | NH | (CH₂)₄ | N | OH | H | H |
| 4961 | 3-NO₂-4-Cl—Ph | NH | (CH₂)₅ | N | OH | H | H |
| 4962 | 3-NO₂-4-Cl—Ph | NH | C12 | O | OH | H | H |
| 4963 | 3-NO₂-4-Cl—Ph | NH | Ph | O | OH | H | H |
| 4964 | 3-NO₂-4-Cl—Ph | NH | C12 | S | OH | H | H |
| 4965 | 3-NO₂-4-Cl—Ph | NH | Ph | S | OH | H | H |

TABLE 1-continued (I-1)

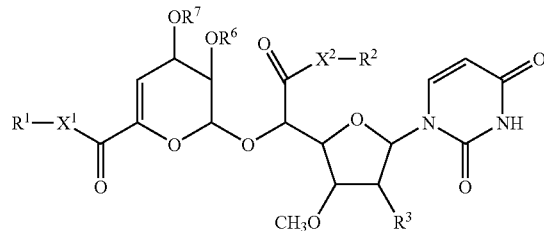

| Exemp. Comp. No. | R¹ | X¹ | R² | X² | R³ | R⁶ | R⁷ |
|---|---|---|---|---|---|---|---|
| 4966 | 3-NO₂-4-Cl—Ph | NMe | H | NH | OH | H | H |
| 4967 | 3-NO₂-4-Cl—Ph | NEt | H | NH | OH | H | H |
| 4968 | 3-NO₂-4-Cl—Ph | NPr | H | NH | OH | H | H |
| 4969 | 3-NO₂-4-Cl—Ph | O | H | NH | OH | H | H |
| 4970 | 3-NO₂-4-Cl—Ph | S | H | NH | OH | H | H |
| 4971 | 4-(F2-O)—Ph | NH | H | NH | H | H | H |
| 4972 | 4-(F2-O)—Ph | NH | H | NH | OH | H | H |
| 4973 | 4-(F2-O)—Ph | NH | H | NH | OA6 | H | H |
| 4974 | 4-(F2-O)—Ph | NH | H | NH | OA8 | H | H |
| 4975 | 4-(F2-O)—Ph | NH | H | NH | OA9 | H | H |
| 4976 | 4-(F2-O)—Ph | NH | H | NH | OA10 | H | H |
| 4977 | 4-(F2-O)—Ph | NH | H | NH | OA12 | H | H |
| 4978 | 4-(F2-O)—Ph | NH | H | NH | OA14 | H | H |
| 4979 | 4-(F2-O)—Ph | NH | H | NH | OA16 | H | H |
| 4980 | 4-(F2-O)—Ph | NH | H | NH | OH | H | A6 |
| 4981 | 4-(F2-O)—Ph | NH | H | NH | OH | H | A8 |
| 4982 | 4-(F2-O)—Ph | NH | H | NH | OH | H | A9 |
| 4983 | 4-(F2-O)—Ph | NH | H | NH | OH | H | A10 |
| 4984 | 4-(F2-O)—Ph | NH | H | NH | OH | H | A12 |
| 4985 | 4-(F2-O)—Ph | NH | H | NH | OH | H | A14 |
| 4986 | 4-(F2-O)—Ph | NH | H | NH | OH | H | A16 |
| 4987 | 4-(F2-O)—Ph | NH | H | NH | OH | A6 | A6 |
| 4988 | 4-(F2-O)—Ph | NH | H | NH | OH | A8 | A8 |
| 4989 | 4-(F2-O)—Ph | NH | H | NH | OH | A10 | A10 |
| 4990 | 4-(F2-O)—Ph | NH | H | NH | OA2 | A2 | A2 |
| 4991 | 4-(F2-O)—Ph | NH | H | NH | OA3 | A3 | A3 |
| 4992 | 4-(F2-O)—Ph | NH | H | NH | OA4 | A4 | A4 |
| 4993 | 4-(F2-O)—Ph | NH | H | NH | OC6 | H | H |
| 4994 | 4-(F2-O)—Ph | NH | H | NH | OC7 | H | H |
| 4995 | 4-(F2-O)—Ph | NH | H | NH | OC8 | H | H |
| 4996 | 4-(F2-O)—Ph | NH | H | NH | OC10 | H | H |
| 4997 | 4-(F2-O)—Ph | NH | H | NH | OC11 | H | H |
| 4998 | 4-(F2-O)—Ph | NH | H | NH | OC12 | H | H |
| 4999 | 4-(F2-O)—Ph | NH | H | NH | OC14 | H | H |
| 5000 | 4-(F2-O)—Ph | NH | H | NH | OC16 | H | H |
| 5001 | 4-(F2-O)—Ph | NH | H | NH | C6CO₃ | H | H |
| 5002 | 4-(F2-O)—Ph | NH | H | NH | C7CO₃ | H | H |
| 5003 | 4-(F2-O)—Ph | NH | H | NH | C8CO₃ | H | H |
| 5004 | 4-(F2-O)—Ph | NH | H | NH | C9CO₃ | H | H |
| 5005 | 4-(F2-O)—Ph | NH | H | NH | C10CO₃ | H | H |
| 5006 | 4-(F2-O)—Ph | NH | H | NH | C12CO₃ | H | H |
| 5007 | 4-(F2-O)—Ph | NH | H | NH | C16CO₃ | H | H |
| 5008 | 4-(F2-O)—Ph | NH | C8 | NH | OH | H | H |
| 5009 | 4-(F2-O)—Ph | NH | C9 | NH | OH | H | H |
| 5010 | 4-(F2-O)—Ph | NH | C10 | NH | OH | H | H |
| 5011 | 4-(F2-O)—Ph | NH | C12 | NH | OH | H | H |
| 5012 | 4-(F2-O)—Ph | NH | C16 | NH | OH | H | H |
| 5013 | 4-(F2-O)—Ph | NH | F1 | NH | OH | H | H |
| 5014 | 4-(F2-O)—Ph | NH | F2 | NH | OH | H | H |
| 5015 | 4-(F2-O)—Ph | NH | F3 | NH | OH | H | H |
| 5016 | 4-(F2-O)—Ph | NH | F4 | NH | OH | H | H |
| 5017 | 4-(F2-O)—Ph | NH | F5 | NH | OH | H | H |
| 5018 | 4-(F2-O)—Ph | NH | F6 | NH | OH | H | H |
| 5019 | 4-(F2-O)—Ph | NH | F7 | NH | OH | H | H |
| 5020 | 4-(F2-O)—Ph | NH | F8 | NH | OH | H | H |
| 5021 | 4-(F2-O)—Ph | NH | F9 | NH | OH | H | H |
| 5022 | 4-(F2-O)—Ph | NH | F10 | NH | OH | H | H |
| 5023 | 4-(F2-O)—Ph | NH | Ph | NH | OH | H | H |
| 5024 | 4-(F2-O)—Ph | NH | Bn | NH | OH | H | H |
| 5025 | 4-(F2-O)—Ph | NH | Pe | NH | OH | H | H |
| 5026 | 4-(F2-O)—Ph | NH | C12 | NMe | OH | H | H |
| 5027 | 4-(F2-O)—Ph | NH | C12 | NEt | OH | H | H |

TABLE 1-continued

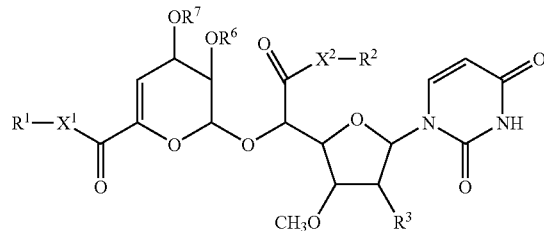

(I-1)

| Exemp. Comp. No. | R¹ | X¹ | R² | X² | R³ | R⁶ | R⁷ |
|---|---|---|---|---|---|---|---|
| 5028 | 4-(F2-O)—Ph | NH | C12 | NPr | OH | H | H |
| 5029 | 4-(F2-O)—Ph | NH | (CH₂)₃ | N | OH | H | H |
| 5030 | 4-(F2-O)—Ph | NH | (CH₂)₄ | N | OH | H | H |
| 5031 | 4-(F2-O)—Ph | NH | (CH₂)₅ | N | OH | H | H |
| 5032 | 4-(F2-O)—Ph | NH | C12 | O | OH | H | H |
| 5033 | 4-(F2-O)—Ph | NH | Ph | O | OH | H | H |
| 5034 | 4-(F2-O)—Ph | NH | C12 | S | OH | H | H |
| 5035 | 4-(F2-O)—Ph | NH | Ph | S | OH | H | H |
| 5036 | 4-(F2-O)—Ph | NMe | H | NH | OH | H | H |
| 5037 | 4-(F2-O)—Ph | NEt | H | NH | OH | H | H |
| 5038 | 4-(F2-O)—Ph | NPr | H | NH | OH | H | H |
| 5039 | 4-(F2-O)—Ph | O | H | NH | OH | H | H |
| 5040 | 4-(F2-O)—Ph | S | H | NH | OH | H | H |
| 5041 | 4-(F3-O)—Ph | NH | H | NH | H | H | H |
| 5042 | 4-(F3-O)—Ph | NH | H | NH | OH | H | H |
| 5043 | 4-(F3-O)—Ph | NH | H | NH | OA6 | H | H |
| 5044 | 4-(F3-O)—Ph | NH | H | NH | OA8 | H | H |
| 5045 | 4-(F3-O)—Ph | NH | H | NH | OA9 | H | H |
| 5046 | 4-(F3-O)—Ph | NH | H | NH | OA10 | H | H |
| 5047 | 4-(F3-O)—Ph | NH | H | NH | OA12 | H | H |
| 5048 | 4-(F3-O)—Ph | NH | H | NH | OA14 | H | H |
| 5049 | 4-(F3-O)—Ph | NH | H | NH | OA16 | H | H |
| 5050 | 4-(F3-O)—Ph | NH | H | NH | OH | H | A6 |
| 5051 | 4-(F3-O)—Ph | NH | H | NH | OH | H | A8 |
| 5052 | 4-(F3-O)—Ph | NH | H | NH | OH | H | A9 |
| 5053 | 4-(F3-O)—Ph | NH | H | NH | OH | H | A10 |
| 5054 | 4-(F3-O)—Ph | NH | H | NH | OH | H | A12 |
| 5055 | 4-(F3-O)—Ph | NH | H | NH | OH | H | A14 |
| 5056 | 4-(F3-O)—Ph | NH | H | NH | OH | H | A16 |
| 5057 | 4-(F3-O)—Ph | NH | H | NH | OH | A6 | A6 |
| 5058 | 4-(F3-O)—Ph | NH | H | NH | OH | A8 | A8 |
| 5059 | 4-(F3-O)—Ph | NH | H | NH | OH | A10 | A10 |
| 5060 | 4-(F3-O)—Ph | NH | H | NH | OA2 | A2 | A2 |
| 5061 | 4-(F3-O)—Ph | NH | H | NH | OA3 | A3 | A3 |
| 5062 | 4-(F3-O)—Ph | NH | H | NH | OA4 | A4 | A4 |
| 5063 | 4-(F3-O)—Ph | NH | H | NH | OC6 | H | H |
| 5064 | 4-(F3-O)—Ph | NH | H | NH | OC7 | H | H |
| 5065 | 4-(F3-O)—Ph | NH | H | NH | OC8 | H | H |
| 5066 | 4-(F3-O)—Ph | NH | H | NH | OC10 | H | H |
| 5067 | 4-(F3-O)—Ph | NH | H | NH | OC11 | H | H |
| 5068 | 4-(F3-O)—Ph | NH | H | NH | OC12 | H | H |
| 5069 | 4-(F3-O)—Ph | NH | H | NH | OC14 | H | H |
| 5070 | 4-(F3-O)—Ph | NH | H | NH | OC16 | H | H |
| 5071 | 4-(F3-O)—Ph | NH | H | NH | C6CO₃ | H | H |
| 5072 | 4-(F3-O)—Ph | NH | H | NH | C7CO₃ | H | H |
| 5073 | 4-(F3-O)—Ph | NH | H | NH | C8CO₃ | H | H |
| 5074 | 4-(F3-O)—Ph | NH | H | NH | C9CO₃ | H | H |
| 5075 | 4-(F3-O)—Ph | NH | H | NH | C10CO₃ | H | H |
| 5076 | 4-(F3-O)—Ph | NH | H | NH | C12CO₃ | H | H |
| 5077 | 4-(F3-O)—Ph | NH | H | NH | C16CO₃ | H | H |
| 5078 | 4-(F3-O)—Ph | NH | C8 | NH | OH | H | H |
| 5079 | 4-(F3-O)—Ph | NH | C9 | NH | OH | H | H |
| 5080 | 4-(F3-O)—Ph | NH | C10 | NH | OH | H | H |
| 5081 | 4-(F3-O)—Ph | NH | C12 | NH | OH | H | H |
| 5082 | 4-(F3-O)—Ph | NH | C16 | NH | OH | H | H |
| 5083 | 4-(F3-O)—Ph | NH | F1 | NH | OH | H | H |
| 5084 | 4-(F3-O)—Ph | NH | F2 | NH | OH | H | H |
| 5085 | 4-(F3-O)—Ph | NH | F3 | NH | OH | H | H |
| 5086 | 4-(F3-O)—Ph | NH | F4 | NH | OH | H | H |
| 5087 | 4-(F3-O)—Ph | NH | F5 | NH | OH | H | H |
| 5088 | 4-(F3-O)—Ph | NH | F6 | NH | OH | H | H |
| 5089 | 4-(F3-O)—Ph | NH | F7 | NH | OH | H | H |

TABLE 1-continued

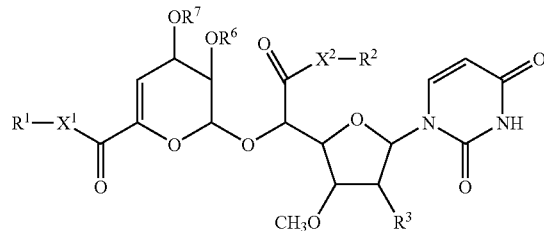

(I-1)

| Exemp. Comp. No. | R¹ | X¹ | R² | X² | R³ | R⁶ | R⁷ |
|---|---|---|---|---|---|---|---|
| 5090 | 4-(F3-O)—Ph | NH | F8 | NH | OH | H | H |
| 5091 | 4-(F3-O)—Ph | NH | F9 | NH | OH | H | H |
| 5092 | 4-(F3-O)—Ph | NH | F10 | NH | OH | H | H |
| 5093 | 4-(F3-O)—Ph | NH | Ph | NH | OH | H | H |
| 5094 | 4-(F3-O)—Ph | NH | Bn | NH | OH | H | H |
| 5095 | 4-(F3-O)—Ph | NH | Pe | NH | OH | H | H |
| 5096 | 4-(F3-O)—Ph | NH | C12 | NMe | OH | H | H |
| 5097 | 4-(F3-O)—Ph | NH | C12 | NEt | OH | H | H |
| 5098 | 4-(F3-O)—Ph | NH | C12 | NPr | OH | H | H |
| 5099 | 4-(F3-O)—Ph | NH | (CH₂)₃ | N | OH | H | H |
| 5100 | 4-(F3-O)—Ph | NH | (CH₂)₄ | N | OH | H | H |
| 5101 | 4-(F3-O)—Ph | NH | (CH₂)₅ | N | OH | H | H |
| 5102 | 4-(F3-O)—Ph | NH | C12 | O | OH | H | H |
| 5103 | 4-(F3-O)—Ph | NH | Ph | O | OH | H | H |
| 5104 | 4-(F3-O)—Ph | NH | C12 | S | OH | H | H |
| 5105 | 4-(F3-O)—Ph | NH | Ph | S | OH | H | H |
| 5106 | 4-(F3-O)—Ph | NMe | H | NH | OH | H | H |
| 5107 | 4-(F3-O)—Ph | NEt | H | NH | OH | H | H |
| 5108 | 4-(F3-O)—Ph | NPr | H | NH | OH | H | H |
| 5109 | 4-(F3-O)—Ph | O | H | NH | OH | H | H |
| 5110 | 4-(F3-O)—Ph | S | H | NH | OH | H | H |
| 5111 | 4-(F7-O)—Ph | NH | H | NH | H | H | H |
| 5112 | 4-(F7-O)—Ph | NH | H | NH | OH | H | H |
| 5113 | 4-(F7-O)—Ph | NH | H | NH | OA6 | H | H |
| 5114 | 4-(F7-O)—Ph | NH | H | NH | OA8 | H | H |
| 5115 | 4-(F7-O)—Ph | NH | H | NH | OA9 | H | H |
| 5116 | 4-(F7-O)—Ph | NH | H | NH | OA10 | H | H |
| 5117 | 4-(F7-O)—Ph | NH | H | NH | OA12 | H | H |
| 5118 | 4-(F7-O)—Ph | NH | H | NH | OA14 | H | H |
| 5119 | 4-(F7-O)—Ph | NH | H | NH | OA16 | H | H |
| 5120 | 4-(F7-O)—Ph | NH | H | NH | OH | H | A6 |
| 5121 | 4-(F7-O)—Ph | NH | H | NH | OH | H | A8 |
| 5122 | 4-(F7-O)—Ph | NH | H | NH | OH | H | A9 |
| 5123 | 4-(F7-O)—Ph | NH | H | NH | OH | H | A10 |
| 5124 | 4-(F7-O)—Ph | NH | H | NH | OH | H | A12 |
| 5125 | 4-(F7-O)—Ph | NH | H | NH | OH | H | A14 |
| 5126 | 4-(F7-O)—Ph | NH | H | NH | OH | H | A16 |
| 5127 | 4-(F7-O)—Ph | NH | H | NH | OH | A6 | A6 |
| 5128 | 4-(F7-O)—Ph | NH | H | NH | OH | A8 | A8 |
| 5129 | 4-(F7-O)—Ph | NH | H | NH | OH | A10 | A10 |
| 5130 | 4-(F7-O)—Ph | NH | H | NH | OA2 | A2 | A2 |
| 5131 | 4-(F7-O)—Ph | NH | H | NH | OA3 | A3 | A3 |
| 5132 | 4-(F7-O)—Ph | NH | H | NH | OA4 | A4 | A4 |
| 5133 | 4-(F7-O)—Ph | NH | H | NH | OC6 | H | H |
| 5134 | 4-(F7-O)—Ph | NH | H | NH | OC7 | H | H |
| 5135 | 4-(F7-O)—Ph | NH | H | NH | OC8 | H | H |
| 5136 | 4-(F7-O)—Ph | NH | H | NH | OC10 | H | H |
| 5137 | 4-(F7-O)—Ph | NH | H | NH | OC11 | H | H |
| 5138 | 4-(F7-O)—Ph | NH | H | NH | OC12 | H | H |
| 5139 | 4-(F7-O)—Ph | NH | H | NH | OC14 | H | H |
| 5140 | 4-(F7-O)—Ph | NH | H | NH | OC16 | H | H |
| 5141 | 4-(F7-O)—Ph | NH | H | NH | C6CO₃ | H | H |
| 5142 | 4-(F7-O)—Ph | NH | H | NH | C7CO₃ | H | H |
| 5143 | 4-(F7-O)—Ph | NH | H | NH | C8CO₃ | H | H |
| 5144 | 4-(F7-O)—Ph | NH | H | NH | C9CO₃ | H | H |
| 5145 | 4-(F7-O)—Ph | NH | H | NH | C10CO₃ | H | H |
| 5146 | 4-(F7-O)—Ph | NH | H | NH | C12CO₃ | H | H |
| 5147 | 4-(F7-O)—Ph | NH | H | NH | C16CO₃ | H | H |
| 5148 | 4-(F7-O)—Ph | NH | C8 | NH | OH | H | H |
| 5149 | 4-(F7-O)—Ph | NH | C9 | NH | OH | H | H |
| 5150 | 4-(F7-O)—Ph | NH | C10 | NH | OH | H | H |
| 5151 | 4-(F7-O)—Ph | NH | C12 | NH | OH | H | H |

TABLE 1-continued (I-1)

| Exemp. Comp. No. | R¹ | X¹ | R² | X² | R³ | R⁶ | R⁷ |
|---|---|---|---|---|---|---|---|
| 5152 | 4-(F7-O)—Ph | NH | C16 | NH | OH | H | H |
| 5153 | 4-(F7-O)—Ph | NH | F1 | NH | OH | H | H |
| 5154 | 4-(F7-O)—Ph | NH | F2 | NH | OH | H | H |
| 5155 | 4-(F7-O)—Ph | NH | F3 | NH | OH | H | H |
| 5156 | 4-(F7-O)—Ph | NH | F4 | NH | OH | H | H |
| 5157 | 4-(F7-O)—Ph | NH | F5 | NH | OH | H | H |
| 5158 | 4-(F7-O)—Ph | NH | F6 | NH | OH | H | H |
| 5159 | 4-(F7-O)—Ph | NH | F7 | NH | OH | H | H |
| 5160 | 4-(F7-O)—Ph | NH | F8 | NH | OH | H | H |
| 5161 | 4-(F7-O)—Ph | NH | F9 | NH | OH | H | H |
| 5162 | 4-(F7-O)—Ph | NH | F10 | NH | OH | H | H |
| 5163 | 4-(F7-O)—Ph | NH | Ph | NH | OH | H | H |
| 5164 | 4-(F7-O)—Ph | NH | Bn | NH | OH | H | H |
| 5165 | 4-(F7-O)—Ph | NH | Pe | NH | OH | H | H |
| 5166 | 4-(F7-O)—Ph | NH | C12 | NMe | OH | H | H |
| 5167 | 4-(F7-O)—Ph | NH | C12 | NEt | OH | H | H |
| 5168 | 4-(F7-O)—Ph | NH | C12 | NPr | OH | H | H |
| 5169 | 4-(F7-O)—Ph | NH | (CH$_2$)$_3$ | N | OH | H | H |
| 5170 | 4-(F7-O)—Ph | NH | (CH$_2$)$_4$ | N | OH | H | H |
| 5171 | 4-(F7-O)—Ph | NH | (CH$_2$)$_5$ | N | OH | H | H |
| 5172 | 4-(F7-O)—Ph | NH | C12 | O | OH | H | H |
| 5173 | 4-(F7-O)—Ph | NH | Ph | O | OH | H | H |
| 5174 | 4-(F7-O)—Ph | NH | C12 | S | OH | H | H |
| 5175 | 4-(F7-O)—Ph | NH | Ph | S | OH | H | H |
| 5176 | 4-(F7-O)—Ph | NMe | H | NH | OH | H | H |
| 5177 | 4-(F7-O)—Ph | NEt | H | NH | OH | H | H |
| 5178 | 4-(F7-O)—Ph | NPr | H | NH | OH | H | H |
| 5179 | 4-(F7-O)—Ph | O | H | NH | OH | H | H |
| 5180 | 4-(F7-O)—Ph | S | H | NH | OH | H | H |
| 5181 | 4-(F8-O)—Ph | NH | H | NH | H | H | H |
| 5182 | 4-(F8-O)—Ph | NH | H | NH | OH | H | H |
| 5183 | 4-(F8-O)—Ph | NH | H | NH | OA6 | H | H |
| 5184 | 4-(F8-O)—Ph | NH | H | NH | OA8 | H | H |
| 5185 | 4-(F8-O)—Ph | NH | H | NH | OA9 | H | H |
| 5186 | 4-(F8-O)—Ph | NH | H | NH | OA10 | H | H |
| 5187 | 4-(F8-O)—Ph | NH | H | NH | OA12 | H | H |
| 5188 | 4-(F8-O)—Ph | NH | H | NH | OA14 | H | H |
| 5189 | 4-(F8-O)—Ph | NH | H | NH | OA16 | H | H |
| 5190 | 4-(F8-O)—Ph | NH | H | NH | OH | H | A6 |
| 5191 | 4-(F8-O)—Ph | NH | H | NH | OH | H | A8 |
| 5192 | 4-(F8-O)—Ph | NH | H | NH | OH | H | A9 |
| 5193 | 4-(F8-O)—Ph | NH | H | NH | OH | H | A10 |
| 5194 | 4-(F8-O)—Ph | NH | H | NH | OH | H | A12 |
| 5195 | 4-(F8-O)—Ph | NH | H | NH | OH | H | A14 |
| 5196 | 4-(F8-O)—Ph | NH | H | NH | OH | H | A16 |
| 5197 | 4-(F8-O)—Ph | NH | H | NH | OH | A6 | A6 |
| 5198 | 4-(F8-O)—Ph | NH | H | NH | OH | A8 | A8 |
| 5199 | 4-(F8-O)—Ph | NH | H | NH | OH | A10 | A10 |
| 5200 | 4-(F8-O)—Ph | NH | H | NH | OA2 | A2 | A2 |
| 5201 | 4-(F8-O)—Ph | NH | H | NH | OA3 | A3 | A3 |
| 5202 | 4-(F8-O)—Ph | NH | H | NH | OA4 | A4 | A4 |
| 5203 | 4-(F8-O)—Ph | NH | H | NH | OC6 | H | H |
| 5204 | 4-(F8-O)—Ph | NH | H | NH | OC7 | H | H |
| 5205 | 4-(F8-O)—Ph | NH | H | NH | OC8 | H | H |
| 5206 | 4-(F8-O)—Ph | NH | H | NH | OC10 | H | H |
| 5207 | 4-(F8-O)—Ph | NH | H | NH | OC11 | H | H |
| 5208 | 4-(F8-O)—Ph | NH | H | NH | OC12 | H | H |
| 5209 | 4-(F8-O)—Ph | NH | H | NH | OC14 | H | H |
| 5210 | 4-(F8-O)—Ph | NH | H | NH | OC16 | H | H |
| 5211 | 4-(F8-O)—Ph | NH | H | NH | C6CO$_3$ | H | H |
| 5212 | 4-(F8-O)—Ph | NH | H | NH | C7CO$_3$ | H | H |
| 5213 | 4-(F8-O)—Ph | NH | H | NH | C8CO$_3$ | H | H |

TABLE 1-continued (I-1)

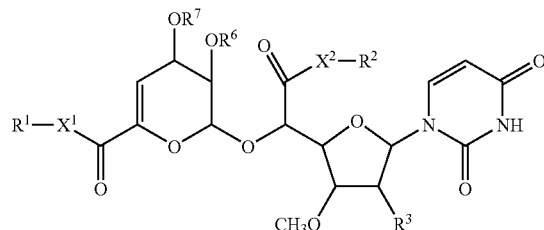

| Exemp. Comp. No. | R¹ | X¹ | R² | X² | R³ | R⁶ | R⁷ |
|---|---|---|---|---|---|---|---|
| 5214 | 4-(F8-O)—Ph | NH | H | NH | C9CO₃ | H | H |
| 5215 | 4-(F8-O)—Ph | NH | H | NH | C10CO₃ | H | H |
| 5216 | 4-(F8-O)—Ph | NH | H | NH | C12CO₃ | H | H |
| 5217 | 4-(F8-O)—Ph | NH | H | NH | C16CO₃ | H | H |
| 5218 | 4-(F8-O)—Ph | NH | C8 | NH | OH | H | H |
| 5219 | 4-(F8-O)—Ph | NH | C9 | NH | OH | H | H |
| 5220 | 4-(F8-O)—Ph | NH | C10 | NH | OH | H | H |
| 5221 | 4-(F8-O)—Ph | NH | C12 | NH | OH | H | H |
| 5222 | 4-(F8-O)—Ph | NH | C16 | NH | OH | H | H |
| 5223 | 4-(F8-O)—Ph | NH | F1 | NH | OH | H | H |
| 5224 | 4-(F8-O)—Ph | NH | F2 | NH | OH | H | H |
| 5225 | 4-(F8-O)—Ph | NH | F3 | NH | OH | H | H |
| 5226 | 4-(F8-O)—Ph | NH | F4 | NH | OH | H | H |
| 5227 | 4-(F8-O)—Ph | NH | F5 | NH | OH | H | H |
| 5228 | 4-(F8-O)—Ph | NH | F6 | NH | OH | H | H |
| 5229 | 4-(F8-O)—Ph | NH | F7 | NH | OH | H | H |
| 5230 | 4-(F8-O)—Ph | NH | F8 | NH | OH | H | H |
| 5231 | 4-(F8-O)—Ph | NH | F9 | NH | OH | H | H |
| 5232 | 4-(F8-O)—Ph | NH | F10 | NH | OH | H | H |
| 5233 | 4-(F8-O)—Ph | NH | Ph | NH | OH | H | H |
| 5234 | 4-(F8-O)—Ph | NH | Bn | NH | OH | H | H |
| 5235 | 4-(F8-O)—Ph | NH | Pe | NH | OH | H | H |
| 5236 | 4-(F8-O)—Ph | NH | C12 | NMe | OH | H | H |
| 5237 | 4-(F8-O)—Ph | NH | C12 | NEt | OH | H | H |
| 5238 | 4-(F8-O)—Ph | NH | C12 | NPr | OH | H | H |
| 5239 | 4-(F8-O)—Ph | NH | (CH₂)₃ | N | OH | H | H |
| 5240 | 4-(F8-O)—Ph | NH | (CH₂)₄ | N | OH | H | H |
| 5241 | 4-(F8-O)—Ph | NH | (CH₂)₅ | N | OH | H | H |
| 5242 | 4-(F8-O)—Ph | NH | C12 | O | OH | H | H |
| 5243 | 4-(F8-O)—Ph | NH | Ph | O | OH | H | H |
| 5244 | 4-(F8-O)—Ph | NH | C12 | S | OH | H | H |
| 5245 | 4-(F8-O)—Ph | NH | Ph | S | OH | H | H |
| 5246 | 4-(F8-O)—Ph | NMe | H | NH | OH | H | H |
| 5247 | 4-(F8-O)—Ph | NEt | H | NH | OH | H | H |
| 5248 | 4-(F8-O)—Ph | NPr | H | NH | OH | H | H |
| 5249 | 4-(F8-O)—Ph | O | H | NH | OH | H | H |
| 5250 | 4-(F8-O)—Ph | S | H | NH | OH | H | H |
| 5251 | 4-(F9-O)—Ph | NH | H | NH | H | H | H |
| 5252 | 4-(F9-O)—Ph | NH | H | NH | OH | H | H |
| 5253 | 4-(F9-O)—Ph | NH | H | NH | OA6 | H | H |
| 5254 | 4-(F9-O)—Ph | NH | H | NH | OA8 | H | H |
| 5255 | 4-(F9-O)—Ph | NH | H | NH | OA9 | H | H |
| 5256 | 4-(F9-O)—Ph | NH | H | NH | OA10 | H | H |
| 5257 | 4-(F9-O)—Ph | NH | H | NH | OA12 | H | H |
| 5258 | 4-(F9-O)—Ph | NH | H | NH | OA14 | H | H |
| 5259 | 4-(F9-O)—Ph | NH | H | NH | OA16 | H | H |
| 5260 | 4-(F9-O)—Ph | NH | H | NH | OH | H | A6 |
| 5261 | 4-(F9-O)—Ph | NH | H | NH | OH | H | A8 |
| 5262 | 4-(F9-O)—Ph | NH | H | NH | OH | H | A9 |
| 5263 | 4-(F9-O)—Ph | NH | H | NH | OH | H | A10 |
| 5264 | 4-(F9-O)—Ph | NH | H | NH | OH | H | A12 |
| 5265 | 4-(F9-O)—Ph | NH | H | NH | OH | H | A14 |
| 5266 | 4-(F9-O)—Ph | NH | H | NH | OH | H | A16 |
| 5267 | 4-(F9-O)—Ph | NH | H | NH | OH | A6 | A6 |
| 5268 | 4-(F9-O)—Ph | NH | H | NH | OH | A8 | A8 |
| 5269 | 4-(F9-O)—Ph | NH | H | NH | OH | A10 | A10 |
| 5270 | 4-(F9-O)—Ph | NH | H | NH | OA2 | A2 | A2 |
| 5271 | 4-(F9-O)—Ph | NH | H | NH | OA3 | A3 | A3 |
| 5272 | 4-(F9-O)—Ph | NH | H | NH | OA4 | A4 | A4 |
| 5273 | 4-(F9-O)—Ph | NH | H | NH | OC6 | H | H |
| 5274 | 4-(F9-O)—Ph | NH | H | NH | OC7 | H | H |
| 5275 | 4-(F9-O)—Ph | NH | H | NH | OC8 | H | H |

TABLE 1-continued (I-1)

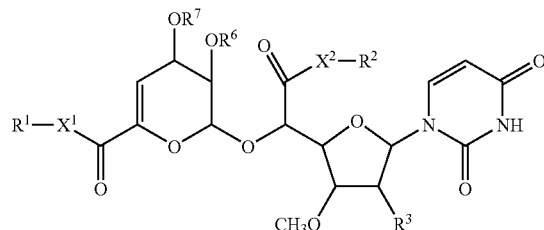

| Exemp. Comp. No. | R¹ | X¹ | R² | X² | R³ | R⁶ | R⁷ |
|---|---|---|---|---|---|---|---|
| 5276 | 4-(F9-O)—Ph | NH | H | NH | OC10 | H | H |
| 5277 | 4-(F9-O)—Ph | NH | H | NH | OC11 | H | H |
| 5278 | 4-(F9-O)—Ph | NH | H | NH | OC12 | H | H |
| 5279 | 4-(F9-O)—Ph | NH | H | NH | OC14 | H | H |
| 5280 | 4-(F9-O)—Ph | NH | H | NH | OC16 | H | H |
| 5281 | 4-(F9-O)—Ph | NH | H | NH | C6CO₃ | H | H |
| 5282 | 4-(F9-O)—Ph | NH | H | NH | C7CO₃ | H | H |
| 5283 | 4-(F9-O)—Ph | NH | H | NH | C8CO₃ | H | H |
| 5284 | 4-(F9-O)—Ph | NH | H | NH | C9CO₃ | H | H |
| 5285 | 4-(F9-O)—Ph | NH | H | NH | C10CO₃ | H | H |
| 5286 | 4-(F9-O)—Ph | NH | H | NH | C12CO₃ | H | H |
| 5287 | 4-(F9-O)—Ph | NH | H | NH | C16CO₃ | H | H |
| 5288 | 4-(F9-O)—Ph | NH | C8 | NH | OH | H | H |
| 5289 | 4-(F9-O)—Ph | NH | C9 | NH | OH | H | H |
| 5290 | 4-(F9-O)—Ph | NH | C10 | NH | OH | H | H |
| 5291 | 4-(F9-O)—Ph | NH | C12 | NH | OH | H | H |
| 5292 | 4-(F9-O)—Ph | NH | C16 | NH | OH | H | H |
| 5293 | 4-(F9-O)—Ph | NH | F1 | NH | OH | H | H |
| 5294 | 4-(F9-O)—Ph | NH | F2 | NH | OH | H | H |
| 5295 | 4-(F9-O)—Ph | NH | F3 | NH | OH | H | H |
| 5296 | 4-(F9-O)—Ph | NH | F4 | NH | OH | H | H |
| 5297 | 4-(F9-O)—Ph | NH | F5 | NH | OH | H | H |
| 5298 | 4-(F9-O)—Ph | NH | F6 | NH | OH | H | H |
| 5299 | 4-(F9-O)—Ph | NH | F7 | NH | OH | H | H |
| 5300 | 4-(F9-O)—Ph | NH | F8 | NH | OH | H | H |
| 5301 | 4-(F9-O)—Ph | NH | F9 | NH | OH | H | H |
| 5302 | 4-(F9-O)—Ph | NH | F10 | NH | OH | H | H |
| 5303 | 4-(F9-O)—Ph | NH | Ph | NH | OH | H | H |
| 5304 | 4-(F9-O)—Ph | NH | Bn | NH | OH | H | H |
| 5305 | 4-(F9-O)—Ph | NH | Pe | NH | OH | H | H |
| 5306 | 4-(F9-O)—Ph | NH | C12 | NMe | OH | H | H |
| 5307 | 4-(F9-O)—Ph | NH | C12 | NEt | OH | H | H |
| 5308 | 4-(F9-O)—Ph | NH | C12 | NPr | OH | H | H |
| 5309 | 4-(F9-O)—Ph | NH | (CH₂)₃ | N | OH | H | H |
| 5310 | 4-(F9-O)—Ph | NH | (CH₂)₄ | N | OH | H | H |
| 5311 | 4-(F9-O)—Ph | NH | (CH₂)₅ | N | OH | H | H |
| 5312 | 4-(F9-O)—Ph | NH | C12 | O | OH | H | H |
| 5313 | 4-(F9-O)—Ph | NH | Ph | O | OH | H | H |
| 5314 | 4-(F9-O)—Ph | NH | C12 | S | OH | H | H |
| 5315 | 4-(F9-O)—Ph | NH | Ph | S | OH | H | H |
| 5316 | 4-(F9-O)—Ph | NMe | H | NH | OH | H | H |
| 5317 | 4-(F9-O)—Ph | NEt | H | NH | OH | H | H |
| 5318 | 4-(F9-O)—Ph | NPr | H | NH | OH | H | H |
| 5319 | 4-(F9-O)—Ph | O | H | NH | OH | H | H |
| 5320 | 4-(F9-O)—Ph | S | H | NH | OH | H | H |
| 5321 | 4-(F11)-Ph | NH | H | NH | H | H | H |
| 5322 | 4-(F11)-Ph | NH | H | NH | OH | H | H |
| 5323 | 4-(F11)-Ph | NH | H | NH | OA6 | H | H |
| 5324 | 4-(F11)-Ph | NH | H | NH | OA8 | H | H |
| 5325 | 4-(F11)-Ph | NH | H | NH | OA9 | H | H |
| 5326 | 4-(F11)-Ph | NH | H | NH | OA10 | H | H |
| 5327 | 4-(F11)-Ph | NH | H | NH | OA12 | H | H |
| 5328 | 4-(F11)-Ph | NH | H | NH | OA14 | H | H |
| 5329 | 4-(F11)-Ph | NH | H | NH | OA16 | H | H |
| 5330 | 4-(F11)-Ph | NH | H | NH | OH | H | A6 |
| 5331 | 4-(F11)-Ph | NH | H | NH | OH | H | A8 |
| 5332 | 4-(F11)-Ph | NH | H | NH | OH | H | A9 |
| 5333 | 4-(F11)-Ph | NH | H | NH | OH | H | A10 |
| 5334 | 4-(F11)-Ph | NH | H | NH | OH | H | A12 |
| 5335 | 4-(F11)-Ph | NH | H | NH | OH | H | A14 |
| 5336 | 4-(F11)-Ph | NH | H | NH | OH | H | A16 |
| 5337 | 4-(F11)-Ph | NH | H | NH | OH | A6 | A6 |

TABLE 1-continued

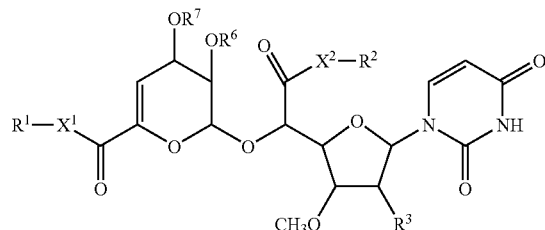

(I-1)

| Exemp. Comp. No. | R¹ | X¹ | R² | X² | R³ | R⁶ | R⁷ |
|---|---|---|---|---|---|---|---|
| 5338 | 4-(F11)-Ph | NH | H | NH | OH | A8 | A8 |
| 5339 | 4-(F11)-Ph | NH | H | NH | OH | A10 | A10 |
| 5340 | 4-(F11)-Ph | NH | H | NH | OA2 | A2 | A2 |
| 5341 | 4-(F11)-Ph | NH | H | NH | OA3 | A3 | A3 |
| 5342 | 4-(F11)-Ph | NH | H | NH | OA4 | A4 | A4 |
| 5343 | 4-(F11)-Ph | NH | H | NH | OC6 | H | H |
| 5344 | 4-(F11)-Ph | NH | H | NH | OC7 | H | H |
| 5345 | 4-(F11)-Ph | NH | H | NH | OC8 | H | H |
| 5346 | 4-(F11)-Ph | NH | H | NH | OC10 | H | H |
| 5347 | 4-(F11)-Ph | NH | H | NH | OC11 | H | H |
| 5348 | 4-(F11)-Ph | NH | H | NH | OC12 | H | H |
| 5349 | 4-(F11)-Ph | NH | H | NH | OC14 | H | H |
| 5350 | 4-(F11)-Ph | NH | H | NH | OC16 | H | H |
| 5351 | 4-(F11)-Ph | NH | H | NH | C6CO$_3$ | H | H |
| 5352 | 4-(F11)-Ph | NH | H | NH | C7CO$_3$ | H | H |
| 5353 | 4-(F11)-Ph | NH | H | NH | C8CO$_3$ | H | H |
| 5354 | 4-(F11)-Ph | NH | H | NH | C9CO$_3$ | H | H |
| 5355 | 4-(F11)-Ph | NH | H | NH | C10CO$_3$ | H | H |
| 5356 | 4-(F11)-Ph | NH | H | NH | C12CO$_3$ | H | H |
| 5357 | 4-(F11)-Ph | NH | H | NH | C16CO$_3$ | H | H |
| 5358 | 4-(F11)-Ph | NH | C8 | NH | OH | H | H |
| 5359 | 4-(F11)-Ph | NH | C9 | NH | OH | H | H |
| 5360 | 4-(F11)-Ph | NH | C10 | NH | OH | H | H |
| 5361 | 4-(F11)-Ph | NH | C12 | NH | OH | H | H |
| 5362 | 4-(F11)-Ph | NH | C16 | NH | OH | H | H |
| 5363 | 4-(F11)-Ph | NH | F1 | NH | OH | H | H |
| 5364 | 4-(F11)-Ph | NH | F2 | NH | OH | H | H |
| 5365 | 4-(F11)-Ph | NH | F3 | NH | OH | H | H |
| 5366 | 4-(F11)-Ph | NH | F4 | NH | OH | H | H |
| 5367 | 4-(F11)-Ph | NH | F5 | NH | OH | H | H |
| 5368 | 4-(F11)-Ph | NH | F6 | NH | OH | H | H |
| 5369 | 4-(F11)-Ph | NH | F7 | NH | OH | H | H |
| 5370 | 4-(F11)-Ph | NH | F8 | NH | OH | H | H |
| 5371 | 4-(F11)-Ph | NH | F9 | NH | OH | H | H |
| 5372 | 4-(F11)-Ph | NH | F10 | NH | OH | H | H |
| 5373 | 4-(F11)-Ph | NH | Ph | NH | OH | H | H |
| 5374 | 4-(F11)-Ph | NH | Bn | NH | OH | H | H |
| 5375 | 4-(F11)-Ph | NH | Pe | NH | OH | H | H |
| 5376 | 4-(F11)-Ph | NH | C12 | NMe | OH | H | H |
| 5377 | 4-(F11)-Ph | NH | C12 | NEt | OH | H | H |
| 5378 | 4-(F11)-Ph | NH | C12 | NPr | OH | H | H |
| 5379 | 4-(F11)-Ph | NH | (CH$_2$)$_3$ | N | OH | H | H |
| 5380 | 4-(F11)-Ph | NH | (CH$_2$)$_4$ | N | OH | H | H |
| 5381 | 4-(F11)-Ph | NH | (CH$_2$)$_5$ | N | OH | H | H |
| 5382 | 4-(F11)-Ph | NH | C12 | O | OH | H | H |
| 5383 | 4-(F11)-Ph | NH | Ph | O | OH | H | H |
| 5384 | 4-(F11)-Ph | NH | C12 | S | OH | H | H |
| 5385 | 4-(F11)-Ph | NH | Ph | S | OH | H | H |
| 5386 | 4-(F11)-Ph | NMe | H | NH | OH | H | H |
| 5387 | 4-(F11)-Ph | NEt | H | NH | OH | H | H |
| 5388 | 4-(F11)-Ph | NPr | H | NH | OH | H | H |
| 5389 | 4-(F11)-Ph | O | H | NH | OH | H | H |
| 5390 | 4-(F11)-Ph | S | H | NH | OH | H | H |
| 5391 | 4-(F12)-Ph | NH | H | NH | H | H | H |
| 5392 | 4-(F12)-Ph | NH | H | NH | OH | H | H |
| 5393 | 4-(F12)-Ph | NH | H | NH | OA6 | H | H |
| 5394 | 4-(F12)-Ph | NH | H | NH | OA8 | H | H |
| 5395 | 4-(F12)-Ph | NH | H | NH | OA9 | H | H |
| 5396 | 4-(F12)-Ph | NH | H | NH | OA10 | H | H |
| 5397 | 4-(F12)-Ph | NH | H | NH | OA12 | H | H |
| 5398 | 4-(F12)-Ph | NH | H | NH | OA14 | H | H |
| 5399 | 4-(F12)-Ph | NH | H | NH | OA16 | H | H |

TABLE 1-continued (I-1)

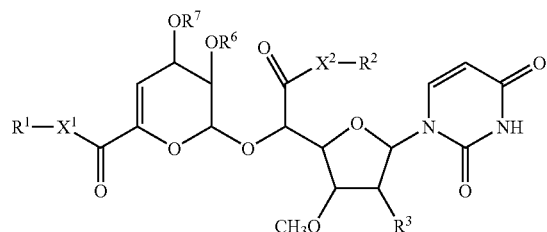

| Exemp. Comp. No. | R¹ | X¹ | R² | X² | R³ | R⁶ | R⁷ |
|---|---|---|---|---|---|---|---|
| 5400 | 4-(F12)-Ph | NH | H | NH | OH | H | A6 |
| 5401 | 4-(F12)-Ph | NH | H | NH | OH | H | A8 |
| 5402 | 4-(F12)-Ph | NH | H | NH | OH | H | A9 |
| 5403 | 4-(F12)-Ph | NH | H | NH | OH | H | A10 |
| 5404 | 4-(F12)-Ph | NH | H | NH | OH | H | A12 |
| 5405 | 4-(F12)-Ph | NH | H | NH | OH | H | A14 |
| 5406 | 4-(F12)-Ph | NH | H | NH | OH | H | A16 |
| 5407 | 4-(F12)-Ph | NH | H | NH | OH | A6 | A6 |
| 5408 | 4-(F12)-Ph | NH | H | NH | OH | A8 | A8 |
| 5409 | 4-(F12)-Ph | NH | H | NH | OH | A10 | A10 |
| 5410 | 4-(F12)-Ph | NH | H | NH | OA2 | A2 | A2 |
| 5411 | 4-(F12)-Ph | NH | H | NH | OA3 | A3 | A3 |
| 5412 | 4-(F12)-Ph | NH | H | NH | OA4 | A4 | A4 |
| 5413 | 4-(F12)-Ph | NH | H | NH | OC6 | H | H |
| 5414 | 4-(F12)-Ph | NH | H | NH | OC7 | H | H |
| 5415 | 4-(F12)-Ph | NH | H | NH | OC8 | H | H |
| 5416 | 4-(F12)-Ph | NH | H | NH | OC10 | H | H |
| 5417 | 4-(F12)-Ph | NH | H | NH | OC11 | H | H |
| 5418 | 4-(F12)-Ph | NH | H | NH | OC12 | H | H |
| 5419 | 4-(F12)-Ph | NH | H | NH | OC14 | H | H |
| 5420 | 4-(F12)-Ph | NH | H | NH | OC16 | H | H |
| 5421 | 4-(F12)-Ph | NH | H | NH | $C6CO_3$ | H | H |
| 5422 | 4-(F12)-Ph | NH | H | NH | $C7CO_3$ | H | H |
| 5423 | 4-(F12)-Ph | NH | H | NH | $C8CO_3$ | H | H |
| 5424 | 4-(F12)-Ph | NH | H | NH | $C9CO_3$ | H | H |
| 5425 | 4-(F12)-Ph | NH | H | NH | $C10CO_3$ | H | H |
| 5426 | 4-(F12)-Ph | NH | H | NH | $C12CO_3$ | H | H |
| 5427 | 4-(F12)-Ph | NH | H | NH | $C16CO_3$ | H | H |
| 5428 | 4-(F12)-Ph | NH | C8 | NH | OH | H | H |
| 5429 | 4-(F12)-Ph | NH | C9 | NH | OH | H | H |
| 5430 | 4-(F12)-Ph | NH | C10 | NH | OH | H | H |
| 5431 | 4-(F12)-Ph | NH | C12 | NH | OH | H | H |
| 5432 | 4-(F12)-Ph | NH | C16 | NH | OH | H | H |
| 5433 | 4-(F12)-Ph | NH | F1 | NH | OH | H | H |
| 5434 | 4-(F12)-Ph | NH | F2 | NH | OH | H | H |
| 5435 | 4-(F12)-Ph | NH | F3 | NH | OH | H | H |
| 5436 | 4-(F12)-Ph | NH | F4 | NH | OH | H | H |
| 5437 | 4-(F12)-Ph | NH | F5 | NH | OH | H | H |
| 5438 | 4-(F12)-Ph | NH | F6 | NH | OH | H | H |
| 5439 | 4-(F12)-Ph | NH | F7 | NH | OH | H | H |
| 5440 | 4-(F12)-Ph | NH | F8 | NH | OH | H | H |
| 5441 | 4-(F12)-Ph | NH | F9 | NH | OH | H | H |
| 5442 | 4-(F12)-Ph | NH | F10 | NH | OH | H | H |
| 5443 | 4-(F12)-Ph | NH | Ph | NH | OH | H | H |
| 5444 | 4-(F12)-Ph | NH | Bn | NH | OH | H | H |
| 5445 | 4-(F12)-Ph | NH | Pe | NH | OH | H | H |
| 5446 | 4-(F12)-Ph | NH | C12 | NMe | OH | H | H |
| 5447 | 4-(F12)-Ph | NH | C12 | NEt | OH | H | H |
| 5448 | 4-(F12)-Ph | NH | C12 | NPr | OH | H | H |
| 5449 | 4-(F12)-Ph | NH | $(CH_2)_3$ | N | OH | H | H |
| 5450 | 4-(F12)-Ph | NH | $(CH_2)_4$ | N | OH | H | H |
| 5451 | 4-(F12)-Ph | NH | $(CH_2)_5$ | N | OH | H | H |
| 5452 | 4-(F12)-Ph | NH | C12 | O | OH | H | H |
| 5453 | 4-(F12)-Ph | NH | Ph | O | OH | H | H |
| 5454 | 4-(F12)-Ph | NH | C12 | S | OH | H | H |
| 5455 | 4-(F12)-Ph | NH | Ph | S | OH | H | H |
| 5456 | 4-(F12)-Ph | NMe | H | NH | OH | H | H |
| 5457 | 4-(F12)-Ph | NEt | H | NH | OH | H | H |
| 5458 | 4-(F12)-Ph | NPr | H | NH | OH | H | H |
| 5459 | 4-(F12)-Ph | O | H | NH | OH | H | H |
| 5460 | 4-(F12)-Ph | S | H | NH | OH | H | H |
| 5461 | 2-$NO_2$—Ph | NH | H | NH | H | H | H |

TABLE 1-continued

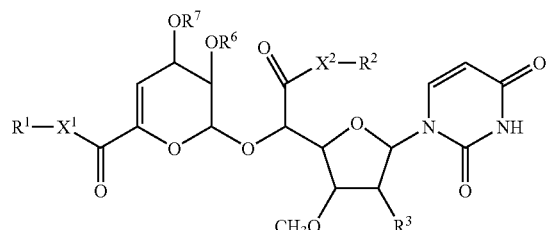

(I-1)

| Exemp. Comp. No. | $R^1$ | $X^1$ | $R^2$ | $X^2$ | $R^3$ | $R^6$ | $R^7$ |
|---|---|---|---|---|---|---|---|
| 5462 | 2-$NO_2$—Ph | NH | H | NH | OH | H | H |
| 5463 | 2-$NO_2$—Ph | NH | H | NH | OA6 | H | H |
| 5464 | 2-$NO_2$—Ph | NH | H | NH | OA8 | H | H |
| 5465 | 2-$NO_2$—Ph | NH | H | NH | OA9 | H | H |
| 5466 | 2-$NO_2$—Ph | NH | H | NH | OA10 | H | H |
| 5467 | 2-$NO_2$—Ph | NH | H | NH | OA12 | H | H |
| 5468 | 2-$NO_2$—Ph | NH | H | NH | OA14 | H | H |
| 5469 | 2-$NO_2$—Ph | NH | H | NH | OA16 | H | H |
| 5470 | 2-$NO_2$—Ph | NH | H | NH | OH | H | A6 |
| 5471 | 2-$NO_2$—Ph | NH | H | NH | OH | H | A8 |
| 5472 | 2-$NO_2$—Ph | NH | H | NH | OH | H | A9 |
| 5473 | 2-$NO_2$—Ph | NH | H | NH | OH | H | A10 |
| 5474 | 2-$NO_2$—Ph | NH | H | NH | OH | H | A12 |
| 5475 | 2-$NO_2$—Ph | NH | H | NH | OH | H | A14 |
| 5476 | 2-$NO_2$—Ph | NH | H | NH | OH | H | A16 |
| 5477 | 2-$NO_2$—Ph | NH | H | NH | OH | A6 | A6 |
| 5478 | 2-$NO_2$—Ph | NH | H | NH | OH | A8 | A8 |
| 5479 | 2-$NO_2$—Ph | NH | H | NH | OH | A10 | A10 |
| 5480 | 2-$NO_2$—Ph | NH | H | NH | OA2 | A2 | A2 |
| 5481 | 2-$NO_2$—Ph | NH | H | NH | OA3 | A3 | A3 |
| 5482 | 2-$NO_2$—Ph | NH | H | NH | OA4 | A4 | A4 |
| 5483 | 2-$NO_2$—Ph | NH | H | NH | OC6 | H | H |
| 5484 | 2-$NO_2$—Ph | NH | H | NH | OC7 | H | H |
| 5485 | 2-$NO_2$—Ph | NH | H | NH | OC8 | H | H |
| 5486 | 2-$NO_2$—Ph | NH | H | NH | OC10 | H | H |
| 5487 | 2-$NO_2$—Ph | NH | H | NH | OC11 | H | H |
| 5488 | 2-$NO_2$—Ph | NH | H | NH | OC12 | H | H |
| 5489 | 2-$NO_2$—Ph | NH | H | NH | OC14 | H | H |
| 5490 | 2-$NO_2$—Ph | NH | H | NH | OC16 | H | H |
| 5491 | 2-$NO_2$—Ph | NH | H | NH | $C6CO_3$ | H | H |
| 5492 | 2-$NO_2$—Ph | NH | H | NH | $C7CO_3$ | H | H |
| 5493 | 2-$NO_2$—Ph | NH | H | NH | $C8CO_3$ | H | H |
| 5494 | 2-$NO_2$—Ph | NH | H | NH | $C9CO_3$ | H | H |
| 5495 | 2-$NO_2$—Ph | NH | H | NH | $C10CO_3$ | H | H |
| 5496 | 2-$NO_2$—Ph | NH | H | NH | $C12CO_3$ | H | H |
| 5497 | 2-$NO_2$—Ph | NH | H | NH | $C16CO_3$ | H | H |
| 5498 | 2-$NO_2$—Ph | NH | C8 | NH | OH | H | H |
| 5499 | 2-$NO_2$—Ph | NH | C9 | NH | OH | H | H |
| 5500 | 2-$NO_2$—Ph | NH | C10 | NH | OH | H | H |
| 5501 | 2-$NO_2$—Ph | NH | C12 | NH | OH | H | H |
| 5502 | 2-$NO_2$—Ph | NH | C16 | NH | OH | H | H |
| 5503 | 2-$NO_2$—Ph | NH | F1 | NH | OH | H | H |
| 5504 | 2-$NO_2$—Ph | NH | F2 | NH | OH | H | H |
| 5505 | 2-$NO_2$—Ph | NH | F3 | NH | OH | H | H |
| 5506 | 2-$NO_2$—Ph | NH | F4 | NH | OH | H | H |
| 5507 | 2-$NO_2$—Ph | NH | F5 | NH | OH | H | H |
| 5508 | 2-$NO_2$—Ph | NH | F6 | NH | OH | H | H |
| 5509 | 2-$NO_2$—Ph | NH | F7 | NH | OH | H | H |
| 5510 | 2-$NO_2$—Ph | NH | F8 | NH | OH | H | H |
| 5511 | 2-$NO_2$—Ph | NH | F9 | NH | OH | H | H |
| 5512 | 2-$NO_2$—Ph | NH | F10 | NH | OH | H | H |
| 5513 | 2-$NO_2$—Ph | NH | Ph | NH | OH | H | H |
| 5514 | 2-$NO_2$—Ph | NH | Bn | NH | OH | H | H |
| 5515 | 2-$NO_2$—Ph | NH | Pe | NH | OH | H | H |
| 5516 | 2-$NO_2$—Ph | NH | C12 | NMe | OH | H | H |
| 5517 | 2-$NO_2$—Ph | NH | C12 | NEt | OH | H | H |
| 5518 | 2-$NO_2$—Ph | NH | C12 | NPr | OH | H | H |
| 5519 | 2-$NO_2$—Ph | NH | $(CH_2)_3$ | N | OH | H | H |
| 5520 | 2-$NO_2$—Ph | NH | $(CH_2)_4$ | N | OH | H | H |
| 5521 | 2-$NO_2$—Ph | NH | $(CH_2)_5$ | N | OH | H | H |
| 5522 | 2-$NO_2$—Ph | NH | C12 | O | OH | H | H |
| 5523 | 2-$NO_2$—Ph | NH | Ph | O | OH | H | H |

TABLE 1-continued (I-1)

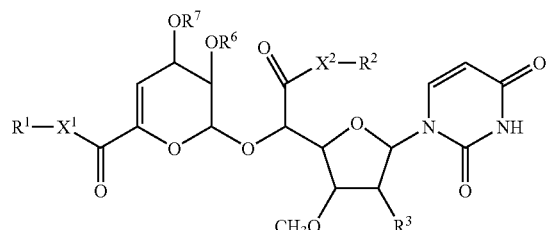

| Exemp. Comp. No. | R¹ | X¹ | R² | X² | R³ | R⁶ | R⁷ |
|---|---|---|---|---|---|---|---|
| 5524 | 2-NO₂—Ph | NH | C12 | S | OH | H | H |
| 5525 | 2-NO₂—Ph | NH | Ph | S | OH | H | H |
| 5526 | 2-NO₂—Ph | NMe | H | NH | OH | H | H |
| 5527 | 2-NO₂—Ph | NEt | H | NH | OH | H | H |
| 5528 | 2-NO₂—Ph | NPr | H | NH | OH | H | H |
| 5529 | 2-NO₂—Ph | O | H | NH | OH | H | H |
| 5530 | 2-NO₂—Ph | S | H | NH | OH | H | H |
| 5531 | 3-NO₂—Ph | NH | H | NH | H | H | H |
| 5532 | 3-NO₂—Ph | NH | H | NH | OH | H | H |
| 5533 | 3-NO₂—Ph | NH | H | NH | OA6 | H | H |
| 5534 | 3-NO₂—Ph | NH | H | NH | OA8 | H | H |
| 5535 | 3-NO₂—Ph | NH | H | NH | OA9 | H | H |
| 5536 | 3-NO₂—Ph | NH | H | NH | OA10 | H | H |
| 5537 | 3-NO₂—Ph | NH | H | NH | OA12 | H | H |
| 5538 | 3-NO₂—Ph | NH | H | NH | OA14 | H | H |
| 5539 | 3-NO₂—Ph | NH | H | NH | OA16 | H | H |
| 5540 | 3-NO₂—Ph | NH | H | NH | OH | H | A6 |
| 5541 | 3-NO₂—Ph | NH | H | NH | OH | H | A8 |
| 5542 | 3-NO₂—Ph | NH | H | NH | OH | H | A9 |
| 5543 | 3-NO₂—Ph | NH | H | NH | OH | H | A10 |
| 5544 | 3-NO₂—Ph | NH | H | NH | OH | H | A12 |
| 5545 | 3-NO₂—Ph | NH | H | NH | OH | H | A14 |
| 5546 | 3-NO₂—Ph | NH | H | NH | OH | H | A16 |
| 5547 | 3-NO₂—Ph | NH | H | NH | OH | A6 | A6 |
| 5548 | 3-NO₂—Ph | NH | H | NH | OH | A8 | A8 |
| 5549 | 3-NO₂—Ph | NH | H | NH | OH | A10 | A10 |
| 5550 | 3-NO₂—Ph | NH | H | NH | OA2 | A2 | A2 |
| 5551 | 3-NO₂—Ph | NH | H | NH | OA3 | A3 | A3 |
| 5552 | 3-NO₂—Ph | NH | H | NH | OA4 | A4 | A4 |
| 5553 | 3-NO₂—Ph | NH | H | NH | OC6 | H | H |
| 5554 | 3-NO₂—Ph | NH | H | NH | OC7 | H | H |
| 5555 | 3-NO₂—Ph | NH | H | NH | OC8 | H | H |
| 5556 | 3-NO₂—Ph | NH | H | NH | OC10 | H | H |
| 5557 | 3-NO₂—Ph | NH | H | NH | OC11 | H | H |
| 5558 | 3-NO₂—Ph | NH | H | NH | OC12 | H | H |
| 5559 | 3-NO₂—Ph | NH | H | NH | OC14 | H | H |
| 5560 | 3-NO₂—Ph | NH | H | NH | OC16 | H | H |
| 5561 | 3-NO₂—Ph | NH | H | NH | C6CO₃ | H | H |
| 5562 | 3-NO₂—Ph | NH | H | NH | C7CO₃ | H | H |
| 5563 | 3-NO₂—Ph | NH | H | NH | C8CO₃ | H | H |
| 5564 | 3-NO₂—Ph | NH | H | NH | C9CO₃ | H | H |
| 5565 | 3-NO₂—Ph | NH | H | NH | C10CO₃ | H | H |
| 5566 | 3-NO₂—Ph | NH | H | NH | C12CO₃ | H | H |
| 5567 | 3-NO₂—Ph | NH | H | NH | C16CO₃ | H | H |
| 5568 | 3-NO₂—Ph | NH | C8 | NH | OH | H | H |
| 5569 | 3-NO₂—Ph | NH | C9 | NH | OH | H | H |
| 5570 | 3-NO₂—Ph | NH | C10 | NH | OH | H | H |
| 5571 | 3-NO₂—Ph | NH | C12 | NH | OH | H | H |
| 5572 | 3-NO₂—Ph | NH | C16 | NH | OH | H | H |
| 5573 | 3-NO₂—Ph | NH | F1 | NH | OH | H | H |
| 5574 | 3-NO₂—Ph | NH | F2 | NH | OH | H | H |
| 5575 | 3-NO₂—Ph | NH | F3 | NH | OH | H | H |
| 5576 | 3-NO₂—Ph | NH | F4 | NH | OH | H | H |
| 5577 | 3-NO₂—Ph | NH | F5 | NH | OH | H | H |
| 5578 | 3-NO₂—Ph | NH | F6 | NH | OH | H | H |
| 5579 | 3-NO₂—Ph | NH | F7 | NH | OH | H | H |
| 5580 | 3-NO₂—Ph | NH | F8 | NH | OH | H | H |
| 5581 | 3-NO₂—Ph | NH | F9 | NH | OH | H | H |
| 5582 | 3-NO₂—Ph | NH | F10 | NH | OH | H | H |
| 5583 | 3-NO₂—Ph | NH | Ph | NH | OH | H | H |
| 5584 | 3-NO₂—Ph | NH | Bn | NH | OH | H | H |
| 5585 | 3-NO₂—Ph | NH | Pe | NH | OH | H | H |

TABLE 1-continued (I-1)

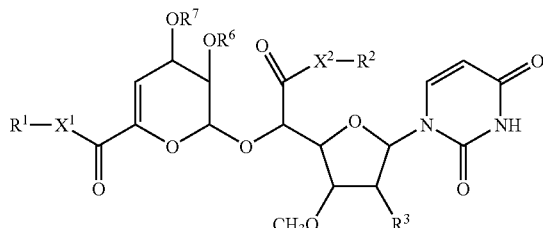

| Exemp. Comp. No. | $R^1$ | $X^1$ | $R^2$ | $X^2$ | $R^3$ | $R^6$ | $R^7$ |
|---|---|---|---|---|---|---|---|
| 5586 | 3-$NO_2$—Ph | NH | C12 | NMe | OH | H | H |
| 5587 | 3-$NO_2$—Ph | NH | C12 | NEt | OH | H | H |
| 5588 | 3-$NO_2$—Ph | NH | C12 | NPr | OH | H | H |
| 5589 | 3-$NO_2$—Ph | NH | $(CH_2)_3$ | N | OH | H | H |
| 5590 | 3-$NO_2$—Ph | NH | $(CH_2)_4$ | N | OH | H | H |
| 5591 | 3-$NO_2$—Ph | NH | $(CH_2)_5$ | N | OH | H | H |
| 5592 | 3-$NO_2$—Ph | NH | C12 | O | OH | H | H |
| 5593 | 3-$NO_2$—Ph | NH | Ph | O | OH | H | H |
| 5594 | 3-$NO_2$—Ph | NH | C12 | S | OH | H | H |
| 5595 | 3-$NO_2$—Ph | NH | Ph | S | OH | H | H |
| 5596 | 3-$NO_2$—Ph | NMe | H | NH | OH | H | H |
| 5597 | 3-$NO_2$—Ph | NEt | H | NH | OH | H | H |
| 5598 | 3-$NO_2$—Ph | NPr | H | NH | OH | H | H |
| 5599 | 3-$NO_2$—Ph | O | H | NH | OH | H | H |
| 5600 | 3-$NO_2$—Ph | S | H | NH | OH | H | H |
| 5601 | 4-$NO_2$—Ph | NH | H | NH | H | H | H |
| 5602 | 4-$NO_2$—Ph | NH | H | NH | OH | H | H |
| 5603 | 4-$NO_2$—Ph | NH | H | NH | OA6 | H | H |
| 5604 | 4-$NO_2$—Ph | NH | H | NH | OA8 | H | H |
| 5605 | 4-$NO_2$—Ph | NH | H | NH | OA9 | H | H |
| 5606 | 4-$NO_2$—Ph | NH | H | NH | OA10 | H | H |
| 5607 | 4-$NO_2$—Ph | NH | H | NH | OA12 | H | H |
| 5608 | 4-$NO_2$—Ph | NH | H | NH | OA14 | H | H |
| 5609 | 4-$NO_2$—Ph | NH | H | NH | OA16 | H | H |
| 5610 | 4-$NO_2$—Ph | NH | H | NH | OH | H | A6 |
| 5611 | 4-$NO_2$—Ph | NH | H | NH | OH | H | A8 |
| 5612 | 4-$NO_2$—Ph | NH | H | NH | OH | H | A9 |
| 5613 | 4-$NO_2$—Ph | NH | H | NH | OH | H | A10 |
| 5614 | 4-$NO_2$—Ph | NH | H | NH | OH | H | A12 |
| 5615 | 4-$NO_2$—Ph | NH | H | NH | OH | H | A14 |
| 5616 | 4-$NO_2$—Ph | NH | H | NH | OH | H | A16 |
| 5617 | 4-$NO_2$—Ph | NH | H | NH | OH | A6 | A6 |
| 5618 | 4-$NO_2$—Ph | NH | H | NH | OH | A8 | A8 |
| 5619 | 4-$NO_2$—Ph | NH | H | NH | OH | A10 | A10 |
| 5620 | 4-$NO_2$—Ph | NH | H | NH | OA2 | A2 | A2 |
| 5621 | 4-$NO_2$—Ph | NH | H | NH | OA3 | A3 | A3 |
| 5622 | 4-$NO_2$—Ph | NH | H | NH | OA4 | A4 | A4 |
| 5623 | 4-$NO_2$—Ph | NH | H | NH | OC6 | H | H |
| 5624 | 4-$NO_2$—Ph | NH | H | NH | OC7 | H | H |
| 5625 | 4-$NO_2$—Ph | NH | H | NH | OC8 | H | H |
| 5626 | 4-$NO_2$—Ph | NH | H | NH | OC10 | H | H |
| 5627 | 4-$NO_2$—Ph | NH | H | NH | OC11 | H | H |
| 5628 | 4-$NO_2$—Ph | NH | H | NH | OC12 | H | H |
| 5629 | 4-$NO_2$—Ph | NH | H | NH | OC14 | H | H |
| 5630 | 4-$NO_2$—Ph | NH | H | NH | OC16 | H | H |
| 5631 | 4-$NO_2$—Ph | NH | H | NH | $C6CO_3$ | H | H |
| 5632 | 4-$NO_2$—Ph | NH | H | NH | $C7CO_3$ | H | H |
| 5633 | 4-$NO_2$—Ph | NH | H | NH | $C8CO_3$ | H | H |
| 5634 | 4-$NO_2$—Ph | NH | H | NH | $C9CO_3$ | H | H |
| 5635 | 4-$NO_2$—Ph | NH | H | NH | $C10CO_3$ | H | H |
| 5636 | 4-$NO_2$—Ph | NH | H | NH | $C12CO_3$ | H | H |
| 5637 | 4-$NO_2$—Ph | NH | H | NH | $C16CO_3$ | H | H |
| 5638 | 4-$NO_2$—Ph | NH | C8 | NH | OH | H | H |
| 5639 | 4-$NO_2$—Ph | NH | C9 | NH | OH | H | H |
| 5640 | 4-$NO_2$—Ph | NH | C10 | NH | OH | H | H |
| 5641 | 4-$NO_2$—Ph | NH | C12 | NH | OH | H | H |
| 5642 | 4-$NO_2$—Ph | NH | C16 | NH | OH | H | H |
| 5643 | 4-$NO_2$—Ph | NH | F1 | NH | OH | H | H |
| 5644 | 4-$NO_2$—Ph | NH | F2 | NH | OH | H | H |
| 5645 | 4-$NO_2$—Ph | NH | F3 | NH | OH | H | H |
| 5646 | 4-$NO_2$—Ph | NH | F4 | NH | OH | H | H |
| 5647 | 4-$NO_2$—Ph | NH | F5 | NH | OH | H | H |

TABLE 1-continued

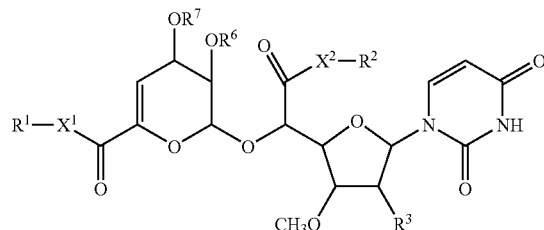

(I-1)

| Exemp. Comp. No. | R¹ | X¹ | R² | X² | R³ | R⁶ | R⁷ |
|---|---|---|---|---|---|---|---|
| 5648 | 4-NO₂—Ph | NH | F6 | NH | OH | H | H |
| 5649 | 4-NO₂—Ph | NH | F7 | NH | OH | H | H |
| 5650 | 4-NO₂—Ph | NH | F8 | NH | OH | H | H |
| 5651 | 4-NO₂—Ph | NH | F9 | NH | OH | H | H |
| 5652 | 4-NO₂—Ph | NH | F10 | NH | OH | H | H |
| 5653 | 4-NO₂—Ph | NH | Ph | NH | OH | H | H |
| 5654 | 4-NO₂—Ph | NH | Bn | NH | OH | H | H |
| 5655 | 4-NO₂—Ph | NH | Pe | NH | OH | H | H |
| 5656 | 4-NO₂—Ph | NH | C12 | NMe | OH | H | H |
| 5657 | 4-NO₂—Ph | NH | C12 | NEt | OH | H | H |
| 5658 | 4-NO₂—Ph | NH | C12 | NPr | OH | H | H |
| 5659 | 4-NO₂—Ph | NH | (CH₂)₃ | N | OH | H | H |
| 5660 | 4-NO₂—Ph | NH | (CH₂)₄ | N | OH | H | H |
| 5661 | 4-NO₂—Ph | NH | (CH₂)₅ | N | OH | H | H |
| 5662 | 4-NO₂—Ph | NH | C12 | O | OH | H | H |
| 5663 | 4-NO₂—Ph | NH | Ph | O | OH | H | H |
| 5664 | 4-NO₂—Ph | NH | C12 | S | OH | H | H |
| 5665 | 4-NO₂—Ph | NH | Ph | S | OH | H | H |
| 5666 | 4-NO₂—Ph | NMe | H | NH | OH | H | H |
| 5667 | 4-NO₂—Ph | NEt | H | NH | OH | H | H |
| 5668 | 4-NO₂—Ph | NPr | H | NH | OH | H | H |
| 5669 | 4-NO₂—Ph | O | H | NH | OH | H | H |
| 5670 | 4-NO₂—Ph | S | H | NH | OH | H | H |
| 5671 | 2-OH—Ph | NH | H | NH | H | H | H |
| 5672 | 2-OH—Ph | NH | H | NH | OH | H | H |
| 5673 | 2-OH—Ph | NH | H | NH | OA6 | H | H |
| 5674 | 2-OH—Ph | NH | H | NH | OA8 | H | H |
| 5675 | 2-OH—Ph | NH | H | NH | OA9 | H | H |
| 5676 | 2-OH—Ph | NH | H | NH | OA10 | H | H |
| 5677 | 2-OH—Ph | NH | H | NH | OA12 | H | H |
| 5678 | 2-OH—Ph | NH | H | NH | OA14 | H | H |
| 5679 | 2-OH—Ph | NH | H | NH | OA16 | H | H |
| 5680 | 2-OH—Ph | NH | H | NH | OH | H | A6 |
| 5681 | 2-OH—Ph | NH | H | NH | OH | H | A8 |
| 5682 | 2-OH—Ph | NH | H | NH | OH | H | A9 |
| 5683 | 2-OH—Ph | NH | H | NH | OH | H | A10 |
| 5684 | 2-OH—Ph | NH | H | NH | OH | H | A12 |
| 5685 | 2-OH—Ph | NH | H | NH | OH | H | A14 |
| 5686 | 2-OH—Ph | NH | H | NH | OH | H | A16 |
| 5687 | 2-OH—Ph | NH | H | NH | OH | A6 | A6 |
| 5688 | 2-OH—Ph | NH | H | NH | OH | A8 | A8 |
| 5689 | 2-OH—Ph | NH | H | NH | OH | A10 | A10 |
| 5690 | 2-OH—Ph | NH | H | NH | OA2 | A2 | A2 |
| 5691 | 2-OH—Ph | NH | H | NH | OA3 | A3 | A3 |
| 5692 | 2-OH—Ph | NH | H | NH | OA4 | A4 | A4 |
| 5693 | 2-OH—Ph | NH | H | NH | OC6 | H | H |
| 5694 | 2-OH—Ph | NH | H | NH | OC7 | H | H |
| 5695 | 2-OH—Ph | NH | H | NH | OC8 | H | H |
| 5696 | 2-OH—Ph | NH | H | NH | OC10 | H | H |
| 5697 | 2-OH—Ph | NH | H | NH | OC11 | H | H |
| 5698 | 2-OH—Ph | NH | H | NH | OC12 | H | H |
| 5699 | 2-OH—Ph | NH | H | NH | OC14 | H | H |
| 5700 | 2-OH—Ph | NH | H | NH | OC16 | H | H |
| 5701 | 2-OH—Ph | NH | H | NH | C6CO₃ | H | H |
| 5702 | 2-OH—Ph | NH | H | NH | C7CO₃ | H | H |
| 5703 | 2-OH—Ph | NH | H | NH | C8CO₃ | H | H |
| 5704 | 2-OH—Ph | NH | H | NH | C9CO₃ | H | H |
| 5705 | 2-OH—Ph | NH | H | NH | C10CO₃ | H | H |
| 5706 | 2-OH—Ph | NH | H | NH | C12CO₃ | H | H |
| 5707 | 2-OH—Ph | NH | H | NH | C16CO₃ | H | H |
| 5708 | 2-OH—Ph | NH | C8 | NH | OH | H | H |
| 5709 | 2-OH—Ph | NH | C9 | NH | OH | H | H |

TABLE 1-continued (I-1)

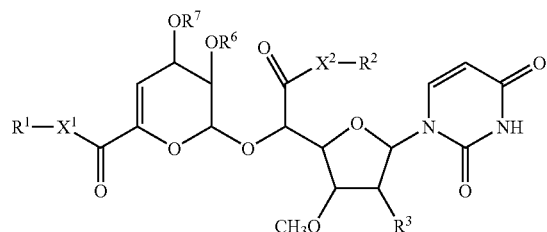

| Exemp. Comp. No. | R¹ | X¹ | R² | X² | R³ | R⁶ | R⁷ |
|---|---|---|---|---|---|---|---|
| 5710 | 2-OH—Ph | NH | C10 | NH | OH | H | H |
| 5711 | 2-OH—Ph | NH | C12 | NH | OH | H | H |
| 5712 | 2-OH—Ph | NH | C16 | NH | OH | H | H |
| 5713 | 2-OH—Ph | NH | F1 | NH | OH | H | H |
| 5714 | 2-OH—Ph | NH | F2 | NH | OH | H | H |
| 5715 | 2-OH—Ph | NH | F3 | NH | OH | H | H |
| 5716 | 2-OH—Ph | NH | F4 | NH | OH | H | H |
| 5717 | 2-OH—Ph | NH | F5 | NH | OH | H | H |
| 5718 | 2-OH—Ph | NH | F6 | NH | OH | H | H |
| 5719 | 2-OH—Ph | NH | F7 | NH | OH | H | H |
| 5720 | 2-OH—Ph | NH | F8 | NH | OH | H | H |
| 5721 | 2-OH—Ph | NH | F9 | NH | OH | H | H |
| 5722 | 2-OH—Ph | NH | F10 | NH | OH | H | H |
| 5723 | 2-OH—Ph | NH | Ph | NH | OH | H | H |
| 5724 | 2-OH—Ph | NH | Bn | NH | OH | H | H |
| 5725 | 2-OH—Ph | NH | Pe | NH | OH | H | H |
| 5726 | 2-OH—Ph | NH | C12 | NMe | OH | H | H |
| 5727 | 2-OH—Ph | NH | C12 | NEt | OH | H | H |
| 5728 | 2-OH—Ph | NH | C12 | NPr | OH | H | H |
| 5729 | 2-OH—Ph | NH | $(CH_2)_3$ | N | OH | H | H |
| 5730 | 2-OH—Ph | NH | $(CH_2)_4$ | N | OH | H | H |
| 5731 | 2-OH—Ph | NH | $(CH_2)_5$ | N | OH | H | H |
| 5732 | 2-OH—Ph | NH | C12 | O | OH | H | H |
| 5733 | 2-OH—Ph | NH | Ph | O | OH | H | H |
| 5734 | 2-OH—Ph | NH | C12 | S | OH | H | H |
| 5735 | 2-OH—Ph | NH | Ph | S | OH | H | H |
| 5736 | 2-OH—Ph | NMe | H | NH | OH | H | H |
| 5737 | 2-OH—Ph | NEt | H | NH | OH | H | H |
| 5738 | 2-OH—Ph | NPr | H | NH | OH | H | H |
| 5739 | 2-OH—Ph | O | H | NH | OH | H | H |
| 5740 | 2-OH—Ph | S | H | NH | OH | H | H |
| 5741 | 3-OH—Ph | NH | H | NH | H | H | H |
| 5742 | 3-OH—Ph | NH | H | NH | OH | H | H |
| 5743 | 3-OH—Ph | NH | H | NH | OA6 | H | H |
| 5744 | 3-OH—Ph | NH | H | NH | OA8 | H | H |
| 5745 | 3-OH—Ph | NH | H | NH | OA9 | H | H |
| 5746 | 3-OH—Ph | NH | H | NH | OA10 | H | H |
| 5747 | 3-OH—Ph | NH | H | NH | OA12 | H | H |
| 5748 | 3-OH—Ph | NH | H | NH | OA14 | H | H |
| 5749 | 3-OH—Ph | NH | H | NH | OA16 | H | H |
| 5750 | 3-OH—Ph | NH | H | NH | OH | H | A6 |
| 5751 | 3-OH—Ph | NH | H | NH | OH | H | A8 |
| 5752 | 3-OH—Ph | NH | H | NH | OH | H | A9 |
| 5753 | 3-OH—Ph | NH | H | NH | OH | H | A10 |
| 5754 | 3-OH—Ph | NH | H | NH | OH | H | A12 |
| 5755 | 3-OH—Ph | NH | H | NH | OH | H | A14 |
| 5756 | 3-OH—Ph | NH | H | NH | OH | H | A16 |
| 5757 | 3-OH—Ph | NH | H | NH | OH | A6 | A6 |
| 5758 | 3-OH—Ph | NH | H | NH | OH | A8 | A8 |
| 5759 | 3-OH—Ph | NH | H | NH | OH | A10 | A10 |
| 5760 | 3-OH—Ph | NH | H | NH | OA2 | A2 | A2 |
| 5761 | 3-OH—Ph | NH | H | NH | OA3 | A3 | A3 |
| 5762 | 3-OH—Ph | NH | H | NH | OA4 | A4 | A4 |
| 5763 | 3-OH—Ph | NH | H | NH | OC6 | H | H |
| 5764 | 3-OH—Ph | NH | H | NH | OC7 | H | H |
| 5765 | 3-OH—Ph | NH | H | NH | OC8 | H | H |
| 5766 | 3-OH—Ph | NH | H | NH | OC10 | H | H |
| 5767 | 3-OH—Ph | NH | H | NH | OC11 | H | H |
| 5768 | 3-OH—Ph | NH | H | NH | OC12 | H | H |
| 5769 | 3-OH—Ph | NH | H | NH | OC14 | H | H |
| 5770 | 3-OH—Ph | NH | H | NH | OC16 | H | H |
| 5771 | 3-OH—Ph | NH | H | NH | $C6CO_3$ | H | H |

TABLE 1-continued (I-1)

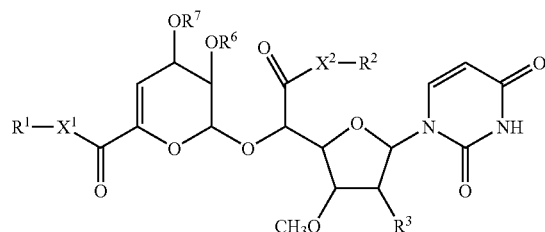

| Exemp. Comp. No. | R$^1$ | X$^1$ | R$^2$ | X$^2$ | R$^3$ | R$^6$ | R$^7$ |
|---|---|---|---|---|---|---|---|
| 5772 | 3-OH—Ph | NH | H | NH | C7CO$_3$ | H | H |
| 5773 | 3-OH—Ph | NH | H | NH | C8CO$_3$ | H | H |
| 5774 | 3-OH—Ph | NH | H | NH | C9CO$_3$ | H | H |
| 5775 | 3-OH—Ph | NH | H | NH | C10CO$_3$ | H | H |
| 5776 | 3-OH—Ph | NH | H | NH | C12CO$_3$ | H | H |
| 5777 | 3-OH—Ph | NH | H | NH | C16CO$_3$ | H | H |
| 5778 | 3-OH—Ph | NH | C8 | NH | OH | H | H |
| 5779 | 3-OH—Ph | NH | C9 | NH | OH | H | H |
| 5780 | 3-OH—Ph | NH | C10 | NH | OH | H | H |
| 5781 | 3-OH—Ph | NH | C12 | NH | OH | H | H |
| 5782 | 3-OH—Ph | NH | C16 | NH | OH | H | H |
| 5783 | 3-OH—Ph | NH | F1 | NH | OH | H | H |
| 5784 | 3-OH—Ph | NH | F2 | NH | OH | H | H |
| 5785 | 3-OH—Ph | NH | F3 | NH | OH | H | H |
| 5786 | 3-OH—Ph | NH | F4 | NH | OH | H | H |
| 5787 | 3-OH—Ph | NH | F5 | NH | OH | H | H |
| 5788 | 3-OH—Ph | NH | F6 | NH | OH | H | H |
| 5789 | 3-OH—Ph | NH | F7 | NH | OH | H | H |
| 5790 | 3-OH—Ph | NH | F8 | NH | OH | H | H |
| 5791 | 3-OH—Ph | NH | F9 | NH | OH | H | H |
| 5792 | 3-OH—Ph | NH | F10 | NH | OH | H | H |
| 5793 | 3-OH—Ph | NH | Ph | NH | OH | H | H |
| 5794 | 3-OH—Ph | NH | Bn | NH | OH | H | H |
| 5795 | 3-OH—Ph | NH | Pe | NH | OH | H | H |
| 5796 | 3-OH—Ph | NH | C12 | NMe | OH | H | H |
| 5797 | 3-OH—Ph | NH | C12 | NEt | OH | H | H |
| 5798 | 3-OH—Ph | NH | C12 | NPr | OH | H | H |
| 5799 | 3-OH—Ph | NH | (CH$_2$)$_3$ | N | OH | H | H |
| 5800 | 3-OH—Ph | NH | (CH$_2$)$_4$ | N | OH | H | H |
| 5801 | 3-OH—Ph | NH | (CH$_2$)$_5$ | N | OH | H | H |
| 5802 | 3-OH—Ph | NH | C12 | O | OH | H | H |
| 5803 | 3-OH—Ph | NH | Ph | O | OH | H | H |
| 5804 | 3-OH—Ph | NH | C12 | S | OH | H | H |
| 5805 | 3-OH—Ph | NH | Ph | S | OH | H | H |
| 5806 | 3-OH—Ph | NMe | H | NH | OH | H | H |
| 5807 | 3-OH—Ph | NEt | H | NH | OH | H | H |
| 5808 | 3-OH—Ph | NPr | H | NH | OH | H | H |
| 5809 | 3-OH—Ph | O | H | NH | OH | H | H |
| 5810 | 3-OH—Ph | S | H | NH | OH | H | H |
| 5811 | 4-OH—Ph | NH | H | NH | H | H | H |
| 5812 | 4-OH—Ph | NH | H | NH | OH | H | H |
| 5813 | 4-OH—Ph | NH | H | NH | OA6 | H | H |
| 5814 | 4-OH—Ph | NH | H | NH | OA8 | H | H |
| 5815 | 4-OH—Ph | NH | H | NH | OA9 | H | H |
| 5816 | 4-OH—Ph | NH | H | NH | OA10 | H | H |
| 5817 | 4-OH—Ph | NH | H | NH | OA12 | H | H |
| 5818 | 4-OH—Ph | NH | H | NH | OA14 | H | H |
| 5819 | 4-OH—Ph | NH | H | NH | OA16 | H | H |
| 5820 | 4-OH—Ph | NH | H | NH | OH | H | A6 |
| 5821 | 4-OH—Ph | NH | H | NH | OH | H | A8 |
| 5822 | 4-OH—Ph | NH | H | NH | OH | H | A9 |
| 5823 | 4-OH—Ph | NH | H | NH | OH | H | A10 |
| 5824 | 4-OH—Ph | NH | H | NH | OH | H | A12 |
| 5825 | 4-OH—Ph | NH | H | NH | OH | H | A14 |
| 5826 | 4-OH—Ph | NH | H | NH | OH | H | A16 |
| 5827 | 4-OH—Ph | NH | H | NH | OH | A6 | A6 |
| 5828 | 4-OH—Ph | NH | H | NH | OH | A8 | A8 |
| 5829 | 4-OH—Ph | NH | H | NH | OH | A10 | A10 |
| 5830 | 4-OH—Ph | NH | H | NH | OA2 | A2 | A2 |
| 5831 | 4-OH—Ph | NH | H | NH | OA3 | A3 | A3 |
| 5832 | 4-OH—Ph | NH | H | NH | OA4 | A4 | A4 |
| 5833 | 4-OH—Ph | NH | H | NH | OC6 | H | H |

TABLE 1-continued

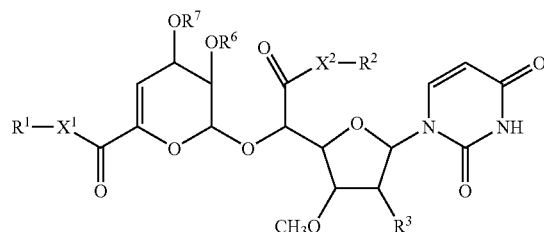

(I-1)

| Exemp. Comp. No. | R¹ | X¹ | R² | X² | R³ | R⁶ | R⁷ |
|---|---|---|---|---|---|---|---|
| 5834 | 4-OH—Ph | NH | H | NH | OC7 | H | H |
| 5835 | 4-OH—Ph | NH | H | NH | OC8 | H | H |
| 5836 | 4-OH—Ph | NH | H | NH | OC10 | H | H |
| 5837 | 4-OH—Ph | NH | H | NH | OC11 | H | H |
| 5838 | 4-OH—Ph | NH | H | NH | OC12 | H | H |
| 5839 | 4-OH—Ph | NH | H | NH | OC14 | H | H |
| 5840 | 4-OH—Ph | NH | H | NH | OC16 | H | H |
| 5841 | 4-OH—Ph | NH | H | NH | C6CO₃ | H | H |
| 5842 | 4-OH—Ph | NH | H | NH | C7CO₃ | H | H |
| 5843 | 4-OH—Ph | NH | H | NH | C8CO₃ | H | H |
| 5844 | 4-OH—Ph | NH | H | NH | C9CO₃ | H | H |
| 5845 | 4-OH—Ph | NH | H | NH | C10CO₃ | H | H |
| 5846 | 4-OH—Ph | NH | H | NH | C12CO₃ | H | H |
| 5847 | 4-OH—Ph | NH | H | NH | C16CO₃ | H | H |
| 5848 | 4-OH—Ph | NH | C8 | NH | OH | H | H |
| 5849 | 4-OH—Ph | NH | C9 | NH | OH | H | H |
| 5850 | 4-OH—Ph | NH | C10 | NH | OH | H | H |
| 5851 | 4-OH—Ph | NH | C12 | NH | OH | H | H |
| 5852 | 4-OH—Ph | NH | C16 | NH | OH | H | H |
| 5853 | 4-OH—Ph | NH | F1 | NH | OH | H | H |
| 5854 | 4-OH—Ph | NH | F2 | NH | OH | H | H |
| 5855 | 4-OH—Ph | NH | F3 | NH | OH | H | H |
| 5856 | 4-OH—Ph | NH | F4 | NH | OH | H | H |
| 5857 | 4-OH—Ph | NH | F5 | NH | OH | H | H |
| 5858 | 4-OH—Ph | NH | F6 | NH | OH | H | H |
| 5859 | 4-OH—Ph | NH | F7 | NH | OH | H | H |
| 5860 | 4-OH—Ph | NH | F8 | NH | OH | H | H |
| 5861 | 4-OH—Ph | NH | F9 | NH | OH | H | H |
| 5862 | 4-OH—Ph | NH | F10 | NH | OH | H | H |
| 5863 | 4-OH—Ph | NH | Ph | NH | OH | H | H |
| 5864 | 4-OH—Ph | NH | Bn | NH | OH | H | H |
| 5865 | 4-OH—Ph | NH | Pe | NH | OH | H | H |
| 5866 | 4-OH—Ph | NH | C12 | NMe | OH | H | H |
| 5867 | 4-OH—Ph | NH | C12 | NEt | OH | H | H |
| 5868 | 4-OH—Ph | NH | C12 | NPr | OH | H | H |
| 5869 | 4-OH—Ph | NH | (CH₂)₃ | N | OH | H | H |
| 5870 | 4-OH—Ph | NH | (CH₂)₄ | N | OH | H | H |
| 5871 | 4-OH—Ph | NH | (CH₂)₅ | N | OH | H | H |
| 5872 | 4-OH—Ph | NH | C12 | O | OH | H | H |
| 5873 | 4-OH—Ph | NH | Ph | O | OH | H | H |
| 5874 | 4-OH—Ph | NH | C12 | S | OH | H | H |
| 5875 | 4-OH—Ph | NH | Ph | S | OH | H | H |
| 5876 | 4-OH—Ph | NMe | H | NH | OH | H | H |
| 5877 | 4-OH—Ph | NEt | H | NH | OH | H | H |
| 5878 | 4-OH—Ph | NPr | H | NH | OH | H | H |
| 5879 | 4-OH—Ph | O | H | NH | OH | H | H |
| 5880 | 4-OH—Ph | S | H | NH | OH | H | H |
| 5881 | 4-Mor-Ph | NH | H | NH | H | H | H |
| 5882 | 4-Mor-Ph | NH | H | NH | OH | H | H |
| 5883 | 4-Mor-Ph | NH | H | NH | OA6 | H | H |
| 5884 | 4-Mor-Ph | NH | H | NH | OA8 | H | H |
| 5885 | 4-Mor-Ph | NH | H | NH | OA9 | H | H |
| 5886 | 4-Mor-Ph | NH | H | NH | OA10 | H | H |
| 5887 | 4-Mor-Ph | NH | H | NH | OA12 | H | H |
| 5888 | 4-Mor-Ph | NH | H | NH | OA14 | H | H |
| 5889 | 4-Mor-Ph | NH | H | NH | OA16 | H | H |
| 5890 | 4-Mor-Ph | NH | H | NH | OH | H | A6 |
| 5891 | 4-Mor-Ph | NH | H | NH | OH | H | A8 |
| 5892 | 4-Mor-Ph | NH | H | NH | OH | H | A9 |
| 5893 | 4-Mor-Ph | NH | H | NH | OH | H | A10 |
| 5894 | 4-Mor-Ph | NH | H | NH | OH | H | A12 |
| 5895 | 4-Mor-Ph | NH | H | NH | OH | H | A14 |

TABLE 1-continued (I-1)

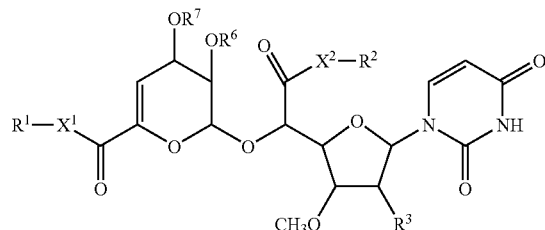

| Exemp. Comp. No. | R¹ | X¹ | R² | X² | R³ | R⁶ | R⁷ |
|---|---|---|---|---|---|---|---|
| 5896 | 4-Mor-Ph | NH | H | NH | OH | H | A16 |
| 5897 | 4-Mor-Ph | NH | H | NH | OH | A6 | A6 |
| 5898 | 4-Mor-Ph | NH | H | NH | OH | A8 | A8 |
| 5899 | 4-Mor-Ph | NH | H | NH | OH | A10 | A10 |
| 5900 | 4-Mor-Ph | NH | H | NH | OA2 | A2 | A2 |
| 5901 | 4-Mor-Ph | NH | H | NH | OA3 | A3 | A3 |
| 5902 | 4-Mor-Ph | NH | H | NH | OA4 | A4 | A4 |
| 5903 | 4-Mor-Ph | NH | H | NH | OC6 | H | H |
| 5904 | 4-Mor-Ph | NH | H | NH | OC7 | H | H |
| 5905 | 4-Mor-Ph | NH | H | NH | OC8 | H | H |
| 5906 | 4-Mor-Ph | NH | H | NH | OC10 | H | H |
| 5907 | 4-Mor-Ph | NH | H | NH | OC11 | H | H |
| 5908 | 4-Mor-Ph | NH | H | NH | OC12 | H | H |
| 5909 | 4-Mor-Ph | NH | H | NH | OC14 | H | H |
| 5910 | 4-Mor-Ph | NH | H | NH | OC16 | H | H |
| 5911 | 4-Mor-Ph | NH | H | NH | C6CO₃ | H | H |
| 5912 | 4-Mor-Ph | NH | H | NH | C7CO₃ | H | H |
| 5913 | 4-Mor-Ph | NH | H | NH | C8CO₃ | H | H |
| 5914 | 4-Mor-Ph | NH | H | NH | C9CO₃ | H | H |
| 5915 | 4-Mor-Ph | NH | H | NH | C10CO₃ | H | H |
| 5916 | 4-Mor-Ph | NH | H | NH | C12CO₃ | H | H |
| 5917 | 4-Mor-Ph | NH | H | NH | C16CO₃ | H | H |
| 5918 | 4-Mor-Ph | NH | C8 | NH | OH | H | H |
| 5919 | 4-Mor-Ph | NH | C9 | NH | OH | H | H |
| 5920 | 4-Mor-Ph | NH | C10 | NH | OH | H | H |
| 5921 | 4-Mor-Ph | NH | C12 | NH | OH | H | H |
| 5922 | 4-Mor-Ph | NH | C16 | NH | OH | H | H |
| 5923 | 4-Mor-Ph | NH | F1 | NH | OH | H | H |
| 5924 | 4-Mor-Ph | NH | F2 | NH | OH | H | H |
| 5925 | 4-Mor-Ph | NH | F3 | NH | OH | H | H |
| 5926 | 4-Mor-Ph | NH | F4 | NH | OH | H | H |
| 5927 | 4-Mor-Ph | NH | F5 | NH | OH | H | H |
| 5928 | 4-Mor-Ph | NH | F6 | NH | OH | H | H |
| 5929 | 4-Mor-Ph | NH | F7 | NH | OH | H | H |
| 5930 | 4-Mor-Ph | NH | F8 | NH | OH | H | H |
| 5931 | 4-Mor-Ph | NH | F9 | NH | OH | H | H |
| 5932 | 4-Mor-Ph | NH | F10 | NH | OH | H | H |
| 5933 | 4-Mor-Ph | NH | Ph | NH | OH | H | H |
| 5934 | 4-Mor-Ph | NH | Bn | NH | OH | H | H |
| 5935 | 4-Mor-Ph | NH | Pe | NH | OH | H | H |
| 5936 | 4-Mor-Ph | NH | C12 | NMe | OH | H | H |
| 5937 | 4-Mor-Ph | NH | C12 | NEt | OH | H | H |
| 5938 | 4-Mor-Ph | NH | C12 | NPr | OH | H | H |
| 5939 | 4-Mor-Ph | NH | (CH₂)₃ | N | OH | H | H |
| 5940 | 4-Mor-Ph | NH | (CH₂)₄ | N | OH | H | H |
| 5941 | 4-Mor-Ph | NH | (CH₂)₅ | N | OH | H | H |
| 5942 | 4-Mor-Ph | NH | C12 | O | OH | H | H |
| 5943 | 4-Mor-Ph | NH | Ph | O | OH | H | H |
| 5944 | 4-Mor-Ph | NH | C12 | S | OH | H | H |
| 5945 | 4-Mor-Ph | NH | Ph | S | OH | H | H |
| 5946 | 4-Mor-Ph | NMe | H | NH | OH | H | H |
| 5947 | 4-Mor-Ph | NEt | H | NH | OH | H | H |
| 5948 | 4-Mor-Ph | NPr | H | NH | OH | H | H |
| 5949 | 4-Mor-Ph | O | H | NH | OH | H | H |
| 5950 | 4-Mor-Ph | S | H | NH | OH | H | H |
| 5951 | 4-PA—Ph | NH | H | NH | H | H | H |
| 5952 | 4-PA—Ph | NH | H | NH | OH | H | H |
| 5953 | 4-PA—Ph | NH | H | NH | OA6 | H | H |
| 5954 | 4-PA—Ph | NH | H | NH | OA8 | H | H |
| 5955 | 4-PA—Ph | NH | H | NH | OA9 | H | H |
| 5956 | 4-PA—Ph | NH | H | NH | OA10 | H | H |
| 5957 | 4-PA—Ph | NH | H | NH | OA12 | H | H |

TABLE 1-continued (I-1)

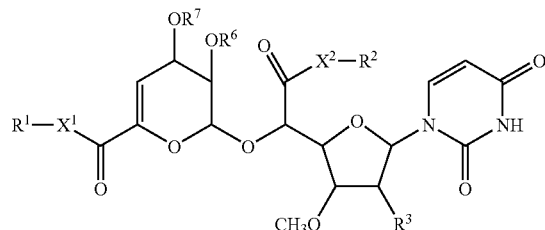

| Exemp. Comp. No. | R¹ | X¹ | R² | X² | R³ | R⁶ | R⁷ |
|---|---|---|---|---|---|---|---|
| 5958 | 4-PA—Ph | NH | H | NH | OA14 | H | H |
| 5959 | 4-PA—Ph | NH | H | NH | OA16 | H | H |
| 5960 | 4-PA—Ph | NH | H | NH | OH | H | A6 |
| 5961 | 4-PA—Ph | NH | H | NH | OH | H | A8 |
| 5962 | 4-PA—Ph | NH | H | NH | OH | H | A9 |
| 5963 | 4-PA—Ph | NH | H | NH | OH | H | A10 |
| 5964 | 4-PA—Ph | NH | H | NH | OH | H | A12 |
| 5965 | 4-PA—Ph | NH | H | NH | OH | H | A14 |
| 5966 | 4-PA—Ph | NH | H | NH | OH | H | A16 |
| 5967 | 4-PA—Ph | NH | H | NH | OH | A6 | A6 |
| 5968 | 4-PA—Ph | NH | H | NH | OH | A8 | A8 |
| 5969 | 4-PA—Ph | NH | H | NH | OH | A10 | A10 |
| 5970 | 4-PA—Ph | NH | H | NH | OA2 | A2 | A2 |
| 5971 | 4-PA—Ph | NH | H | NH | OA3 | A3 | A3 |
| 5972 | 4-PA—Ph | NH | H | NH | OA4 | A4 | A4 |
| 5973 | 4-PA—Ph | NH | H | NH | OC6 | H | H |
| 5974 | 4-PA—Ph | NH | H | NH | OC7 | H | H |
| 5975 | 4-PA—Ph | NH | H | NH | OC8 | H | H |
| 5976 | 4-PA—Ph | NH | H | NH | OC10 | H | H |
| 5977 | 4-PA—Ph | NH | H | NH | OC11 | H | H |
| 5978 | 4-PA—Ph | NH | H | NH | OC12 | H | H |
| 5979 | 4-PA—Ph | NH | H | NH | OC14 | H | H |
| 5980 | 4-PA—Ph | NH | H | NH | OC16 | H | H |
| 5981 | 4-PA—Ph | NH | H | NH | C6CO₃ | H | H |
| 5982 | 4-PA—Ph | NH | H | NH | C7CO₃ | H | H |
| 5983 | 4-PA—Ph | NH | H | NH | C8CO₃ | H | H |
| 5984 | 4-PA—Ph | NH | H | NH | C9CO₃ | H | H |
| 5985 | 4-PA—Ph | NH | H | NH | C10CO₃ | H | H |
| 5986 | 4-PA—Ph | NH | H | NH | C12CO₃ | H | H |
| 5987 | 4-PA—Ph | NH | H | NH | C16CO₃ | H | H |
| 5988 | 4-PA—Ph | NH | C8 | NH | OH | H | H |
| 5989 | 4-PA—Ph | NH | C9 | NH | OH | H | H |
| 5990 | 4-PA—Ph | NH | C10 | NH | OH | H | H |
| 5991 | 4-PA—Ph | NH | C12 | NH | OH | H | H |
| 5992 | 4-PA—Ph | NH | C16 | NH | OH | H | H |
| 5993 | 4-PA—Ph | NH | F1 | NH | OH | H | H |
| 5994 | 4-PA—Ph | NH | F2 | NH | OH | H | H |
| 5995 | 4-PA—Ph | NH | F3 | NH | OH | H | H |
| 5996 | 4-PA—Ph | NH | F4 | NH | OH | H | H |
| 5997 | 4-PA—Ph | NH | F5 | NH | OH | H | H |
| 5998 | 4-PA—Ph | NH | F6 | NH | OH | H | H |
| 5999 | 4-PA—Ph | NH | F7 | NH | OH | H | H |
| 6000 | 4-PA—Ph | NH | F8 | NH | OH | H | H |
| 6001 | 4-PA—Ph | NH | F9 | NH | OH | H | H |
| 6002 | 4-PA—Ph | NH | F10 | NH | OH | H | H |
| 6003 | 4-PA—Ph | NH | Ph | NH | OH | H | H |
| 6004 | 4-PA—Ph | NH | Bn | NH | OH | H | H |
| 6005 | 4-PA—Ph | NH | Pe | NH | OH | H | H |
| 6006 | 4-PA—Ph | NH | C12 | NMe | OH | H | H |
| 6007 | 4-PA—Ph | NH | C12 | NEt | OH | H | H |
| 6008 | 4-PA—Ph | NH | C12 | NPr | OH | H | H |
| 6009 | 4-PA—Ph | NH | (CH₂)₃ | N | OH | H | H |
| 6010 | 4-PA—Ph | NH | (CH₂)₄ | N | OH | H | H |
| 6011 | 4-PA—Ph | NH | (CH₂)₅ | N | OH | H | H |
| 6012 | 4-PA—Ph | NH | C12 | O | OH | H | H |
| 6013 | 4-PA—Ph | NH | Ph | O | OH | H | H |
| 6014 | 4-PA—Ph | NH | C12 | S | OH | H | H |
| 6015 | 4-PA—Ph | NH | Ph | S | OH | H | H |
| 6016 | 4-PA—Ph | NMe | H | NH | OH | H | H |
| 6017 | 4-PA—Ph | NEt | H | NH | OH | H | H |
| 6018 | 4-PA—Ph | NPr | H | NH | OH | H | H |
| 6019 | 4-PA—Ph | O | H | NH | OH | H | H |

TABLE 1-continued (I-1)

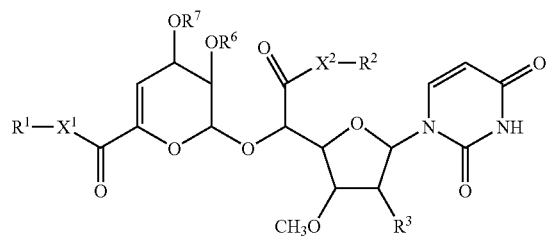

| Exemp. Comp. No. | R¹ | X¹ | R² | X² | R³ | R⁶ | R⁷ |
|---|---|---|---|---|---|---|---|
| 6020 | 4-PA—Ph | S | H | NH | OH | H | H |
| 6021 | 3-CN—Ph | NH | H | NH | H | H | H |
| 6022 | 3-CN—Ph | NH | H | NH | OH | H | H |
| 6023 | 3-CN—Ph | NH | H | NH | OA6 | H | H |
| 6024 | 3-CN—Ph | NH | H | NH | OA8 | H | H |
| 6025 | 3-CN—Ph | NH | H | NH | OA9 | H | H |
| 6026 | 3-CN—Ph | NH | H | NH | OA10 | H | H |
| 6027 | 3-CN—Ph | NH | H | NH | OA12 | H | H |
| 6028 | 3-CN—Ph | NH | H | NH | OA14 | H | H |
| 6029 | 3-CN—Ph | NH | H | NH | OA16 | H | H |
| 6030 | 3-CN—Ph | NH | H | NH | OH | H | A6 |
| 6031 | 3-CN—Ph | NH | H | NH | OH | H | A8 |
| 6032 | 3-CN—Ph | NH | H | NH | OH | H | A9 |
| 6033 | 3-CN—Ph | NH | H | NH | OH | H | A10 |
| 6034 | 3-CN—Ph | NH | H | NH | OH | H | A12 |
| 6035 | 3-CN—Ph | NH | H | NH | OH | H | A14 |
| 6036 | 3-CN—Ph | NH | H | NH | OH | H | A16 |
| 6037 | 3-CN—Ph | NH | H | NH | OH | A6 | A6 |
| 6038 | 3-CN—Ph | NH | H | NH | OH | A8 | A8 |
| 6039 | 3-CN—Ph | NH | H | NH | OH | A10 | A10 |
| 6040 | 3-CN—Ph | NH | H | NH | OA2 | A2 | A2 |
| 6041 | 3-CN—Ph | NH | H | NH | OA3 | A3 | A3 |
| 6042 | 3-CN—Ph | NH | H | NH | OA4 | A4 | A4 |
| 6043 | 3-CN—Ph | NH | H | NH | OC6 | H | H |
| 6044 | 3-CN—Ph | NH | H | NH | OC7 | H | H |
| 6045 | 3-CN—Ph | NH | H | NH | OC8 | H | H |
| 6046 | 3-CN—Ph | NH | H | NH | OC10 | H | H |
| 6047 | 3-CN—Ph | NH | H | NH | OC11 | H | H |
| 6048 | 3-CN—Ph | NH | H | NH | OC12 | H | H |
| 6049 | 3-CN—Ph | NH | H | NH | OC14 | H | H |
| 6050 | 3-CN—Ph | NH | H | NH | OC16 | H | H |
| 6051 | 3-CN—Ph | NH | H | NH | C6CO$_3$ | H | H |
| 6052 | 3-CN—Ph | NH | H | NH | C7CO$_3$ | H | H |
| 6053 | 3-CN—Ph | NH | H | NH | C8CO$_3$ | H | H |
| 6054 | 3-CN—Ph | NH | H | NH | C9CO$_3$ | H | H |
| 6055 | 3-CN—Ph | NH | H | NH | C10CO$_3$ | H | H |
| 6056 | 3-CN—Ph | NH | H | NH | C12CO$_3$ | H | H |
| 6057 | 3-CN—Ph | NH | H | NH | C16CO$_3$ | H | H |
| 6058 | 3-CN—Ph | NH | C8 | NH | OH | H | H |
| 6059 | 3-CN—Ph | NH | C9 | NH | OH | H | H |
| 6060 | 3-CN—Ph | NH | C10 | NH | OH | H | H |
| 6061 | 3-CN—Ph | NH | C12 | NH | OH | H | H |
| 6062 | 3-CN—Ph | NH | C16 | NH | OH | H | H |
| 6063 | 3-CN—Ph | NH | F1 | NH | OH | H | H |
| 6064 | 3-CN—Ph | NH | F2 | NH | OH | H | H |
| 6065 | 3-CN—Ph | NH | F3 | NH | OH | H | H |
| 6066 | 3-CN—Ph | NH | F4 | NH | OH | H | H |
| 6067 | 3-CN—Ph | NH | F5 | NH | OH | H | H |
| 6068 | 3-CN—Ph | NH | F6 | NH | OH | H | H |
| 6069 | 3-CN—Ph | NH | F7 | NH | OH | H | H |
| 6070 | 3-CN—Ph | NH | F8 | NH | OH | H | H |
| 6071 | 3-CN—Ph | NH | F9 | NH | OH | H | H |
| 6072 | 3-CN—Ph | NH | F10 | NH | OH | H | H |
| 6073 | 3-CN—Ph | NH | Ph | NH | OH | H | H |
| 6074 | 3-CN—Ph | NH | Bn | NH | OH | H | H |
| 6075 | 3-CN—Ph | NH | Pe | NH | OH | H | H |
| 6076 | 3-CN—Ph | NH | C12 | NMe | OH | H | H |
| 6077 | 3-CN—Ph | NH | C12 | NEt | OH | H | H |
| 6078 | 3-CN—Ph | NH | C12 | NPr | OH | H | H |
| 6079 | 3-CN—Ph | NH | (CH$_2$)$_3$ | N | OH | H | H |
| 6080 | 3-CN—Ph | NH | (CH$_2$)$_4$ | N | OH | H | H |
| 6081 | 3-CN—Ph | NH | (CH$_2$)$_5$ | N | OH | H | H |

TABLE 1-continued (I-1)

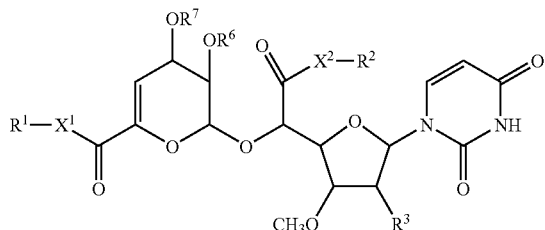

| Exemp. Comp. No. | $R^1$ | $X^1$ | $R^2$ | $X^2$ | $R^3$ | $R^6$ | $R^7$ |
|---|---|---|---|---|---|---|---|
| 6082 | 3-CN—Ph | NH | C12 | O | OH | H | H |
| 6083 | 3-CN—Ph | NH | Ph | O | OH | H | H |
| 6084 | 3-CN—Ph | NH | C12 | S | OH | H | H |
| 6085 | 3-CN—Ph | NH | Ph | S | OH | H | H |
| 6086 | 3-CN—Ph | NMe | H | NH | OH | H | H |
| 6087 | 3-CN—Ph | NEt | H | NH | OH | H | H |
| 6088 | 3-CN—Ph | NPr | H | NH | OH | H | H |
| 6089 | 3-CN—Ph | O | H | NH | OH | H | H |
| 6090 | 3-CN—Ph | S | H | NH | OH | H | H |
| 6091 | F1 | NH | H | NH | H | H | H |
| 6092 | F1 | NH | H | NH | OH | H | H |
| 6093 | F1 | NH | H | NH | OA6 | H | H |
| 6094 | F1 | NH | H | NH | OA8 | H | H |
| 6095 | F1 | NH | H | NH | OA9 | H | H |
| 6096 | F1 | NH | H | NH | OA10 | H | H |
| 6097 | F1 | NH | H | NH | OA12 | H | H |
| 6098 | F1 | NH | H | NH | OA14 | H | H |
| 6099 | F1 | NH | H | NH | OA16 | H | H |
| 6100 | F1 | NH | H | NH | OH | H | A6 |
| 6101 | F1 | NH | H | NH | OH | H | A8 |
| 6102 | F1 | NH | H | NH | OH | H | A9 |
| 6103 | F1 | NH | H | NH | OH | H | A10 |
| 6104 | F1 | NH | H | NH | OH | H | A12 |
| 6105 | F1 | NH | H | NH | OH | H | A14 |
| 6106 | F1 | NH | H | NH | OH | H | A16 |
| 6107 | F1 | NH | H | NH | OH | A6 | A6 |
| 6108 | F1 | NH | H | NH | OH | A8 | A8 |
| 6109 | F1 | NH | H | NH | OH | A10 | A10 |
| 6110 | F1 | NH | H | NH | OA2 | A2 | A2 |
| 6111 | F1 | NH | H | NH | OA3 | A3 | A3 |
| 6112 | F1 | NH | H | NH | OA4 | A4 | A4 |
| 6113 | F1 | NH | H | NH | OC6 | H | H |
| 6114 | F1 | NH | H | NH | OC7 | H | H |
| 6115 | F1 | NH | H | NH | OC8 | H | H |
| 6116 | F1 | NH | H | NH | OC10 | H | H |
| 6117 | F1 | NH | H | NH | OC11 | H | H |
| 6118 | F1 | NH | H | NH | OC12 | H | H |
| 6119 | F1 | NH | H | NH | OC14 | H | H |
| 6120 | F1 | NH | H | NH | OC16 | H | H |
| 6121 | F1 | NH | H | NH | C6CO$_3$ | H | H |
| 6122 | F1 | NH | H | NH | C7CO$_3$ | H | H |
| 6123 | F1 | NH | H | NH | C8CO$_3$ | H | H |
| 6124 | F1 | NH | H | NH | C9CO$_3$ | H | H |
| 6125 | F1 | NH | H | NH | C10CO$_3$ | H | H |
| 6126 | F1 | NH | H | NH | C12CO$_3$ | H | H |
| 6127 | F1 | NH | H | NH | C16CO$_3$ | H | H |
| 6128 | F1 | NH | C8 | NH | OH | H | H |
| 6129 | F1 | NH | C9 | NH | OH | H | H |
| 6130 | F1 | NH | C10 | NH | OH | H | H |
| 6131 | F1 | NH | C12 | NH | OH | H | H |
| 6132 | F1 | NH | C16 | NH | OH | H | H |
| 6133 | F1 | NH | F1 | NH | OH | H | H |
| 6134 | F1 | NH | F2 | NH | OH | H | H |
| 6135 | F1 | NH | F3 | NH | OH | H | H |
| 6136 | F1 | NH | F4 | NH | OH | H | H |
| 6137 | F1 | NH | F5 | NH | OH | H | H |
| 6138 | F1 | NH | F6 | NH | OH | H | H |
| 6139 | F1 | NH | F7 | NH | OH | H | H |
| 6140 | F1 | NH | F8 | NH | OH | H | H |
| 6141 | F1 | NH | F9 | NH | OH | H | H |
| 6142 | F1 | NH | F10 | NH | OH | H | H |
| 6143 | F1 | NH | Ph | NH | OH | H | H |

TABLE 1-continued (I-1)

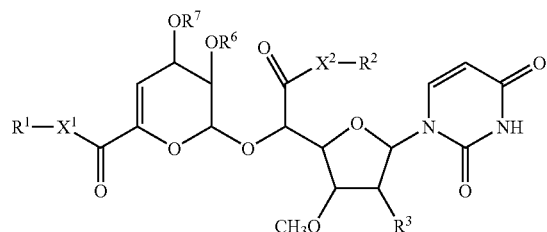

| Exemp. Comp. No. | R¹ | X¹ | R² | X² | R³ | R⁶ | R⁷ |
|---|---|---|---|---|---|---|---|
| 6144 | F1 | NH | Bn | NH | OH | H | H |
| 6145 | F1 | NH | Pe | NH | OH | H | H |
| 6146 | F1 | NH | C12 | NMe | OH | H | H |
| 6147 | F1 | NH | C12 | NEt | OH | H | H |
| 6148 | F1 | NH | C12 | NPr | OH | H | H |
| 6149 | F1 | NH | (CH₂)₃ | N | OH | H | H |
| 6150 | F1 | NH | (CH₂)₄ | N | OH | H | H |
| 6151 | F1 | NH | (CH₂)₅ | N | OH | H | H |
| 6152 | F1 | NH | C12 | O | OH | H | H |
| 6153 | F1 | NH | Ph | O | OH | H | H |
| 6154 | F1 | NH | C12 | S | OH | H | H |
| 6155 | F1 | NH | Ph | S | OH | H | H |
| 6156 | F1 | NMe | H | NH | OH | H | H |
| 6157 | F1 | NEt | H | NH | OH | H | H |
| 6158 | F1 | NPr | H | NH | OH | H | H |
| 6159 | F1 | O | H | NH | OH | H | H |
| 6160 | F1 | S | H | NH | OH | H | H |
| 6161 | F7 | NH | H | NH | H | H | H |
| 6162 | F7 | NH | H | NH | OH | H | H |
| 6163 | F7 | NH | H | NH | OA6 | H | H |
| 6164 | F7 | NH | H | NH | OA8 | H | H |
| 6165 | F7 | NH | H | NH | OA9 | H | H |
| 6166 | F7 | NH | H | NH | OA10 | H | H |
| 6167 | F7 | NH | H | NH | OA12 | H | H |
| 6168 | F7 | NH | H | NH | OA14 | H | H |
| 6169 | F7 | NH | H | NH | OA16 | H | H |
| 6170 | F7 | NH | H | NH | OH | H | A6 |
| 6171 | F7 | NH | H | NH | OH | H | A8 |
| 6172 | F7 | NH | H | NH | OH | H | A9 |
| 6173 | F7 | NH | H | NH | OH | H | A10 |
| 6174 | F7 | NH | H | NH | OH | H | A12 |
| 6175 | F7 | NH | H | NH | OH | H | A14 |
| 6176 | F7 | NH | H | NH | OH | H | A16 |
| 6177 | F7 | NH | H | NH | OH | A6 | A6 |
| 6178 | F7 | NH | H | NH | OH | A8 | A8 |
| 6179 | F7 | NH | H | NH | OH | A10 | A10 |
| 6180 | F7 | NH | H | NH | OA2 | A2 | A2 |
| 6181 | F7 | NH | H | NH | OA3 | A3 | A3 |
| 6182 | F7 | NH | H | NH | OA4 | A4 | A4 |
| 6183 | F7 | NH | H | NH | OC6 | H | H |
| 6184 | F7 | NH | H | NH | OC7 | H | H |
| 6185 | F7 | NH | H | NH | OC8 | H | H |
| 6186 | F7 | NH | H | NH | OC10 | H | H |
| 6187 | F7 | NH | H | NH | OC11 | H | H |
| 6188 | F7 | NH | H | NH | OC12 | H | H |
| 6189 | F7 | NH | H | NH | OC14 | H | H |
| 6190 | F7 | NH | H | NH | OC16 | H | H |
| 6191 | F7 | NH | H | NH | C6CO₃ | H | H |
| 6192 | F7 | NH | H | NH | C7CO₃ | H | H |
| 6193 | F7 | NH | H | NH | C8CO₃ | H | H |
| 6194 | F7 | NH | H | NH | C9CO₃ | H | H |
| 6195 | F7 | NH | H | NH | C10CO₃ | H | H |
| 6196 | F7 | NH | H | NH | C12CO₃ | H | H |
| 6197 | F7 | NH | H | NH | C16CO₃ | H | H |
| 6198 | F7 | NH | C8 | NH | OH | H | H |
| 6199 | F7 | NH | C9 | NH | OH | H | H |
| 6200 | F7 | NH | C10 | NH | OH | H | H |
| 6201 | F7 | NH | C12 | NH | OH | H | H |
| 6202 | F7 | NH | C16 | NH | OH | H | H |
| 6203 | F7 | NH | F1 | NH | OH | H | H |
| 6204 | F7 | NH | F2 | NH | OH | H | H |
| 6205 | F7 | NH | F3 | NH | OH | H | H |

TABLE 1-continued

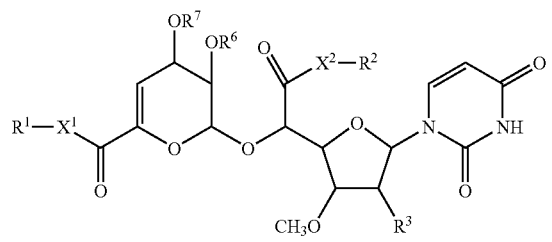

(I-1)

| Exemp. Comp. No. | R¹ | X¹ | R² | X² | R³ | R⁶ | R⁷ |
|---|---|---|---|---|---|---|---|
| 6206 | F7 | NH | F4 | NH | OH | H | H |
| 6207 | F7 | NH | F5 | NH | OH | H | H |
| 6208 | F7 | NH | F6 | NH | OH | H | H |
| 6209 | F7 | NH | F7 | NH | OH | H | H |
| 6210 | F7 | NH | F8 | NH | OH | H | H |
| 6211 | F7 | NH | F9 | NH | OH | H | H |
| 6212 | F7 | NH | F10 | NH | OH | H | H |
| 6213 | F7 | NH | Ph | NH | OH | H | H |
| 6214 | F7 | NH | Bn | NH | OH | H | H |
| 6215 | F7 | NH | Pe | NH | OH | H | H |
| 6216 | F7 | NH | C12 | NMe | OH | H | H |
| 6217 | F7 | NH | C12 | NEt | OH | H | H |
| 6218 | F7 | NH | C12 | NPr | OH | H | H |
| 6219 | F7 | NH | (CH$_2$)$_3$ | N | OH | H | H |
| 6220 | F7 | NH | (CH$_2$)$_4$ | N | OH | H | H |
| 6221 | F7 | NH | (CH$_2$)$_5$ | N | OH | H | H |
| 6222 | F7 | NH | C12 | O | OH | H | H |
| 6223 | F7 | NH | Ph | O | OH | H | H |
| 6224 | F7 | NH | C12 | S | OH | H | H |
| 6225 | F7 | NH | Ph | S | OH | H | H |
| 6226 | F7 | NMe | H | NH | OH | H | H |
| 6227 | F7 | NEt | H | NH | OH | H | H |
| 6228 | F7 | NPr | H | NH | OH | H | H |
| 6229 | F7 | O | H | NH | OH | H | H |
| 6230 | F7 | S | H | NH | OH | H | H |
| 6231 | F10 | NH | H | NH | H | H | H |
| 6232 | F10 | NH | H | NH | OH | H | H |
| 6233 | F10 | NH | H | NH | OA6 | H | H |
| 6234 | F10 | NH | H | NH | OA8 | H | H |
| 6235 | F10 | NH | H | NH | OA9 | H | H |
| 6236 | F10 | NH | H | NH | OA10 | H | H |
| 6237 | F10 | NH | H | NH | OA12 | H | H |
| 6238 | F10 | NH | H | NH | OA14 | H | H |
| 6239 | F10 | NH | H | NH | OA16 | H | H |
| 6240 | F10 | NH | H | NH | OH | H | A6 |
| 6241 | F10 | NH | H | NH | OH | H | A8 |
| 6242 | F10 | NH | H | NH | OH | H | A9 |
| 6243 | F10 | NH | H | NH | OH | H | A10 |
| 6244 | F10 | NH | H | NH | OH | H | A12 |
| 6245 | F10 | NH | H | NH | OH | H | A14 |
| 6246 | F10 | NH | H | NH | OH | H | A16 |
| 6247 | F10 | NH | H | NH | OH | A6 | A6 |
| 6248 | F10 | NH | H | NH | OH | A8 | A8 |
| 6249 | F10 | NH | H | NH | OH | A10 | A10 |
| 6250 | F10 | NH | H | NH | OA2 | A2 | A2 |
| 6251 | F10 | NH | H | NH | OA3 | A3 | A3 |
| 6252 | F10 | NH | H | NH | OA4 | A4 | A4 |
| 6253 | F10 | NH | H | NH | OC6 | H | H |
| 6254 | F10 | NH | H | NH | OC7 | H | H |
| 6255 | F10 | NH | H | NH | OC8 | H | H |
| 6256 | F10 | NH | H | NH | OC10 | H | H |
| 6257 | F10 | NH | H | NH | OC11 | H | H |
| 6258 | F10 | NH | H | NH | OC12 | H | H |
| 6259 | F10 | NH | H | NH | OC14 | H | H |
| 6260 | F10 | NH | H | NH | OC16 | H | H |
| 6261 | F10 | NH | H | NH | C6CO$_3$ | H | H |
| 6262 | F10 | NH | H | NH | C7CO$_3$ | H | H |
| 6263 | F10 | NH | H | NH | C8CO$_3$ | H | H |
| 6264 | F10 | NH | H | NH | C9CO$_3$ | H | H |
| 6265 | F10 | NH | H | NH | C10CO$_3$ | H | H |
| 6266 | F10 | NH | H | NH | C12CO$_3$ | H | H |
| 6267 | F10 | NH | H | NH | C16CO$_3$ | H | H |

TABLE 1-continued

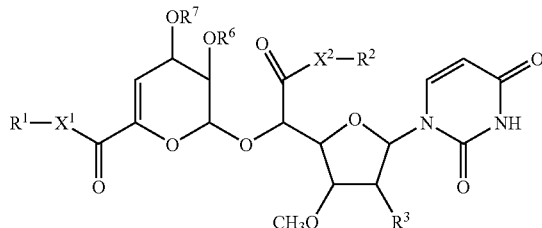

(I-1)

| Exemp. Comp. No. | $R^1$ | $X^1$ | $R^2$ | $X^2$ | $R^3$ | $R^6$ | $R^7$ |
|---|---|---|---|---|---|---|---|
| 6268 | F10 | NH | C8 | NH | OH | H | H |
| 6269 | F10 | NH | C9 | NH | OH | H | H |
| 6270 | F10 | NH | C10 | NH | OH | H | H |
| 6271 | F10 | NH | C12 | NH | OH | H | H |
| 6272 | F10 | NH | C16 | NH | OH | H | H |
| 6273 | F10 | NH | F1 | NH | OH | H | H |
| 6274 | F10 | NH | F2 | NH | OH | H | H |
| 6275 | F10 | NH | F3 | NH | OH | H | H |
| 6276 | F10 | NH | F4 | NH | OH | H | H |

TABLE 2

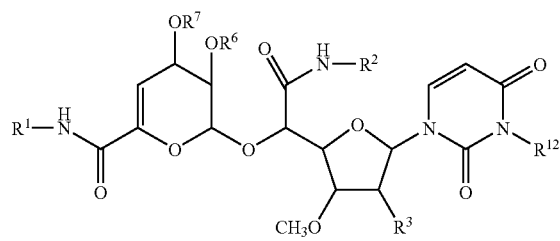

(I-2)

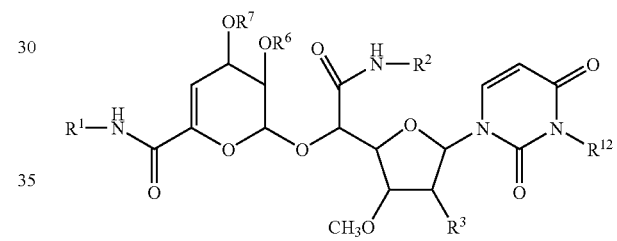

(I-2)

| Exemp. Comp. No. | $R^1$ | $R^2$ | $R^3$ | $R^6$ | $R^7$ | $R^{12}$ | Exemp. Comp. No. | $R^1$ | $R^2$ | $R^3$ | $R^6$ | $R^7$ | $R^{12}$ |
|---|---|---|---|---|---|---|---|---|---|---|---|---|---|
| 6632 | 3-NH$_2$—Ph | H | H | H | H | H | 6662 | 3-NH$_2$—Ph | H | OC14 | H | H | H |
| 6633 | 3-NH$_2$—Ph | H | OH | H | H | H | 6663 | 3-NH$_2$—Ph | H | OC16 | H | H | H |
| 6634 | 3-NH$_2$—Ph | H | OA6 | H | H | H | 6664 | 4-Me$_2$N—Ph | H | H | H | H | H |
| 6635 | 3-NH$_2$—Ph | H | OA8 | H | H | H | 6665 | 4-Me$_2$N—Ph | H | OH | H | H | H |
| 6636 | 3-NH$_2$—Ph | H | OA9 | H | H | H | 6666 | 4-Me$_2$N—Ph | H | OA6 | H | H | H |
| 6637 | 3-NH$_2$—Ph | H | OA10 | H | H | H | 6667 | 4-Me$_2$N—Ph | H | OA8 | H | H | H |
| 6638 | 3-NH$_2$—Ph | H | OA12 | H | H | H | 6668 | 4-Me$_2$N—Ph | H | OA9 | H | H | H |
| 6639 | 3-NH$_2$—Ph | H | OA14 | H | H | H | 6669 | 4-Me$_2$N—Ph | H | OA10 | H | H | H |
| 6640 | 3-NH$_2$—Ph | H | OA16 | H | H | H | 6670 | 4-Me$_2$N—Ph | H | OA12 | H | H | H |
| 6641 | 3-NH$_2$—Ph | H | OH | H | A6 | H | 6671 | 4-Me$_2$N—Ph | H | OA14 | H | H | H |
| 6642 | 3-NH$_2$—Ph | H | OH | H | A8 | H | 6672 | 4-Me$_2$N—Ph | H | OA16 | H | H | H |
| 6643 | 3-NH$_2$—Ph | H | OH | H | A9 | H | 6673 | 4-Me$_2$N—Ph | H | OH | H | A6 | H |
| 6644 | 3-NH$_2$—Ph | H | OH | H | A10 | H | 6674 | 4-Me$_2$N—Ph | H | OH | H | A8 | H |
| 6645 | 3-NH$_2$—Ph | H | OH | H | A12 | H | 6675 | 4-Me$_2$N—Ph | H | OH | H | A9 | H |
| 6646 | 3-NH$_2$—Ph | H | OH | H | A14 | H | 6676 | 4-Me$_2$N—Ph | H | OH | H | A10 | H |
| 6647 | 3-NH$_2$—Ph | H | OH | H | A16 | H | 6677 | 4-Me$_2$N—Ph | H | OH | H | A12 | H |
| 6648 | 3-NH$_2$—Ph | H | OH | A6 | A6 | H | 6678 | 4-Me$_2$N—Ph | H | OH | H | A14 | H |
| 6649 | 3-NH$_2$—Ph | H | OH | A8 | A8 | H | 6679 | 4-Me$_2$N—Ph | H | OH | H | A16 | H |
| 6650 | 3-NH$_2$—Ph | H | OH | A10 | A10 | H | 6680 | 4-Me$_2$N—Ph | H | OH | A6 | A6 | H |
| 6651 | 3-NH$_2$—Ph | C8 | OH | H | H | H | 6681 | 4-Me$_2$N—Ph | H | OH | A8 | A8 | H |
| 6652 | 3-NH$_2$—Ph | C9 | OH | H | H | H | 6682 | 4-Me$_2$N—Ph | H | OH | A10 | A10 | H |
| 6653 | 3-NH$_2$—Ph | C10 | OH | H | H | H | 6683 | 4-Me$_2$N—Ph | C8 | OH | H | H | H |
| 6654 | 3-NH$_2$—Ph | C12 | OH | H | H | H | 6684 | 4-Me$_2$N—Ph | C9 | OH | H | H | H |
| 6655 | 3-NH$_2$—Ph | C16 | OH | H | H | H | 6685 | 4-Me$_2$N—Ph | C10 | OH | H | H | H |
| 6656 | 3-NH$_2$—Ph | H | OC6 | H | H | H | 6686 | 4-Me$_2$N—Ph | C12 | OH | H | H | H |
| 6657 | 3-NH$_2$—Ph | H | OC7 | H | H | H | 6687 | 4-Me$_2$N—Ph | C16 | OH | H | H | H |
| 6658 | 3-NH$_2$—Ph | H | OC8 | H | H | H | 6688 | 4-Me$_2$N—Ph | H | OC6 | H | H | H |
| 6659 | 3-NH$_2$—Ph | H | OC10 | H | H | H | 6689 | 4-Me$_2$N—Ph | H | OC7 | H | H | H |
| 6660 | 3-NH$_2$—Ph | H | OC11 | H | H | H | 6690 | 4-Me$_2$N—Ph | H | OC8 | H | H | H |
| 6661 | 3-NH$_2$—Ph | H | OC12 | H | H | H | 6691 | 4-Me$_2$N—Ph | H | OC10 | H | H | H |

TABLE 2-continued

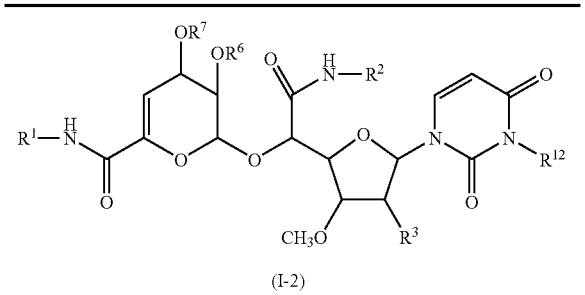

(I-2)

| Exemp. Comp. No. | R$^1$ | R$^2$ | R$^3$ | R$^6$ | R$^7$ | R$^{12}$ |
|---|---|---|---|---|---|---|
| 6692 | 4-Me$_2$N—Ph | H | OC11 | H | H | H |
| 6693 | 4-Me$_2$N—Ph | H | OC12 | H | H | H |
| 6694 | 4-Me$_2$N—Ph | H | OC14 | H | H | H |
| 6695 | 4-Me$_2$N—Ph | H | OC16 | H | H | H |
| 6696 | Ph | H | OH | H | H | POM |
| 6697 | Ph | H | OH | H | H | ECE |
| 6698 | Ph | H | OH | H | H | HCE |
| 6699 | Ph | H | OH | H | H | DCE |
| 6700 | Ph | H | OH | H | H | CCE |
| 6701 | Ph | H | OH | H | H | HOE |
| 6702 | 3,4-F$_2$—Ph | H | OH | H | H | POM |
| 6703 | 3,4-F$_2$—Ph | H | OH | H | H | ECE |
| 6704 | 3,4-F$_2$—Ph | H | OH | H | H | HCE |
| 6705 | 3,4-F$_2$—Ph | H | OH | H | H | DCE |
| 6706 | 3,4-F$_2$—Ph | H | OH | H | H | CCE |
| 6707 | 3,4-F$_2$—Ph | H | OH | H | H | HOE |
| 6708 | 4-Bu—Ph | H | OH | H | H | POM |
| 6709 | 4-Bu—Ph | H | OH | H | H | ECE |
| 6710 | 4-Bu—Ph | H | OH | H | H | HCE |
| 6711 | 4-Bu—Ph | H | OH | H | H | DCE |
| 6712 | 4-Bu—Ph | H | OH | H | H | CCE |
| 6713 | 4-Bu—Ph | H | OH | H | H | HOE |
| 6714 | 4-NO$_2$—Ph | H | OH | H | H | POM |
| 6715 | 4-NO$_2$—Ph | H | OH | H | H | ECE |
| 6716 | 4-NO$_2$—Ph | H | OH | H | H | HCE |
| 6717 | 4-NO$_2$—Ph | H | OH | H | H | DCE |
| 6718 | 4-NO$_2$—Ph | H | OH | H | H | CCE |
| 6719 | 4-NO$_2$—Ph | H | OH | H | H | HOE |
| 6720 | 4-F—Ph | H | OH | H | H | POM |
| 6721 | 4-F—Ph | H | OH | H | H | ECE |
| 6722 | 4-F—Ph | H | OH | H | H | HCE |
| 6723 | 4-F—Ph | H | OH | H | H | DCE |
| 6724 | 4-F—Ph | H | OH | H | H | CCE |
| 6725 | 4-F—Ph | H | OH | H | H | HOE |

TABLE 3

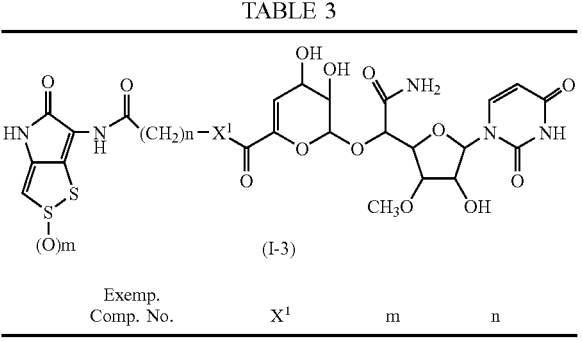

(I-3)

| Exemp. Comp. No. | X$^1$ | m | n |
|---|---|---|---|
| 6726 | NH | 0 | 1 |
| 6727 | NH | 0 | 2 |
| 6728 | NH | 0 | 3 |
| 6729 | NH | 0 | 4 |
| 6730 | NH | 0 | 5 |
| 6731 | NH | 0 | 6 |
| 6732 | NH | 0 | 7 |
| 6733 | NH | 0 | 8 |

TABLE 3-continued

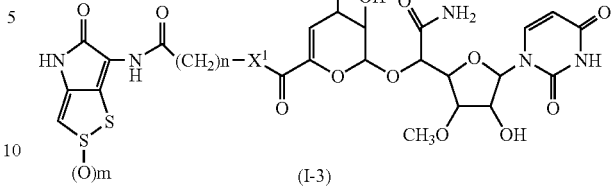

(I-3)

| Exemp. Comp. No. | X$^1$ | m | n |
|---|---|---|---|
| 6734 | NH | 0 | 9 |
| 6735 | NH | 0 | 10 |
| 6736 | NH | 0 | 11 |
| 6737 | O | 0 | 1 |
| 6738 | O | 0 | 2 |
| 6739 | O | 0 | 3 |
| 6740 | O | 0 | 4 |
| 6741 | O | 0 | 5 |
| 6742 | O | 0 | 6 |
| 6743 | O | 0 | 7 |
| 6744 | O | 0 | 8 |
| 6745 | O | 0 | 9 |
| 6746 | O | 0 | 10 |
| 6747 | O | 0 | 11 |
| 6748 | NH | 2 | 1 |
| 6749 | NH | 2 | 2 |
| 6750 | NH | 2 | 3 |
| 6751 | NH | 2 | 4 |
| 6752 | NH | 2 | 5 |
| 6753 | NH | 2 | 6 |
| 6754 | NH | 2 | 7 |
| 6755 | NH | 2 | 8 |
| 6756 | NH | 2 | 9 |
| 6757 | NH | 2 | 10 |
| 6758 | NH | 2 | 11 |
| 6759 | O | 2 | 1 |
| 6760 | O | 2 | 2 |
| 6761 | O | 2 | 3 |
| 6762 | O | 2 | 4 |
| 6763 | O | 2 | 5 |
| 6764 | O | 2 | 6 |
| 6765 | O | 2 | 7 |
| 6766 | O | 2 | 8 |
| 6767 | O | 2 | 9 |
| 6768 | O | 2 | 10 |
| 6769 | O | 2 | 11 |

Throughout the tables following abbreviations are used with the following meanings.

Exemp. Comp. No.: exemplification compound number,

Me: methyl,

Et: ethyl,

Pr: propyl, iPr: isopropyl,

Bu: butyl, tBu: tert-butyl, sBu: sec-butyl,

Pen: pentyl,

Hex: hexyl, cHex: cyclohexyl,

Hep: heptyl,

Vin: vinyl,

Ph: phenyl,

Bn: benzyl,

Pe: phenethyl,

Nap: naphthyl,

C8 and Oct: octyl,

C9: nonyl,

C10 and Dec: decyl,

C11: undecyl,

C12: dodecyl,

C14: tetradecyl,

C16: hexadecyl,

C18: octadecyl,

OC6: hexyloxy,

OC7: heptyloxy,

OC8: octyloxy,

OC10: decyloxy,

OC12: dodecyloxy,

OC14: tetradecyloxy,

OC16: hexadecyloxy, $C6CO_3$: hexyloxycarbonyloxy, $C7CO_3$: heptyloxycarbonyloxy, $C8CO_3$: octyloxycarbonyloxy, $C9CO_3$: nonyloxycarbonyloxy, $C10CO_3$: decyloxycarbonyloxy, $C12CO_3$: dodecyloxycarbonyloxy, $C16CO_3$: hexadecyloxycarbonyloxy, A2: acetyl, A3: propionyl, A4: butyryl, A6: hexanoyl, A8: octanoyl, A9: nonanoyl, A10: decanoyl, A12: dodecanoyl, A14: tetradecanoyl, A16: hexadecanoyl, OA2: acetyloxy, OA3: propionyloxy, OA4: butyryloxy, OA6: hexanoyloxy, OA8: octanoyloxy, OA9: nonanoyloxy, OA10: decanoyloxy, OA12: dodecanoyloxy, OA14: tetradecanoyloxy, OA16: hexadecanoyloxy,

F1: $H(CF_2)_2CH_2$,

F2: $CF_3CF_2CH_2$,

F3: $CF_3(CF_2)_2CH_2$,

F4: $CF_3(CF_2)_5CH_2$,

F5: $CF_3(CF_2)_6CH_2$,

F6: $CF_3(CF_2)_7CH_2$,

F7: $CF_3(CF_2)_3CH_2CH_2$,

F8: $CF_3(CF_2)_5CH_2CH_2$,

F9: $CF_3(CF_2)_7CH_2CH_2$,

F10: $CF_3(CF_2)_9CH_2CH_2$,

F11: $FCH_2CH_2$,

F12: $FCH_2CH_2CH_2CH_2$,

Mor: morpholino,

PA: phenylazo,

CHE: 2-(1-cyclohexenyl)ethyl,

COD: cis-octadecen-9-yl,

Py: pyridyl,

Tp: thienyl,

Fu: furyl,

Ta: thiazolyl,

DHT: 4,5-dihydrothiazolyl,

CTD: 5-cyclopropyl-1,3,4-thiadiazolyl,

Qin: quinolyl,

DTP: 4H-1,2-dithiolo-[4,3-b]-5-oxo-pyrrolyl,

POM: pivaloyloxymethyl,

ECE: 1-(ethoxycarbonyloxy)ethyl,

HCE: 1-(hexyloxycarbonyloxy)ethyl,

DCE: 1-(decyloxycarbonyloxy)ethyl,

CCE: 1-(cyclohexyloxycarbonyloxy)ethyl,

HOE: 1-(hexanoyloxy)ethyl.

In Tables 1 to 3:

Exemplification compound numbers of preferred compounds are 1 to 420, 491 to 1120, 1401 to 1540, 1611 to 1748, 1961 to 2520, 2591 to 2870, 2941 to 3430, 3711 to 3850, 4131 to 5460, 5531 to 5670, 5741 to 6090, and 6631.

Exemplification compound numbers of more preferred compounds are 2 to 55, 72 to 125, 142 to 195, 212 to 265, 282 to 335, 352 to 405, 492 to 545, 562 to 615, 632 to 685, 702 to 755, 772 to 825, 842 to 895, 912 to 965, 982 to 1035, 1052 to 1105, 1402 to 1455, 1472 to 1525, 1612 to 1665, 1682 to 1735, 1962 to 2015, 2032 to 2085, 2102 to 2155, 2172 to 2225, 2242 to 2295, 2312 to 2365, 2382 to 2435, 2452 to 2505, 2592 to 2645, 2662 to 2715, 2732 to 2785, 2802 to 2855, 2942 to 2995, 3012 to 3065, 3082 to 3135, 3152 to 3205, 3222 to 3275, 3292 to 3345, 3362 to 3415, 3712 to 3765, 3782 to 3835, 4132 to 4185, 4202 to 4255, 4272 to 4325, 4342 to 4395, 4412 to 4465, 4482 to 4535, 4552 to 4605, 4622 to 4675, 4692 to 4745, 4762 to 4815, 4832 to 4885, 4902 to 4955, 4972 to 5025, 5042 to 5095, 5112 to 5165, 5182 to 5235, 5252 to 5305, 5322 to 5375, 5392 to 5445, 5532 to 5585, 5602 to 5655, 5742 to 5795, 5812 to 5865, 5882 to 5935, 5952 to 6005, 6022 to 6075, and 6631.

Exemplification compound numbers of more preferred compounds are 2 to 9, 72 to 79, 142 to 149, 212 to 219, 282 to 289, 352 to 459, 492 to 599, 562 to 569, 632 to 639, 702 to 709, 772 to 779, 842 to 849, 912 to 919, 982 to 989, 1052 to 1059, 1402 to 1409, 1472 to 1479, 1612 to 1619, 1682 to 1689, 1962 to 1969, 2032 to 2039, 2102 to 2109, 2172 to 2179, 2242 to 2249, 2312 to 2319, 2382 to 2389, 2452 to 2459, 2592 to 2599, 2662 to 2669, 2732 to 2739, 2802 to 2809, 2942 to 2949, 3012 to 3019, 3082 to 3089, 3152 to 3159, 3222 to 3229, 3292 to 3299, 3362 to 3369, 3712 to 3719, 3782 to 3789, 4132 to 4139, 4202 to 4209, 4272 to 4279, 4342 to 4349, 4412 to 4419, 4482 to 4489, 4552 to 4559, 4622 to 4629, 4692 to 4699, 4762 to 4769, 4832 to 4839, 4902 to 4909, 4972 to 4979, 5042 to 5049, 5112 to 5119, 5182 to 5189, 5252 to 5259, 5322 to 5329, 5392 to 5399, 5532 to 5539, 5602 to 5609, 5742 to 5749, 5812 to 5819, 5882 to 5889, 5952 to 5959, 6022 to 6029, and 6631.

Exemplification compound numbers of still more preferred compounds are 2 to 9, 142 to 149, 562 to 569, 982 to 989, 1472 to 1479, 2242 to 2249, 2312 to 2319, 2382 to 2389, 3012 to 3019, 3712 to 3719, 4132 to 4139, 4202 to 4209, 4762 to 4769, 4832 to 4839, and 5532 to 5539.

Exemplification compound numbers of particularly preferred compounds are 2, 6, 142, 146, 562, 982, 1472, 1476, 2242, 2312, 2382, 3012, 3016, 3712, 3716, 4132, 4136, 4202, 4206, 4762, 4766, 4832, 4836, 5532 and 5536.

Particularly preferred compounds of formula (I') are:

a compound wherein $R^1$ is phenyl, $R^2$ is hydrogen, $X^1$ and $X^2$ are —NH—, and $R^3$ is hydroxyl (exemplification compound number 2, Example 43), a compound wherein $R^1$ is phenyl, $R^2$ is hydrogen, $X^1$ and $X^2$ are —NH—, and $R^3$ is decanoyloxy (exemplification compound number 6, Example 81), a compound wherein $R^1$ is 4-ethylphenyl, $R^2$ is hydrogen, $X^1$ and $X^2$ are —NH—, and $R^3$ is hydroxyl (exemplification compound number 142, Example 44), a compound wherein $R^1$ is 4-ethylphenyl, $R^2$ is hydrogen, $X^1$ and $X^2$ are —NH—, and $R^3$ is decanoyloxy (exemplification compound number 146), a compound wherein $R^1$ is 4-pentylphenyl, $R^2$ is hydrogen, $X^1$ and $X^2$ are —NH—, and $R^3$ is hydroxyl (exemplification compound number 562, Example 55), a compound wherein $R^1$ is 3-ethylphenyl, $R^2$ is hydrogen, $X^1$ and $X^2$ are —NH—, and $R^3$ is hydroxyl (exemplification compound number 982, Example 58), a compound wherein $R^1$ is 4-trifluoromethylphenyl, $R^2$ is hydrogen, $X^1$ and $X^2$ are —NH—, and $R^3$ is hydroxyl (exemplification compound number 1472, Example 50), a compound wherein $R^1$ is 4-trifluoromethylphenyl, $R^2$ is hydrogen, $X^1$ and $X^2$ are —NH—, and $R^3$ is decanoyloxy (exemplification compound number 1476), a compound wherein $R^1$ is 4-butoxyphenyl, $R^2$ is hydrogen, $X^1$ and $X^2$ are —NH—, and $R^3$ is hydroxyl (exemplification compound number 2242, Example 62), a compound wherein $R^1$ is 4-pentyloxyphenyl, $R^2$ is hydrogen, $X^1$ and $X^2$ are —NH—, and $R^3$ is hydroxyl (exemplification compound number 2312, Example 64), a compound wherein $R^1$ is 4-hexyloxyphenyl, $R^2$ is hydrogen, $X^1$ and $X^2$ are —NH—, and $R^3$ is hydroxyl (exemplification compound number 2832, Example 63), a compound wherein $R^1$ is 4-fluorophenyl, $R^2$ is hydrogen, $X^1$ and $X^2$ are —NH—, and $R^3$ is hydroxyl (exemplification compound number 3012, Example 45), a compound wherein $R^1$ is 4-fluorophenyl, $R^2$ is hydrogen, $X^1$ and $X^2$ are —NH—, and $R^3$ is decanoyloxy (exemplification compound number 3016), compound wherein $R^1$ is 3,4-difluorophenyl, $R^2$ is hydrogen, $X^1$ and $X^2$ are —NH—, and $R^3$ is hydroxyl (exemplification compound number 3712, Example 57), a compound wherein $R^1$ is 3,4-difluorophenyl, $R^2$ is hydrogen, $X^1$ and $X^2$ are —NH—, and $R^3$ is decnoyloxy (exemplification compound number 3716), a compound wherein $R^1$ is 3-chloro-4-fluorophenyl, $R^2$ is hydrogen, $X^1$ and $X^2$ are —NH—, and $R^3$ is hydroxyl (exemplification compound number 4132, Example 60), a compound wherein $R^1$ is 3-chloro-4-fluorophenyl, $R^2$ is hydrogen, $X^1$ and $X^2$ are —NH—, and $R^3$ is decanoyloxy (exemplification compound number 4136), a compound wherein $R^1$ is 3-trifluoromethyl-4-fluorophenyl, $R^2$ is hydrogen, $X^1$ and $X^2$ are —NH—, and $R^3$ is hydroxyl (exemplification compound number 4202, Example 65)

a compound wherein $R^1$ is 3-trifluoromethyl-4-fluorophenyl, $R^2$ is hydrogen, $X^1$ and $X^2$ are —NH—, and $R^3$ is decanoyloxy (exemplification compound number 4206), a compound wherein $R^1$ is 3-methyl-4-bromophenyl, $R^2$ is hydrogen, $X^1$ and $X^2$ are —NH—, and $R^3$ is hydroxyl (exemplification compound number 4762, Example 96), a compound wherein $R^1$ is 3-methyl-4-bromophenyl, $R^2$ is hydrogen, $X^1$ and $X^2$ are —NH—, and $R^3$ is decanoyloxy (exemplification compound number 4766), a compound wherein $R^1$ is 3-nitro-4-fluorophenyl, $R^2$ is hydrogen, $X^1$ and $X^2$ are —NH—, and $R^3$ is hydroxyl (exemplification compound number 4832, Example 97), a compound wherein $R^1$ is 3-nitro-4-fluorophenyl, $R^2$ is hydrogen, $X^1$ and $X^2$ are —NH—, and $R^3$ is decanoyloxy (exemplification compound number 4836), a compound wherein $R^1$ is 3-nitrophenyl, $R^2$ is hydrogen, $X^1$ and $X^2$ are —NH—, and $R^3$ is hydroxyl (exemplification compound number 5532, Example 95) and a compound wherein $R^1$ is 3-nitrophenyl, $R^2$ is hydrogen, $X^1$ and $X^2$ are —NH—, and $R^3$ is decanoyloxy (exemplification compound number 5536).

The compounds of formula (I) and pharmaceutically acceptable ethers, esters and N-alkyl derivatives thereof can be prepared by one of Methods A to H or an appropriate combination of these methods.

[Method A]

A compound of formula (Ia), which is a compound of formula (I) wherein $R^1$—$X^1$ is a group of formula $R^1R^4N$—, $R^2$—$X^2$ is amino and $R^3$ is hydroxyl, is prepared by Method A.

Method A

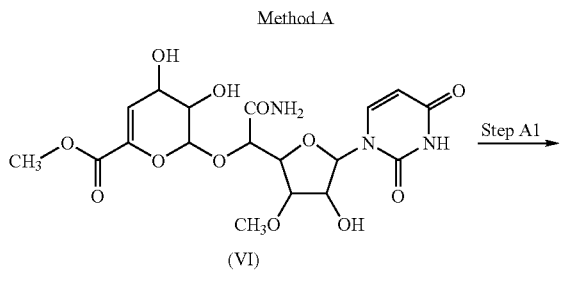

(VI) Step A1

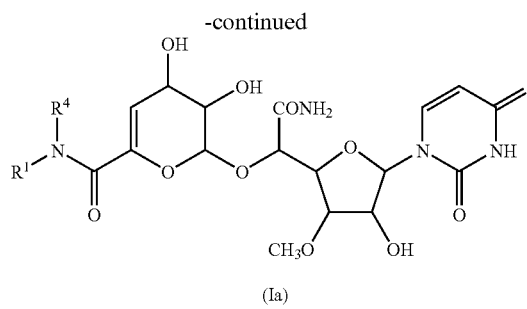

(Ia)

wherein $R^1$ and $R^4$ are as defined above.

A compound of formula (Ia) is prepared according to Step A1 from a compound of formula (VI). This step can be accomplished by reaction of the compound of formula (VI) with a compound of formula $R^1R^4NH$ in a solvent.

The compound of formula (VI) can be isolated from a product of a micro-organism described later.

The compound of formula $R^1R^4NH$ is required to be sufficiently nucleophilic, and a preferred compound is a primary amine or cyclic amine. Where the compound of formula $R^1R^4NH$ is not sufficiently nucleophilic, a compound of formula (Ia) is prepared by Method B described below.

The solvent in this step is not particularly limited provided that it has no adverse effect on the reaction and dissolves the starting material and the reagent to some extent. Examples of such solvents include alcohols such as methanol and ethanol; and amides such as N,N-dimethylformamide and N,N-dimethylacetamide. Preferred solvents are alcohols, and a particularly preferred solvent is methanol.

The temperature of this step depends on the amine, the solvent employed and the like and is usually between 0° C. and 150° C., preferably between 20° C. and 100° C.

The reaction time of this step depends on the reaction temperature and the like and is usually from 30 minutes to 2 days, preferably from 5 hours to 1 day.

After the reaction of this step, the desired compound of formula (Ia) can be isolated from the reaction mixture by a conventional technique. For example, the reaction mixture is appropriately neutralized, filtered when there are insoluble materials, and concentrated in vacuo. The residue is then partitioned between water and an organic solvent immiscible with water such as ethyl acetate or dichloromethane. The extract is appropriately washed with dilute hydrochloric acid, aqueous sodium hydrogencarbonate solution, aqueous sodium chloride solution and the like, dried over anhydrous magnesium sulfate and the like, and then concentrated to give the desired product. If desired, the product can be further purified by recrystallization, reprecipitation or chromatography.

The product of formula (Ia) can be converted to a compound wherein $R^3$ is hydrogen or to an ether or ester derivative thereof by a procedure described later.

[Method B]

A compound of formula (Ib), which is a compound of formula (I) wherein $R^2$—$X^2$ is amino and $R^3$ is hydroxyl, is prepared by Method B.

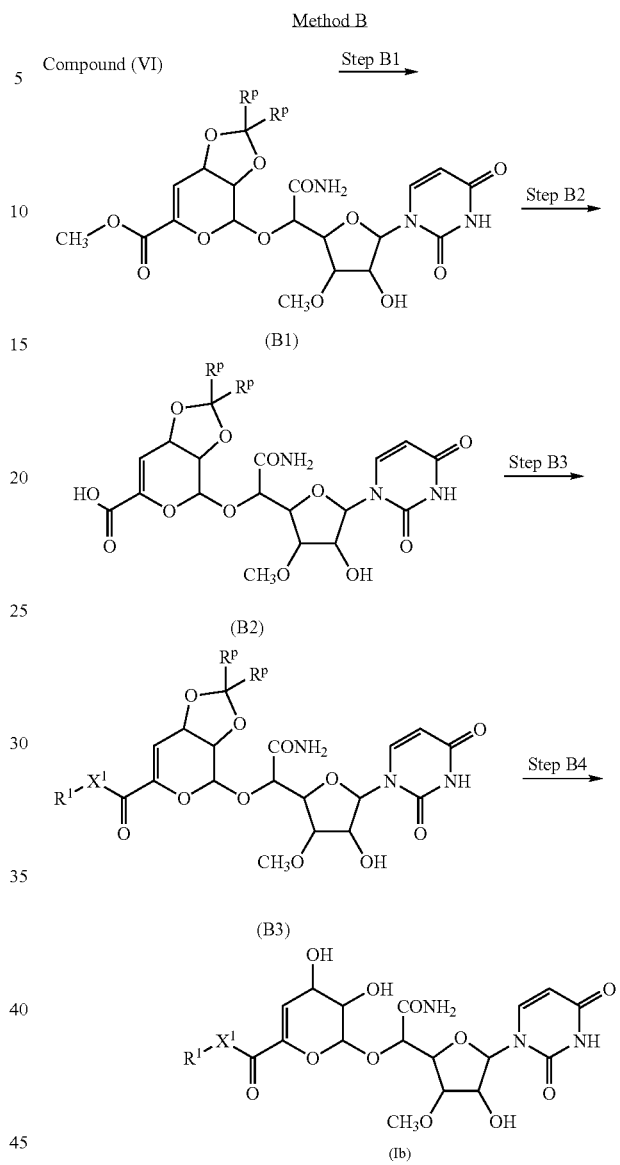

(Ib)

wherein $R^1$ and $X^1$ are as defined above, and the two groups $R^p$ are the same or different and each is hydrogen or $C_1$–$C_3$ alkyl, or the two groups $R^p$, together with the carbon to which they are attached, form a 5- or 6-membered cycloalkyl ring.

A compound of formula (B1) is prepared according to Step B1 from a compound of formula (VI). This step can be accomplished by reaction of the compound of formula (VI) with an acetalization reagent in the presence of an acid catalyst in a solvent.

Preparation of the compound of formula (VI) will be described later.

An acetalization reagent is a compound having the formula $(R^p)_2C$=O or a compound equivalent to $(R^p)_2C$=O. Examples of such compounds include formaldehyde, acetaldehyde, acetone, methyl ethyl ketone, diethyl ketone, dipropyl ketone, methoxyisopropene, 2,2-dimethoxypropane, cyclopentanone, cyclohexanone, 1,1-dimethoxycyclopentane, and 1,1-dimethoxycyclohexane. A preferred acetalization reagent is acetone, 2,2-dimethoxypropane, cyclopentanone or 1,1-dimethoxycyclopentane.

The solvent employed in this step is not particularly limited provided that it has no adverse effect on the reaction and dissolves the starting material and the reagent to some extent. A preferred example of such a solvent is the acetalization reagent of formula $(R^p)_2C=O$ employed in this step. A more preferable solvent is acetone or cyclopentanone.

Examples of the acid catalyst employed in this step include inorganic acids such as hydrogen chloride, nitric acid and sulfuric acid; organic acids such as acetic acid, trifluoroacetic acid, methanesulfonic acid and p-toluenesulfonic acid; Lewis acids such as boron trifluoride; or acidic resins such as Amberlyst 15. A preferred acid is an organic acid or an acidic resin, and a more preferred acid is p-toluenesulfonic acid or Amberlyst 15.

The temperature of this step depends on the acetalization reagent, the acid catalyst employed and the like and is usually between 0° C. and 100° C., preferably between 20° C. and 50° C.

The reaction time of this step depends on the reaction temperature and the like and is usually from 1 hour to 7 days, preferably from 10 hours to 3 days.

After the reaction of this step, the desired compound of formula (Ib) can be isolated from the reaction mixture by a conventional technique. For example, the reaction mixture is appropriately neutralized, filtered when there are insoluble materials, and concentrated in vacuo. The residue is partitioned between water and an organic solvent immiscible with water such as ethyl acetate or dichloromethane. The extract is appropriately washed with dilute hydrochloric acid, aqueous sodium hydrogencarbonate solution, aqueous sodium chloride solution and the like, dried over anhydrous magnesium sulfate and the like, and then concentrated to give the desired product. If desired, the product can be further purified by recrystallization, reprecipitation or chromatography.

A compound of formula (B2) is prepared according to Step B2 from the compound of formula (B1). This step can be accomplished by reaction of the compound of formula (B1) with a base in a solvent.

Examples of bases employed in this step include alkali metal hydroxides such as sodium hydroxide and potassium hydroxide. A preferred base is sodium hydroxide.

Examples of solvents employed in this step include water; mixtures of water and an alcohol such as methanol, ethanol and propanol; and mixtures of water and an ether miscible with water such as dioxane and tetrahydrofuran. A preferred solvent is a mixture of water and an alcohol (particularly methanol).

The temperature of this step is usually between −20° C. and 50° C., preferably between 0° C. and 20° C.

The reaction time of this step depends on the reaction temperature and the like and is usually from 1 minute to 1 hour, preferably 5 minutes to 20 minutes After the reaction of this step the desired compound of formula (B2) can be isolated by conversion to the free carboxylic acid using an acidic resin such as Dowex 50WX8 and then by a conventional technique. For example, the reaction mixture is filtered in order to remove insoluble material. The filtrate is then concentrated in vacuo or partitioned between water and an organic solvent immiscible with water such as ethyl acetate or dichloromethane. The extract is appropriately washed with dilute hydrochloric acid, aqueous sodium chloride solution and the like, dried over anhydrous magnesium sulfate and the like, and then concentrated to give the desired product. If desired, the product can be further purified by recrystallization, reprecipitation or chromatography.

A compound of formula (B3) is prepared according to Step B3 from the compound of formula (B2). This step can be accomplished by reaction of the compound of formula (B2) with a compound of formula $R^1-X^1H$ in the presence of a coupling reagent in an inert solvent.

A compound of formula $R^1-X^1H$ is an alcohol, thiol or amine each of which has desired groups $R^1$ and $X^1$.

Examples of coupling reagents employed in this step include carbodiimides such as dicyclohexylcarbodiimide and diisopropylcarbodiimide (DIPC); sulfonic acid chlorides such as benzenesulfonyl chloride and p-toluenesulfonyl chloride; phosphonium salts such as benzotriazol-1-yloxytris(dimethylamino)phosphonium hexafluorophosphate; and uronium salts such as O-benzotriazol-1-yl-N,N,N',N'-tetramethyluronium hexafluorophosphate. A preferred coupling reagent is a carbodiimide and a particularly preferred reagent is DIPC. When the coupling reagent is a carbodiimide, 1-hydroxybenzotriazole (HOBT) can be added to the reaction mixture.

The solvent employed in this step is not particularly limited provided that it has no adverse effect on the reaction and dissolves the starting material and the reagent to some extent. Examples of such a solvent include amides such as N,N-dimethylformamide and N,N-dimethylacetamide; halogenated hydrocarbons such as dichloromethane and chloroform; and ethers such as dioxane and tetrahydrofuran. A preferred solvent is an amide, and a particularly preferred solvent is N,N-dimethylformamide.

The reaction temperature of this step is usually between −20° C. and 80° C., preferably between 0° C. and 50° C.

The reaction time of this step, depends on the reaction temperature and the like and is usually from 1 hour to 2 days, preferably from 3 hours to 1 day.

After the reaction of this step, the desired compound of formula (B3) can be isolated from the reaction mixture by a conventional technique. For example, the reaction mixture is appropriately neutralized, filtered when there are insoluble materials, and then concentrated in vacuo. The residue is partitioned between water and an organic solvent immiscible with water such as ethyl acetate or dichloromethane. The extract is appropriately washed with dilute hydrochloric acid, aqueous sodium hydrogencarbonate solution, aqueous sodium chloride solution and the like, dried over anhydrous magnesium sulfate and the like, and then concentrated to give the desired product. If desired, the product can be further purified by recrystallization, reprecipitation or chromatography.

A compound of formula (Ib) is prepared according to Step B4 from the compound of formula (B3). This step can be accomplished by hydrolysis of the compound of formula (B3) in the presence of an acid catalyst in a solvent.

Examples of the acid catalyst employed in this step include inorganic acids such as hydrogen chloride, nitric acid and sulfuric acid; organic acids such as acetic acid, trifluoroacetic acid, methanesulfonic acid, and p-toluenesulfonic acid; Lewis acids such as boron trifluoride; or acidic resins such as Amberlyst 15. A preferred acid is an organic acid or an acidic resin, and a more preferred acid is trifluoroacetic acid, p-toluenesulfonic acid or Amberlyst 15.

Examples of solvents employed in this step include water; alcohols such as methanol, ethanol and propanol; mixtures of water and an alcohol; mixtures of water and an ether miscible with water such as dioxane or tetrahydrofuran; halogenated hydrocarbons such as methylene chloride and chloroform; and mixtures of water and a halogenohydrocarbon. A preferred solvent is an alcohol (particularly methanol) or a halogenohydrocarbon (particularly methylene chloride).

The reaction temperature of this step is usually between 0° C. and 120° C., preferably between 20° C. and 100° C.

The reaction time of this step depends on the reaction temperature and the like and is usually from 1 hour to 2 days, preferably from 3 hours to 1 day.

After the reaction of this step, the desired compound of formula (Ib) can be isolated from the reaction mixture by a conventional technique. For example, the reaction mixture is appropriately neutralized, filtered when there are insoluble materials, and concentrated in vacuo. The residue is partitioned between water and an organic solvent immiscible with water such as ethyl acetate or dichloromethane. The extract is appropriately washed with dilute hydrochloric acid, aqueous sodium hydrogencarbonate solution, aqueous sodium chloride solution and the like, dried over anhydrous magnesium sulfate and the like, and then concentrated to give the desired product. If desired, the product can be further purified by recrystallization, reprecipitation or chromatography.

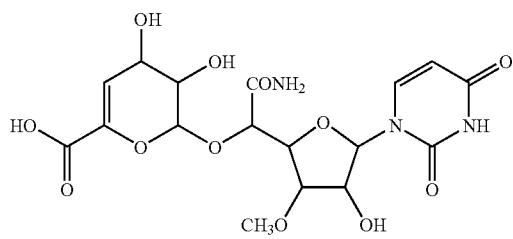

(VII)

In addition, when the acetalization reaction (Step B1) and the deacetalization reaction (Step B4) are not needed, the compound of formula (Ib) can also be prepared from the compound of formula (VI) by hydrolysis (Step B2) to afford a compound of formula (VII) and then by introduction of an $R^1$—$X^1$ group into the compound of formula (VII). The compound of formula (VII) can also be isolated from a product of a micro-organism.

The product of formula (Ib) can be converted to a compound (Id) wherein $R^3$ is hydrogen or to an ether or ester derivative thereof by a procedure described later.

[Method C]

A compound of formula (Ic), which is a compound of formula (I) wherein $R^3$ is hydroxyl, is prepared by Method C.

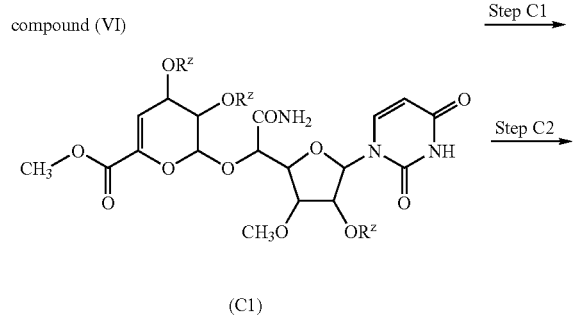

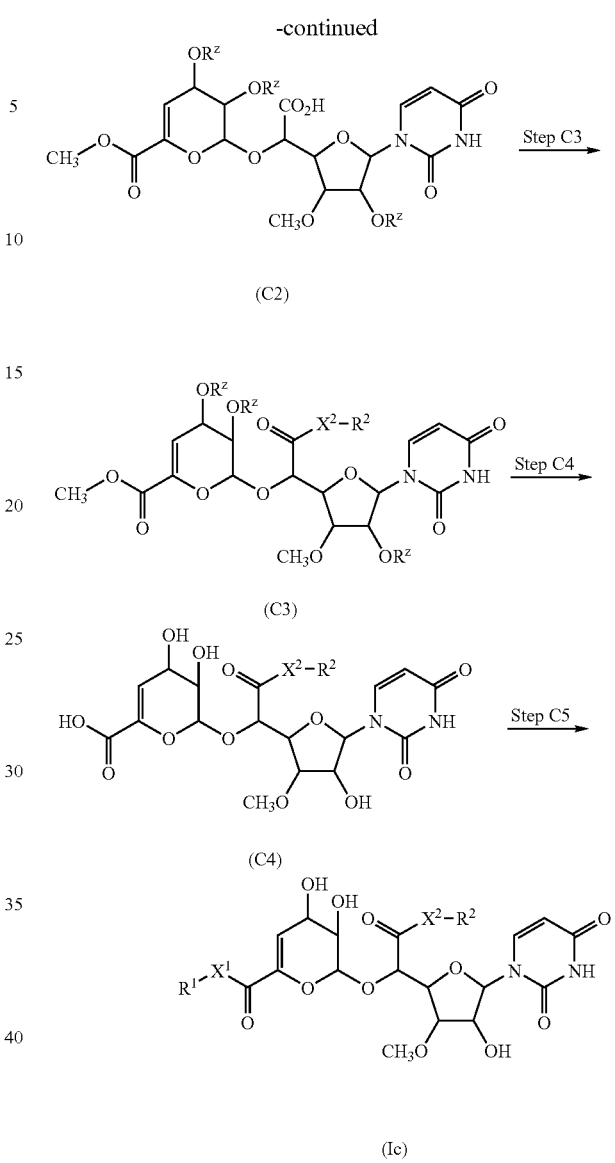

wherein $R^1$, $R^2$, $X^1$, and $X^2$ are as defined above, and $R^z$ is an acyl group.

A compound of formula (C1), which is obtained by protection of the hydroxyl groups of compound (VI) with acyl groups, is prepared according to Step C1. This step can be accomplished by reaction of compound (VI) with an acylating reagent in the presence of a base in an inert solvent.

The solvent employed in this step is not particularly limited provided that it has no adverse effect on the reaction and can dissolve the starting material and the reagent to some extent. Examples of such solvents include ethers such as diethyl ether, tetrahydrofuran and dioxane; amides such as N,N-dimethylformamide and N,N-dimethylacetamide; halogenated hydrocarbons such as dichloromethane and chloroform; acetonitrile; ethyl acetate; pyridine and lutidine. Preferable solvents are N,N-dimethylacetamide and pyridine.

Examples of bases employed in this step include pyridine, lutidine, collidine, and N,N-dimethylaminopyridine. Preferred bases are pyridine and N,N-dimethylaminopyridine.

Examples of acylating reagents include $C_1$–$C_4$ aliphatic acyl halides or acid anhydrides such as acetyl chloride, propionyl chloride and acetic anhydride; $C_6$–$C_{10}$ aromatic acyl halides or anhydrides such as benzoyl chloride, benzoyl bromide and benzoic anhydride. A preferred acylating reagent is benzoyl chloride or benzoic anhydride.

The reaction temperature of this step depends on the acylating reagent, the base employed and the like and is usually between −20° C. and 100° C., preferably between 0° C. and 50° C.

The reaction time of this step depends on the reaction temperature and the like and is usually from 30 minutes to 1 day, preferably from 1 hour to 10 hours After the reaction of this step the desired compound of formula (C1) can be isolated from the reaction mixture by a conventional technique. For example, the reaction mixture is appropriately neutralized, filtered when there are insoluble materials, and concentrated in vacuo. The residue is partitioned between water and an organic solvent immiscible with water such as ethyl acetate or dichloromethane. The extract is appropriately washed with dilute hydrochloric acid, aqueous sodium hydrogencarbonate solution, aqueous sodium chloride solution and the like, dried over anhydrous magnesium sulfate and the like, and then concentrated to give the desired product. If desired, the product can be further purified by recrystallization, reprecipitation or chromatography.

A compound of formula (C2) is prepared by hydrolysis of the carbamoyl group of the compound of formula (C1) according to Step C2. This step can be accomplished by reaction of the compound of formula (C1) with nitrosylsulfuric acid.

Examples of solvents employed in this step include mixtures of water and dichloromethane.

The temperature of this step depends on the solvent employed and the like and is usually between −20° C. and 100° C., preferably between 0° C. and 50° C.

The reaction time of this step depends on the reaction temperature and the like and is usually from 10 minute to 5 hours, preferably 20 minutes to 2 hours.

After the reaction of this step, the desired compound of formula (C2) can be isolated by a conventional technique. For example, the reaction mixture is appropriately neutralized, filtered when there are insoluble materials, and concentrated in vacuo. The residue is partitioned between water and an organic solvent immiscible with water such as ethyl acetate or dichloromethane. The extract is appropriately washed with dilute hydrochloric acid, aqueous sodium hydrogencarbonate solution, aqueous sodium chloride solution and the like, dried over anhydrous magnesium sulfate and the like, and then concentrated to give the desired product. If desired, the product can be further purified by recrystallization, reprecipitation or chromatography.

In Step C3, a compound of formula (C3) is prepared by introducing a group $R^2$—$X^2$ into the compound of formula (C2). This step can be accomplished by reaction of compound (C2) in a similar manner to that described in Step B3.

In Step C4, a compound (C4) is prepared by alkaline hydrolysis of the compound of formula (C3). This step can be accomplished by reaction of compound (C3) in a similar manner to that described in Step B2.

In Step C5, a compound of formula (Ic) is prepared by introducing a group $R^1$—$X^1$ into the compound of formula (C4). This step can be accomplished by reaction of compound (C4) in a similar manner to that described in Step B3.

The product of formula (Ic) can be converted to a compound wherein $R^3$ is hydrogen or to an ether or ester derivative thereof by a procedure described later.

[Method D]

A compound of formula (Id), which is a compound of formula (I) wherein $R^3$ is hydrogen, is prepared by Method D.

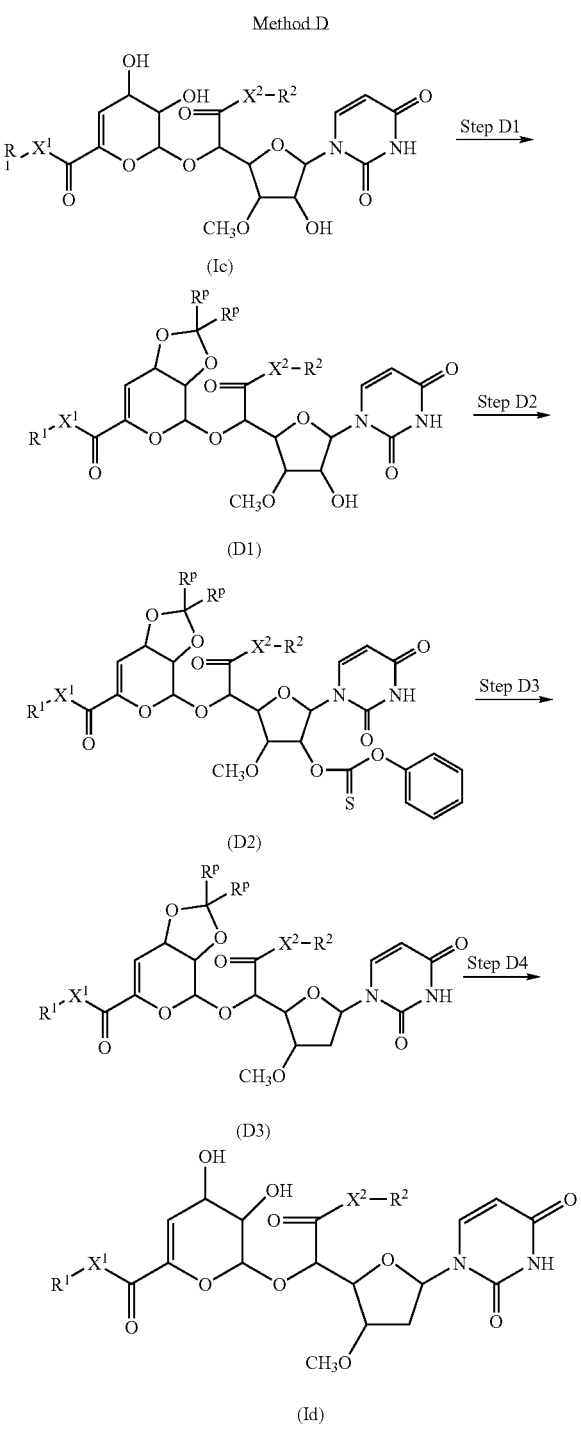

wherein $R^1$, $R^2$, $X^1$, $X^2$ and RP are as defined above.

In Step D1, a compound of formula (D1) is prepared by protection of the two hydroxyl groups on the dihydropyran ring of the compound of formula (Ic) using an acetal-forming reagent. This step can be accomplished by reaction of compound (Ic) in a similar manner to that described in Step B1.

In step D2, a compound of formula (D2) is prepared by introducing a phenoxythiocarbonyl group into the compound of formula (D1). This step can be accomplished by reaction of compound (D1) with a phenoxythiocarbonylation reagent in the presence of a base in an inert solvent.

Examples of phenoxythiocarbonylation reagents employed in this step include phenoxythiocarbonyl halides or phenoxythiocarboxylic acid anhydrides. A preferred phenoxythiocarbonylation reagent is phenoxythiocarbonyl chloride.

The solvent employed in this step is not particularly limited provided that it has no adverse effect on the reaction and dissolves the starting material and the reagent to some extent. Examples of such solvents include halogenated hydrocarbons such as dichloromethane and chloroform; ethers such as diethyl ether, dioxane and tetrahydrofuran; aromatic hydrocarbons such as benzene and toluene; and pyridine. Preferred solvents are halogenated hydrocarbons.

Examples of bases employed in this step include pyridine, lutidine, collidine, triethylamine, and 4-N,N-dimethylaminopyridine. A preferred base is 4-N,N-dimethylaminopyridine.

The reaction temperature of this step depends on the solvent and the base employed in this step and the like and is usually between −20° C. and 10° C., preferably between 0° C. and 50° C.

The reaction time of this step depends on the reaction temperature and the like and is usually from 30 minutes to 10 hours, preferably from 1 hour to 3 hours.

After the reaction of this step, the desired compound of formula (D2) can be isolated from the reaction mixture by a conventional technique. For example, the reaction mixture is appropriately neutralized, filtrated when there are insoluble materials, and concentrated in vacuo. The residue is partitioned between water and an organic solvent immiscible with water such as ethyl acetate and dichloromethane. The extract is appropriately washed with dilute hydrochloric acid, aqueous sodium hydrogencarbonate solution, aqueous sodium chloride solution and the like, dried over anhydrous magnesium sulfate and the like, and then concentrated to give the desired product. If desired, the product can be further purified by recrystallization, reprecipitation or chromatography.

In step D3, a compound of formula (D3) is prepared by reductive removal of the phenoxythiocarbonyloxy group of the compound of formula (D2). This step can be accomplished by reaction of the compound of formula (D2) with a tin hydride in the presence of a radical initiating reagent in an inert solvent.

Examples of tin hydrides employed in this step include tributyltin hydride and triphenyltin hydride. A preferred tin hydride is tributyltin hydride.

Examples of solvents employed in this step include halogenated hydrocarbons such as dichloromethane and chloroform; ethers such as diethyl ether, dioxane and tetrahydrofuran; and aromatic hydrocarbons such as benzene and toluene. A preferred solvent is toluene.

A preferred example of a radical initiating reagent is 2,2'-azobis(isobutyronitrile) (AIBN).

The reaction temperature of this step depends on the solvent and base employed in this step and the like and is usually between 20° C. and 150° C., preferably between 80° C. and 120° C.

The reaction time of this step, depends on the reaction temperature and the like and is usually from 1 hour to 3 days, preferably from 5 hours to 1 day.

After the reaction of this step the desired compound of formula (D3) can be isolated from the reaction mixture by a conventional technique. For example, the reaction mixture is appropriately neutralized, filtered when there are insoluble materials, and concentrated in vacuo. The residue is partitioned between water and an organic solvent immiscible with water such as ethyl acetate or dichloromethane. The extract is appropriately washed with dilute hydrochloric acid, aqueous sodium hydrogencarbonate solution, aqueous sodium chloride solution and the like, dried over anhydrous magnesium sulfate and the like, and then concentrated to give the desired product. If desired, the product can be further purified by recrystallization, reprecipitation or chromatography.

In Step D4, a compound of formula (Id) is prepared by deprotection of the acetal group at the two hydroxy groups on the dihydropyran ring of the compound of formula (D3). This step can be accomplished by reaction of the compound of formula (D3) in a similar manner to that described in Step B4.

The product of formula (Id) can be converted to an ether or ester derivative thereof by a procedure described later.

[Method E]

In Method E, ether derivatives of formula (E4) of the compounds defined by the general formula (I) are synthesized.

Method E

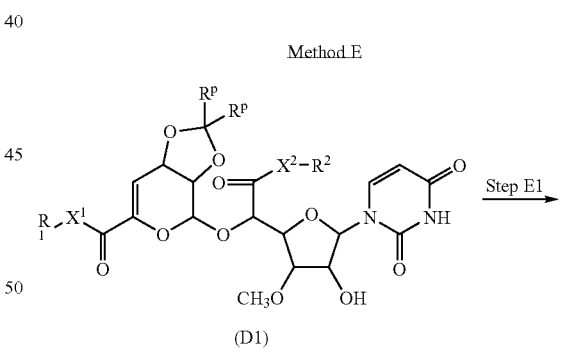

(D1)

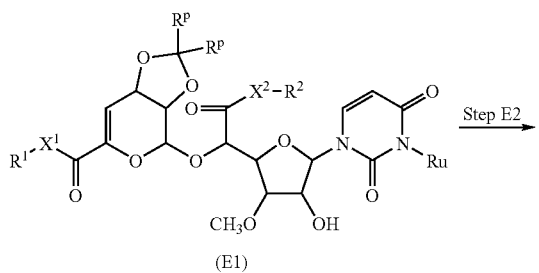

(E1)

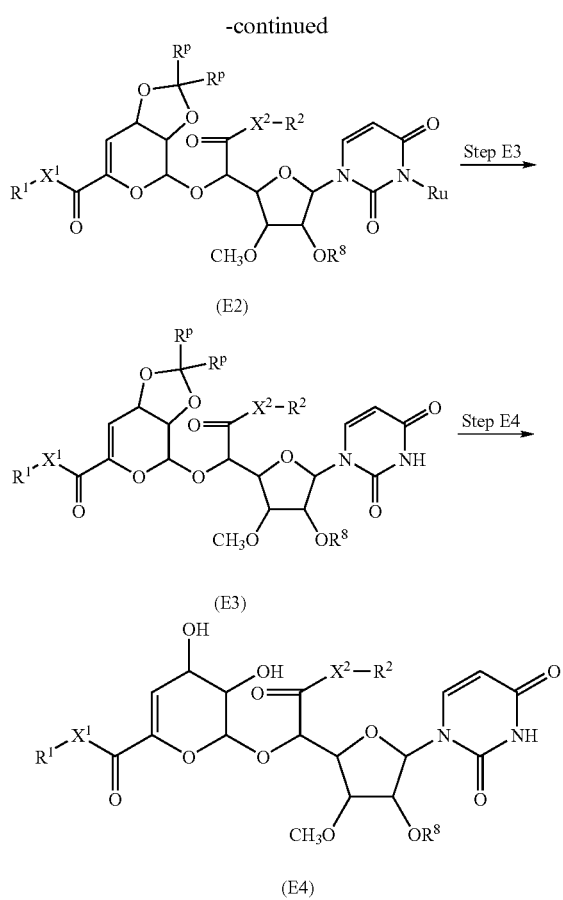

In the above reaction scheme, $R^1$, $R^2$, $X^1$, $X^2$ and $R^u$ are as defined earlier, $R^B$ is an ether residue, and $R^u$ is a protecting group for a uracil residue.

In Step E1, a compound of formula (E1) is synthesized by introducing a protecting group for a uracil residue into the compound of formula (D1). This step is carried out by reaction of the compound of formula (D1) with a protecting agent for a uracil residue in the presence of a base in an inert solvent.

In this reaction, p-methoxybenzyl chloromethyl ether is preferably used as the protecting agent of the uracil residue.

The inert solvent used in this reaction is not particularly limited provided that it has no adverse effect on the reaction and dissolves the starting material and reactant to some extent. Examples of the solvent employed in this reaction include ethers such as diethyl ether, tetrahydrofuran or dioxane; amides such as N,N-dimethylformamide or N,N-dimethylacetamide; halogenated hydrocarbons such as dichloromethane or chloroform; or acetonitrile. N,N-dimethylformamide and acetonitrile are preferred.

Examples of the base employed in this reaction include tertiary amines such as 1,8-diazabicyclo[5.4.0]undec-7-ene (DBU) or 1,5-diazabicyclo[4.3.0]non-5-ene (DBN); or alkali metal hydrides such as sodium hydride or potassium hydride, and 1,8-diazabicyclo[5.4.0]undec-7-ene (DBU) is preferred.

The temperature of this reaction mainly depends on the protecting agent and base employed. However, it is usually between 0° C. and 100° C., and is preferably between 20° C. and 50° C.

The reaction time mainly depends on the reaction temperature employed. However, it is usually from 30 min to one day, and is preferably from 1 hr to 5 hr.

After the reaction is complete, the desired compound of this reaction is isolated from the reaction mixture using a conventional technique. For example, the reaction mixture is neutralized appropriately or insoluble matter, if present, is removed by filtration, and the neutralized reaction mixture or the filtrate of the reaction mixture is evaporated under reduced pressure. The residue obtained is dissolved in an organic solvent that is immiscible with water such as ethyl acetate or dichloromethane, washed appropriately with dilute hydrochloric acid, aqueous sodium hydrogencarbonate or aqueous sodium chloride, dried over anhydrous magnesium sulfate or the like and then evaporated to give the desired product. The product thus obtained can, if necessary, be purified by a conventional technique such as recrystallization, reprecipitation or chromatography.

In Step E2, a compound of formula (E2) is synthesized by introducing an ether residue to a free hydroxyl group of the compound of formula (E1). This step can be carried out by reaction of the compound of formula (E1) with an etherification agent in the presence of a base in an inert solvent.

The etherification agent employed in this reaction is a compound of formula $R^8L$ (wherein $R^8$ is an ether residue defined earlier and L is a leaving group) and is, for example, a halide derivative or triflate derivative of $R^8$, and an iodide derivative of $R^8$ is preferred.

Examples of the inert solvent employed in this reaction include ethers such as diethyl ether, tetrahydrofuran or dioxane; amides such as N,N-dimethylformamide or N,N-dimethylacetamide; halogenated hydrocarbons such as dichloromethane or chloroform; or acetonitrile; and N,N-dimethylformamide is preferred.

Examples of the base employed in this reaction include tertiary amines such as 1,8-diazabicyclo[5.4.0]undec-7-ene (DBU) or 1,5-diazabicyclo[4.3.0]non-5-ene (DBN); or alkali metal hydrides such as sodium hydride or potassium hydride; and alkali metal hydrides are preferred.

The temperature of this reaction mainly depends on various factors such as the etherification agent and base employed. However, it is usually between −30° C. and 100° C., and is preferably between −10° C. and 30° C.

The reaction time for the reaction mainly depends on the reaction temperature employed. However, it is usually from 30 min to one day, and is preferably from 1 hr to 5 hr.

After the reaction is complete, the desired compound of this reaction is isolated from the reaction mixture using a conventional technique. For example, the reaction mixture is neutralized appropriately or insoluble matters, if present, are removed by filtration, and the neutralized reaction mixture or the filtrate of the reaction mixture is evaporated under reduced pressure. The residue obtained is dissolved in an organic solvent that is immiscible with water such as ethyl acetate or dichloromethane, washed appropriately with dilute hydrochloric acid, aqueous sodium hydrogencarbonate or aqueous sodium chloride, dried over anhydrous magnesium sulfate or the like, and evaporated to give the desired product. The product thus obtained can, if necessary, be further purified using a conventional technique such as recrystallization, reprecipitation or chromatography.

In Step E3, a compound of formula (E3) is synthesized from the compound of formula (E2) by removing the protecting group for the uracil residue. This step is conducted by reaction of the compound of formula (E2) with an agent for the removal of the protecting group in an inert solvent.

The agent for the removal of the protecting group used in this reaction is, for example, 2,3-dichloro-5,6-dicyano-1,4-benzoquinone (DDQ) or ammonium cerium (IV) nitrate (CAN), and 2,3-dichloro-5,6-dicyano-1,4-benzoquinone (DDQ) is preferred.

The inert solvent employed in this reaction is not particularly limited provided that it has no adverse effect on the reaction and dissolves the starting material and reactant to some extent. Examples of the solvent employed in this reaction include water; alcohols such as methanol or ethanol; ethers such as diethyl ether, tetrahydrofuran or dioxane; halogenated hydrocarbons such as dichloromethane or chloroform; or a mixture thereof, and a mixed solvent of water and dichloromethane is preferred.

The temperature of this reaction mainly depends on various factors such as the agent for the removal of the protecting group employed. It is usually between 0° C. and 150° C., and is preferably between 10° C. and 100° C.

The reaction time mainly depends on the reaction temperature employed. It is usually from 1 hr to two days, and is preferably from 1 hr to 10 hr.

After the reaction is complete, the desired compound of this reaction is isolated from the reaction mixture using a conventional technique. For example, the reaction mixture is neutralized appropriately or insoluble matter, if present, is removed by filtration, and the neutralized reaction mixture or the filtrate of the reaction mixture is evaporated under reduced pressure. The residue obtained is dissolved in an organic solvent that is immiscible with water such as ethyl acetate or dichloromethane, washed appropriately with dilute hydrochloric acid, aqueous sodium hydrogencarbonate or aqueous sodium chloride, dried over anhydrous magnesium sulfate or the like, and evaporated to give the desired product. The product thus obtained can, if necessary, be further purified by a conventional technique such as recrystallization, reprecipitation or chromatography.

In Step E4, a compound of formula (E4) is synthesized from the compound of formula (E3) by removing the protecting group of the two hydroxyl groups on the dihydropyran ring. This step can be carried out using the compound of formula (E3) as the starting material in a manner similar to that mentioned in Step B4.

By the synthetic method employed in this step, the ether compound of formula (E4) having the ether residue only at the hydroxyl group at the 3-position of the oxolane ring of the compound of formula (I) can be prepared.

The ether compound of formula (E4) thus obtained can, if necessary, be converted into an ester derivative by procedures mentioned later. That is, by reaction of the ether compound of formula (E4) with an esterification reagent, a derivative having the ether residue at the hydroxyl group at the 3-position of the oxolane ring and additionally, ester residue(s) introduced to the hydroxyl groups on the dihydropyran ring can be prepared.

[Method F]

In Method F, ester derivatives of formula (F2) of the compounds defined by the general formula (I) are synthesized.

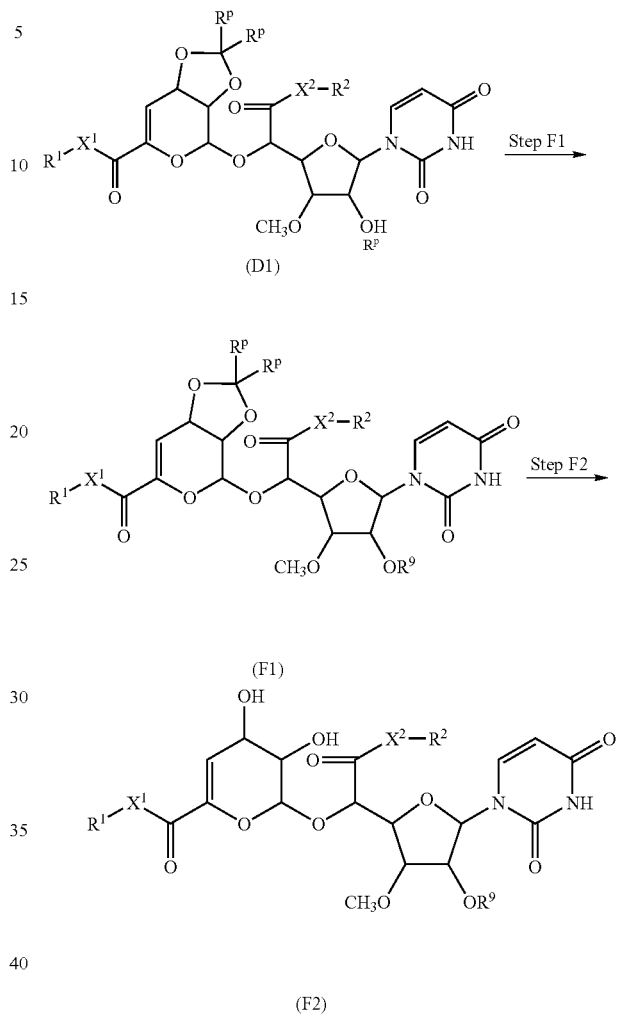

In the above reaction scheme, $R^1$, $R^2$, $X^1$, $X^2$ and Rp are as defined earlier, and $R^9$ is an ester residue defined earlier.

In Step F1, a compound of formula (F1) is synthesized from the compound of formula (D1) by introducing an ester residue to a hydroxyl group. This step is carried out by reaction of the compound (D1) with an acid halide or acid anhydride, either of which has a desired ester residue, in the presence of a base in an inert solvent.

The acid halide or acid anhydride used in this reaction is, for example, a compound having formula $R^aCO$—Y, $R^aCO_2CO_2R^{10}$, $R^aCO$—O—$COR^a$ or $R^aOCO$—Y [wherein $R^a$ is as defined earlier, Y is a halogen atom (a chlorine atom or bromine atom is preferred), and $R^{10}$ is an alkyl group having from 1 to 4 carbon atoms (an ethyl or propyl group is preferred)], a mixed acid anhydride prepared from formic acid and acetic acid, a cyclic acid anhydride such as succinic anhydride, glutaric anhydride, or adipic anhydride, or a compound having the formula $(R^{11a}O)(R^{11b}O)PO$—Y which is used as a phosphorylating agent [wherein Y is as defined above, and $R^{11a}$ and $R^{11b}$ are the same or different and each is an alkyl group having from 2 to 16 carbon atoms], and a compound having the formula $R^aCO$—Y, $R^aCO_2CO_2R^{10}$, $R^aCO$—O—$COR^a$ or $R^aOCO$—Y (wherein $R^a$, Y and $R^{10}$ are as defined above] is preferred.

Examples of the base employed include alkali metal hydroxides such as lithium hydroxide, sodium hydroxide or potassium hydroxide; alkali metal carbonates such as lithium carbonate, sodium carbonate or potassium carbonate; alkali metal hydrogencarbonates such as sodium hydrogencarbonate or potassium hydrogencarbonate; alkali metal alkoxides such as lithium methoxide, sodium methoxide, sodium ethoxide or potassium t-butoxide; or organic amines such as triethylamine, tributylamine, N-methylmorpholine, pyridine, 4-dimethylaminopyridine, picoline, lutidine, collidine, 1,5-diazobicyclo[4.3.0]non-5-ene or 1,8-diazabicyclo[5,4,0]undec-7-ene. Of these, organic amines are preferred, and triethylamine, tributylamine, pyridine or lutidine is particularly preferred. When liquid organic amines are employed in the reaction, a large excess of amine can be used since it can be also used as the reaction solvent.

Of the esterification reactions mentioned above, the phosphorylation reaction can be also carried out as follows. That is, the compound of formula (D1) is reacted with a phosphite having the desired ester residue in the presence of acid or base in an inert solvent, and subsequently the obtained intermediate is oxidized with an oxidizing agent to afford the desired phosphoric acid ester derivative.

The phosphite used in this reaction is, for example, a compound having a formula of $(R^{11a}O)(R^{11b}O)P-Z$ [wherein, $R^{11a}$ is an alkyl group having from 2 to 16 carbon atoms, $R^{11b}$ is an alkyl group having from 2 to 16 carbon atoms or a 2-cyanoethyl group, and Z is a halogen atom or a group having a formula of $-N(isopropyl)_2$].

When Z in the formula shown above is a halogen atom, the base defined earlier is used as the catalyst. On the other hand, when Z is not a halogen atom, any acid can be used as the catalyst provided that its acidity is comparable to that of acetic acid, and tetrazole is preferably used.

The oxidizing agent used in this reaction is, for example, m-chloroperbenzoic acid, t-butyl hydroperoxide or peracetic acid, and m-chloroperbenzoic acid is preferred.

The inert solvent employed in this reaction is not particularly limited provided that it has no effect on the reaction. Examples of the inert solvent employed include hydrocarbons such as hexane, benzene or toluene; halogenated hydrocarbons such as dichloromethane, chloroform, carbon tetrachloride or 1,2-dichloroethane; ethers such as ether, tetrahydrofuran or dioxane; ketones such as acetone or methyl ethyl ketone; nitrites such as acetonitrile; amides such as N,N-dimethylformamide, N,N-dimethylacetamide, N-methyl-2-pyrrolidone or hexamethylphosphoramide; sulfoxides such as dimethyl sulfoxide; or a mixture thereof, and hydrocarbons or amides are preferred.

The temperature of this reaction mainly depends on various factors such as the compound (D1) used as the starting material and the type of the acid halide and solvent used in the reaction. However, it is usually between −10° C. and 100° C., and is preferably between 0° C. and 50° C. The reaction time for the reaction mainly depends on the reaction temperature employed. It is usually from 10 min to two days, and is preferably from 30 min to 10 hr.

When a phosphite having the formula in which $R^{11b}$ is a 2-cyanoethyl group is used in the phosphorylation reaction, a phosphoric acid ester derivative having a 2-cyanoethyl group is obtained after the oxidation reaction. Subsequently, by hydrolysis of the 2-cyanoethyl group of the ester derivative by treatment with an aqueous basic solution such as ammonia solution, the corresponding mono-alkylphosphoric acid ester derivative is afforded.

Furthermore, the esterification reaction may also be carried out by reaction of the compound of formula (D1) with a carboxylic acid having the desired ester residue in the presence of a condensing agent in an inert solvent.

Examples of the condensing agent employed in this reaction are carbodiimides such as N,N'-dicyclohexylcarbodiimide, 1,1'-carbonyldiimidazole; or 1-(N,N-dimethylaminopropyl)-3-methylcarbodiimide hydrochloride; and N,N'-dicyclohexylcarbodiimide is preferred.

The inert solvent employed in this reaction is not particularly limited provided that it has no effect on the reaction. Examples of the inert solvent employed include hydrocarbons such as hexane, benzene or toluene; halogenated hydrocarbons such as dichloromethane, chloroform, carbon tetrachloride or 1,2-dichloroethane; ethers such as ether, tetrahydrofuran or dioxane; ketones such as acetone or methyl ethyl ketone; nitrites such as acetonitrile; amides such as N,N-dimethylformamide, N,N-dimethylacetamide, N-methyl-2-pyrrolidone or hexamethylphosphoramide; sulfoxides such as dimethyl sulfoxide; or a mixture thereof, and hydrocarbons, halogenated hydrocarbons or amides are preferred.

The temperature of this reaction mainly depends on various factors such as the compound of formula (D1) used as the starting material and type of carboxylic acid and solvent used in the reaction. However, it is usually between −10° C. and 100° C., and is preferably between 0° C. and 50° C. The reaction time for the reaction mainly depends on the reaction temperature employed. It is usually from 10 min to two days, and is preferably from 30 min to 10 hr.

After the reaction is complete, the desired compound of this reaction is isolated from the reaction mixture using a conventional technique. For example, the reaction mixture is neutralized appropriately or insoluble matter, if present, is removed by filtration, and the neutralized reaction mixture or the filtrate of the reaction mixture is evaporated under reduced pressure. The residue obtained is dissolved in an organic solvent that is immiscible with water such as ethyl acetate or dichloromethane, washed appropriately with dilute hydrochloric acid, aqueous sodium hydrogencarbonate or aqueous sodium chloride, dried over anhydrous magnesium sulfate or the like, and evaporated to give the desired product. The product thus obtained can, if necessary, be further purified by a conventional technique such as recrystallization, reprecipitation or chromatography.

In Step F2, a compound of formula (F2) is synthesized from the compound of formula (F1) by removing the protecting group of the two hydroxyl groups on the dihydropyran ring. This step can be carried out using the compound of formula (F1) as the starting material in a manner similar to that mentioned in Step B4.

By the synthetic method employed in this step, the ester derivative of formula (F2) having the ester residue only at the hydroxyl group at the 3-position of the oxolane ring of the compound (I) can be prepared.

In addition, an ester derivative having an ester residue at one or more hydroxyl groups of the dihydropyran ring, in addition to the ester residue at the hydroxyl group at the 3-position of the oxolane ring, can be prepared from the ester derivative of formula (F2) by reacting with an amount of one molar equivalent of the esterification agent. Furthermore, by reaction of the diester derivative thus obtained with an additional amount of one molar equivalent of the esterification agent, a derivative having ester residues at all the hydroxyl groups can be prepared. The ester residues in these derivatives thus synthesized may be the same or different.

On the other hand, a derivative having an ester residue at the hydroxyl group at the 3-position of the oxolane ring and ether residue(s) at the hydroxyl groups of the dihydropyran ring can be prepared from the ester derivative of formula (F2) by conducting the following reactions successively. That is, the uracil residue of the ester derivative of formula (F2) is protected with a protecting agent; subsequently, the intermediate obtained is reacted with an etherification agent;

and finally, the protecting group of the uracil residue is removed to afford the desired derivative.

Furthermore, a mixture of compounds of which one to three hydroxyl groups are esterified is obtained from the compound defined by the formula (I) by a reaction with amounts from one to three molar equivalents of the esterification agent. Subsequently, by the isolation and purification of the compounds in the mixture obtained above by column chromatography and the like, the derivative having only one esterified hydroxyl group, that having two esterified hydroxyl groups and that having three esterified hydroxyl groups can be afforded, respectively. As occasion demands, the ester derivative having two esterified hydroxyl groups and that having three esterified hydroxyl groups can be synthesized from the derivative having one esterified hydroxyl group or that having two esterified hydroxyl groups by reacting with amount of one or two molar equivalents of the esterification agent, respectively. The ester residues in these derivatives synthesized by either of the reactions mentioned above may be the same or different.

In addition, derivatives having both an ester residue and an ether residue can be synthesized from the derivative having one esterified hydroxyl group or that having two esterified hydroxyl groups, respectively, as follows. That is, the uracil residue of these derivatives used as starting substances is protected with a protecting agent; subsequently, the intermediate obtained are reacted with an etherification agent, and finally, the protecting group of the uracil residue is removed to afford the desired derivatives.

[Method G]

In Method G, a compound of formula (G3), which is a compound defined by the general formula (I), in which $X^2$ is an —NH— group and $R^3$ is a hydroxyl group, is synthesized.

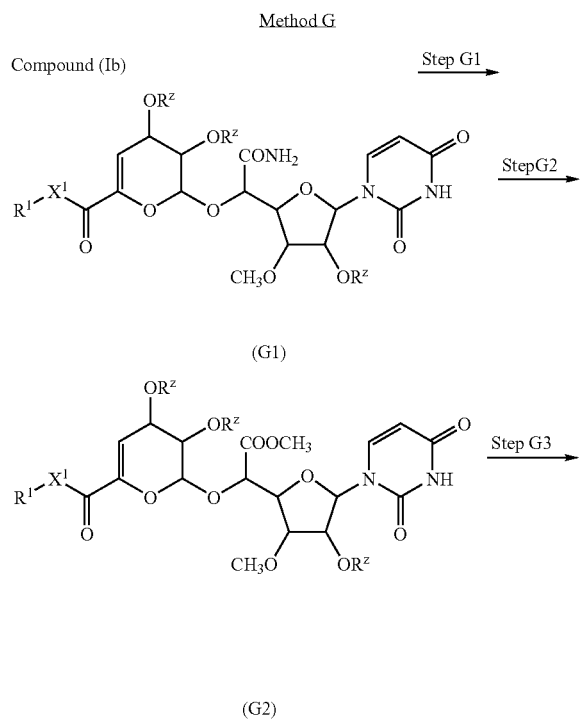

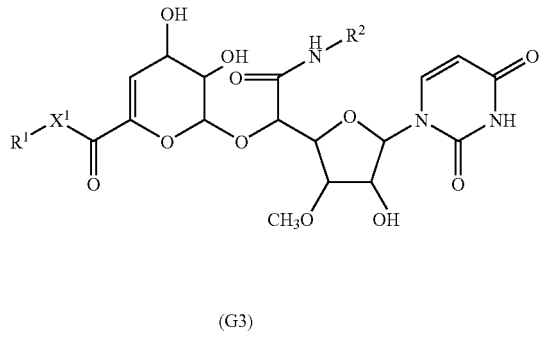

In the above reaction scheme, $R^1$, $R^2$, $X^1$ and $R^z$ are as defined earlier.

In Step G1, a compound of formula (G1) is synthesized by introducing a protecting group $R^z$ to a hydroxyl group of the compound of formula (Ib) prepared by Method B described previously. This step can be carried out using the compound of formula (Ib) as the starting substance in a manner similar to that mentioned previously in Step C1.

In Step G2, a compound of formula (G2) is synthesized by hydrolysis of the carbamoyl group of the compound of formula (G1) to a carboxyl group, followed by methylation of the carboxyl group. The hydrolysis reaction in this step is carried out in a manner similar to that mentioned in Step C2, and the methylation step is conducted by reaction of the obtained carboxylic acid compound with diazomethane in solvent.

Examples of the solvent used in the methylation reaction include dichloromethane, diethyl ether, tertahydrofuran and a mixture thereof, and a mixed solvent of dichloromethane and diethyl ether is preferred.

The temperature of this reaction mainly depends on the solvent employed in the reaction. However, it is usually between −20° C. and 100° C., and is preferably between 0° C. and 50° C.

The reaction time for the reaction mainly depends on the reaction temperature employed. It is usually from 5 min to 2 hr, and is preferably from 10 min to 30 min.

After the reaction is complete, the desired compound of this reaction is isolated from the reaction mixture using a conventional technique. For example, the reaction mixture is neutralized appropriately or insoluble matter, if present, is removed by filtration, and the neutralized reaction mixture or the filtrate of the reaction mixture is evaporated under reduced pressure. The residue obtained is dissolved in an organic solvent that is immiscible with water such as ethyl acetate or dichloromethane, washed appropriately with dilute hydrochloric acid, aqueous sodium hydrogencarbonate or aqueous sodium chloride, dried over anhydrous magnesium sulfate or the like, and evaporated to give the desired product. The product thus obtained can, if necessary, be further purified by a conventional technique such as recrystallization, reprecipitation or chromatography.

In Step G3, a compound of formula (G3) is synthesized by converting the ester moiety of the compound of formula (G2) into an amide moiety. This step is carried out by reaction of the compound of formula (G2) with an amine having the desired substituent group $R^2$ in a solvent.

The solvent used in this reaction is, for example, an alcohol such as methanol or ethanol, and methanol is preferred.

The temperature of this reaction mainly depends on various factors such as the amine and solvent used in the reaction. However, it is usually between 0° C. and 100° C., and is preferably between 20° C. and 50° C.

The reaction time for the reaction mainly depends on the reaction temperature employed. It is usually from 1 hr to 5 days, and is preferably from 10 hr to 2 days.

After the reaction is complete, the desired compound of this reaction is isolated from the reaction mixture using a conventional technique. For example, the reaction mixture is neutralized appropriately or insoluble matter, if present, is removed by filtration, and the neutralized reaction mixture or the filtrate of the reaction mixture is evaporated under reduced pressure. The residue obtained is dissolved in an organic solvent that is immiscible with water such as ethyl acetate or dichloromethane, washed appropriately with dilute hydrochloric acid, aqueous sodium hydrogencarbonate or aqueous sodium chloride, dried over anhydrous magnesium sulfate or the like, and evaporated to give the desired product. The product thus obtained can, if necessary, be further purified by a conventional technique such as recrystallization, reprecipitation or chromatography.

[Method H]

In Method H, an N-alkyl derivative of formula (H4) of the compound defined by the general formula (I) is synthesized.

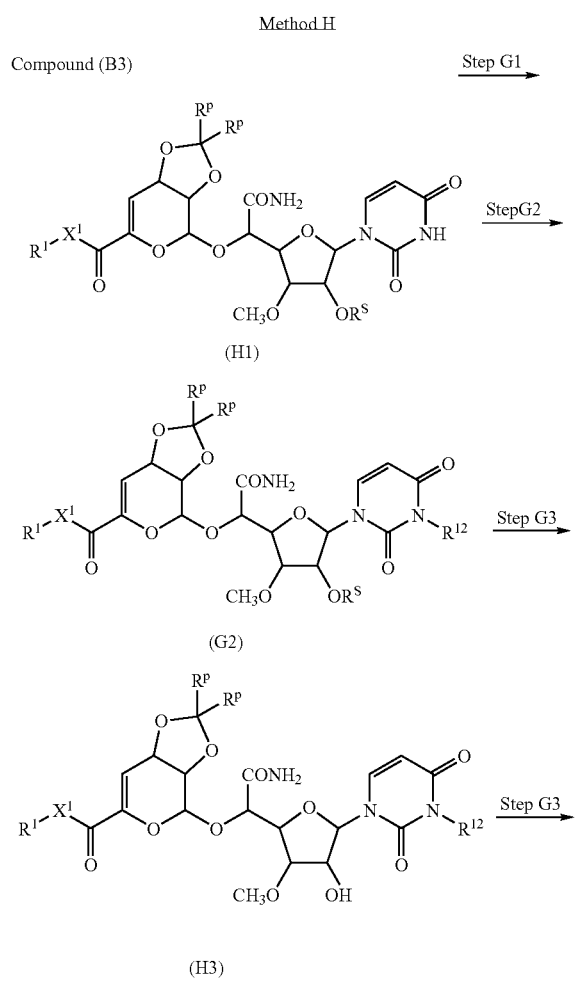

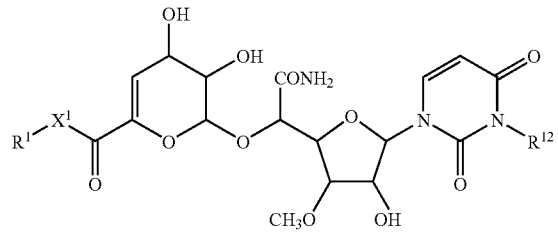

(H4)

In the above reaction scheme, $R^1$, $R^p$ and $X^1$ are as defined earlier; $R^s$ is a protecting group for a hydroxyl group (silyl groups), and trialkylsilyl groups such as the trimethylsilyl, triethylsilyl or t-butyldimethylsilyl groups are preferred, and the t-butylsilyl group is particularly preferred; and $R^{12}$ is a straight- or branched chain alkyl group having from 1 to 21 carbon atoms, a straight- or branched chain unsaturated alkyl group having from 2 to 21 carbon atoms, a 1-[($C_2$–$C_{20}$) alkanoyloxy]alkyl group having from 1 to 3 carbon atoms, or a 1-[($C_1$–$C_{20}$)alkoxycarbonyloxy]alkyl group having from 1 to 3 carbon atoms.

In Step H1, a compound of formula (H1) is synthesized by introducing a protecting group, $R^s$, into a hydroxyl group of the compound of formula (B3). In this step, the compound of formula (H1) is afforded by reaction of the compound of formula (B3) with a protecting agent for the hydroxyl group in the presence of a base in an inert solvent.

The protecting agent for the hydroxyl group employed in this reaction is, for example, a trialkylsilyl halide such as trimethylsilyl chloride or t-butyldimethylsilyl chloride; or a trialkylsilyl triflate such as t-butyldimethylsilyl triflate, and t-butyldimethylsilyl chloride is preferred.

The inert solvent employed in this reaction is, for example, a halogenated hydrocarbon such as dichloromethane or chloroform; dimethylformamide; dimethylacetamide; or pyridine; and dimethylformamide or pyridine is preferred.

Examples of the base employed in this reaction include imidazole, pyridine or 4-dimethylaminopyridine, and imidazole or pyridine is preferred.

The temperature of this reaction mainly depends on the solvent used in the reaction. However, it is usually between −20° C. and 100° C., and is preferably between 0° C. and 50° C.

The reaction time for the reaction mainly depends on the reaction temperature employed. However, it is usually from 30 min to 1 day, and is preferably from 1 hr to 5 hr.

After the reaction is complete, the desired compound of this reaction is isolated from the reaction mixture using a conventional technique. For example, the reaction mixture is neutralized appropriately or insoluble matter, if present, is removed by filtration, and the neutralized reaction mixture or the filtrate of the reaction mixture is evaporated under reduced pressure. The residue obtained is dissolved in an organic solvent that is immiscible with water such as ethyl acetate or dichloromethane, washed appropriately with dilute hydrochloric acid, aqueous sodium hydrogencarbonate or aqueous sodium chloride, dried over anhydrous magnesium sulfate or the like, and evaporated to give the desired product. The product thus obtained can, if necessary, be further purified by a conventional technique such as recrystallization, reprecipitation or chromatography.

In Step H2, a compound of formula (H2) is synthesized by introducing the desired alkyl group ($R^{12}$) to the nitrogen atom at the 3-position of the uracil residue of the compound of formula (H1). In this step, the compound of formula (H2) is afforded by reaction of the compound of formula (H1) with an N-alkylating agent in the presence of a base in an inert solvent.

The N-alkylating agent preferably used in this reaction is an alkyl halide such as an alkyl chloride, alkyl bromide or alkyl iodide.

Examples of the base used in this reaction include alkali metal carbonates such as sodium carbonate or potassium carbonate; sodium hydrogencarbonate; alkali metal hydrides such as sodium hydride or lithium hydride; or tertiary amines such as 1,8-diazabicyclo[5,4,0]undec-7-ene (DBU) or 1,5-diazobicyclo[4.3.0]non-5-ene (DBN), and potassium carbonate or DBU is preferred.

The inert solvent employed in this reaction is, for example, a halogenated hydrocarbon such as dichloromethane or chloroform; dimethylformamide; dimethylacetamide; or pyridine, and dimethylformamide is preferred.

The temperature of this reaction mainly depends on the solvent used in the reaction. However, it is usually between −20° C. and 120° C., and is preferably between 20° C. and 80° C.

The reaction time for the reaction mainly depends on the reaction temperature employed. However, it is usually from 1 hr to 1 day, and is preferably from 3 hr to 10 hr.

After the reaction is complete, the desired compound of this reaction is isolated from the reaction mixture using a conventional technique. For example, the reaction mixture is neutralized appropriately or insoluble matter, if present, is removed by filtration, and the neutralized reaction mixture or the filtrate of the reaction mixture is evaporated in under reduced pressure. The residue obtained is dissolved in an organic solvent that is immiscible with water such as ethyl acetate or dichloromethane, washed appropriately with dilute hydrochloric acid, aqueous sodium hydrogencarbonate or aqueous sodium chloride, dried over anhydrous magnesium sulfate or the like, and evaporated to give the desired product. The product thus obtained can, if necessary, be further purified by a conventional technique such as recrystallization, reprecipitation or chromatography.

In Step H3, a compound of formula (H3) is synthesized by removal of the protecting group, $R^s$, of the hydroxyl group of the compound of formula (H2). This step is carried out by reaction of the compound (H2) with an agent for removal of the protecting group $R^s$ in an inert solvent.

The agent for removal of the protecting group $R^s$ used in this reaction is, for example, tetrabutylammonium fluoride or cesium fluoride, and tetrabutylammonium fluoride is preferred.

The inert solvent used in this reaction is, for example, tetrahydrofuran, diethyl ether or acetonitrile, and tetrahydrofuran is preferred.

The temperature of this reaction mainly depends on the solvent used in the reaction. However, it is usually between −20° C. and 100° C., and is preferably between 0° C. and 50° C.

The reaction time for the reaction mainly depends on the reaction temperature employed. However, it is usually from 30 min to 10 hr, and is preferably from 1 hr to 3 hr.

After the reaction is complete, the desired compound of this reaction is isolated from the reaction mixture using a conventional technique. For example, the reaction mixture is neutralized appropriately or insoluble matter, if present, is removed by filtration, and the neutralized reaction mixture or the filtrate of the reaction mixture is evaporated under reduced pressure. The residue obtained is dissolved in an organic solvent that is immiscible with water such as ethyl acetate or dichloromethane, washed appropriately with dilute hydrochloric acid, aqueous sodium hydrogencarbonate or aqueous sodium chloride, dried over anhydrous magnesium sulfate or the like, and evaporated to give the desired product. The product thus obtained can, if necessary, be further purified by a conventional technique such as recrystallization, reprecipitation or chromatography.

In step H4, a compound of formula (H4) is synthesized from the compound of formula (H3) by removal of the protecting group, $R^p$, of the two hydroxyl groups on the dihydropyran ring. This step can be carried out using the compound (H3) as the starting substance in a manner similar to that mentioned in the Step B4.

On the other hand, Compounds (VI) and (VII), which are used as starting materials in Methods A to C, are available by the method described in WO0/02892. In other words, they are obtained by culturing a microorganism belonging to the *Streptomyces* spp., producing the said compounds in a proper medium, and then collecting the compounds from the cultured broth. *Streptomyces griseus* Strain SANK60196 (which will hereinafter be called "Strain SANK60196"), which is a preferred microorganism capable of producing Compounds (VI) and (VII), has been collected and separated from the soil of Mt. Tsukuba/Ibaraki-ken in a manner known to those skilled in the art. The mycological properties of Strain SANK60196 are as follows:

1) Morphological Appearance

Strain SANK60196 showed the morphological appearance as described below after cultivation at 28° C. for 14 days on a medium specified by the International *Streptomyces* Project (which will hereinafter be abbreviated as "ISP") (refer to Shirling, E. B. and Gottlieb, D., Int. J. Syst. Bacteriol. 16, 313–340 (1996)). Observation through an optical microscope indicates that the substrate mycelia of SANK60196 are favorably grown and branched and show yellowish gray, yellowish brown or pale olive color, but are different from the strain belonging to *Nocardia* spp., in that they are free from cleavage or zigzag extension. Aerial mycelia exhibit simple branching. The form of the spore chain is straight or curved and its chain is formed of 10 to 50 or greater spores. Observation through a scanning electron microscope shows that the spore has an oval shape and it has a smooth surface structure. The spore is 0.6–0.8× 0.7–1.2 mm in dimension. The spore is formed only on the aerial mycelia. Formation of sporangia, axial division of aerial mycelia, cleavage of aerial mycelia and sclerotia are not recognized.

2) Growth Characteristics on Various Culture Media

The growth characteristics of Strain SANK60196 on an agar medium after cultivation at 28° C. for 14 days are as described below in Table 4. In the Table, the composition of the medium attached with ISP No. is as specified by ISP. In the items, the abbreviations G, AM, R and SP stand for growth, aerial mycelia, reverse color and soluble pigment, respectively. The color tone is described in accordance with "Color Standards", ed. by Japan Color Laboratory. The indication of the color tone in parentheses is a color number in accordance with the Munsell color system. The pale yellow soluble pigment produced in a water-agar medium changes into colorless by 0.05N hydrochloric acid, but shows no change by 0.05N aqueous sodium hydroxide.

(Table 4)

Nature of Medium;
  Item: characteristics

Yeast extract•malt extract agar (ISP 2);
  G: Excellent, flat, yellowish brown (10YR 5/6)
  AM: Abundantly formed, velvety, pale brown (2.5Y 8/2)
  R: Yellowish brown (10YR 5/8)
  SP: Yellowish brown (10YR 6/8)

Oatmeal—agar (ISP 3);
  G: Excellent, flat, yellowish brown (2.5Y 6/6)
  AM: Abundantly formed, velvety, pale yellowish orange (5Y 9/2)
  R: Dark yellow (2.5Y 8/8)
  SP: Not produced Starch•inorganic salt agar (ISP 4);
  G: Good, flat, yellowish brown (2.5Y 6/4)
  AM: Abundantly formed, velvety, yellowish gray (7.5Y 9/2)
  R: Yellowish brown (2.5Y 6/4)

Glycerin•asparagine agar (ISP 5);
  G: Excellent, flat, pale yellowish brown (2.5Y 7/6)
  AM: Abundantly formed, velvety, yellowish gray (5Y 8/2)
  R: Pale yellowish brown (2.5Y 8/6)
  SP: Not produced Peptone•yeast extract•iron agar (ISP 6);
  G: Excellent, flat, pale olive color (5Y 8/3)
  AM: Slightly produced, velvety, yellowish gray (5Y 9/1)
  R: Pale yellow (5Y 8/6)
  SP: Not produced Tyrosine agar (ISP 7);
  G: Good, flat, grayish yellow brown (2.5Y 5/4)
  AM: Abundantly formed, velvety, light olive gray (7.5Y 8/2)
  R: Yellowish brown (10YR 5/4)
  SP: Grayish yellow brown (2.5Y 4/3)

Sucrose•nitrate agar;
  G: Not so good, flat, pale yellow (5Y 8/6)
  AM: Abundantly formed, velvety, light olive gray (7.5Y 8/2)
  R: Dark yellow (5Y 8/8)
  SP: Pale yellow (5Y 9/6)

Glucose•asparagine agar;
  G: Good, flat, pale yellow (5Y 9/3)
  AM: Not so good, velvety, yellowish gray (5Y 9/1)
  R: Yellowish gray (7.5Y 9/3)
  SP: Not produced Nutrient agar (product of Difco Laboratories);
  G: Good, flat, pale yellowish brown (2.5Y 8/3)
  AM: Good, velvety, yellowish gray (5Y 9/1)
  R: Yellowish gray (5Y 9/4)
  SP: Not produced Potato extract•carrot extract agar;
  G: Not so good, flat, yellowish gray (7.5Y 9/2)
  AM: Not so good, velvety, yellowish gray (5Y 9/2)
  R: yellowish gray (7.5Y 9/3)
  SP: Yellowish gray (7.5Y 9/3)

Water agar;
  G: Not good, flat, yellowish gray (5Y 9/1)
  AM: Not good, velvety, yellowish gray (5ZY 9/1)
  R: Yellowish gray (7.5Y 9/4)
  SP: Pale yellow (5Y 9/6)

3) Physiological Characteristics

The physiological characteristics of the present strain observed for 2 to 21 days after cultivation at 28° C. are as shown in Table 5. In the Table, Medium 1 is a yeast extract malt extract agar medium (ISP 2).

TABLE 5

| | |
|---|---|
| Hydrolysis of starch | positive |
| Liquefaction of gelatin | positive |
| Reduction of nitrates | positive |
| Coagulation of milk | negative |
| Peptonization of milk | positive |
| Formation of melanine-like pigment | positive |
| Substrate decomposition: | positive |
| casein | positive |
| tyrosine | positive |
| xanthine | negative |
| Growth temperature range (Medium 1) | 6 to 35° C. |
| Optimum growth temperature (Medium 1) | 18 to 30° C. |
| Growth in the presence of salt (Medium 1) | 10% |

Assimilation of a carbon source by Strain SANK60196 observed after cultivation at 28° C. for 14 days on a Pridham-Gottlieb agar medium (ISP 9) is as described in Table 6. In the table, "+" means assimilable, while "−" means non-assimilable.

TABLE 6

| | |
|---|---|
| D-glucose | + |
| L-arabinose | − |
| D-xylose | + |
| Inositol | − |
| D-mannitol | + |
| D-fructose | + |
| L-rhamnose | − |
| Sucrose | − |
| Raffinose | − |
| Control | − |

4) Chemotaxonomic Properties

The cell wall of the present strain was investigated in accordance with the method of Hasegawa, et al. (refer to Hasegawa, T., et al., *The Journal of General and Applied Microbiology,* 29, 319–322 (1983)), resulting in the detection of L,L-diaminopimelic acid. The main sugar component in the whole cells of the present strain was investigated in accordance with the method of M. P. Lechevalier (refer to Lechevalier, M. P., *Journal of Laboratory and Clinical Medicine,* 71, 934–944 (1968)). As a result, no characteristic component was detected.

The above-described mycological properties have revealed that the present strain belongs to *Streptomyces* spp. among the *Actinomyces*. It has been made clear that the present strain is markedly related to *Streptomyces griseus*, as a result of comparison with the the microorganism described in the ISP strains by Shirling and Gottlieb (refer to Shirling, E. B. and Gottlieb, D., *International Journal of Systematic Bacteriology,* 18, 68–189 and 279–392 (1968); 19, 391–512 (1969); 22, 265–394 (1972)), the microorganism described in "The actinomycetes Vol. 2" written by Waksman (refer to Waksman, S. A., "The actinomycetes 2 (1961)"), the microorganism described in Bergey's Manual edited by Buchanan and Gibbons (refer to R. E. Buchanan and N. E. Gibbons, "Bergey's Manual of Determinative Bacteriology", 8th edition (1974)), the microorganism described in "Bergey's Manual of Systematic Bacteriology", edited by Williams (refer to Williams, S. T., et al., "Bergey's Manual of Systematic Bacteriology 4 (1989)") and the microorganism described in the recent literature about *Actinomyces* belonging to *Streptomyces* spp. It has however been recognized to be different from *Streptomyces griseus*, because it produces a yellowish gray soluble pigment on a glycerin asparagine agar medium and a pale yellowish brown soluble pigment on a peptone yeast extract iron agar medium but produces a soluble pigment neither on a potato extract carrot extract agar medium nor on a water agar medium; the maximum growth temperature is 40° C.; and it is grown in the presence of 7% of salt.

The present strain having such mycological characteristics is considered to be a novel strain different from *Streptomyces griseus*, but it is impossible to distinguish them based on only the above-described differences. The present inventors therefore identified the present strain as *Streptomyces griseus* SANK60196.

This strain was internationally deposited with Agency of Industrial Science and Technology, Ministry of International Trade and Industry (1–3, Higashi 1-chome, Tsukuba-shi, Ibaraki-ken, 305; JAPAN) as of Feb. 22, 1996 and deposited under the name of FERM BP-5420.

A description of Strain SANK60196 is given above. It is known that various properties of *Actinomyces* are not fixed but easily change naturally or artificially. The strain usable in the present invention embraces all such variants. In other words, the present invention embraces all strains belonging to the *Streptomyces* spp. and capable of producing the compounds of formulae (VI) or (VII).

As a medium usable for cultivation of microorganisms capable of producing the compounds of formulae (VI) or (VII) of the present invention, any synthetic or natural medium can be used insofar as it contains, as needed, a substance selected from carbon sources, nitrogen sources, inorganic ions and organic nutrition sources.

As such nutrition sources, known carbon sources, nitrogen sources and inorganic salts conventionally employed for the cultivation of a strain of the *Eumycetes* or *Actinomycetes* and are assimilable by a microorganism can be used.

Specific examples of carbon sources include glucose, fructose, maltose, sucrose, mannitol, glycerol, dextrin, oats, rye, corn starch, potato, corn flour, soybean powder, cotton seed oil, thick malt syrup, theriac, soybean oil, citric acid and tartaric acid. They may be used either singly or in combination. The amount of the carbon source to be added usually varies, but is not limited to, within a range of from 1 to 10 wt. % of the amount of the medium.

As the nitrogen source, a substance containing protein or hydrolyzates thereof can usually be employed. Preferred examples of the nitrogen source include soybean powder, wheat bran, peanut flour, cotton seed flour, skimmed milk, casein hydrolyzate, Farmamine (product of Sheffield Chemical), fish flour, corn steep liquor, peptone, meat extract, raw yeast, dry yeast, yeast extract, malt extract, potato, ammonium sulfate, ammonium nitrate and sodium nitrate. It is preferred to use the nitrogen source either singly or in combination in an amount ranging from 0.2 to 6 wt. % of the amount of the medium.

As the nutrition inorganic salt, ordinarily employed salts from which an ion is available, such as sodium salts, ammonium salts, calcium salts, phosphates, sulfates, chlorides and carbonates can be used. In addition, trace metals such as potassium, calcium, cobalt, manganese, iron and magnesium are usable.

For the production of the compounds of formulae (VI) or (VII), the addition of cobalt, skimmed milk or yeast extract is particularly effective.

Upon culturing the microorganism capable of producing the compounds of formulae (VI) and (VII), an antibiotic biosynthesis inhibitor can be added. The compounds of formulae (VI) and (VII) can be produced, for example, by using, as a medium additive, S-(2-aminoethyl)-L-cysteine or a salt thereof which is an aspartate kinase inhibitor, singly or in combination with cobalt, skimmed milk or yeast extract. A combination of the said medium additive with skimmed milk especially accelerates production of the compounds of formulae (VI) and (VII). The additive can be added to give its final concentration ranging from 1 to 100 mM. Preferably, use of it to give a final concentration of 10 mM permits favorable production of the compounds of formulae (VI) and (VII).

Upon liquid culture, a silicone oil, vegetable oil or surfactant can be added as an antifoamer.

The medium used for the cultivation of Strain SANK60196 to produce the compounds of formulae (VI) and (VII) preferably has a pH of 5.0 to 8.0.

The growth temperature of Strain SANK60196 is 12 to 36° C. It is preferred to cultivate the strain at 18 to 28° C. in order to produce the compounds of formulae (VI) and (VII), of which 19 to 23° C. is more preferred.

The compounds of formulae (VI) and (VII) are available by aerobic culture of Strain SANK60196. As such a culturing method, ordinarily-employed solid culture, shake culture, and aeration agitation culture can be used.

For small-scale culturing, agitation culture for several days at 19 to 23° C. is preferred. Culturing is started from a growing step of seed cultures in the first to second stage in an Erlenmeyer flask equipped with a baffle (water flow adjusting wall) or an ordinarily-employed Erlenmeyer flask. As a medium in the seed culture growing stage, a carbon source and a nitrogen source can be used in combination. The seed flask may be shaken at 19 to 23° C. for 5 days in a thermostat incubator or shaken until the seed cultures grow sufficiently. The seed cultures thus grown are used for inoculation on the second seed medium or a production medium. When the seed cultures under an intermediate growing step are used, they are allowed to grow essentially in a similar manner, followed by inoculation of a part of them on a production medium. The flask into which the seeds have been inoculated is subjected to shake culture at a constant temperature for several days and after completion of the culturing, the cultured product in the flask is centrifuged or filtered.

For large-scale culturing, on the other hand, culturing in a jar fermenter or tank equipped with a stirrer and an aeration apparatus is preferred. Prior to culturing in such a container, the culture medium is heated at 121 to 130° C. for sterilization. After cooling, the seed cultures which have been allowed to grow in advance by the above-described method are inoculated on the sterilized medium. Then, aeration and agitation is effected at 19 to 23° C. for culturing. This method is suited for obtaining a large amount of the desired compounds.

The compounds of formulae (VI) and (VII) can be produced by adding, as an aspartate kinase inhibitor, an aqueous solution of S-(2-aminoethyl)-L-cysteine or salt thereof which has been filter sterilized in advance to a sterilized medium at the commencement of the cultivation or during cultivation.

The amount of the compounds of formulae (VI) and (VII) produced with the passage of cultivation can be measured by sampling a portion of the cultured broth and subjecting it to high performance liquid chromatography. The production amount of the compounds of formulae (VI) and (VII) usually reaches a peak in 3 to 15 days.

After completion of the cultivation, the cell component is separated from the cultured broth by filtration with the aid of diatomaceous earth or by centrifugation. The compounds of formulae (VI) and (VII) present in the filtrate or supernatant are purified by utilizing its physicochemical properties with HPLC analytical data as an index. As diatomaceous earth, "Celite 545" (trade name; product of Celite Corporation) is preferably used. The compounds of formulae (VI) and (VII) present in the filtrate can be purified by using adsorbents singly or in combination, for example, activated charcoal and an adsorbing resin such as "Amberlite XAD-2 or XAD-4" (trade name; product of Rohm & Haas), and "Diaion HP-10, HP-20, CHP-20P, HP-50 or SP207" (trade name; product of Mitsubishi Chemical). The compounds of formulae (VI) and (VII) can be separated by causing a solution containing them to pass through the layer of such an adsorbent, and removing the impurities adsorbed thereto from the solution; or by eluting the adsorbed compounds with aqueous methanol, aqueous acetone, aqueous normal butanol, aqueous ammonia, aqueous methanol containing ammonia or aqueous acetone containing ammonia.

The compounds of formulae (VI) and (VII) thus obtained can be purified by adsorption column chromatography using a carrier such as silica gel, "Florisil" (trade name), "Cosmosil" (trade name; product of Nacalai Tesque), or "Diaion CHP-20P or SP207" (trade name; product of Mitsubishi Chemical); gel filtration chromatography using "Sephadex GH-10" (trade name; product of Pharmacia Biotech) or "Toyopearl HW40F" (trade name; product of TOSOH Corp); anion exchange chromatography using "Dowex1 or SBR-P" (trade name; product of Dow Chemical) or "Diaion PA316" (trade name; product of Mitsubishi Chemical), or high performance liquid chromatography using a normal phase or reversed phase column; or the like.

The compounds of formulae (VI) and (VII) according to the present invention can be separated and purified by using the above-exemplified separation and purification means singly or in combination as needed, or in some cases, by using one of them in repetition.

Typical preparation processes for the compounds of formula (I), an ester, ether or N-alkyl derivative thereof, and the compounds of formulae (VI) and (VII) which are used as a starting material have been described above, but preparation processes are not limited thereto and other processes already known to those skilled in the art may also be employed.

Compounds of formula (I), esters, ethers and N-alkyl derivatives thereof thus obtained are novel compounds not published in the literature and show potent antibacterial activity against Gram-positive and Gram-negative bacteria. Examples of Gram-positive bacteria against which these compounds are expected to show potent antibacterial activity, include *Mycobacteria* such as *Mycobacterium smegmatis, Mycobacterium avium, Mycobacterium intracellulae, Mycobacterium kansaii, Mycobacterium marinum, Mycobacterium scrofulaceum, Mycobacterium chelonae, Mycobacterium fortuitum* and *Mycobacterium tuberculosis*; *Bacillus subtilis* and Gram-positive cocci such as *Staphylococcus aureus, Streptococcus pyrogenes, Streptococcus pneumoniae, Enterococcus faecalis* and *Enterococcus faecium*. Examples of Gram-negative bacteria against which these compounds are expected to show potent antibacterial activity, include *Moraxella catarrhalis* and *Haemophilus influenzae*. Out of these, more potent antibacterial activity is demonstrated against *Mycobacteria*, particularly *Mycobacterium avium, Mycobacterium intracellulae, Mycobacterium kansaii* and *Mycobacterium tuberculosis*.

Their growth inhibitory activity against general Gram positive bacteria or Gram negative bacteria can be determined by the disk assay method using normal agar medium (product of Eiken Chemical) or heart infusion agar medium (product of Difco Laboratories). Growth inhibitory activity against *Mycobacteria*, Gram positive bacteria belonging to the *Actinomycetales*, can be determined similarly on the above-described medium added further with glycerin.

Typical evaluation methods of biological activity of Compound (I) are described above, but the evaluation method is not limited thereto: other evaluation methods already known to those skilled in the art can also be employed.

The compound of formula (I) of the present invention, a pharmaceutically acceptable ester, ether or N-alkyl derivative thereof, or a pharmaceutically acceptable salt thereof, may be administered alone or as a mixture of said compound and a pharmaceutically acceptable carrier, such as an excipient or diluent in various forms which include tablets, capsules, granules, powders, syrups, injections, ointments, liquids and solutions, suspensions, aerosols, troches and the like, to a warm-blooded animal, such as a human. Medicaments of the present invention can be administered orally or parenterally. But it is preferable that Compound (I), an active component or a pharmaceutically acceptable salt thereof is administered by delivery to the lung or airway (including spraying in the mouth and intranasal administration).

These formulations can be prepared, in a conventional manner, by adding, to a medicament, ordinarily employed carriers known in the field of pharmaceutical formulation technique such as an excipient, binder, disintegrator, lubricant, corrigent, adjuvant for solubilization, suspending agent, coating agent and/or the like.

For the formation of tablets, various carriers known conventionally in this field can be employed. Examples include excipients such as lactose, sucrose, sodium chloride, glucose, urea, starch, calcium carbonate, kaolin, crystalline cellulose and silicic acid; binders such as water, ethanol, propanol, simple syrup, glucose solution, starch solution, gelatin solution, carboxymethylcellulose, shellac, methylcellulose, potassium phosphate and polyvinyl pyrrolidone; disintegrators such as dry starch, sodium alginate, agar powder, laminaran powder, sodium bicarbonate, calcium carbonate, polyoxyethylene sorbitan fatty acid ester, sodium lauryl sulfate, stearic acid monoglyceride, starch and lactose; disintegration suppressants such as sucrose, stearin, cacao butter and hydrogenated oil; absorption facilitators such as quaternary ammonium salts and sodium lauryl sulfate; humectants such as glycerin and starch; adsorbents such as starch, lactose, kaolin, bentonite and colloidal silicic acid; and lubricants such as purified talc, stearates, boric acid powder and polyethylene glycol. Tablets can be formed as those having ordinary coating as needed such as sugar coated tablets, gelatin encapsulated tablets, enteric coated tablets, film coated tablets, or double or multiple layer tablets.

For the formation of pills, various carriers conventionally known in this field can be used. Examples include excipients such as glucose, lactose, cacao butter, starch, hardened vegetable oil, kaolin and talc; binders such as gum arabic powder, tragacanth powder, gelatin and ethanol; and disintegrators such as laminaran agar.

For the formation of suppositories, various carriers conventionally known in this field can be employed. Examples include polyethylene glycol, cacao butter, higher alcohols and esters thereof, gelatin and semi-synthetic glyceride.

Upon formulation as injections, it is preferred that solutions or suspensions are sterilized and they are made isotonic with the blood. Solutions, emulsions or suspensions can be formed using any diluent conventionally used in this field. Examples include water, ethanol, propylene glycol, ethoxylated isostearyl alcohol, polyoxylated isostearyl alcohol and polyoxyethylene sorbitan fatty acid ester. It is also possible to incorporate, in a pharmaceutical preparation, salt, glucose or glycerin in an amount sufficient for preparing an isotonic solution, or to add an ordinarily employed adjuvant for solubilization, buffer, soothing agent and/or the like.

When liquids and solutions, and suspensions are used for a pulmonary drug delivery system, aqueous solutions and suspensions are adopted and they are prepared using water alone (for example, sterilized or pyrogen-free water) or water and a physiologically acceptable solvent (for example ethanol, propylene glycol, and polyethylene glycol including PEG 400). It is also possible to incorporate, in liquids and solutions, and suspensions, additional excipients including antiseptics (for example benzalkonium chloride), adjuvants for solubilization (for example polysorbate)/surfactants (for example Tween 80, Span 80, benzalkonium chloride), buffers, isotonicity regulating agents (for example sodium chloride), absorption facilitators, viscosity increasing agents and/or the like. It is also possible to incorporate, in suspensions, suspending agents (for example fine crystalline cellulose and sodium carboxymethylcellulose). Liquids and solutions, and suspensions are directly administered intranasally or sprayed in the mouth by ordinary methods using syringes, pipettes and atomizers. These pharmaceutical preparations can be administered as single or multiple doses. In the latter case, use of a dose measuring device is preferable. When a syringe or pipette is used, the dose needed for a patient can be administered by application of a prescribed volume of liquids and solutions, and suspensions. When an atomizer is used, it works with a metered-dose spray pump as a dose measuring device. Administration to the airway or lung can be performed by a pressurized aerosol canister with a chlorofluorocarbon (CFC, for example dichlorodifluoromethane, trichlorofluoromethane or dichlorotetrafluoroethane), carbon dioxide or another suitable gas propellant. An aerosol formulation containing surfactants such as lecithin is preferred. The dose can be controlled by a metered valve.

For the formation of powders for a pulmonary drug delivery system, the compound may be mixed with dry powder. Examples include lactose, starch and starch derivatives (for example hydroxypropylmethylcellulose), and polyvinylpyrrolidone (PVP). It is preferable that carrier particles form gel in nasal. Powders can be administered in a unit dose form such as a capsule or cartilage which is made of gelatin, or a blister pack (from which powders can be administered using an inhaler). In powders for a pulmonary delivery system including nasal formulations, the particle size is generally small, for example, not more than 5 μm. The particle size can be obtained by methods already known in the art, such as ultra-pulverization. If necessary, powders which continuously release an active ingredient may be used.

If necessary, a colorant, preservative, flavor, sweetener or other medicaments may be incorporated.

There is no particular limitation on the content of the compound incorporated as an active ingredient in the above-described pharmaceutical preparation. It can be chosen suitably from a wide range. In general, it is desired to be contained in an amount of 1 to 70 wt. %, preferably 1 to 30 wt. % in the whole composition.

There is no particular limitation on the method of administration of the above-described pharmaceutical preparation and it is determined depending on the dosage form or age, sex or other conditions of a patient (such as a human patient) to be administered or seriousness of the disease of the patient. For example, tablets, pills, solutions, suspensions, emulsions, granules or capsules are administered orally. Injections are administered intravenously either alone or as a mixture with an ordinarily employed fluid such as glucose or an amino acid. If necessary, they are alone administered intramuscularly, subcutaneously, intracutaneously or intraperitoneally. A suppository is administered rectally.

Although the dose of the active ingredient differs with the conditions, age, and weight of the patient, administration route or dosage form, the daily dose usually ranges from 2000 mg (preferably 100 mg) as the upper limit to 0.1 mg (preferably 1 mg, more preferably 10 mg) as the lower limit per adult. It can be administered once or in several portions a day according to the conditions.

EXAMPLES

The present invention will hereinafter be described in more detail by way of the Examples, Test Examples and Preparation Examples below.

Example 1

Exemplification Compound Number 6306

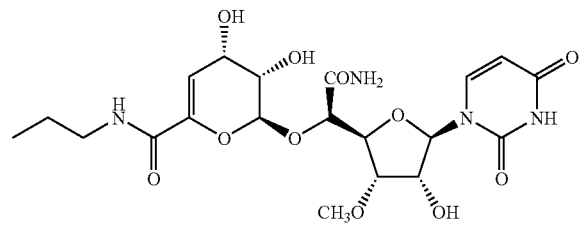

To a solution of the compound of formula (VI) (57 mg) in methanol (1.5 mL) was added n-propylamine (99 μL) and the mixture was stirred at room temperature. After 2 days, the solvent was evaporated under reduced pressure. The residue was purified by high performance liquid chromatography (HPLC; Intersil PREP-ODS, 30×250 mm) using 12% aqueous acetonitrile as the eluant. The aqueous solution was lyophilized to give the desired compound (41 mg).

$^1$H NMR (CD$_3$OD) δ ppm: 7.87 (d, J=8.1 Hz, 1H), 5.94 (d, J=2.5 Hz, 1H), 5.80 (d, J=4.3 Hz, 1H), 5.75 (d, J=8.1 Hz, 1H), 5.21 (d, J=4.4 Hz, 1H), 4.69 (d, J=2.1 Hz, 1H), 4.50 (dd, J=2.0 and 5.2 Hz, 1H), 4.38 (t, J=3.9 Hz, 1H), 4.24 (t, J=4.6 Hz, 1H), 4.03 (m, 1H), 3.70 (t, J=5.1 Hz, 1H), 3.37 (s, 3H), 3.24 (m, 2H), 1.57 (m, 2H), 0.93 (t, J=7.5 Hz, 3H).

IR (KBr) ν cm$^{-1}$: 3360, 2963, 2935, 2878, 2835, 1685, 1535, 1463, 1387, 1267, 1139, 1116, 1094, 1058, 1023, 978.

Example 2

Exemplification Compound Number 6321

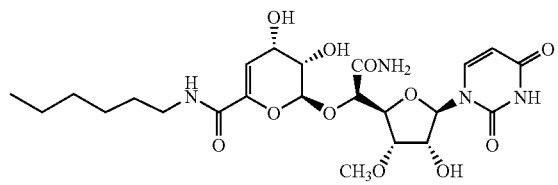

To a solution of the compound of formula (VI) (47 mg) in methanol (1 mL) was added n-hexylamine (132 μL) and the mixture was stirred at room temperature. After 2 days, the solvent was evaporated under reduced pressure. The residue was purified by high performance liquid chromatography (HPLC; Intersil PREP-ODS, 30×250 mm) using 50% aqueous acetonitrile as the eluant. The aqueous solution was lyophilized to give the desired compound (23 mg).

$^1$H NMR (CD$_3$OD) δ ppm: 7.86 (d, J=8.1 Hz, 1H), 5.94 (d, J=2.5 Hz, 1H), 5.80 (d, J=4.3 Hz, 1H), 5.75 (d, J=8.1 Hz, 1H), 5.21 (d, J=4.4 Hz, 1H), 4.69 (d, J=2.1 Hz, 1H), 4.50 (dd, J=1.8 and 5.4 Hz, 1H), 4.38 (t, J=3.9 Hz, 1H), 4.23 (t, J=4.6 Hz, 1H), 4.03 (m, 1H), 3.70 (t. J=5.1 Hz, 1H), 3.37 (s, 3H), 3.25 (m, 2H), 1.54 (m, 2H), 1.33 (m, 6H), 0.91 (t, J=6.7 Hz, 3H).

IR (KBr) ν cm$^{-1}$: 3352, 2956, 2931, 2872, 2858, 1685, 1532, 1464, 1386, 1267, 1137, 1115, 1094, 1058, 992.

Example 3

Exemplification Compound Number 6336

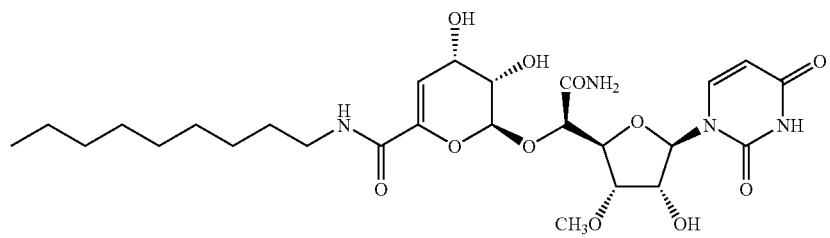

To a solution of the compound of formula (VI) (47 mg) in methanol (1 mL) was added n-nonylamine (200 μL) and the mixture was stirred at 50° C. After 4 hours, the solvent was evaporated under reduced pressure. The residue was purified by high performance liquid chromatography (HPLC; Intersil PREP-ODS, 30×250 mm) using 50–80% aqueous acetonitrile as the eluant. The aqueous solution was lyophilized to give the desired compound (31 mg).

$^1$H NMR (CD$_3$OD) δ ppm: 7.86 (d, J=8.1 Hz, 1H), 5.94 (d, J=2.9 Hz, 1H), 5.81 (d, J=4.2 Hz, 1H), 5.75 (d, J=8.1 Hz, 1H), 5.21 (d, J=4.6 Hz, 1H), 4.69 (d, J=2.1 Hz, 1H), 4.50 (dd, J=1.9 and 5.2 Hz, 1H), 4.38 (m, 1H), 4.23 (t, J=4.6 Hz, 1H), 4.03 (m, 1H), 3.70 (t, J=5.1 Hz, 1H), 3.38 (s, 3H), 3.25 (m, 2H), 1.54 (m, 2H), 1.33 (m, 12H), 0.90 (t, J=6.6 Hz, 3H).

IR (KBr) ν cm$^{-1}$: 3339, 2960, 2926, 2855, 1686, 1533, 1464, 1383, 1262, 1203, 1095, 1058, 1025.

Example 4

Exemplification Compound Number 6346

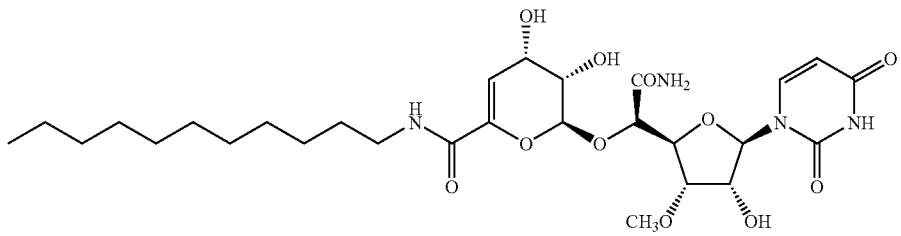

The desired compound (10 mg) was obtained using n-undecylamine (200 μL) in a similar manner to that described in Example 3.

$^1$H NMR (CD$_3$OD) δ ppm: 7.86 (d, J=8.1 Hz, 1H), 5.94 (d, J=4.0 Hz, 1H), 5.80 (d, J=4.3 Hz, 1H), 5.75 (d, J=8.1 Hz, 1H), 5.21 (d, J=4.5 Hz, 1H), 4.69 (d, J=2.1 Hz, 1H), 4.50 (dd, J=2.0 and 5.2 Hz, 1H), 4.38 (t, J=4.0 Hz, 1H), 4.23 (t, J=4.7 Hz, 1H), 4.03 (m, 1H), 3.70 (t, J=5.1 Hz, 1H), 3.38 (s, 3H), 3.25 (m, 2H), 1.54 (m, 2H), 1.33 (m, 16H), 0.90 (t, J=6.6 Hz, 3H).

IR (KBr) ν cm$^{-1}$: 3404, 2955, 2925, 2854, 1682, 1531, 1466, 1408, 1385, 1266, 1115, 1095, 1059.

Example 5

Exemplification Compound Number 6351

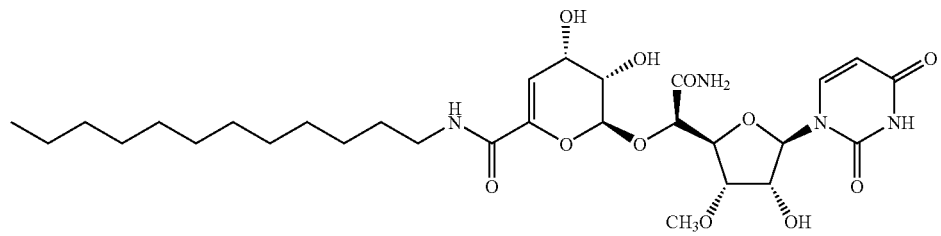

The desired compound (45 mg) was obtained using n-dodecylamine (200 μL) in a similar manner to that described in Example 3.

$^1$H NMR (CD$_3$OD) δ ppm: 7.86 (d, J=8.1 Hz, 1H), 5.94 (d, J=2.9 Hz, 1H), 5.81 (d, J=4.4 Hz, 1H), 5.75 (d, J=8.1 Hz, 1H), 5.21 (d, J=4.4 Hz, 1H), 4.70 (d, J=2.2 Hz, 1H), 4.50 (m, 1H), 4.38 (m, 1H), 4.23 (t, J=4.4 Hz, 1H), 4.04 (t, J=4.4 Hz, 1H), 3.70 (t, J=5.1 Hz, 1H), 3.38 (s, 3H), 3.25 (m, 2H), 1.54 (m, 2H), 1.33 (m, 18H), 0.90 (t, J=7.0 Hz, 3H).

IR (KBr) ν cm$^{-1}$: 3350, 2954, 2925, 2854, 1686, 1532, 1465, 1391, 1267, 1139, 1116, 1094, 1057.

Example 6

Exemplification Compound Number 6361

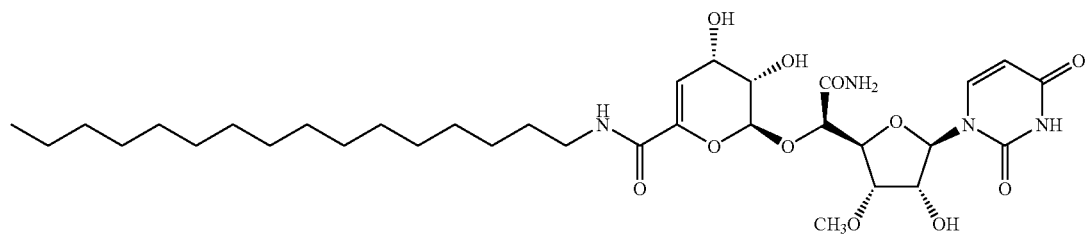

The desired compound (11 mg) was obtained using n-hexadecylamine (200 μL) in a similar manner to that described in Example 3.

$^1$H NMR (CD$_3$OD) δ ppm: 7.86 (d, J=8.1 Hz, 1H), 5.95 (d, J=4.0 Hz, 1H), 5.81 (d, J=4.2 Hz, 1H), 5.75 (d, J=8.1 Hz, 1H), 5.21 (d, J=4.5 Hz, 1H), 4.69 (d, J=1.9 Hz, 1H), 4.50 (dd, J=1.9 and 5.2 Hz, 1H), 4.38 (t, J=3.9 Hz, 1H), 4.23 (t, J=4.7 Hz, 1H), 4.03 (t, J=4.3 Hz, 1H), 3.70 (t, J=5.1 Hz, 1H), 3.38 (s, 3H), 3.25 (m, 2H), 1.54 (m, 2H), 1.33 (m, 26H), 0.90 (t, J=6.8 Hz, 3H).

IR (KBr) ν cm$^{-1}$: 3349, 2924, 2853, 1686, 1531, 1466, 1385, 1267, 1115, 1095, 1057.

Example 7

Exemplification Compound Number 6371

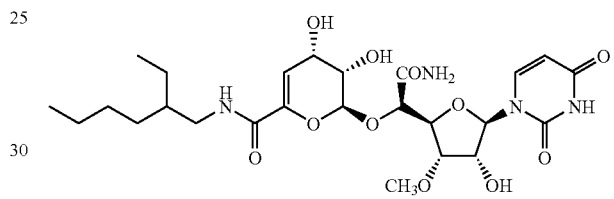

The desired compound (26 mg) was obtained using 2-ethylhexylamine (200 μL) in a similar manner to that described in Example 3.

$^1$H NMR (CD$_3$OD) δ ppm: 7.88 (d, J=8.1 Hz, 1H), 5.94 (m, 1H), 5.81 (d, J=4.4 Hz, 1H), 5.75 (d, J=8.1 Hz, 1H), 5.21 (d, J=4.5 Hz, 1H), 4.69 (d, J=2.0 Hz, 1H), 4.50 (dd, J=2.1 and 5.1 Hz, 1H), 4.38 (t, J=4.9 Hz, 1H), 4.24 (t, J=4.7 Hz, 1H), 4.03 (t, J=4.3 Hz, 1H), 3.71 (t, J=5.0 Hz, 1H), 3.38 (s, 3H), 3.25 (m, 2H), 1.55 (m, 1H), 1.33 (m, 8H), 0.90 (m, 6H).

IR (KBr) ν cm$^{-1}$: 3365, 2959, 2930, 2874, 2860, 1684, 1530, 1463, 1385, 1266, 1139, 1116, 1093, 1057.

Example 8

Exemplification Compound Number 6376

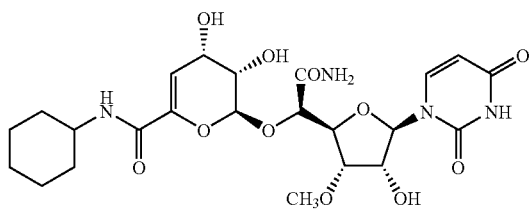

The desired compound (12 mg) was obtained using cyclohexylamine (114 μL) in a similar manner to that described in Example 3.

$^1$H NMR (CD$_3$OD) δ ppm: 7.86 (d, J=8.1 Hz, 1H), 5.94 (d, J=4.0 Hz, 1H), 5.81 (d, J=4.3 Hz, 1H), 5.75 (d, J=8.1 Hz, 1H), 5.21 (d, J=4.8 Hz, 1H), 4.72 (d, J=1.7 Hz, 1H), 4.51 (dd, J=1.8 and 5.1 Hz, 1H), 4.34 (t, J=3.9 Hz, 1H), 4.23 (t, J=4.7 Hz, 1H), 4.02 (t, J=4.2 Hz, 1H), 3.75 (m, 1H), 3.71 (t, J=5.1 Hz, 1H), 3.38 (s, 3H), 1.90–1.15 (m, 9H).

IR (KBr) ν cm$^{-1}$: 3408, 3352, 2933, 2855, 1686, 1527, 1462, 1386, 1327, 1267, 1115, 1090, 1060, 1021.

Example 9

Exemplification Compound Number 6381

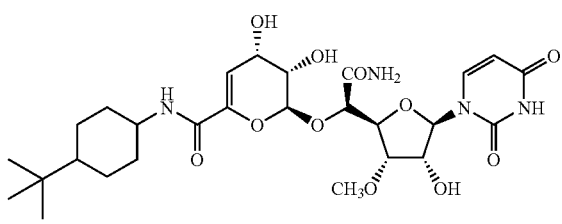

Example (9-1)

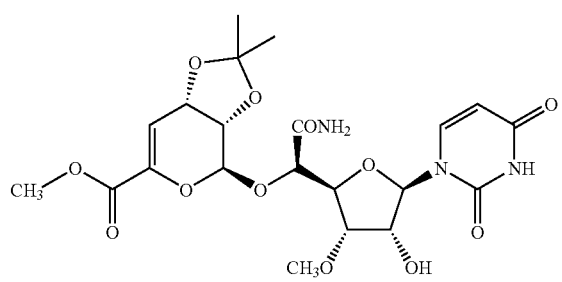

To a solution of the compound of formula (VI) (5 g) in acetone (500 mL) were added 2,2-dimethoxypropane (52 mL) and "Amberlyst 15" (1.25 g), and the mixture was stirred at room temperature. After 19 hours, the reaction mixture was filtered through Celite and the solvent of the filtrate evaporated under reduced pressure. The residue was purified by chromatography on a silica gel (250 g) column using 4% methanol in methylene chloride as the eluant to give the desired compound (3.82 g).

$^1$H NMR (CDCl$_3$) δ ppm: 8.42 (br s, 1H), 7.70 (d, J=8.1 Hz, 1H), 7.13 (br s, 1H), 6.40 (d, J=4.4 Hz, 1H), 5.94 (d, J=5.1 Hz, 1H), 5.80 (br s, 1H), 5.74 (dd, J=2.2 and 8.1 Hz, 1H), 4.75 (m, 2H), 4.56 (d, J=8.1 Hz, 1H), 4.53 (s, 1H), 4.23 (m, 1H), 4.15 (m, 1H), 4.03 (t, J=7.0 Hz, 1H), 3.82 (s, 3H), 3.58 (s, 3H), 3.09 (d, J=7.3 Hz, 1H), 1.51 (s, 3H), 1.46 (s, 3H).

Example (9-2)

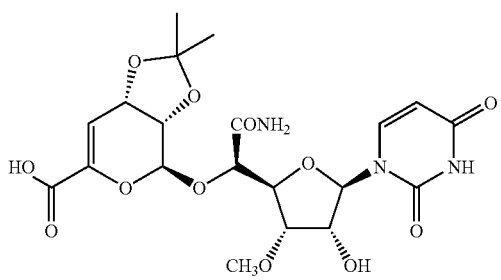

To a solution of the compound obtained in Example (9-1) (3.82 g) in 50% aqueous methanol (744 mL) was added 0.2N aqueous sodium hydroxide solution (186 mL) and the mixture was stirred at room temperature. After 10 minutes, the reaction mixture was purified through a Dowex 50W x 8 (H$^+$) column using 50% aqueous methanol as the eluant to give the desired compound (3.68 g).

$^1$H NMR (CD$_3$OD) δ ppm: 7.87 (d, J=8.1 Hz, 1H), 6.30 (d, J=3.7 Hz, 1H), 5.88 (d, J=5.1 Hz, 1H), 5.73 (d, J=8.1 Hz, 1H), 4.93 (d, J=5.9 Hz, 1H), 4.81 (m, 1H), 4.63 (d, J=2.2 Hz, 1H), 4.56 (m, 1H), 4.27 (m, 2H), 4.00 (t, J=5.1 Hz, 1H), 3.50 (s, 3H), 1.47 (s, 3H), 1.45 (s, 3H).

Example (9-3)

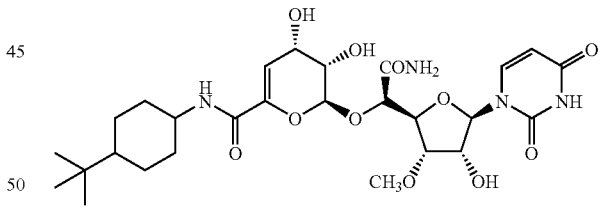

To a solution of the compound obtained in Example (9-2) (150 mg) in dimethylformamide (DMF) (2.6 mL) were added 4-t-butylcyclohexylamine (101 μL), 1-hydroxybenzotriazole (HOBT) (61 mg) and diisopropylcarbodiimide (DIPC) (102 μL), and the mixture was stirred at room temperature. After 6 hours, the solvent was evaporated under reduced pressure. To the residue was added ethyl acetate (30 mL). The resulting mixture was washed with 0.01N hydrochloric acid (30 mL), saturated aqueous sodium hydrogen carbonate solution (30 mL) and saturated aqueous sodium chloride solution (30 mL), dried over anhydrous sodium sulfate and then concentrated by evaporation under reduced pressure. A solution of the residue in methanol (5.5 mL) was refluxed with "Amberlyst 15" (225 mg) for 2.5 hours. After the insoluble material was filtered off, the solvent of the filtrate was evaporated under reduced pressure. The residue was purified by chromatography on a silica gel (8 g) column using 5% methanol in methylene chloride as the eluant to give the desired compound (diastereoisomeric mixture consisting of an about 7:3 mixture) (78 mg).

$^1$H NMR (CD$_3$OD) δ ppm: 7.89 (d, J=8.1 Hz, 0.3H), 7.86 (d, J=8.1 Hz, 0.7H), 5.95 (d, J=2.5 Hz, 0.3H), 5.93 (d, J=4.0 Hz, 0.7H), 5.81 (d, J=4.4 Hz, 0.7H), 5.79 (d, J=3.9 Hz, 0.3H), 5.75 (d, J=8.1 Hz, 1H), 5.27 (d, J=4.4 Hz, 0.3H), 5.20 (d, J=4.6 Hz, 0.7H), 4.72 (d, J=1.7 Hz, 0.7H), 4.61 (d, J=1.7 Hz, 0.3H), 4.51 (dd, J=1.8 and 5.2 Hz, 0.7H), 4.47 (dd, J=1.9 and 5.5 Hz, 0.3H), 4.38 (m, 1H), 4.25 (m, 1H), 4.02 (m, 1H), 3.70 (m, 1H), 3.64 (s, 0.9H), 3.39 (s, 2.1H), 1.97–1.82 (m, 3H), 1.70–1.53 (m, 1H), 1.40–0.97 (m, 5H), 0.87 (s, 9H).

IR (KBr) ν cm$^{-1}$: 3408, 2944, 2864, 1686, 1524, 1463, 1385, 1366, 1329, 1266, 1190, 1116, 1090, 1060, 1022, 987.

Example 10

Exemplification Compound Number 6386

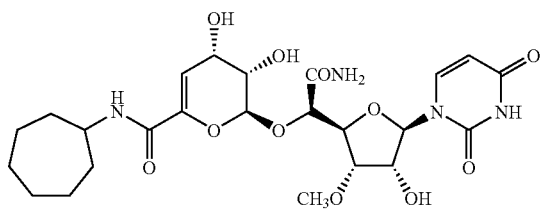

The desired compound (47 mg) was obtained using cycloheptylamine (200 μL) instead of 4-t-butylcyclohexylamine in a similar manner to that described in Example (9-3).

$^1$H NMR (CD$_3$OD) δ ppm: 7.87 (d, J=8.1 Hz, 1H), 5.93 (d, J=4.0 Hz, 1H), 5.81 (d, J=4.2 Hz, 1H), 5.75 (d, J=8.1 Hz, 1H), 5.21 (d, J=4.7 Hz, 1H), 4.71 (d, J=2.1 Hz, 1H), 4.51 (dd, J=1.9 and 5.2 Hz, 1H), 4.37 (t, J=3.9 Hz, 1H), 4.24 (t, J=4.7 Hz, 1H), 4.02 (m, 1H), 3.92 (m, 1H), 3.70 (m, 1H), 3.39 (s, 3H), 1.89 (m, 2H), 1.75–1.45 (m, 10H).

IR (KBr) ν cm$^{-1}$: 3403, 2929, 2857, 1685, 1525, 1462, 1385, 1330, 1267, 1115, 1091, 1060, 1018, 994, 978.

Exemplification Compound Number 6396

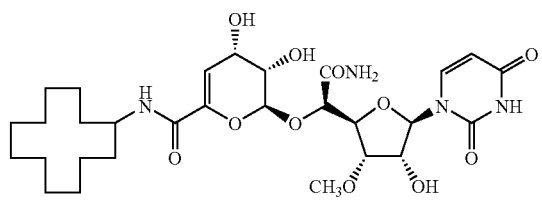

The desired compound (22 mg) was obtained using cyclododecylamine (200 μL) instead of 4-t-butylcyclohexylamine in a similar manner to that described in Example (9-3).

$^1$H NMR (CD$_3$OD) δ ppm: 7.88 (d, J=8.1 Hz, 1H), 5.92 (d, J=2.7 Hz, 1H), 5.82 (d, J=4.4 Hz, 1H), 5.75 (d, J=8.1 Hz, 1H), 5.21 (d, J=4.5 Hz, 1H), 4.71 (d, J=2.0 Hz, 1H), 4.51 (dd, J=2.0 and 5.0 Hz, 1H), 4.38 (t, J=3.9 Hz, 1H), 4.24 (t, J=4.7 Hz, 1H), 4.02 (t, J=4.2 Hz, 1H), 3.65 (m, 1H), 3.39 (s, 3H), 1.73 (m, 2H), 1.60–1.27 (m, 22H).

IR (KBr) ν cm$^{-1}$: 3363, 2935, 2864, 1685, 1529, 1469, 1446, 1332, 1262, 1206, 1186, 1137, 1095, 1064, 1024.

Exemplification Compound Number 6401

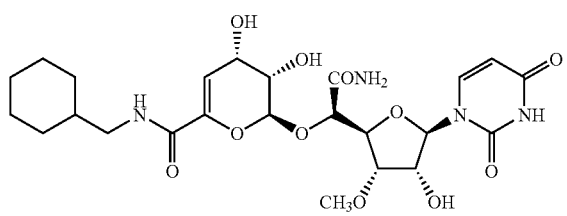

The desired compound (28 mg) was obtained using (aminomethyl)cyclohexane (200 μL) in a similar manner to that described in Example 3.

$^1$H NMR (CD$_3$OD) δ ppm: 7.87 (d, J=8.1 Hz, 1H), 5.94 (m, 1H), 5.81 (d, J=4.4 Hz, 1H), 5.75 (d, J=8.1 Hz, 1H), 5.21 (d, J=4.4 Hz, 1H), 4.69 (d, J=2.1 Hz, 1H), 4.50 (dd, J=2.0 and 5.2 Hz, 1H), 4.38 (dd, J=3.3 and 4.2 Hz, 1H), 4.23 (t, J=4.7 Hz, 1H), 4.02 (m, 1H), 3.70 (t, J=5.0 Hz, 1H), 3.38 (s, 3H), 3.10 (m, 2H), 2.81 (t, J=7.3 Hz, 1H), 1.98 (m, 2H), 1.75–1.50 (m, 6H), 1.22 (m, 2H).

IR (KBr) ν cm$^{-1}$: 3333, 2925, 2853, 1684, 1530, 1462, 1451, 1386, 1263, 1137, 1116, 1093, 1058.

Example 13

Exemplification Compound Number 6406

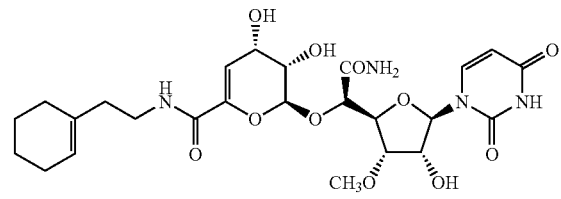

The desired compound (30 mg) was obtained using 2-(1-cyclohexenyl)ethylamine (200 μL) in a similar manner to that described in Example 3.

$^1$H NMR (CD$_3$OD) δ ppm: 7.87 (d, J=8.1 Hz, 1H), 5.94 (m, 1H), 5.80 (d, J=4.2 Hz, 1H), 5.75 (d, J=8.1 Hz, 1H), 5.48 (br s, 1H), 5.20 (d, J=4.7 Hz, 1H), 4.65 (d, J=2.1 Hz, 1H), 4.48 (m, 1H), 4.38 (t, J=3.9 Hz, 1H), 4.24 (t, J=4.7 Hz, 1H), 4.02 (t, J=4.2 Hz, 1H), 3.70 (t, J=5.2 Hz, 1H), 3.38 (s, 3H), 3.30 (m, 2H), 2.17 (t, J=7.4 Hz, 1H), 1.98 (m, 4H), 1.65–1.53 (m, 4H).

IR (KBr) ν cm$^{-1}$: 3348, 2929, 2858, 2836, 1685, 1530, 1462, 1389, 1267, 1137, 1115, 1093, 1059.

Example 14

Exemplification Compound Number 6411

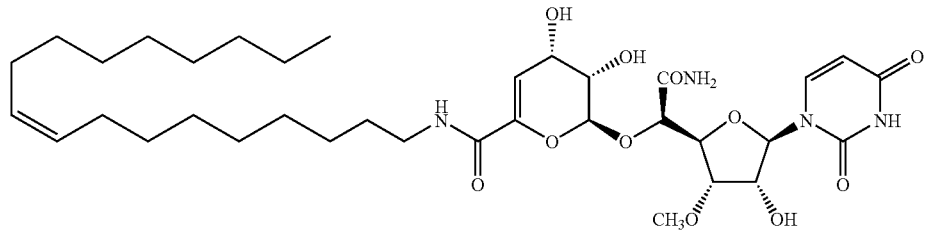

The desired compound (32 mg) was obtained using cis-octadecen-9-ylamine (200 μL) in a similar manner to that described in Example 3.

$^1$H NMR (CD$_3$OD) δ ppm: 7.87 (d, J=8.1 Hz, 1H), 5.94 (m, 1H), 5.81 (d, J=4.1 Hz, 1H), 5.75 (d, J=8.1 Hz, 1H), 5.34 (t, J=4.5 Hz, 2H), 5.21 (d, J=4.4 Hz, 1H), 4.69 (d, J=2.1 Hz, 1H), 4.50 (dd, J=2.0 and 5.2 Hz, 1H), 4.38 (t, J=4.0 Hz, 1H), 4.23 (t, J=4.5 Hz, 1H), 4.03 (t, J=4.2 Hz, 1H), 3.70 (t, J=5.1 Hz, 1H), 3.38 (s, 3H), 2.79 (t, J=7.4 Hz, 1H), 2.00 (m, 6H), 1.55 (m, 4H), 1.32 (m, 20H), 0.90 (d, J=6.2 Hz, 3H).

IR (KBr) ν cm$^{-1}$: 3308, 3006, 2925, 2854, 1685, 1533, 1466, 1385, 1098.

Example 15

Exemplification Compound Number 6416

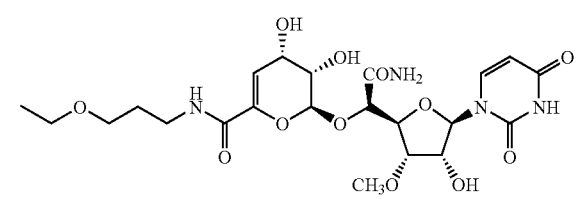

The desired compound (35 mg) was obtained using 3-(ethoxy)propylamine (200 μL) in a similar manner to that described in Example 3.

$^1$H NMR (CD$_3$OD) δ ppm: 7.86 (d, J=8.1 Hz, 1H), 5.94 (m, 1H), 5.79 (d, J=1.9 Hz, 1H), 5.75 (d, J=8.1 Hz, 1H), 5.21 (d, J=4.2 Hz, 1H), 4.65 (d, J=1.6 Hz, 1H), 4.49 (dd, J=2.0 and 5.6 Hz, 1H), 4.38 (dd, J=3.2 and 4.3 Hz, 1H), 4.24 (t, J=4.3 Hz, 1H), 4.03 (m, 1H), 3.69 (t, J=5.2 Hz, 2H), 3.50 (m, 4H), 3.37 (s, 3H), 1.89 (m, 2H), 1.18 (t J=7.2 Hz, 3H).

IR (KBr) ν cm$^{-1}$: 3351, 2972, 2933, 2874, 1685, 1532, 1462, 1386, 1267, 1221, 1136, 1115, 1058, 1023.

Example 16

Exemplification Compound Number 6421

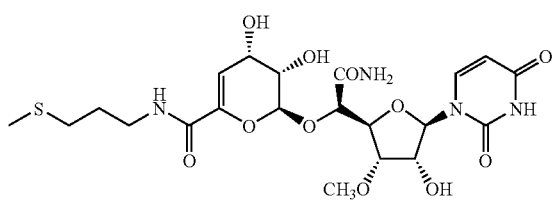

The desired compound (30 mg) was obtained using 3-(methylthio)propylamine (200 μL) in a similar manner to that described in Example 3.

$^1$H NMR (CD$_3$OD) δ ppm: 7.87 (d, J=8.1 Hz, 1H), 5.95 (m, 1H), 5.79 (d, J=4.0 Hz, 1H), 5.75 (d, J=8.1 Hz, 1H), 5.21 (d, J=4.4 Hz, 1H), 4.68 (d, J=2.1 Hz, 1H), 4.50 (dd, J=2.0 and 5.6 Hz, 1H), 4.38 (dd, J=3.2 and 4.3 Hz, 1H), 4.24 (t, J=4.6 Hz, 1H), 4.04 (t, J=4.2 Hz, 1H), 3.70 (t, J=5.2 Hz, 1H), 3.38 (m, 2H), 3.37 (s, 3H), 2.52 (t, J=7.4 Hz, 2H), 2.08 (s, 3H), 1.84 (m, 2H).

IR (KBr) νcm$^{-1}$: 3351, 2925, 1685, 1532, 1462, 1390, 1267, 1137, 1115, 1094, 1057, 976.

Example 17

Exemplification Compound Number 6431

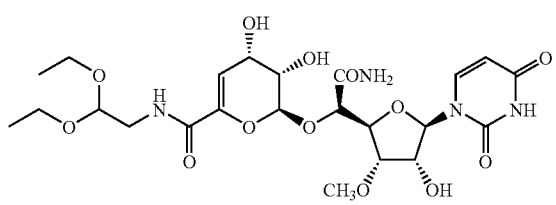

The desired compound (21 mg) was obtained using 2,2-(diethoxy)ethylamine (200 μL) in a similar manner to that described in Example 3.

$^1$H NMR (CD$_3$OD) δ ppm: 7.88 (d, J=8.1 Hz, 1H), 5.97 (m, 1H), 5.81 (d, J=4.3 Hz, 1H), 5.75 (d, J=8.1 Hz, 1H), 5.22 (d, J=4.7 Hz, 1H), 4.66 (d, J=2.1 Hz, 1H), 4.62 (t, J=5.3 Hz, 1H), 4.50 (dd, J=2.0 and 5.2 Hz, 1H), 4.38 (t, J=4.0 Hz, 1H), 4.24 (t, J=4.7 Hz, 1H), 4.02 (m, 1H), 3.70 (m, 3H), 3.55 (m, 2H), 3.47–3.33 (m, 2H), 3.37 (s, 3H), 1.20 (m, 6H).

IR (KBr) ν cm$^{-1}$: 3350, 2877, 2935, 1686, 1531, 1462, 1385, 1268, 1122, 1091, 1058.

Example 18

Exemplification Compound Number 6436

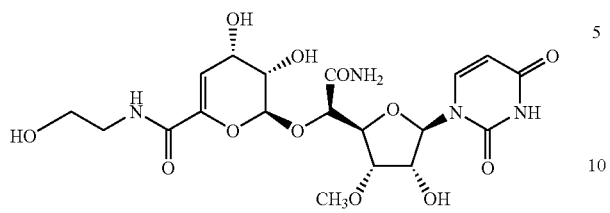

The desired compound (28 mg) was obtained using 2-hydroxyethylamine (200 μL) in a similar manner to that described in Example 3.

$^1$H NMR (CD$_3$OD) δ ppm: 7.87 (d, J=8.1 Hz, 1H), 5.97 (d, J=2.4 Hz, 1H), 5.81 (d, J=4.4 Hz, 1H), 5.75 (d, J=8.1 Hz, 1H), 5.21 (d, J=4.6 Hz, 1H), 4.69 (d, J=2.1 Hz, 1H), 4.51 (dd, J=1.8 and 5.1 Hz, 1H), 4.38 (t, J=4.0 Hz, 1H), 4.24 (t, J=4.7 Hz, 1H), 4.02 (m, 1H), 3.73 (t, J=5.1 Hz, 1H), 3.63 (m, 4H), 3.37 (s, 3H).

IR (KBr) ν cm$^{-1}$: 3337, 2937, 1684, 1535, 1462, 1426, 1394, 1361, 1264, 1139, 1115, 1092, 1058.

Example 19

Exemplification Compound Number 6441

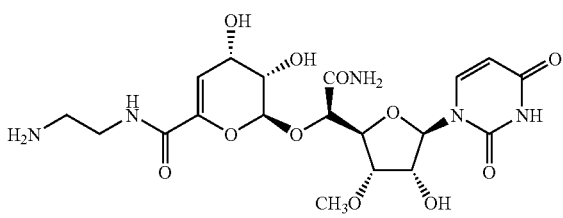

The desired compound (26 mg) was obtained using 1,2-diaminoethane (200 μL) in a similar manner to that described in Example 3.

$^1$H NMR (CD$_3$OD) δ ppm: 7.85 (d, J=8.1 Hz, 1H), 5.98 (m, 1H), 5.77 (d, J=3.8 Hz, 1H), 5.74 (d, J=8.1 Hz, 1H), 5.23 (d, J=4.2 Hz, 1H), 4.65 (d, J=1.8 Hz, 1H), 4.48 (dd, J=2.0 and 5.7 Hz, 1H), 4.40 (dd, J=3.2 and 4.3 Hz, 1H), 4.25 (t, J=3.9 Hz, 1H), 4.06 (m, 1H), 3.70 (m, 2H), 3.37 (s, 3H), 2.95 (m, 2H).

IR (KBr) ν cm$^{-1}$: 3305, 2940, 1682, 1532, 1464, 1428, 1396, 1265, 1203, 1180, 1136, 1095, 1060, 1021.

Example 20

Exemplification Compound Number 6451

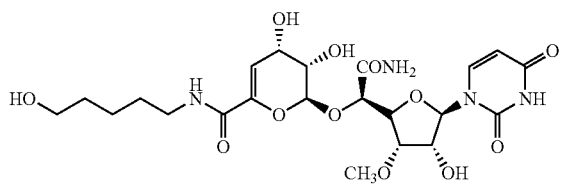

The desired compound (19 mg) was obtained using 5-hydroxypentylamine (200 μL) in a similar manner to that described in Example 3.

$^1$H NMR (CD$_3$OD) δ ppm: 7.86 (d, J=8.1 Hz, 1H), 5.94 (m, 1H), 5.80 (d, J=4.2 Hz, 1H), 5.75 (d, J=8.1 Hz, 1H), 5.21 (d, J=4.4 Hz, 1H), 4.69 (d, J=2.0 Hz, 1H), 4.50 (dd, J=1.9 and 5.4 Hz, 1H), 4.38 (dd, J=3.3 and 4.3 Hz, 1H), 4.23 (t, J=4.6 Hz, 1H), 4.03 (m, 1H), 3.55 (m, 2H), 3.38 (s, 3H), 2.75 (t, J=7.0 Hz, 2H), 1.55 (m, 6H).

IR (KBr) ν cm$^{-1}$: 3336, 2935, 1684, 1644, 1532, 1461, 1391, 1264, 1139, 1115, 1091, 1057.

Example 21

Exemplification Compound Number 6456

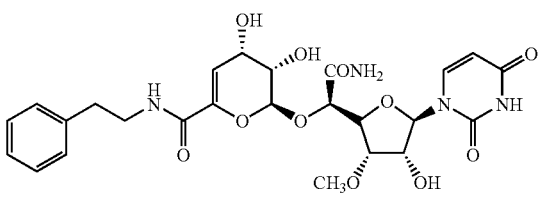

The desired compound (35 mg) was obtained using 2-phenylethylamine (200 μL) in a similar manner to that described in Example 3.

$^1$H NMR (CD$_3$OD) δ ppm: 7.87 (d, J=8.1 Hz, 1H), 7.30 (m, 2H), 7.22 (m, 3H), 5.96 (m, 1H), 5.80 (d, J=4.1 Hz, 1H), 5.75 (d, J=8.1 Hz, 1H), 5.20 (d, J=4.7 Hz, 1H), 4.64 (d, J=2.0 Hz, 1H), 4.50 (dd, J=2.0 and 5.3 Hz, 1H), 4.38 (dd, J=3.3 and 4.2 Hz, 1H), 4.23 (t, J=4.5 Hz, 1H), 4.02 (t, J=4.1 Hz, 1H), 3.69 (t, J=5.1 Hz, 1H), 3.48 (m, 2H), 3.35 (s, 3H), 2.84 (t, J=7.6 Hz, 2H).

IR (KBr) ν cm$^{-1}$: 3392, 3368, 2932, 1685, 1532, 1497, 1458, 1390, 1267, 1136, 1115, 1094, 1059, 1029.

Example 22

Exemplification Compound Number 6461

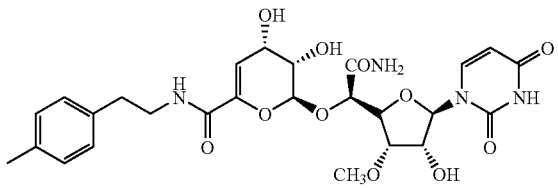

The desired compound (29 mg) was obtained using 2-(4-methylphenyl)ethylamine (200 μL) in a similar manner to that described in Example 3.

$^1$H NMR (CD$_3$OD) δ ppm: 7.86 (d, J=8.1 Hz, 1H), 7.10 (s, 4H), 5.96 (m, 1H), 5.80 (d, J=4.1 Hz, 1H), 5.75 (d, J=8.1 Hz, 1H), 5.19 (d, J=4.7 Hz, 1H), 4.64 (d, J=2.1 Hz, 1H), 4.49 (dd, J=2.0 and 5.5 Hz, 1H), 4.38 (t, J=3.9 Hz, 1H), 4.23 (t, J=4.5 Hz, 1H), 4.02 (m, 1H), 3.69 (t, J=5.1 Hz, 1H), 3.45 (m, 2H), 3.34 (s, 3H), 2.79 (t, J=6.6 Hz, 2H), 2.29 (s, 3H).

IR (KBr) ν cm$^{-1}$: 3400, 2930, 1684, 1531, 1517, 1463, 1385, 1267, 1137, 1115, 1095, 1060.

Example 23

Exemplification Compound Number 6466

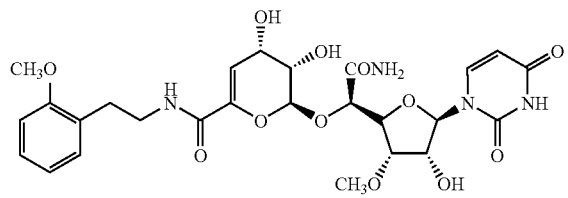

The desired compound (28 mg) was obtained using 2-(2-methoxyphenyl)ethylamine (200 μL) in a similar manner to that described in Example 3.

$^1$H NMR (CD$_3$OD) δ ppm: 7.86 (d, J=8.1 Hz, 1H), 7.19 (t, J=7.8 Hz, 1H), 7.14 (d, J=7.4 Hz, 1H), 6.93 (d, J=8.4 Hz, 1H), 6.87 (t, J=7.4 Hz, 1H), 5.95 (m, 1H), 5.80 (d, J=4.2 Hz, 1H), 5.75 (d, J=8.1 Hz, 1H), 5.19 (d, J=4.5 Hz, 1H), 4.63 (d, J=2.0 Hz, 1H), 4.48 (dd, J=1.9 and 5.6 Hz, 1H), 4.38 (t, J=4.0 Hz, 1H), 4.22 (t, J=4.5 Hz, 1H), 4.02 (m, 1H), 3.83 (s, 3H), 3.66 (t, J=5.2 Hz, 1H), 3.46 (m, 2H), 3.34 (s, 3H), 2.86 (m, 2H).

IR (KBr) ν cm$^{-1}$: 3365, 2933, 1685, 1531, 1495, 1464, 1389, 1266, 1245, 1118, 1054, 1024.

Example 24

Exemplification Compound Number 6476

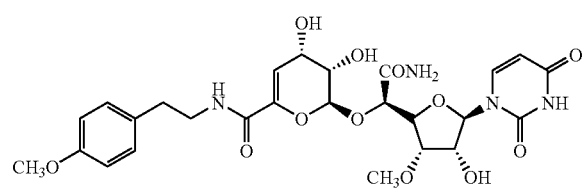

The desired compound (35 mg) was obtained using 2-(4-methoxyphenyl)ethylamine (200 μL) in a similar manner to that described in Example 3.

$^1$H NMR (CD$_3$OD) δ ppm: 7.87 (d, J=8.1 Hz, 1H), 7.14 (d, J=8.7 Hz, 2H), 6.85 (d, J=8.7 Hz, 2H), 5.96 (m, 1H), 5.80 (d, J=4.0 Hz, 1H), 5.75 (d, J=8.1 Hz, 1H), 5.20 (d, J=4.6 Hz, 1H), 4.64 (d, J=1.7 Hz, 1H), 4.50 (dd, J=2.0 and 5.3 Hz, 1H), 4.38 (m, 1H), 4.23 (t, J=4.6 Hz, 1H), 4.02 (t, J=4.2 Hz, 1H), 3.76 (s, 3H), 3.69 (t, J=5.2 Hz, 1H), 3.45 (m, 2H), 3.34 (s, 3H), 2.76 (m, 2H).

IR (KBr) ν cm$^{-1}$: 3342, 2935, 1685, 1513, 1461, 1391, 1361, 1301, 1247, 1178, 1138, 1115, 1093, 1059, 1031.

Example 25

Exemplification Compound Number 6481

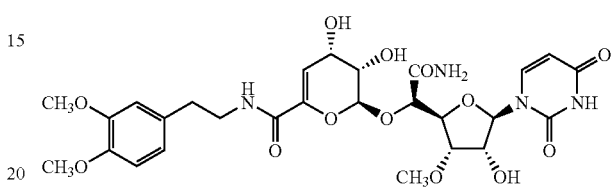

The desired compound (39 mg) was obtained using 2-(3,4-dimethoxyphenyl)ethylamine (200 μL) in a similar manner to that described in Example 3.

$^1$H NMR (CD$_3$OD) δ ppm: 7.86 (d, J=8.1 Hz, 1H), 6.88 (d, J=8.1 Hz, 1H), 6.84 (d, J=1.7 Hz, 1H), 6.77 (dd, J=1.7 and 8.1 Hz, 1H), 5.96 (m, 1H), 5.79 (d, J=4.1 Hz, 1H), 5.75 (d, J=8.1 Hz, 1H), 5.20 (d, J=4.4 Hz, 1H), 4.64 (d, J=2.1 Hz, 1H), 4.49 (dd, J=1.9 and 5.3 Hz, 1H), 4.38 (t, J=3.9 Hz, 1H), 4.23 (t, J=4.5 Hz, 1H), 4.02 (t, J=4.2 Hz, 1H), 3.82 (s, 3H), 3.80 (s, 3H), 3.68 (t, J=5.2 Hz, 1H), 3.45 (m, 2H), 3.33 (s, 3H), 2.78 (t, J=7.4 Hz, 2H).

IR (KBr) ν cm$^{-1}$: 3350, 2937, 2837, 1685, 1516, 1464, 1418, 1389, 1263, 1237, 1141, 1116, 1094, 1059, 1026.

Example 26

Exemplification Compound Number 6486

The desired compound (33 mg) was obtained using 2-(4-fluorophenyl)ethylamine (200 μL) in a similar manner to that described in Example 3.

$^1$H NMR (CD$_3$OD) δ ppm: 7.87 (d, J=8.1 Hz, 1H), 7.23 (m, 2H), 7.01 (t, J=8.8 Hz, 2H), 5.95 (m, 1H), 5.80 (d, J=4.1 Hz, 1H), 5.75 (d, J=8.1 Hz, 1H), 5.20 (d, J=4.5 Hz, 1H), 4.65 (d, J=1.7 Hz, 1H), 4.50 (dd, J=2.0 and 5.3 Hz, 1H), 4.38 (dd, J=3.3 and 4.2 Hz, 1H), 4.23 (t, J=4.6 Hz, 1H), 4.03 (t, J=4.2 Hz, 1H), 3.69 (t, J=5.1 Hz, 1H), 3.45 (m, 2H), 3.35 (s, 3H), 2.83 (t, J=7.5 Hz, 2H).

IR (KBr) ν cm$^{-1}$: 3349, 2935, 1685, 1531, 1510, 1463, 1391, 1266, 1222, 1137, 1116, 1098, 1059.

Example 27

Exemplification Compound Number 6496

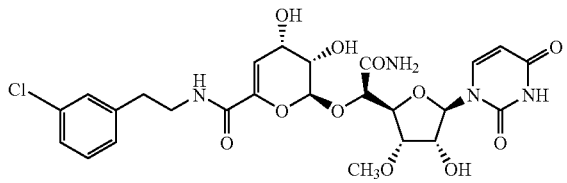

The desired compound (33 mg) was obtained using 2-(3-chlorophenyl)ethylamine (200 μL) in a similar manner to that described in Example 3.

$^{1}$H NMR (CD$_3$OD) δ ppm: 7.86 (d, J=8.1 Hz, 1H), 7.30–7.15 (m, 4H), 5.96 (m, 1H), 5.80 (d, J=4.2 Hz, 1H), 5.75 (d, J=8.1 Hz, 1H), 5.20 (d, J=4.4 Hz, 1H), 4.65 (d, J=2.1 Hz, 1H), 4.50 (dd, J=2.0 and 5.3 Hz, 1H), 4.38 (t, J=3.9 Hz, 1H), 4.23 (t, J=4.6 Hz, 1H), 4.02 (m, 1H), 3.69 (t, J=5.2 Hz, 1H), 3.45 (m, 2H), 3.35 (s, 3H), 2.84 (t, J=7.4 Hz, 2H).

IR (KBr) ν cm$^{-1}$: 3401, 2934, 1684, 1599, 1574, 1530, 1463, 1389, 1267, 1136, 1116, 1096, 1059.

Example 28

Exemplification Compound Number 6506

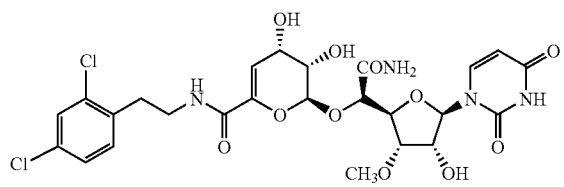

The desired compound (33 mg) was obtained using 2-(2,4-dichlorophenyl)ethylamine (200 μL) in a similar manner to that described in Example 3.

$^{1}$H NMR (CD$_3$OD) δ ppm: 7.87 (d, J=8.1 Hz, 1H), 7.44 (d, J=1.8 Hz, 1H), 7.29 (m, 2H), 5.94 (d, J=2.5 Hz, 1H), 5.80 (d, J=4.1 Hz, 1H), 5.75 (d, J=8.1 Hz, 1H), 5.20 (d, J=4.5 Hz, 1H), 4.66 (d, J=2.0 Hz, 1H), 4.49 (dd, J=1.8 and 5.4 Hz, 1H), 4.38 (t, J=3.9 Hz, 1H), 4.23 (t, J=4.4 Hz, 1H), 4.02 (t, J=4.2 Hz, 1H), 3.69 (t, J=5.2 Hz, 1H), 3.50 (m, 2H), 3.35 (s, 3H), 2.98 (m, 2H).

IR (KBr) ν cm$^{-1}$: 3402, 2931, 1684, 1591, 1530, 1473, 1386, 1268, 1115, 1054.

Example 29

Exemplification Compound Number 6511

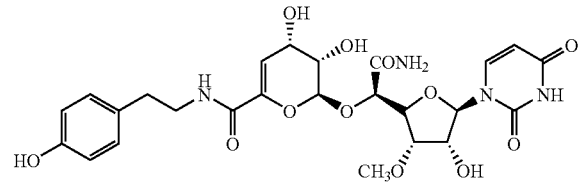

The desired compound (43 mg) was obtained using 2-(4-hydroxyphenyl)ethylamine (200 μL) in a similar manner to that described in Example 3.

$^{1}$H NMR (CD$_3$OD) δ ppm: 7.88 (d, J=8.1 Hz, 1H), 7.42–7.25 (m, 4H), 5.98 (d, J=3.5 Hz, 1H), 5.83 (t, J=4.9 Hz, 1H), 5.75 (d, J=8.1 Hz, 1H), 5.20 (t, J=5.1 Hz, 1H), 4.75 (m, 1H), 4.67 (m, 1H), 4.52 (m, 1H), 4.48 (m, 1H), 4.26 (m, 1H), 4.00 (m, 1H), 3.75 (m, 1H), 3.55 (m, 2H), 3.40 and 3.35 (2 s, 3H), 3.33 (m, 1H).

IR (KBr) ν cm$^{-1}$: 3339, 2934, 1681, 1532, 1495, 1455, 1389, 1267, 1199, 1138, 1115, 1094, 1062, 1027.

Example 30

Exemplification Compound Number 6516

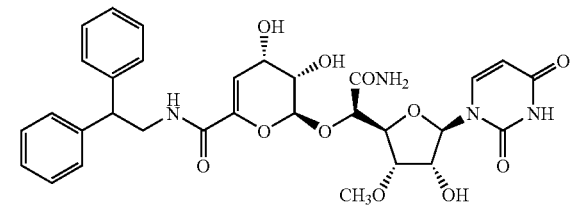

The desired compound (22 mg) was obtained using 2,2-diphenylethylamine (200 μL) in a similar manner to that described in Example 3.

$^{1}$H NMR (CD$_3$OD) δ ppm: 7.84 (d, J=8.1 Hz, 1H), 7.28 (m, 8H), 7.20 (m, 2H), 5.91 (d, J=2.4 Hz, 1H), 5.80 (d, J=4.3 Hz, 1H), 5.73 (d, J=8.1 Hz, 1H), 5.11 (d, J=4.8 Hz, 1H), 4.53 (d, J=2.1 Hz, 1H), 4.45 (dd, J=2.1 and 5.2 Hz, 1H), 4.35 (m, 2H), 4.20 (t, J=4.5 Hz, 1H), 3.95 (m, 2H), 3.85 (m, 1H), 3.63 (t, J=5.1 Hz, 1H), 3.31 (s, 3H).

IR (KBr) ν cm$^{-1}$: 3416, 3062, 3028, 2934, 1685, 1527, 1495, 1454, 1385, 1268, 1115, 1092, 1059.

Example 31

Exemplification Compound Number 6521

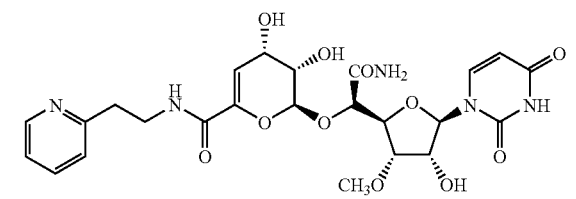

The desired compound (25 mg) was obtained using 2-(2-pyridyl)ethylamine (200 μL) in a similar manner to that described in Example 3.

¹H NMR (CD$_3$OD) δ ppm: 8.48 (d, J=5.4 Hz, 1H), 7.87 (d, J=8.2 Hz, 1H), 7.78 (m, 1H), 7.34 (d, J=8.0 Hz, 1H), 7.28 (m, 1H), 5.94 (m, 1H), 5.80 (d, J=4.3 Hz, 1H), 5.75 (d, J=8.2 Hz, 1H), 5.20 (d, J=4.5 Hz, 1H), 4.65 (d, J=1.7 Hz, 1H), 4.49 (dd, J=2.0 and 5.3 Hz, 1H), 4.38 (t, J=3.8 Hz, 1H), 4.23 (t, J=4.7 Hz, 1H), 4.02 (m, 1H), 3.70 (t, J=5.1 Hz, 1H), 3.64 (m, 2H), 3.34 (s, 3H), 3.02 (t, J=7.0 Hz, 2H).

IR (KBr) ν cm$^{-1}$: 3367, 2935, 1684, 1596, 1570, 1531, 1462, 1438, 1387, 1265, 1139, 1116, 1094, 1058.

Example 32

Exemplification Compound Number 6526

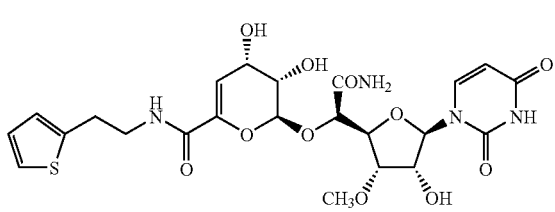

The desired compound (29 mg) was obtained using 2-(2-thienyl)ethylamine (200 μL) in a similar manner to that described in Example 3.

¹H NMR (CD$_3$OD) δ ppm: 7.87 (d, J=8.1 Hz, 1H), 7.21 (d, J=5.1 Hz, 1H), 6.93 (dd, J=3.7 and 5.1 Hz, 1H), 6.88 (d, J=3.7 Hz, 1H), 5.96 (d, J=4.0 Hz, 1H), 5.81 (d, J=4.3 Hz, 1H), 5.75 (d, J=8.1 Hz, 1H), 5.20 (d, J=4.8 Hz, 1H), 4.66 (d, J=2.1 Hz, 1H), 4.50 (dd, J=1.9 and 5.2 Hz, 1H), 4.39 (t, J=4.0 Hz, 1H), 4.24 (t, J=4.6 Hz, 1H), 4.02 (m, 1H), 3.71 (t, J=5.1 Hz, 1H), 3.52 (m, 2H), 3.35 (s, 3H), 3.07 (t, J=7.3 Hz, 2H).

IR (KBr) 3335, 2933, 1685, 1529, 1462, 1390, 1266, 1115, 1094, 1059.

Example 33

Exemplification Compound Number 6531

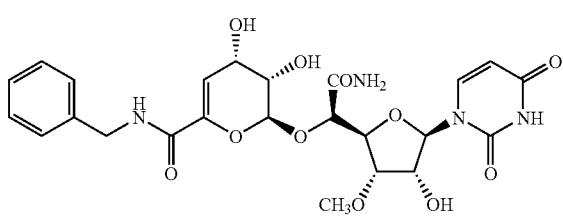

The desired compound (28 mg) was obtained using benzylamine (109 μL) in a similar manner to that described in Example 3.

¹H NMR (CD$_3$OD) δ ppm: 7.86 (d, J=8.1 Hz, 1H), 7.31 (m, 4H), 7.24 (m, 1H), 5.98 (m, 1H), 5.79 (d, J=4.3 Hz, 1H), 5.75 (d, J=8.1 Hz, 1H), 5.21 (d, J=4.5 Hz, 1H), 4.68 (d, J=2.1 Hz, 1H), 4.46 (m, 2H), 4.35 (m, 1H), 4.21 (t, J=4.5 Hz, 1H), 4.04 (t, J=4.4 Hz, 1H), 3.67 (t, J=5.1 Hz, 1H), 3.20 (s, 3H).

IR (KBr) ν cm$^{-1}$: 3350, 2929, 1685, 1529, 1457, 1391, 1267, 1115, 1093, 1059, 1022.

Example 34

Exemplification Compound Number 6536

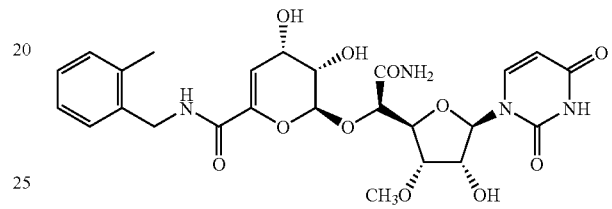

The desired compound (29 mg) was obtained using 2-methylbenzylamine (200 μL) in a similar manner to that described in Example 3.

¹H NMR (CD$_3$OD) δ ppm: 7.87 (d, J=8.1 Hz, 1H), 7.24 (m, 1H), 7.15 (m, 3H), 5.98 (d, J=3.9 Hz, 1H), 5.80 (d, J=4.3 Hz, 1H), 5.75 (d, J=8.1 Hz, 1H), 5.22 (d, J=4.7 Hz, 1H), 4.69 (d, J=2.0 Hz, 1H), 4.48 (m, 3H), 4.40 (m, 1H), 4.22 (t, J=4.6 Hz, 1H), 4.03 (m, 1H), 3.69 (t, J=5.1 Hz, 1H), 3.21 (s, 3H), 2.33 (s, 3H).

IR (KBr) ν cm$^{-1}$: 3349, 2935, 1685, 1527, 1462, 1386, 1268, 1116, 1091, 1058.

Example 35

Exemplification Compound Number 6546

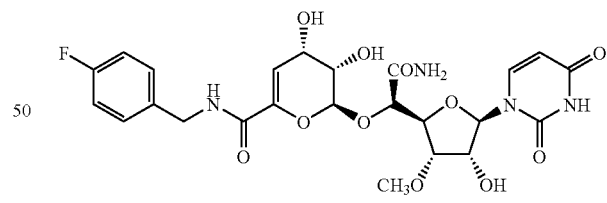

The desired compound (13 mg) was obtained using 4-fluorobenzylamine (200 μL) in a similar manner to that described in Example 3.

¹H NMR (CD$_3$OD) δ ppm: 7.85 (d, J=8.1 Hz, 1H), 7.34 (m, 2H), 7.05 (m, 2H), 5.98 (m, 1H), 5.78 (d, J=4.2 Hz, 1H), 5.75 (d, J=8.1 Hz, 1H), 5.22 (d, J=4.4 Hz, 1H), 4.67 (d, J=2.0 Hz, 1H), 4.43 (d, J=3.5 Hz, 2H), 4.39 (dd, J=3.2 and 4.3 Hz, 1H), 4.22 (t, J=4.5 Hz, 1H), 4.04 (t, J=4.3 Hz, 1H), 3.66 (t, J=5.1 Hz, 1H), 3.20 (s, 3H).

IR (KBr) ν cm$^{-1}$: 3351, 2935, 1684, 1526, 1510, 1462, 1416, 1387, 1359, 1266, 1222, 1137, 1115, 1095, 1059, 1020.

Example 36

Exemplification Compound Number 6561

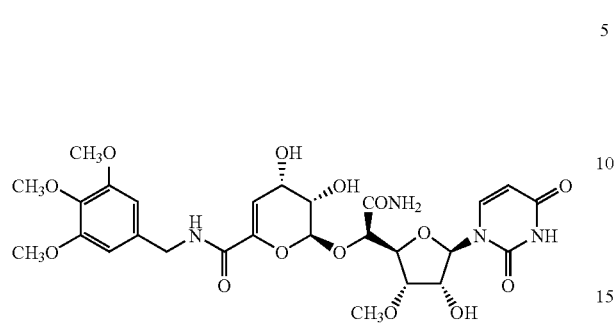

The desired compound (29 mg) was obtained using 3,4,5-trimethoxybenzylamine (200 μL) in a similar manner to that described in Example 3.

$^1$H NMR (CD$_3$OD) δ ppm: 7.85 (d, J=8.1 Hz, 1H), 6.65 (s, 2H), 5.99 (m, 1H), 5.77 (d, J=4.0 Hz, 1H), 5.75 (d, J=8.1 Hz, 1H), 5.22 (d, J=4.3 Hz, 1H), 4.66 (d, J=2.0 Hz, 1H), 4.47–4.34 (m, 4H), 4.21 (t, J=4.3 Hz, 1H), 4.05 (t, J=4.4 Hz, 1H), 3.82 (s, 6H), 3.73 (s, 3H), 3.64 (t, J=5.5 Hz, 1H), 3.18 (s, 3H).

IR (KBr) ν cm$^{-1}$: 3349, 2939, 2838, 1686, 1594, 1527, 1507, 1462, 1423, 1387, 1357, 1330, 1265, 1237, 1125, 1058, 1020.

Example 37

Exemplification Compound Number 6566

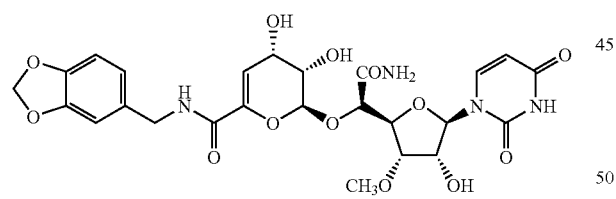

The desired compound (31 mg) was obtained using 3,4-methylenedioxybenzylamine (200 μL) in a similar manner to that described in Example 3.

$^1$H NMR (CD$_3$OD) δ ppm: 7.85 (d, J=8.1 Hz, 1H), 6.75 (m, 3H), 5.97 (m, 1H), 5.90 (s, 2H), 5.79 (d, J=4.3 Hz, 1H), 5.74 (d, J=8.1 Hz, 1H), 5.20 (d, J=4.5 Hz, 1H), 4.67 (d, J=2.1 Hz, 1H), 4.47 (dd, J=1.8 and 5.4 Hz, 1H), 4.41–4.31 (m, 3H), 4.20 (t, J=4.6 Hz, 1H), 4.02 (m, 1H), 3.66 (t, J=5.1 Hz, 1H), 3.23 (s, 3H).

IR (KBr) ν cm$^{-1}$: 3350, 2935, 1685, 1528, 1503, 1491, 1462, 1444, 1386, 1253, 1115, 1096, 1056, 1039.

Example 38

Exemplification Compound Number 6571

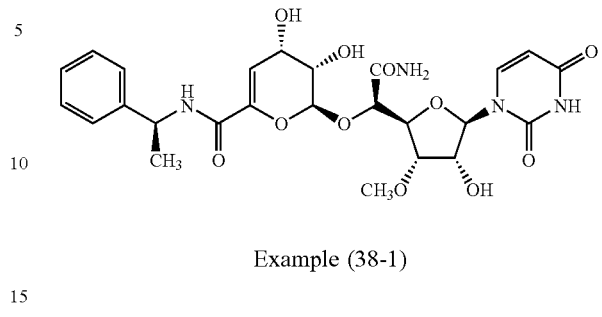

Example (38-1)

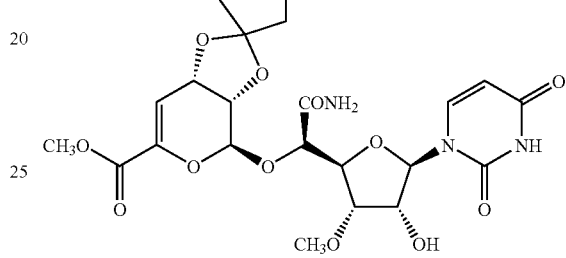

To a solution of the compound of formula (VI) (1.5 g) in cyclopentanone (75 mL) were added 1,1-dimethoxycyclopentane (16.5 g) and "Amberlyst 15" (350 mg), and the mixture was stirred at room temperature for 3 hours. After insoluble material was filtered off, the solvent of the filtrate was evaporated under reduced pressure. The residue was purified by chromatography on a silica gel (86 g) column using 3% methanol in methylene chloride as the eluant to give the desired compound (1.31 g).

$^1$H NMR (CDCl$_3$) δ ppm: 8.94 (br s, 1H), 7.71 (d, J=8.1 Hz, 1H), 8.18 (br s, 1H), 6.39 (d, J=4.4 Hz, 1H), 6.31 (m, 1H), 5.94 (d, J=4.9 Hz, 1H), 5.75 (d, J=8.1 Hz, 1H), 4.70 (m, 1H), 4.60 (m, 2H), 4.52 (m, 1H), 4.25 (t, J=5.3 Hz, 1H), 4.15 (m, 1H), 3.99 (m, 1H), 3.82 (s, 3H), 3.58 (s, 3H), 2.05–1.60 (m, 8H).

Example (38-2)

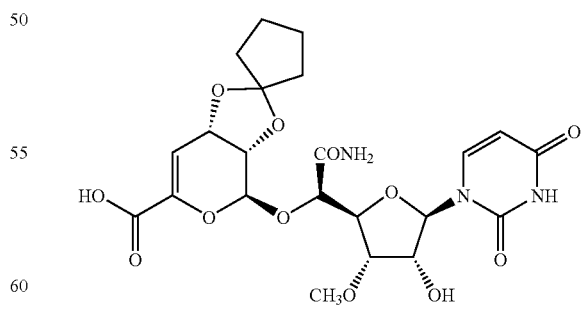

To a solution of the compound obtained in Example (38-1) (1.31 g) in methanol (200 mL) and water (200 mL) was added 0.2N aqueous sodium hydroxide solution (100 mL), and the mixture was stirred at room temperature. After 4 minutes, the reaction mixture was purified through a Dowex 50W x 8 (H+) column using 50% aqueous methanol as the eluant to give the desired compound.

Example (38-3)

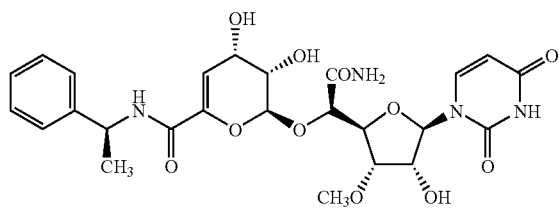

To a solution of the compound obtained in Example (38-2) (80 mg) in DMF (1.4 mL) were added L-(−)-α-phenethylamine (38 μL), HOBT (33 mg) and DIPC (54 μL), and the mixture was stirred at room temperature for 2 hours. After addition of methanol (1 mL), the solvent was evaporated under reduced pressure. The residue was dissolved in methylene chloride (33 mL). The solution was stirred with trifluoroacetic acid (TFA) (1.76 mL) at room temperature for 5.5 hours. After the solvent was evaporated under reduced pressure, the residue was purified by chromatography on a silica gel (9 g) column using 7% methanol in methylene chloride as the eluant to give the desired compound (79 mg).

$^1$H NMR (CD$_3$OD) δ ppm: 7.85 (d, J=8.1 Hz, 1H), 7.35 (m, 4H), 7.22 (m, 1H), 5.95 (m, 1H), 5.78 (d, J=4.4 Hz, 1H), 5.74 (d, J=8.1 Hz, 1H), 5.24 (d, J=4.6 Hz, 1H), 5.14 (quartet, J=6.9 Hz, 1H), 4.71 (d, J=2.0 Hz, 1H), 4.47 (dd, J=1.7 and 5.1 Hz, 1H), 4.38 (t, J=3.9 Hz, 1H), 4.18 (t, J=4.7 Hz, 1H), 4.03 (m, 1H), 3.61 (t, J=5.0 Hz, 1H), 3.02 (s, 3H), 1.52 (d, J=7.2 Hz, 3H).

IR (KBr) ν cm$^{-1}$: 3339, 2927, 2853, 1685, 1524, 1462, 1386, 1332, 1269, 1205, 1137, 1117, 1060, 1022.

Example 39

Exemplification Compound Number 6576

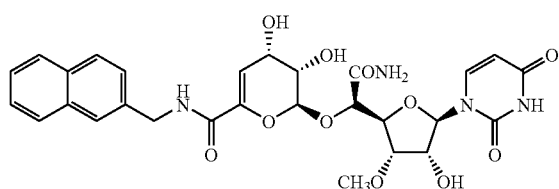

The desired compound (28 mg) was obtained using 2-(aminomethyl)naphthalene (200 μL) in a similar manner to that described in Example 3.

$^1$H NMR (CD$_3$OD) δ ppm: 7.85 (m, 3H), 7.50 (m, 4H), 6.02 (d, J=3.9 Hz, 1H), 5.77 (d, J=4.3 Hz, 1H), 5.73 (d, J=8.1 Hz, 1H), 5.19 (d, J=4.9 Hz, 1H), 5.00 (d, J=15 Hz, 1H), 4.90 (d, J=15.0 Hz, 1H), 4.65 (d, J=2.1 Hz, 1H), 4.43 (dd, J=2.0 and 5.2 Hz, 1H), 4.40 (t, J=3.5 Hz, 1H), 4.16 (t, J=4.6 Hz, 1H), 4.02 (t, J=4.9 Hz, 1H), 3.62 (t, J=5.1 Hz, 1H), 3.05 (s, 3H).

IR (KBr) ν cm$^{-1}$: 3349, 2935, 1685, 1527, 1462, 1397, 1266, 1116, 1094, 1060, 1023.

Example 40

Exemplification Compound Number 6581

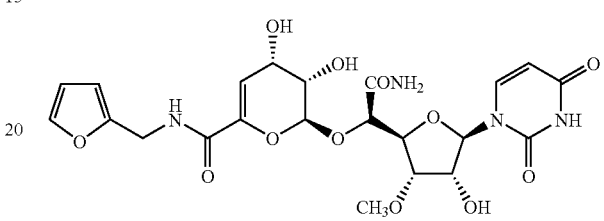

The desired compound (26 mg) was obtained using 2-(aminomethyl)furan (200 μL) in a similar manner to that described in Example 3.

$^1$H NMR (CD$_3$OD) δ ppm: 7.85 (m, 3H), 7.40 (d, J=2.4 Hz, 1H), 6.33 (m, 1H), 6.27 (m, 1H), 5.98 (m, 1H), 5.80 (d, J=4.4 Hz, 1H), 5.75 (d, J=8.1 Hz, 1H), 5.20 (d, J=4.7 Hz, 1H), 4.68 (d, J=2.1 Hz, 1H), 4.51–4.37 (m, 4H), 4.21 (t, J=4.7 Hz, 1H), 4.02 (m, 1H), 3.68 (t, J=5.1 Hz, 1H), 3.27 (s, 3H).

IR (KBr) ν cm$^{-1}$: 3365, 2934, 1685, 1528, 1463, 1391, 1332, 1268, 1140, 1115, 1093, 1059, 1019.

Example 41

Exemplification Compound Number 6586

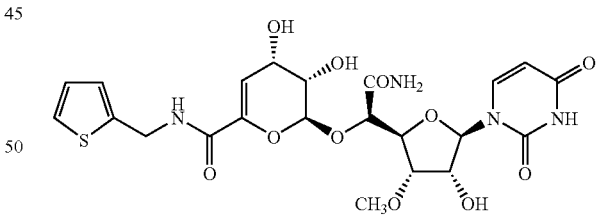

The desired compound (22 mg) was obtained using 2-aminomethylthiophene (200 μL) in a similar manner to that described in Example 3.

$^1$H NMR (CD$_3$OD) δ ppm: 7.85 (d, J=8.1 Hz, 1H), 7.27 (d, J=5.1 Hz, 1H), 7.02 (m, 1H), 6.92 (m, 1H), 5.98 (d, J=2.4 Hz, 1H), 5.79 (d, J=4.4 Hz, 1H), 5.75 (d, J=8.1 Hz, 1H), 5.20 (d, J=4.4 Hz, 1H), 4.67 (d, J=2.2 Hz, 1H), 4.65 (d, J=15.0 Hz, 1H), 4.59 (d, J=15.0 Hz, 1H), 4.47 (dd, J=1.7 and 5.1 Hz, 1H), 4.39 (t, J=4.9 Hz, 1H), 4.20 (t, J=4.6 Hz, 1H), 4.02 (m, 1H), 3.66 (t, J=5.1 Hz, 1H), 3.21 (s, 3H).

IR (KBr) ν cm$^{-1}$: 3334, 2930, 1684, 1522, 1462, 1390, 1267, 1223, 1115, 1092, 1059.

Example 42

Exemplification Compound Number 6591

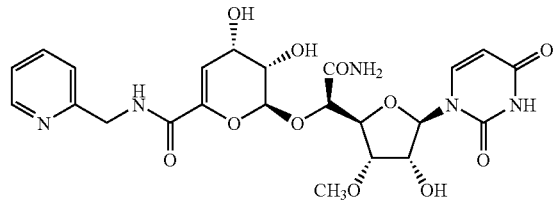

The desired compound (79 mg) was obtained using 2-(aminomethyl)pyridine (108 µL) instead of 4-t-butylcyclohexylamine in a similar manner to that described in Example (9-3).

$^1$H NMR (CD$_3$OD) δ ppm: 8.49 (d, J=5.2 Hz, 1H), 7.88 (d, J=8.1 Hz, 1H), 7.80 (m, 1H), 7.42 (m, 1H), 7.30 (m, 1H), 6.01 (m, 1H), 5.81 (d, J=4.4 Hz, 1H), 5.75 (d, J=8.1 Hz, 1H), 5.25 (d, J=4.5 Hz, 1H), 4.70 (d, J=2.0 Hz, 1H), 4.59 (s, 2H), 4.51 (dd, J=2.0 and 5.2 Hz, 1H), 4.41 (t, J=4.0 Hz, 1H), 4.26 (t, J=4.5 Hz, 1H), 4.02 (m, 1H), 3.75 (t, J=5.0 Hz, 1H), 3.30 (s, 3H).

IR (KBr) ν cm$^{-1}$: 3334, 2932, 1684, 1597, 1572, 1528, 1463, 1438, 1392, 1266, 1139, 1116, 1095, 1059, 1021.

Example 43

Exemplification Compound Number 2

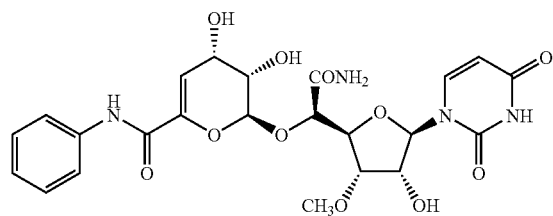

The compound obtained in Example (38-2) (50 mg) was reacted with aniline (108 µL) instead of L-(−)-α-phenethylamine in a similar manner to that described in Example (38-3). After purification by high performance liquid chromatography (HPLC; Intersil PREP-ODS, 30×250 mm) using 15% aqueous acetonitrile as the eluant, the aqueous solution was lyophilized to give the desired compound (22 mg).

$^1$H NMR (CD$_3$OD) δ ppm: 7.87 (d, J=8.1 Hz, 1H), 7.64 (d, J=8.8 Hz, 2H), 7.34 (t, J=7.5 Hz, 2H), 7.15 (t, J=7.3 Hz, 1H), 6.09 (m, 1H), 5.77 (d, J=3.7 Hz, 1H), 5.75 (d, J=8.1 Hz, 1H), 5.30 (d, J=4.3 Hz, 1H), 4.85 (m, 1H), 4.52 (dd, J=1.8 and 6.0 Hz, 1H), 4.45 (m, 1H), 4.26 (t, J=4.2 Hz, 1H), 4.10 (m, 1H), 3.75 (t, J=5.5 Hz, 1H), 3.28 (s, 3H).

IR (KBr) ν cm$^{-1}$: 3339, 2936, 1685, 1599, 1534, 1497, 1462, 1444, 1391, 1323, 1269, 1113, 1060, 1018, 977.

Example 44

Exemplification Compound Number 142

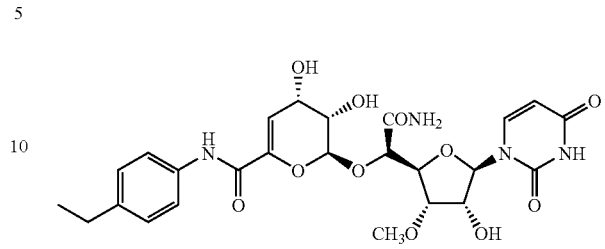

The compound obtained in Example (38-2) (120 mg) was reacted with 4-ethylaniline (57 µL) instead of L-(−)-α-phenethylamine in a similar manner to that described in Example (38-3). After purification by high performance liquid chromatography (HPLC; Intersil PREP-ODS, 30×250 mm) using 30% aqueous acetonitrile as the eluant, the aqueous solution was lyophilized to give the desired compound (48 mg).

$^1$H NMR (CD$_3$OD) δ ppm: 7.86 (d, J=8.1 Hz, 1H), 7.53 (d, J=8.5 Hz, 2H), 7.18 (d, J=8.5 Hz, 2H), 6.14 (m, 1H), 5.77 (d, J=3.7 Hz, 1H), 5.75 (d, J=8.1 Hz, 1H), 5.29 (d, J=4.4 Hz, 1H), 4.85 (m, 1H), 4.52 (dd, J=1.9 and 6.1 Hz, 1H), 4.44 (m, 1H), 4.26 (t, J=4.4 Hz, 1H), 4.08 (t, J=4.3 Hz, 1H), 3.75 (t, J=5.5 Hz, 1H), 3.28 (s, 3H), 2.62 (quartet, J=7.6 Hz, 2H), 1.22 (t, J=7.6 Hz, 3H).

IR (KBr) ν cm$^{-1}$: 3341, 2963, 2932, 1685, 1594, 1527, 1462, 1413, 1392, 1319, 1268, 1112, 1060, 1019, 977.

Example 45

Exemplification Compound Number 3012

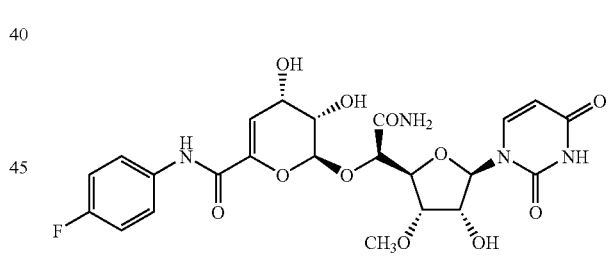

The compound obtained in Example (38-2) (120 mg) was reacted with 4-fluoroaniline (43 µL) instead of L-(−)-α-phenethylamine in a similar manner to that described in Example (38-3). After purification by high performance liquid chromatography (HPLC; Intersil PREP-ODS, 30×250 mm) using 30% aqueous acetonitrile as the eluant, the aqueous solution was lyophilized to give the desired compound (122 mg).

$^1$H NMR (CD$_3$OD) δ ppm: 7.86 (d, J=8.1 Hz, 1H), 7.65 (m, 2H), 7.08 (m, 2H), 6.08 (m, 1H), 5.77 (d, J=3.7 Hz, 1H), 5.75 (d, J=8.1 Hz, 1H), 5.30 (d, J=4.3 Hz, 1H), 4.85 (m, 1H), 4.51 (dd, J=1.9 and 6.2 Hz, 1H), 4.44 (dd, J=3.2 and 4.3 Hz, 1H), 4.25 (dd, J=3.8 and 4.8 Hz, 1H), 4.10 (m, 1H), 3.74 (t, J=5.5 Hz, 1H), 3.28 (s, 3H).

IR (KBr) ν cm$^{-1}$: 3342, 2969, 2936, 1686, 1624, 1576, 1533, 1510, 1464, 1410, 1391, 1326, 1314, 1269, 1215, 1129, 1115, 1060, 1018.

Example 46

Exemplification Compound Number 3152

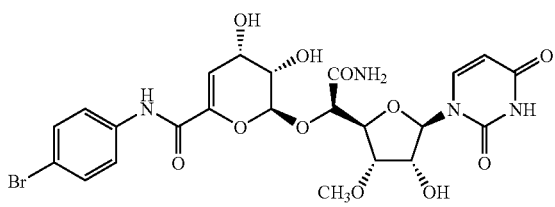

The compound obtained in Example (38-2) (120 mg) was reacted with 4-bromoaniline (79 mg) instead of L-(−)-α-phenethylamine in a similar manner to that described in Example (38-3). After purification by high performance liquid chromatography (HPLC; Intersil PREP-ODS, 30×250 mm) using 30% aqueous acetonitrile as the eluant, the aqueous solution was lyophilized to give the desired compound (52 mg).

$^1$H NMR (CD$_3$OD) δ ppm: 7.86 (d, J=8.1 Hz, 1H), 7.61 (d, J=8.9 Hz, 2H), 7.48 (d, J=8.9 Hz, 2H), 6.08 (m, 1H), 5.76 (d, J=3.7 Hz, 1H), 5.75 (d, J=8.1 Hz, 1H), 5.30 (d, J=4.0 Hz, 1H), 4.85 (m, 1H), 4.51 (dd, J=2.0 and 6.0 Hz, 1H), 4.44 (dd, J=3.2 and 4.3 Hz, 1H), 4.25 (dd, J=3.7 and 4.8 Hz, 1H), 4.09 (m, 1H), 3.73 (m, 1H), 3.27 (s, 3H).

IR (KBr) ν cm$^{-1}$: 3400, 2933, 1685, 1591, 1527, 1490, 1464, 1397, 1310, 1271, 1243, 1113, 1061, 1017, 977.

Example 47

Exemplification Compound Number 2452

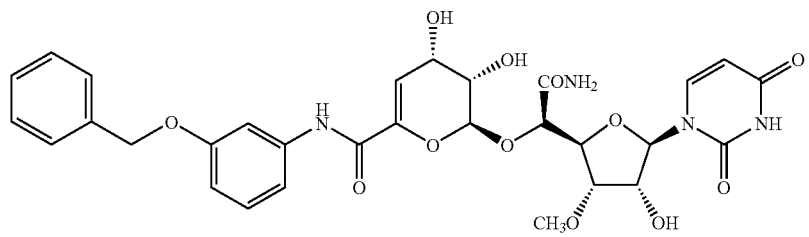

The compound obtained in Example (38-2) (120 mg) was reacted with 3-benzyloxyaniline (90 mg) instead of L-(−)-α-phenethylamine in a similar manner to that described in Example (38-3). After purification by high performance liquid chromatography (HPLC; Intersil PREP-ODS, 30×250 mm) using 30% aqueous acetonitrile as the eluant, the aqueous solution was lyophilized to give the desired compound (106 mg).

$^1$H NMR (CD$_3$OD) δ ppm: 7.86 (d, J=8.1 Hz, 1H), 7.44 (m, 3H), 7.37 (m, 2H), 7.30 (m, 1H), 7.23 (m, 2H), 6.80 (m, 1H), 6.09 (m, 1H), 5.77 (d, J=3.6 Hz, 1H), 5.75 (d, J=8.1 Hz, 1H), 5.29 (d, J=4.3 Hz, 1H), 5.08 (s, 2H), 4.85 (m, 1H), 4.52 (dd, J=1.9 and 6.2 Hz, 1H), 4.44 (t, J=4.3 Hz, 1H), 4.25 (t, J=4.2 Hz, 1H), 4.08 (m, 1H), 3.74 (t, J=5.5 Hz, 1H), 3.26 (s, 3H).

IR (KBr) ν cm$^{-1}$: 3342, 2929, 1685, 1605, 1537, 1493, 1456, 1444, 1426, 1386, 1269, 1206, 1183, 1157, 1138, 1115, 1060, 1022.

Example 48

Exemplification Compound Number 5462

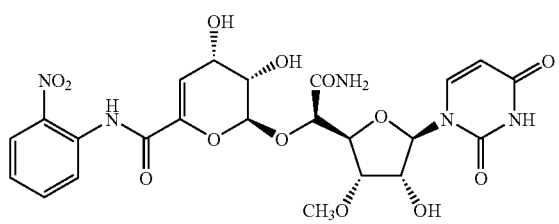

The compound obtained in Example (38-2) (120 mg) was reacted with 2-nitroaniline (63 mg) instead of L-(−)-α-phenethylamine in a similar manner to that described in Example (38-3). After purification by high performance liquid chromatography (HPLC; Intersil PREP-ODS, 30×250 mm) using 30% aqueous acetonitrile as the eluant, the aqueous solution was lyophilized to give the desired compound (8 mg).

$^1$H NMR (CD$_3$OD) δ ppm: 8.73 (d, J=8.6 Hz, 1H), 8.28 (d, J=8.6 Hz, 1H), 7.96 (d, J=8.1 Hz, 1H), 7.76 (t, J=7.2 Hz, 1H), 7.34 (t, J=7.2 Hz, 1H), 6.22 (d, J=3.8 Hz, 1H), 5.88 (d, J=5.2 Hz, 1H), 5.75 (d, J=8.1 Hz, 1H), 5.34 (d, J=5.8 Hz, 1H), 4.73 (d, J=2.1 Hz, 1H), 4.57 (m, 1H), 4.45 (t, J=4.1 Hz, 1H), 4.32 (t, J=5.1 Hz, 1H), 4.05 (t, J=5.1 Hz, 1H), 3.91 (t, J=4.5 Hz, 1H), 3.36 (s, 3H).

IR (KBr) ν cm$^{-1}$: 3402, 3342, 2932, 1687, 1608, 1586, 1505, 1460, 1436, 1385, 1341, 1274, 1243, 1111, 1088, 1060, 1018.

Example 49

Exemplification Compound Number 1822

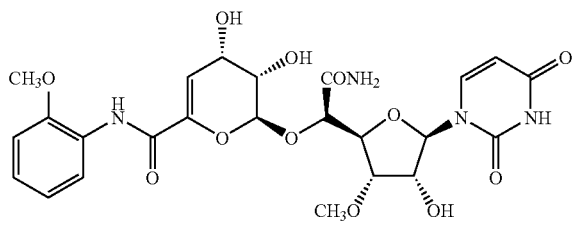

The compound obtained in Example (38-2) (120 mg) was reacted with 2-methoxyaniline (51 μl) instead of L-(−)-α-phenethylamine in a similar manner to that described in Example (38-3). After purification by high performance liquid chromatography (HPLC; Intersil PREP-ODS, 30×250 mm) using 25% aqueous acetonitrile as the eluant, the aqueous solution was lyophilized to give the desired compound (77 mg).

$^1$H NMR (CD$_3$OD) δ ppm: 8.15 (d, J=9.0 Hz, 1H), 7.89 (d, J=8.2 Hz, 1H), 7.13 (m, 1H), 7.05 (m, 1H), 6.95 (m, 1H), 6.12 (d, J=3.6 Hz, 1H), 5.81 (d, J=4.0 Hz, 1H), 5.75 (d, J=8.2 Hz, 1H), 5.33 (d, J=5.0 Hz, 1H), 4.64 (d, J=1.8 Hz, 1H), 4.53 (dd, J=2.0 and 5.4 Hz, 1H), 4.44 (t, J=4.0 Hz, 1H), 4.23 (t, J=4.5 Hz, 1H), 4.06 (m, 1H), 3.78 (t, J=5.3 Hz, 1H), 3.28 (s, 3H).

IR (KBr) ν cm$^{-1}$: 3401, 3319, 2975, 2937, 2840, 1686, 1603, 1531, 1486, 1464, 1437, 1386, 1332, 1291, 1254, 1219, 1203, 1117, 1060, 1022.

Example 50

Exemplification Compound Number 1472

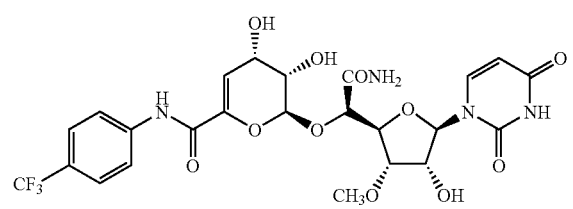

The compound obtained in Example (38-2) (120 mg) was reacted with 4-(trifluoromethyl)aniline (57 μL) instead of L-(−)-α-phenethylamine in a similar manner to that described in Example (38-3). After purification by high performance liquid chromatography (HPLC; Intersil PREP-ODS, 30×250 mm) using 32% aqueous acetonitrile as the eluant, the aqueous solution was lyophilized to give the desired compound (49 mg).

$^1$H NMR (CD$_3$OD) δ ppm: 7.89 (d, J=8.7 Hz, 2H), 7.86 (d, J=8.1 Hz, 1H), 7.64 (d, J=8.7 Hz, 2H), 6.12 (m, 1H), 5.76 (d, J=3.1 Hz, 1H), 5.75 (d, J=8.1 Hz, 1H), 5.32 (d, J=4.2 Hz, 1H), 4.85 (m, 1H), 4.52 (dd, J=2.0 and 6.2 Hz, 1H), 4.46 (m, 1H), 4.23 (t, J=4.2 Hz, 1H), 4.11 (m, 1H), 3.73 (dd, J=5.0 and 6.2 Hz, 1H), 3.26 (s, 3H).

IR (KBr) ν cm$^{-1}$: 3401, 3349, 2936, 1686, 1617, 1602, 1532, 1464, 1412, 1326, 1266, 1251, 1163, 1114, 1066, 1017.

Example 51

Exemplification Compound Number 1542

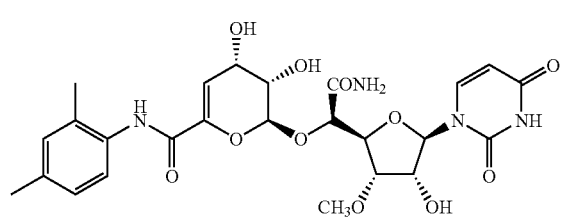

The desired compound (118 mg) was prepared from the compound obtained in Example (38-2) (120 mg) after reacting with 2,4-dimethylaniline (56 μl) instead of L-(−)-α-phenethylamine in a similar manner to that described in Example (38-3).

$^1$H NMR (CD$_3$OD) δ ppm: 7.90 (d, J=8.1 Hz, 2H), 7.27 (d, J=8.1 Hz, 1H), 7.08 (s, 1H), 7.01 (d, J=8.1 Hz, 1H), 6.07 (m, 1H), 5.81 (d, J=3.9 Hz, 1H), 5.75 (d, J=8.1 Hz, 1H), 5.31 (d, J=4.5 Hz, 1H), 4.74 (d, J=2.0 Hz, 1H), 4.53 (dd, J=1.8 and 5.7 Hz, 1H), 4.44 (t, J=4.3 Hz, 1H), 4.28 (t, J=4.4 Hz, 1H), 4.18 (m, 1H), 3.80 (t, J=3.3 Hz, 1H), 3.31 (s, 3H), 2.30 (s, 3H), 2.24 (s, 3H).

IR (KBr) ν cm$^{-1}$: 3408, 3349, 2925, 2854, 1685, 1598, 1525, 1462, 1395, 1265, 1205, 1183, 1135, 1113, 1061, 1019.

Example 52

Exemplification Compound Number 4622

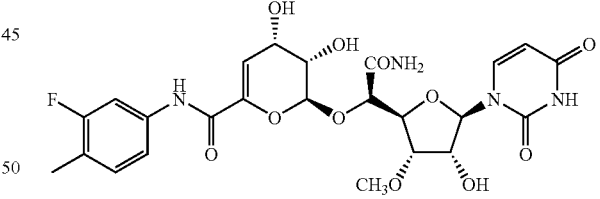

The desired compound (104 mg) was prepared from the compound obtained in Example (38-2) (120 mg) by reacting with 3-fluoro-4-methylaniline (52 μL) instead of L-(−)-α-phenethylamine in a similar manner to that described in Example (38-3).

$^1$H NMR (CD$_3$OD) δ ppm: 7.85 (d, J=8.1 Hz, 2H), 7.52 (dd, J=2.0 and 11.8 Hz, 1H), 7.30 (dd, J=2.0 and 8.2 Hz, 1H), 7.18 (t, J=8.4 Hz, 1H), 6.07 (m, 1H), 5.77 (d, J=3.6 Hz, 1H), 5.75 (d, J=8.1 Hz, 1H), 5.29 (d, J=4.2 Hz, 1H), 4.85 (m, 1H), 4.51 (dd, J=1.8 and 6.1 Hz, 1H), 4.44 (m, 1H), 4.25 (m, 1H), 4.08 (m, 1H), 3.73 (t, J=5.5 Hz, 1H), 3.27 (s, 3H), 2.23 (s, 3H).

IR (KBr) ν cm$^{-1}$: 3332, 2927, 2854, 1685, 1599, 1530, 1462, 1414, 1316, 1268, 1204, 1119, 1060, 1020.

Example 53

Exemplification Compound Number 212

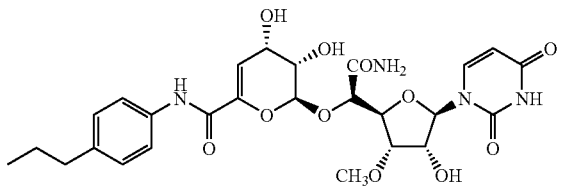

The desired compound (93 mg) was prepared from the compound obtained in Example (38-2) (150 mg) by reacting with 4-n-propylaniline (81 μL) instead of L-(−)-α-phenethylamine in a similar manner to that described in Example (38-3).

$^1$H NMR (CD$_3$OD) δ ppm: 7.87 (d, J=8.1 Hz, 2H), 7.53 (d, J=8.5 Hz, 2H), 7.16 (d, J=8.5 Hz, 2H), 6.07 (d, J=2.4 Hz, 1H), 5.77 (d, J=3.7 Hz, 1H), 5.75 (d, J=8.1 Hz, 1H), 5.29 (d, J=4.4 Hz, 1H), 4.85 (m, 1H), 4.52 (dd, J=1.9 and 6.1 Hz, 1H), 4.44 (dd, J=3.3 and 4.2 Hz, 1H), 4.25 (dd, J=3.9 and 4.8 Hz, 1H), 4.09 (t, J=4.3 Hz, 1H), 3.75 (t, J=5.4 Hz, 1H), 3.28 (s, 3H), 2.57 (t, J=7.8 Hz, 2H), 1.64 (m, 2H), 0.93 (t, J=7.4 Hz, 3H).

IR (KBr) ν cm$^{-1}$: 3400, 3351, 2958, 2932, 2972, 1685, 1595, 1527, 1463, 1413, 1385, 1320, 1269, 1112, 1060, 1018.

Example 54

Exemplification Compound Number 352

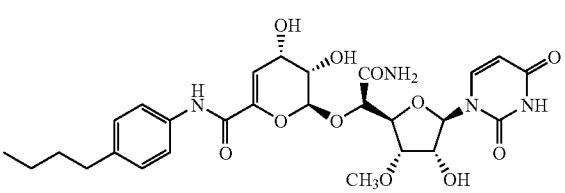

The desired compound (38 mg) was prepared from the compound obtained in Example (38-2) (150 mg) by reacting with 4-n-butylaniline (81 μL) instead of L-(−)-α-phenethylamine in a similar manner to that described in Example (38-3).

$^1$H NMR (CD$_3$OD) δ ppm: 7.87 (d, J=8.1 Hz, 1H), 7.52 (d, J=8.5 Hz, 2H), 7.16 (d, J=8.5 Hz, 2H), 6.07 (d, J=2.4 Hz, 1H), 5.77 (d, J=3.7 Hz, 1H), 5.75 (d, J=8.1 Hz, 1H), 5.29 (d, J=4.3 Hz, 1H), 4.85 (m, 1H), 4.52 (dd, J=1.9 and 6.1 Hz, 1H), 4.44 (m, 1H), 4.25 (t, J=4.2 Hz, 1H), 4.09 (t, J=4.4 Hz, 1H), 3.74 (t, J=5.5 Hz, 1H), 3.28 (s, 3H), 2.59 (t, J=7.6 Hz, 2H), 1.60 (m, 2H), 1.35 (m, 2H), 0.93 (t, J=7.3 Hz, 3H).

IR (KBr) ν cm$^{-1}$: 3390, 2957, 2929, 2873, 2859, 1685, 1595, 1527, 1465, 1413, 1385, 1353, 1320, 1259, 1107, 1060, 1019.

Example 55

Exemplification Compound Number 562

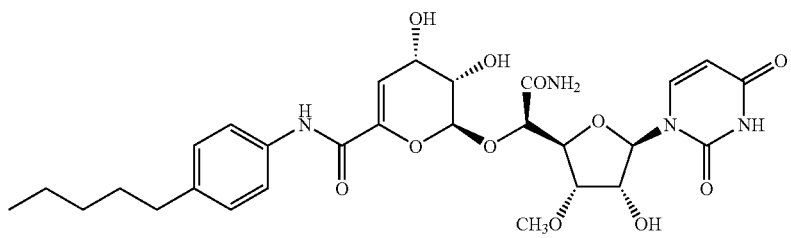

The desired compound (27 mg) was obtained using 4-n-pentylaniline (81 μL) instead of 4-t-butylcyclohexylamine in a similar manner to that described in Example (9-3).

$^1$H NMR (CD$_3$OD) δ ppm: 7.87 (d, J=8.1 Hz, 1H), 7.52 (d, J=8.6 Hz, 2H), 7.15 (d, J=8.6 Hz, 2H), 6.07 (d, J=2.5 Hz, 1H), 5.77 (d, J=3.7 Hz, 1H), 5.75 (d, J=8.1 Hz, 1H), 5.29 (d, J=4.3 Hz, 1H), 4.85 (m, 1H), 4.52 (dd, J=2.0 and 6.0 Hz, 1H), 4.44 (t, J=3.9 Hz, 1H), 4.25 (t, J=4.2 Hz, 1H), 4.09 (m, 1H), 3.75 (t, J=5.4 Hz, 1H), 3.28 (s, 3H), 2.59 (t, J=7.7 Hz, 2H), 1.60 (m, 2H), 1.33 (m, 4H), 0.90 (t, J=6.9 Hz, 3H).

IR (KBr) ν cm$^{-1}$: 3323, 2957, 2930, 2857, 1687, 1595, 1526, 1464, 1413, 1386, 1320, 1262, 1111, 1060, 1018.

Example 56

Exemplification Compound Number 2662

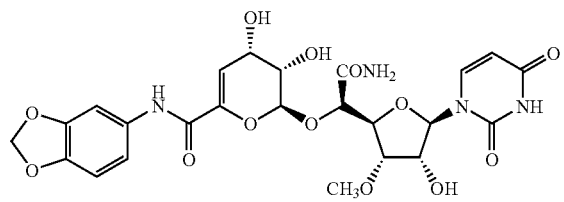

The desired compound (98 mg) was obtained using 3,4-methylenedioxyaniline (109 mg) instead of 4-t-butylcyclohexylamine in a similar manner to that described in Example (9-3).

$^1$H NMR (CD$_3$OD) δ ppm: 7.86 (d, J=8.1 Hz, 1H), 7.26 (d, J=2.1 Hz, 1H), 7.03 (dd, J=2.1 and 8.2 Hz, 1H), 6.78 (d, J=8.2 Hz, 1H), 6.06 (m, 1H), 5.94 (s, 1H), 5.77 (d, J=3.7 Hz, 1H), 5.75 (d, J=8.1 Hz, 1H), 5.28 (d, J=4.3 Hz, 1H), 4.83 (m, 1H), 4.52 (dd, J=1.9 and 6.0 Hz, 1H), 4.43 (m, 1H), 4.25 (m, 1H), 4.07 (m, 1H), 3.73 (t, J=5.5 Hz, 1H), 3.29 (s, 3H).

IR (KBr) ν cm$^{-1}$: 3332, 2925, 2853, 1685, 1538, 1503, 1491, 1462, 1434, 1385, 1269, 1245, 1194, 1139, 1111, 1060, 1038, 1020.

Example 57

Exemplification Compound Number 3712

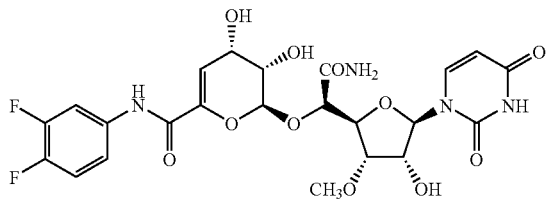

The desired compound (20 mg) was prepared from the compound obtained in Example (38-2) (200 mg) after reacting with 3,4-difluoroaniline (75 μL) instead of L-(−)-α-phenethylamine in a similar manner to that described in Example (38-3).

$^1$H NMR (CD$_3$OD) δ ppm: 7.85 (d, J=8.1 Hz, 1H), 7.76 (m, 1H), 7.40 (m, 1H), 7.23 (quartet, J=9.5 Hz, 1H), 6.09 (m, 1H), 5.75 (d, J=3.3 Hz, 1H), 5.74 (d, J=8.1 Hz, 1H), 5.30 (d, J=4.2 Hz, 1H), 4.82 (m, 1H), 4.50 (dd, J=2.0 and 6.4 Hz, 1H), 4.44 (m, 1H), 4.25 (dd, J=3.7 and 4.7 Hz, 1H), 4.10 (m, 1H), 3.72 (m, 1H), 3.26 (s, 3H).

IR (KBr) ν cm$^{-1}$: 3396, 3334, 2938, 2837, 1685, 1618, 1536, 1518, 1463, 1414, 1386, 1327, 1267, 1242, 1210, 1115, 1060, 1019.

Example 58

Exemplification Compound Number 982

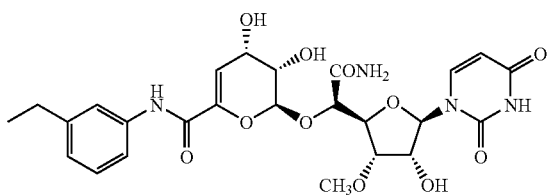

The desired compound (111 mg) was prepared from the compound obtained in Example (38-2) (200 mg) by reacting with 3-ethylaniline (75 μL) instead of L-(−)-α-phenethylamine in a similar manner to that described in Example (38-3).

$^1$H NMR (CD$_3$OD) δ ppm: 7.86 (d, J=8.1 Hz, 1H), 7.48 (s, 1H), 7.47 (d, J=8.0 Hz, 1H), 7.24 (dd, J=7.5 and 8.0 Hz, 1H), 7.00 (d, J=7.5 Hz, 1H), 6.08 (m, 1H), 5.77 (d, J=3.7 Hz, 1H), 5.75 (d, J=8.1 Hz, 1H), 5.30 (d, J=4.4 Hz, 1H), 4.84 (m, 1H), 4.53 (dd, J=1.9 and 6.1 Hz, 1H), 4.44 (m, 1H), 4.26 (m, 1H), 4.08 (m, 1H), 3.76 (t, J=5.5 Hz, 1H), 3.29 (s, 3H), 2.64 (quartet, J=7.6 Hz, 2H), 1.23 (t, J=7.6 Hz, 3H).

IR (KBr) ν cm$^{-1}$: 3410, 2964, 2930, 1685, 1611, 1595, 1542, 1490, 1462, 1448, 1422, 1385, 1330, 1307, 1266, 1113, 1059, 1020.

Example 59

Exemplification Compound Number 5742

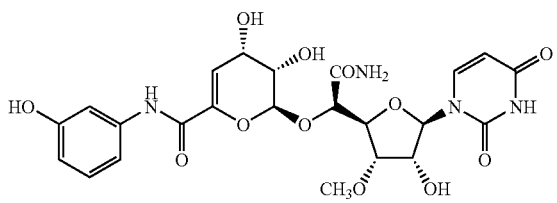

The desired compound (118 mg) was obtained using 3-aminophenol (87 μL) instead of 4-t-butylcyclohexylamine in a similar manner to that described in Example (9-3).

$^1$H NMR (CD$_3$OD) δ ppm: 7.87 (d, J=8.1 Hz, 1H), 7.23 (t, J=2.1 Hz, 1H), 7.13 (t, J=8.1 Hz, 1H), 7.03 (dd, J=2.1 and 8.0 Hz, 1H), 6.58 (dd, J=2.1 and 8.0 Hz, 1H), 6.07 (m, 1H), 5.77 (d, J=3.7 Hz, 1H), 5.75 (d, J=8.1 Hz, 1H), 5.29 (d, J=4.4 Hz, 1H), 4.83 (m, 1H), 4.52 (dd, J=1.9 and 6.0 Hz, 1H), 4.44 (m, 1H), 4.26 (m, 1H), 4.08 (m, 1H), 3.76 (t, J=5.4 Hz, 1H), 3.30 (s, 3H).

IR (KBr) ν cm$^{-1}$: 3390, 2936, 2836, 1684, 1604, 1541, 1494, 1455, 1386, 1334, 1271, 1175, 1113, 1060, 1020.

Example 60

Exemplification Compound Number 4132

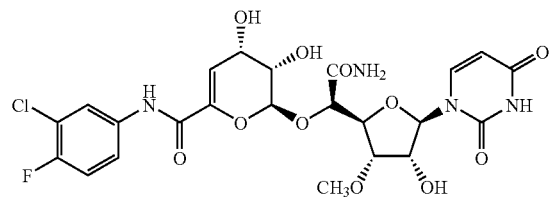

The desired compound (27 mg) was obtained using 3-chloro-4-fluoroaniline (116 μL) instead of 4-t-butylcyclohexylamine in a similar manner to that described in Example (9-3).

$^1$H NMR (CD$_3$OD) δ ppm: 7.90 (dd, J=2.7 and 6.6 Hz, 1H), 7.85 (d, J=8.1 Hz, 1H), 7.15 (m, 2H), 6.09 (m, 1H), 5.76 (d, J=3.0 Hz, 1H), 5.75 (d, J=8.1 Hz, 1H), 5.30 (d, J=3.9 Hz, 1H), 4.83 (m, 1H), 4.51 (dd, J=2.0 and 6.2 Hz, 1H), 4.44 (dd, J=3.2 and 4.2 Hz, 1H), 4.26 (m, 1H), 4.11 (m, 1H), 3.73 (m, 1H), 3.26 (s, 3H).

IR (KBr) ν cm$^{-1}$: 3409, 2957, 2928, 2854, 1685, 1604, 1537, 1502, 1466, 1400, 1385, 1260, 1138, 1116, 1065, 1007.

Example 61

Exemplification Compound Number 1192

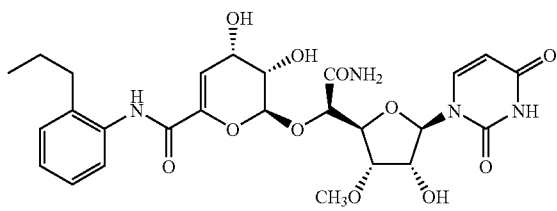

The desired compound (44 mg) was obtained using 2-n-propylaniline (135 μL) instead of 4-t-butylcyclohexylamine in a similar manner to that described in Example (9-3).

$^1$H NMR (CD$_3$OD) δ ppm: 7.91 (d, J=8.1 Hz, 1H), 7.44 (m, 1H), 7.27 (m, 1H), 7.22 (m, 2H), 6.09 (m, 1H), 5.80 (d, J=3.7 Hz, 1H), 5.76 (d, J=8.1 Hz, 1H), 5.33 (d, J=4.5 Hz, 1H), 4.72 (d, J=2.0 Hz, 1H), 4.52 (dd, J=2.0 and 5.7 Hz, 1H), 4.45 (m, 1H), 4.29 (t, J=4.5 Hz, 1H), 4.10 (t, J=4.3 Hz, 1H), 3.80 (t, J=5.3 Hz, 1H), 3.34 (s, 3H), 2.61 (t, J=7.2 Hz, 2H), 1.63 (m, 2H), 0.95 (t, J=7.3 Hz, 3H).

IR (KBr) ν cm$^{-1}$: 3423, 2960, 2933, 2873, 1685, 1588, 1525, 1455, 1385, 1267, 1111, 1060, 1019.

Example 62

Exemplification Compound Number 2242

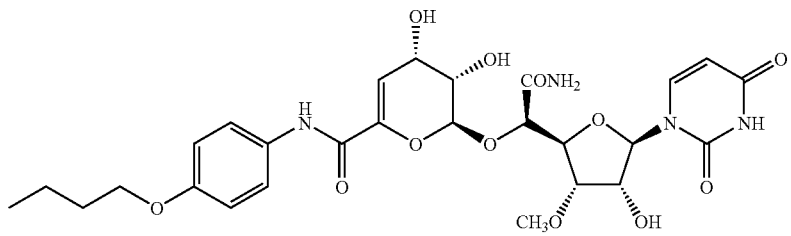

The desired compound (47 mg) was obtained using 4-n-butoxyaniline (95 μL) instead of 4-t-butylcyclohexylamine in a similar manner to that described in Example (9-3).

$^1$H NMR (CD$_3$OD) δ ppm: 7.87 (d, J=8.1 Hz, 1H), 7.51 (d, J=8.9 Hz, 2H), 6.89 (d, J=8.9 Hz, 2H), 6.06 (m, 1H), 5.77 (d, J=3.7 Hz, 1H), 5.75 (d, J=8.1 Hz, 1H), 5.29 (d, J=4.4 Hz, 1H), 4.83 (d, J=2.1 Hz, 1H), 4.52 (dd, J=2.0 and 5.9 Hz, 1H), 4.44 (dd, J=3.3 and 4.2 Hz, 1H), 4.25 (m, 1H), 4.08 (t, J=4.4 Hz, 1H), 3.96 (t, J=6.5 Hz, 2H), 3.74 (t, J=5.4 Hz, 1H), 3.29 (s, 3H), 1.74 (m, 2H), 1.50 (m, 2H), 0.98 (t, J=7.6 Hz, 3H).

IR (KBr) ν cm$^{-1}$: 3407, 3358, 2958, 2935, 2874, 1685, 1597, 1528, 1512, 1465, 1414, 1385, 1245, 1173, 1112, 1061.

Example 63

Exemplification Compound Number 2382

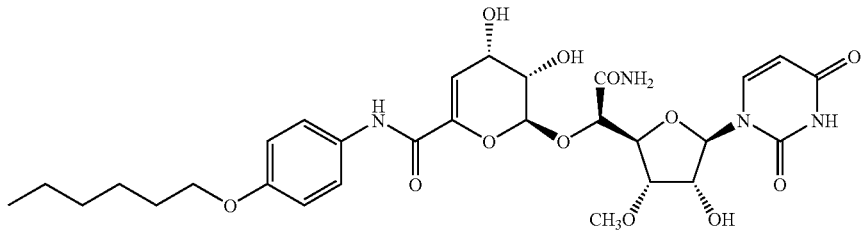

The desired compound (46 mg) was obtained using 4-n-hexyloxyaniline (110 mg) instead of 4-t-butylcyclohexylamine in a similar manner to that described in Example (9-3).

$^1$H NMR (CD$_3$OD) δ ppm: 7.86 (d, J=8.1 Hz, 1H), 7.50 (m, 2H), 6.89 (m, 2H), 6.06 (m, 1H), 5.77 (d, J=3.7 Hz, 1H), 5.75 (d, J=8.1 Hz, 1H), 5.28 (d, J=4.2 Hz, 1H), 4.83 (d, J=1.7 Hz, 1H), 4.52 (dd, J=2.1 and 5.9 Hz, 1H), 4.44 (t, J=4.3 Hz, 1H), 4.25 (m, 1H), 4.08 (m, 1H), 3.96 (t, J=6.5 Hz, 2H), 3.74 (t, J=5.4 Hz, 1H), 3.29 (s, 3H), 1.75 (m, 2H), 1.48 (m, 2H), 1.37 (m, 4H), 0.98 (t, J=7.1 Hz, 3H).

IR (KBr) ν cm$^{-1}$: 3348, 2933, 2871, 1685, 1597, 1528, 1513, 1467, 1414, 1385, 1245, 1111, 1078, 1060, 1019.

Example 64

Exemplification Compound Number 2312

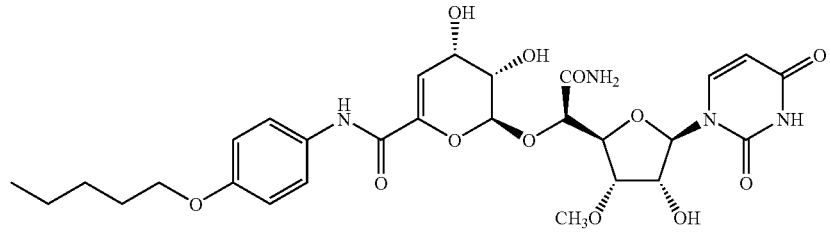

The desired compound (105 mg) was obtained using 4-n-pentoxyaniline (105 μL) instead of 4-t-butylcyclohexylamine in a similar manner to that described in Example (9-3).

$^1$H NMR (CD$_3$OD) δ ppm: 7.86 (d, J=8.1 Hz, 1H), 7.51 (m, 2H), 6.89 (m, 2H), 6.07 (m, 1H), 5.77 (d, J=3.8 Hz, 1H), 5.75 (d, J=8.1 Hz, 1H), 5.29 (d, J=4.3 Hz, 1H), 4.83 (d, J=2.0 Hz, 1H), 4.52 (dd, J=1.9 and 5.9 Hz, 1H), 4.44 (m, 1H), 4.25 (m, 1H), 4.09 (t, J=4.3 Hz, 1H), 3.96 (t, J=6.3 Hz, 2H), 3.74 (t, J=5.4 Hz, 1H), 3.29 (s, 3H), 1.76 (m, 2H), 1.44 (m, 2H), 0.95 (t, J=7.2 Hz, 3H).

IR (KBr) ν cm$^{-1}$: 3407, 2956, 2934, 2872, 1685, 1597, 1528, 1513, 1466, 1414, 1386, 1247, 1112, 1060, 1019.

Example 65

Exemplification Compound Number 4202

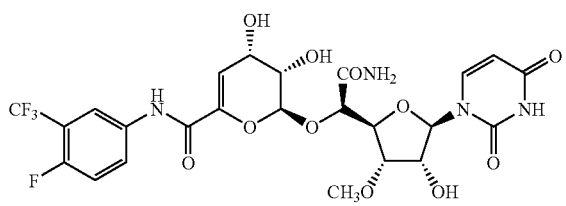

The desired compound (114 mg) was obtained using 3-trifluoromethyl-4-fluoroaniline (73 μL) instead of 4-t-butylcyclohexylamine in a similar manner to that described in Example (9-3).

$^1$H NMR (CD$_3$OD) δ ppm: 8.09 (dd, J=2.6 and 6.3 Hz, 1H), 7.97 (m, 1H), 7.86 (d, J=8.1 Hz, 1H), 7.33 (t, J=9.6 Hz, 1H), 6.11 (m, 1H), 5.75 (m, 2H), 5.31 (d, J=3.8 Hz, 1H), 4.82 (d, J=2.1 Hz, 1H), 4.51 (dd, J=2.0 and 6.3 Hz, 1H), 4.45 (dd, J=3.2 and 4.3 Hz, 1H), 4.26 (t, J=4.0 Hz, 1H), 4.12 (m, 1H), 3.72 (t, J=5.5 Hz, 1H), 3.25 (s, 3H).

IR (KBr) ν cm$^{-1}$: 3407, 2932, 1686, 1542, 1508, 1464, 1429, 1386, 1329, 1269, 1243, 1136, 1056, 1019.

Example 66

Exemplification Compound Number 6596

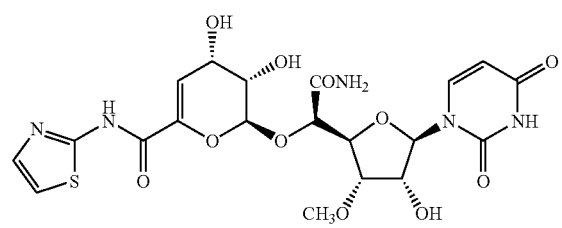

The desired compound (81 mg) was prepared from the compound obtained in Example (38-2) (120 mg) by reacting with 2-aminothiazole (45 mg) instead of L-(−)-α-phenethylamine in a similar manner to that described in Example (38-3).

$^1$H NMR (CD$_3$OD) δ ppm: 7.84 (d, J=8.1 Hz, 1H), 7.50 (d, J=3.6 Hz, 1H), 7.18 (d, J=3.6 Hz, 1H), 6.19 (m, 1H), 5.76 (d, J=3.9 Hz, 1H), 5.74 (d, J=8.1 Hz, 1H), 5.32 (d, J=4.4 Hz, 1H), 4.83 (m, 1H), 4.50 (dd, J=2.3 and 5.8 Hz, 1H), 4.45 (m, 1H), 4.27 (m, 1H), 4.08 (m, 1H), 3.75 (t, J=5.3 Hz, 1H), 3.27 (s, 3H).

IR (KBr) ν cm$^{-1}$: 3334, 2937, 2834, 1685, 1541, 1463, 1393, 1322, 1269, 1224, 1138, 1113, 1059, 1019.

Example 67

Exemplification Compound Number 6601

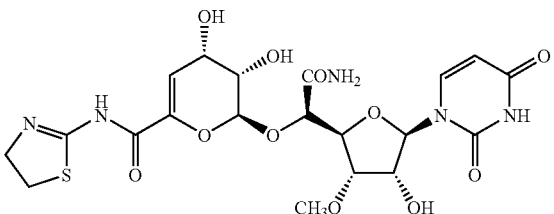

The desired compound (54 mg) was prepared from the compound obtained in Example (38-2) (120 mg) by reacting with 2-amino-4,5-dihydrothiazole (45 mg) instead of L-(−)-α-phenethylamine in a similar manner to that described in Example (38-3).

$^1$H NMR (CD$_3$OD) δ ppm: 7.87 (d, J=8.1 Hz, 1H), 6.24 (d, J=3.5 Hz, 1H), 5.84 (d, J=4.9 Hz, 1H), 5.74 (d, J=8.1 Hz, 1H), 5.16 (d, J=5.1 Hz, 1H), 4.67 (d, J=2.1 Hz, 1H), 4.51

(dd, J=2.1 and 4.8 Hz, 1H), 4.38 (t, J=4.1 Hz, 1H), 4.24 (t, J=4.9 Hz, 1H), 3.97 (t, J=4.8 Hz, 1H), 3.86 (t, J=4.9 Hz, 1H), 3.78 (t, J=7.9 Hz, 2H), 3.41 (s, 3H), 3.34 (m, 2H).

IR (KBr) ν cm$^{-1}$: 3313, 2939, 1685, 1614, 1549, 1465, 1442, 1395, 1333, 1266, 1224, 1204, 1113, 1058, 1018.

Example 68

Exemplification Compound Number 6606

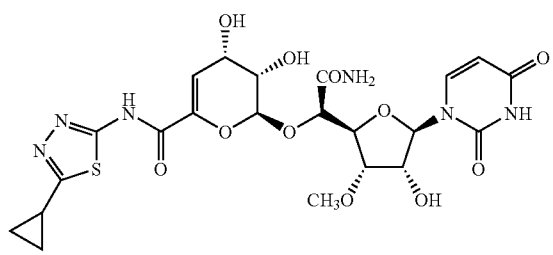

The desired compound (59 mg) was prepared from the compound obtained in Example (38-2) (80 mg) by reacting with 2-amino-5-cyclopropyl-1,3,4-thiadiazole (42 mg) instead of L-(−)-α-phenethylamine in a similar manner to that described in Example (38-3).

$^1$H NMR (CD$_3$OD) δ ppm: 7.84 (d, J=8.1 Hz, 1H), 6.19 (d, J=2.4 Hz, 1H), 5.76 (d, J=3.9 Hz, 1H), 5.73 (d, J=8.1 Hz, 1H), 5.32 (d, J=4.2 Hz, 1H), 4.83 (d, J=2.2 Hz, 1H), 4.50 (dd, J=2.2 and 5.8 Hz, 1H), 4.45 (dd, J=2.3 and 4.2 Hz, 1H), 4.24 (m, 1H), 4.10 (m, 1H), 3.73 (t, J=5.4 Hz, 1H), 3.27 (s, 3H), 2.47 (m, 1H), 1.22 (m, 2H), 1.06 (m, 2H).

IR (KBr) ν cm$^{-1}$: 3333, 2935, 2853, 1685, 1536, 1483, 1464, 1393, 1308, 1273, 1204, 1137, 1115, 1058, 1017.

Example 69

Exemplification Compound Number 6611

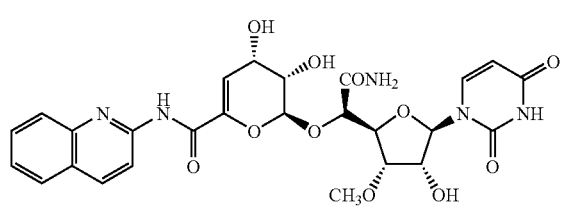

The desired compound (56 mg) was prepared from the compound obtained in Example (38-2) (120 mg) by reacting with 2-aminoquinoline (42 mg) instead of L-(−)-α-phenethylamine in a similar manner to that described in Example (38-3).

$^1$H NMR (CD$_3$OD) δ ppm: 9.07 (d, J=2.2 Hz, 1H), 8.77 (d, J=2.5 Hz, 1H), 7.87 (d, J=8.1 Hz, 1H), 7.67 (m, 4H), 6.18 (m, 1H), 5.76 (m, 2H), 5.36 (d, J=3.8 Hz, 1H), 4.87 (m, 1H), 4.54 (dd, J=2.0 and 6.1 Hz, 1H), 4.49 (dd, J=2.1 and 4.2 Hz, 1H), 4.27 (dd, J=3.6 and 4.9 Hz, 1H), 4.15 (m, 1H), 3.76 (dd, J=5.1 and 6.2 Hz, 1H), 3.27 (s, 3H).

Example 70

Exemplification Compound Number 6616

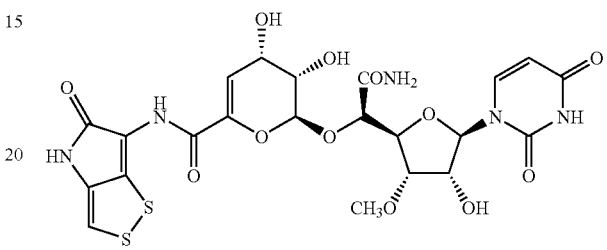

The desired compound (81 mg) was obtained using horothin hydrochloride (153 mg) and triethylamine (204 μL) instead of 4-t-butylcyclohexylamine in a similar manner to that described in Example (9-3).

$^1$H NMR (CD$_3$OD) δ ppm: 7.88 (d, J=8.1 Hz, 1H), 7.19 (s, 1H), 6.08 (d, J=3.6 Hz, 1H), 5.82 (d, J=4.4 Hz, 1H), 5.74 (d, J=8.1 Hz, 1H), 5.28 (d, J=5.0 Hz, 1H), 4.79 (d, J=2.1 Hz, 1H), 4.54 (dd, J=2.2 and 5.1 Hz, 1H), 4.43 (t, J=4.0 Hz, 1H), 4.28 (m, 1H), 4.05 (m, 1H), 3.79 (t, J=5.0 Hz, 1H), 3.41 (s, 3H).

IR (KBr) ν cm$^{-1}$: 3379, 3071, 2936, 2834, 1683, 1520, 1462, 1385, 1316, 1268, 1190, 1110, 1060, 1018.

Example 71

Exemplification Compound Number 6621

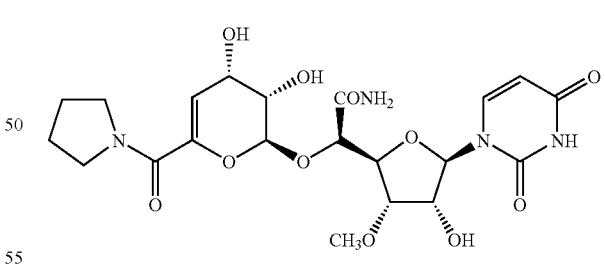

The desired compound (12 mg) was obtained using pyrrolidine (82 μL) in a similar manner to that described in Example 3.

$^1$H NMR (CD$_3$OD) δ ppm: 7.95 (d, J=8.1 Hz, 1H), 5.85 (d, J=4.0 Hz, 1H), 5.75 (d, J=8.1 Hz, 1H), 5.56 (d, J=4.4 Hz, 1H), 5.15 (d, J=6.6 Hz, 1H), 4.55 (m, 2H), 4.33 (t, J=4.4 Hz, 1H), 4.28 (t, J=4.6 Hz, 1H), 3.90 (m, 2H), 3.68 (m, 2H), 3.45 (m, 2H), 3.42 (s, 3H), 1.93 (m, 4H).

IR (KBr) ν cm$^{-1}$: 3389, 2935, 2883, 1687, 1614, 1515, 1455, 1389, 1338, 1268, 1196, 1136, 1114, 1091, 1060.

Example 72

Exemplification Compound Number 66

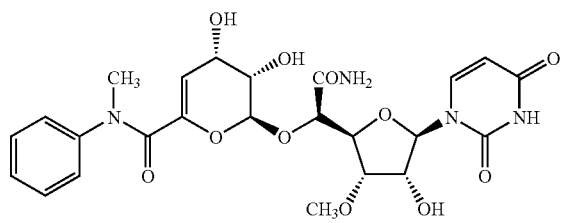

The desired compound (40 mg) was prepared from the compound obtained in Example (38-2) (80 mg) by reacting with N-methylaniline (32 μL) instead of L-(−)-α-phenethylamine in a similar manner to that described in Example (38-3).

$^1$H NMR (CD$_3$OD) δ ppm: 7.88 (d, J=8.1 Hz, 1H), 7.45–7.05 (m, 5H), 5.87 (d, J=5.2 Hz, 1H), 5.69 (d, J=8.1 Hz, 1H), 5.66 (d, J=5.2 Hz, 1H), 4.85 (m, 1H), 4.40 (m, 1H), 4.23 (m, 2H), 3.18 (m, 1H), 3.13 (m, 1H), 3.55 (s, 3H), 3.36 (s, 3H).

IR (KBr) ν cm$^{-1}$: 3335, 2935, 2833, 1685, 1593, 1496, 1463, 1390, 1271, 1203, 1134, 1089, 1060.

Example 73

Exemplification Compound Number 6626

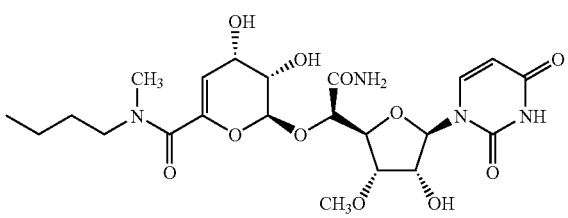

The desired compound (61 mg) was prepared from the compound obtained in Example (38-2) (160 mg) by reacting with N-methyl-n-butylamine (300 μL) instead of L-(−)-α-phenethylamine in a similar manner to that described in Example (38-3).

$^1$H NMR (CD$_3$OD) δ ppm: 7.95 (d, J=8.1 Hz, 1H), 5.88 (m, 1H), 5.74 (d, J=8.1 Hz, 1H), 5.27 (dd, J=4.3 and 18.0 Hz, 1H), 5.15 (m, 1H), 4.52 (m, 2H), 4.31 (t, J=4.4 Hz, 1H), 4.29 (br s, 1H), 3.91 (m, 2H), 3.44 and 3.42 (2s, 3H), 3.10 and 2.92 (2s, 3H), 1.58 (m, 2H), 1.32 (m, 2H), 0.94 (t, J=7.3 Hz, 3H).

IR (KBr) ν cm$^{-1}$: 3403, 2958, 2933, 2874, 1686, 1625, 1492, 1463, 1408, 1386, 1268, 1111, 1091, 1061, 1024.

Example 74

Exemplification Compound Number 6627

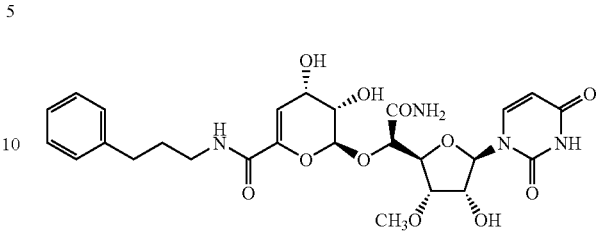

The desired compound (30 mg) was obtained using 3-phenylpropylamine (200 μL) in a similar manner to that described in Example 3.

$^1$H NMR (CD$_3$OD) δ ppm: 7.87 (d, J=8.1 Hz, 1H), 7.28–7.14 (m, 5H), 5.95 (m, 1H), 5.79 (d, J=4.2 Hz, 1H), 5.75 (d, J=8.1 Hz, 1H), 5.21 (d, J=4.4 Hz, 1H), 4.68 (d, J=2.0 Hz, 1H), 4.49 (m, 1H), 4.38 (m, 1H), 4.23 (t, J=4.5 Hz, 1H), 4.03 (m, 1H), 3.70 (t, J=5.2 Hz, 1H), 3.34 (s, 3H), 3.32 (m, 2H), 2.65 (t, J=7.5 Hz, 2H).

IR (KBr) ν cm$^{-1}$: 3350, 2935, 1685, 1532, 1496, 1462, 1391, 1267, 1136, 1116, 1094, 1058.

Example 75

Exemplification Compound Number 6628

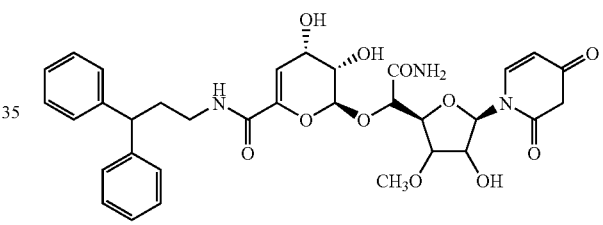

The desired compound (36 mg) was obtained using 3,3-diphenylpropylamine (200 μL) in a similar manner to that described in Example 3.

$^1$H NMR (CD$_3$OD) δ ppm: 7.86 (d, J=8.1 Hz, 1H), 7.30–7.12 (m, 10H), 5.93 (m, 1H), 5.79 (d, J=4.0 Hz, 1H), 5.75 (d, J=8.1 Hz, 1H), 5.19 (d, J=4.4 Hz, 1H), 4.67 (d, J=2.1 Hz, 1H), 4.49 (m, 1H), 4.37 (m, 1H), 4.23 (t, J=4.5 Hz, 1H), 4.00 (m, 2H), 3.68 (t, J=5.2 Hz, 1H), 3.30 (s, 3H), 3.35–3.17 (m, 2H), 2.32 (quartet, J=7.7 Hz, 2H).

IR (KBr) ν cm$^{-1}$: 3344, 3061, 3027, 2936, 1685, 1529, 1495, 1453, 1390, 1268, 1136, 1115, 1095, 1057, 1030.

Example 76

Exemplification Compound Number 69

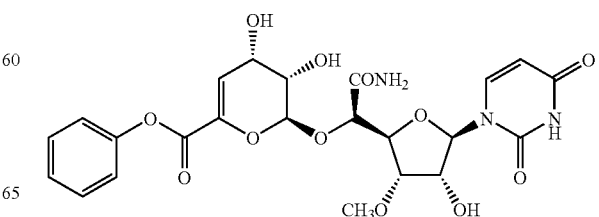

305

The desired compound (14 mg) was obtained using phenol (160 mg) instead of 4-t-butylcyclohexylamine in a similar manner to that described in Example (9-3).

$^1$H NMR (CD$_3$OD) δ ppm: 7.93 (d, J=8.1 Hz, 1H), 7.42 (m, 2H), 7.28 (m, 1H), 7.14 (m, 2H), 6.34 (d, J=4.0 Hz, 1H), 5.85 (d, J=4.4 Hz, 1 h), 5.75 (d, J=8.1 Hz, 1H), 5.23 (d, J=5.8 Hz, 1H), 4.62 (d, J=1.6 Hz, 1H), 4.57 (m, 1H), 4.45 (t, J=4.3 Hz, 1H), 4.27 (t, J=4.7 Hz, 1H), 4.00 (m, 2H), 3.42 (s, 3H).

IR (KBr) ν cm$^{-1}$: 3404, 2925, 2852, 1684, 1591, 1487, 1460, 1386, 1301, 1248, 1195, 1162, 1111, 1064, 1019.

Example 77

Exemplification Compound Number 6629

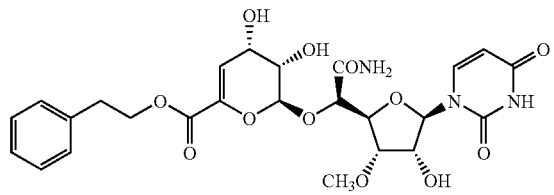

The desired compound (38 mg) was obtained using phenethyl alcohol (191 µL) instead of 4-t-butylcyclohexylamine in a similar manner to that described in Example (9-3).

$^1$H NMR (CD$_3$OD) δ ppm: 7.89 (d, J=8.1 Hz, 1H), 7.25 (m, 5H), 6.07 (d, J=4.0 Hz, 1H), 5.83 (d, J=4.6 Hz, 1H), 5.72 (d, J=8.1 Hz, 1H), 5.12 (d, J=5.8 Hz, 1H), 4.55 (m, 2H), 4.39 (t, J=6.8 Hz, 2H), 4.35 (t, J=4.2 Hz, 1H), 4.21 (t, J=4.7 Hz, 1H), 3.92 (m, 1H), 3.86 (t, J=4.9 Hz, 1H), 3.37 (s, 3H), 2.98 (t, J=6.8 Hz, 2H).

IR (KBr) ν cm$^{-1}$: 3420, 2934, 1684, 1462, 1389, 1265, 1113, 1088, 1062, 1026.

Example 78

Exemplification Compound Number 6630

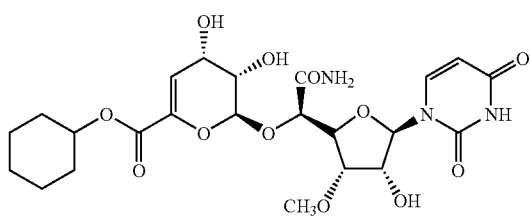

The desired compound (33 mg) was obtained using cyclohexanol (169 µL) instead of 4-t-butylcyclohexylamine in a similar manner to that described in Example (9-3).

$^1$H NMR (CD$_3$OD) δ ppm: 7.91 (d, J=8.1 Hz, 1H), 6.10 (d, J=4.0 Hz, 1H), 5.85 (d, J=4.6 Hz, 1H), 5.73 (d, J=8.1 Hz, 1H), 5.14 (d, J=5.8 Hz, 1H), 4.56 (m, 2H), 4.36 (t, J=4.3 Hz, 1H), 4.24 (t, J=5.0 Hz, 1H), 3.92 (m, 2H), 3.46 (s, 3H), 1.88 (m, 2H), 1.75 (m, 2H), 1.60–1.30 (m, 6H).

306

Example 79

Exemplification Compound Number 6631

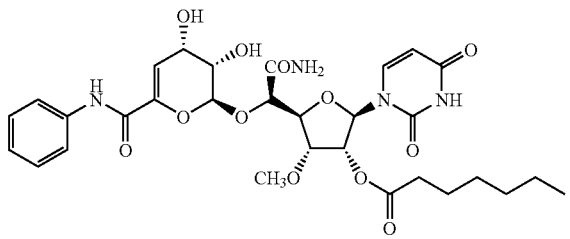

Example (79-1)

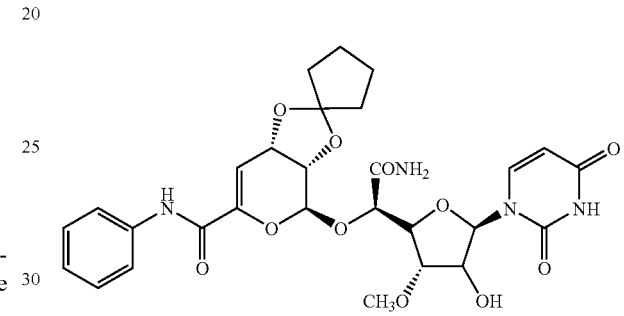

To a solution of the compound obtained in Example (38-2) (2 g) in DMF (30 mL) were added aniline (1.04 mL), HOBT (820 mg) and DIPC (1.37 mL), and the mixture was stirred at room temperature for 1 hour. After addition of methanol (1 mL), the solvent was evaporated under reduced pressure. The residue was purified by chromatography on a silica gel (80 g) column using 3% methanol in methylene chloride as the eluant to give the desired compound (1.5 g).

$^1$H NMR (CD$_3$OD) δ ppm: 7.87 (d, J=8.1 Hz, 1H), 7.65 (m, 2H), 7.35 (m, 2H), 7.16 (t, J=7.3 Hz, 1H), 6.23 (d, J=3.8 Hz, 1H), 5.80 (d, J=3.7 Hz, 1H), 5.72 (d, J=8.1 Hz, 1H), 5.20 (d, J=5.0 Hz, 1H), 4.78 (dd, J=3.8 and 5.9 Hz, 1H), 4.56 (dd, J=1.8 and 6.1 Hz, 1H), 4.38 (t, J=5.6 Hz, 1H), 4.29 (m, 1H), 3.84 (t, J=5.5 Hz, 1H), 3.30 (s, 3H), 1.88 (m, 4H), 1.72 (m, 4H).

IR (KBr) ν cm$^{-1}$: 3331, 3100, 3064, 2959, 2940, 1690, 1599, 1533, 1498, 1445, 1388, 1321, 1300, 1268, 1243, 1207, 1101, 1072.

Example (79-2)

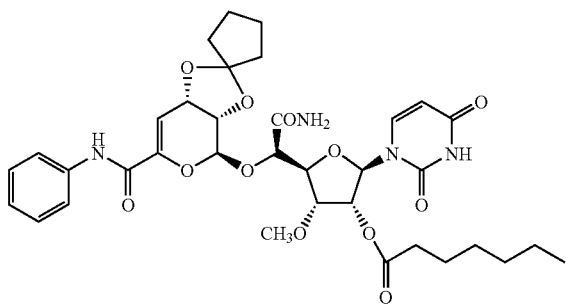

To a solution of the compound obtained in Example (79-1) (150 mg) in pyridine (4.5 mL) were added n-heptanoic anhydride (131 μL) and dimethylaminopyridine (3 mg). The mixture was stirred at room temperature for 4 hours. After addition of methanol (1 mL), the solvent was evaporated under reduced pressure. The residue was then dissolved in ethyl acetate (150 mL) and the solution was washed with saturated aqueous sodium hydrogen carbonate solution (150 mL) and saturated aqueous sodium chloride solution (150 mL). After drying over anhydrous sodium sulfate, the solvent was evaporated under reduced pressure. The residue was purified by chromatography on a silica gel (8 g) column using 1.5% methanol in methylene chloride as the eluant to give the desired compound (155 mg).

$^1$H NMR (CD$_3$OD) δ ppm: 7.84 (d, J=8.1 Hz, 1H), 7.63 (d, J=7.5 Hz, 2H), 7.34 (t, J=8.0 Hz, 2H), 7.16 (t, J=7.3 Hz, 1H), 6.22 (d, J=3.8 Hz, 1H), 5.94 (d, J=4.7 Hz, 1H), 5.74 (d, J=8.1 Hz, 1H), 5.38 (t, J=4.7 Hz, 1H), 5.22 (d, J=5.0 Hz, 1H), 4.85 (m, 2H), 4.55 (m, 1H), 4.39 (t, J=5.5 Hz, 1H), 4.09 (t, J=5.0 Hz, 1H), 3.30 (s, 3H), 2.38 (t, J=7.2 Hz, 2H), 1.88 (m, 4H), 1.72 (m, 4H), 1.60 (m, 2H), 1.30 (m, 6H), 0.88 (t, J=6.8 Hz, 3H).

Example (79-3)

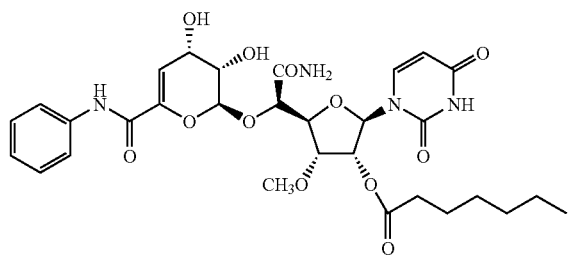

To a solution of the compound obtained in Example (79-2) (155 mg) in methylene chloride (73 mL) was added trifluoroacetic acid (3 mL), and the mixture was stirred at room temperature for 4 hours. After the solvent was evaporated under reduced pressure, azeotropic distillation was carried out with ethanol several times. Then the residue was purified by chromatography on a silica gel (8 g) column using 6% methanol in methylene chloride as the eluant to give the desired compound (121 mg).

$^1$H NMR (CD$_3$OD) δ ppm: 7.86 (d, J=8.1 Hz, 1H), 7.64 (m, 2H), 7.35 (m, 2H), 7.15 (t, J=7.4 Hz, 1H), 6.08 (d, J=2.5 Hz, 1H), 5.90 (d, J=4.4 Hz, 1H), 5.76 (d, J=8.1 Hz, 1H), 5.37 (t, J=4.7 Hz, 1H), 5.31 (d, J=4.5 Hz, 1H), 4.85 (m, 1H), 4.50 (m, 2H), 4.10 (m, 1H), 4.02 (t, J=5.2 Hz, 1H), 3.26 (s, 3H), 2.36 (t, J=7.3 Hz, 2H), 1.60 (m, 2H), 1.30 (m, 6H), 0.87 (t, J=6.8 Hz, 3H).

IR (KBr) ν cm$^{-1}$: 3342, 3100, 3065, 2958, 2931, 2957, 1689, 1599, 1534, 1498, 1462, 1444, 1384, 1322, 1263, 1238, 1206, 1158, 1109, 1060, 1021.

Example 80

Exemplification Compound Number 5

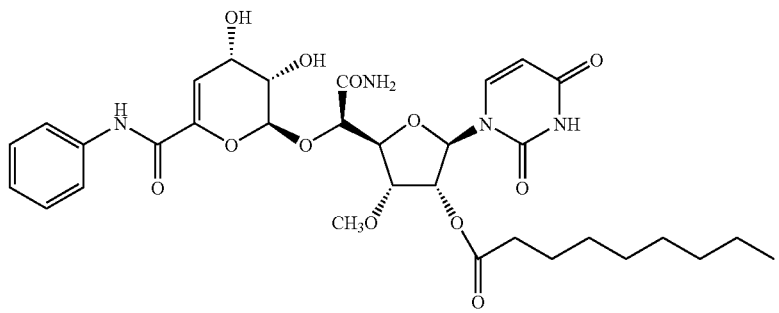

To a solution of the compound obtained in Example (79-1) (150 mg) in pyridine (4.5 mL) were added pelargonic anhydride (180 μL) and dimethylaminopyridine (8 mg). The mixture was stirred at room temperature for 1 hour. After the solvent was evaporated under reduced pressure, the residue was dissolved in ethyl acetate (100 mL). The solution was washed with saturated aqueous sodium hydrogen carbonate solution (100 mL) and saturated aqueous sodium chloride solution (100 mL). After drying over anhydrous sodium sulfate, the solvent was evaporated under reduced pressure. The residue was dissolved in methylene chloride (77 mL). The solution was stirred with trifluoroacetic acid (3.85 mL) at room temperature for 1.5 hours. After the solvent was evaporated under reduced pressure, azeotropic distillation was carried out with toluene several times. The residue was purified by chromatography on a silica gel (25 g) column using 10% methanol in methylene chloride as the eluant to give the desired compound (41 mg).

$^1$H NMR (CD$_3$OD) δ ppm: 7.86 (d, J=8.1 Hz, 1H), 7.64 (m, 2H), 7.34 (m, 2H), 7.15 (m, 1H), 6.09 (m, 1H), 5.90 (d, J=4.4 Hz, 1H), 5.76 (d, J=8.1 Hz, 1H), 5.37 (t, J=4.7 Hz, 1H), 5.31 (d, J=4.6 Hz, 1H), 4.85 (m, 1H), 4.50 (m, 2H), 4.10 (m, 1H), 4.02 (t, J=5.2 Hz, 1H), 3.26 (s, 3H), 2.36 (t, J=7.3 Hz, 2H), 1.58 (m, 2H), 1.28 (m, 10H), 0.88 (t, J=6.8 Hz, 3H).

IR (KBr) ν cm$^{-1}$: 3357, 3100, 3063, 2955, 2927, 2855, 1687, 1600, 1535, 1498, 1465, 1444, 1385, 1322, 1270, 1243, 1154, 1113, 1060, 1021.

Example 81

Exemplification Compound Number 6

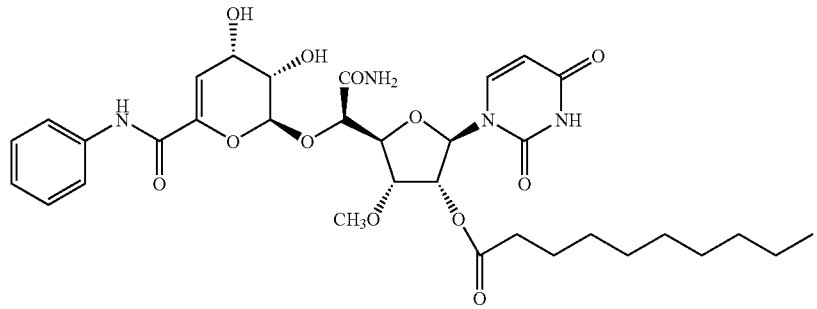

The desired compound (120 mg) was obtained using n-decanoic anhydride instead of pelargonic anhydride in a similar manner to that described in Example 80.

$^1$H NMR (CD$_3$OD) δ ppm: 7.86 (d, J=8.1 Hz, 1H), 7.63 (m, 2H), 7.33 (t, J=7.8 Hz, 2H), 7.14 (t, J=7.4 Hz, 1H), 6.08 (d, J=4.0 Hz, 1H), 5.90 (d, J=4.3 Hz, 1H), 5.76 (d, J=8.1 Hz, 1H), 5.37 (t, J=4.7 Hz, 1H), 5.31 (d, J=4.5 Hz, 1H), 4.85 (m, 1H), 4.50 (m, 2H), 4.09 (t, J=4.3 Hz, 1H), 4.02 (t, J=5.2 Hz, 1H), 3.26 (s, 3H), 2.36 (t, J=7.3 Hz, 2H), 1.60 (m, 2H), 1.27 (m, 12H), 0.89 (t, J=6.8 Hz, 3H).

IR (KBr) ν cm$^{-1}$: 3343, 3098, 3064, 2955, 2927, 2854, 1690, 1599, 1534, 1498, 1463, 1444, 1383, 1321, 1266, 1243, 1152, 1112, 1060, 1021.

Example 82

Exemplification Compound Number 7

The desired compound (79 mg) was obtained using n-dodecanoic anhydride instead of pelargonic anhydride in a similar manner to that described in Example 80.

$^1$H NMR (CD$_3$OD) δ ppm: 7.86 (d, J=8.1 Hz, 1H), 7.64 (m, 2H), 7.33 (m, 2H), 7.14 (m, 1H), 6.08 (d, J=4.0 Hz, 1H), 5.90 (d, J=4.4 Hz, 1H), 5.76 (d, J=8.1 Hz, 1H), 5.37 (t, J=4.7 Hz, 1H), 5.31 (d, J=4.5 Hz, 1H), 4.85 (m, 1H), 4.50 (m, 2H), 4.09 (m, 1H), 4.02 (t, J=5.2 Hz, 1H), 3.26 (s, 3H), 2.36 (t, J=7.3 Hz, 2H), 1.60 (m, 2H), 1.27 (m, 16H), 0.89 (t, J=7.4 Hz, 3H).

IR (KBr) ν cm$^{-1}$: 3343, 3098, 3064, 2926, 2854, 1689, 1600, 1534, 1498, 1464, 1444, 1384, 1322, 1269, 1243, 1149, 1113, 1060, 1021.

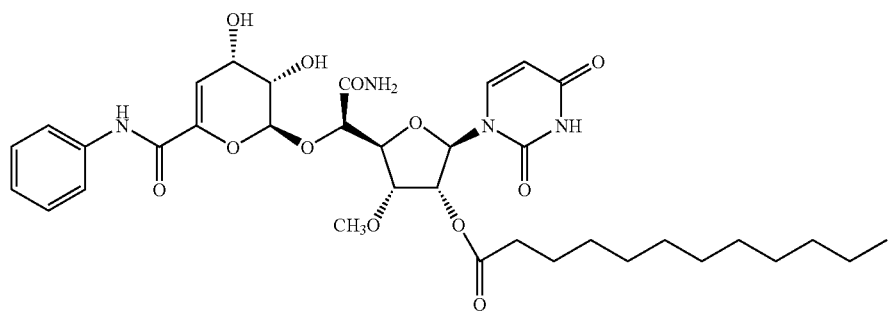

Example 83

Exemplification Compound Number 9

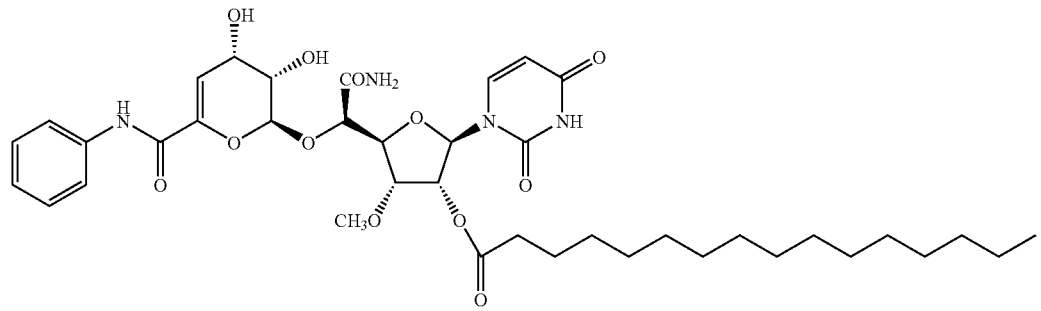

The desired compound (297 mg) was prepared from the compound obtained in Example (79-1) (270 mg) by reacting with palmitic anhydride (465 mg) instead of pelargonic anhydride in a similar manner to that described in Example 80.

$^1$H NMR (CD$_3$OD) δ ppm: 7.86 (d, J=8.1 Hz, 1H), 7.63 (m, 2H), 7.34 (m, 2H), 7.14 (m, 1H), 6.08 (d, J=2.5 Hz, 1H), 5.90 (d, J=4.4 Hz, 1H), 5.76 (d, J=8.1 Hz, 1H), 5.37 (t, J=4.7 Hz, 1H), 5.31 (d, J=4.6 Hz, 1H), 4.85 (m, 1H), 4.50 (m, 2H), 4.10 (m, 1H), 4.02 (t, J=5.2 Hz, 1H), 3.26 (s, 3H), 2.36 (t, J=7.3 Hz, 2H), 1.60 (m, 2H), 1.27 (m, 24H), 0.89 (t, J=6.8 Hz, 3H).

IR (KBr) ν cm$^{-1}$: 3346, 3099, 3064, 2925, 2853, 1691, 1599, 1534, 1498, 1464, 1444, 1412, 1382, 1320, 1268, 1242, 1148, 1113, 1086, 1060, 1021.

Example 84

Exemplification Compound Number 567

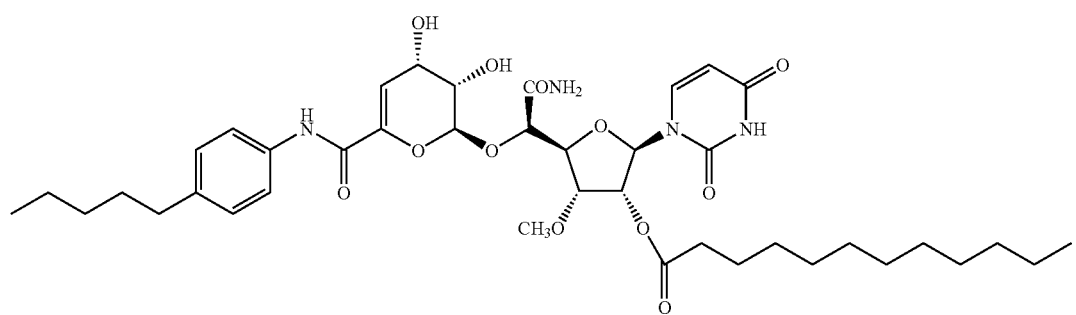

Example (84-1)

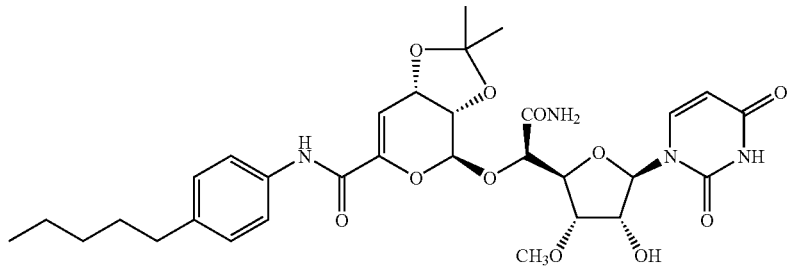

To a solution of the compound obtained in Example (9-2) (700 mg) in DMF (9 mL) were added 4-n-amylaniline (497 μL), HOBT (303 mg) and DIPC (504 μL), and the mixture was stirred at room temperature for 105 minutes. After the solvent was evaporated under reduced pressure, the residue was dissolved in ethyl acetate (200 mL). The solution was washed with 0.01N hydrochloric acid (200 mL), saturated aqueous sodium hydrogen carbonate solution (200 mL) and saturated aqueous sodium chloride solution (200 mL), dried over anhydrous sodium sulfate and concentrated under reduced pressure. The residue was purified by chromatography on a silica gel (103 g) column using 4% methanol in methylene chloride as the eluant to give the desired compound (764 mg).

$^1$H NMR (CDCl$_3$) δ ppm: 9.06 (br s, 1H), 8.40 (s, 1H), 7.70 (d, J=8.8 Hz, 1H), 7.49 (d, J=8.1 Hz, 2H), 7.14 (d, J=8.1 Hz, 2H), 7.10 (br s, 1H), 6.48 (d, J=4.4 Hz, 1H), 6.10 (br s, 1H), 5.79 (d, J=2.9 Hz, 1H), 5.73 (d, J=8.1 Hz, 1H), 4.80 (dd, J=4.4 and 5.9 Hz, 1H), 4.75 (m, 2H), 4.42 (m, 1H), 4.12 (t, J=6.6 Hz, 1H), 4.03 (m, 1H), 3.60 (br s, 1H), 3.42 (s, 3H), 2.56 (t, J=7.3 Hz, 2H), 1.58 (m, 2H), 1.49 (s, 3H), 1.45 (s, 3H), 1.35 (m, 4H), 0.88 (t, J=6.8 Hz, 3H).

Example (84-2)

To a solution of the compound obtained in Example (84-1) (760 mg) in pyridine (25 mL) were added dodecanoic anhydride (677 mg) and dimethylaminopyridine (15 mg). The mixture was stirred at room temperature for 2 hours and 40 minutes. After the solvent was evaporated under reduced pressure, the residue was dissolved in methylene chloride (200 mL) and the solution was washed with 0.01N hydrochloric acid (200 mL), saturated aqueous sodium hydrogen carbonate solution (200 mL) and saturated aqueous sodium chloride solution (200 mL). After drying over anhydrous sodium sulfate, the solvent was evaporated under reduced pressure. The residue was then dissolved in methanol (50 mL) and the solution was refluxed with "Amberlyst 15" (700 mg) for 6 hours. The reaction mixture was filtered through Celite and evaporated under reduced pressure. The residue was purified by chromatography on a silica gel (104 g) column using 7% methanol in methylene chloride as the eluant to give the desired compound (665 mg).

$^1$H NMR (CD$_3$OD) δ ppm: 7.86 (d, J=8.1 Hz, 1H), 7.51 (d, J=8.5 Hz, 2H), 7.15 (d, J=8.5 Hz, 2H), 6.07 (d, J=3.8 Hz, 1H), 5.91 (d, J=4.5 Hz, 1H), 5.76 (d, J=8.1 Hz, 1H), 5.36 (t, J=4.7 Hz, 1H), 5.30 (d, J=4.6 Hz, 1H), 4.85 (m, 1H), 4.52 (dd, J=1.6 and 5.1 Hz, 1H), 4.48 (t, J=3.9 Hz, 1H), 4.08 (m, 1H), 4.03 (t, J=5.1 Hz, 1H), 3.27 (s, 3H), 2.59 (t, J=7.7 Hz, 2H), 2.36 (t, J=7.3 Hz, 2H), 1.60 (m, 4H), 1.40–1.25 (m, 20H), 0.90 (m, 6H).

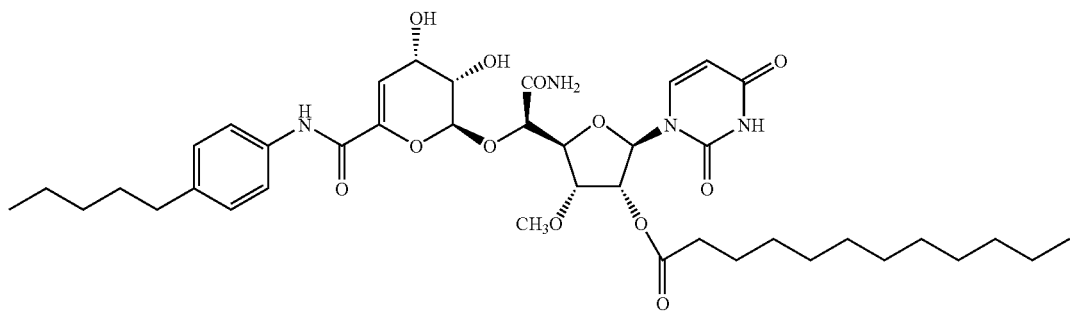

IR (KBr) ν cm$^{-1}$: 3344, 2956, 2926, 2854, 1690, 1595, 1527, 1464, 1413, 1381, 1319, 1269, 1242, 1150, 1112, 1060, 1021.

Example 85

Exemplification Compound Number 20

IR (KBr) ν cm$^{-1}$: 3342, 3098, 3064, 2935, 2850, 1750, 1693, 1600, 1534, 1498, 1445, 1375, 1322, 1238, 1114, 1053.

Example 86

Exemplification Compound Number 163

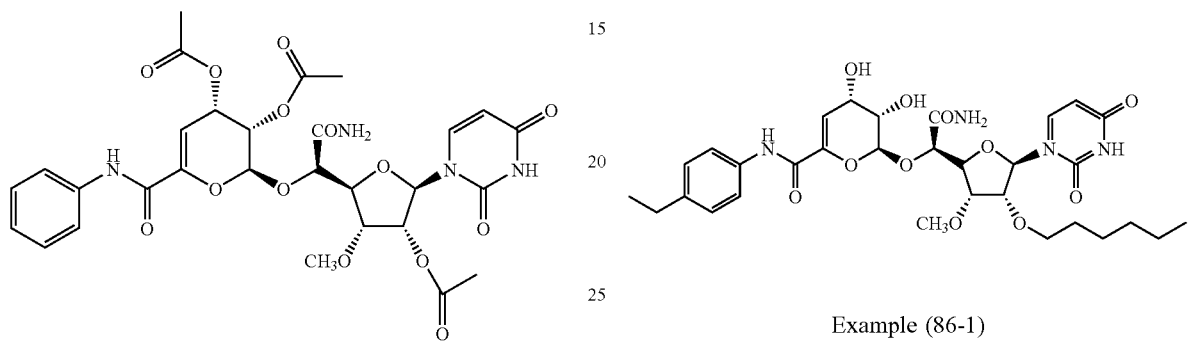

Example (86-1)

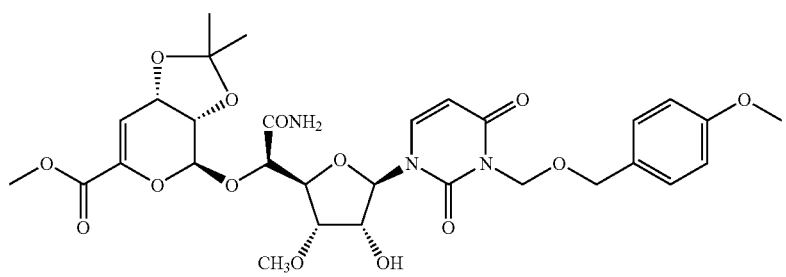

To a solution of the compound obtained in Example 43 (300 mg) in pyridine (3 mL) were added acetic anhydride (0.15 mL) and dimethylaminopyridine (4 mg). The mixture was stirred at room temperature for 1 hour. After the solvent was evaporated under reduced pressure, the residue was dissolved in ethyl acetate (50 mL) and the solution was washed twice with saturated aqueous sodium hydrogen carbonate solution (50 mL). After drying over anhydrous sodium sulfate, the solvent was evaporated under reduced pressure. The residue was purified by chromatography on a silica gel (8 g) column using 3% methanol in methylene chloride as the eluant to give the desired compound (270 mg).

$^1$H NMR (CD$_3$OD) δ ppm: 7.71 (d, J=8.1 Hz, 1H), 7.64 (d, J=8.5 Hz, 2H), 7.35 (t, J=8.0 Hz, 2H), 7.16 (t, J=7.3 Hz, 1H), 6.09 (t, J=1.9 Hz, 1H), 5.89 (d, J=8.1 Hz, 1H), 5.84 (d, J=3.6 Hz, 1H), 5.80 (m, 1H), 5.70 (m, 1H), 5.51 (d, J=2.7 Hz, 1H), 5.34 (dd, J=3.7 and 5.1 Hz, 1H), 4.85 (m, 1H), 4.41 (dd, J=2.0 and 6.5 Hz, 1H), 3.91 (dd, J=5.4 and 6.3 Hz, 1H), 3.19 (s, 3H), 2.11 (s, 3H), 2.08 (s, 6H).

To a solution of the compound obtained in Example (9-1) (206 mg) and 1,8-diazabicyclo[5.4.0]undec-7-ene (DBU) (120 μL) in DMF (4 mL) was added 4-methoxybenzyl chloromethyl ether (T. Benneche, P. Strande and K. Undeheim, *Synthesis*, 9, 762–763, (1983)) (130 mg) and the mixture was stirred at room temperature for 2.5 hours. After the solvent was evaporated under reduced pressure, the residue was dissolved in methylene chloride (100 mL) and the solution was washed with 0.01N hydrochloric acid (100 mL) and saturated aqueous sodium hydrogen carbonate solution (100 mL). After drying over anhydrous magnesium sulfate, the solvent was evaporated under reduced pressure. The residue was purified by chromatography on a silica gel (30 g) column using 1.5% methanol in methylene chloride as the eluant to give the desired compound (224 mg).

$^1$H NMR (CDCl$_3$) δ ppm: 7.67 (d, J=8.1 Hz, 1H), 7.31 (d, J=8.8 Hz, 2H), 7.12 (br s, 1H), 6.85 (m, 2H), 6.40 (d, 4.4 Hz, 1H), 5.95 (d, J=4.4 Hz, 1H), 5.75 (d, J=8.1 Hz, 1H), 5.59 (br s, 1H), 5.44 (dd, J=9.5 and 16.1 Hz, 2H), 4.73 (m, 2H), 4.62 (s, 2H), 4.56 (d, J=8.1 Hz, 1H), 4.52 (d, J=1.5 Hz, 1H), 4.25 (m, 1H), 4.13 (t, J=5.1 Hz, 1H), 4.02 (dd, J=5.9 and 8.1 Hz, 1H), 3.82 (s, 3H), 3.79 (s, 3H), 3.59 (s, 3H), 3.02 (d, J=6.6 Hz, 1H), 1.50 (s, 3H), 1.45 (s, 3H).

IR (KBr) ν cm$^{-1}$: 3449, 3362, 3104, 2988, 2934, 2853, 1715, 1669, 1612, 1514, 1457, 1412, 1371, 1304, 1280, 1248, 1219, 1167, 1086, 1065, 1015.

Example (86-2)

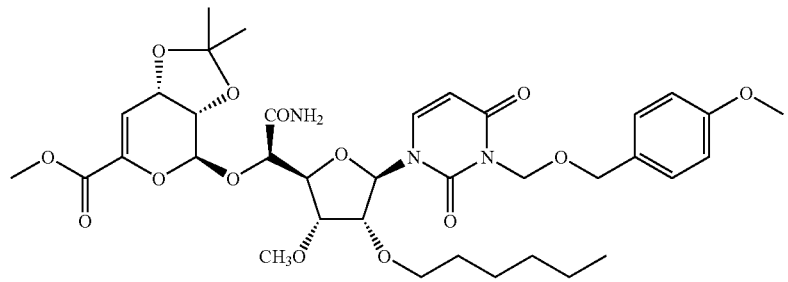

To a solution of the compound obtained in Example (86-1) (224 mg) in DMF (2 mL) were added 60% sodium hydride (20 mg) and 1-iodohexane (497 μL) under a nitrogen atomosphere at 0° C. The temperature of the reaction mixture was allowed to rise back to room temperature in 5 minutes. After 35 minutes, the solvent was evaporated under reduced pressure. The residue was then dissolved in methylene chloride (100 mL) and the solution was washed with 0.01N hydrochloric acid (100 mL) and saturated aqueous sodium hydrogen carbonate solution (100 mL). After drying over anhydrous magnesium sulfate, the solvent was evaporated under reduced pressure. The residue was purified by chromatography on a silica gel (40 g) column using 1% methanol in methylene chloride as the eluant to give the desired compound (64 mg).

$^1$H NMR (CDCl$_3$) δ ppm: 7.92 (d, J=8.1 Hz, 1H), 7.31 (d, J=8.8 Hz, 2H), 7.19 (br s, 1H), 6.86 (d, J=8.8 Hz, 2H), 6.39 (d, J=4.4 Hz, 1H), 5.88 (d, J=1.5 Hz, 1H), 5.72 (d, J=8.1 Hz, 1H), 5.68 (br s, 1H), 5.43 (dd, J=10.3 and 17.5 Hz, 2H), 4.75 (m, 2H), 4.63 (s, 2H), 4.60 (d, J=8.1 Hz, 1H), 4.55 (d, J=1.5 Hz, 1H), 4.00 (m, 2H), 3.95 (m, 1H), 3.83 (m, 1H), 3.81 (s, 3H), 3.79 (s, 3H), 3.65 (m, 1H), 3.50 (s, 3H), 1.62 (m, 2H), 1.50 (s, 3H), 1.46 (s, 3H), 1.40–1.22 (m, 6H), 0.88 (m, 3H).

IR (KBr) ν cm$^{-1}$: 3450, 3342, 3103, 2932, 2858, 1713, 1699, 1670, 1612, 1514, 1456, 1411, 1371, 1304, 1278, 1248, 1220, 1167, 1092, 1067, 1017.

Example (86-3)

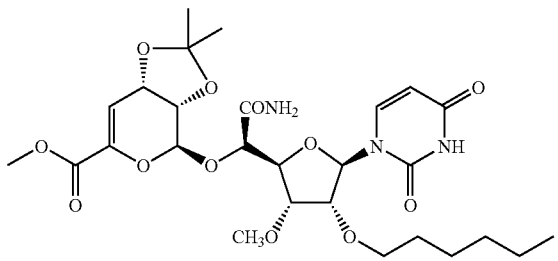

To a solution of the compound obtained in Example (86-2) (64 mg) in methylene chloride (1 mL) were added water (50 μL) and 2,3-dichloro-5,6-dicyano-1,4-benzoquinone (98 mg) and the mixture was stirred at room temperature for 4 hours. After insoluble material was filtered off, the filtrate was diluted with methylene chloride (100 mL). The solution was then washed with saturated aqueous sodium hydrogen carbonate solution (100 mL) and saturated aqueous sodium chloride solution (100 mL). After drying over anhydrous magnesium sulfate, the solvent was evaporated under reduced pressure. The residue was purified by chromatography on a silica gel (10 g) column using 3% methanol in methylene chloride as the eluant to give the desired compound (40 mg).

$^1$H NMR (CDCl$_3$) δ ppm: 8.33 (br s, 1H), 7.92 (d, J=8.1 Hz, 1H), 7.19 (br s, 1H), 6.39 (d, J=4.4 Hz, 1H), 5.91 (d, J=2.2 Hz, 1H), 5.77 (br s, 1H), 5.71 (d, J=8.1 Hz, 1H), 4.75 (dd, J=4.4 and 6.6 Hz, 2H), 4.59 (d, J=8.1 Hz, 1H), 4.54 (d, J=1.5 Hz, 1H), 4.00 (m, 3H), 3.81 (s, 3H), 3.75 (m, 1H), 3.60 (m, 1H), 3.51 (s, 3H), 1.60 (m, 2H), 1.50 (s, 3H), 1.46 (s, 3H), 1.40–1.22 (m, 6H), 0.88 (t, J=6.6 Hz, 3H).

IR (KBr) ν cm$^{-1}$: 3454, 3199, 3098, 3063, 2988, 2934, 2859, 1696, 1458, 1383, 1307, 1265, 1248, 1220, 1166, 1122, 1092, 1066, 1016.

Example (86-4)

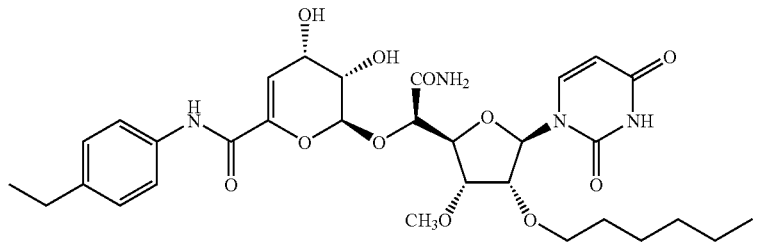

To a solution of the compound obtained in Example (86-3) (40 mg) in methanol (6 mL) and water (3 mL) was added 1N aqueous sodium hydroxide (334 μL), and the mixture was stirred at room temperature. After 8 minutes, the reaction mixture was passed through a Dowex 50W x 8 (H+) column (10 mL) using 50% aqueous methanol (100 mL). After the solvent was evaporated under reduced pressure, azeotropic distillation of the residue was carried out with toluene. To a solution of the resulting residue in DMF (0.6 mL) were added HOBT (14 mg), DIPC (24 μL) and 4-ethylaniline (0.6 mL), and the mixture was stirred at room temperature for 2 hours. The solvent was evaporated under reduced pressure. The residue was then dissolved in methylene chloride (100 mL), and the solution was washed with 0.01N hydrochloric acid (100 mL) and saturated aqueous sodium hydrogen carbonate solution (100 mL). After drying over anhydrous magnesium sulfate, the solvent was evaporated under reduced pressure. The residue was dissolved in methanol (2 mL) and the solution was refluxed with "Amberlyst 15" (60 mg) for 7 hours. After insoluble material was filtered off, the desired compound (30 mg) was obtained by preparative thin layer chromatography (TLC) on a silica gel plate using methylene chloride-methanol (12:1) as the developing solvent.

$^1$H NMR (CD$_3$OD) δ ppm: 7.88 (d, J=8.1 Hz, 1H), 7.54 (d, J=8.5 Hz, 2H), 7.18 (d, J=8.5 Hz, 2H), 6.06 (d, J=2.5 Hz, 1H), 5.84 (d, J=3.4 Hz, 1H), 5.76 (d, J=8.1 Hz, 1H), 5.30 (d, J=4.2 Hz, 1H), 4.84 (m, 1H), 4.54 (m, 1H), 4.45 (m, 1H), 4.11 (t, J=4.4 Hz, 1H), 4.00 (m, 1H), 3.77 (m, 1H), 3.68 (m, 1H), 3.55 (m, 1H), 3.24 (s, 3H), 2.62 (quartet, J=7.6 Hz, 2H), 1.55 (m, 2H), 1.40–1.20 (m, 6H), 1.22 (t, J=7.6 Hz, 3H), 0.87 (m, 3H).

IR (KBr) ν cm$^{-1}$: 3333, 2960, 2932, 2872, 2860, 1686, 1595, 1527, 1464, 1413, 1386, 1319, 1268, 1102, 1060, 1019.

Example 87

Exemplification Compound Number 5042

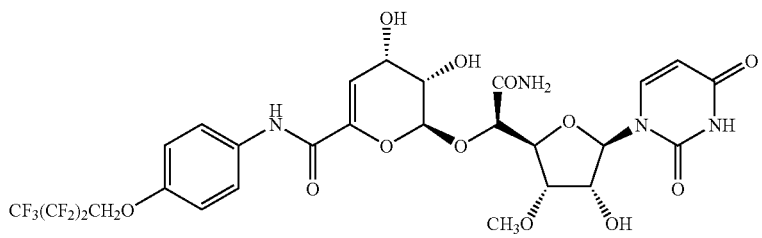

Example (87-1)

To a solution of 1H,1H-heptafluorobutanol (1.2 mL) in tetrahydrofuran (10 mL) were added sodium hydroxide (400 mg) and 4-fluoronitrobenzene (1.27 mL), and the mixture was stirred at room temperature for 4 hours. After addition of ethyl acetate (100 mL), the mixture was washed with water (100 mL) and saturated aqueous sodium chloride solution (100 mL). After drying over anhydrous magnesium sulfate, the solvent was evaporated under reduced pressure. The residue was purified by chromatography on a silica gel (150 g) column using hexane:ethyl acetate (30:1) as the eluant to give 1H,1H-heptafluorobutyl 4-nitrophenyl ether (2.0189 g).

$^1$H NMR (CDCl$_3$) δ ppm: 8.26 (d, J=9.1 Hz, 2H), 7.05 (d, J=9.1 Hz, 2H), 4.56 (t, J=12.4 Hz, 2H).

Example (87-2)

To a solution of hydrazine monohydrate (3.12 g) in methanol (20 mL) was added the compound obtained in Example (87-1) (2 g) in methanol (16 mL) and tetrahydrofuran (4 mL). After addition of 10% palladium on carbon (667 mg), the mixture was stirred at room temperature for 80 minutes. The reaction mixture was then filtered through Celite and evaporated under reduced pressure. The residue was purified by chromatography on a silica gel (60 g)

column using hexane:ethyl acetate (15:1~7:2) as the eluant to give 1H,1H-heptafluorobutyl 4-aminophenyl ether (1.7178 g).

¹H NMR (CDCl₃) δ ppm: 6.79 (d, J=8.8 Hz, 2H), 6.65 (d, J=8.8 Hz, 2H), 4.37 (t, J=13.2 Hz, 2H), 3.52 (br s, 1H), 1.57 (br s, 1H)

Example (87-3)

The desired compound (226 mg) was prepared using the compound obtained in Example (87-2) instead of 4-t-butyl-cyclohexylamine in a similar manner to that described in Example (9-3).

¹H NMR (CD₃OD) δ ppm: 7.86 (d, J=8.1 Hz, 1H), 7.61 (d, J=8.8 Hz, 2H), 7.02 (d, J=8.8 Hz, 2H), 6.07 (m, 1H), 5.68 (m, 2H), 5.30 (d, J=3.0 Hz, 1H), 4.83 (m, 1H), 4.64 (t, J=13.2 Hz, 2H), 4.52 (m, 1H), 4.45 (m, 1H), 4.25 (m, 1H), 4.09 (m, 1H), 3.74 (m, 1H), 3.28 (s, 3H).

IR (KBr) ν cm⁻¹: 3398, 3348, 3101, 2935, 2852, 1687, 1602, 1530, 1513, 1462, 1414, 1393, 1354, 1228.

Example 88

Exemplification Compound Number 2942

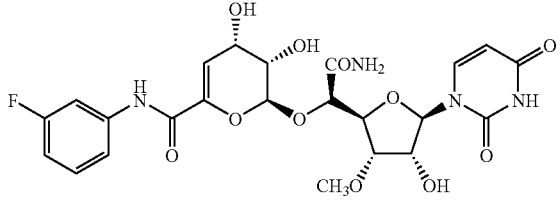

The desired compound (90 mg) was obtained using 3-fluoroaniline instead of 4-t-butylcyclohexylamine in a similar manner to that described in Example (9-3).

¹H NMR (CD₃OD) δ ppm: 7.86 (d, J=8.1 Hz, 1H), 7.61 (m, 1H), 7.42 (m, 1H), 7.34 (m, 1H), 6.88 (m, 1H), 6.09 (m, 1H), 5.76 (m, 2H), 5.30 (d, J=4.1 Hz, 1H), 4.84 (d, J=2.0 Hz, 1H), 4.52 (dd, J=1.9 and 6.2 Hz, 1H), 4.45 (t, J=3.9 Hz, 1H), 4.25 (dd, J=3.8 and 4.9 Hz, 1H), 4.09 (m, 1H), 3.74 (t, J=5.5 Hz, 1H), 3.26 (s, 3H).

IR (KBr) ν cm⁻¹: 3401, 2937, 2836, 1685, 1614, 1604, 1537, 1493, 1463, 1446, 1425, 1393, 1319, 1267.

Example 89

Exemplification Compound Number 3502

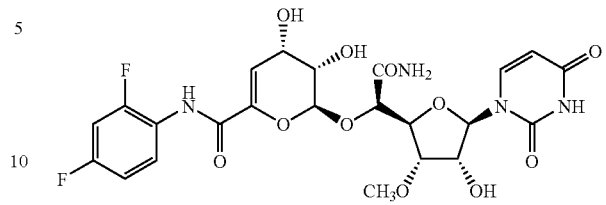

The desired compound (131 mg) was obtained using 2,4-difluoroaniline instead of 4-t-butylcyclohexylamine in a similar manner to that described in Example (9-3).

¹H NMR (CD₃OD) δ ppm: 7.88 (d, J=8.1 Hz, 1H), 7.74 (m, 1H), 7.08 (m, 1H), 6.99 (m, 1H), 6.10 (d, J=3.9, 1H), 5.81 (d, J=4.0 Hz, 1H), 5.75 (d, J=8.1 Hz, 1H), 5.30 (d, J=4.6 Hz, 1H), 4.76 (d, J=1.7 Hz, 1H), 4.53 (dd, J=1.8 and 5.3 Hz, 1H), 4.44 (t, J=3.9 Hz, 1H), 4.27 (t, J=4.5 Hz, 1H), 4.08 (t, J=4.2 Hz, 1H), 3.78 (t, J=5.1 Hz, 1H), 3.31 (s, 3H).

IR (KBr) ν cm⁻¹: 3417, 2936, 2836, 1686, 1611, 1534, 1498, 1463, 1432, 1386, 1330, 1263.

Example 90

Exemplification Compound Number 3852

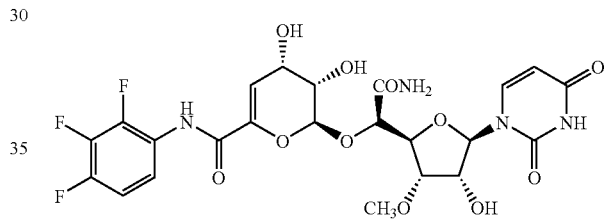

The desired compound (168 mg) was obtained using 2,3,4-trifluoroaniline instead of 4-t-butylcyclohexylamine in a similar manner to that described in Example (9-3).

¹H NMR (CD₃OD) δ ppm: 7.88 (d, J=8.1 Hz, 1H), 7.47 (m, 1H), 7.15 (m, 1H), 6.10 (m, 1H), 5.80 (d, J=3.9 Hz, 1H), 5.75 (d, J=8.1 Hz, 1H), 5.31 (d, J=4.4 Hz, 1H), 4.76 (d, J=1.8 Hz, 1H), 4.52 (m, 1H), 4.45 (m, 1H), 4.26 (m, 1H), 4.10 (m, 1H), 3.77 (t, J=5.3 Hz, 1H), 3.36 (s, 3H).

IR (KBr) ν cm⁻¹: 3414, 2939, 2838, 1686, 1623, 1547, 1516, 1468, 1385, 1294, 1265.

Example 91

Exemplification Compound Number 5322

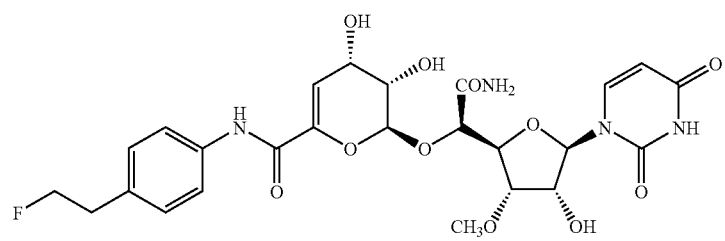

Example (91-1)

A solution of 2-(4-nitrophenyl)ethanol (835 mg) in methylene chloride (30 mL) was stirred at −78° C. under a nitrogen atomosphere. To this solution, diethylaminosulfur trifluoride (1.98 mL) in methylene chloride (20 mL) was added dropwise over 10 minutes. With stirring, the temperature of the reaction mixture was allowed to rise back to room temperature. After 30 minutes, the reaction was stopped by the addition of saturated aqueous sodium hydrogen carbonate solution (50 mL) in an ice bath. The methylene chloride solution was washed with saturated aqueous sodium hydrogen carbonate solution (50 mL). After drying over anhydrous magnesium sulfate, the solvent was evaporated under reduced pressure. The residue was purified by chromatography on a silica gel (25 g) column using hexane:ethyl acetate (7:2) as the eluant to give 1-fluoro-2-(4-nitrophenyl)ethane (359 mg).

$^1$H NMR (CDCl$_3$) δ ppm: 8.20 (s, 2H), 7.40 (s, 2H), 4.67 (m, 2H), 3.10 (m, 2H).

Example (91-2)

To a solution of hydrazine monohydrate (1.014 mL) in methanol (5 mL) was added the compound of Example (91-1) (353 mg) in methanol (4 mL) and tetrahydrofuran (1 mL). After addition of 10% palladium on carbon (200 mg), the mixture was stirred at room temperature overnight. The reaction mixture was then refluxed at 80° C. overnight. After addition of 10% palladium on carbon (200 mg), the refluxing was continued for 9 hours. The reaction mixture was then filtered through Celite and the solvent of the filtrate was evaporated under reduced pressure. The residue was dissolved in ethyl acetate (50 mL). The resulting solution was washed with water (50 mL) twice, dried over anhydrous sodium sulfate and concentrated. The residue was purified by chromatography on a silica gel (30 g) column using hexane:ethyl acetate (4:1) as the eluant to give 1-fluoro-2-(4-aminophenyl)ethane (207 mg).

$^1$H NMR (CDCl$_3$) δ ppm: 6.10 (m, 2H), 5.75 (m, 2H), 3.70 (m, 1H), 3.58 (m, 1H), 2.68 (br s, 2H), 1.99 (m, 2H).

Example (91-3)

A solution of the compound of Example (91-2) (207 mg), the compound of formula (VII) (367 mg), DIPC (254 μL) and HOBT (162 mg) in DMF (8 mL) was stirred at 0° C. for 1 hour and allowed to stand at room temperature overnight. After the solvent was evaporated under reduced pressure, the residue was purified by chromatography on a silica gel (30 g) column using methylene chloride:methanol (93:7) as the eluant to give a crude product. The product was further purified by high performance liquid chromatography (HPLC; Intersil PREP-ODS, 30×250 mm) using 30% aqueous acetonitrile as the eluant. The aqueous solution was lyophilized to give the desired compound (359 mg).

$^1$H NMR (CD$_3$OD) δ ppm: 7.86 (d, J=8.1 Hz, 1H), 7.58 (d, J=8.4 Hz, 2H), 7.24 (d, J=8.4 Hz, 2H), 6.08 (m, 1H), 5.77 (d, J=3.7 Hz, 1H), 5.75 (d, J=8.1 Hz, 1H), 5.30 (d, J=4.3 Hz, 1H), 4.84 (d, J=2.1 Hz, 1H), 4.64 (t, J=6.5 Hz, 1H), 4.53 (m, 2H), 4.44 (t, J=3.9 Hz, 1H), 4.25 (t, J=4.3 Hz, 1H), 4.09 (m, 1H), 3.74 (t, J=5.5 Hz, 1H), 3.28 (s, 3H), 3.00 (t, J=6.3 Hz, 1H), 2.94 (t, J=6.3 Hz, 1H).

IR (KBr) ν cm$^{-1}$: 3385, 2937, 2835, 1685, 1596, 1528, 1464, 1414, 1389, 1323, 1269.

Example 92

Exemplification Compound Number 4412

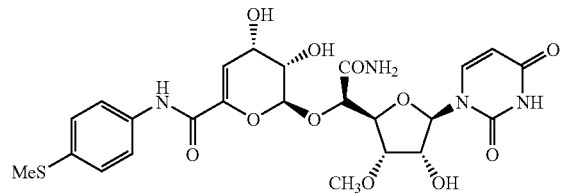

The desired compound (51 mg) was prepared from 4-methylthioaniline (118 μL), the compound of formula (VII) (218 mg), DIPC (169 μl) and HOBT (102 mg) in DMF (3 mL) in a similar manner to that described in Example (91-3).

$^1$H NMR (CD$_3$OD) δ ppm: 7.86 (d, J=8.1 Hz, 1H), 7.59 (d, J=8.8 Hz, 2H), 7.26 (d, J=8.8 Hz, 2H), 6.08 (d, J=2.9 Hz, 1H), 5.76 (m, 2H), 5.30 (d, J=4.4 Hz, 1H), 4.83 (m, 1H), 4.52 (m, 1H), 4.44 (m, 1H), 4.25 (t, J=4.4 Hz, 1H), 4.09 (t, J=4.4 Hz, 1H), 3.74 (t, J=5.5 Hz, 1H), 3.22 (s, 3H), 2.46 (s, 3H).

IR (KBr) ν cm$^{-1}$: 3401, 2924, 2834, 1685, 1587, 1522, 1496, 1463, 1400, 1326, 1312, 1271, 1243.

Example 93

Exemplification Compound Number 4342

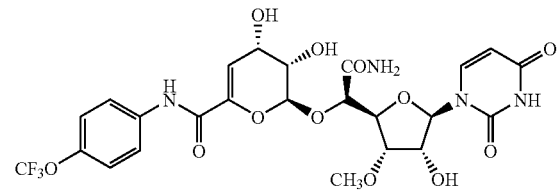

The desired compound of formula (201 mg) was prepared from 4-trifluoromethoxyaniline (117 μL), the compound of formula (VII) (201 mg), DIPC (158 μL) and HOBT (95 mg) in DMF (2.9 mL) in a similar manner to that described in Example (91-3).

$^1$H NMR (CD$_3$OD) δ ppm: 7.86 (d, J=8.2 Hz, 1H), 7.76 (d, J=8.6 Hz, 2H), 7.26 (d, J=8.6 Hz, 2H), 6.10 (m, 1H), 5.76 (m, 2H), 5.31 (d, J=4.0 Hz, 1H), 4.83 (d, J=2.0 Hz, 1H), 4.52 (dd, J=1.9 and 6.2 Hz, 1H), 4.45 (dd, J=3.2 and 4.3 Hz, 1H), 4.26 (dd, J=3.8 and 4.8 Hz, 1H), 4.11 (t, J=4.5 Hz, 1H), 3.74 (t, J=5.5 Hz, 1H), 3.27 (s, 3H).

IR (KBr) ν cm$^{-1}$: 3409, 2938, 2836, 1686, 1609, 1533, 1511, 1464, 1413, 1268, 1223, 1203.

Example 94

Exemplification Compound Number 4482

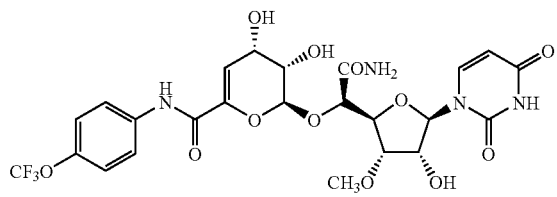

The desired compound of formula (102 mg) was prepared from 4-trifluoromethylthioaniline (121 μL), the compound of formula (VII) (195 mg), DIPC (151 μL) and HOBT (94 mg) in DMF (2.8 mL) in a similar manner to that described in Example (91-3).

$^1$H NMR (CD$_3$OD) δ ppm: 7.86 (d, J=8.4 Hz, 1H), 7.83 (d, J=8.7 Hz, 2H), 7.66 (d, J=8.7 Hz, 2H), 6.12 (m, 1H), 5.75 (m, 2H), 5.31 (d, J=4.2 Hz, 1H), 4.83 (d, J=2.1 Hz, 1H), 4.51 (dd, J=1.9 and 4.3 Hz, 1H), 4.45 (m, 1H), 4.26 (m, 1H), 4.10 (m, 1H), 3.73 (t, J=5.5 Hz, 1H), 3.26 (s, 3H).

IR (KBr) ν cm$^{-1}$: 3408, 3352, 3104, 2936, 2836, 1686, 1589, 1522, 1463, 1401, 1315, 1271, 1243.

Example 95

Exemplification Compound Number 5532

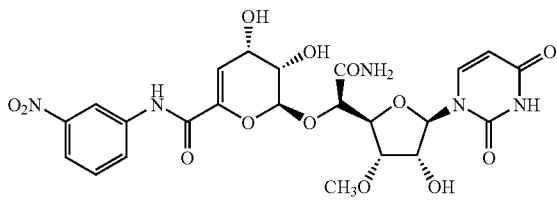

The desired compound of formula (103 mg) was prepared from 3-nitroaniline (102 μL), the compound of formula (VII) (169 mg), DIPC (133 μL) and HOBT (83 mg) in DMF (2.9 mL) in a similar manner to that described in Example (91-3).

$^1$H NMR (CD$_3$OD) δ ppm: 8.70 (m, 1H), 8.07 (dd, J=2.1 and 7.9 Hz, 1H), 8.01 (dd, J=2.0 and 9.0 Hz, 1H), 7.86 (d, J=8.1 Hz, 1H), 7.59 (t, J=8.2 Hz, 1H), 6.13 (m, 1H), 5.75 (m, 2H), 5.33 (d, J=3.9 Hz, 1H), 4.85 (m, 1H), 4.51 (dd, J=2.0 and 6.4 Hz, 1H), 4.46 (dd, J=3.2 and 4.3 Hz, 1H), 4.26 (m, 1H), 4.12 (m, 1H), 3.74 (t, J=5.5 Hz, 1H), 3.26 (s, 3H).

IR (KBr) ν cm$^{-1}$: 3351, 2937, 2835, 1685, 1595, 1533, 1463, 1430, 1391, 1355, 1328, 1300, 1268, 1248.

Example 96

Exemplification Compound Number 4762

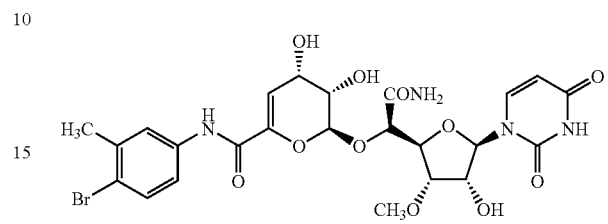

The desired compound (132 mg) was prepared from 4-bromo-3-methylaniline (164 mg), the compound of formula (VII) (203 mg), DIPC (158 μL) and HOBT (95 mg) in DMF (2.9 mL) in a similar manner to that described in Example (91-3).

$^1$H NMR (CD$_3$OD) δ ppm: 7.86 (d, J=8.2 Hz, 1H), 7.61 (d, J=2.4 Hz, 1H), 7.49 (d, J=8.7 Hz, 1H), 7.44 (dd, J=2.4 and 8.7 Hz, 1H), 6.08 (m, 1H), 5.75 (m, 2H), 5.30 (d, J=4.3 Hz, 1H), 4.83 (d, J=2.0 Hz, 1H), 4.52 (dd, J=2.0 and 6.0 Hz, 1H), 4.44 (dd, J=3.2 and 4.2 Hz, 1H), 4.25 (dd, J=3.8 and 4.8 Hz, 1H), 4.09 (m, 1H), 3.73 (dd, J=5.2 and 6.0 Hz, 1H), 3.27 (s, 3H), 2.37 (s, 3H).

IR (KBr) ν cm$^{-1}$: 3338, 2934, 2834, 1685, 1605, 1583, 1530, 1478, 1463, 1403, 1390, 1305, 1270.

Example 97

Exemplification Compound Number 4832

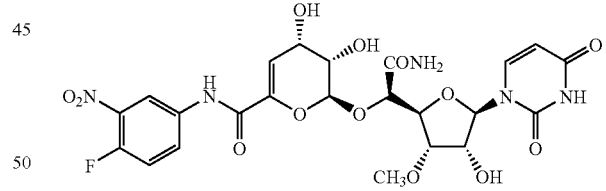

The desired compound (75 mg) was prepared from 4-fluoro-3-nitroaniline (156 mg), the compound (VII) (229 mg), DIPC (180 μL) and HOBT (108 mg) in DMF (3.3 mL) in a similar manner to that described in Example (91-3).

$^1$H NMR (CD$_3$OD) δ ppm: 8.55 (dd, J=2.6 and 6.8 Hz, 1H), 8.03 (m, 1H), 7.85 (d, J=8.1 Hz, 1H), 7.42 (dd, J=9.0 and 10.7 Hz, 1H), 6.13 (m, 1H), 5.75 (m, 2H), 5.32 (d, J=3.8 Hz, 1H), 4.82 (d, J=2.1 Hz, 1H), 4.50 (dd, J=2.0 and 6.2 Hz, 1H), 4.46 (dd, J=3.1 and 4.3 Hz, 1H), 4.26 (dd, J=3.5 and 4.5 Hz, 1H), 4.12 (m, 1H), 3.72 (dd, J=5.1 and 6.2 Hz, 1H), 3.26 (s, 3H).

IR (KBr) ν cm$^{-1}$: 3370, 2937, 2836, 1685, 1604, 1540, 1501, 1463, 1406, 1353, 1265, 1223.

Example 98

Exemplification Compound Number 842

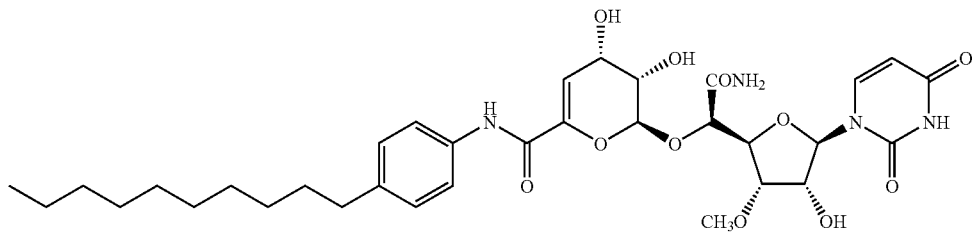

The desired compound (157 mg) was prepared from 4-decylaniline (211 mg), the compound of formula (VII) (208 mg), DIPC (162 μL) and HOBT (97 mg) in DMF (3 mL) in a similar manner to that described in Example (91-3).

$^1$H NMR (CD$_3$OD) δ ppm: 7.86 (d, J=8.1 Hz, 1H), 7.52 (d, J=8.4 Hz, 2H), 7.16 (d, J=8.4 Hz, 2H), 6.07 (m, 1H), 5.77 (d, J=3.7 Hz, 1H), 5.75 (d, J=8.1 Hz, 1H), 5.29 (d, J=4.3 Hz, 1H), 4.84 (d, J=2.0 Hz, 1H), 4.52 (dd, J=1.8 and 6.0 Hz, 1H), 4.44 (dd, J=3.3 and 4.3 Hz, 1H), 4.26 (m, 1H), 4.09 (t, J=4.3 Hz, 1H), 3.75 (t, J=5.5 Hz, 1H), 3.29 (s, 3H), 2.59 (t, J=7.6 Hz, 2H), 1.60 (m, 2H), 1.30 (m, 14H), 0.89 (t, J=6.7 Hz, 3H).

IR (KBr) ν cm$^{-1}$: 3340, 2925, 2853, 1687, 1611, 1595, 1526, 1464, 1413, 1319, 1269.

Example 99

Exemplification Compound Number 6633

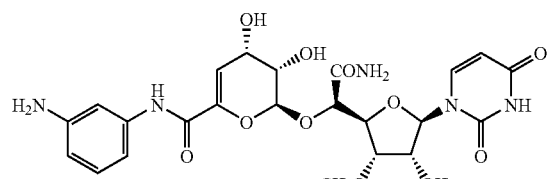

The desired compound (103 mg) was prepared from 1,3-phenylenediamine (115 mg), the compound of formula (VII) (242 mg), DIPC (191 μL) and HOBT (119 mg) in DMF (3.5 mL) in a similar manner to that described in Example (91-3).

$^1$H NMR (CD$_3$OD) δ ppm: 7.87 (d, J=8.1 Hz, 1H), 7.08 (m, 1H), 7.05 (d, J=8.0 Hz, 1H), 6.90 (dd, J=2.0 and 8.0 Hz, 1H), 6.52 (dd, J=2.0 and 8.0 Hz, 1H), 6.06 (d, J=2.5 Hz, 1H), 5.78 (d, J=3.7 Hz, 1H), 5.75 (d, J=8.1 Hz, 1H), 5.28 (d, J=4.5 Hz, 1H), 4.83 (d, J=1.9 Hz, 1H), 4.53 (dd, J=2.0 and 5.9 Hz, 1H), 4.43 (t, J=3.9 Hz, 1H), 4.26 (t, J=4.2 Hz, 1H), 4.07 (t, J=4.3 Hz, 1H), 3.75 (t, J=5.4 Hz, 1H), 3.30 (s, 3H).

IR (KBr) ν cm$^{-1}$: 3351, 2936, 2833, 1685, 1610, 1540, 1497, 1459, 1391, 1325, 1269.

Example 100

Exemplification Compound Number 6665

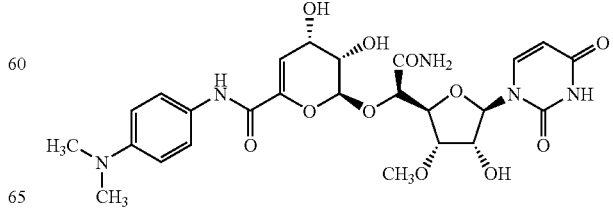

Example (100-1)

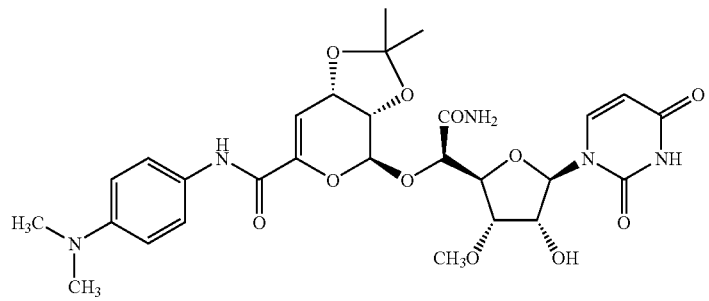

A solution of the compound of Example (9-2) (301 mg), N,N-dimethyl-1,4-phenylenediamine dihydrochloride (252 mg), triethylamine (336 µL), DIPC (216 µL) and HOBT (130 mg) in DMF (4 mL) was stirred at room temperature for 5 hours. After the solvent was evaporated under reduced pressure, the residue was purified by chromatography on a silica gel (30 g) column using methylene chloride:methanol (97.5:2.5) as the eluant to give the desired compound (231 mg).

$^1$H NMR (CD$_3$OD) δ ppm: 7.86 (d, J=8.1 Hz, 1H), 7.46 (d, J=9.0 Hz, 2H), 6.76 (d, J=9.0 Hz, 2H), 6.19 (d, J=4.4 Hz, 1H), 5.80 (d, J=3.7 Hz, 1H), 5.72 (d, J=8.1 Hz, 1H), 5.21 (d, J=5.1 Hz, 1H), 4.88 (m, 1H), 4.84 (m, 1H), 4.56 (dd, J=2.2 and 5.9 Hz, 1H), 4.45 (m, 1H), 4.27 (m, 1H), 3.82 (t, J=5.5 Hz, 1H), 3.30 (s, 3H), 2.92 (s, 6H).

Example (100-2)

A solution of the compound obtained in Example (100-1) in a mixture of acetic acid (1.4 mL), water (0.6 mL) and ethylene glycol (0.3 mL) was refluxed for 2 hours. After the solvent was evaporated under reduced pressure, the residue was purified by chromatography on a silica gel (3 g) column using methylene chloride:methanol (95:5) as the eluant to give the desired compound (93 mg).

$^1$H NMR (CD$_3$OD) δ ppm: 7.87 (d, J=8.1 Hz, 1H), 7.45 (d, J=9.3 Hz, 2H), 6.76 (d, J=9.3 Hz, 2H), 6.05 (m, 1H), 5.78 (d, J=3.7 Hz, 1H), 5.75 (d, J=8.1 Hz, 1H), 5.28 (d, J=4.4 Hz, 1H), 4.83 (d, J=2.0 Hz, 1H), 4.52 (dd, J=1.9 and 5.8 Hz, 1H), 4.43 (t, J=3.9 Hz, 1H), 4.25 (t, J=4.4 Hz, 1H), 4.08 (t, J=4.3 Hz, 1H), 3.75 (t, J=5.4 Hz, 1H), 3.34 (s, 3H), 2.91 (s, 6H).

IR (KBr) ν cm$^{-1}$: 3340, 2930, 2853, 2802, 1685, 1616, 1591, 1525, 1461, 1408, 1386, 1324, 1267.

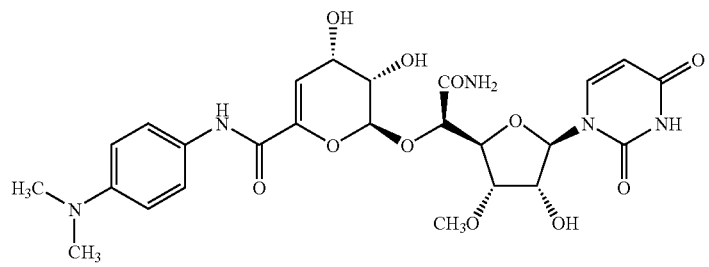

Example 101

Exemplification Compound Number 6162

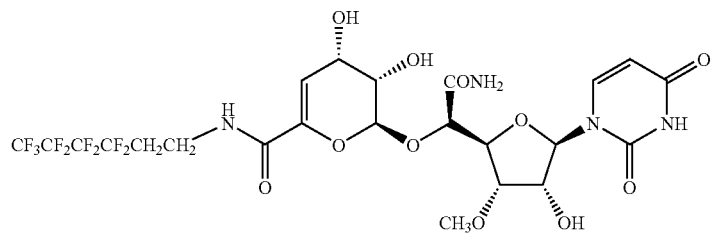

The desired compound (94 mg) was obtained using 2-(perfluorobutyl)ethylamine (F. Szonyi, F. Guennouni and A. Cambon, *Journal of Fluorine Chemistry*, 55(1), 85–92 (1991)) instead of 4-t-butylcyclohexylamine in a similar manner to that described in Example (9-3).

$^1$H NMR (CD$_3$OD) δ ppm: 7.86 (d, J=8.1 Hz, 1H), 5.97 (m, 1H), 5.80 (d, J=4.2 Hz, 1H), 5.75 (d, J=8.1 Hz, 1H), 5.22 (d, J=4.4 Hz, 1H), 4.66 (d, J=2.0 Hz, 1H), 4.49 (dd, J=2.0 and 5.4 Hz, 1H), 4.39 (dd, J=3.2 and 4.2 Hz, 1H), 4.24 (t, J=4.6 Hz, 1H), 4.04 (t, J=4.4 Hz, 1H), 3.70 (t, J=5.3 Hz, 1H), 3.65 (m, 1H), 3.57 (m, 1H), 3.37 (s, 3H), 2.48 (m, 2H).

IR (KBr) ν cm$^{-1}$: 3352, 3101, 2928, 2854, 1688, 1532, 1463, 1395, 1357, 1332, 1237.

Example 102

Exemplification Compound Number 561

A solution of the compound obtained in Example (84-1) (845 mg), 4-dimethylaminopyridine (480 mg) and phenyl chlorothioformate (353 μL) in methylene chloride (30 mL) dried over alumina was stirred at room temperature. After 2 hours, the reaction mixture was diluted with methylene chloride (300 mL). The solution was then washed with 0.1N hydrochloric acid (300 mL), saturated aqueous sodium hydrogen carbonate solution (300 mL) and saturated aqueous sodium chloride solution (300 mL). After drying over anhydrous sodium sulfate, the solvent was evaporated under reduced pressure. The residue was purified by chromatography on a silica gel (110 g) column using methylene chloride:methanol (97:3) as the eluant to give the desired compound (950 mg).

$^1$H NMR (CD$_3$OD) δ ppm: 7.81 (d, J=8.1 Hz, 1H), 7.53 (d, J=8.5 Hz, 2H), 7.41 (t, J=7.9 Hz, 2H), 7.29 (t, J=7.3 Hz, 1H), 7.18 (d, J=8.5 Hz, 2H), 7.10 (d, J=7.5 Hz, 2H), 6.19 (d, J=3.7 Hz, 1H), 6.09 (d, J=4.9 Hz, 1H), 5.89 (t, J=5.1 Hz, 1H), 5.75 (d, J=8.1 Hz, 1H), 5.29 (d, J=4.6 Hz, 1H), 4.93 (m, 1H), 4.61 (m, 1H), 4.48 (t, J=5.2 Hz, 1H), 4.27 (t, J=4.8 Hz, 1H), 3.35 (s, 3H), 2.60 (t, J=7.6 Hz, 2H), 1.62 (m, 2H), 1.45 (s, 6H), 1.33 (m, 4H), 0.90 (t, J=7.0 Hz, 3H).

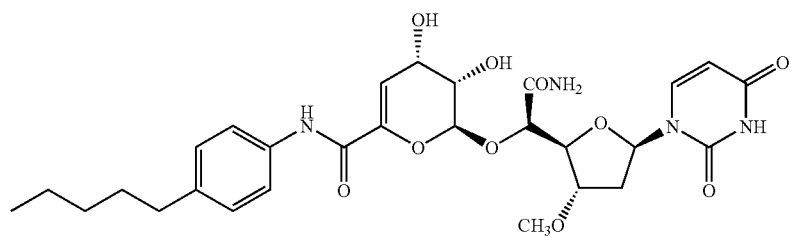

Example (102-1)

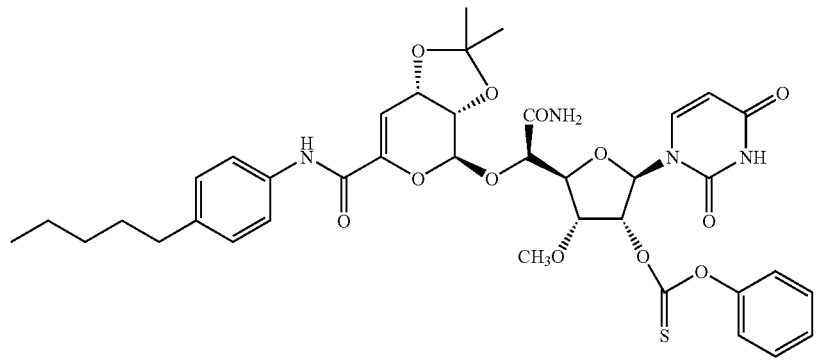

Example (102-2)

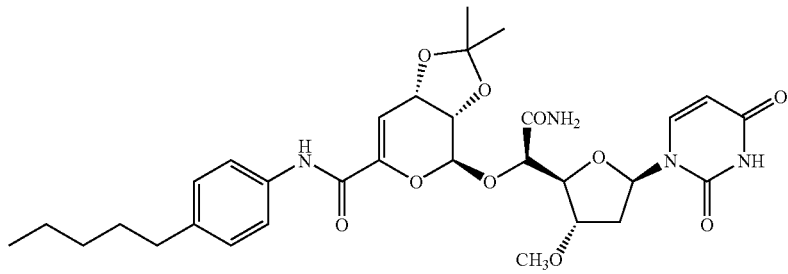

To a solution of the compound (113 mg) obtained in Example (102-1) in toluene (5 mL) were added tributyltin hydride (113 μL) and azobis(isobutyronitrile) (6 mg). After refluxing for 1.5 hours, the solvent was evaporated under reduced pressure. The residue was purified by chromatography on a silica gel (8 g) column using methylene chloride:methanol (99:1) as the eluant to give the desired compound (68 mg).

$^1$H NMR (CD$_3$OD) δ ppm: 7.88 (d, J=8.1 Hz, 1H), 7.52 (d, J=8.6 Hz, 2H), 7.17 (d, J=8.6 Hz, 2H), 6.22 (d, J=3.7 Hz, 1H), 6.16 (dd, J=6.0 and 7.8 Hz, 1H), 5.73 (d, J=8.1 Hz, 1H), 5.20 (d, J=4.8 Hz, 1H), 4.50 (m, 1H), 4.44 (t, J=5.5 Hz, 1H), 4.06 (m, 1H), 3.24 (s, 3H), 2.59 (t, J=7.7 Hz, 2H), 2.40 (m, 1H), 2.05 (m, 1H), 1.61 (m, 2H), 1.45 (s, 6H), 1.34 (m, 4H), 0.90 (t, J=7.0 Hz, 3H).

Example (102-3)

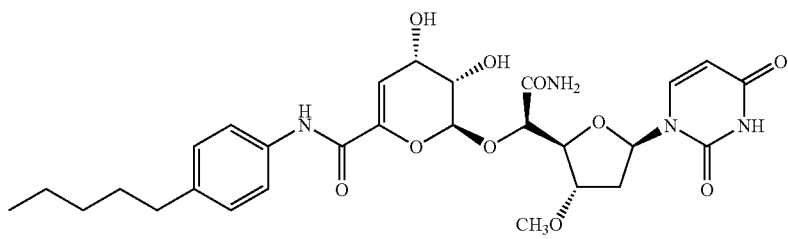

A solution of the compound obtained in Example (102-2) (68 mg) in methanol (2.5 mL) was refluxed with "Amberlyst 15" (H$^+$) (110 mg) for 140 minutes. After insoluble material was filtered off, the solvent of the filtrate was evaporated under reduced pressure. The residue was purified by preparative TLC using methylene chloride:methanol (85:15) as the developing solvent to give the desired compound (39 mg).

$^1$H NMR (CD$_3$OD) δ ppm: 7.90 (d, J=8.1 Hz, 1H), 7.52 (d, J=8.4 Hz, 2H), 7.17 (d, J=8.4 Hz, 2H), 6.14 (dd, J=6.0 and 7.8 Hz, 1H), 6.06 (d, J=2.5 Hz, 1H), 5.76 (d, J=8.1 Hz, 1H), 5.27 (d, J=4.6 Hz, 1H), 449 (m, 1H), 4.39 (m, 1H), 4.06 (m, 1H), 4.00 (m, 1H), 3.23 (s, 3H), 2.59 (t, J=7.7 Hz, 2H), 2.39 (m, 1H), 2.00 (m, 1H), 1.61 (m, 2H), 1.32 (m, 4H), 0.90 (t, J=7.0 Hz, 3H).

Example 103

Exemplification Compound Number 41

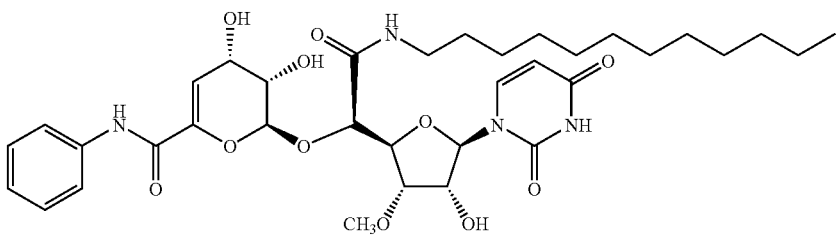

Example (103-1)

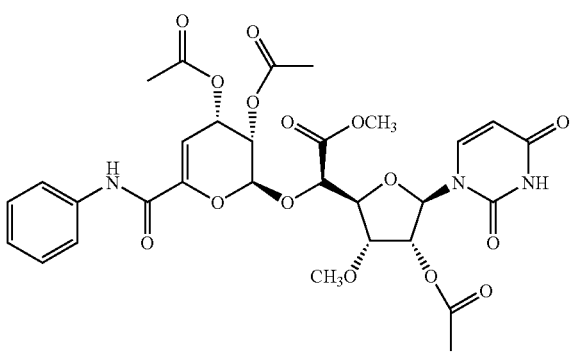

To a solution of the compound obtained in Example 85 (222 mg) in methylene chloride (6 mL) was added water (3.5 mL) and the mixture was stirred at room temperature. Nitrosylsulfuric acid (2.99 g) was added to the solution in portions over 20 minutes. After stirring for 5 minutes, the reaction mixture was diluted with methylene chloride (10 mL) and the aqueous layer was removed. The solution was then washed with water (4 mL) twice and saturated aqueous sodium chloride solution (5 mL). The solvent was evaporated under reduced pressure. To a solution of the residue in methylene chloride (10 mL), diazomethane solution (1.66 mmol) in ether was added. After stirring for 15 minutes at room temperature, the solvent was evaporated under reduced pressure. The residue was purified by chromatography on a silica gel (7 g) column using methylene chloride: methanol (99:1) as the eluant to give the desired compound (123 mg).

$^1$H NMR (CD$_3$OD) δ ppm: 7.64 (m, 3H), 7.36 (m, 2H), 7.16 (t, J=7.3 Hz, 1H), 6.08 (m, 1H), 5.94 (d, J=8.1 Hz, 1H), 5.90 (d, J=3.7 Hz, 1H), 5.77 (m, 1H), 5.60 (m, 1H), 5.34 (m, 1H), 5.15 (m, 1H), 4.56 (m, 1H), 3.92 (m, 1H), 3.86 (s, 3H), 3.21 (s, 3H), 2.11 (s, 3H), 2.08 (s, 3H), 2.03 (s, 3H).

Example (103-2)

To a solution of the compound (120 mg) obtained in Example (103-1) in methanol (4.2 mL) was added n-dodecylamine (1.19 g) and the mixture was stirred at room temperature overnight. After the reaction mixture was passed through a Dowex 50W x 8 (H$^+$) column (10 g) using 50% aqueous methanol, the solvent was evaporated under reduced pressure. The residue was purified by chromatography on a silica gel (5 g) column using methylene chloride: methanol (91:1) as the eluant to give the desired compound (11.9 mg).

$^1$H NMR (CD$_3$OD) δ ppm: 7.86 (d, J=8.1 Hz, 1H), 7.63 (d, J=8.5 Hz, 2H), 7.34 (t, J=7.9 Hz, 2H), 7.15 (m, 1H), 6.09 (d, J=3.5 Hz, 1H), 5.79 (d, J=4.1 Hz, 1H), 5.75 (d, J=8.1 Hz, 1H), 5.23 (d, J=5.0 Hz, 1H), 4.53 (dd, J=2.0 and 5.7 Hz, 1H), 4.44 (t, J=4.1 Hz, 1H), 4.27 (t, J=4.5 Hz, 1H), 4.07 (t, J=4.7 Hz, 1H), 3.80 (t, J=5.3 Hz, 1H), 3.30 (m, 5H), 1.55 (m, 2H), 1.27 (m, 18H), 0.89 (t, J=6.8 Hz, 3H).

IR (KBr) ν cm$^{-1}$: 3351, 3098, 3062, 2925, 2854, 1684, 1600, 1535, 1498, 1464, 1444, 1385, 1321, 1269.

Example 104

Exemplification Compound Number 6696

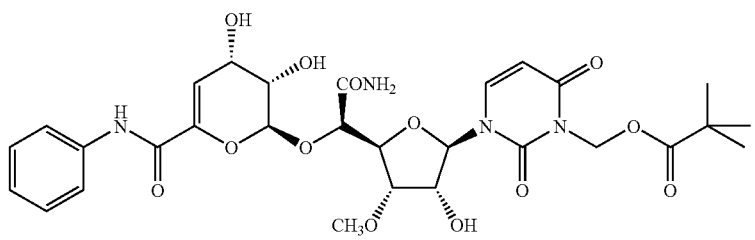

Example 104-1)

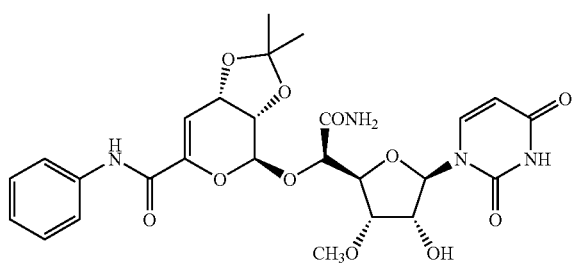

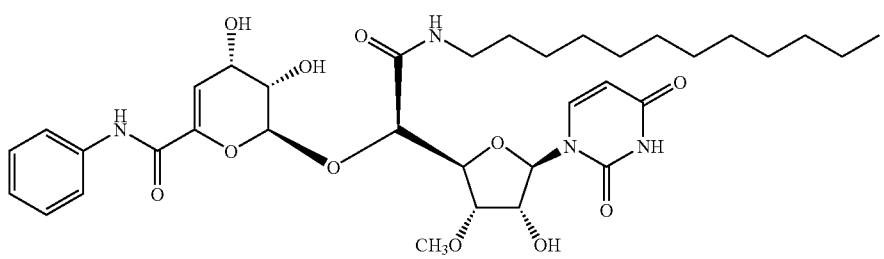

A solution of the compound obtained in Example (9-2) (807 mg), aniline (265 μL), DIPC (496 μL) and HOBT (393 mg) in DMF (16 mL) was stirred in an ice bath for 1 hour and then at room temperature for 14 hours. After the solvent was evaporated under reduced pressure, the residue was dissolved in ethyl acetate (200 mL). The solution was washed with 0.05N hydrochloric acid (200 mL) and saturated aqueous sodium hydrogen carbonate solution (200 mL). After drying over anhydrous magnesium sulfate, the solvent was concentrated under reduced pressure. The residue was then purified by chromatography on a silica gel (80 g) column using methylene chloride:methanol (96:4) as the eluant to give the desired compound (596 mg).

$^1$H NMR (CDCl$_3$:CD$_3$OD; 19:1) δ ppm: 8.53 (s, 1H), 7.77 (d, J=8.1 Hz, 1H), 7.61 (m, 2H), 7.35 (m, 2H), 7.16 (m, 1H), 6.48 (d, J=3.7 Hz, 1H), 5.77 (d, J=2.9 Hz, 1H), 5.74 (d, J=8.1 Hz, 1H), 4.78 (m, 4H), 4.37 (m, 1H), 4.12 (m, 1H), 3.99 (dd, J=5.1 and 6.6 Hz, 1H), 3.41 (s, 3H), 1.51 (s, 3H), 1.47 (s, 3H).

IR (KBr) ν cm$^{-1}$: 3418, 3341, 3100, 3064, 2989, 2936, 2833, 1691, 1599, 1533, 1498, 1445, 1383, 1321, 1299, 1269, 1244, 1218.

Example (104-2)

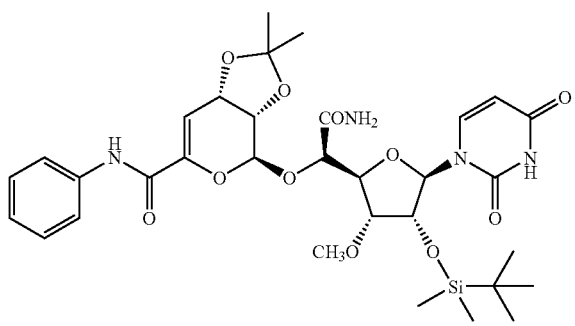

To a solution of the compound obtained in Example (104-1) (593 mg) in DMF (2 mL) were added t-butyldimethylsilyl chloride (311 mg) and imidazole (140 mg), and the mixture was stirred at room temperature for 5 hours. After further addition of t-butyldimethylsilyl chloride (165 mg) and imidazole (70 mg), stirring was continued for 16 hours. The solvent was then evaporated under reduced pressure and the residue was dissolved in ethyl acetate (100 mL). The solution was washed with water (100 mL). After drying over anhydrous magnesium sulfate, the solvent was concentrated under reduced pressure. The residue was then purified by chromatography on a silica gel (80 g) column using methylene chloride:methanol (98:2) as the eluant to give the desired compound (632 mg).

$^1$H NMR (CDCl$_3$) δ ppm: 8.47 (br s, 1H), 8.42 (br s, 1H), 7.86 (d, J=7.8 Hz, 1H), 7.62 (d, J=7.8 Hz, 2H), 7.36 (m, 2H), 7.17 (m, 1H), 7.07 (br s, 1H), 6.52 (d, J=3.9 Hz, 1H), 5.87 (br s, 1H), 5.72 (m, 1H), 5.62 (s, 1H), 4.85 (m, 1H), 4.82 (m, 1H), 4.70 (d, J=7.8 Hz, 1H), 4.65 (d, J=2.9 Hz, 1H), 4.48 (m, 1H), 4.08 (dd, J=5.9 and 7.8 Hz, 1H), 3.85 (dd, J=3.9 and 4.9 Hz, 1H), 3.31 (s, 3H), 1.52 (s, 3H), 1.47 (s, 3H), 0.92 (s, 9H), 0.21 (s, 3H), 0.15 (s, 3H).

IR (KBr) ν cm$^{-1}$: 3458, 3417, 3340, 3198, 3098, 3064, 2988, 2952, 2933, 2897, 2857, 1695, 1600, 1533, 1499, 1444, 1382, 1320, 1298, 1251, 1220.

Example (104-3)

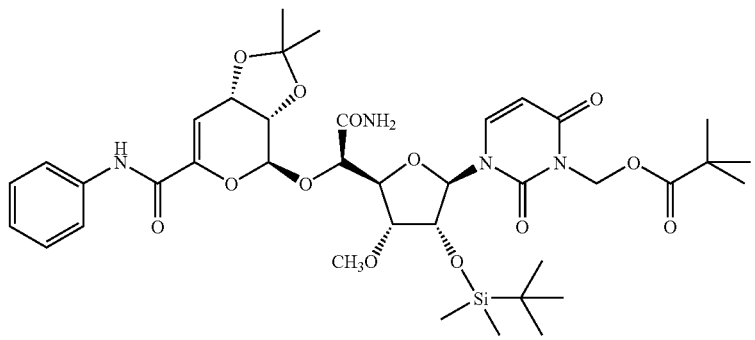

To a solution of the compound obtained in Example (104-2) (318 mg) in DMF (5 mL) were added 1,8-diazabicyclo[5.4.0]undec-7-ene (102 μL) and pivaloyloxymethyl chloride (100 μL), and the mixture was stirred at room temperature for 23 hours. After addition of 1,8-diazabicyclo [5.4.0]undec-7-ene (102 μL) and pivaloyloxymethyl chloride (100 μL), stirring was continued for 4 hours. The solvent was then evaporated under reduced pressure and the residue was dissolved in ethyl acetate (200 mL). The solution was washed with water (200 mL). After drying over anhydrous magnesium sulfate, the solvent was concentrated under reduced pressure. The residue was then purified by chromatography on a silica gel (40 g) column using hexane: ethyl acetate (1:1) as the eluant to give the desired compound (273 mg).

$^1$H NMR (CDCl$_3$) δ ppm: 8.40 (br s, 1H), 7.90 (d, J=8.0 Hz, 1H), 7.61 (d, J=7.8 Hz, 2H), 7.36 (t, J=7.8 Hz, 2H), 7.17 (m, 1H), 7.05 (br s, 1H), 6.53 (d, J=3.9 Hz, 1H), 5.93 (s, 1H), 5.79 (d, J=8.0 Hz, 1H), 5.74 (br s, 1H), 5.68 (s, 1H), 4.89 (m, 1H), 4.81 (m, 1H), 4.71 (d, J=7.8 Hz, 1H), 4.62 (d, J=2.0 Hz, 1H), 4.38 (m, 1H), 4.08 (m, 1H), 3.84 (m, 1H), 3.31 (s, 3H), 1.52 (s, 3H), 1.47 (s, 3H), 1.10 (s, 9H), 0.94 (s, 9H), 0.22 (s, 3H), 0.13 (s, 3H).

IR (KBr) ν cm$^{-1}$: 3466, 3422, 3350, 3194, 3103, 3064, 2958, 2934, 2906, 2858, 1731, 1685, 1600, 1533, 1499, 1480, 1456, 1445, 1404, 1375, 1321, 1279, 1251, 1220.

Example (104-4)

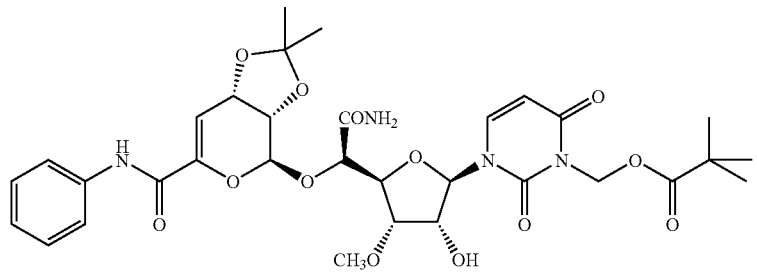

To a solution of the compound obtained in Example (104-3) (272 mg) in tetrahydrofuran (340 μL) was added 1M tetrabutylammonium fluoride solution (340 μL) in tetrahydrofuran, and the mixture was allowed to stand at room temperature for 30 minutes. After further addition of 1M tetrabutylammonium fluoride solution (100 μL) in tetrahydrofuran, the reaction mixture was further allowed to stand at room temperature for 1 hour. The solvent was then evaporated under reduced pressure, and the residue was purified by chromatography on a silica gel (40 g) column using methylene chloride-methanol (99:1) as the eluant to give the desired compound (218 mg).

$^1$H NMR (CDCl$_3$) δ ppm: 8.31 (s, 1H), 7.75 (d, J=8.1 Hz, 1H), 7.58 (d, J=8.1 Hz, 2H), 7.35 (m, 2H), 7.17 (t, J=7.3 Hz, 1H), 7.07 (br s, 1H), 6.51 (d, J=4.4 Hz, 1H), 5.92 (m, 2H), 5.86 (d, J=2.9 Hz, 1H), 5.81 (d, J=8.1 Hz, 1H), 5.76 (br s, 1H), 4.81 (m, 2H), 4.72 (m, 2H), 4.40 (br s, 1H), 4.10 (m, 1H), 4.05 (m, 1H), 3.44 (s, 3H), 2.17 (br s, 1H), 1.51 (s, 3H), 1.47 (s, 3H), 1.19 (s, 9H).

IR (KBr) ν cm$^{-1}$: 3459, 3422, 3355, 3105, 3063, 2982, 2935, 2877, 1728, 1682, 1600, 1533, 1499, 1481, 1456, 1445, 1404, 1376, 1321, 1280, 1241, 1219.

Example (104-5)

A solution of the compound obtained in Example (104-4) (216 mg) in methanol (3 mL) was refluxed with "Amberlyst 15" (100 mg) for 3 hours. After insoluble material was filtered off, the solvent of the filtrate was evaporated under reduced pressure. The residue was purified by chromatography on a silica gel (20 g) column using methylene chloride:methanol (96:4) as the eluant to give the desired compound (146 mg).

$^1$H NMR (CD$_3$OD) δ ppm: 7.94 (d; J=8.1 Hz, 1H), 7.64 (d, J=8.7 Hz, 2H), 7.34 (d, J=8.0 Hz, 2H), 7.15 (t, J=7.3 Hz, 1H), 6.08 (m, 1H), 5.89 (m, 3H), 5.79 (d, J=3.4 Hz, 1H), 5.31 (d, J=4.3 Hz, 1H), 4.55 (dd, J=1.9 and 6.2 Hz, 1H), 4.44 (t, J=3.9 Hz, 1H), 4.27 (m, 1H), 4.10 (m, 1H), 3.73 (dd, J=5.1 and 6.2 Hz, 1H), 3.27 (s, 3H), 1.17 (s, 9H).

IR (KBr) ν cm$^{-1}$: 3411, 3368, 3108, 2973, 2935, 2877, 1726, 1671, 1599, 1534, 1497, 1481, 1458, 1445, 1405, 1376, 1324, 1280, 1240.

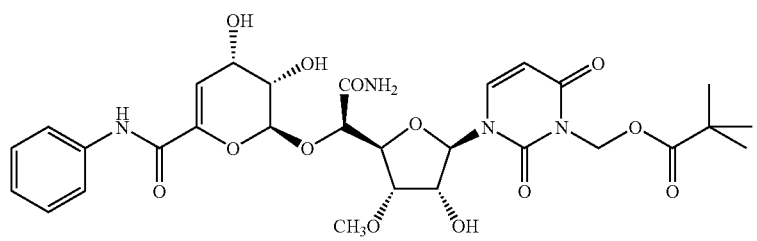

Example 105

Exemplification Compound Number 6707

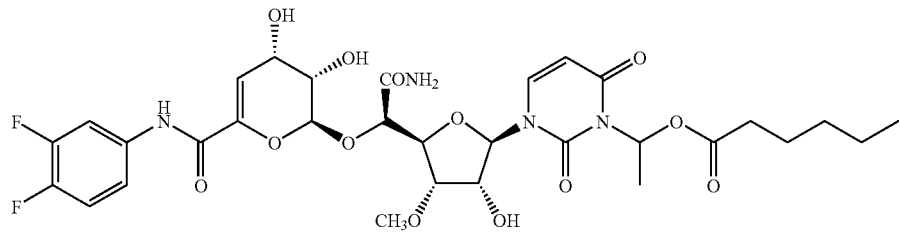

Example (105-1)

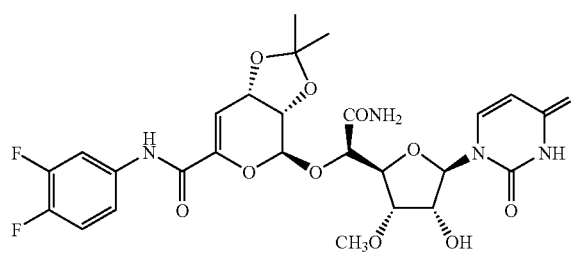

The desired compound (1.405 g) was obtained using 3,4-difluoroaniline instead of aniline in a similar manner to that described in Example (104-1).

$^1$H NMR (CD$_3$OD) δ ppm: 7.84 (d, J=8.1 Hz, 1H), 7.76 (m, 1H), 7.40 (m, 1H), 7.23 (m, 1H), 6.23 (d, J=3.7 Hz, 1H), 5.79 (d, J=3.7 Hz, 1H), 5.72 (d, J=8.1 Hz, 1H), 5.26 (d, J=4.4 Hz, 1H), 4.83 (m, 1H), 4.52 (m, 1H), 4.47 (m, 1H), 4.27 (dd, J=3.7 and 5.1 Hz, 1H), 3.80 (m, 1H), 3.27 (s, 3H), 1.45 (s, 3H), 1.44 (s, 3H).

Example (105-2)

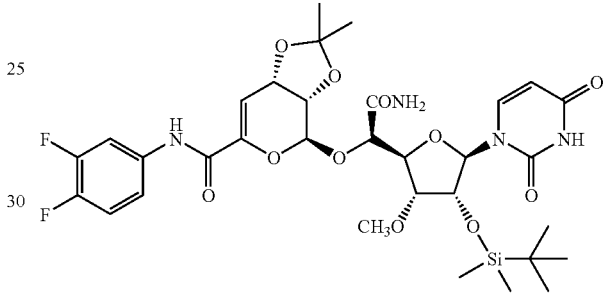

The desired compound (981 mg) was obtained using the compound obtained in Example (105-1) (1 g) in a similar manner to that described in Example (104-2).

$^1$H NMR (CD$_3$OD) δ ppm: 7.92 (d, J=8.1 Hz, 1H), 7.76 (m, 1H), 7.40 (m, 1H), 7.25 (m, 1H), 6.22 (d, J=3.7 Hz, 1H), 5.72 (d, J=8.1 Hz, 1H), 7.72 (d, J=3.7 Hz, 1H), 5.24 (d, J=4.4 Hz, 1H), 4.88 (d, J=2.2 Hz, 1H), 4.85 (m, 1H), 4.58 (m, 1H), 4.43 (m, 1H), 4.38 (m, 1H), 3.72 (m, 1H), 3.26 (s, 3H), 1.46 (s, 3H), 1.45 (s, 3H), 0.89 (s, 9H), 0.13 (s, 3H), 0.10 (s, 3H).

IR (KBr) ν cm$^{-1}$: 3415, 3341, 3101, 2988, 2933, 2897, 2858, 1694, 1617, 1518, 1461, 1439, 1413, 1383, 1265.

Example (105-3)

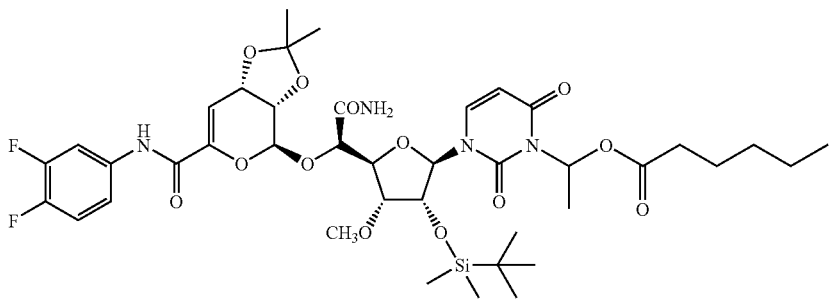

To a solution of the compound obtained in Example (105-2) (717 mg) and potassium carbonate (232 mg) in DMF (18 mL) was added 1-chloroethyl hexanoate (530 mg), and the mixture was stirred in an ice bath for 5 minutes and then at 60° C. for 6 hours. After the solvent was evaporated under reduced pressure, the residue was purified by chromatography on a silica gel (32 g) column using methylene chloride:methanol (98.5:1.5) as the eluant to give the desired compound (230 mg).

$^1$H NMR (CDCl$_3$) δ ppm: 8.54 (s, 1H), 7.78 (m, 2H), 7.22–7.00 (m, 5H), 6.51 (m, 1H), 5.85 (m, 1H), 5.72 (d, J=8.1 Hz, 1H), 5.67 (s, 1H), 4.85 (m, 1H), 4.80 (m, 1H), 4.65 (m, 1H), 4.60 (m, 1H), 4.37 (m, 1H), 4.07 (m, 1H), 3.81 (m, 1H), 3.30 (s, 3H), 2.33 (m, 2H), 1.79 (m, 2H), 1.48 (s, 3H), 1.25 (m, 4H), 0.95 (s, 9H), 0.85 (m, 3H), 0.23 (s, 3H), 0.18 and 0.17 (2s, 3H).

Example (105-4)

The desired compound (177 mg) was prepared from the compound obtained in Example (105-3) (282 mg) in a similar manner to that described in Example (104-4).

$^1$H NMR (CD$_3$OD) δ ppm: 7.85 (d, J=8.1 Hz, 1H), 7.78 (m, 1H), 7.40 (m, 1H), 7.22 (m, 2H), 6.21 (m, 1H), 5.76 (m, 2H), 5.27 (m, 1H), 4.82 (m, 1H), 4.57 (m, 2H), 4.47 (m, 1H), 4.28 (m, 1H), 3.78 (m, 1H), 3.26 (s, 3H), 2.32 (t, J=7.3 Hz, 2H), 1.76 (d, J=6.6 Hz, 2H), 1.59 (m, 2H), 1.43 (m, 6H), 1.30 (m, 5H), 0.90 (m, 3H).

IR (KBr) ν cm$^{-1}$: 3442, 3106, 2987, 2957, 2935, 2874, 1718, 1677, 1617, 1537, 1518, 1444, 1414, 1383, 1280, 1239, 1214.

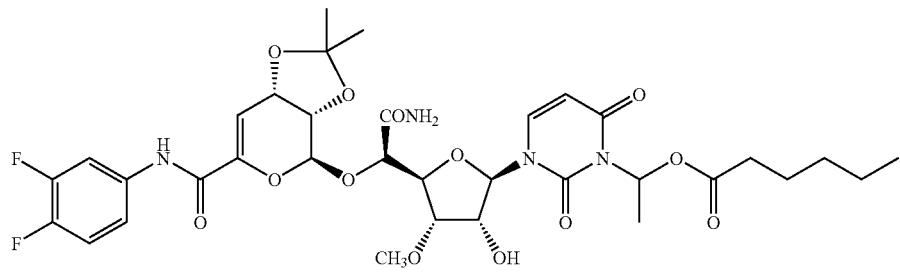

Example (105-5)

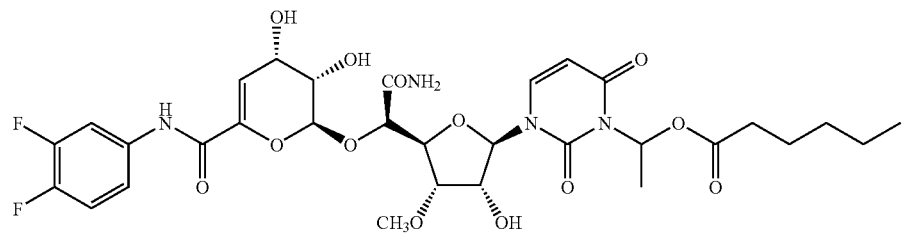

The desired compound (54 mg) was prepared from the compound obtained in Example (105-4) (175 mg) in a similar manner to that described in Example (104-5).

¹H NMR (CD₃OD) δ ppm: 7.86 (d, J=8.1 Hz, 1H), 7.77 (m, 1H), 7.41 (m, 1H), 7.22 (m, 2H), 6.08 (m, 1H), 5.75 (m, 2H), 5.30 (d, J=4.4 Hz, 1H), 4.82 (d, J=2.2 Hz, 1H), 4.52 (m, 1H), 4.42 (m, 1H), 4.24 (m, 1H), 4.10 (m, 1H), 3.68 (m, 1H), 3.24 (s, 3H), 2.32 (t, J=7.3 Hz, 2H), 1.75 (d, J=5.9 Hz, 3H), 1.59 (m, 2H), 1.29 (m, 4H), 0.89 (m, 3H).

IR (KBr) ν cm⁻¹: 3412, 3349, 3105, 2957, 2935, 2873, 1719, 1665, 1617, 1536, 1518, 1444, 1414, 1384, 1320, 1279, 1241, 1210.

Example (106

Exemplification Compound Number 6703

The desired compound (152 mg) was obtained using 1-chloroethyl ethyl carbonate instead of 1-chloroethyl hexanoate in a similar manner to that described in Example (105-3).

¹H NMR (CDCl₃) δ ppm: 8.54 (s, 1H), 7.78 (m, 2H), 7.15 (m, 3H), 7.00 (m, 1H), 6.50 (m, 1H), 5.73 (m, 2H), 5.67 (d, J=3.7 Hz, 1H), 4.85 (m, 1H), 4.80 (m, 2H), 4.65 (m, 1H), 4.59 (d, J=2.2 Hz, 1H), 4.39 (m, 1H), 4.18 (m, 3H), 4.08 (m, 1H), 3.82 (m, 1H), 3.31 (s, 3H), 1.85 (m, 2H), 1.51 (s, 3H), 1.46 (s, 3H), 1.30 (m, 5H), 0.95 (s, 9H), 0.24 and 0.23 (2s, 3H), 0.15 (s, 3H).

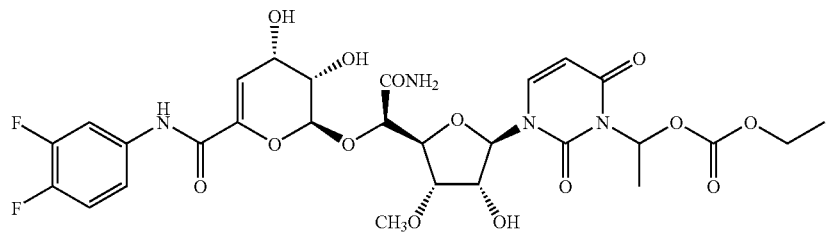

Example (106-1)

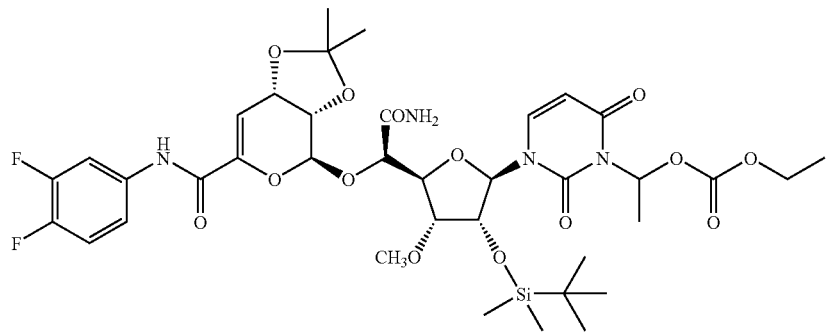

Example (106-2)

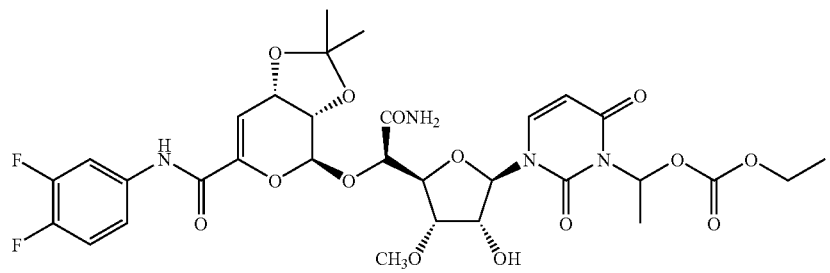

The desired compound (111 mg) was prepared from the compound obtained in Example (106-1) (194 mg) in a similar manner to that described in Example (104-4).

$^1$H NMR (CD$_3$OD) δ ppm: 7.84 (m, 1H), 7.77 (m, 1H), 7.40 (m, 1H), 7.23 (m, 1H), 7.12 (m, 1H), 7.21 (m, 1H), 5.75 (m, 2H), 5.26 (m, 1H), 4.83 (m, 1H), 4.54 (m, 1H), 4.46 (m, 1H), 4.28 (m, 1H), 4.15 (m, 2H), 3.78 (m, 1H), 3.27 (s, 3H), 1.80 (d, J=6.6 Hz, 3H), 1.45 (s, 3H), 1.44 (s, 3H), 1.26 (m, 3H).

Example (106-3)

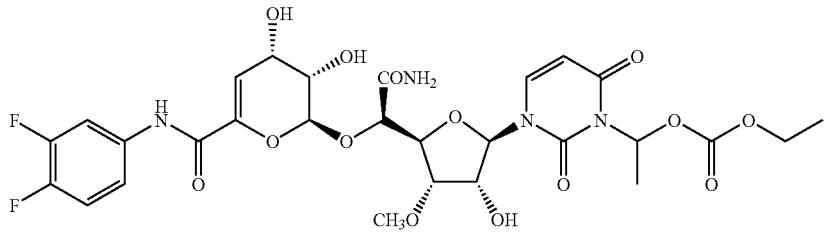

The desired compound (42 mg) was prepared from the compound obtained in Example (106-2) (110 mg) in a similar manner to that described in Example (104-5).

$^1$H NMR (CD$_3$OD) δ ppm: 7.86 (d, J=8.1 Hz, 1H), 7.77 (m, 1H), 7.41 (m, 1H), 7.23 (m, 1H), 7.12 (m, 1H), 6.08 (m, 1H), 5.77 (d, J=8.1 Hz, 1H), 5.74 (m, 1H), 5.30 (d, J=3.7 Hz, 1H), 4.82 (d, J=2.2 Hz, 1H), 4.52 (m, 1H), 4.43 (m, 1H), 4.24 (m, 1H), 4.15 (m, 2H), 4.10 (m, 1H), 3.68 (m, 1H), 3.24 (s, 3H), 1.79 (d, J=5.9 Hz, 3H), 1.25 (m, 3H).

Example (107

Exemplification Compound Number 6706

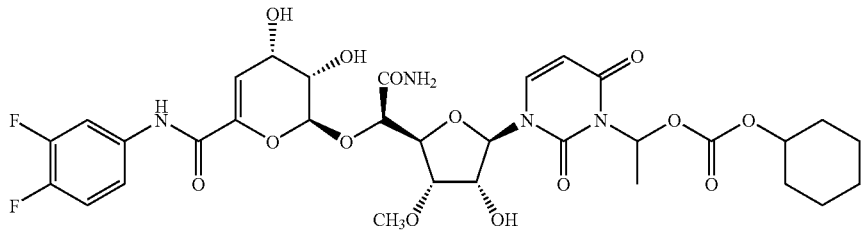

Example (107-1)

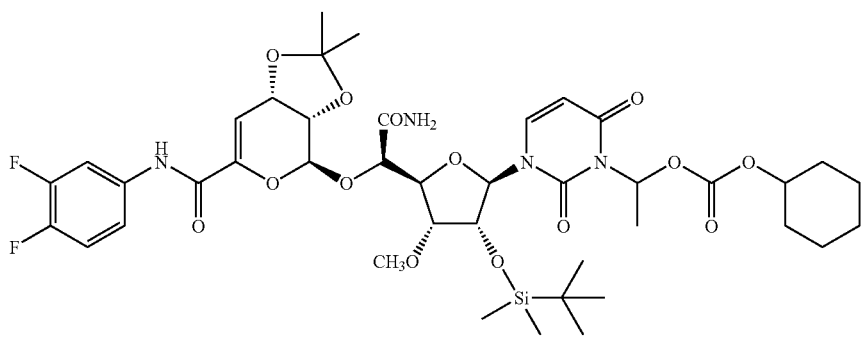

The desired compound (194 mg) was obtained using 1-chloroethyl cyclohexyl carbonate instead of 1-chloroethyl hexanoate in a similar manner to that described in Example (105-3).

Example (107-2)

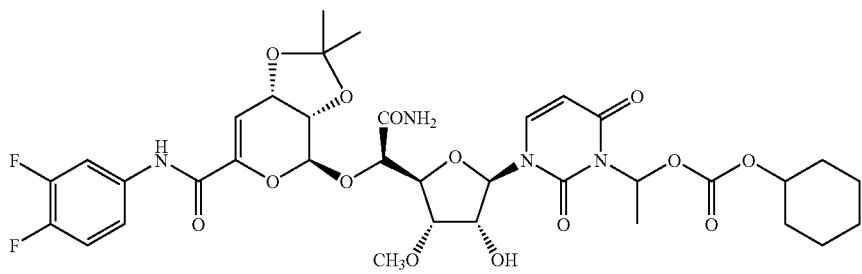

The desired compound (122 mg) was prepared from the compound obtained in Example (107-1) (193 mg) in a similar manner to that described in Example (1044).

Example (107-3)

$^1$H NMR (CD$_3$OD) δ ppm: 7.87 (d, J=8.1 Hz, 1H), 7.78 (m, 1H), 7.42 (m, 1H), 7.23 (m, 1H), 7.12 (m, 1H), 6.08 (m, 1H), 5.79 (d, J=8.1 Hz, 1H), 5.75 (m, 1H), 5.31 (d, J=4.4 Hz, 1H), 4.82 (m, 1H), 4.58 (m, 1H), 4.52 (m, 1H), 4.42 (m, 1H), 4.25 (m, 1H), 4.10 (m, 1H), 3.68 (m, 1H), 3.24 (s, 3H), 1.85 (m, 2H), 1.79 (d, J=5.9 Hz, 3H), 1.72 (m, 2H), 1.55–1.25 (m, 6H).

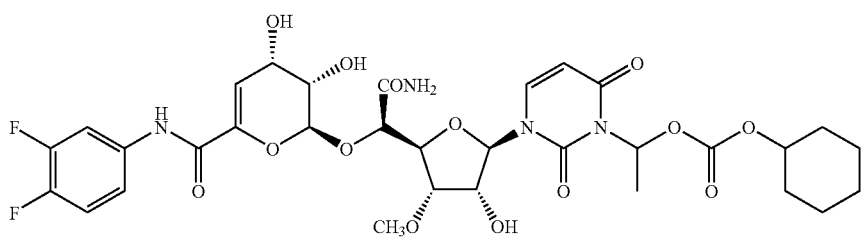

The desired compound (51 mg) was prepared from the compound obtained in Example (107-2) (120 mg) in a similar manner to that described in Example (104-5).

Example (108

Exemplification Compound Number 6708

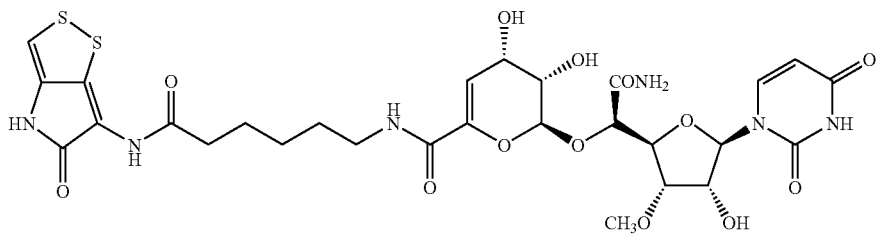

Example (108-1)

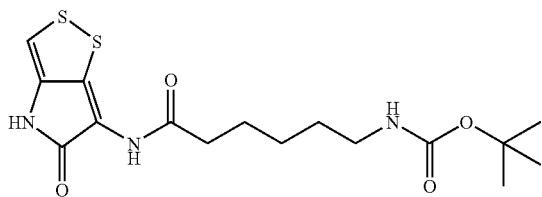

A solution of N-t-butoxycarbonyl-6-aminohexanoic acid (106 mg) and triethylamine (77 μL) in methylene chloride (16 mL) was stirred at −78° C. under a nitrogen atomosphere. To this solution was added ethyl chloroformate (53 μL). After 1 hour, the temperature of the reaction mixture was allowed to rise to 0° C. and the mixture was stirred for 40 minutes. A solution of horothin hydrochloride (115 mg) and triethylamine (154 μL) in DMF (14 mL) was then added dropwise to the reaction mixture. After 30 minutes, the temperature of the reaction mixture was allowed to rise back to room temperature. The stirring was continued for 90 minutes. After the solvent was evaporated under reduced pressure, the residue was dissolved in ethyl acetate (50 mL). The ethyl acetate solution was washed with water (50 mL) and saturated aqueous sodium chloride solution (50 mL). After drying over anhydrous magnesium sulfate, the solvent was evaporated under reduced pressure. The residue was purified by chromatography on a silica gel (5 g) column using methylene chloride:methanol (99:1) as the eluant to give the desired compound (84 mg).

$^1$H NMR (CDCl$_3$) δ ppm: 8.96 (br s, 1H), 8.21 (br s, 1H), 6.79 (s, 1H), 4.63 (br s, 1H), 3.10 (m, 2H), 2.38 (t, J=7.6 Hz, 2H), 1.75–1.40 (m, 15H).

Example (108-9)

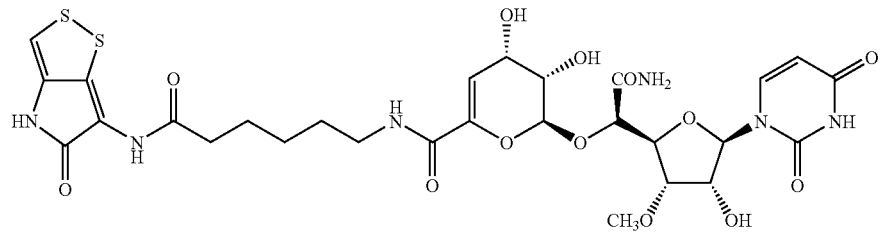

A solution of the compound obtained in Example (108-1) (84 mg) in trifluoroacetic acid:water (4:1) (30 mL) was stirred at room temperature for 15 minutes. After the solvent was evaporated under reduced pressure, azeotropic distillation was carried out with ethanol several times to give a yellow substance. To the substance were added the compound of formula (VII) (107 mg) and HOBT (48 mg). After the mixture was dissolved in DMF (1.5 mL), triethylamine (46 μL) and DIPC (70 μL) were added to the solution. After stirring at room temperature for 3 hours, the solvent was evaporated under reduced pressure. The residue was purified by chromatography on a silica gel (6 g) column using methylene chloride:methanol (4:1) as the eluant to give the desired compound (75 mg).

$^1$H NMR (CD$_3$OD) δ ppm: 7.87 (d, J=8.2 Hz, 1H), 5.94 (m, 1H), 5.81 (d, J=4.2 Hz, 1H), 5.75 (d, J=8.2 Hz, 1H), 5.21 (d, J=4.7 Hz, 1H), 4.69 (d, J=1.8 Hz, 1H), 4.50 (dd, J=2.0 and 5.2 Hz, 1H), 4.38 (m, 1H), 4.24 (t, J=4.5 Hz, 1H), 4.02 (t, J=4.3 Hz, 1H), 3.71 (t, J=5.1 Hz, 1H), 3.38 (s, 3H), 3.30 (m, 2H), 2.40 (t, J=7.4 Hz, 2H), 1.70 (m, 2H), 1.60 (m, 2H), 1.40 (m, 2H).

Example (109)

Exemplification Compound Number 6732

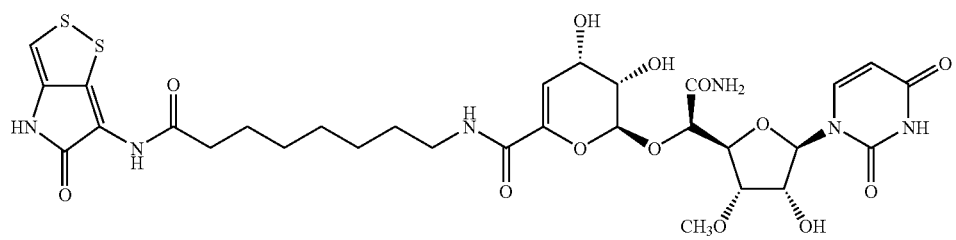

Example (109-1)

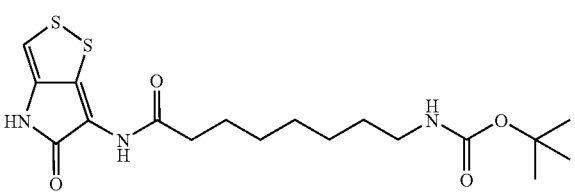

The desired compound (162 mg) was obtained using N-t-butoxycarbonyl-8-aminooctanoic acid instead of N-t-butoxycarbonyl-6-aminohexanoic acid in a similar manner to that described in Example (108-1).

$^1$H NMR (CDCl$_3$) δ ppm: 8.62 (br s, 1H), 7.78 (br s, 1H), 6.76 (s, 1H), 4.53 (br s, 1H), 3.08 (m, 2H), 2.35 (t, J=7.3 Hz, 2H), 1.75–1.30 (m, 19H).

Example (109-2)

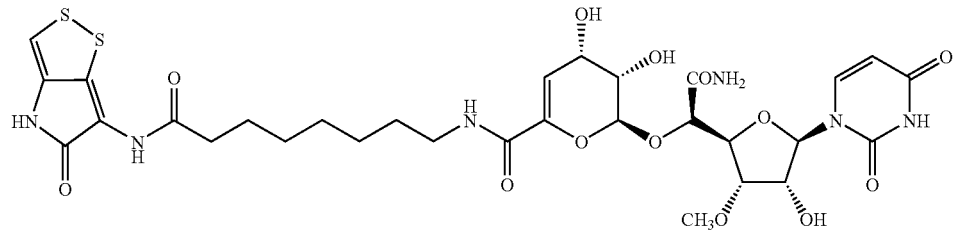

The desired compound (43 mg) was prepared from the compound obtained in Example (109-1) instead of the compound obtained in Example (108-1) in a similar manner to that described in Example (108-2).

$^1$H NMR (CD$_3$OD) δ ppm: 7.87 (d, J=8.8 Hz, 1H), 7.06 (s, 1H), 5.94 (d, J=4.4 Hz, 1H), 5.81 (d, J=4.4 Hz, 1H), 5.75 (d, J=8.8 Hz, 1H), 5.21 (d, J=4.4 Hz, 1H), 4.69 (d, J=1.5 Hz, 1H), 4.50 (dd, J=2.2 and 5.1 Hz, 1H), 4.38 (m, 1H), 4.24 (m, 1H), 4.02 (t, J=4.4 Hz, 1H), 3.71 (t, J=5.1 Hz, 1H), 3.38 (s, 3H), 3.25 (m, 2H), 2.39 (t, J=7.4 Hz, 2H), 1.65 (m, 2H), 1.55 (m, 2H), 1.38 (br s, 6H).

Manufacturing Example 1

Cultivation of *Streptomyces griseus* Strain SANK60196 (FERM BP-5420)

Into each of four 2 L Erlenmeyer flasks (seed flasks), each containing 500 mL of a preculture medium made sterile prior to inoculation and having the composition described below, was inoculated four loopfuls of strain SANK60196 followed by shaking in a rotary shaker at 23° C. and 210 revolutions/min (revolutions per minute: which will hereinafter be abbreviated as "rpm"). Preculture was thus conducted for 3 days.

| Preculture medium | |
|---|---|
| Maltose | 30 g |
| Meat extract | 5 g |
| Polypeptone | 5 g |
| Sodium chloride | 5 g |
| CaCO$_3$ | 3 g |
| Antifoamer ("CB442"; product of NOF Corporation) | 50 mg |
| Tap water | 1000 mL |
| pH before sterilization: | 7.4 |
| Sterilization: at 121° C. for 30 minutes. | |

The culture was conducted as described below. Described specifically, the seed broth was inoculated at 3% (v/v) into each of two 30 L jar fermenters, each containing 15 L of a sterilized main culture medium having the composition described below. Six hours after the initiation of cultivation at 23° C., filter-sterilized S-(2-aminoethyl)-L-cysteine hydrochloride was added to give a final concentration of 10 mM, followed by culture with aeration and agitation at 23° C. for 6 days.

| Main culture medium | |
|---|---|
| Maltose | 30 g |
| Yeast extract (product of Difco Laboratories) | 5 g |
| Meat extract | 5 g |
| Polypeptone | 5 g |
| Sodium chloride | 5 g |
| CaCO$_3$ | 3 mg |
| Antifoamer ("CB442"; product of NOF Corporation) | 50 mg |
| Tap water | 1000 mL |
| pH before sterilization: | 7.4 |
| Sterilization: at 125° C. for 30 minutes | |

Manufacturing Example 2

Purification of Compound (VI)

After completion of the cultivation, the broth (30 L) obtained above in Manufacturing Example 1 was filtered with the aid of "Celite 545" (product of Celite Corporation).

Upon purification as described later, the active substance of each fraction was monitored by HPLC under the following conditions.

| | |
|---|---|
| Column: | "Senshu Pak ODS-H-2151" 6ϕ × 150 mm (product of Senshu Scientific Co., Ltd.) |
| Solvent: | 4% aqueous acetonitrile containing 0.04% trifluoroacetic acid |
| Flow rate: | 1.0 mL/min |
| Detection: | UV 210 nm |
| Retention time: | 21.2 min |

The resulting concentrate (30 L) was charged on a "Diaion HP-20P" column (product of Mitsubishi Chemical Corporation; 6 L). After the column was washed with 12 L of pure water, the non-bound fraction passing through and the wash fraction were combined (hereinafter the combined fraction is referred to as the "non-bound/wash fraction". The active fraction was eluted with 10% aqueous acetone. The eluate was concentrated to remove acetone and then lyophilized to give 39 g of a crude powdery product.

The crude powdery product was dissolved in 200 mL of pure water. The resulting solution was charged on a "Diaion CHP-20P" column (product of Mitsubishi Chemical Corporation; 2 L). After washing the column with 4 L of pure water and 4 L of 10% aqueous methanol, the active fraction was eluted with 4 L of 15% aqueous methanol and 4 L of 20% aqueous methanol. A 2 to 4 L portion eluted with 15% aqueous methanol and all portions eluted with 20% aqueous methanol were combined and concentrated to remove methanol and then lyophilized to give 8.9 g of a powdery product.

The powdery product was dissolved in 200 mL of pure water. The resulting solution was charged on a "Toyopearl HW-40F" column (product of Tosoh Corporation; 1 L), followed by development with pure water. As a result of fractionation of the eluate to 100 mL portions each, an active substance having a peak at a retention time of 21.2 minutes in the above-described HPLC was eluted in Fractions No. 5 to 10. These fractions were collected and concentrated and the resulting concentrate was lyophilized to give 2.7 g of a powdery product.

The powdery product thus obtained was dissolved in 200 mL of pure water. The resulting solution was charged on an HPLC column ("YMC-Pack ODS-1050-20-SR" (100φ×500 mm; product of YMC Co., Ltd.)) equilibrated with a 4% aqueous solution of acetonitrile containing 0.04% trifluoroacetic acid, followed by development with a 4% aqueous solution of acetonitrile containing 0.04% trifluoroacetic acid at a flow rate of 208 mL/min. As a result of fractionation of the eluate to 1 L portions each, the active substance was eluted in Fractions No. 6 to 7.

The resulting fractions were concentrated by "Evapor" (product of Okawara Seisakujo) into 200 mL, followed by lyophilization, whereby 99 mg of a substance was obtained as a powdery product. After the powdery product was dissolved in 5 mL of distilled water, insoluble matter was filtered off. The filtrate was concentrated to 2 mL by a rotary evaporator and the resulting concentrate was lyophilized to give 87 mg of the compound of formula (VI) as a pure product. The following data are physico-chemical properties of the resulting substance.

1) Appearance of the substance: white powder

2) Solubility: soluble in water; slightly soluble in methanol; insoluble in normal hexane and chloroform 3) Molecular formula: $C_{18}H_{23}N_3O_{12}$ 4) Molecular weight: 473 (measured by the FAB mass spectrum method)

5) Precise mass, $[M+H]^+$, as measured by high-resolution FAB mass spectrum method is as follows:
   Found: 474.1349
   Calculated: 474.1359

6) Ultraviolet absorption spectrum: ultraviolet absorption spectrum measured in water exhibits the following maximum absorption:
   251 nm (ε10,000)

7) Optical rotation: optical rotation measured in water exhibits the following value:
   $[\alpha]_D^{20}$: +115° (c 1.00, $H_2O$)

8) Infrared absorption spectrum: Infrared absorption spectrum as measured by the potassium bromide (KBr) tablet method exhibits the following maximum absorptions: 3410, 2955, 1683, 1464, 1441, 1396, 1309, 1267, 1206, 1138, 1115, 1088, 1062, 1023 $cm^{-1}$.

9) $^1H$ nuclear magnetic resonance spectrum was measured in deuterated dimethyl sulfoxide with tetramethylsilane as an internal standard. $^1H$ nuclear magnetic resonance spectrum is as follows:
   3.24 (3H, s), 3.52 (1H, dd, J=4.5, 6.1 Hz), 3.72 (3H, s), 3.98 (1H, m), 4.10 (1H, m), 4.25 (1H, m), 4.29 (1H, d, J=2.0 Hz), 4.33 (1H, dd, J=2.0, 6.1 Hz), 5.05 (1H, d, J=3.9 Hz), 5.16 (1H, d, J=6.8 Hz), 5.45 (1H, d, J=4.2 Hz), 5.54 (1H, d, J=5.9 Hz), 5.61 (1H, d, J=3.3 Hz), 5.61 (1H, d, J=8.1 Hz), 5.93 (1H, dd, J=1.3, 2.9 Hz), 7.56 (1H, br. s), 7.69 (1H, br. s), 7.74 (1H, d, J=8.1 Hz) ppm.

10) $^{13}C$ nuclear magnetic resonance spectrum was measured in deuterated dimethyl sulfoxide with tetramethylsilane as an internal standard. $^{13}C$ nuclear magnetic resonance spectrum is as follows:
   52.0 (q), 57.3 (q), 61.5 (d), 64.9 (d), 72.1 (d), 75.4 (d), 78.2 (d), 81.3 (d), 89.0 (d), 99.2 (d), 101.2 (d), 114.2 (d), 139.2 (s), 139.8 (d), 150.3 (s), 161.8 (s), 163.1 (s), 170.1 (s) ppm.

11) High performance liquid chromatography

| | |
|---|---|
| Column: | "Senshu Pak ODS-H-2151" 6φ × 150 mm (product of Senshu Scientific Co., Ltd.) |
| Solvent: | 4% aqueous acetonitrile containing 0.04% trifluoroacetic acid |
| Flow rate: | 1.0 mL/min |
| Detection: | UV 210 nm |
| Retention time: | 21 min |

Manufacturing Example 3

Purification of Compound (VII)

Upon purification as described later, the active substance of each fraction was monitored by HPLC under the following conditions.

| | |
|---|---|
| Column: | "Senshu Pak ODS-H-2151" 6φ ×150 mm (product of Senshu Scientific Co., Ltd.) |
| Solvent: | 0.04% aqueous trifluoroacetic acid |
| Flow rate: | 1.5 mL/min |
| Detection: | UV 210 nm |
| Retention time: | 18 min |

The pH of the "non-bound/wash fraction" (42 L) in Manufacturing Example 2 was adjusted to 9 with 6N aqueous sodium hydroxide solution. The resulting solution was charged on a "Diaion PA316 ($Cl^-$)" column (product of Mitsubishi Chemical; 8.5 L). After washing the column with 27 L of pure water, the active substance was eluted with 27 L of 0.1N hydrochloric acid.

The pH of the eluate was adjusted to 7 with 6N aqueous sodium hydroxide. The resulting solution was charged on an active charcoal column (2 L). After washing the column with 10 L of pure water, the active substance was eluted with 8 L of 10% aqueous solution of acetone containing 0.5N aqueous ammonia. The eluate was concentrated to remove acetone and then lyophilized to give 28 g of a powdery product.

After the powdery product was dissolved in 400 mL of distilled water, the pH of the solution was adjusted to 3.0. The resulting solution was charged on a "Diaion CHP-20P" column (product of Mitsubishi Chemical Corporation; 2 L)

washed with sufficient pure water. The non-bound fraction passing through and wash fraction were combined, concentrated and lyophilized to give 12 g of a sticky product.

The sticky product thus obtained was dissolved in 200 mL of distilled water. After the pH was adjusted to 3.3 with trifluoroacetic acid, the resulting solution was charged on a "Diaion CHP-20P" column (product of Mitsubishi Chemical Corporation; 1 L) equilibrated with 0.04% aqueous trifluoroacetic acid, followed by development with 0.04% aqueous trifluoroacetic acid (2 L). After a 0.8 to 1.4 L portion (H fraction) was collected, the eluant was changed to distilled water (2 L). A portion (F fraction, 2 L) eluted with distilled water was concentrated and lyophilized to give 605 mg of a powdery product.

The powdery product thus obtained from the F fraction was dissolved in 15 mL of water. Each 1 mL was charged on an HPLC column ("Senshu Pak ODS-H-5251" 20ϕ×250 mm (product of Senshu Scientific Co., Ltd.)) equilibrated with 0.04% aqueous trifluoroacetic acid, followed by development at a flow rate of 10 mL/min. The active fraction detected by UV at 210 nm was eluted with a retention time of 29~31 minutes. The procedure was repeated 15 times. The combined fractions were concentrated by a rotary evaporator and the resulting concentrate was lyophilized to give 134 mg of the compound of formula (VII) as a pure product. The following data are physico-chemical properties of the resulting substance.

1) Appearance of the substance: white powder

2) Solubility: soluble in water; slightly soluble in methanol; insoluble in normal hexane and chloroform 3) Molecular formula: $C_{17}H_{21}N_3O_{12}$ 4) Molecular weight: 459 (measured by the FAB mass spectrum method)

5) Precise mass, $[M+H]^+$, as measured by the high-resolution FAB mass spectrum method is as follows:
Found: 460.1201
Calculated: 460.1203

6) Ultraviolet absorption spectrum: ultraviolet absorption spectrum measured in water exhibits the following maximum absorption:
262 nm (ε7,000)

7) Optical rotation: optical rotation measured in water exhibits the following value:
$[α]_D^{20}$: +111° (c 0.41, $H_2O$)

8) Infrared absorption spectrum: Infrared absorption spectrum as measured by the potassium bromide (KBr) tablet method exhibits the following maximum absorptions: 3391, 2941, 1684, 1466, 1400, 1333, 1269, 1205, 1137, 1115, 1062, 1020 $cm^{-1}$.

9) $^1H$ nuclear magnetic resonance spectrum was measured in deuterated water using the proton signal of water as 4.75 ppm. $^1H$ nuclear magnetic resonance spectrum is as follows:
3.37 (3H, s), 3.79 (1H, dd, J=5.1, 6.4 Hz), 4.17 (1H, ddd, J=1.6, 3.4, 4.6 Hz), 4.38 (1H, dd, J=3.5, 5.1 Hz), 4.48 (1H, dd, J=2.4, 6.4 Hz), 4.49 (1H, ddd, J=0.6, 2.7, 4.6 Hz), 4.69 (1H, d, J=2.4 Hz), 5.32 (1H, dd, J=0.6, 3.4 Hz), 5.77 (1H, d, J=3.5 Hz), 5.90 (1H, d, J=8.1 Hz), 6.11 (1H, dd, J=1.6, 2.7 Hz), 7.75 (1H, d, J=8.1 Hz) ppm.

10) $^{13}C$ nuclear magnetic resonance spectrum was measured in deuterated water using 1,4-dioxane (67.4 ppm) as an internal standard. $^{13}C$ nuclear magnetic resonance spectrum is as follows:

58.6 (q), 62.7 (d), 65.5 (d), 72.7 (d), 76.3 (d), 78.8 (d), 91.2 (d), 100.0 (d), 102.7 (d), 114.8 (d), 140.7 (s), 141.9 (d), 152.1 (s), 165.4 (s), 167.0 (s), 173.9 (s) ppm.

11) High performance liquid chromatography

| | |
|---|---|
| Column: | "Senshu Pak ODS-H-2151" 6ϕ × 150 mm (product of Senshu Scientific Co., Ltd.) |
| Solvent: | 0.04% aqueous trifluoroacetic acid |
| Flow rate: | 1.5 mL/min |
| Detection: | UV 210 nm |
| Retention time: | 18 min |

Manufacturing Example 4

Manufacturing Method of Compound (VII)
(Hydrolysis of Compound (VI))

The compound of formula (VI) (4.4 mg) obtained in Manufacturing Example 2 above was dissolved in distilled water (0.5 mL). After addition of 0.5 mL of 0.02N aqueous sodium hydroxide, 1 mL of 0.1N aqueous sodium hydroxide was added to the solution. The resulting solution was allowed to stand at room temperature for 50 minutes. After neutralization with 1N hydrochloric acid, the solution was charged on an active charcoal column (2 mL). The column was washed with 8 mL of distilled water and the reaction product was eluted with 8 mL of a 10% aqueous solution of acetone containing 0.5N aqueous ammonia.

The eluate was concentrated to 700 μL and divided into three parts. Each 230 μL was charged on an HPLC column ("Senshu Pak ODS-H-4251" 10ϕ×250 mm (product of Senshu Scientific Co., Ltd.)) equilibrated with 0.04% aqueous trifluoroacetic acid, followed by development at a flow rate of 4 mL/min. The active substance detected by UV at 210 nm was eluted with a retention time of 25~30 minutes. This procedure was repeated 3 times. The combined fractions were concentrated by a rotary evaporator and the resulting concentrate was lyophilized to give 2.6 mg of the compound of formula (VII) as a pure product.

Test Example 1

In Vitro Antibacterial Activity (1)

The minimum inhibitory concentration of compounds of this invention against *Mycobacterium avium* Strain NIHJ 1605 was determined. Described specifically, Tween 80 (0.1%) was added to Middlebrook 7H9 broth. After high-pressure steam sterilization, Middlebrook ADC enrichment was added (20%). Into each of the micro-test tubes was poured a 0.8 mL portion of the resulting mixture. To each of the test tubes was added a 0.1 mL portion of each of the tested compounds of this invention diluted by two-fold dilution system (which will hereinafter be abbreviated as "the medicament-containing medium"). Aside from this, a colony obtained by preculturing *Mycobacterium avium* NIHJ1605 on a Tween egg medium for 10 to 14 days was charged in a test tube containing Tween 80 and glass beads. After sufficient mixing, Middlebrook 7H9 broth was added to form a uniform microorganism solution. The microorganism solution was adjusted to $OD_{625nm}$=0.10 (viable cell count: about $1×10^8$ CFU/mL), followed by dilution 100-fold. A 0.1 mL portion of the resulting microorganism solution was inoculated into the above-described medicament-containing medium (final viable cell count: about $1\times10^5$ CFU/mL), followed by aerobic culture at 37° C. for 6 days. The minimum medicament amount at which no colony having a diameter of 1 mm or greater was recognized on the bottom of the test tube was determined as MIC (μg/mL). The results are shown in Table 7.

TABLE 7

Antibacterial activities against *Mycobacterium avium* NIHJ 1605

| Exemplification Compound No. | Minimum inhibitory concentration (μg/mL) |
|---|---|
| Capuramycin | 8 |
| 5 (Example 80) | 0.25 |
| 6 (Example 81) | 0.5 |
| 7 (Example 82) | 1 |
| 9 (Example 83) | 2 |
| 20 (Example 85) | 4 |
| 142 (Example 44) | 2 |
| 163 (Example 86) | 4 |
| 352 (Example 54) | 4 |
| 562 (Example 55) | 1 |
| 982 (Example 58) | 2 |
| 1472 (Example 50) | 2 |
| 2242 (Example 62) | 1 |
| 2312 (Example 64) | 0.25 |
| 2382 (Example 63) | 0.5 |
| 3012 (Example 45) | 4 |
| 3712 (Example 57) | 2 |
| 4132 (Example 60) | 2 |
| 5742 (Example 59) | 4 |
| 6351 (Example 5) | 4 |
| 6411 (Example 14) | 1 |
| 6526 (Example 32) | 4 |
| 6631 (Example 79) | 0.5 |

Test Example 2

In Vitro Antibacterial Activity (2)

The minimum inhibitory concentration (MICs) of the test compounds against *Mycobacterium tuberculosis* was determined by the broth dilution method. After the solution of a test compound in dimethyl sulfoxide (DMSO) or distilled water was diluted with 50% aqueous acetone or distilled water, each two-fold dilution of the solution was carried out with Middlebrook 7H9 broth containing 0.05% Tween 80, 0.2% dextrose and Middlebrook ADC enrichment. The final concentrations of DMSO and acetone did not exceed 0.05% and 2.5% respectively. The microorganisms cultivated on Ogawa medium were suspended uniformly in Middlebrook 7H9 broth containing 0.05% Tween 80, 0.2% dextrose and Middlebrook ADC enrichment. The microorganism solution was adjusted to about $1\times10^7$ CFU/mL using a spectrophotometer. The resulting microorganism solution was further diluted with Middlebrook 7H9 broth containing 0.05% Tween 80, 0.2% dextrose and Middlebrook ADC enrichment (final viable cell count: about $1\times10^5$ CFU/mL). After mixing the diluted microorganism solution with the diluted test compound solution in the test tube, cultivation was performed at 35° C. for 10–21 days. When significant growth was found in the control test tube with no test compound, the MIC was determined as the minimum concentration of the compound at which no colony was recognized macroscopically in the test tube.

The minimum inhibitory concentrations (MICs) of the test compound against *Mycobacterium tuberculosis* is shown in Table 8.

TABLE 8

MICs (μg/mL) of Compound 3712 against *Mycobacterium tuberculosis*

| Exemplification Compound No. | *M. tuberculosis* Kato | *M. tuberculosis* No. 74 |
|---|---|---|
| 3712 (Example 57) | 1 | 8 |

While *M. tuberculosis* No. 74 is a rifampicin-resistant strain (MIC: 128 μg/mL), Exemplification Compound No. 3712 (Example 57) demonstrated excellent antibacterial activity against the strain.

| | |
|---|---|
| Compound of Example 43 | 100 mg |
| Lactose | 100 mg |
| Corn starch | 148.8 mg |
| Magnesium stearate | 1.2 mg |
| Total amount | 350 mg |

A capsule is obtained by mixing the powders described above, sieving the resulting mixture through a 60-mesh sieve, and then charging the resulting powder in a gelatin capsule.

Preparation Example 2

Solution 1

A solution is prepared to the following composition:

| | |
|---|---|
| Compound of Example 57 | 10% (w/w) |
| Benzalkonium chloride | 0.04% (w/w) |
| Phenethyl alcohol | 0.40% (w/w) |
| Purified water | 89.56% (w/w) |

Preparation Example 3

Solution 2

A solution is prepared to the following composition:

| | |
|---|---|
| Compound of Example 57 | 10% (w/w) |
| Benzalkonium chloride | 0.04% (w/w) |
| Polyethylene glycol 400 | 10% (w/w) |
| Propylene glycol | 30% (w/w) |
| Purified water | 39.96% (w/w) |

Preparation Example 4

Powder

A powder is prepared to the following composition:

| | |
|---|---|
| Compound of Example 57 | 40% (w/w) |
| Lactose | 60% (w/w) |

Preparation Example 5

Aerosol

An aerosol is prepared to the following composition:

| | |
|---|---|
| Compound of Example 57 | 10% (w/w) |
| Lecithin | 0.5% (w/w) |
| Flon 11 | 34.5% (w/w) |
| Flon 12 | 55% (w/w) |

The present invention relates to a compound of formula (I), a pharmaceutically ether or ester of the compound and a pharmaceutically acceptable salt thereof. These compounds exhibit excellent antibacterial activity against many kinds of bacteria (preferably acid-fast bacteria and particularly preferably *Mycobacterium tuberculosis*). Therefore, they are useful in the prevention or treatment (preferably treatment) of bacterial infections attributable to these bacteria.

What is claimed is:

1. A compound of formula (I), a pharmaceutically acceptable ester or ether thereof, or a pharmaceutically acceptable salt thereof:

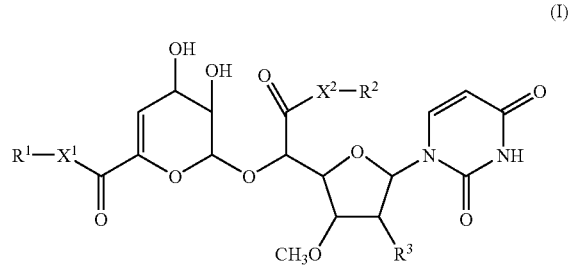

(I)

wherein
$X^1$ represents an oxygen atom, a sulfur atom or a group of formula $N(R^4)$—, in which $R^4$ is a hydrogen atom, a $C_1$–$C_3$ alkyl group, or $R^4$, together with $R^1$ and the nitrogen atom to which they are attached, forms a 3 to 7 membered cyclic amine which optionally has a ring oxygen or sulfur atom;

$X^2$ represents an oxygen atom, a sulfur atom or a group of formula —$N(R^5)$—, in which $R^5$ is a hydrogen atom, a $C_1$–$C_3$ alkyl group, or $R^5$, together with $R^2$ and the nitrogen atom to which they are attached, forms a 3- to 7-membered cyclic amine which optionally has a ring oxygen or sulfur atom;

$R^1$ and $R^2$ are the same or different and each represents:

(1) a hydrogen atom, (2) a $C_6$–$C_{10}$ aryl group which is unsubstituted or has one or more substituents of a Substituent Group A selected from the group consisting of a halogen atom; a hydroxyl group; an amino group; a nitro group; a cyano group; a carboxyl group; a $C_1$–$C_4$ alkoxycarbonyl group; a carbamoyl group; a $C_1$–$C_{10}$ alkylenedloxy group, a $C_7$–$C_{14}$ aralkyloxy group; a $C_1$–$C_{18}$ alkyl group, said alkyl group being unsubstituted or substituted with one or more halogen atoms; a $C_2$–$C_{16}$ alkenyl group; a $C_1$–$C_{16}$ alkoxy group, said alkoxy group being unsubstituted or substituted with one or more halogen atoms; a $C_1$–$C_{16}$ alkylthio group, said alkylthio group being unsubstituted or substituted with one or more halogen atoms; a $C_6$–$C_{10}$ arylazo group; and a heterocyclic group which has 1–4 ring nitrogen, sulfur or oxygen atoms, (3) a heterocyclic group which has 1–4 nitrogen, sulfur or oxygen atoms and which is unsubstituted or substituted by one or more substituents of a Substituent Group B selected from the group consisting of an oxo group; a thiooxo group; an imino group; a halogen atom; a hydroxyl group; an amino group; a nitro group; a cyano group; a carboxyl group; a $C_1$–$C_4$ alkoxycarbonyl group, a carbamoyl group; a $C_7$–$C_{14}$ aralkyloxy group; a $C_1$–$C_{16}$ alkyl group; said alkyl group being unsubstituted or substituted with one or more halogen atoms; a $C_1$–$C_{16}$ alkenyl group; a $C_1$–$C_{18}$ alkoxy group, said alkoxy group being unsubstituted or substituted with one or more halogen atoms; and a $C_1$–$C_{16}$ alkylthio group, said alkylthio group being unsubstituted or substituted with one or more halogen atoms;

(4) a $C_1$–$C_{14}$ alkyl group which is substituted with one to three $C_6$–$C_{10}$ aryl groups which are the same or different and each is unsubstituted or have one or more substituents from the Substituent Group A;

(5) a $C_1$–$C_{14}$ alkyl group which is substituted with one to three heterocyclic groups which are the same or different, have 1–4 nitrogen, sulfur or oxygen atoms and are unsubstituted or have one or more substituents from the Substituent Group B on the heterocyclic group;

(6) a $C_1$–$C_{22}$ alkyl group which is unsubstituted or have one or more substituents of a Substituent Group C selected from the group consisting of a halogen atom, a hydroxyl group, an amino group, a nitro group, a cyano group, a carboxyl group, a $C_1$–$C_4$ alkoxycarbonyl group, a carbamoyl group, a $C_1$–$C_{18}$ alkoxy group, said alkoxy group being unsubstituted or substituted with one or more halogen atoms, and a $C_1$–$C_{16}$ alkylthio group, said alkylthio group being unsubstituted or substituted with one or more halogen atoms; or (7) a $C_2$–$C_{22}$ alkenyl group which is unsubstituted or has one or more substituents, said one or more substituents are selected from those listed in (2) or (3) above or from said Substituent Group C; and $R^3$ represents a hydrogen atom or a hydroxyl group;

with the proviso that excluded are:

a compound wherein $X^1$ and $X^2$ represent a group of formula —NH—, $R^1$ represents a hydrogen atom or a group of the following formulae (II), (III), (IV) or (V), $R^2$ is a hydrogen atom and $R^3$ is a hydroxyl group, and a compound wherein $X^1$ is an oxygen atom, $X^2$ represents a group of formula —NH—, $R^1$ represents a hydrogen atom or a methyl group, $R^z$ is a hydrogen atom and $R^3$ is a hydroxyl group

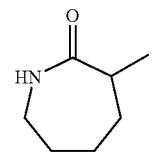

(II)

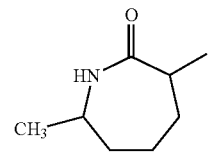

(III)

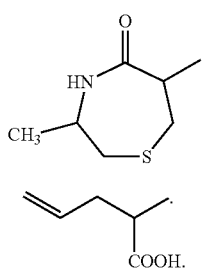

2. A compound, a pharmaceutically acceptable ester or ether thereof or a pharmaceutically acceptable salt thereof according to claim 1, wherein $X^1$ represents a group of formula —N($R^4$)—.

3. A compound, a pharmaceutically acceptable ester or ether thereof or a pharmaceutically acceptable salt thereof according to claim 1, wherein $X^1$ represents a group of formula —N($R^4$)—, in which $R^4$ represents a hydrogen atom or a $C_1$–$C_3$ alkyl group.

4. A compound, a pharmaceutically acceptable ester or ether thereof or a pharmaceutically acceptable salt thereof according to claim 1, wherein $X^1$ represents a group of formula —NH—.

5. A compound, a pharmaceutically acceptable ester or ether thereof or a pharmaceutically acceptable salt thereof according to claim 1, wherein $X^2$ represents a group of formula —N($R^5$)—.

6. A compound, a pharmaceutically acceptable ester or ether thereof or a pharmaceutically acceptable salt thereof according to claim 1, wherein $X^2$ represents a group of formula —N($R^5$)—, in which $R^5$ represents a hydrogen atom or a $C_1$–$C_3$ alkyl group.

7. A compound, a pharmaceutically acceptable ester or ether thereof or a pharmaceutically acceptable salt thereof according to claim 1, wherein $X^2$ represents a group of the formula —NH—.

8. A compound, a pharmaceutically acceptable ester or ether thereof or a pharmaceutically acceptable salt thereof according to claim 1, wherein $R^1$ represents a hydrogen atom.

9. A compound, a pharmaceutically acceptable ester or ether thereof or a pharmaceutically acceptable salt thereof according to claim 1, wherein $R^1$ represents a $C_6$–$C_{10}$ aryl group which is unsubstituted or has one or more substituents from said Substituent Group A.

10. A compound, a pharmaceutically acceptable ester or ether thereof or a pharmaceutically acceptable salt thereof according to claim 9, wherein $R^1$ represents a phenyl, 1-naphthyl or 2-naphthyl group which is unsubstituted or has one or more substituents from said Substituent Group A.

11. A compound, a pharmaceutically acceptable ester or ether thereof or a pharmaceutically acceptable salt thereof according to claim 9, wherein $R^1$ represents a phenyl group which is unsubstituted or has one or more substituents from said Substituent Group A.

12. A compound, a pharmaceutically acceptable ester or ether thereof or a pharmaceutically acceptable salt thereof according to claim 1, wherein $R^1$ represents a heterocyclic group which has 1–4 ring nitrogen, sulfur or oxygen atoms and which is unsubstituted or has one or more substituents from said Substituent Group B.

13. A compound, a pharmaceutically acceptable ester or ether thereof or a pharmaceutically acceptable salt thereof according to claim 12, wherein $R^1$ represents a 5- or 6-membered aromatic heterocyclic group or a 5- or 6-membered aromatic heterocyclic group fused to a benzene ring, which has 1–4 ring nitrogen, sulfur or oxygen atoms and which is unsubstituted or has one or more substituents from said Substituent Group B.

14. A compound, a pharmaceutically acceptable ester or ether thereof or a pharmaceutically acceptable salt thereof according to claim 1, wherein $R^1$ represents a $C_1$–$C_{14}$ alkyl group which is substituted with one to three $C_6$–$C_{10}$ aryl groups which are the same or different and which are unsubstituted or have one or more substituents from said Substituent Group A.

15. A compound, a pharmaceutically acceptable ester or ether thereof or a pharmaceutically acceptable salt thereof according to claim 14, wherein $R^1$ is said aryl group and is a phenyl, 1-naphthyl or 2-naphthyl group which is unsubstituted or has one or more substituents from said Substituent Group A.

16. A compound, a pharmaceutically acceptable ester or ether thereof or a pharmaceutically acceptable salt thereof according to claim 14, wherein $R^1$ is said aryl group and is a phenyl group which is unsubstituted or has one or more substituents from said Substituent Group A.

17. A compound, a pharmaceutically acceptable ester or ether thereof or a pharmaceutically acceptable salt thereof according to claim 14, wherein $R^{11}$ is said alkyl group and is a $C_1$–$C_8$ alkyl group.

18. A compound, a pharmaceutically acceptable ester or ether thereof or a pharmaceutically acceptable salt thereof according to claim 14, wherein $R^1$ is said alkyl group and is a $C_1$–$C_4$ alkyl group.

19. A compound, a pharmaceutically acceptable ester or ether thereof or a pharmaceutically acceptable salt thereof according to claim 14, wherein $R^1$ is said alkyl group and is a $C_2$ alkyl group.

20. A compound, a pharmaceutically acceptable ester or ether thereof, or a pharmaceutically acceptable salt thereof according to claim 1, wherein $R^1$ represents a $C_1$–$C_{14}$ alkyl group which is substituted with one to three heterocyclic groups which are the same or different and each have 1–4 ring nitrogen, sulfur or oxygen atoms and are unsubstituted or have one or more substituents from said Substituent Group B.

21. A compound, a pharmaceutically acceptable ester or ether thereof or a pharmaceutically acceptable salt thereof according to claim 20, wherein $R^1$ is said heterocyclic group and is a 5- or 6-membered aromatic heterocyclic group or a 5- or 6-membered aromatic heterocyclic group fused to a benzene ring, which is unsubstituted or has one or more substituents from said Substituent Group B.

22. A compound, a pharmaceutically acceptable ester or ether thereof or a pharmaceutically acceptable salt thereof according to claim 20, wherein $R^1$ is said alkyl group and is a $C_1$–$C_8$ alkyl group.

23. A compound, a pharmaceutically acceptable ester or ether thereof or a pharmaceutically acceptable salt thereof according to claim 20, wherein $R^1$ is said alkyl group and is a $C_1$–$C_4$ alkyl group.

24. A compound, a pharmaceutically acceptable ester or ether thereof or a pharmaceutically acceptable salt thereof according to claim 20, wherein $R^1$ is said alkyl group and is a $C_2$ alkyl group.

25. A compound, a pharmaceutically acceptable ester or ether thereof or a pharmaceutically acceptable salt thereof according to claim 21, wherein $R^1$ is said alkyl group and is a $C_1$–$C_8$ alkyl group.

26. A compound, a pharmaceutically acceptable ester or ether thereof or a pharmaceutically acceptable salt thereof according to claim 21, wherein $R^1$ is said alkyl group and is a $C_1$–$C_4$ alkyl group.

27. A compound, a pharmaceutically acceptable ester or ether thereof or a pharmaceutically acceptable salt thereof according to claim 21, wherein $R^1$ is said alkyl group and is a $C_2$ alkyl group.

28. A compound, a pharmaceutically acceptable ester or ether thereof, or a pharmaceutically acceptable salt thereof according to claim 1, wherein $R^1$ represents a $C_1$–$C_{22}$ alkyl group which is unsubstituted or has one or more substituents from said Substituent Group C.

29. A compound, a pharmaceutically acceptable ester or ether thereof or a pharmaceutically acceptable salt thereof according to claim 28, wherein $R^1$ represents a $C_1$–$C_{18}$ alkyl group which is unsubstituted or has one or more substituents from said Substituent Group C.

30. A compound, a pharmaceutically acceptable ester or ether thereof or a pharmaceutically acceptable salt thereof according to claim 1, wherein $R^1$ represents a $C_2$–$C_{22}$ alkenyl group which is unsubstituted or has one or more substituents, said one or more substituents are from the substituents set forth in groups (2) or (3) in the definition of $R^1$ in claim 1, or a substituent from said Substituent Group C.

31. A compound, a pharmaceutically acceptable ester or ether thereof or a pharmaceutically acceptable salt thereof according to claim 30, wherein $R^1$ represents a $C_2$–$C_{22}$ alkenyl group which has no substituent.

32. A compound, a pharmaceutically acceptable ester or ether thereof or a pharmaceutically acceptable salt thereof according to claim 30, wherein $R^1$ represents a $C_2$–$C_{18}$ alkenyl group which has no substituent.

33. A compound, a pharmaceutically acceptable ester or ether thereof, or a pharmaceutically acceptable salt thereof according to claim 1, wherein $R^2$ represents a hydrogen atom, a $C_1$–$C_{22}$ alkyl group which is unsubstituted or has one or more substituents from said Substituent Group C or a $C_2$–$C_{22}$ alkenyl group which is unsubstituted or has one or more substituents from said Substituent Group C.

34. A compound, a pharmaceutically acceptable ester or ether thereof or a pharmaceutically acceptable salt thereof according to claim 1, wherein $R^2$ represents a hydrogen atom, a $C_1$–$C_{22}$ alkyl group which has no substituent or a $C_2$–$C_{22}$ alkenyl group which has no substituent.

35. A compound or a pharmaceutically acceptable ester or ether thereof or a pharmaceutically acceptable salt thereof according to claim 1, wherein $R^2$ represents a hydrogen atom, a $C_1$–$C_{20}$ alkyl group which has no substituent or a $C_{10}$–$C_{20}$ alkenyl group which has no substituent.

36. A compound, a pharmaceutically acceptable ester or ether thereof or a pharmaceutically acceptable salt thereof according to claim 1, wherein $R^2$ represents a hydrogen atom or a $C_8$–$C_{20}$ alkyl group which has no substituent.

37. A compound, a pharmaceutically acceptable ester or ether thereof or a pharmaceutically acceptable salt thereof according to claim 1, wherein $R^2$ represents a hydrogen atom.

38. A compound, a pharmaceutically acceptable ester or ether thereof or a pharmaceutically acceptable salt thereof according to claim 1, wherein $R^3$ represents a hydroxyl group.

39. A compound, a pharmaceutically acceptable ester or ether thereof or a pharmaceutically acceptable salt thereof according to claim 1, wherein:

$X^1$ is represented by the formula —$N(R^4)$—;

$X^2$ is represented by the formula —$N(R^5)$—;

$R^1$ represents (2) a $C_6$–$C_{10}$ aryl group which is unsubstituted or has one or more substituents from said Substituent Group A; a $C_1$–$C_{14}$ alkyl group which is substituted with one to three $C_6$–$C_{10}$ aryl groups which are the same or different and each is unsubstituted or has one or more substituents from said Substituent Group A; a $C_1$–$C_{14}$ alkyl group which is substituted with one to three heterocyclic groups which are the same or different and each have 1–4 ring nitrogen, sulfur or oxygen atoms and are unsubstituted or have one or more substituents from said Substituent Group B; a $C_1$–$C_{22}$ alkyl group which is unsubstituted or has one or more substituents from said Substituent Group C; or a $C_2$–$C_{22}$ alkenyl group which is unsubstituted or has one or more substituents, said one or more substituents are from the substituents set forth in groups (2) or (3) in the definition of $R^1$ in claim 1, or a substituent from said Substituent Group C;

$R^2$ represents a hydrogen atom or a $C_6$–$C_{20}$ alkyl group which has no substituent and $R^3$ represents a hydrogen atom or a hydroxyl group.

40. A compound, a pharmaceutically acceptable ester or ether thereof or a pharmaceutically acceptable salt thereof according to claim 1, wherein:

$X^1$ and $X^2$ are represented by the formula —NH—;

$R^1$ represents a $C_8$–$C_{10}$ aryl group which is unsubstituted or has one or more substituents from said Substituent Group A; a $C_1$–$C_{14}$ alkyl group which is substituted with one to three $C_8$–$C_{10}$ aryl groups which are the same or different and each may have one or more substituents from said Substituent Group A; a $C_1$–$C_{14}$ alkyl group which is substituted with one to three heterocyclic groups which are the same or different and each have 1–4 ring nitrogen, sulfur or oxygen atoms and are unsubstituted or have one or more substituents from said Substituent Group B; a $C_1$–$C_{22}$ alkyl group which is unsubstituted or has one or more substituents from said Substituent Group C; or a $C_2$–$C_{22}$ alkenyl group which is unsubstituted or has one or more substituents, said one or more substituents are from the substituents set forth in groups (2) or (3) in the definition of $R^1$ in claim 1, or a substituent from said Substituent Group C;

$R^2$ represents a hydrogen atom or a $C_6$–$C_{20}$ alkyl group which has no substituent; and $R^3$ represents a hydrogen atom or a hydroxyl group.

41. A compound, a pharmaceutically acceptable ester or ether thereof or a pharmaceutically acceptable salt thereof according to claim 1, wherein:

$X^1$ and $X^2$ are represented by the formula —NH—;

$R^1$ represents a $C_6$–$C_{10}$ aryl group which is unsubstituted or has one or more substituents from said Substituent Group A; a $C_1$–$C_{22}$ alkyl group which is unsubstituted or has one or more substituents from said Substituent Group C, or a $C_2$–$C_{22}$ alkenyl group which is unsubstituted or has one or more substituents from said Substituent Group C;

$R^2$ represents a hydrogen atom or a $C_6$–$C_{20}$ alkyl group which has no substituent; and $R^3$ represents a hydrogen atom or a hydroxyl group.

42. A compound, a pharmaceutically acceptable ester or ether thereof or a pharmaceutically acceptable salt thereof according to claim 1, wherein:

$X^1$ and $X^2$ are represented by the formula —NH—, $R^1$ represents a $C_6$–$C_{10}$ aryl group which is unsubstituted or has one or more substituents from said Substituent Group A or a $C_1$–$C_{20}$ alkyl group which is unsubstituted or has one or more substituents from said Substituent Group C;

$R^2$ represents a hydrogen atom or a $C_6$–$C_{20}$ alkyl group which has no substituent; and $R^3$ represents a hydrogen atom or a hydroxyl group.

43. A compound, a pharmaceutically acceptable ester or ether thereof or a pharmaceutically acceptable salt thereof according to claim 1, wherein:

$X^1$ and $X^2$ are represented by the formula —NH—;

$R^1$ represents a $C_6$–$C_{10}$ aryl group which is unsubstituted or has one or more substituents from said Substituent Group A;

$R^2$ represents a hydrogen atom or a $C_6$–$C_{20}$ alkyl group which has no substituent, and $R^3$ represents a hydrogen atom or a hydroxyl group.

44. A compound, a pharmaceutically acceptable ester or ether thereof or a pharmaceutically acceptable salt thereof according to claim 1, wherein:

$X^1$ and $X^2$ are represented by the formula —NH—;

$R^1$ represents a phenyl group which is unsubstituted or has one or more substituents from said Substituent Group A;

$R^2$ represents a hydrogen atom; and $R^3$ represents a hydroxyl group.

45. A compound, a pharmaceutically acceptable ester or ether thereof or a pharmaceutically acceptable salt thereof according to claim 1, wherein:

$X^1$ and $X^2$ are represented by the formula —NH—;

$R^1$ represents a phenyl group which is unsubstituted or has one or more substituents from said Substituent Group A;

$R^2$ represents a $C_6$–$C_{20}$ alkyl group which has no substituent; and $R^3$ represents a hydrogen atom.

46. A compound, a pharmaceutically acceptable ester or ether thereof or a pharmaceutically acceptable salt thereof according to claim 1, wherein:

$X^1$ and $X^2$ are represented by the formula —NH—;

$R^1$ represents a phenyl group which is unsubstituted or has one or more substituents from said Substituent Group A; and $R^2$ and $R^3$ represent hydrogen atoms.

47. A compound of the following formula (I') in which $R^1$, $R^2$, $R^3$, $X^1$ and $X^2$ are as defined in claim 1, a pharmaceutically acceptable ester or ether thereof, or a pharmaceutically acceptable salt thereof:

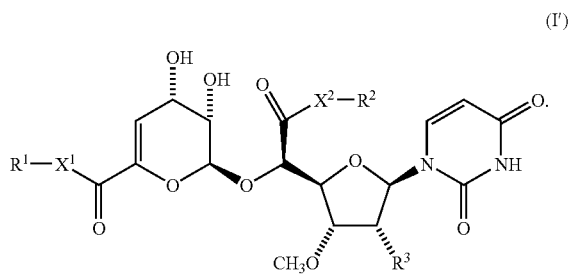

(I')

48. A compound according to claim 47, a pharmaceutically acceptable ester or ether thereof, wherein $R^1$ represents a phenyl group, $R^2$ represents a hydrogen atom, $X^1$ and $X^2$ are represented by the formula —NH— and $R^3$ represents a hydroxyl group, or a pharmaceutically acceptable salt thereof.

49. A compound according to claim 47, a pharmaceutically acceptable ester or ether thereof, wherein $R^1$ represents a phenyl group, $R^2$ represents a hydrogen atom, $X^1$ and $X^2$ are represented by the formula —NH— and $R^3$ represents a decanoyloxy group, or a pharmaceutically acceptable salt thereof.

50. A compound according to claim 47, a pharmaceutically acceptable ester or ether thereof, wherein $R^1$ represents a 4-ethylphenyl group, $R^2$ represents a hydrogen atom, $X^1$ and $X^2$ are represented by the formula —NH— and $R^3$ represents a hydroxyl group, or a pharmaceutically acceptable salt thereof.

51. A compound according to claim 47, a pharmaceutically acceptable ester or ether thereof, wherein $R^1$ represents a 4-ethylphenyl group, $R^2$ represents a hydrogen atom, $X^1$ and $X^2$ are represented by the formula —NH— and $R^3$ represents a decanoyloxy group, or a pharmaceutically acceptable salt thereof.

52. A compound according to claim 47, a pharmaceutically acceptable ester or ether thereof, wherein $R^1$ represents a 4-pentylphenyl group, $R^2$ represents a hydrogen atom, $X^1$ and $X^2$ are represented by the formula —NH— and $R^3$ represents a hydroxyl group, or a pharmaceutically acceptable salt thereof.

53. A compound according to claim 47, a pharmaceutically acceptable ester or ether thereof, wherein $R^1$ represents a 3-ethylphenyl group, $R^2$ represents a hydrogen atom, $X^1$ and $X^2$ are represented by the formula —NH— and $R^3$ represents a hydroxyl group, or a pharmaceutically acceptable salt thereof.

54. A compound according to claim 47, a pharmaceutically acceptable ester or ether thereof, wherein $R^1$ represents a 4-trifluoromethylphenyl group, $R^2$ represents a hydrogen atom, $X^1$ and $X^2$ are represented by the formula —NH— and $R^3$ represents a hydroxyl group, or a pharmaceutically acceptable salt thereof.

55. A compound according to claim 47, a pharmaceutically acceptable ester or ether thereof, wherein $R^1$ represents a 4-trifluoromethylphenyl group, $R^2$ represents a hydrogen atom, $X^1$ and $X^2$ are represented by the formula —NH— and $R^3$ represents a decanoyloxy group, or a pharmaceutically acceptable salt thereof.

56. A compound according to claim 47, a pharmaceutically acceptable ester or ether thereof, wherein $R^1$ represents a 4-butoxyphenyl group, $R^2$ represents a hydrogen atom, $X^1$ and $X^2$ are represented by the formula —NH— and $R^3$ represents a hydroxy group, or a pharmaceutically acceptable salt thereof.

57. A compound according to claim 47, a pharmaceutically acceptable ester or ether thereof, wherein $R^1$ represents a 4-pentyloxyphenyl group, $R^2$ represents a hydrogen atom, $X^1$ and $X^2$ are represented by the formula —NH— and $R^3$ represents a hydroxyl group, or a pharmaceutically acceptable salt thereof.

58. A compound according to claim 47, a pharmaceutically acceptable ester or ether thereof, wherein $R^1$ represents a 4-hexyloxyphenyl group, $R^2$ represents a hydrogen atom, $X^1$ and $X^2$ are represented by the formula —NH— and $R^3$ represents a hydroxyl group, or a pharmaceutically acceptable salt thereof.

59. A compound according to claim 47, a pharmaceutically acceptable ester or ether thereof, wherein $R^1$ represents a 4-fluorophenyl group, $R^2$ represents a hydrogen atom, $X^1$ and X² are represented by the formula —NH— and R³ represents a hydroxyl group, or a pharmaceutically acceptable salt thereof.

60. A compound according to claim 47, a pharmaceutically acceptable ester or ether thereof, wherein R¹ represents a 4-fluorophenyl group, R² represents a hydrogen atom, X¹ and X² are represented by the formula —NH— and R³ represents a decanoyloxy group, or a pharmaceutically acceptable salt thereof.

61. A compound according to claim 47, a pharmaceutically acceptable ester or ether thereof, wherein R¹ represents a 3,4-difluorophenyl group, R² represents a hydrogen atom, X¹ and X² are represented by the formula —NH— and R³ represents a hydroxyl group, or a pharmaceutically acceptable salt thereof.

62. A compound according to claim 47, a pharmaceutically acceptable ester or ether thereof, wherein R¹ represents a 3,4-difluorophenyl group, R² represents a hydrogen atom, X¹ and X² are represented by the formula —NH— and R³ represents a decanoyloxy group, or a pharmaceutically acceptable salt thereof.

63. A compound according to claim 47, a pharmaceutically acceptable ester or ether thereof, wherein R¹ represents a 3-chloro-4-fluorophenyl group, R² represents a hydrogen atom, X¹ and X² are represented by the formula —NH— and R³ represents a hydroxyl group, or a pharmaceutically acceptable salt thereof.

64. A compound according to claim 47, a pharmaceutically acceptable ester or ether thereof, wherein R¹ represents a 3-chloro-4-fluorophenyl group, R² represents a hydrogen atom, X¹ and X² are represented by the formula —NH— and R³ represents a decanoyloxy group, or a pharmaceutically acceptable salt thereof.

65. A compound according to claim 47, a pharmaceutically acceptable ester or ether thereof, wherein R¹ represents a 3-trifluoromethyl-4-fluorophenyl group, R² represents a hydrogen atom, X¹ and X² are represented by the formula —NH— and R³ represents a hydroxyl group, or a pharmaceutically acceptable salt thereof.

66. A compound according to claim 47, a pharmaceutically acceptable ester or ether thereof, wherein R¹ represents a 3-trifluoromethyl-4-fluorophenyl group, R² represents a hydrogen atom, X¹ and X² are represented by the formula —NH— and R³ represents a decanoyloxy group, or a pharmaceutically acceptable salt thereof.

67. A compound according to claim 47, a pharmaceutically acceptable ester or ether thereof, wherein R¹ represents a 3-methyl-4-bromophenyl group, R² represents a hydrogen atom, X¹ and X² are represented by the formula —NH— and R³ represents a hydroxyl group, or a pharmaceutically acceptable salt thereof.

68. A compound according to claim 47, a pharmaceutically acceptable ester or ether thereof wherein R¹ represents a 3-methyl-4-bromophenyl group, R² represents a hydrogen atom, X¹ and X² are represented by the formula —NH— and R³ represents a decanoyloxy group, or a pharmaceutically acceptable salt thereof.

69. A compound according to claim 47, a pharmaceutically acceptable ester or ether thereof, wherein R¹ represents a 3-nitro-4-fluorophenyl group, R² represents a hydrogen atom, X¹ and X² are represented by the formula —NH— and R³ represents a hydroxyl group, or a pharmaceutically acceptable salt thereof.

70. A compound according to claim 47, a pharmaceutically acceptable ester or ether thereof, wherein R¹ represents a 3-nitro-4-fluorophenyl group, R² represents a hydrogen atom, X¹ and X² are represented by the formula —NH— and R³ represents a decanoyloxy group, or a pharmaceutically acceptable salt thereof.

71. A compound according to claim 47, a pharmaceutically acceptable ester or ether thereof, wherein R¹ represents a 3-nitrophenyl group, R² represents a hydrogen atom, X¹ and X² are represented by the formula —NH— and R³ represents a hydroxyl group, or a pharmaceutically acceptable salt thereof.

72. A compound according to claim 47, a pharmaceutically acceptable ester or ether thereof, wherein R¹ represents a 3-nitrophenyl group, R² represents a hydrogen atom, X¹ and X² are represented by the formula —NH— and R³ represents a decanoyloxy group, or a pharmaceutically acceptable salt thereof.

73. A pharmaceutical composition for the prevention or treatment of a bacterial infection comprising as an active ingredient an antibacterially effective amount of a compound of the formula (I) according to claim 1, a pharmaceutically acceptable ester or ether thereof, or a pharmaceutically acceptable salt thereof, in combination with a pharmaceutically acceptable carrier.

74. A pharmaceutical composition for the prevention or treatment of a bacterial infection comprising as an active ingredient an antibacterially effective amount of a compound of the formula (I') according to claim 47, a pharmaceutically acceptable ester or ether thereof or a pharmaceutically acceptable salt thereof, in combination with a pharmaceutically acceptable carrier.

75. A composition according to claim 74, wherein the compound is selected from the group consisting of
- a compound wherein R¹ represents a phenyl group, R² represents a hydrogen atom, X¹ and X² are represented by the formula —NH— and R³ represents a hydroxyl group;
- a compound wherein R¹ represents a phenyl group, R² represents a hydrogen atom, X¹ and X² are represented by the formula —NH— and R³ represents a decanoyloxy group;
- a compound wherein R¹ represents a 4-ethylphenyl group, R² represents a hydrogen atom, X¹ and X² are represented by the formula —NH— and R³ represents a hydroxyl group;
- a compound wherein R¹ represents a 4-ethylphenyl group, R² represents a hydrogen atom, X¹ and X² are represented by the formula —NH— and R³ represents a decanoyloxy group;
- a compound wherein R¹ represents a 4-pentylphenyl group, R² represents a hydrogen atom, X¹ and X² are represented by the formula —NH— and R³ represents a hydroxyl group;
- a compound wherein R¹ represents a 3-ethylphenyl group, R² represents a hydrogen atom, X¹ and X² are represented by the formula —NH— and R³ represents a hydroxyl group;
- a compound wherein R¹ represents a 4-trifluoromethylphenyl group, R² represents a hydrogen atom, X¹ and X² are represented by the formula —NH— and R³ represents a hydroxyl group;
- a compound wherein R¹ represents a 4-trifluoromethylphenyl group, R² represents a hydrogen atom, X¹ and X² are represented by the formula —NH— and R³ represents a decanoyloxy group;
- a compound wherein R¹ represents a 4-butoxyphenyl group, R² represents a hydrogen atom, X¹ and X² are represented by the formula —NH— and R¹ represents a hydroxy group;

a compound wherein R¹ represents a 4-pentyloxyphenyl group, R² represents a hydrogen atom, X¹ and X² are represented by the formula —NH— and R³ represents a hydroxyl group;

a compound wherein R¹ represents a 4-hexyloxyphenyl group, R² represents a hydrogen atom, X¹ and X² are represented by the formula —NH— and R³ represents a hydroxyl group;

a compound wherein R¹ represents a 4-fluorophenyl group, R² represents a hydrogen atom, X¹ and X² are represented by the formula —NH— and R³ represents a hydroxyl group;

a compound wherein R¹ represents a 4-fluorophenyl group, R² represents a hydrogen atom, X¹ and X² are represented by the formula —NH— and R³ represents a decanoyloxy group;

a compound wherein R¹ represents a 3,4-difluorophenyl group, R² represents a hydrogen atom, X¹ and X² are represented by the formula —NH— and R³ represents a hydroxyl group;

a compound wherein R¹ represents a 3,4-difluorophenyl group, R² represents a hydrogen atom, X¹ and X² are represented by the formula —NH— and R³ represents a decanoyloxy group;

a compound wherein R¹ represents a 3-chloro-4-fluorophenyl group, R² represents a hydrogen atom, X¹ and X² are represented by the formula —NH— and R³ represents a hydroxyl group;

a compound wherein R¹ represents a 3-chloro-4-fluorophenyl group, R² represents a hydrogen atom, X¹ and X² are represented by the formula —NH— and R³ represents a decanoyloxy group;

a compound wherein R¹ represents a 3-trifluoromethyl-4-fluorophenyl group, R² represents a hydrogen atom, X¹ and X² are represented by the formula —NH— and R³ represents a hydroxyl group;

a compound wherein R¹ represents a 3-trifluoromethyl-4-fluorophenyl group, R² represents a hydrogen atom, X¹ and X² are represented by the formula —NH— and R³ represents a decanoyloxy group;

a compound wherein R¹ represents a 3-methyl-4-bromophenyl group, R² represents a hydrogen atom, X¹ and X² are represented by the formula —NH— and R³ represents a hydroxyl group;

a compound wherein R¹ represents a 3-methyl-4-bromophenyl group, R² represents a hydrogen atom, X¹ and X² are represented by the formula —NH— and R³ represents a decanoyloxy group;

a compound wherein R¹ represents a 3-nitro-4-fluorophenyl group, R² represents a hydrogen atom, X¹ and X² are represented by the formula —NH— and R³ represents a hydroxyl group;

a compound wherein R¹ represents a 3-nitro-4-fluorophenyl group, R² represents a hydrogen atom, X¹ and X² are represented by the formula —NH— and R³ represents a decanoyloxy group;

a compound wherein R¹ represents a 3-nitrophenyl group, R² represents a hydrogen atom, X¹ and X² are represented by the formula —NH— and R³ represents a hydroxyl group; and a compound wherein R¹ represents a 3-nitrophenyl group, R² represents a hydrogen atom, X¹ and X² are represented by the formula —NH— and R³ represents a decanoyloxy group, or a pharmaceutically acceptable ester or ether thereof, or a pharmaceutically acceptable salt thereof.

76. A method for the treatment of a bacterial infection in a warm-blooded animal, which comprises administering to said warm-blooded animal an antibacterially effective amount of a compound of formula (I) according to claim 1, a pharmaceutically acceptable ester or ether thereof or a pharmaceutically acceptable salt thereof.

77. A method according to claim 76, wherein the warm-blooded animal is a human.

78. A method according to claim 77, wherein the bacterial infection is a *Mycobacterium* bacterial infection.

79. A method according to claim 77, wherein the bacterial infection is a *Mycobacterium tuberculosis* infection.

80. A method for the treatment of a bacterial infection in a warm-blooded animal, which comprises administering to said warm-blooded animal an antibacterially effective amount of a compound of formula (I') according to claim 47, a pharmaceutically acceptable ester or ether thereof or a pharmaceutically acceptable salt thereof.

81. A method according to claim 80, wherein the warm-blooded animal is a human.

82. A method according to claim 81, wherein the bacterial infection is a *Mycobacterium* bacterial infection.

83. A method according to claim 81, wherein the bacterial infection is a *Mycobacterium tuberculosis* infection.

84. A method according to claim 81, wherein the compound is selected from the group consisting of a compound wherein R¹ represents a phenyl group, R² represents a hydrogen atom, X¹ and X² are represented by the formula —NH— and R³ represents a hydroxyl group;

a compound wherein R¹ represents a phenyl group, R² represents a hydrogen atom, X¹ and X² are represented by the formula —NH— and R³ represents a decanoyloxy group;

a compound wherein R¹ represents a 4-ethylphenyl group, R² represents a hydrogen atom, X¹ and X² are represented by the formula —NH— and R³ represents a hydroxyl group;

a compound wherein R¹ represents a 4-ethylphenyl group, R² represents a hydrogen atom, X¹ and X² are represented by the formula —NH— and R³ represents a decanoyloxy group;

a compound wherein R¹ represents a 4-pentylphenyl group, R² represents a hydrogen atom, X¹ and X² are represented by the formula —NH— and R³ represents a hydroxyl group;

a compound wherein R¹ represents a 3-ethylphenyl group, R² represents a hydrogen atom, X¹ and X² are represented by the formula —NH— and R³ represents a hydroxyl group;

a compound wherein R¹ represents a 4-trifluoromethylphenyl group, R² represents a hydrogen atom, X¹ and X² are represented by the formula —NH— and R³ represents a hydroxyl group;

a compound wherein R¹ represents a 4-trifluoromethylphenyl group, R² represents a hydrogen atom, X¹ and X² are represented by the formula —NH— and R³ represents a decanoyloxy group;

a compound wherein R¹ represents a 4-butoxyphenyl group, R² represents a hydrogen atom, X¹ and X² are represented by the formula —NH— and R³ represents a hydroxy group;

a compound wherein R¹ represents a 4-pentyloxyphenyl group, R² represents a hydrogen atom, X¹ and X² are represented by the formula —NH— and R³ represents a hydroxyl group;

a compound wherein R¹ represents a 4-hexyloxyphenyl group, R² represents a hydrogen atom, X¹ and X² are represented by the formula —NH— and R³ represents a hydroxyl group;

a compound wherein $R^1$ represents a 4-fluorophenyl group, $R^2$ represents a hydrogen atom, $X^1$ and $X^2$ are represented by the formula —NH— and $R^3$ represents a hydroxyl group;

a compound wherein $R^1$ represents a 4-fluorophenyl group, $R^2$ represents a hydrogen atom, $X^1$ and $X^2$ are represented by the formula —NH— and $R^3$ represents a decanoyloxy group;

a compound wherein $R^1$ represents a 3,4-difluorophenyl group, $R^2$ represents a hydrogen atom, $X^1$ and $X^2$ are represented by the formula —NH— and $R^3$ represents a hydroxyl group;

a compound wherein $R^1$ represents a 3,4-difluorophenyl group, $R^2$ represents a hydrogen atom, $X^1$ and $X^2$ are represented by the formula —NH— and $R^3$ represents a decanoyloxy group;

a compound wherein $R^1$ represents a 3-chloro-4-fluorophenyl group, $R^2$ represents a hydrogen atom, $X^1$ and $X^2$ are represented by the formula —NH— and $R^3$ represents a hydroxyl group;

a compound wherein $R^1$ represents a 3-chloro-4-fluorophenyl group, $R^2$ represents a hydrogen atom, $X^1$ and $X^2$ are represented by the formula —NH— and $R^3$ represents a decanoyloxy group;

a compound wherein $R^1$ represents a 3-trifluoromethyl-4-fluorophenyl group, $R^2$ represents a hydrogen atom, $X^1$ and $X^2$ are represented by the formula —NH— and $R^3$ represents a hydroxyl group;

a compound wherein $R^1$ represents a 3-trifluoromethyl-4-fluorophenyl group, $R^2$ represents a hydrogen atom, $X^1$ and $X^2$ are represented by the formula —NH— and $R^3$ represents a decanoyloxy group;

a compound wherein $R^1$ represents a 3-methyl-4-bromophenyl group, $R^2$ represents a hydrogen atom, $X^1$ and $X^2$ are represented by the formula —NH— and $R^3$ represents a hydroxyl group;

a compound wherein $R^1$ represents a 3-methyl-4-bromophenyl group, $R^2$ represents a hydrogen atom, $X^1$ and $X^2$ are represented by the formula —NH— and $R^3$ represents a decanoyloxy group;

a compound wherein $R^1$ represents a 3-nitro-4-fluorophenyl group, $R^2$ represents a hydrogen atom, $X^1$ and $X^2$ are represented by the formula —NH— and $R^3$ represents a hydroxyl group;

a compound wherein $R^1$ represents a 3-nitro-4-fluorophenyl group, $R^2$ represents a hydrogen atom, $X^1$ and $X^2$ are represented by the formula —NH— and $R^3$ represents a decanoyloxy group;

a compound wherein $R^1$ represents a 3-nitrophenyl group, $R^2$ represents a hydrogen atom, $X^1$ and $X^2$ are represented by the formula —NH— and $R^3$ represents a hydroxyl group; and a compound wherein $R^1$ represents a 3-nitrophenyl group, $R^2$ represents a hydrogen atom, $X^1$ and $X^2$ are represented by the formula —NH— and $R^3$ represents a decanoyloxy group, or a pharmaceutically acceptable ester or ether thereof, or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 7,157,442 B2 |
| APPLICATION NO. | : 10/080191 |
| DATED | : January 2, 2007 |
| INVENTOR(S) | : Hotoda et al. |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (710) days Delete the phrase "by 710" and insert --by 781 days--

Signed and Sealed this

Twelfth Day of June, 2007

JON W. DUDAS
*Director of the United States Patent and Trademark Office*